United States Patent
Kitazawa et al.

(10) Patent No.: US 7,071,201 B2
(45) Date of Patent: Jul. 4, 2006

(54) QUINOLINE DERIVATIVES

(75) Inventors: Noritaka Kitazawa, Ibaraki (JP); Kohshi Ueno, Ibaraki (JP); Keiko Takahashi, Ibaraki (JP); Teiji Kimura, Ibaraki (JP); Atsushi Sasaki, Ibaraki (JP); Koki Kawano, Ibaraki (JP); Tadashi Okabe, Ibaraki (JP); Makoto Komatsu, Ibaraki (JP); Manabu Matsunaga, Ibaraki (JP); Atsuhiko Kubota, Ibaraki (JP)

(73) Assignee: Eisai Co., Ltd., Tokyo (JP)

( * ) Notice: Subject to any disclaimer, the term of this patent is extended or adjusted under 35 U.S.C. 154(b) by 270 days.

(21) Appl. No.: 09/846,259

(22) Filed: May 2, 2001

(65) Prior Publication Data

US 2002/0086999 A1 Jul. 4, 2002

Related U.S. Application Data

(62) Division of application No. 09/367,227, filed as application No. PCT/JP98/01481 on Mar. 31, 1998, now Pat. No. 6,448,243.

(30) Foreign Application Priority Data

Mar. 31, 1997 (JP) ............................................... 9-98433
Dec. 26, 1997 (JP) ............................................. 9-366764

(51) Int. Cl.
 *A61K 31/435* (2006.01)
 *A61K 31/55* (2006.01)
 *C07D 211/68* (2006.01)
 *C07D 401/00* (2006.01)

(52) U.S. Cl. ..................... 514/277; 514/291; 514/310; 514/312; 514/320; 514/321; 514/322; 514/323; 514/191; 514/252; 544/333; 544/392; 544/71; 544/165; 546/153; 546/155; 546/192; 546/193; 546/195; 546/197; 546/198; 546/199; 546/200; 546/201; 546/202; 546/205

(58) Field of Classification Search ................ 546/210, 546/218.9, 153, 155, 192, 193, 195, 197, 546/198, 199, 200, 201, 202, 205; 544/71, 544/165, 1, 357, 392, 333; 514/191, 252, 514/398, 277, 291, 310, 312, 320, 321, 322, 514/323
See application file for complete search history.

(56) References Cited

U.S. PATENT DOCUMENTS 5,883,252 A * 3/1999 Tung et al. ................... 544/71
5,945,413 A * 8/1999 Tung et al. .................. 514/193

FOREIGN PATENT DOCUMENTS

| EP | A 1466585 | 1/1992 |
|---|---|---|
| EP | A 2470039 | 2/1992 |
| EP | WO9734895 | 9/1997 |
| EP | WO9828293 | 7/1998 |
| WO | 9210192 | 6/1992 |
| WO | 9533721 | 12/1992 |
| WO | 9623784 | 8/1996 |
| WO | 9706155 | 2/1997 |
| WO | 9747601 | 12/1997 |

OTHER PUBLICATIONS

Sasakura K. et al. "Simple Synthesis of 1–(azacycloalkyl)indoles using exclusive ortho.alpha.–chloroacetylation of N–(azacycloalkyl)anilines" Synth. Commun.; vol. 18(3); pp. 265–273 (1998).

* cited by examiner

*Primary Examiner*—D. Margaret Seaman
*Assistant Examiner*—Raymond Covington
(74) *Attorney, Agent, or Firm*—Birch, Stewart, Kolasch & Birch, LLP

(57) ABSTRACT

A novel compound of the formula:

wherein A, B, C, D, T, Y, and Z represent each methine or nitrogen; $R^1$, $R^2$, $R^3$, $R^4$, and $R^5$ represent each a substituent; n represents 0 or an integer of 1 to 3; m represents 0 or an integer of 1 to 6; and p represents an integer of 1 to 3; and pharmacologically acceptable salts thereof. The compound has a serotonin antagonism and is clinically useful as medicament, in particular, for treating, ameliorating and preventing spastic paralysis or central muscle relaxants for ameliorating myotonia.

19 Claims, No Drawings

QUINOLINE DERIVATIVES

This application is a divisional of co-pending application Ser. No. 09/367,227, filed on Aug. 11, 1999, for which priority is claimed under 35 U.S.C. §120. application Ser. No. 09/367,227 issued as U.S. Pat. No. 6,448,243 B1 on Sep. 10, 2002. application Ser. No. 09/367,227 is the U.S. national phase under 35 U.S.C. §371 of PCT International Application No. PCT/JP98/01481 filed on Mar. 31, 1998. The entire contents of each of the above-identified applications are hereby incorporated by reference. This application also claims priority under 35 U.S.C. §119 to Application No. JP 9-98433 and JP 9-366764 filed in Japan on Mar. 31, 1997 and Dec. 26, 1997, respectively.

BACKGROUND OF THE INVENTION

This invention relates to clinically useful medicaments having a serotonin antagonism, in particular for treating, ameliorating, andpreventing spastic paralysis or central muscle relaxants for ameliorating myotonia.

Myotonia, which seriously restrains daily life, is induced by any of a number of factors or a combination thereof, for example, cervico-omo-brachial syndromes accompanying stiffness or pain in the neck, shoulder, arm, lumbar, and dorsal skeletal muscles due to abnormal posture, fatigue, changes in the backbone with ageing, etc., shoulder periarthritis accompanying inflammation in the tissues constituting the shoulder joint due to changes in the shoulder joint caused by trauma, etc., and spastic paralysis wherein accelerated limb muscle tonus hinders voluntary movements.

In particular, spastic paralysis is a disease which accompanies limb muscle tonus, stiffening, walking difficulty, etc., and thus seriously restrains daily life.

It has been a practice to treat these diseases mainly with the use of medicaments. At the present stage, central muscle relaxants or peripheral muscle relaxants are administered to patients with these diseases. Particular examples of such central muscle relaxants include Tolperisone hydrochloride, Baclofen, Tizanidine hydrochloride, Chlorzoxazone, and Diazepam. Particular examples of such peripheral muscle relaxants include suxamethonium chloride, Pancuronium bromide, and dantrolene sodium.

Central muscle relaxants act selectively on the central nervous system so as to relaxmuscles. Therefore, it is expected that those action on the upper center would exhibit a more potent muscle relaxant effect. However, there arise at the same time some problems including extrapyramidal symptoms and neurologic manifestations such as sleepiness, sluggishness, and atony. No medicament capable of achieving well-balanced principal action and side effects has been known hitherto.

Diazepam, which is inherently a minor tranquilizer, is efficacious against diseases accompanying mental symptoms such as anxiety, tension and depression. However, its effect is too potent to merely ameliorate myotonia. With the use of diazepam, therefore, spastic paralysis can be relieved but there arise some problems such as dizziness. Suxamethonium chloride and Pancuronium bromide, which are peripheral muscle relaxants, are marketed exclusively as injections, which makes the chronic administration thereof difficult. Dantrolene sodium is processed into injections and preparations for oral use and has a relatively potent muscle relaxant effect. However, it has only a lowmarginof safetyand frequently induces muscular atony. Accordingly, it is difficult for those other than medical specialists to administer this medicine.

SUMMARY OF THE INVENTION

In view of the lack of a clinically useful, highly safe medicament for treating and amelioriating mytonia in spastic paralysis and the like, as discussed above, the present inventors have developed medicaments for treating, ameliorating, and preventing spastic paralysis or central muscle relaxants which have a potent effect of ameliorating myotonia while sustaining a high safety profile. It has been found that a novel class of 1,4-substituted cyclic amine derivatives represented by the following formula, and pharmacologically acceptable salts thereof, have an excellent central muscle relaxant effect while maintaining a high safety safety profile. This discovery makes it possible to solve the above problems, thus completing the present invention.

Accordingly, the present invention aims at providing clinically useful novel medicaments which have well-balanced principal action and side effects and make it possible to overcome the problem encountering in the prior art that those acting on the upper center would exhibit a more potent muscle relaxant effect but at the same time suffer from some problems including extrapyramidal symptoms and neurologic manifestations such as sleepiness, sluggishness and weakness.

Because of the anti-serotonin effect, it is expected that the 1,4-substituted cyclic amine derivative (I) of the present invention is moreover usable in preventing, treating and ameliorating depression, emotional disorders, schizophrenia, sleep disturbance, anxiety, spinal cord injury, thrombosis, hypertension, brain circulatory disturbances, peripheral circulatory disturbances, drug addiction, etc.

The 1,4-substituted cyclic amine derivative (I) according to the present invention is represented by the following formula:

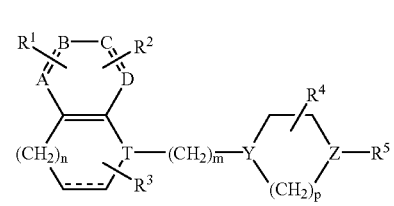

(I)

wherein A, B, C and D are the same or different from one another and each represents methine or nitrogen, provided at least two of them are methine;

the bond represented by the following formula:

----- represents a single or double bond;

T represents methine or nitrogen;

Y and Z are the same or different from each other and each represents methine, nitrogen, a group represented by the following formula:

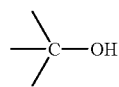

or a group represented by the following formula:

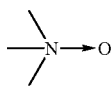

provided at least one of them represents nitrogen;

R$^1$ and R$^2$ are the same or different from each other and each represents hydrogen, halogeno, hydroxy, lower alkylsulfonylaminoalkyl, lower halogenated-alkylsulfonylaminoalkyl, 2-pyrrolidinon-1-yl, 1-hydroxy-1-(methoxypyridyl)methyl, methoxypyridylcarbonyl, 1,3-propanesultum-2-yl, lower hydroxypiperidylcarbonylalkyl, lower hydroxyalkylamidoalkyl, lower halogenated-alkylamidoalkyl, lower dihalogenated-alkylamidoalkyl, lower heteroarylamidoalkyl, lower hydroxyalkylamidoalkyl, optionally substituted amino, nitro, lower alkyl, lower alkoxy, lower acyl, lower alkoxyalkoxy, cyano, lower alkylsulfonyl, sulfonylamido, hydroxy-lower alkyl, hydroxy-lower alkoxy, lower alkoxycarbonylamino, lower alkylsulfonylamino, N-lower alkylalkylsulfonylamino, lower acylamino, optionally substituted aminoalkyl, optionally N-substituted lower acylaminoalkyl, optionally substituted aryl, optionally substituted arylsulfonylamino, lower alkylsulfonyloxy, hydroxyiminomethyl, (2-pyrrolidon-1-yl)methyl, (2-piperidon-1-yl)methyl, optionally substituted heteroaryl, optionally substituted aralkyl, optionally substituted heteroarylalkyl, cycloalkylcarbonylaminoalkyl, optionally substituted ureido, optionally substituted ureido-lower alkyl, succinimido, (succinimido-1-yl)-lower alkyl, amido, optionally substituted carbamoyl, optionally substituted carbamoyl-lower alkyl, optionally substituted thiocarbamoyl-lower alkyl, formyl, aromatic acyl, heteroarylcarbonyl, halogenated lower alkyl, (2-imidazolidinon-1-yl)methyl, (2,4-imidazolidinedion-3-yl)methyl, (2-oxazolidon-3-yl)methyl, (glutarimido-1-yl)methyl, optionally substituted heteroarylhydroxyalkyl, cyano-lower alkyl, 1-hydroxy lower cycloalkyl, (2,4-thiazolidinedion-3-yl)methyl, optionally substituted 4-piperidylmethyl, heteroarylacyl, pyrrolidinylcarbonyl-lower alkyl, optionally substituted aminosulfonylalkyl, carboxy-lower alkyl or lower alkylamidoalkyl; or alternatively R$^1$ and R$^2$ together may form optionally substituted alicycle, optionally substituted heterocycle or alkylenedioxy, provided these rings may be substituted;

R$^3$ represents hydrogen, halogeno, lower alkyl, hydroxy, hydroxy-lower alkyl, lower alkoxy, formyl, optionally substituted aralkyloxy, hydroxy-lower alkoxy, optionally substituted sulfamoyl or optionally N-substituted sulfamoyl-lower alkyl;

R$^4$ represents hydrogen, lower alkyl, hydroxy-lower alkyl, lower alkoxyalkyl, optionally aryl-substituted aryloxyalkyl or optionally aryl-substituted aralkyloxyalkyl;

R$^5$ represents lower alkyl, lower acyl, lower alkoxycarbonyl, aromatic acyl or a group represented by the following formula:

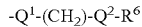

[wherein
Q$^1$ and Q$^2$ are both single bonds, or one of them is a single bond while the other represents oxygen, carbonyl, a group represented by —NHCO—, a group represented by —NHSO$_2$— or a group represented by >CH—R$^7$ (wherein R$^7$ represents hydroxy, lower alkyl or halogeno):
s represents 0 or an integer of 1 to 6; and R$^6$ represents optionally substituted aryl, optionally substituted heteroaryl, optionally substituted benzoheteroaryl, 1,4-benzodioxanyl, 1,3-benzodioxolyl, benzothiazolyl or cyano];
n represents 0 or an integer of 1 to 3;
m represents 0 or an integer of 1 to 6; and
p represents an integer of 1 to 3.

DETAILED DESCRIPTION OF THE INVENTION

The term "halogens" as used in the above definition particularly means chloro, fluoro, bromo and iodo.

The term "optionally substituted amino" particularly means amino optionally substituted by lower alkyl, optionally substituted aryl, etc.

The term "lower alkyl" particularly means C$_{1-6}$ alkyl such asmethyl, ethyl, n-propyl, i-propyl, n-butyl, i-butyl, t-butyl, pentyl and hexyl. The term "lower alkoxy" particularly means those consisting of the above lower alkyl and oxygen bonded thereto such as methoxy, ethoxy and propoxy. The term "lower acyl" particularly means those consisting of lower alkoxy and carbonyl bonded thereto such as acetyl, propionyl and butyryl. The term "lower alkoxyalkoxy" particularly means the above lower alkoxy further substituted by lower alkoxy such as methoxymethoxy, methoxyethoxy and methoxypropoxy. The term "lower alkylsulfonyl" particularly means the above lower alkyl bonded to sulfonyl (—SO$_2$—) such as methanesulfonyl and ethanesulfonyl. The term "sulfonylamido" means those represented by the formula (—SO$_2$NH$_2$). The term "hydroxy-lower alkyl" particularly means the above lower alkyl substituted by one or more hydroxy groups such as hydroxymethyl, hydroxyethyl and hydroxypropyl. The term "lower alkylsulfonylamino" particularly means the above lower alkyl bonded to sulfonylamino (—SO$_2$N<) such as methanesulfonylamino, ethanesulfonylamino, propanesulfonylamino, butanesulfonylamino and N-methylmethanesulfonylamino. The term "lower acylamino" particularly means amino bonded to lower (C$_{2-6}$) fatty acids such as acetamido, propionamido and butyrylamido.

The term "optionally N-substituted lower acylaminoalkyl" particularly means the above lower acyl bonded to amino-lower alkyl such as acetamidomethyl, acetamidoethyl, propionamidomethyl and butrylamidomethyl which may be further N-substituted by lower alkyl, etc.

The term "optionally substituted arylsulfonylamino" particularly means aryl bonded to sulfonylamino (—SO$_2$NH—) and optionally further substituted such as benzenesulfonylamino and toluenesulfonylamino. The term "lower alkylsulfonyloxy" particularly means the above lower alkyl bonded to sulfonyloxy (—SO$_3$—). The term "optionally substituted aminoalkyl" particularly means amino bonded to the above lower alkyl which may be further N-substituted by lower alkyl, lower alkylsulfonyl, etc.

The term "optionally substituted aryl" particularly means optionally substituted phenyl, optionally substituted naphthyl, etc. Preferable substituents are a halogen or a lower alkoxy, and further preferable are fluorine, chlorine and methoxy. And plural substituents may be used, which are the same as or different from one another. The term "optionally substituted heteroaryl" particularly means optionally substitutedpyridyl, pyrazyl, pyrimidyl, pyrrolyl, imidazolyl, pyrazolyl, quinolyl, isoquinolyl, furyl, thienyl, thiazolyl, etc. The term "optionally substituted aralkyl" particularly means optionally substituted benzyl, phenethyl, phenylpropyl, etc. The term "optionally substituted heteroarylalkyl" particularly means optionally substituted pyridylmethyl, pyridylethyl, pyrazylethyl, pyridonemethyl, pyrrolidonemethyl, pyrrolylmethyl, imidazolylmethyl, triazolylmethyl, thiazolylmethyl, etc. The term "cycloalkylcarbonylaminoalkyl" means carbonylaminoalkyl bonded to $C_{3-8}$ cycloalkyl.

The term "optionally substituted carbamoyl-lower alkyl" particularly means, for example, carbamoylmethyl ($H_2NCOCH_2$—) optionally N-substituted by lower alkyl, cycloalkyl, lower hydorxyalkyl, lower dihydroxyalkyl, lower carbamoylalkylcarbamoylalkyl, lower dialkylaminoalkyl, lower cyanoalkyl, lower alkoxyalkyl, lower halogenated-alkyl, etc. at the 1 or 2 position. The term "optionally substituted thiocarbamoyl-lower alkyl" particularly means, for example, thiocarbamoylmethyl ($H_2NCSCH_2$—) optionally N-substituted by lower alkyl, etc.

The term "heteroarylcarbonyl" particularly means pyridylcarbonyl, pyrrolylcarbonyl, thaizolylcarbonyl, etc. The term "halogenated lower alkyl" means lower alkyl substituted with halogeno such as chloromethyl, fluoromethyl, fluoroethyl, etc.

The term "optionally substituted heteroarylhydroxyalkyl" particularly means pyridylhydroxymethyl, thiazolylhydroxymethyl, pyrimidylhydroxymethyl, pyrrolylhydroxymethyl, etc.

More particularly, the 1,4-substituted cyclic amine derivatives (I) of the present invention are exemplified by the following compounds, though the present invention is not restricted thereto:

(1) 1-[1-(4-fluorophenyl)piperidin-4-yl]indoline,
(2) 1-[1-(4-fluorobenzyl)piperidin-4-yl]indoline,
(3) 1-(1-phenethylpiperidin-4-yl)indoline,
(4) 1-[1-(4-bromophenethyl)piperidin-4-yl]indoline,
(5) 1-[1-(3-chlorophenethyl)piperidin-4-yl]indoline,
(6) 1-[1-(4-chlorophenethyl)piperidin-4-yl]indoline,
(7) 1-[1-(2-fluorophenethyl)piperidin-4-yl]indoline,
(8) 1-[1-(3-fluorophenethyl)piperidin-4-yl]indoline,
(9) 1-[1-(4-fluorophenethyl)piperidin-4-yl]indoline,
(10) 1-[1-(2,4-difluorophenethyl)piperidin-4-yl]indoline,
(11) 1-[1-(3,4-difluorophenethyl)piperidin-4-yl]indoline,
(12) 1-[1-(3,5-difluorophenethyl)piperidin-4-yl]indoline,
(13) 1-[1-(4-fluorophenylpropyl)piperidin-4-yl]indoline,
(14) 1-{1-[2-(4-fluorophenyl)propyl]piperidin-4-yl}indoline,
(15) 1-[1-(4-fluorophenylbutyl)piperidin-4-yl]indoline,
(16) 1-[1-(4-fluorophenethyl)piperidin-4-yl]methylindoline,
(17) 1-{2-[1-(4-fluorophenethyl)piperidin-4-yl]ethyl}indoline,
(18) 1-[1-(4-methoxyphenethyl)piperidin-4-yl]indoline,
(19) 1-[1-(3-methoxyphenethyl)piperidin-4-yl]indoline,
(20) 1-[1-(4-hydroxyphenethyl)piperidin-4-yl]indoline,
(21) 1-[1-(4-cyanophenethyl)piperidin-4-yl]indoline,
(22) 1-[1-(3-hydroxymethylphenethyl)piperidin-4-yl]indoline,
(23) 1-[1-(4-hydroxymethylphenethyl)piperidin-4-yl]indoline,
(24) 1-{1-[4-(2-hydroxyethyl)phenethyl]piperidin-4-yl}indoline,
1-{1-[14-(1-hydroxyethyl)phenethyl]piperidin-4-yl}indoline,
(26) 1-{1-[4-(2-hydroxyethoxy)phenethyl]piperidin-4-yl}indoline,
(27) 1-[1-(4-trifluoromethylphenethyl)piperidin-4-yl]indoline,
(28) 1-[1-(4-methanesulfonylphenethyl)piperidin-4-yl]indoline,
(29) 1-[1-(4-nitrophenethyl)piperidin-4-yl]indoline,
(30) 1-[1-(4-aminophenethyl)piperidin-4-yl]indoline,
(31) 1-[1-(4-methylsulfonylaminophenethyl)piperidin-4-yl]indoline and 1-{1-[4-bis(methylsulfonyl)aminophenethyl]piperidin-4-yl}indoline,
(32) 1-[1-(4-acetamidophenethyl)piperidin-4-yl]indoline,
(33) 1-[1-(4-ethylaminophenethyl)piperidin-4-yl]indoline,
(34) 1-[1-(4-hydroxyiminomethylphenethyl)piperidin-4-yl]indoline,
(35) 1-[1-(4-aminomethylphenethyl)piperidin-4-yl]indoline,
(36) 1-[1-(4-acetamidomethylphenethyl)piperidin-4-yl]indoline,
(37) 1-[1-(4-chloroacetamidomethylphenethyl)piperidin-4-yl]indoline,
(38) 1-[1-(4-methanesulfonylaminomethylphenethyl)-piperidin-4-yl]indoline,
(39) 1-[1-(4-propionylaminomethylphenethyl)piperidin-4-yl]-3-methylindoline,
(40) 1-[1-(4-carbamoylphenethyl)piperidin-4-yl]indoline,
(41) 1-[1-(4-N-isopropylcarbamoylmethylphenethyl)piperidin-4-yl]indoline,
(42) 1-[1-(4-sulfamoylphenethyl)piperidin-4-yl]indoline,
1-{1-[2-hydroxyethoxy)phenethyl]piperidin-4-yl}indoline,
(44) 1-{1-[4-(2-dimethylaminoethoxy)phenethyl]piperidin-4-yl}indoline,
(45) 1-{1-[3,4-di(hydroxymethyl)phenethyl]piperidin-4-yl}indoline,
(46) 1-{1-[3,4-(methylenedioxy)phenethyl]piperidin-4-yl}indoline,
(47) 1-{1-[2-(4-chlorophenylsulfonylamino)ethyl]-piperidin-4-yl}indoline,
(48) 1-{1-[2-(4-methoxyphenylsulfonylamino)ethyl]-piperidin-4-yl}indoline,
(49) 1-{1-[2-(4-pyridyl)ethyl]piperidin-4-yl}indoline,
(50) 1-{1-[2-(2-pyridyl)ethyl]piperidin-4-yl}indoline,
(51) 1-{1-[2-(3-pyridyl)ethyl]piperidin-4-yl}indoline,
(52) 1-{1-[2-(2-methoxy-5-pyridyl)ethyl]piperidin-4-yl}indoline,
(53) 1-{1-[2-(3-methoxypyridin-5-yl)ethyl]piperidin-4-yl}indoline,
(54) 1-{1-[2-(2-cyanopyridin-5-yl)ethyl]piperidin-4-yl}indoline,
(55) 1-{1-[2-(2-hydroxymethylpyridin-5-yl)ethyl]-piperidin-4-yl}indoline,
(56) 1-{1-[2-(3-hydroxymethylpyridin-5-yl)ethyl]-piperidin-4-yl}indoline,
(57) 1-[1-(2,6-difluoro-3-pyridylethyl)piperidin-4-yl]indoline,
(58) 1-{1-[2-(2-thienyl)ethyl]piperidin-4-yl}indoline,
(59) 1-{1-[2-(3-thienyl)ethyl]piperidin-4-yl}indoline,
(60) 1-[1-(2-thiazolylethyl)piperidin-4-yl]indoline,
(61) 1-[1-(4-methyl-5-thiazolylethyl)piperidin-4-yl]indoline,
(62) 1-{1-[(indol-3-yl)ethyl]piperidin-4-yl}indoline,
(63) 1-{1-[2-(6-benzothiazolyl)ethyl]piperidin-4-yl}indoline,
(64) 1-[1-(5-methoxy-2-thienyl)ethylpiperidin-4-yl]indoline,
(65) 1-[1-(2-methoxy-5-thiazolyl)ethylpiperidin-4-yl]indoline,
(66) 1-[1-(2-cyano-5-thiazolyl)ethylpiperidin-4-yl]indoline,
(67) 1-(1-pyrazinylethylpiperidin-4-yl)indoline,
(68) 1-{1-[2-(4-bromopyrazol-1-yl)ethyl]piperidin-4-yl}indoline,
(69) 1-{1-[3-(4-fluorophenoxy)propyl]piperidin-4-yl}indoline,

(70) 1-{1-[3-(4-hydroxymethylphenoxy)propyl]piperidin-4-yl}indoline,
(71) 1-{1-[3-(4-hydroxyethylphenoxy)propyl]piperidin-4-yl}indoline,
(72) 1-{1-[4-(4-fluorophenyl)-4-oxobutyl]piperidin-4-yl}indoline,
(73) 1-{1-[4-(4-fluorophenyl)-4-hydroxybutyl]piperidin-4-yl}indoline,
(74) 1-[1-(phthalimido-1-yl)ethylpiperidin-4-yl]indoline,
(75) 1-[1-(4-fluorobenzamido)ethylpiperidin-4-yl]indoline,
(76) 1-{1-[1-(3,4-dimethoxyphenyl)propan-2-yl]piperidin-4-yl}indoline,
(77) 1-{1-[(1,4-benzodioxan-2-yl)methyl]piperidin-4-yl}indoline,
(78) 1-{1-[3-(3,4-methylenedioxyphenoxy)propyl]piperidin-4-yl}indoline,
(79) 1-[1-(4-fluorophenethyl)-3-methylpiperidin-4-yl]indoline,
(80) 1-(1-benzyl-3-hydroxymethylpiperidin-4-yl)indoline,
(81) 1-[1-(4-fluorophenethyl)-3-hydroxymethylpiperidin-4-yl]indoline,
(82) 1-[1-(4-fluorophenethyl)-3-hydroxymethylpiperidin-4-yl]indoline,
(83) 1-[2-(4-acetamidomethylphenyl)ethyl]-4-(indan-1-yl)piperidin-1-oxide,
(84) 1-[1-ethyl-3-(4-fluorophenoxymethyl)piperidin-4-yl]indoline,
(85) 1-[1-ethyl-3-(4-fluorobenzyloxymethyl)piperidin-4-yl]indoline,
(86) 1-[1-ethyl-3-(4-fluorobenzyloxymethyl)piperidin-4-yl]indoline,
(87) 1-(1-acetylpiperidin-4-yl) indoline -7-carbaldehyde,
1-[1-(t-butoxycarbonyl)piperidin-4-yl]-6-bromoindoline,
1-[1-(t-butoxycarbonyl)piperidin-4-yl]-6-hydroxymethylindoline,
1-[1-(t-butoxycarbonyl)piperidin-4-yl]-6-aminomethylindoline,
(91) 1-(1-benzylpiperidin-4-yl)-6-bromoindoline,
(92) 1-(1-benzylpiperidin-4-yl)-6-fluoroindoline,
(93) 1-(1-benzylpiperidin-4-yl)-6-formyindoline,
(94) 1-(1-benzylpiperidin-4-yl)-6-hydroxyiminomethylindoline,
(95) 1-(1-benzylpiperidin-4-yl)-6-aminomethylindoline,
(96) 1-(1-benzylpiperidin-4-yl)-6-acetamidomethylindoline,
(97) 1-[1-(4-methoxyphenethyl)piperidin-4-yl]-6-acetamidomethylindoline,
(98) 1-[1-(4-chlorophenethyl)piperidin-4-yl]-6-acetamidornethylindoline,
(99) 1-[1-(4-fluorophenethyl)piperidin-4-yl]-5-methoxyindolime,
(100) 1-[1-(4-fluorophenethyl)piperidin-4-yl]-6-bromnoindoline,
(101) 1-[1-(4-fluorophenethyl)piperidin-4-yl]-6-bromoindoline,
(102) 1-[1-(4-fluorophenethyl)piperidin-4-yl]-6-chloroindoline,
(103) 1-[1-(4-fluorophenethyl)piperidin-4-yl]-6-fluoroindoline,
(104) 1-[1-(4-fluorophenethyl)piperidin-4-yl]-6-hydroxyindoline,
(105) 1-[1-(4-fluorophenethyl)piperidin-4-yl]-4-methoxyindolime,
(106) 1-[1-(4-fluorophenethyl)piperidin-4-yl]-6-methoxyindoline,
(107) 1-[1-(4-fluorophenethyl)piperidin-4-yl]-7-methoxyindoline,
(108) 1-[1-(4-fluorophenethyl)piperidin-4-yl]-6,7-dimethoxyindoline,
(109) 1-[1-(4-fluorophenethyl)piperidin-4-yl]-6-nitroindoline,
(110) 1-[1-(4-fluorophenethyl)piperidin-4-yl]-6-aminoindoline:
(111) 1-[1-(4-fluorophenethyl)piperidin-4-yl]-6-methylaminoindoline,
(112) 1-[1-(4-fluorophenethyl)piperidin-4-yl]-6-ethylaminoindoline,
(113) 1-[1-(4-fluorophenethyl)piperidin-4-yl]-6-isopropylaminoindoline,
(114) 1-[1-(4-fluorophenethyl)piperidin-4-yl]-6-dimethylaminoindoline,
(115) 1-[1-(4-fluorophenethyl)piperidin-4-yl]-6-acetamidoindoline,
(116) 1-[1-(4-fluorophenethyl)piperidin-4-yl]-6-methanesulfonylaminoindoline,
(117) 1-[1-(4-fluorophenethyl)piperidin-4-yl]-6-ethanesulfonylaminoindoline,
(118) 1-[1-(4-fluorophenethyl)piperidin-4-yl]-6-propanesulfonylaminoindoline,
(119) 1-[1-(4-fluorophenethyl)piperidin-4-yl]-6-(4-fluorobenzenesulfonylamino)indoline,
(120) 1-[1-(4-fluorophenethyl)piperidin-4-yl]-6-(N-methylmethanesulfonylamino)indoline,
(121) 1-[1-(4-fluorophenethyl)piperidin-4-yl]-6-hydroxyethoxyindoline,
(122) 1-[1-(4-fluorophenethyl)piperidin-4-yl]-6-methanesulfonyloxyindoline,
(123) 1-[1-(4-fluorophenethyl)piperidin-4-yl]-7-hydroxyethoxyindoline,
(124) 1-[1-(4-fluorophenethyl)piperidin-4-yl]-6-cyanoindoline,
(125) 1-[1-(4-fluorophenethyl)piperidin-4-yl]-6-carbamoylindoline,
(126) 1-[1-(4-fluorophenethyl)piperidin-4-yl]-6-(1-pyrrolylcarbonyl)indoline,
(127) 1-[1-(4-fluorophenethyl)piperidin-4-yl]-6-acetylindoline,
(128) 1-[1-(4-fluorophenethyl)piperidin-4-yl]-6-methanesulfonylindoline,
(129) 1-[1-(4-fluorophenethyl)piperidin-4-yl]-6-thiocarbamoylmethylindoline,
(130) 1-[1-(4-fluorophenethyl)piperidin-4-yl]-6-formylindoline,
(131) 1-[1-(4-fluorophenethyl)piperidin-4-yl]-6-hydroxyiminomethylindoline,
(132) 1-[1-(4-fluorophenethyl)piperidin-4-yl]-6-aminomethylindoline,
(133) 1-[1-(4-fluorophenethyl)piperidin-4-yl]-6-acetamidomethylindoline,
(134) 1-[1-(2-fluorophenethyl)piperidin-4-yl]-6-acetamidomethylindoline,
(135) 1-[1-(3-fluorophenethyl)piperidin-4-yl]-6-acetamidomethylindoline,
(136) 1-[1-(4-fluorophenethyl)piperidin-4-yl]-6-hydroxymethylindoline,
(137) 1-[1-(4-fluorophenethyl)piperidin-4-yl]-6-(1-hydroxyethyl)indoline,
(138) 1-[1-(4-fluorophenethyl)piperidin-4-yl]-6-(1-hydroxypropyl)indoline,
(139) 1-[1-(4-fluorophenethyl)piperidin-4-yl]-6-(1-hydroxy-1-methylethyl)indoline,
(140) 1-[1-(4-fluorophenethyl)piperidin-4-yl]-6-(1-hydroxycyclobutyl)indoline,
(141) 1-[1-(4-fluorophenethyl)piperidin-4-yl]-6-(1-hydroxycyclopentyl)indoline,
(142) 1-[1-(4-fluorophenethyl)piperidin-4-yl]-6-chloromethylindoline, (143) 1-[1-(4-fluorophenethyl)piperidin-4-yl]-6-fluoromethylindoline,
(144) 1-[1-(4-fluorophenethyl)piperidin-4-yl]-6-(1-fluoroethyl)indoline,
(145) 1-[1-(4-fluorophenethyl)piperidin-4-yl]-6-cyanomethylindoline,
(146) 1-[1-(4-fluorophenethyl)piperidin-4-yl]-6-carboxymethylindoline,
(147) 1-[1-(4-fluorophenethyl)piperidin-4-yl]-6-carbamoylmethylindoline,
(148) 1-[1-(4-fluorophenethyl)piperidin-4-yl]-6-(methylcarbamoylmethyl)indoline,
(149) 1-[1-(4-fluorophenethyl)piperidin-4-yl]-6-(ethylcarbamoylmethyl)indoline,
(150) 1-[1-(4-fluorophenethyl)piperidin-4-yl]-6-(n-propylcarbamoylmethyl)indoline,
(151) 1-[1-(4-fluorophenethyl)piperidin-4-yl]-6-(isopropylcarbamoylmethyl)indoline,
(152) 1-[1-(4-fluorophenethyl)piperidin-4-yl]-6-(isobutylcarbamoylmethyl)indoline,
(153) 1-[1-(4-fluorophenethyl)piperidin-4-yl]-6-(t-butylcarbamoylmethyl)indoline,
(154) 1-[1-(4-fluorophenethyl)piperidin-4-yl]-6-(cyclopropylcarbamoylmethyl)indoline,
(155) 1-[1-(4-fluorophenethyl)piperidin-4-yl]-6-(tetramethylenecarbamoylmethyl)indoline,
(156) 1-[1-(4-fluorophenethyl)piperidin-4-yl]-6-propionylaminomethylindoline,
(157) 1-[1-(4-fluorophenethyl)piperidin-4-yl]-6-(n-butyryl)aminomethylindoline,
(158) 1-[1-(4-fluorophenethyl)piperidin-4-yl]-6-isobutyrylaminomethylindoline,
(159) 1-[1-(4-fluorophenethyl)piperidin-4-yl]-6-cyclopropanecarboxamidomethylindoline,
(160) 1-[1-(4-fluorophenethyl)piperidin-4-yl]-6-methylsulfonylaminomethylindoline,
(161) 1-[1-(4-fluorophenethyl)piperidin-4-yl]-6-ureidomethylindoline,
(162) 1-[1-(4-fluorophenethyl)piperidin-4-yl]-6-N-methylaminomethylindoline,
(163) 1-[1-(4-fluorophenethyl)piperidin-4-yl]-6-N-methylacetamidomethylindoline,
(164) 1-[1-(4-fluorophenethyl)piperidin-4-yl]-6-(N-methylsulfamoylmethyl)indoline,
(165) 1-[1-(4-fluorophenethyl)piperidin-4-yl]-6-(1-acetamidoethyl)indoline,
(166) 1-[1-(4-fluorophenethyl)piperidin-4-yl]-6-acetamidoethylindoline,
(167) 1-[1-(4-fluorophenethyl)piperidin-4-yl]-6-[(piperidin-4-yl)methyl]indoline,
(168) 1-[1-(4-fluorophenethyl)piperidin-4-yl]-6-[(1-acetylpiperidin-4-yl)methyl]indoline,
(169) 1-[1-(4-fluorophenethyl)piperidin-4-yl]-6-[(1-ethylpiperidin-4-yl)methyl]indoline,
(170) 1-[1-(4-fluorophenethyl)piperidin-4-yl]-6-[(1-methylpiperidin-4-yl)methyl]indoline,
(171) 1-[1-(4-fluorophenethyl)piperidin-4-yl]-6-(2-pyridyl)indoline,
(172) 1-[1-(4-fluorophenethyl)piperidin-4-yl]-6-(2-thiazolyl)indoline,
(173) 1-[1-(4-fluorophenethyl)piperidin-4-yl]-6-(1-methylpyrrol-2-yl)indoline,
(174) 1-[1-(4-fluorophenethyl)piperidin-4-yl]-6-[1-hydroxy-1-(2-pyridyl)methyl]indoline,
(175) 1-[1-(4-fluorophenethyl)piperidin-4-yl]-6-[(2-pyridyl)methyl]indoline,
(176) 1-[1-(4-fluorophenethyl)piperidin-4-yl]-6-[1-hydroxy-1-(3-pyridyl)methyl]indoline,
(177) 1-[1-(4-fluorophenethyl)piperidin-4-yl]-6-[1-(3-pyridyl)methyl]indoline,
(178) 1-[1-(4-fluorophenethyl)piperidin-4-yl]-6-(1-hydroxy-4-pyridylmethyl)indoline,
(179) 1-[1-(4-fluorophenethyl)piperidin-4-yl]-6-(4-pyridylmethyl)indoline,
(180) 1-[1-(4-fluorophenethyl)piperidin-4-yl]-6-(2-pyridylcarbonyl)indoline,
(181) 1-[1-(4-fluorophenethyl)piperidin-4-yl]-6-[1-hydroxy-1-(2-pyridyl)ethyl]indoline,
(182) 1-[1-(4-fluorophenethyl)piperidin-4-yl]-6-[1-(2-pyridyl)ethyl]indoline,
(183) 1-[1-(4-fluorophenethyl)piperidin-4-yl]-6-(3-pyridylcarbonyl)indoline,
(185) 1-[1-(4-fluorophenethyl)piperidin-4-yl]-6-[1-(2-methoxypyridin-3-yl) methyl]indoline,
(186) 1-[1-(4-fluorophenethyl)piperidin-4-yl]-6-[1-hydroxy-1-(2-methoxypyridin-6-yl)methyl]indoline,
(187) 1-[1-(4-fluorophenethyl)piperidin-4-yl)-6-[1-(2-methoxypyridin-6-yl)methyl]indoline,
(188) 1-[1-(4-fluorophenethyl)piperidin-4-yl]-6-[1-hydroxy-1-(2-methoxypyridin-5-yl)methyl]indoline,
(189) 1-[1-(4-fluorophenethyl)piperidin-4-yl]-6-[1-(2-methoxypyridin-5-yl)methyl]indoline,
(190) 1-[1-(4-fluorophenethyl)piperidin-4-yl]-6-[1-hydroxy-1-(2-pyridon-5-yl)methyl]indoline,
(191) 1-[1-(4-fluorophenethyl)piperidin-4-yl]-6-[1-hydroxy-1-(2-dimethylaminopyridin-5-yl)methyl]indoline,
(192) 1-[1-(4-fluorophenethyl)piperidin-4-yl]-6-[1-hydroxy-1-(2-chloropyridin-5-yl)methyl]indoline,
(193) 1-[1-(4-fluorophenethyl)piperidin-4-yl]-6-[2-(2-thiazolyl)-1-hydroxymethyl]indoline,
(194) 1-[1-(4-fluorophenethyl)piperidin-4-yl]-6-(2-thiazolylcarbonyl)indoline,
(195) 1-[1-(4-fluorophenethyl)piperidin-4-yl]-6-[1-(4-thiazolyl)-1-hydroxymethyl]indoline,
(196) 1-[1-(4-fluorophenethyl)piperidin-4-yl]-6-[1-(5-thiazolyl)-1-hydroxymethyl)indoline,
(197) 1-[1-(4-fluorophenethyl)piperidin-4-yl]-6-[1-hydroxy-1-(pyrimidin-2-yl)methyl]indoline,
(198) 1-[1-(4-fluorophenethyl)piperidin-4-yl]-6-[1-hydroxy-1-(pyrimidin-5-yl)methyl]indoline,
(199) 1-[1-(4-fluorophenethyl)piperidin-4-yl]-6-[1-hydroxy-1-(2-pyrrolyl)methyl]indoline,
(200) 1-[1-(4-fluorophenethyl)piperidin-4-yl]-6-N,N-dimethylaminomethylindoline,
(201) 1-[1-(4-fluorophenethyl)piperidin-4-yl]-6-(4-fluorophenyl)indoline,
(202) 1-[1-(4-fluorophenethyl)piperidin-4-yl]-6-(2-pyrrolidon-1-yl)methylindoline,
(203) 1-[1-(4-fluorophenethyl)piperidin-4-yl]-6-(2-piperidon-1-yl)methylindoline,
(204) 1-[1-(4-fluorophenethyl)piperidin-4-yl]-6-(succinimido-1-yl)methylindoline,
(205) 1-[1-(4-fluorophenethyl)piperidin-4-yl]-6-(glutarimido-1-yl)methylindoline,
(206) 1-[1-(4-fluorophenethyl)piperidin-4-yl]-6-(2-imidazolidonyl)methylindoline,
(207) 1-[1-(4-fluorophenethyl)piperidin-4-yl]-6-(2,4-imidazolidinedion-3-yl)methylindoline,
(208) 1-[1-(4-fluorophenethyl)piperidin-4-yl]-6-(2-oxazolidon-3-yl)methylindoline,
(209) 1-[1-(4-fluorophenethyl)piperidin-4-yl]-6-(2,4-thiazolidinedion-3-yl)methylindoline,
(210) 1-[1-(4-fluorophenethyl)piperidin-4-yl]-6-(pyrrol-1-yl)methylindoline,
(211) 1-[1-(4-fluorophenethyl)piperidin-4-yl]-6-(imidazol-1-yl)methylindoline, (212) 1-[1-(4-fluorophenethyl)piperidin-4-yl]-6-(1,2,3-triazol-1-yl)methylindoline and 1-[1-(4-fluorophenethyl)piperidin-4-yl]-6-(1,2,3-triazol-2-yl)methylindoline,
(213) 1-[1-(4-fluorophenethyl)piperidin-4-yl]-6-(1,2,4-triazol-2-yl)methylindoline,
(214) 1-[1-(4-fluorophenethyl)piperidin-4-yl]-6-(2-thiazolyl)methylindoline,
(215) 1-[1-(4-fluorophenethyl)piperidin-4-yl]-3-(4-methoxybenzyl)indoline,
(216) 1-[1-(4-fluorophenethyl)piperidin-4-yl]-3-methylindoline,
(217) 1-[1-(4-fluorophenethyl)piperidin-4-yl]-5-chloro-6-aminoindoline,
(218) 1-[1-(4-fluorophenethyl)piperidin-4-yl]-5-chloro-6-methanesulfonylaminoindoline,
(219) 1-[1-(4-fluorophenethyl)piperidin-4-yl]-5-chloro-6-methoxyindoline,
(220) 1-[1-(2,4-difluorophenethyl)piperidin-4-yl]-6-aminoindoline,
(221) 1-[1-(2,4-difluorophenethyl)piperidin-4-yl]-6-methanesulfonylaminoindoline,
(222) 1-[1-(2,4-difluorophenethyl)piperidin-4-yl]-6-acetamidoindoline,
(223) 1-[1-(2,4-difluorophenethyl)piperidin-4-yl]-6-bromoindoline,
(224) 1-[1-(2,4-difluorophenethyl)piperidin-4-yl]-6-acetamidomethylindoline,
(225) 1-[1-(2,4-difluorophenethyl)piperidin-4-yl]-6-carbamoylmethylindoline,
(226) 1-{1-[3-(4-fluorophenyl)propyl]piperidin-4-yl}-6-acetamidomethylindoline,
(227) 1-{1-[4-(4-fluorophenyl)butyl]piperidin-4-yl}-6-acetamidomethylindoline,
(228) 1-[1-(4-methoxyphenethyl)piperidin-4-yl]-6-methoxyindoline,
(229) 1-[1-(4-methoxyphenethyl)piperidin-4-yl]-6-fluoroindoline,
(230) 1-[1-(4-sulfamoylphenethyl)piperidin-4-yl]-6-methoxyindoline,
(231) 1-[1-(4-fluorophenoxypropyl)piperidin-4-yl]-6-bromoindoline,
(232) 1-[1-(4-fluorophenoxypropyl)piperidin-4-yl]-6-acetamidomethylindoline,
(233) 1-{1-[2-(6-benzothiazolyl)ethyl]piperidin-4-yl}-6-methoxyindoline,
(234) 1-{1-(4-fluorophenethyl)piperidin-4-yl}thiazolo[5,4-]indoline,
(235) 1-[1-(4-fluorophenethyl)piperidin-4-yl]-6-aminothiazolo[5,4-f]indoline,
(236) 1-[1-(4-fluorophenethyl)piperidin-4-yl]-7-hydroxy-(4a,7a)-cyclohexanoindoline and 1-[1-(4-fluorophenethyl)piperidin-4-yl]-4-hydroxy-(3b,6a)-cyclohexanoindoline,
(237) 1-(1-methylpiperidin-4-yl)-6-(4-fluorobenzenesulfonylamino)indoline,
(238) 1-(1-ethylpiperidin-4-yl)-6-(4-fluorobenzenesulfonylamino)indoline,
(239) 1-(1-ethylpiperidinyl)-4-(4-fluorophenyl)indoline,
(240) 1-(1-ethylpiperidin-4-yl)-3-(4-fluorophenyl)-indoline,
(241) 1-(1-ethylpiperidin-4-yl)-3-(4-methoxyphenyl)-indoline,
(242) 1-(1-ethylpiperidin-4-yl)-3-(4-methoxybenzyl)-indoline,
(243) 1-[(1-ethylpiperidin-4-yl)methyl]-3-(4-methoxybenzyl)indoline,
(244) 1-(1-ethylpiperidin-4-yl)-3-(4-fluorobenzyl)-indoline,
(245) 1-(1-ethylpiperidin-4-yl)-3-(3-pyridylmethyl)-indoline,
(246) 1-(1-ethylpiperidin-4-yl)-3-(3-methoxyphenethyl)-indoline,
(247) 1-(1-ethylpiperidin-4-yl)-3-(3-fluorophenethyl)-indoline,
(248) 1-[1-(4-fluorophenethyl)piperidin-4-yl]indan,
(249) 1-[1-(4-methoxyphenethyl)piperidin-4-yl]indan,
(250) 1-{4-[2-(4-fluorophenyl)ethyl]piperazin-1-yl}-6-methoxyindan,
(251) 1-(4-ethylpiperazin-1-yl)-6-methoxyindan,
(252) 1-(4-ethylpiperazin-1-yl)-2-ethoxycarboxyaminoindan,
(253) 1-(4-ethylpiperazin-1-yl)-2-methylaminoindan,
(254) 1-(4-ethylpiperazin-1-yl)-2-[methyl-(4-trifluorobenzyl)amino]indan,
(255) 7-[4-hydroxy-1-(4-fluorophenethyl)piperidin-4-yl]-5,6-dihydro-7H-pyrindine,
(256) 7-[1-(4-fluorophenethyl)piperidin-4-ylidene]-5,6-dihydropyrindine,
(2 57) 7-[1-(4-fluorophenethyl)piperidin-4-yl]-5,6-dihydro-7H -pyrindine,
(258) 7-[4-(4-fluorophenethyl)piperazin-1-yl]-5,6-dihydro-7H-pyrindine,
(259) 1-[1-(4-fluorophenethyl)piperidin-4-yl]-6-chloro-7-azaindoline,
(260) 1-[1-(4-fluorophenethyl)piperidin-4-yl]-7-azaindoline,
(261) 1-[1-(4-fluorophenethyl)piperidin-4-yl]-6-fluoro-7-azaindoline,
(262) 1-(1-(2,4-difluorophenethyl)piperidin-4-yl]-6-chloro-7-azaindoline,
(263) 1-[1-(4-methoxyphenethyl)piperidin-4-yl]-6-chloro-7-azaindoline,
(264) 1-[1-(4-fluorophenethyl)piperidin-4-yl]-6-azaindoline,
(265) 5-[1-(4-fluorophenethyl)piperidin-4-ylidene]-7-methyl-5,6-dihydrocyclopentapyrazine,
(266) 5-[1-(4-fluorophenethyl)piperidin-4-yl]-7-methyl-5,6-dihydro-5H-cyclopentapyrazine,
(267) 1-{1-[2-(4-methoxyphenyl)ethyl]piperidin-4-yl}-7-methoxy-1,2,3,4-tetrahydroquinoline,
(268) 1-{1-[2-(4-fluorophenyl) ethyl piperidin -4-yl}-7-methoxy-1,2,3,4-tetrahydroquinoline,
(269) 1-[1-(4-cyanopropyl)piperidin-4-yl]-7-methoxy-1,2,3,4-tetrahydroquinoline,
(270) 1-{1-[2-(2-thienyl)ethyl]lpiperidin-4-yl}-7-methoxy-1,2,3,4-tetrahydroquinoline,
(271) 1-{1-[2-(4-fluorophenyl)ethyl]piperidin-4-yl}-7,8-dimethoxy-1,2,3,4-tetrahydroquinoline,
(272) 1-{1-[2-(4-fluorophenyl)ethyl]piperidin-4-yl}-7,8-methylenedioxy-1,2,3,4-tetrahydroquinoline,
(267) 1-{-[2-(4-fluorophenyl)ethyl]piperidin-4-yl}-7-methoxy-8-methyl-1,2,3,4-tetrahydroquinoline,
(274) 1-{1-[2-(4-fluorophenyl)-2-oxoethyl]piperidin-4-yl}-7-methoxy-1,2,3,4-tetrahydroquinoline,
(275) 1-{1-[2-(4-fluorophenyl)-2-hydroxyethyl]piperidin-4-yl}-7-methoxy-1,2,3,4-tetrahydroquinoline,
(276) 1-{l-[2-(4-fluorophenyl)-2-fluoroethyl]piperidin-4-yl}-7-methoxy-1,2,3,4-tetrahydroquinoline,
(277) 1-[2-(4-fluorophenyl)ethyl]-4-(6-methoxy-1,2,3,4-tetrahydronaphthalen-1-yl)piperidine,
(278) 1-[2-(4-fluorophenyl)ethyl]-4-[6-(2-hydroxy)ethoxy-1,2,3,4-tetrahydronaphthalen-1-yl]piperidine,
(279) trans-1-(4-ethylpiperazin-1-yl)-7-methoxy-2-(4-trifluoromethylphenoxy)-1,2,3,4-tetrahydronaphthalene,
(280) 1-{4-[2-(4-fluorophenyl)ethyl]piperazin-1-yl}-7-methoxy-1,2,3,4-tetrahydronaphthalene, (281) 1-{4-[2-(4-fluorophenyl)-2-oxoethyl]piperazin-1-yl}-7-methoxy-1,2,3,4-tetrahydronaphthalene,
(282) 1-(4-fluorophenethyl)-4-(2-methoxybenzocycloheptan-9-yl)piperazine,
(283) 5-{4-[2-(4-fluorophenyl)ethyl]piperazin-1-yl}-5,6,7,8-tetrahydroisoquinoline,
(284) 1-[1-(4-fluorophenethyl)piperidin-4-yl]-5,6-methylenedioxyindoline,
(285) 1-[1-(4-fluorophenethyl)piperidin-4-yl]-6-acetamidomethylindole,
(286) 1-[1-(4-fluorophenethyl)piperidin-4-yl]-6-(N-isopropylcarbamoylmethyl)indole,
(287) 1-[1-(4-fluorophenethyl)piperidin-4-yl]-6-(1-methylpyrrol-2-yl)indole,
(288) 1-[1-(4-acetamidomethylphenethyl)piperidin-4-yl]indole,
(289) 1-[1-(4-fluorophenethyl)piperidin-4-yl]-6-cyanoindole,
(290) 1-[1-(4-fluorophenethyl)-3-methylpiperidin-4-yl]indole,
(291) 1-[1-(4-fluorophenethyl)homopiperidin-4-yl]-6-methoxyindoline,
(292) 1-[1-(4-fluorophenethyl)pyrrolidin-3-yl]-6-methoxyindoline,
(293) 3,3-dimethyl-1-[1-(4-fluorophene thyl) piperidin -4-yl]-6-bromoindoline,
(294) 1-[1-(4-fluorophenethyl)piperidin-4-yl]-6-(ethylcarbamoylmethyl)indoline,
(295) 1-[1-(4-fluorophenethyl)piperidin-4-yl]-6-[N-(cyclopropylcarbamoyl)methyl]indole,
(296) 1-[1-(4-fluorophenethyl)piperidin-4-yl]-6-[N-(isobutylcarbamoyl)methyl]indole,
(297) 1-[1-(4-fluorophenethyl)piperidin-4-yl]-6-(n-propylcarbamoylmethy)indoline,
(298) 1-[-(4-fluorophenethyl)piperidin-4-yl]-6-(tetramethylenecarbamoylmethyl)indole,
(299) 1-[1-(2,4-difluorophenethyl)piperidin-4-yl]-6-carbamoylmethylindole,
(300) 1-[1-(4-fluorophenethyl)piperidin-4-yl]-6-(2-hydroxyethyl)carbamoylmethylindole,
(301) 1-[1-(4-fluorophenethyl)piperidin-4-yl]-6-dimethylcarbamoylmethylindole,
(302) 1-[1-(4-fluorophenethyl)piperidin-4-yl]-6-(4-hydroxypiperidin-1-yl)carbonylmethylindole,
(303) 1-[1-(4-fluorophenethyl)piperidin-4-yl]-6-[bis(2-hydroxyethyl)carbamoylmethyl]indole,
(304) 1-[1-(4-fluorophenethyl)piperidin-4-yl]-6-(1,3-dihydroxypropan-2-yl)carbamoylmethylindole,
(305) 1-[1-(4-fluorophenethyl)piperidin-4-yl]-6-carbaoylmethylindole,
(306) 1-[1-(4-fluorophenethyl)piperidin-4-yl]-6-(carbamoylmethyl) carbaoylmethylindole,
(307) 1-(1-(4-fluorophenethyl)piperidin-4-yl]-6-(2-dimnethylamninoethyl)carbarnoylmnethylindole,
(308) 1-[1-(4-fluorophenethyl)piperidin-4-yl]-6-cyanormethylcarbaoylrmethylindolei,
(309) 1-[1-(4-fluorophenethyl)piperidin-4-yl]-6-(2-methoxyethyl)lcarbarboylmethylindole,
(310) 1-[1-(4-fluorophenethyl)piperidin-4-yl]-6-(2-fluoroethyl)carbamoylmethylindole,
(311) 1-[1-(4-fluorophenethyl)piperidin-4-yl]-6-[2-(ethylcarbamoyl)ethyl]indole,
(312) 1-[1-(4-fluorophenethyl)piperidin-4-yl]-6-[2-(pyrrolidin-1-yl)ethyl]carbamoylmethylindole,
(313) 1-[1-(4-fluorophenethyl)piperidin-4-yl]-6-[2-(morpholin-4-yl)ethyl]carbamoylmethylindole,
(314) 1-[1-(4-fluorophenethyl)piperidin-4-yl]-6-(pyridin-4-yl)methylcarbamoylmethylindole,
(315) 1-[1-(4-fluorophenethyl)piperidin-4-yl]-6-[2-(pyridin-2-yl)ethyl]carbamoylmethylindole,
(316) 1-[1-(4-fluorophenethyl)piperidin-4-yl]-6-methylcarbamoylmethylindole,
(317) 1-[1-(4-fluorophenethyl)piperidin-4-yl]-6-(2-methoxypyridin-5-yl)carbonylindole,
(318) 1-[1-(4-fluorophenethyl)piperidin-4-yl]-6-[(2-methoxypyridin-5-yl)hydroxymethyl]indole,
(319) 1-[1-(4-fluorophenethyl)piperidin-4-yl]-6-(1-hydroxyproyl)indole,
(320) 1-[1-(4-fluorophenethyl)piperidin-4-yl]-6-(1-hydroxy-1-methylethyl)indoline,
(321) 1-[1-(4-fluorophenethyl)piperidin-4-yl]-6-(3-hydroxypropyl)indole,
(322) 1-[1-(4-fluorophenethyl)piperidin-4-yl]-6-methanesulfonamidomethylindole,
(323) 1-[1-(4-fluorophenethyl)piperidin-4-yl]-6-isopropylsulfonamidomethylindole,
(324) 1-[1-(4-fluorophenethyl)piperidin-4-yl]-6-n-propylsulfonamidomethylindole,
(325) 1-[1-(4-fluorophenethyl)piperidin-4-yl]-6-(3-chloropropyl)sulfonamidomethylindole,
(326) 1-[1-(4-fluorophenethyl)piperidin-4-yl]-6-(1,3-propanesultam-2-yl)methylindole,
(327) 1-[1-(4-fluorophenethyl)piperidin-4-yl]-6-propionylaminomethylindole,
(328) 3-chloro-1-[1-(4-fluorophenethyl)-piperidin-4-yl]-6-acetamidomethylindole,
(329) 1-[1-(4-fluorophenethyl)piperidin-4-yl]-6-(4-hydroxybutyroylamidomethyl)indole,
(330) 1-[1-(4-fluorophenethyl)piperidin-4-yl]-6-hydroxyethoxyindole,
(331) 1-[1-(4-fluorophenethyl)piperidin-4-yl]-6-methanesulfonylindole,
(332) 1-[1-(2,6-difluoro-3-pyridylethyl)piperidin-4-yl]indole,
(333) 1-[1-(4-fluorophenethyl)piperidin-4-yl]-6-fluoroindole,
(334) 1-[1-(4-fluorophenethyl)piperidin-4-yl]thiazolo-[5,4-f]indole,
(335) 1-[1-(4-fluorophenethyl)piperidin-4-yl]-6-(N-methylmethanesulfonylamino)indole,
(336) 1-[1-(4-fluorophenethyl)piperidin-4-yl]-6-methanesulfonyloxyindole,
(337) 1-[1-(4-fluorophenethyl)piperidin-4-yl]-6-carbamoylindole,
(338) 1-[1-(4-fluorophenethyl)piperidin-4-yl]-6-(N-methylsulfamoylmethyl)indole,
(339) 1-[1-(4-fluorophenethyl)piperidin-4-yl]-6-acetamidoindole,
(340) 1-[1-(4-fluorophenethyl)piperidin-4-yl]-6-(1,2-dihydroxypropan-3-yl)carbamoylmethylindole,
(341) 1-[1-(4-fluorophenethyl)piperidin-4-yl]-6-(pyridin-2-yl)methylcarbamoylmethylindole,
(342) 1-[1-(2-fluorophenethyl)piperidin-4-yl]-6-methylcarbamoylmethylindole,
(343) 1-[1-(2-fluorophenethyl)piperidin-4-yl]-6-(1-acetylpiperidin-4-yl)methylcarbamoylmethylindole,
(344) 1-[1-(2-fluorophenethyl)piperidin-4-yl]-6-ethylcarbamoylmethylindole,
(345) 1-[1-(4-fluorophenethyl)piperidin-4-yl]-6-(1-ethylpiperidin-4-yl)methylcarbamoylmethylindole,
(346) 1-[1-(2-fluorophenethyl)piperidin-4-yl]-6-(2-hydroxyethyl)carbamoylmethylindole,
(347) 1-[1-(4-fluorophenethyl)piperidin-4-yl]-6-(1,3-dioxolan-2-yl)methylcarbamoylmethylindole,
(348) 1-[1-(2-fluorophenethyl)piperidin-4-yl]-6-aminomethylindole, (349) 1-[1-(4-chlorophenethyl)piperidin-4-yl]-6-acetamidomethylindole,
(350) 1-[1-(3-fluorophenethyl)piperidin-4-yl]-6-acetamidomethylindole,
(351) 1-[1-(4-methoxyphenethyl)piperidin-4-yl]-6-acetamnidomethylindoie,
(352) 1-[1-(2-fluorophenethyl)piperidin-4-yl]-6-acetamidomethylindole,
(353) 1-[1-(4-fluorophenethyl)piperidin-4-yl]-6-(2,4-imidazolidinedion-3-yl)methylindole,
(354) 1-[1-(4-fluorophenethyl)piperidin-4-yl]-6-isobutyrylaminomethylindole,
(355) 1-[1-(4-fluorophenethyl)piperidin-4-yl]-6-(2-imidazolidonyl)methylindole,
(356) 1-{1-[4-(4-fluorophenyl)butyl]piperidin-4-yl}-6-acetamidomethylindole,
(357) 1-[1-(2,4-difluorophenethyl)piperidin-4-yl]-6-acetamidomethylindole,
(358) 1-[1-(4-fluorophenethyl)piperidin-4-yl]-6-(2-pyrrolidon-1-yl)methylindole,
(359) 1-[1-(4-fluorophenethyl)piperidin-4-yl]-6-N-methylacetamidomethylindole,
(360) 1-{1-[3-(4-fluorophenyl)propyl]piperidin-4-yl}-6-acetamidomethylindole,
(361) 1-[1-(4-fluorophenethyl)piperidin-4-yl]-6-N-methylaminomethylindole,
(362) 1-[1-(4-fluorophenethyl)piperidin-4-yl]-6-(n-butyryl)aminomethylindole,
(363) 1-[1-(4-fluorophenethyl)piperidin-4-yl]-6-cyclopropanecarboxamidomethylindole,
(364) 1-[1-(4-fluorophenethyl)piperidin-4-yl]-6-hydroxyacetamidomethylindole,
(365) 1-[1-(4-fluorophenethyl)piperidin-4-yl]-6-fluoroacetamidomethylindole,
(366) 1-[1-(4-fluorophenethyl)piperidin-4-yl]-6-(3-fluoroacetamidomethylindole,
(367) 1-[1-(4-fluorophenethyl)piperidin-4-yl]-6-(3-chloropropionylamino)methylindole,
(368) 1-[1-(4-fluorophenethyl)piperidin-4-yl]-6-imidazocarbonylaminomethylindole,
(369) 1-[1-(4-fluorophenethyl)piperidin-4-yl]-6-(3-hydroxypropionylamino)methylindole,
(370) 1-[1-(4-fluorophenethyl)piperidin-4-yl]-3-formyl-6-acetamidomethylindole,
(371) 1-[1-(4-fluorophenethyl)piperidin-4-yl]-3-hydroxyimino-6-acetamidomethylindole,.
(372) 1-[1-(4-fluorophenethyl)piperidin-4-yl]-3-hydroxymethyl-6-acetamidomethylindole,
(373) 1-[1-(4-fluorophenethyl)piperidin-4-yl]-6-chloroacetamidomethylindole,
(374) 1-[1-(4-fluorophenethyl)piperidin-4-yl]-6-bromoacetamidomethylindole,
(375) 1-[1-(4-fluorophenethyl)piperidin-4-yl]-6-(N,N-dimethylaminoacetamido)methylindole,
(376) 1-[1-(4-fluorophenethyl)piperidin-4-yl]-6-[(piperidin-1-yl)acetamido]methylindole,
(377) 1-[1-(4-fluorophenethyl)piperidin-4-yl]-6-(3-bromopropionylamino)methylindole,
(378) 1-[1-(4-fluorophenethyl)piperidin-4-yl]-6-(3-N,N-dimethylarninopropionyl)aminomethylindole,
(379) 1-[1-(4-fluorophenethyl)piperidin-4-yl]-6-[3-(piperidin-1-yl)propionylamino]methylindole,
(380) 1-[1-(2-fluorophenethyl)piperidin-4-yl]-6-propionylaminomethylindole,
(381) 1-[1-(2-fluorophenethyl)piperidin-4-yl]-6-fluoroacetamidomethylindole,
(382) 1-[1-(2-fluorophenethyl)piperidin-4-yl]-6-(3-hydroxypropionylamino)methylindole,
(383) 1-[1-(2-fluorophenethyl)piperidin-4-yl]-6-hydroxyacetamidomethylindole,
(384) 1-[1-(4-fluorophenethyl)piperidin-4-yl]-6-methoxycarbonylaminomethylindole,
(385) 1-[1-(4-fluorophenethyl)piperidin-4-yl]-6-N,N-dimethylaminocarbonylaminomethylindole,
(386) 1-{1-[2-(3-pyridyl)ethyl]piperidin-4-yl}-6-acetamidomethylindole,
(387) 3-cyano-1-[1-(4-fluorophenethyl)piperidin-4-yl]-6-acetamidomethylindole,
(388) 1-{4-[(1-hydroxyethyl)phenethyl]piperidin-4-yl}-6-acetamidomethylindole,
(389) 1-[1-(4-bromophenethyl)piperidin-4-yl]-6-acetamidomethylindole,
(390) 1-[1-(2-fluorophenethyl)piperidin-4-yl]-6-formylindole,
(391) 1-[1-(2-fluorophenethyl)piperidin-4-yl]-6-hydroxymethylindole,
(392) 1-[1-(4-fluorophenethyl)piperidin-4-yl]-6-(1-hydroxyethyl)indole,
(393) 1-[1-(4-fluorophenethyl)piperidin-4-yl]-6-ureidomethylindole,
(394) 1-[1-(4-fluorophenethyl)piperidin-4-yl]-6-(3-methylureido)methylindole,
(395) 3,3-dimethyl-1-[1-(4-fluorophenethyl)piperidin-4-yl]-6-acetamidoindoline,
(396) 2,2-dimethyl-1-[1-(4-fluorophenethyl)piperidin-4-yl]-6-methoxyindoline and
(397) 1-[1-(4-fluorophenethyl)piperidin-4-yl]-6-(3-methylureido)methylindole.

Although some of the 1,4-substituted cyclic amine derivatives (I) of the present invention occur as optical isomers or geometrical isomers, either one of these optical isomers or a mixture thereof may be used in the present invention without restriction. Similarly, either one of geometrical isomers or a mixture thereof may be employed herein without any restriction. In the case of polymorphic crystals, either one of the crystal forms or a mixture thereof may be used in the present invention without restriction, too. Moreover, use may be made of both anhydrides and hydrates.

The pharmacologically acceptable salts to be used in the present invention may be arbitrary salts of the 1,4-substituted cyclic amine derivatives (I) of the present invention without particular restriction. Examples thereof include inorganic acid addition salts such as hydrochlorides, sulfates, nitrates, hydrobromides, hydriodides, perchlorates and phosphates, organic acid addition salts such as oxalates, maleates, fumarates and succinates, sulfonic acid addition salts such as methanesulfonates, ethanesulfonates, benzenesulfonates, p-toluenesulfonates and camphorsulfonates, and amino acid addition salts. Among all, it is preferable to use hydrochlorides and oxalates thereof.

The 1,4-substituted cyclic amine derivative (II) according to the present invention is represented by the following formula:

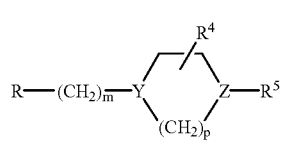

(II)

R represents a substituent selected from among the following ones:

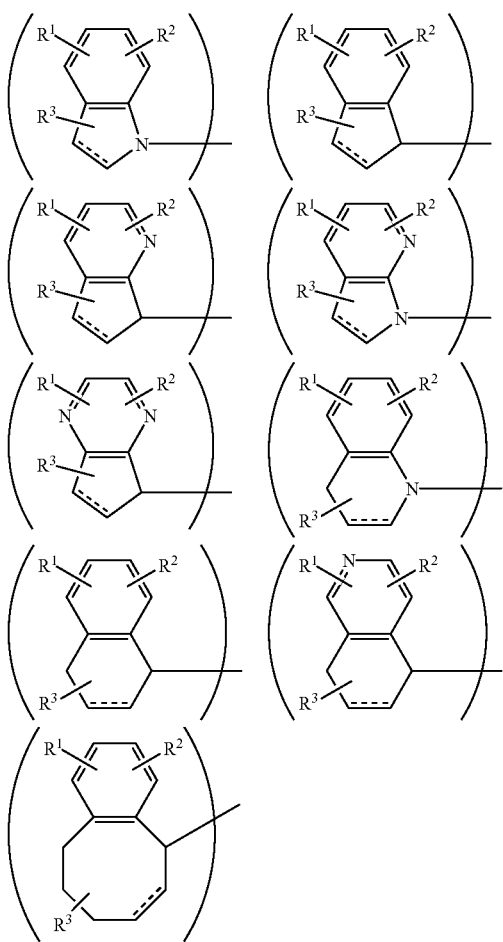

(wherein the bond represented by the following formula:

and $R^1$, $R^2$ and $R^3$ are each as defined above); and $R^4$, $R^5$, Y, Z, m and p are each as defined above.

Examples of the 1,4-substituted cyclic amine derivatives (II) include compounds similar to those cited above as the examples of the 1,4-substituted cyclic amine derivatives (I), though the present invention is not restricted thereto.

The 1,4-substituted cyclic amine derivative (III) according to the present invention is represented by the following formula:

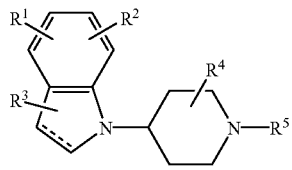

wherein the bond represented by the following formula:

and $R^1$, $R^2$, $R^3$, $R^4$ and $R^5$ are each as defined above.

Further, the 1,4-substituted cyclic amine derivative (IV) of the present invention is represented by the following formula:

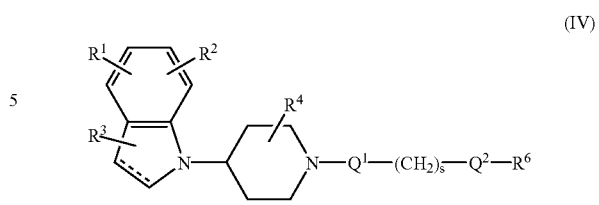

wherein the bond represented by the following formula:

and $R^1$, $R^2$, $R^3$, $R^4$, $R^6$, $Q^1$, $Q^2$ and s are each as defined above.

Next, the 1,4-substituted cyclic amine derivative (V) according to the present invention is represented by the following formula:

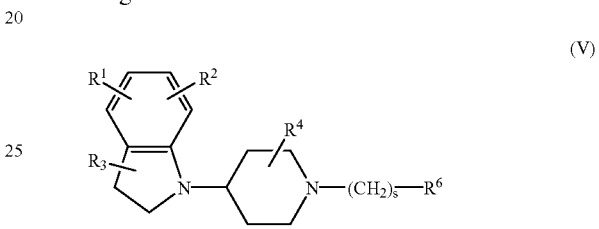

wherein $R^1$, $R^2$, $R^3$, $R^4$, $R^6$ and s are each as defined above.

Finally, the 1,4-substituted cyclic amine derivative (VI) according to the present invention is represented by the following formula:

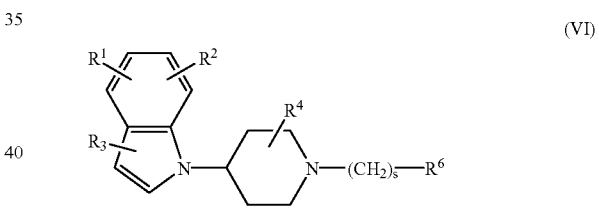

wherein $R^1$, $R^2$, $R^3$, $R^4$, $R^6$ and s are each as defined above.

Among the 1,4-substituted cyclic amine derivatives (I) to (VI) according to the present invention, those which are particularly preferable from the viewpoint of pharmacological effects or safety are, for example, the following ones:

(1) 1-[1-(4-acetamidomethylphenethyl)piperidin-4-yl]indoline, (2) 1-[1-(4-fluorophenethyl)piperidin-4-yl]-6-carbamoylindoline, (3) 1-[1-(4-fluorophenethyl)piperidin-4-yl]-6-methanesulfonylindoline, (4) 1-[1-(4-fluorophenethyl)piperidin-4-yl]-6-acetamidomethylindoline, (5) 1-[1-(4-fluorophenethyl)piperidin-4-yl]-6-(1-hydroxyethyl)indoline, (6) 1-[1-(4-fluorophenethyl)piperidin-4-yl]-6-(n-propylcarbamoylmethyl)indoline, (7) 1-[1-(4-fluorophenethyl)piperidin-4-yl]-6-(isopropylcarbamoylmethyl)indoline, (8) 1-[1-(4-fluorophenethyl)piperidin-4-yl]-6-ureidomethylindoline, (9) 1-[1-(4-fluorophenethyl)piperidin-4-yl]-6-N-methylacetamidomethylindoline,

(10) 1-[1-(4-fluorophenethyl)piperidin-4-yl]-6-[1-(4-thiazolyl)-1-hydroxymethyl]indoline, and

(11) 1-[1-(4-fluorophenethyl)piperidin-4-yl]-6-acetamidomethylindole.

The compounds of the present invention are each a highly safe one having an extremely high $LD_{50}$.

Although compounds having the indoline or indan skeleton are disclosed in WO96/23784, JP-A 8-512,299 (WO95/01976), WO97/06155, etc., these compounds are completely different in structure from the 1,4-substituted cyclic amine derivatives (I) to (VI) of the present invention.

The present invention provides the method for treating the disease which serotonin antagonism is efficacious, by administering the effective dose of the compound as set forth or pharmacologically acceptable salts thereof to a person, and the use of the compound as set forth or pharmacologically acceptable salts thereof for treating the disease which serotonin antagonism is efficacious.

The present invention includes the following mode:

(1) 1,4-Substituted cyclic amine derivatives, which the bond represented by the following formula in the formula (I):

is a single bond, represented by the formula (XXI):

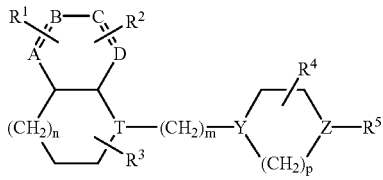

(XXI)

or pharmacologically acceptable salts thereof.

(2) 1,4-Substituted cyclic amine derivatives, which m is 0 in the formula (I), represented by the formula (XXII):

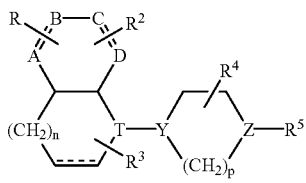

(XXII)

or pharmacologically acceptable salts thereof.

(3) 1,4-Substituted cyclic amine derivatives represented by the formula (I), in which m is 1 to 6 selected from the following compounds:

(16) 1-[1-(4-fluorophenethyl)piperidin-4-yl]methylindoline,

(17) 1-{2-[1-(4-fluorophenethyl)piperidin-4-yl]ethyl}indoline, and (243) 1-[(1-ethylpiperidin-4-yl)methyl]-3-(4-methoxybenzyl)indoline or pharmacologically acceptable salts thereof.

(4) 1,4-Substituted cyclic amine derivatives represented by the formula (XXIII):

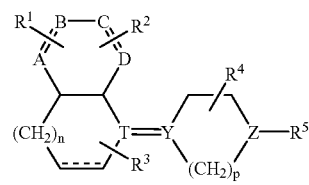

(XXIII)

selected from the following compounds:

(256) 7-[1-(4-fluorophenethyl)piperidin-4-ylidene]-5,6-dihydropyrindine and (265) 5-[1-(4-fluorophenethyl)piperidin-4-ylidene]-7-methyl-5,6-dihydrocyclopentapyrazine or pharmacologically acceptable salts thereof.

(5) 1,4-Substituted cyclic amine derivatives, which the bond represented by the following formula in the formula (I)

is a double bond, represented by the formula (XXIV):

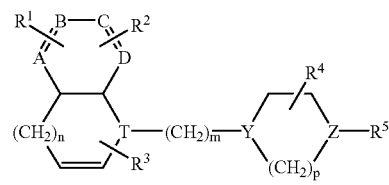

(XXIV)

or pharmacologically acceptable salts thereof.

The 1,4-substituted cyclic amine derivatives (I) of the present invention can be produced by, for example, the following processes, though the present invention is not restricted thereto.

(1) The case where T=N, m=0, Y=methine, and Z=N

In this case, the aimed compounds can be synthesized in accordance with the conventional method of reductive amination, for example, the one described in "Shin Jikken Kagaku Koza 14-III", p. 1380 (Maruzen Co., Ltd.), by reacting a fused cyclic amine (VII) with a cyclic ketone (VIII) in the presence of a reducing agent to thereby give a 1,4-substituted cyclic amine derivative (IX), removing the protecting group theretrom if necessary, and then introducing a substituent $R^5$ thereinto. This reaction is represented by the following chemical reaction formula:

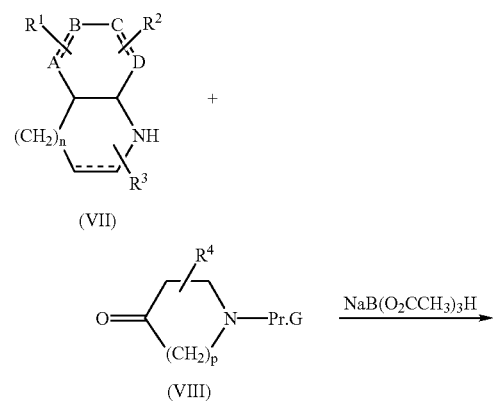

-continued

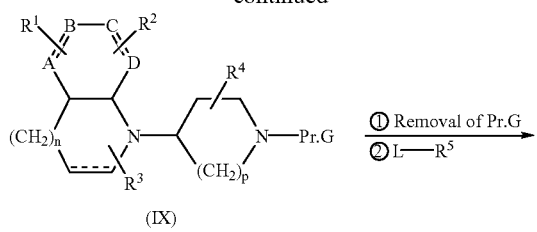
(IX)

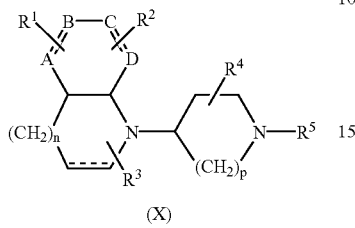
(X)

[wherein the bond represented by the following formula:

- - - - - represents a single or double bond;

A, B, C, D, $R^1$, $R^2$, $R^3$, $R^4$, $R^5$, n and p are each as defined above; Pr.G represents hydrogen or a protecting group; and L represents a leaving group such as hydroxy, halogeno or methanesulfonyloxy].

It is also possible to chemically modify the substituents $R^1$, $R^2$, $R^3$ and $R^4$ to thereby synthesize analogs of the 1,4-substituted cyclic amine derivatives.

The reducing agent to be used herein may be an arbitrary one, so long as it is one commonly employed in reductive N-alkylation. Preferable examples thereof include sodium triacetoxyborohydride, sodium cyanoborohydride and lithium aluminum hydride.

(2) The case where T=N, n=0, m=0, Y=methine, and Z=N

An alternative method of (1) for synthesizing, in particular, the 1,4-substituted cyclic amine derivatives (I) wherein n=0 comprises treating the amine (XI) successively with oxalyl chloride and aluminum chloride to thereby give a diketone (XII), reducing the same to thereby give an indole derivative (XIII), removing the protecting group therefrom if necessary, then introducing a substituent $R^5$ thereinto to thereby give an indole derivative (XIV), and reducing the same to thereby give an indoline derivative (XV). This reaction is represented by the following chemical reaction formula:

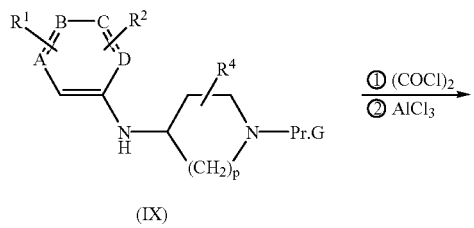
(IX)

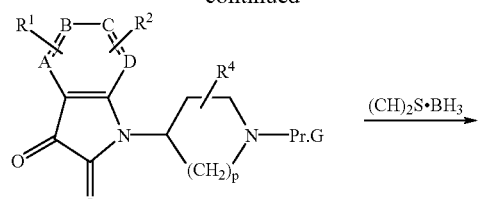
(XII)

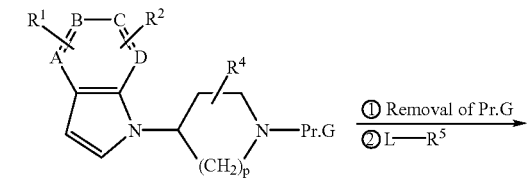
(XIII)

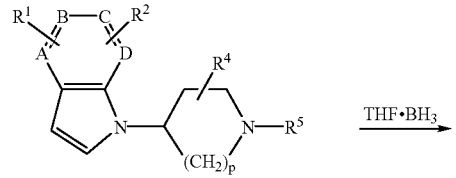
(XIV)

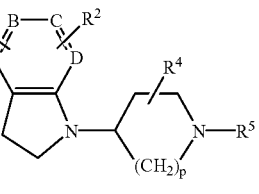
(XV)

[wherein the bond represented by the following formula:

- - - - - and A, B, C, D, $R^1$, $R^2$, $R^4$, $R^5$, p, Pr.G and L are each as defined above.]

(1) The case of indole derivatives wherein T=N, n=0, m=0, Y=methine, and Z=N

The indole derivatives (XIV) can be obtained not only by the above method (2) but also by oxidizing the indoline derivatives (XV) in a conventional manner. Although the reagent and catalyst to be used in such a case are not particularly restricted, it is preferable to use activated manganese dioxide.

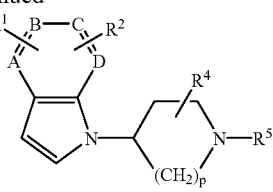

(XIV)

(4) The case where T=mehtine, n=0, m=0, Y=methine, and Z=N

The aimed compounds can be synthesized by introducing a substituent $R^5$ into 1-(piperidin-4-yl) indan derivatives (XVI). This reaction is represented by the following chemical reaction formula:

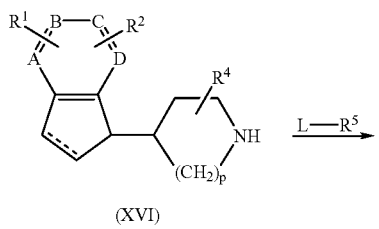

(XVI)

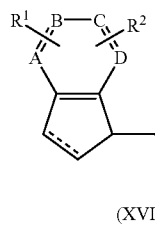

(XVII)

[wherein the bond represented by the following formula:

- - - - - and A, B, C, D, $R^1$, $R^2$, $R^4$, $R^5$, p and L are each as defined above.]

(5) The case where T=N, n=1, m=0, Y=methine, and Z=N

The aimed compounds can be synthesized by introducing a substituent $R^5$ into 1-(4-piperidinyl)-1,2,3,4-tetrahydroquinoline derivatives (XVIII) This reaction is represented by the following chemical reaction formula:

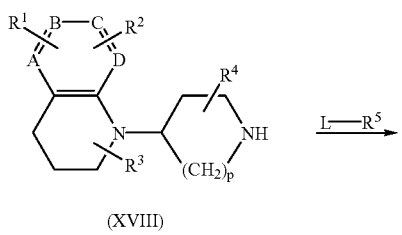

(XVIII)

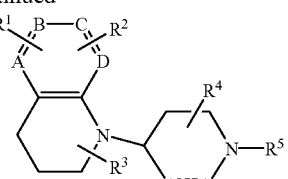

(XIX)

[wherein the bond represented by the following formula:

- - - - - and A, B, C, D, $R^1$, $R^2$, $R^3$, $R^4$, $R^5$, p and L are each as defined above.]

Among the 1,4-substituted cyclic amine derivatives (I) according to the present invention, compounds having structures other than those as defined in the above cases (1) to (5) can be produced by the same methods as the ones as will be described in Examples hereinafter.

To produce the 1,4-substituted cyclic amine derivatives (I) of the present invention, 4-substituted cyclic amine derivatives (XX) represented by the following formula are novel compounds which are useful as intermediates in the production of the 1,4-substituted cyclic amine derivatives (I) to (VI) having a serotonin antagonism and being clinically useful as medicaments for, in particular, treating, ameliorating and preventing spastic paralysis or central muscle relaxants for ameliorating myotonia:

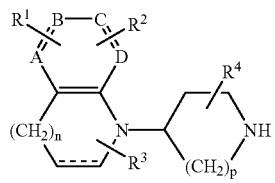

(XX)

wherein the bond represented by the following formula:

- - - - - and A, B, C, D, $R^1$, $R^2$, $R^3$, $R^4$, n and p are each as defined above, provided that the case where $R^1$, $R^2$, $R^3$ and $R^4$ are all hydrogen is excluded.

More particularly speaking, the 4-substituted cyclic amine derivatives (XX) are exemplified by the following compounds, though the present invention is not restricted thereto:

(1) 1-(piperidin-4-yl)-6-fluoroindoline,
(2) 1-(piperidin-4-yl)-6-bromoindoline,
(3) 1-(piperidin-4-yl)-6-nitroindoline,
(4) 1-(piperidin-4-yl)-6-methoxyindoline,
(5) 1-(piperidin-4-yl)-6-acetamidomethylindoline,
(6) 1-(piperidin-4-yl)-6-fluoroindole,
(7) 1-(piperidin-4-yl)-6-bromoindole,
(8) 1-(piperidin-4-yl)-6-nitroindole,
(9) 1-(piperidin-4-yl)-6-methoxyindole, and
(10) 1-(piperidin-4-yl)-6-acetamidomethylindole.

Examples of the dosage forms of the compounds of the present invention include oral preparations such as powders, fine granules, granules, tablets, coated tablets and capsules, external preparations such as ointments, patches and suppositories, and injections. These preparations may be produced by the conventional methods with the use of pharmaceutical carriers commonly employed in the art.

Namely, oral preparations may be produced by blending the 1,4-substituted cyclic amine derivative or a pharmacologically acceptable salt thereof with fillers optionally together with binders, disintegrating agents, lubricating agents, coloring agents, corrigents, etc. and then processing the resultant blends into powders, fine granules, granules, tablets, coated tablets, capsules, etc. by the conventional methods.

As the fillers, use may be made of, for example, lactose, corn starch, sucrose, glucose, mannitol, sorbitol, crystalline cellulose and silicon dioxide. As the binders, use may be made of, for example, polyvinyl alcohol, polyvinyl ether, methylcellulose, ethylcellulose, acacia, tragacanth, gelatin, shellac, hydroxypropylmethylcellulose, hydroxypropylcellulose, polyvinylpyrrolidone, polypropylene glycol/polyoxyethylene block polymers and meglumine. As the disintegrating agents, use may be made of, for example, starch, agar, gelatin powder, crystalline cellulose, calcium carbonate, sodium hydrogencarbonate, calcium citrate, dextrin, pectin and calcium carboxymethylcellulose. As the lubricating agents, use may be made of, for example, magnesium stearate, talc, polyethylene glycol, silica and hardened vegetable oils. As the coloring agents, use may be made of those authorized as pharmaceutical additives. As the corrigents, use may be made of, for example, cocoa powder, mentha, aromatic powder, mentha oil, borneol and powdered cinnamon bark. Needless to say, these tablets and granules may be appropriately coated with sugar, etc., if necessary.

Injections are produced by blending the 1,4-substituted cyclic amine derivative or a pharmacologically acceptable salt thereof with pH regulating agents, resolvents, tonicity agents, etc., optionally together with dissolution aids, stabilizers, etc. and processing the resultant blends into preparations by the conventional methods.

External preparations may be produced by the conventional methods without restriction. As the bases, therefore, use can be made of various materials commonly used in drugs, quasi drugs, cosmetics, etc.

Particular examples of the base materials include animal and vegetable oils, mineral oils, ester oils, waxes, higher alcohols, fatty acids, silicone oils, surfactants, phospholipids, alcohols, polyhydric alcohols, water-soluble polymers, clay minerals and purified water. If needed, it is possible to further add pH regulating agents, antioxidants, chelating agents, antiseptics, fungicides, coloring agents, perfumes, etc., though the materials usable as the base in the external preparations of the present invention are not restricted thereto. If necessary, it is also possible to furthermore add other ingredients capable of inducing differentiation, blood flow accelerators, bactericides, antiinflammatory agents, cell activators, vitamins, amino acids, humectants, keratolytic agents, etc. The above materials may be added in such amounts as to give the concentrations thereof commonly employed in the production of external preparations.

The clinical dose of the 1,4-substituted cyclic amine derivative of the present invention or a pharmacologically acceptable salt thereof is not restricted but varies depending on the symptoms, severity, age, complications, etc. Also, the dose thereof varies depending on the type of the salt, administration route, etc. In general, these compounds are administered to an adult in a dose of from 0.01 to 1000 mg, preferably from 0.1 to 500 mg and still preferably from 0.5 to 100 mg, per day orally, intravenously, as suppositories or percutaneously.

Next, the results of a binding test on the compounds of the present invention to serotonin 1A and serotonin 2 receptors will be given so as to illustrate the effects of the present invention. Moreover, the results of a binding test on these compounds to an α1 adrenalin receptor will be given so as to illustrate the safety thereof.

It is reported in, for example, the following publications that compounds with a serotonin antagonism are usable as medicament for treating, ameliorating and preventing spastic paralysis or central muscle relaxants for ameliorating myotonia:

(1) Saishin Igaku Jiten, 3rd impression of 1st edition, p. 809 "SEROTONIN", Iyaku Shuppan
(2) Stedman's Medical Dictionary, 24th edition, p. 1227 "serotonin", Williams & Wilkins
(3) Shinkei Shinpo, 37(3), 459–467, 1993.
(4) Iyaku Journal, 30(8), 2030–2068, 1994.
(5) DN & P, 5(8), 453–460, 1992.
(6) Annals of Neurology, 30(4), 533–541, 1991.

Compounds poor in the ability to bind to an α1 adrenalin receptor are medicines which would scarcely affect blood pressure in orthostatic hypotension, etc. and have a higher safety.

Effect of the Invention:

(1) Binding test on serotonin 1A, serotonin 2 and α1 adrenalin receptors

Method (Reagent)

The following reagents were employed in this test.
1) Serotonin binoxalate (5-HT binoxalate, mfd. by Sigma Chemical Co.).
2) Methysergide maleate (mfd. by RBI).

As radioisotope-labeled compounds, use was made of the following reagents (mfd. by NEN).
3) [$^3$H] 8-Hydroxy-dipropylaminotetralin (8-OH-DPAT).
4) [$^3$H] Ketanserin hydrochloride.
5) [$^3$H] Prazosin.

These compounds and test compounds, when insoluble in water, were dissolved in ethanol and then dilutedwith distilled water so as to each give an ethanol concentration of 10%. Methysergide maleate was dissolved in distilled water before using.

(Animal)

Use was made of SD rats aged 6 to 8 weeks.

(Preparation of receptor source)

The rats were sacrificed by dcapitation to extirpate the cerebra. The hippocampus and cortex were separated therefrom and employed in the binding tests respectively on the serotonin 1A receptor and the serotonin 2 receptor.

The hippocampus was mixed with 50 times (on the wet weight basis) as much a 0.32 M sucrose solution while the cortex was mixed with 10 times as much the same solution. Each mixture was homogenized by using a Teflon glass homogenizer and centrifuged at 1,000×g for 10 min. The supernatant thus obtained was further centrifuged at 20,000×g for 20 min. The obtained precipitate was re-suspended in 50 times (based on the intial wet weight; in the case of the hippocampus) or 10 times (in the case of the cortex) as much a 50 mM Tris hydrochloride (pH 7.4) and incubated at room temperature for 30 min. After centrifuging at 20,000×g for 20 min, the obtained precipitate was further suspended and centrifuged twice each in the same manner. The precipitate thus obtained was suspended in 100 times (based on the initial wet weight; in the case of the hippocampus) or 20 times (in the case of the cortex) as much a 50 mM Tris hydrochloride solution (pH 7.4) to thereby give a receptor fraction. This receptor fraction was stored at −80° C. until using.

(Binding test on [³H] 8-hydroxy-dipropylaminotetralin)

To the receptor fraction of the hippocampus were added a test compound and 0.5 nM of [³H] 8-hydroxy-dipropylaminotetralin and the resultant mixture was incubated at room temperature for 30 min. Next, it was filtered through a glass filter with the use of a cell harvester. After washing the glass filter with 50 mM Tris hydrochloride (pH 7.4), the radioactivity of the receptor was measured with a liquid scintillation counter. The binding detected in the presence of 10 μM of serotonin binoxalate was referred to as the nonspecific binding.

(Binding test on [³H] ketanserin)

To the receptor fraction of the cerebral cortex were added a test compound and 0.3 nM of [³H] ketanserin and the resultant mixture was incubated at 37° C. for 15 min. Next, it was filtered through a glass filter with the use of a cell harvester. After washing the glass filterwith 50 mM Tris hydrochloride (pH 7.4), the radioactivity of the receptor was measured with a liquid scintillation counter. The binding detected in the presence of 1 μM of methysergide was referred to as the nonspecific binding.

$IC_{50}$ was calculated by the probit method, while Ki was determined in accordance with the following formula:

$$Ki = IC_{50}/(1+c/Kd)$$

wherein c represents the concentration of the radioisotope-labeled compound, and Kd represents the dissociation constant of the radioisotope-labeled compound with respect to-the receptor determined by Scatchard's analysis.

(Binding test on [³H] prazosin)

To the receptor fraction of the cerebral cortex were added a test compound and about 0.2 nM of [³H] prazosin and the resultant mixture was incubated at room temperature for 60 min. Next, it was filtered through a glass filter with the use of a cell harvester. After washing the glass filter with 50 mM Tris hydrochloride (pH 7.4), the radioactivity of the receptor was measured with a liquid scintillation counter. The binding detected in the presence of 10 μM of phentolamine was referred to as the nonspecific binding.

The following tables show the abilities of typical examples of the compounds of the present invention to bind to the serotonin 1A and serotonin 2 receptors, wherein the number of each compound corresponds to the Example number. Also, comparison was made with cyproheptadine hydrochloride (CAS Registry No.: 969-33-5) and cyclobenzaprine hydrochloride (CAS Registy No.: 6202-23-9) which were employed as positive controls having anti-serotonin effects.

TABLE 1

| Ex. no. | 5HT1a (nM) | 5HT2 (nM) | Ex. no. | 5HT1a (nM) | 5HT2 (nM) |
|---|---|---|---|---|---|
| 1 | 623.94 | >200 | 28 | 46.90 | 8.10 |
| 3 | 28.70 | 17.40 | 29 | — | 36.50 |
| 4 | 6.00 | 24.90 | 30 | 21.90 | 15.70 |
| 5 | 10.10 | 8.10 | 31 | 20.80 | 4.10 |
| 6 | 4.50 | 17.40 | 32 | 30.20 | 30.20 |
| 7 | 34.30 | 12.80 | 33 | 5.70 | 24.30 |
| 8 | 13.50 | 26.90 | 34 | 1.90 | 9.10 |
| 9 | 3.00 | 11.60 | 35 | 16.60 | 37.60 |
| 10 | 8.10 | 6.00 | 36 | 4.50 | 14.90 |
| 11 | 5.70 | 27.90 | 37 | 4.60 | 14.80 |
| 12 | 8.50 | 16.30 | 38 | 15.00 | 21.80 |
| 13 | 24.20 | >200 | 39 | 1.60 | 8.90 |
| 15 | 28.60 | 28.60 | 40 | 43.66 | >200 |
| 16 | 109.32 | 13.85 | 41 | 19.81 | 5.03 |
| 17 | 19.01 | 16.36 | 42 | 35.80 | 5.70 |

TABLE 1-continued

| Ex. no. | 5HT1a (nM) | 5HT2 (nM) | Ex. no. | 5HT1a (nM) | 5HT2 (nM) |
|---|---|---|---|---|---|
| 18 | 0.13 | 0.12 | 43 | 4.20 | 37.90 |
| 19 | 8.80 | 7.00 | 44 | 4.00 | 43.70 |
| 20 | 15.20 | 0.22 | 45 | 15.20 | 6.40 |
| 21 | 1.90 | 42.70 | 46 | 1.10 | 4.20 |
| 22 | 24.00 | 12.20 | 47 | 206.20 | 92.30 |
| 23 | 7.40 | 14.60 | 48 | 15.30 | 35.00 |
| 24 | 26.50 | 174.20 | 49 | 54.50 | 29.90 |
| 25 | 8.30 | 13.10 | 50 | 31.20 | 52.20 |
| 26 | 2.90 | 19.50 | 52 | 2.50 | 5.60 |
| 27 | >200 | 28.80 | 53 | 21.50 | 2.10 |

TABLE 2

| Ex. no. | 5HT1a (nM) | 5HT2 (nM) | Ex. no. | 5HT1a (nM) | 5HT2 (nM) |
|---|---|---|---|---|---|
| 54 | 7.10 | 10.30 | 81 | 44.30 | 119.00 |
| 55 | 41.90 | 17.80 | 82 | 71.20 | 5.30 |
| 56 | 20.70 | 1.70 | 84 | >200 | 133.70 |
| 57 | 14.60 | 1.10 | 85 | 169.60 | 56.20 |
| 58 | 26.20 | 34.80 | 99 | — | 8.70 |
| 59 | 12.00 | 28.90 | 102 | 2.70 | 28.40 |
| 60 | 60.80 | >200 | 103 | 3.90 | 15.80 |
| 61 | 5.00 | 12.50 | 104 | 2.40 | 6.00 |
| 62 | 6.20 | 7.40 | 105 | >200 | 17.40 |
| 63 | 3.20 | 1.20 | 106 | 0.70 | 6.40 |
| 64 | 14.80 | 14.20 | 107 | 7.70 | 1.70 |
| 65 | 8.80 | 4.80 | 108 | 172.30 | 2.20 |
| 66 | 50.90 | 85.00 | 110 | 23.30 | 16.00 |
| 67 | 262.50 | 27.10 | 111 | 5.50 | 74.20 |
| 68 | 47.20 | 39.50 | 112 | 3.20 | 165.20 |
| 69 | 9.70 | 29.90 | 113 | 13.70 | >200 |
| 70 | 41.90 | 27.60 | 114 | 5.80 | 23.20 |
| 71 | 25.40 | 28.20 | 116 | 0.50 | 14.30 |
| 72 | 25.90 | 21.10 | 117 | 0.60 | 10.70 |
| 73 | 34.90 | 7.20 | 118 | 0.70 | 10.40 |
| 75 | 3.60 | 30.30 | 119 | 0.20 | 45.50 |
| 76 | 43.20 | >200 | 120 | 1.00 | 11.20 |
| 77 | 44.50 | 13.70 | 121 | 0.50 | 22.80 |
| 78 | 2.40 | 29.60 | 122 | 0.20 | 15.20 |
| 79 | 115.40 | 26.50 | 123 | 251.10 | 2.70 |

TABLE 3

| Ex. no. | 5HT1a (nM) | 5HT2 (nM) | Ex. no. | 5HT1a (nM) | 5HT2 (nM) |
|---|---|---|---|---|---|
| 124 | 1.10 | 45.80 | 152 | 16.40 | 0.27 |
| 125 | 0.10 | 4.76 | 153 | 15.48 | 4.24 |
| 126 | 1.23 | 129.30 | 154 | 6.52 | 0.0006 |
| 127 | 0.21 | 5.08 | 155 | 14.83 | 1.33 |
| 128 | 0.34 | 4.70 | 156 | 7.80 | 2.60 |
| 129 | 0.95 | 0.65 | 157 | 4.11 | 0.18 |
| 130 | 0.49 | 9.12 | 158 | 8.18 | 0.16 |
| 131 | 0.17 | 15.21 | 159 | 5.58 | 0.76 |
| 132 | 2.08 | 14.27 | 160 | 3.86 | 8.00 |
| 133 | 3.70 | 0.05 | 161 | 3.23 | 0.43 |
| 136 | 3.40 | 6.20 | 162 | 0.98 | 27.08 |
| 137 | 0.65 | 6.68 | 163 | 2.41 | 7.75 |
| 138 | 1.98 | 5.93 | 164 | 0.54 | 34.06 |
| 139 | 2.31 | 8.80 | 165 | 5.50 | 1.22 |
| 140 | 6.23 | 35.07 | 166 | 0.79 | 17.07 |
| 141 | 3.03 | 342.74 | 167 | 6.49 | 18.43 |
| 143 | 1.86 | 3.36 | 168 | 3.84 | 4.06 |
| 144 | 1.49 | 3.38 | 169 | 16.39 | 13.78 |
| 145 | 8.07 | 48.77 | 170 | 47.45 | 16.26 |
| 146 | 163.97 | >200 | 171 | 0.39 | 178.00 |
| 147 | 1.31 | 0.77 | 172 | 0.12 | 52.43 |
| 148 | 9.58 | 0.25 | 173 | 0.06 | 70.07 |

TABLE 3-continued

| Ex. no. | 5HT1a (nM) | 5HT2 (nM) | Ex. no. | 5HT1a (nM) | 5HT2 (nM) |
|---|---|---|---|---|---|
| 149 | 7.44 | 0.50 | 174 | 0.24 | 1.85 |
| 150 | 13.00 | 0.16 | 175 | 1.49 | 0.35 |
| 151 | 8.84 | 0.57 | 176 | 1.67 | 0.05 |

TABLE 4

| Ex. no. | 5HT1a (nM) | 5HT2 (nM) | Ex. no. | 5HT1a (nM) | 5HT2 (nM) |
|---|---|---|---|---|---|
| 177 | 0.25 | 0.92 | 204 | 1.06 | 4.49 |
| 178 | 10.17 | 2.53 | 205 | 2.76 | 0.12 |
| 179 | 0.17 | 0.41 | 206 | 1.49 | 2.17 |
| 181 | 1029.00 | 9.62 | 207 | 0.81 | 2.69 |
| 182 | 4.28 | 2.91 | 208 | 2.33 | 1.05 |
| 183 | 1.18 | 3.86 | 209 | 6.98 | 4.72 |
| 184 | 15.13 | 3.06 | 210 | 2.50 | 4.93 |
| 185 | 14.58 | 4.73 | 211 | 0.53 | 1.21 |
| 186 | 14.55 | 3.32 | 212 | 0.82 | 0.36 |
| 187 | 65.03 | 5.01 | 213 | 1.03 | 0.18 |
| 189 | 7.72 | 2.02 | 214 | 3.50 | 0.90 |
| 190 | 0.49 | 0.33 | 215 | 126.40 | 1.00 |
| 191 | 29.06 | 0.32 | 216 | 4.70 | 42.90 |
| 192 | 1.02 | 2.90 | 218 | 4.50 | 11.70 |
| 193 | 6.92 | 2.88 | 219 | 19.60 | 30.90 |
| 194 | 4.59 | >200 | 221 | 1.90 | 2.40 |
| 195 | 5.73 | 1.15 | 222 | 0.04 | 18.10 |
| 196 | 1.67 | 1.17 | 224 | 3.09 | 5.11 |
| 197 | 10.40 | 1.27 | 225 | 5.74 | 7.61 |
| 198 | 13.70 | 2.21 | 228 | 0.34 | >200 |
| 199 | 1.98 | 1.19 | 229 | 2.50 | >200 |
| 200 | 4.84 | 233.98 | 230 | 13.30 | >200 |
| 201 | 7.05 | >200 | 232 | 37.65 | 48.19 |
| 202 | 2.57 | 5.13 | 233 | 0.60 | >200 |
| 203 | 0.55 | 4.61 | 234 | 1.10 | 3.30 |

TABLE 5

| Ex. no. | 5HT1a (nM) | 5HT2 (nM) | Ex. no. | 5HT1a (nM) | 5HT2 (nM) |
|---|---|---|---|---|---|
| 235 | 0.20 | 14.60 | 262 | 1.50 | 2.10 |
| 236 | 29.20 | 10.60 | 263 | 0.46 | >200 |
| 237 | 30.40 | >200 | 264 | 11.30 | 138.90 |
| 238 | 86.60 | >200 | 265 | 25.20 | 34.20 |
| 240 | >200 | 27.60 | 266 | 31.60 | 22.60 |
| 241 | 360.00 | 1658.30 | 277 | 22.80 | 3.90 |
| 242 | >200 | 2.30 | 278 | >200 | 3.90 |
| 243 | >200 | 53.00 | 279 | 0.22 | 90.40 |
| 244 | >200 | 2.50 | 281 | 35.19 | 11.20 |
| 245 | >200 | 11.20 | 282 | 58.70 | 150.00 |
| 246 | >200 | 60.00 | 283 | 39.50 | 40.90 |
| 247 | >200 | 52.90 | 284 | 4.50 | 4.70 |
| 248 | 2.90 | 6.80 | 285 | 0.44 | 1.39 |
| 249 | 2.10 | 20.20 | 286 | 3.74 | 3.12 |
| 250 | 1.60 | 18.80 | 287 | 0.10 | >200 |
| 251 | 58.50 | >200 | 288 | 0.2 | 0.1 |
| 254 | >200 | 176.80 | 291 | 6.9 | 100.6 |
| 255 | >200 | 15.70 | 292 | 92.0 | 58.8 |
| 256 | 0.40 | 12.10 | A | 25 | 29 |
| 257 | 2.80 | 0.61 | B | 29.5 | 1.68 |
| 258 | 35.20 | 4.80 | C | 72.5 | 0.4 |
| 259 | 0.60 | 5.90 | A: Cyclobenzaprine | | |
| 260 | 1.30 | 12.90 | B: Cyproheptadine | | |
| 261 | 1.50 | 5.30 | C: Co. No. 5 given in WO96/23784 | | |
| 294 | 1.05 | 2.86 | 318 | 1.49 | 8.3 |
| 295 | 0.85 | 3.64 | 319 | 0.56 | 24.5 |
| 296 | 0.32 | 2.73 | 320 | 0.55 | 44 |
| 297 | 0.98 | 4.17 | 321 | 0.14 | >20 |
| 298 | 1.86 | 21.3 | 322 | 0.08 | 30.36 |
| 299 | 0.11 | 2.54 | 323 | 0.14 | >20 |

TABLE 5-continued

| Ex. no. | 5HT1a (nM) | 5HT2 (nM) | Ex. no. | 5HT1a (nM) | 5HT2 (nM) |
|---|---|---|---|---|---|
| 300 | 1.73 | 3.55 | 324 | 0.1 | >20 |
| 301 | 0.8 | 21.93 | 325 | 0.65 | 10.86 |
| 302 | 2.92 | 60.48 | 326 | 0.4 | >20 |
| 303 | 3.6 | 35.85 | 327 | 1.04 | 2.64 |
| 304 | 8.37 | 6.26 | 328 | 2.06 | >20 |
| 305 | 0.06 | 3.29 | 329 | 2.06 | 2.41 |
| 306 | 2.82 | 3.87 | 330 | 0.11 | >20 |
| 307 | 7.02 | 0.83 | 331 | 0.11 | 8.28 |
| 308 | 0.73 | 3.84 | 332 | 2.24 | 16.17 |
| 309 | 3.85 | 1.02 | 333 | 1.08 | >20 |
| 310 | 1.34 | 2.29 | 334 | 0.04 | >20 |
| 311 | 1.08 | 46.39 | 335 | 0.22 | >20 |
| 312 | 8.27 | 0.56 | 336 | <0.2 | >20 |
| 313 | 13.07 | 1.58 | 337 | <0.2 | >20 |
| 314 | 0.72 | 1.1 | 338 | 0.07 | >20 |
| 315 | 6.74 | 1.18 | 339 | <0.2 | >20 |
| 316 | 1.82 | 1.26 | | | |
| 317 | 0.76 | >20 | | | |
| 340 | 3.02 | 2.84 | 370 | >20 | >20 |
| 341 | 2.08 | 0.67 | 372 | >20 | >20 |
| 342 | 0.65 | 38.15 | 373 | 0.24 | 1.77 |
| 343 | 1.54 | 1.64 | 375 | 1.56 | 3.37 |
| 344 | 1.78 | 1.64 | 376 | 0.91 | 2.1 |
| 345 | 4.82 | 0.29 | 378 | 14.2 | 1.54 |
| 346 | 13.46 | 1.49 | 379 | 9.65 | 1.25 |
| 347 | 2.24 | 0.65 | 380 | 2.87 | 1.56 |
| 349 | 0.22 | 8.12 | 381 | 1.37 | 2.02 |
| 350 | 1.92 | 11.44 | 382 | 7.59 | 3.31 |
| 351 | 0.27 | >20 | 383 | 5.34 | 1.81 |
| 352 | 1.58 | 0.75 | 384 | 0.13 | 0.25 |
| 353 | 0.78 | 12.57 | 385 | 2.41 | 0.97 |
| 354 | 1.22 | 4.79 | 386 | 5.38 | >20 |
| 355 | 0.35 | 6.87 | 387 | 63.5 | >20 |
| 356 | 1.52 | >20 | 388 | 2.26 | >20 |
| 357 | 0.38 | 1.3 | 389 | 0.53 | 15.46 |
| 358 | 0.73 | 14.02 | 390 | 0.99 | 11.56 |
| 359 | 0.71 | 7.39 | 391 | 1.72 | 6.83 |
| 360 | 26.6 | >20 | 392 | 0.65 | 38.15 |
| 361 | 0.27 | >20 | 393 | 0.85 | 2.54 |
| 362 | 0.46 | 3.54 | 394 | 1.18 | 0.96 |
| 363 | 1.5 | 3.39 | 397 | 1.28 | 2.27 |
| 364 | 1.73 | 4.23 | | | |
| 365 | 0.42 | 3.11 | | | |
| 366 | 0.48 | 2.05 | | | |
| 367 | 1.63 | 1.76 | | | |
| 368 | 1.63 | 0.56 | | | |
| 369 | 2.02 | 2.88 | | | |

Subsequently, the abilities of typical examples of the compounds of the present invention to bind to the α1 adrenalin receptor were evaluated by the test method described above. The following table shows the results, wherein the number of each compound corresponds to the Example number.

Also, comparison was made with Co. No. 5, as a typical example of the known compounds with a serotonin antagonism, disclosed in Table 2 of WO96/23784 and having the following chemical formula. This compound was produced in accordance with the mehtod described in WO96/23784 (see Referential Example 1 as will be given hereinbelow).

TABLE 6
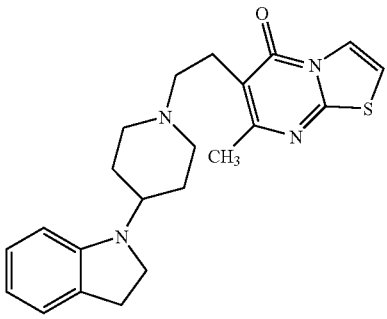
| Ex. no. | α1 (nM) |
|---|---|
| 9 | 76.5 |
| 11 | 147 |
| 13 | 188 |
| 19 | 55.5 |
| 22 | 113 |
| 26 | 51.1 |
| 36 | 39 |
| 38 | 244.2 |
| 42 | 230 |
| 65 | 55.7 |
| 68 | 223.4 |
| 75 | 88.6 |
| 77 | 248.7 |
| 103 | 77.7 |
| 106 | 71.3 |
| 121 | 58.2 |
| 125 | 46.37 |
| 133 | 261.65 |
| 137 | 125.59 |
| 147 | 156.84 |
| 149 | 304.15 |
| 151 | 292.16 |
| 162 | 222.63 |
| 164 | 638.02 |
| 166 | 193.71 |
| 168 | 72.56 |
| 182 | 70.07 |
| 184 | 188.42 |
| 187 | >200 |
| 189 | 442.24 |
| 197 | 68.59 |
| 204 | 183.23 |
| 206 | 104.75 |
| 216 | 81.59 |
| 235 | 77.8 |
| 236 | 72.2 |
| 248 | 75.3 |
| 250 | 263 |
| 277 | 354.41 |
| 280 | 222 |
| 283 | 197 |
| 285 | 26.8 |
| 291 | 171.5 |
| 292 | 178.3 |
| Cyclobenzaprine | — |
| Cyproheptadine | 1900 |
| Co. No. 5 given in WO96/23784 | 16.8 |
| 294 | 80.7 |
| 295 | 195.3 |
| 296 | 238.5 |
| 297 | 226.3 |
| 298 | 27.9 |
| 300 | 224.6 |
| 301 | 66.9 |
| 302 | 142.9 |
| 303 | 306.9 |
| 304 | 141 |
| 305 | 35.9 |
| 306 | 147.5 |
| 307 | 51.5 |
TABLE 6-continued
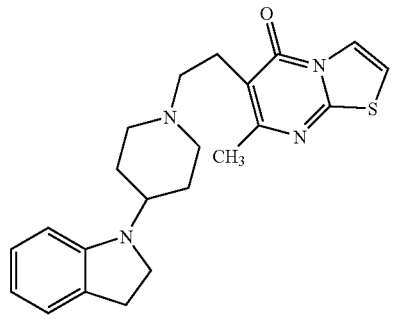
| Ex. no. | α1 (nM) |
|---|---|
| 308 | 59.4 |
| 309 | 122.9 |
| 310 | 84.4 |
| 311 | 85 |
| 312 | 53.3 |
| 313 | 144 |
| 314 | 51.3 |
| 316 | 63.7 |
| 317 | 400 |
| 318 | 46.6 |
| 319 | 42.5 |
| 320 | 26.1 |
| 321 | 203 |
| 322 | 41.3 |
| 323 | 86.9 |
| 324 | 60.9 |
| 325 | 47 |
| 326 | 167 |
| 327 | 99 |
| 328 | 140 |
| 329 | 149 |
| 330 | 338.7 |
| 331 | 77 |
| 332 | 65.9 |
| 333 | 247.1 |
| 334 | 212.2 |
| 335 | 28.4 |
| 336 | 53.7 |
| 338 | 21.3 |
| 339 | 31.7 |
| 340 | 339.8 |
| 341 | 47.6 |
| 342 | 25 |
| 343 | 38.1 |
| 344 | 74.9 |
| 345 | 103.2 |
| 346 | 115.5 |
| 347 | 44.3 |
| 349 | 88.5 |
| 350 | 123.4 |
| 351 | 175 |
| 352 | 96.7 |
| 353 | 144.1 |
| 354 | 90.5 |
| 355 | 39.5 |
| 358 | 41.8 |
| 359 | 75.9 |
| 360 | 690 |
| 361 | 77.4 |
| 362 | 144 |
| 363 | 106 |
| 364 | 289 |
| 365 | 61.6 |
| 366 | 74.6 |
| 367 | 45.8 |
| 368 | 37.6 |
| 369 | 121.4 |
| 370 | 255.5 |
| 372 | 206.4 |
| 375 | 61.4 |
| 376 | 46.7 |

TABLE 6-continued

[Chemical structure]

| Ex. no. | α1 (nM) |
|---|---|
| 378 | 43.7 |
| 379 | 30.3 |
| 380 | 116 |
| 381 | 100.7 |
| 382 | 163.1 |
| 383 | 120.1 |
| 385 | 21.6 |
| 386 | 26.2 |
| 387 | 26.2 |
| 388 | 365.8 |
| 389 | 45 |
| 390 | 34.3 |
| 391 | 116.2 |
| 392 | 25 |
| 393 | 37.8 |
| 397 | 27.1 |

Tables 1 to 6 indicate that the 1,4-substituted cyclic amine derivatives of the present invention are useful as medicaments with a serotonin antagonism and have clinical usefulness and a high safety, in particular, those for treating, ameliorating and preventing spastic paralysis or central muscle
relaxants for ameliorating myotonia.

Moreover, the compounds of the present invention are superior in safety to the Co. No.5 disclosed in WO96/23784 which is a typical example of the known compounds, since the compounds in the present invention have low abilities to bond to the α1 adrenalin receptor and scarcely affect blood pressure.

(2) Morphine induced Straub's tail phenomenon in mice

By using mice, typical examples of the compounds of the present invention were evaluated in the effect of relaxing rigidity in accordance with the method reported in Drug Dev. Res., 11:53–57, 1987.

In this test, use was made of male ddY mice aged 4 to 5 weeks (SLC, Shizuoka) which were divided into groups each comprising 8 animals. Also, use was made, as positive controls, of cyproheptadine hydrochloride, cylcobenzaprine hydrochloride, tizanidine hydrochloride (CAS Registry No.: 51322-75-9) and baclofen (CAS Registry No.: 1134-47-0). The test compounds and the positive controls were each dissolved in a 5% glucose solution for injection or suspended in a 0.5% methylcellulose solution. Morphine hydrochloride was dissolved in physiological saline for injection.

The test compounds of the given concentrations were administered per os (p.o.) or intraperitoneally (i.p.) to the mice, while the media were orally administered to the control group. After 15 min of the administration of the test compounds, 12.5 mg/kg of morphine hydrochloride was subcutaneously injected into the animals. After 15, 30 and 45 min of the administration of morphine hydrochloride, the hyper-muscle tone in the tail was observed and those showing hyper-muscle tone were judged as positive in Straub's tail reaction.

The rate of those showing Straub's tail reaction in each test group was compared with that of the control group at each observation point and analyzed by the $\chi$ square calibration method to thereby determine the statistically significant ($p<0.05$) minimal effective dose.

Now, the results of the evaluation will be shown.

TABLE 7

| Ex. no. | i.p. (mg/kg) | p.o. (mg/kg) | Ex. no. | i.p. (mg/kg) | p.o. (mg/kg) |
|---|---|---|---|---|---|
| 9 | 10 | — | 168 | — | 10 |
| 22 | — | >10 | 182 | — | 10 |
| 34 | ≦10 | 30 | 184 | — | 3 |
| 36 | 1 | ≦3 | 186 | — | 10 |
| 42 | ≦10 | 10 | 189 | — | 10 |
| 65 | — | 30 | 197 | — | 10 |
| 103 | ≦10 | >30 | 204 | 3 | 3 |
| 106 | 10 | >30 | 206 | — | 10 |
| 121 | — | 10 | 235 | — | >10 |
| 125 | 1 | 3 | 248 | ≦10 | 30 |
| 133 | 0.3 | ≦0.3 | 250 | 10 | 30 |
| 137 | — | 1 | 277 | <1 | 30 |
| 147 | ≦0.3 | ≦3 | 285 | 1 | 1 |
| 149 | 1 | ≦3 | Cyclobenzaprine | 10 | — |
| 151 | — | 3 | Cyproheptadine | 3 | — |
| 162 | 1 | >10 | Tizanidine | 1 | 1 |
| 166 | 3 | 3 | Baclofen | 3 | 10 |

As Table 7 clearly shows, the compounds of the present invention have excellent effects of relaxing rigidity in vivo.

To further illustrate the present invention in greater detail, the following Production Examples and Examples will be given. However, it is needless to say that the present invention is not restricted thereto.

PRODUCTION EXAMPLE

Production Example 1: Synthesis of 4-flourophenethyl bromide

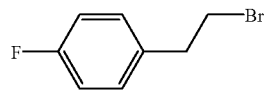

Triphenylphosphine (222 g) and N-bromosuccinimide (151 g) were added to a solution of 4-fluorophenethyl alcohol (100 g) in methylene chloride (1 1) under ice cooing, followed by stirring for 1 hr. After concentrating the resultant solution under reduced pressure, the precipitated crystals were filtered off and the filtrate was concentrated to give the title compound (133 g) as a colorless oil (yield: 92%).

$^1$H-NMR (400 MHz, CDCl$_3$)

δ(ppm) 3.14(2H, t, J=8 Hz), 3.54(2H, t, J=8 Hz), 6.98–7.03(2H, m), 7.15–7.18(2H, m).

Production Example 2 Synthesis of 1-bromo-1-(4-fluorophenyl)-propane

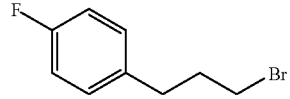

Thionyl chloride (6.8 ml) was added dropwise into ethanol (20 ml) under ice cooling, followed by stirring for 15 min. Then 3-(4-fluorophenyl)propionic acid (2.853 g) was added to the resultant solution, which was stirred at room temperature for 11 hr and concentrated under reduced pressure. The residue was diluted with ethyl acetate (500 ml), washed with a saturated aqueous solution of sodium bicarbonate and brine (a saturated aqueous solution of sodium chloride), dried over anhydrous sodium sulfate, and then concentrated under reduced pressure to give a colorless oil (3.456 g). The product was dissolved in tetrahydrofuran (90 ml) and lithium aluminum hydride (0.863 g) was added to the solution under ice cooling. After stirring the mixture for 1 hr, water (0.9 ml), a 5 N aqueous solution of sodium hydroxide (0.9 ml) and further water (2.7 ml) were added thereto. The resulting precipitate was filtered off and the filtrate was concentrated under reduced pressure to give a pale yellow oil (2.577 g). This oil was treated as in Example 1 to give the title compound (2.354 g) as a yellow oil (yield: 63.6%).

$^1$H-NMR (400 MHz, CDCl$_3$):

δ(ppm) 2.14(2H, tt, J=6.6, 7.0 Hz), 2.76(2H, t, J=7.0 Hz), 3.38(2H, t, J=6.6 Hz), 6.98(2H, t, J=8.8 Hz), 7.16(2H, m).

Production Example 3: Synthesis of 1-bromo-4-(4-flourophenyl)-butane (3-1) 3-(4-Flourophenyl)propyl -1,1-dicarboxylic acid

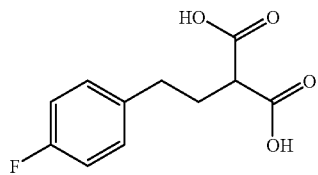

Sodium (0.7 g) was dissolved in ethanol (17.5 ml) and diethyl malonate (9.1 ml) and 4-fluorophenethyl bromide (4.1 g) were added thereto. Then the resultant mixture was heated under reflux for 2.5 hr and allowed to cool. Next, it was diluted with ethyl acetate (500 ml), washed with brine, dried over anhydrous sodium sulfate and concentrated under reduced pressure. The residue was dissolved in ethanol (10 ml) followed by the addition of potassium hydroxide (10.2 g) dissolved in water (10 ml) thereto. The resultant mixture was stirred at 80° C. for 3 hr. After allowing to cool, it was acidified with hydrochloric acid, diethyl ether was added thereto. The organic layer was separated and washed with brine, dried over anhydrous magnesium sulfate. It was then concentrated under reduced pressure to give the title compound (6.938 g) as a pale yellow oil.

$^1$H-NMR (400 MHz, CDCl$_3$):

δ(ppm) 2.25(2H, dt, J=7.6 Hz), 2.70(2H, t, J=7.6 Hz), 3.42(1H, t, J=7.6 Hz), 6.97(2H, t, J=8.8 Hz), 7.12(2H, m).

(3-2) 4-(4-Fluorophenyl)butyric acid

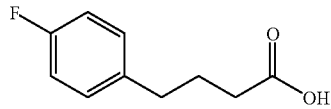

The above 3-(4-fluorophenyl)propyl-1,1-dicarboxylic acid (6.938 g) was stirred at 180° C. for 40 min to give the title compound (4.877 g) as a brown oil.

$^1$H-NMR (400 MHz, CDCl$_3$)

δ(ppm) 1.94(2H, m), 2.37(2H, t, J=7.6 Hz), 2.65(2H, t, J=7.6 Hz), 6.97(2H, t, J=8.8 Hz), 7.15(2H, m).

(3-3) Ethyl 4-(4-fluorophenyl)butyrate

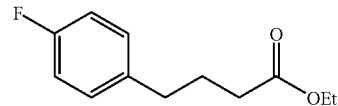

Under ice cooling, thionyl chloride (6.8 ml) was dropped into ethanol (20 ml) and the resultant solution was stirred at room temperature for 11 hr and concentrated under reduced pressure. Next, it was diluted with ethyl acetate (500 ml) washed with a saturated aqueous solution of sodium bicarbonate and brine, dried over anhydrous sodium sulfate and concentrated under reduced pressure to give the title compound (7.178 g) as a brown oil.

$^1$H-NMR (400 MHz, CDCl$_3$):

δ(ppm) 1.34(3H, dt, J=2.0, 7.0 Hz), 1.93(2H, m), 2.31 (2H, dt, J=0, 7.2 Hz), 2.63(2H, t, J=7.2 Hz), 4.12(2H, dq, J=2.0, 7.0 Hz), 6.97(2H, t, J=8.8 Hz), 7.13(2H, m).

(3-4) 4-(4-Fluorophenyl)butan-1-ol

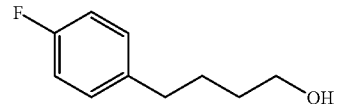

The above ethyl 4-(4-fluorophenyl)butyrate (7.178 g) was dissolved in tetrahydrofuran (120 ml) and then aluminum lithium hydride (1.55 g) was added thereto under ice cooling followed by stirring for 1 hr. After adding water (1.5 ml), 5 N aqueous solution of sodium hydroxide (1.5 ml) and further water (4.5 ml), the resulting precipitate was filtered off and the filtrate was concentrated under reduced pressure to give the title compound (3.890 g) as a brown oil.

$^1$H-NMR (400 MHz, CDCl$_3$)

δ(ppm) 1.58–1.71(4H, m), 2.61(2H, t, J=7.0 Hz), 3.66 (2H, dt, J=2.8, 6.4 Hz), 6.96(2H, t, J=8.8 Hz), 7.13(2H, m).

(3–5) 1-Bromo-4-(4-fluorophenyl)butane

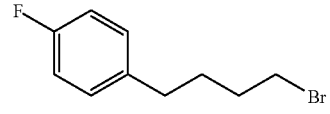

The above 4-(4-fluorophenyl)butan-1-ol (7.178 g) was treated as in the above Production Example 1 to give the title compound (4.250 g) as a yellow oil (yield: 91.9%).

$^1$H-NMR (400 MHz, CDCl$_3$)

δ(ppm) 1.75(2H, m), 1.88(2H, m), 2.62(2H, t, J=7.6 Hz), 3.42(2H, t, J=7.0 Hz), 6.97(2H, t, J=8.8 Hz), 7.13(2H, m).

Production Examnple 4 Syntbpsis of 4-bromophenethyl bromide

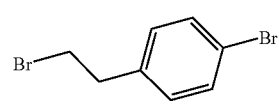

4-Bromophenethyl alcohol (1.3 ml) was treated as in Production Example 1 to give the title compound (2.345 g) as a pale yellow oil (yield: 88.8%).

$^1$H-NMR (400 MHz, CDCl$_3$)

δ(ppm) 3.12(2H, t, J=7.4 Hz), 3.54(2H, t, J=7.4 Hz), 7.09(2H, d, J=8.4 Hz), 7.45(2H, d, J=8.4 Hz).

Production Example 5 Synthesis of 3-chlorophenethyl bromide

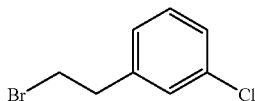

3-Chlorophenethyl alcohol (1.0 ml) was treated as in Production Example 1 to give the title compound (1.417 g) as a pale yellow oil (yield: 64.6%).

$^1$H-NMR (400 MHz, CDCl$_3$):

δ(ppm) 3.14(2H, t, J=8.6 Hz), 3.56(2H, t, J=8.6 Hz), 7.11(1H, m), 7.21(1H, s), 7.45 (2H, m).

Production Example 6 Synthesis of 4-chlorophenethyl bromide

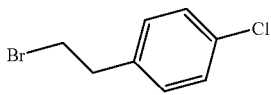

4-Chlorophenethyl alcohol (5 ml) was treated as in Production Example 1 to give the title compound (2.639 g) as a pale yellow oil (yield: 32.6%).

(no NMR)

Production Example 7 Synethesis of 4-methoxyphenethyl bromide

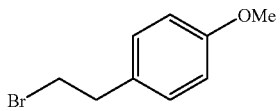

4-Methoxyphenethyl alcohol (0.61 g) was treated as in Production Example 1 to give the title compound (0.838 g) as a pale yellow oil (yield: 97.4%).

$^1$H-NMR (400 MHz, CDCl$_3$):

δ(ppm) 3.10(2H, t, J=7.6 Hz), 3.53(2H, t, J=7.6 Hz), 3.80(3H, s), 6.86(2H, d, J=8.2 Hz), 7.13(2H, d, J=8.2 Hz).

Production Example 8 Synthesis of 4-(2-bromoethyl) benzyl) alcohol

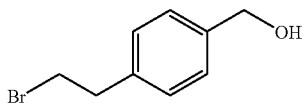

(2-Bromoethyl)benzaldehyde (1.178 g) was dissolved in ethanol (20 ml) After adding sodium borohydride (0.189 g) the resultant mixture was stirred at room temperature for 1 hr. Then it was diluted with ethyl acetate (200 ml), washed with brine, dried over anhydrous sodium sulfate and concentrated under reduced pressure. The residue was purified by silica gel column chromatography (hexane/ethyl acetate system) to give the title compound (0.439 g) as a pale yellow oil (yield: 40.1%).

$^1$H-NMR (400 MHz, CDCl$_3$)

δ(ppm) 2.02(1H, br-s), 3.16(2H, t, J=7.6 Hz), 3.56(2H, t, J=7.6 Hz), 7.20(2H, d, J=8.4 Hz), 7.31(2H, d, J=8.4 Hz).

Production Example 9 Synthesis of 4-(2-bromoethyl-benzaldehyde

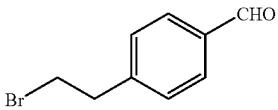

(2-Bromoethyl)benzene (2.72 ml) was dissolved in methylene chloride (20 ml). Subsequently, a 1.0 M solution (40 ml) of titanium tetrachloride in methylene chloride and dichloromethyl methyl ether (2.72 ml) were successively added dropwise thereinto while maintaining the reaction temperature at −10° C. or below. After stirring at room temperature for 6 hr, the reaction solution was poured into ice, extracted with ethyl acetate, washed successively with a saturated aqueous solution of sodium chloride, a saturated aqueous solution of sodium bicarbonate and a saturated aqueous solution of sodium chloride again, dried over anhydrous magnesium sulfate and concentrated under reduced pressure to give the title compound (5.408 g) as a brown oil.

$^1$H-NMR (400 MHz, CDCl$_3$):

δ(ppm) 3.26(2H, t, J=7.2 Hz), 3.61(2H, t, J=7.2 Hz), 7.40(2H, d, J=8.4 Hz), 7.86(2H, d, J=8.4 Hz), 10.01(1H, s).

Production Example 10 Synthesis of 4-(2-bromoethyl)-benzaldoxime

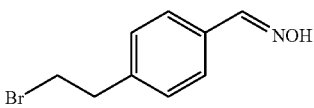

The above 4-(2-bromoethyl)benzaldehyde (2.72 g) was dissolved in ethanol (80 ml). After adding water (20 ml), hydroxylamine hydrochloride (1.53 g) and sodium acetate trihydrate (2.99 g), the resultant mixture was heated under reflux for 30 min. Then it was allowed to cool and the reaction mixture was partitioned between water and ethyl acetate (500 ml). The organic layer was washed with brine, dried over anhydrous sodium sulfate and concentrated under reduced pressure to give the title compound (5.408 g) as a brown oil.

$^1$H-NMR (400 MHz, CDCl$_3$):

δ(ppm) 3.18(2H, t, J=7.4 Hz), 3.57(2H, t, J=7.4 Hz), 7.24(2H, d, J=8.0 Hz), 7.52(2H, d, J=8.0 Hz), 8.13(1H, s).

Prodction Example 11 Synthesis of 4-cyanonphenethyl bromide

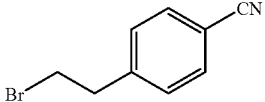

4-(2-Bromoethyl)benzaldoxime (1.0 g) was treated as in Example 20 to give the title compound (0.977 g) as a brown oil.

$^1$H-NMR (400 MHz, CDCl$_3$)

δ(ppm) 3.23(2H, t, J=7.2 Hz), 3.59(2H, t, J=7.2 Hz), 7.34(2H, d, J=7.4 Hz), 7.63(2H, d, J=7.4 Hz).

Production Example 12 Synthesis of 4-carbamoylphenethyl bromide

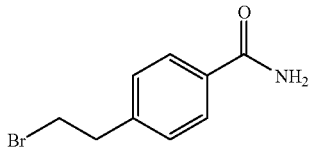

4-Cyanophenethyl bromide (0.997 g) was dissolved in sulfuric acid (20 ml) and stirred at room temperature for 15 hr. Then it was poured into ice, diethyl ether was added thereto and the layers were separated. The organic layer was washed with a saturated aqueous solution of sodium bicarbonate and brine, dried over anhydrous magnesium sulfate and concentrated under reduced pressure. The residue was purified by silica gel column chromatography (hexane/ethyl acetate system) to give the title compound (0.619 g) as colorless crystals (yield: 62.0%).
$^1$H-NMR (400 MHz, CDCl$_3$):
δ(ppm) 3.23(2H, t, J=7.3 Hz), 3.59(2H, t, J=7.3 Hz), 7.31(2H, d, J=8.4 Hz), 7.78(2H, d, J=8.4 Hz).
Production Example 13 Synthesis of N-isopropyl-4-(2-bromoethyl)phenylacetamide (13-1) N-Isopropyl-4-bromophenylacetamide

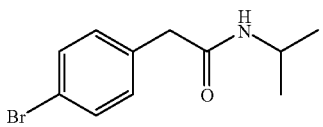

4-Bromophenylacetic acid (10 g) was dissolved in tetrahydrofuran (200 ml). After adding N,N-carbonyldiimidazole (7.54 g) thereto, the resultant mixture was stirred at room temperature for 15 min. Next, isopropylamine (3.96 ml) was further added and the resultant mixture was stirred at room temperature for 24 hr and then concentrated under reduced pressure. The residue was partitioned between ethyl acetate (500 ml) and a saturated aqueous solution of sodium bicarbonate, the organic layer was washed with brine, dried over anhydrous magnesium sulfate and concentrated under reduced pressure to give colorless crystals (11.3 g) of the title compound (yield: 94.8%).
$^1$H-NMR (400 MHz, CDCl$_3$):
δ(ppm) 1.08 (6H, d, J=6.8 Hz), 3.47 (2H, s), 4.06 (1H, m), 5.17(1H, br-s), 7.13(2H, d, J=8.8 Hz), 7.47(2H, d, J=8.8 Hz).
(13-2) N-Isopropyl-4-vinylphenylacetamide

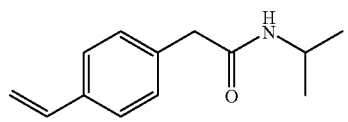

N-Isopropyl-4-bromophenylacetamide (1.0 g) and vinyltributyltin (1.4 ml) were dissolved in toluene (12 ml). After adding tetrakistriphenylphosphinepalladium (0.5 g) thereto, the resultant mixture was heated under reflux for 4 hr. Then it was allowed to cool and diluted with ethyl acetate. The resulting solid was filtered off and the filtrate was concentrated under reduced pressure. The obtained residue was purified by silica gel column chromatography (hexane/ethyl acetate system) to give colorless crystals (0.578 g) of the title compound (yield: 72.8%).
$^1$H-NMR (400 MHz, CDCl$_3$)
δ(ppm) 1.08(6H, d, J=6.4 Hz), 3.55(2H, s), 4.07(1H, m), 5.21 (1H, br-s), 5.28 (1H, dd, J=0.8, 10.8 Hz), 5.76 (H, dd, J=0.8, 17.6 Hz), 6.718(1H, dd, J=10.8, 17.6 Hz), 7.21(2H, J=8.0 Hz), 7.40(2H, d, J=8.8 Hz).
(13-3) N-Isopropyl-4-(2-hydroxyethyl)phenylacetamide

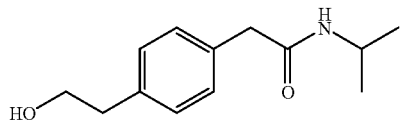

N-Isopropyl-4-vinylphenylacetamide (0.378 g) was dissolved in tetrahydrofuran (4.4 ml). Under ice cooling, a 1.0 M solution (5.6 ml) of a borane/tetrahydrofuran complex in tetrahydrofuran was added dropwise thereinto and then the resultant mixture was stirred for 2 hr. After adding a 5 N aqueous solution (3 ml) of sodium hydroxide and a 30% aqueous solution (3 ml) of hydrogen peroxide, the mixture was stirred for 10 hr. Then ethyl acetate and water were added thereto and the mixture was distributed between two liquid layers. The organic layer was washed with brine, dried over anhydrous magnesium sulfate and concentrated under reduced pressure. The residue was purified by silica gel column chromatography (hexane/ethyl acetate-methanol system) to give colorless crystals (0.134 g) of the title compound (yield: 32.6%).
$^1$H-NMR (400 MHz, CDCl$_3$):
δ(ppm) 1.08(6H, dd, J=1.6, 6.8 Hz), 2.87(2H, t, J=6.6 Hz) 3.51(2H, s), 3.87 (2H, t, J=6.6 Hz), 4.07 (1H, m), 5.26(1H, br-s) 7.19(2H, J=8.6 Hz), 7.22(2H, d, J=8.6 Hz).
(13-4) N-Isopropyl-4-(2-bromoethyl)phenylacetamide

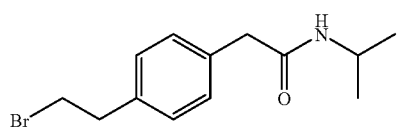

N-Isopropyl-4-(2-hydroxyethyl)phenylacetamide (0.134 g) was treated as in production Example 1 to give colorless crystals (0.029 g) of the title compound (yield: 16.9%).
$^1$H-NMR (400 MHz, CDCl$_3$)
δ(ppm) 1.08(6H, d, J=6.4 Hz), 3.16(2H, t, J=7.4 Hz), 3.15(2H, s), 3.57(2H, t, J=7.4 Hz), 4.06(1H, m), 5.20(1H, br-s) 7.21(4H,
Production Example 14 Synthesis of 3-[2-(t-butyl)dimethylsilyloxyethoxy]phenethyl bromide

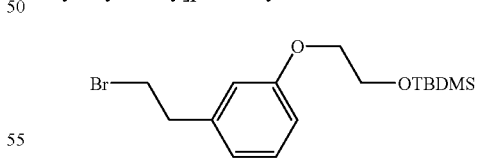

[wherein TBDMS means (t-butyl)dimethylsilyl.]
3-Hydroxyphenethyl alcohol (1.5 g) and 1-bromo-2-(t-butyl)dimethylsilyloxyethane (3.4 g) were treated as in Example 35 to give a pale yellow oil. Then this product was treated as in the above Production Example 1 to give the title compound (1.996 g) as a pale yellow oil (yield: 55.4%).
$^1$H-NMR (400 MHz, CDCl$_3$):
δ(ppm) 0.11(6H, s), 0.92(9H, s), 3.13(2H, t, J=7.6 Hz), 3.56(2H, t, J=7.6 Hz), 3.97(2H, m), 4.04(2H, m), 6.78(3H, m), 7.21(1H, m).

Production Example 19 Synthesis of 1,2-dihydroxymethyl)-4-bromobenzene
(15-1) Dimethyl 4-bromophthalate

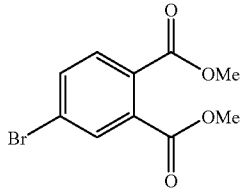

Methanol (500 ml) was added to 4-bromophthalic anhydride (50.25 g). Further, chlorosulfonic acid (1 ml) was added thereto. The resultant mixture was heated under reflux overnight and then concentrated under reduced pressure. The residue was purified by silica gel column chromatography (hexane/ethyl acetate system) to give the title compound (39.98 g) as a colorless oil (yield: 66.1%).
$^1$H-NMR (400 MHZ, CDCl$_3$):
δ(ppm) 3.90(3H, s), 3.92(3H, s), 7.63(1H, d, J=8.4 Hz), 7.68(1H, dd, J=2.0, 8.4 Hz), 7.84(1H, d, J=2.0 Hz).
(15-2) 1,2-Dihydroxymethyl-4-bromobenzene

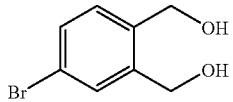

Lithium aluminum hydride (8.77 g) was suspended in tetrahydrofuran (400 ml) and the obtained suspension was stirred under ice cooling. Into the resultant suspension was added dropwise a solution of dimethyl 4-bromophthalate (39.98 g) in tetrahydrofuran (100 ml). After stirring for additional 30 min, water (8.8 ml), a 5 N aqueous solution of sodiumhydroxide (8.8 ml) and further water (26.4 ml) were successively added thereto. The resultant mixture was diluted with ethyl acetate and the insoluble matter was filtered off followed by concentration under reduced pressure. The residue was purified by silica gel column chromatography (hexane/ethyl acetate system) to give the title compound (13.7 g) as a colorless powder (yield: 43.1%).
$^1$H-NMR (400 MHz, CDCl$_3$)
δ(ppm) 3.18(1H, br-t), 3.27(1H, br-t), 4.63–4.65(2H, m), 7.20(1H, d, J=8.0 Hz), 7.43(1H, dd, J=2.0, 8.0 Hz), 7.49(1H, d, J=2.0 Hz).
Production Example 1 6 Synthesis of 3,4-di[t-butyl) dimethyl-silyloxymethyl]phenethyl bromide
(16-1) 3,4-Di[(t-butyl)dimethylsilyloxymethyl]phenethyl alcohol

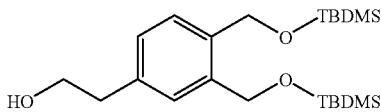

1,2-Dihydroxymethyl-4-bromobenzene (3.110 g) was treated as reported in J. Am. Chem. Soc., 6190 (1972). togiveacolorless oil (6.000 g). This product was dissolved in tetrahydrofuran (56 ml) and a solution (4.2 ml) of n-butyllithium in n-hexane and ethylene oxide (1.36 ml) were successively added thereto in a nitrogen atmosphere at −78° C. followed by stirring for 3 hr. After adding water and diethyl ether to separate the layers, the organic layer was washed with brine, dried over anhydrous magnesium sulfate and concentrated under reduced pressure. The residue was purified by silica gel column chromatography (hexane/ethyl acetate system) to give the title compound-(2.214 g) as a colorless oil (yield: 37.6%).
$^1$H-NMR (400 MHz, CDCl$_3$):
δ(ppm) 0.11(6H, s), 0.95(9H, s), 2.87(2H, t, J=6.4 Hz), 3.85(2H, q, J=6.4 Hz), 4.72(2H, s), 4.74 (2H, s), 7.11(1H, dd, J=1.6, 7.6 Hz), 7.29(1H, d, J=1.6 Hz), 7.36(1H, d, J=7.6 Hz).
(16-2) 3,4-Di[(t-butyl)dimethylsilyloxymethyl]phenethyl bromide

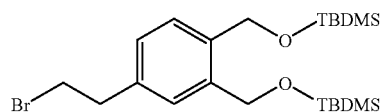

Pyridine (0.16 ml) was added to 3,4-dihydroxymethylphenethyl alcohol (0.41 g) and the resultant mixture was treated as in the above Production Example 1 to give the title compound (0.421 g) as a colorless oil (yield: 88.9%).
$^1$H-NMR (400 MHZ, CDCl$_3$):
δ(ppm) 0.11 (6H, s), 0.95(9H, s), 3.16 (2H, t, J=7.8 Hz), 3.56(2H, t, J=7.8 Hz), 4.71(2H, s), 4.74(2H, s), 7.10(1H, dd, J=1.6, 7.6 Hz), 7.27(1H, d, J=1.6 Hz), 7.36(1H, d, J=7.6 Hz).
Production Example 17 Synthesis of 3-(t-butyl)-dimethylsiloxymethyl]phenyl bromide
(17-1) 3-(t-Butyl)dimethylsilyloxymethylbenzyl alcohol

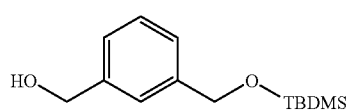

1,3-Benzenedimethanol (10 g) was dissolved in tetrahydrofuran (210 ml). Under ice cooling, sodium hydride (1.16 g) was added thereto. Next, (t-butyl)dimethyl-chlorosilane (4.36 g) dissolved in tetrahydrofuran (40 ml) was added dropwise thereinto and the resultant mixture was stirred at room temperature for 3 hr. After adding water, the resultant mixture was concentrated under reduced pressure. After adding ethyl acetate (200 ml) to the residue, the organic layer was washed with brine, dried over anhydrous magnesium sulfate and concentrated under reduced pressure. The residue was purified by silica gel column chromatography (hexane/ethyl acetate system) to give the title compound (2.108 g) as a colorless oil (yield: 29.1%).
$^1$H-NMR (400 MHz, CDCl$_3$)
δ(ppm) 0.10(6H, s), 0.95(9H, s), 1.57(1H, br-s), 4.70(2H, s), 4.75(2H, s), 7.23–7.35(4H, m).
(17-2) 3-(t-Butyl)dimethyldilyloxymethylbenzaldehyde

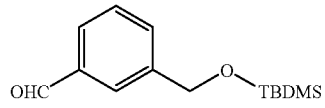

Dimethyl sulfoxide (1.43 ml) was dissolved in methylene chloride (31 ml). In a nitrogen atmosphere, oxalyl chloride (0.88 ml) was added dropwise thereinto at −78° C. and the resultant mixture was stirred for 30 min. After successively adding thereto 3-(t-butyl)dimethylsilyloxymethylbenzyl alcohol (2.108 g) dissolved in methylene chloride (10 ml) and diisopropylethylamine (4.4 ml), the obtained mixture was stirred at room temperature for 1 hr. Then the reaction solution was concentrated under reduced pressure and purified by silica gel column chromatography (hexane/ethyl acetate system) to give the title compound (2.132 g) as a colorless oil (yield: 100%).

$^1$H-NMR (400 MHz, CDCl$_3$)

δ(ppm) 0.12(6H, s), 0.95(9H, s), 4.81(2H, s), 7.50(1H, t, J=7.6 Hz), 7.61(1H, d, J=7.6 Hz), 7.77(1H, d, J=7.6 Hz), 7.83(1H, s), 10.02 (H, s).

(17-3) 3-(t-Butyl)dimethyldilyloxymethylstyrene

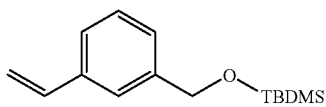

Methyltriphenylphosphonium bromide (3.16 g) was suspended in tetrahydrofuran (30 ml). Under ice cooling, potassium t-butoxide (0.99 g) was added thereto and the resultant mixture was stirred at room temperature for 10 min. Then it was ice cooled again followed by the addition of 3-(t-butyl) dimethyl silyloxybenzaldehyde (2.132 g) dissolved in tetrahydrofuran (0.88 ml). The resultant mixture was stirred at room temperature for 5 hr. After adding water and ethyl acetate, the layers were separated and the organic layer was washed with brine, dried over anhydrous magnesium sulfate and concentrated under reduced pressure. The residue was purified by silica gel column chromatography (hexane/ethyl acetate system) to give the title compound (1.930 g) as a yellow oil (yield: 93.0%).

$^1$H-NMR (400 MHz, CDCl$_3$)

δ(ppm) 0.10(6H, s), 0.95(9H, s), 4.74(2H, s), 5.24(1H, dd, J=1.2, 11.2 Hz), 5.75(1H, dd, J=1.2, 17.6 Hz), 6.72(1H, dd, J=11.2, 17.6 Hz), 7.21(1H, m), 7.29(2H, m), 7.38(1H, S).

(17-4) 3-(t-Butyl)dimethylsilyloxymethylphenethyl alcohol

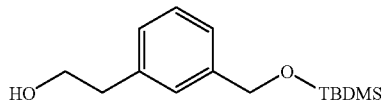

By using a 0.5 M solution of (9-boranebicyclo-[3.3.1] nonane) in tetrahydrofuran, 3-(t-butyl) dimethylsilyloxymethylstyrene (0.5 g) was treated as reported in J. Am. Chem. Soc., 7765 (1974). to give the title compound (0.494 g) as a colorless oil (yield: 92.2%).

$^1$H-NMR (400 MHz, CDCl$_3$)

δ(ppm) 0.110(6H, S), 0.95(9H, s), 2.88(2H, t, J=6.4 Hz), 3.87(2H, q, J=6.4 Hz), 4.73(2H, s), 7.09–7.34(4H, m).

(17-5) 3-(t-Butyl)dimethylsilyloxymethylphenethyl bromide

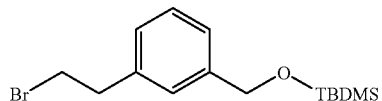

3-(t-Butyl)dimethylsilyloxymethylphenethyl alcohol (0.494 g) was treated as in the above Production Example 1 to give the title compound (0.390 g) as a colorless oil (yield: 63.7%).

Production Example 18 Synthesis of 4-[2-(t-butyl)-dimethyldilyloxyethyl]phenethyl bromide (18-1) Dimethyl 1,4-phenylenediacetate

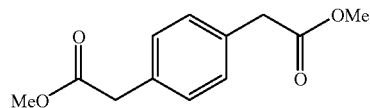

Under ice cooling, thionyl chloride (6.6 ml) was added dropwise into methanol (26 ml) and the resultant mixture was stirred for 15 min. Next, 1,4-phenylenediacetic acid (5.0 g) was added thereto and the resultant mixture was stirred at room temperature for 35 hr and then concentrated under reduced pressure. Then it was diluted with ethyl acetate (500 ml), washed with a saturated aqueous solution of sodium bicarbonate and brine, dried over anhydrous sodium sulfate and concentrated under reduced pressure to give the title compound as colorless crystals.

$^1$H-NMR (400 MHz, CDCl$_3$):

δ(ppm) 3.61(4H, s), 3.69(6H, s), 7.25(4H, d, J=6.4 Hz)

(18-2) 1,4-Benzenediethanol

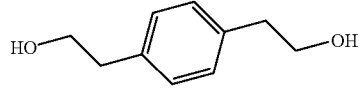

All the dimethyl 1,4-phenylenediacetate synthesized in Production Example 18-1 was dissolved in tetrahydrofuran (100 ml). Under ice cooling, lithium aluminum hydride (2.44 g) was added thereto and the resultant mixture was stirred at room temperature for 3 hr. Then it was ice cooled and water (2.5 ml), a 5 N aqueous solution of sodium hydroxide (2.5 ml) and further water (7.5 ml) were added thereto. The resulting precipitate was filtered off and the filtrate was concentrated under reduced pressure to give the title compound (4.555 g) as colorless crystals.

$^1$H-NMR (400 MHz, CDCl$_3$):

δ(ppm) 1.40(2H, t, J=6.0 Hz), 2.85(4H, t, J=6.4 Hz), 3.86(4H, q, J=6.4 Hz), 7.19 (4H, s)

(18-3) 4-[2-t-Butyl)dimethylsilyloxyethyl]phenethyl alcohol

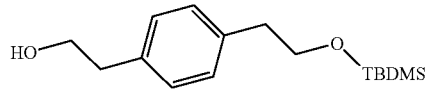

1,4-Benzenediethanol (4.555 g) was treated as in the above Production Example 17-1 to give the title compound (0.869 g) as a colorless oil (yield: 30.1%).

$^1$H-NMR (400 MHz, CDCl$_3$)

δ(ppm) −0.01(6H, s), 0.91(9H, s), 2.80(2H, t, J=7.2 Hz), 2.84(2H, t, J=6.4 Hz), 3.79(2H, t, J=7.2 Hz), 3.84(2H, q, J=6.4 Hz), 7.15(4H, s).

(18-4) 4-[2-(t-Butyl)dimethyldilyloxyethyl]phenethyl bromide

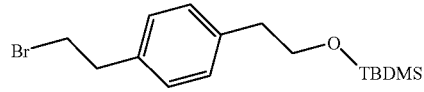

4-[2-(t-Butyl)dimethylsilyloxyethyl]phenethyl alcohol (0.869 g) was treated as in the above Production Example 1 to give the title compound (0.700 g) as a colorless oil (yield: 65.8%).

Production Example 19 Synthesis of 4-(1-hydroxyethyl)-phenethyl bromide

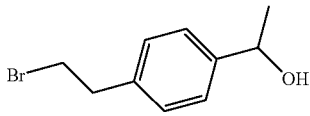

4-(2-Bromoethyl)benzaldehyde (3.245 g) was dissolved in tetrahydrofuran (60 ml). Under ice cooling, a 3 M solution (4.9 ml) of methylmagnesium bromide in diethyl ether was added dropwise thereinto and the resultant mixture was stirred for 1.5 hr. After adding water and ethyl acetate, the layers were separated and the organic layer was washed with brine, dried over anhydrous magnesium sulfate and concentrated under reduced pressure. The residue was then purified by silica gel column chromatography (hexane/ethyl acetate system) to give the title compound (2.745 g) as a brown oil (yield: 83.8%).
$^1$H-NMR (400 MHz, CDCl$_3$):
δ(ppm) 1.49(3H, d, J=6.4 Hz), 1.81(1H, br-s), 3.16(2H, t, J=7.6 Hz), 3.57 (2H, t, J=7.6 Hz), 4.89 (1H, q, J=6.4 Hz), 7.20 (2H, d), 7.33(2H, d).

Production Example 20 Synthesis of 4-methanesulfonylphenethyl bromide (20-1) 4-2t-Butyldimethylsiloxyethyl)-1-bromobenzene

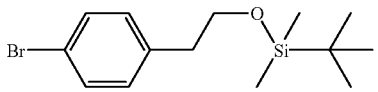

A solution of 4-bromophenethyl alcohol (10 g), imidazole (4.0 g) and (t-butyl)dimethylsilyl chloride (9.0 g) in dimethylformamide (50 ml) was stirred at room temperature for 3 hr. Then the reaction solution was concentrated under reduced pressure. After adding water and ethyl acetate, the layers were separated and the organic layer was washed with brine and dried over anhydrous magnesium sulfate. After evaporating the solvent, the residue was purified by silica gel column chromatography (hexane/ethyl acetate system) to give the title compound (13.9 g) as a colorless oil (yield: 88%).
$^1$H-NMR (400 MHz, CDCl$_3$):
δ(ppm) −0.02(6H, s), 0.89(9H, s), 2.79(2H, t, J=7 Hz), 3.80(2H, t, J=7 Hz), 7.10(2H, d, J=8 Hz), 7.42(2H, d, J=8 Hz).

(20-2) 4-Methanesulfonylphenethyl alcohol

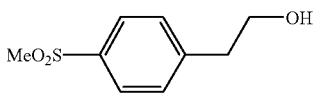

A 2.5 M solution (7.6 ml) of (n-butyllithium) in hexane was added dropwise at −78° C. into a solution of 4-[2-(t-butyl)-dimethylsiloxyethyl]-1-bromobenzene (5.0 g) in tetrahydrofuran (50 ml) over 10 min. After 10 min, a saturated solution of sulfur dioxide in tetrahydrofuran (200 ml) was added thereto and the resultant mixture was warmed to room temperature. After concentrating the reaction solution under reduced pressure, dimethylformamide (100 ml) and methyl iodide (2.7 g) were added to the obtained residue followed by stirring at 50° C. for 6 hr. After concentrating under reduced pressure, a saturated aqueous solution of sodium bicarbonate and ethyl acetate were added thereto and the layers were separated. The organic layer was washed with brine, dried over anhydrous magnesium sulfate and concentrated under reduced pressure. To the residue was added tetrahydrofuran and tetrabutylammonium fluoride followed by stirring at 0° C. for 2 hr. After adding water and ethyl acetate to the reaction solution, the layers were separated and the organic layer was washed with brine and dried over anhydrous magnesium sulfate. The residue was purified by silica gel column chromatography (methylene chloride/ethanol system) to give the title compound (1.9 g) as a colorless oil (yield: 60%).
$^1$H-NMR (400 MHz, CDCl$_3$):
δ(ppm) 1.45(1H, t, J=7 Hz), 2.85(2H, t, J=7 Hz), 3.04(3H, s), 3.92(2H, q, J=7 Hz), 7.44(2H, d, J=8 Hz), 7.89(2H, d, J=8 Hz).

(20-3) 4-Methanesulfonylphenethyl bromide

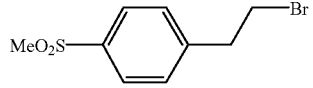

4-Methanesulfonylphenethyl alcohol (1.9 g) was treated as in the above Production Example 1 to give the title compound (1.9 g) as a colorless oil (yield: 76%).
$^1$H-NMR (400 MHz, CDCl$_3$):
δ(ppm) 3.05(3H, s), 3.27(2H, t, J=7 Hz), 3.61(2H, t, J=7 Hz), 7.43(2H, d, J=8 Hz), 7.90(2H, d, J=8 Hz).

Production Example 21 Synthesis of 4-sulfamoylphenethyl bromide

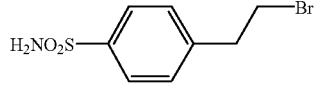

Under ice cooling, phenethyl bromide (5.0 g) was added dropwise into chlorosulfonic acid (15 ml) followed by stirring for 1 hr. The reaction solution was diluted with ice water and ethyl acetate and the layers were separated. Then the organic layer was washed with brine. Then aqueous ammonia (10 ml) was added thereto and the resultant mixture was stirred for 1 hr. The organic layer was washed with brine, dried over anhydrous magnesium sulfate and concentrated under reduced pressure. The crystalline precipitates were washed with isopropyl ether and air-dried to give the title compound (1.4 g) as white crystals (yield: 22%).
$^1$H-NMR (400 MHz, DMSO-d$_6$):
δ(ppm) 3.20(2H, t, J=7 Hz), 3.31(2H, br-s), 3.77(2H, t, J=7 Hz), 7.48(2H, d, J=8 Hz), 7.74(2H, d, J=8 Hz).

Production Example 22 Synthesis of 1-bromo-3-(4-fluorophenoxy)propane

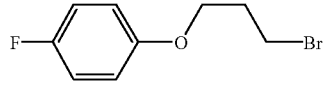

A mixture of 4-fluorophenol (11 g), 1,3-dibromopropane (61 g), sodium hydroxide (8.0 g), tetra-n-butylammonium bromide (6.0 g), methylene chloride (200 ml) and water (200 ml) was vigorously stirred at room temperature overnight. After separating the organic layer, it was washed with brine and dried over anhydrous magnesium sulfate. The residue was then purified by silica gel column chromatography (hexane/isopropyl ether system) to give the title compound (16.5 g) as a colorless oil (yield: 71%).

¹H-NMR (400 MHz, CDCl₃):

δ(ppm) 2.24–2.36(2H, m), 3.60(2H, t, J=7 Hz), 4.08(2H, t, J=7 Hz), 6.80–6.89(2H, m), 6.93–7.00(2H, m).

Production Example 23 Synthesis of 3-bromopropoxy-1,2-methylenedioxybenzene

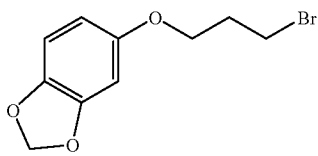

3,4-Methylenedioxyphenol (4.144 g) was dissolved in N,N-dimethylformamide (40 ml). Under ice cooling, 60% sodium hydride (1.2 g) was added thereto and the resultant mixture was stirred. After 1 hr, 1,3-dibromopropane (9.1 ml) was added thereto followed by stirring at room temperature overnight. The reaction mixture was diluted with ethyl acetate and water and the layers were separated. Then the organic layer was washed with water, dried over magnesium sulfate and concentrated under reduced pressure. The residue was purified by silica gel column chromatography (ethyl acetate/hexane system) to give the title compound (1.341 g) as a colorless solid (yield: 17%).

¹H-NMR (400 MHz, CDCl₃):

δ(ppm) 2.25–2.32(2H, m), 3.59(2H, t, J=6.4 Hz), 4.03 (2H, t, J=5.8 Hz), 5.92(2H, s), 6.33(1H, dd, J=8.8 Hz, 2.4 Hz), 6.49(1H, d, J=2.4 Hz), 6.71(1H, d, J=8.8 Hz).

Production Example 24 Synthesis of 4-(3-bromopropoxy)-phenethyl alcohol

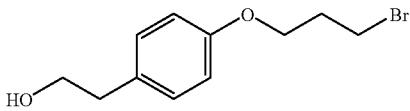

4-Hydroxyphenethyl alcohol (4.145 g), 1,3-dibromopropane (9.1 ml) and tetrabutylammonium bromide (967 mg) were added to methylene chloride (100 ml) and a solution of sodium hydroxide (2.4 g) in water (100 ml) and the resultant mixture was vigorously stirred at room temperature overnight. The methylene chloride layer was washed with water, dried over magnesium sulfate and concentrated under reduced pressure. The residue was purified by silica gel column chromatography (ethyl acetate/hexane system) to give the title compound (1.005 g) as a colorless solid (yield: 13%).

¹H-NMR (400 MHz, CDCl₃):

δ(ppm) 2.31(2H, qui, J=6 Hz), 2.81(2H, t, J=6.4 Hz), 3.60(2H, t, J=6.4 Hz), 3.83(2H, t, J=6.4 Hz), 4.09(2H, t, J=6 Hz), 6.86(2H, d, J=8.6 Hz), 7.08(2H, d, J=8.6 Hz).

Production Example 25 Synthesis of 4-(3-bromopropoxy) benzyl alcohol

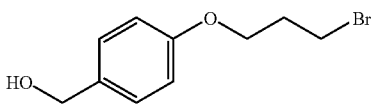

4-Hydroxybenzyl alcohol (3.724 g) was treated as in the above Production Example 24 to give the title compound (314 mg) as a pale yellow solid (yield: 4%).

¹H-NMR (400 MHz, CDCl₃):

δ(ppm) 2.31(2H, qui, J=6.3 Hz), 3.30(2H, t, J=6.3 Hz), 4.10(2H, t, J=6.3 Hz), 4.60(2H, d, J=5.8 Hz), 6.90(2H, d, J=8.9 Hz), 7.30(2H, d, J=8.9 Hz).

Production Example 26 Synthesis of 3-(2-bromoethyl) pyridine (26-1) 3-Pyridylethanol

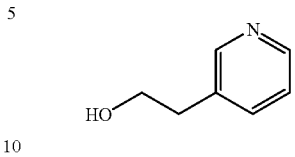

Ethyl 3-pyridylacetate (2.0 ml) was dissolved in tetrahydrofuran (66 ml). Under ice cooling, lithium aluminum hydride (0.5 g) was added thereto followed by stirring for 30 min. After adding water (0.5 ml), a 5 N aqueous solution of sodium hydroxide (0.5 ml) and further water (1.5 ml), the resulting precipitate was filtered off and washed with ethyl acetate. The filtrate was concentrated under reduced pressure to give the title compound (1.636 g) as a pale yellow oil (1.636 g) (yield: quantitative).

¹H-NMR (400 MHz, CDCl₃):

δ(ppm) 2.84(2H, t, J=6.4 Hz), 3.85(2H, t, J=6.4 Hz), 7.20(1H, m), 7.57(1H, m), 8.36(2H, m)

(26-2) 3-(2-Bromoethyl)pyridine

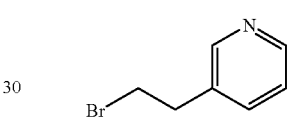

3-Pyridylethanol (0.4 g) was treated as in the above Production Example 1. The liquid reaction mixture was reverse extracted with 1 N hydrochloric acid and then basified with an aqueous solution of sodium hydroxide. Next, it was extracted with chloroform, washed with brine, dried over anhydrous magnesium sulfate and concentrated under reduced pressure to give the title compound (0.481 g) as a brown oil (yield: 79.5%).

¹H-NMR (400 MHz, CDCl₃):

δ(ppm) 3.18(2H, t, J=7.2 Hz), 3.58(2H, t, J=7.2 Hz), 7.47(1H, m), 7.55(1H, dt, J=1.6, 7.2 Hz), 7.67(1H, ddd, J=1.6, 7.2, 10.8 Hz), 8.51(1H, m).

Production Example 27 Synthesis of 1-bromo-2-(2-methoxy-pyridin-5-yl)ethane (27-1) 2-(2-Methoxypyridin-5-yl)ethanol

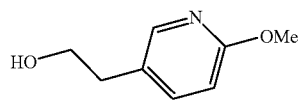

5-Bromo-2-methoxypyridine (2.628 g) synthesized as reported in Tetrahedron, 1373 (1985). was dissolved in diethyl ether (40 ml) and then treated as in the above Production Example 16-1 to give the title compound (1.342 g) as a pale yellow oil (yield: 62.7%).

¹H-NMR (400 MHz, CDCl₃)

δ(ppm) 2.79 (2H, t, J=6.4 Hz), 3.82 (2H, br-t), 3.91(3H, s), 6.71(1H, d, J=8.4 Hz), 7.46(1H, dd, J=2.4, 8.4 Hz), 8.01(1H, d, J=2.4 Hz).

(27-2) 1-Bromo-2-(2-methoxypyridin-5-yl)ethane

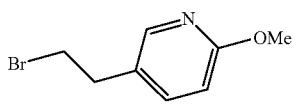

2-(2-Methoxypyridin-5-yl)ethanol (1.342 g) was treated as in the above Production Example 1. After the completion of the reaction, reverse extraction method was effected to give the title compound (1.221 g) as a brown oil (yield: 64.5%).
$^1$H-NMR (400 MHz, CDCl$_3$):
δ(ppm) 3.09(2H, t, J=7.4 Hz), 3.52(2H, t, J=7.4 Hz), 3.93(3H, s), 6.71(1H, d, J=8.4 Hz), 7.44(1H, dd, J=2.4, 8.4 Hz), 8.02(1H, d, J=2.4 Hz).
Production Example 28 Synthesis of 1-bromo-2-(2-cyanopyridin-5-yl)ethane
(28-1) 2-(3-Pyridyl)ethanol

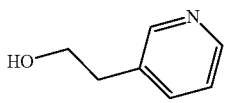

3-Pyridylacetic acid hydrochloride (25 g) was treated successively as in the above Production Examples 3-3 and 3-4 to give the title compound (16.938 g) as a yellow oil (yield: 95.5%).
$^1$H-NMR (400 MHz, CDCl$_3$):
δ(ppm) 2.86(2H, t, J=6.8 Hz), 3.88(2H, t, J=6.8 Hz), 7.22(1H, dd, J=4.8, 7.6 Hz), 7.527(1H, d, J=7.6 Hz), 8.42(1H, dd, J=2.0, 4.8 Hz), 8.44(1H, d, J=2.0 Hz).
(28-2) 2-(Pyridyl)-1-triphenylmethyloxyethane

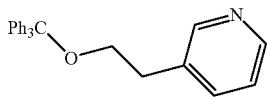

2-(3-Pyridyl)ethanol (5.0 g) was treated as reported in Tetrahedron Lett., 579 (1986). to give the title compound (10.096 g) as a yellow oil (yield: 68.0%).
$^1$H-NMR (400 MHz, CDCl$_3$)
δ(ppm) 2.86(2H, t, J=6.4 Hz), 3.32(2H, t, J=6.4 Hz), 7.08–7.38(16H, m), 7.53(1H, d, J=8.0 Hz), 8.46(2H, m).
(28-3) 3-(2-Triphenylmethyloxyethyl)pyridin N-oxide

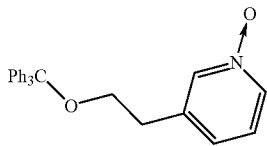

2-(3-Pyridyl)-1-triphenylmethyloxyethane (10.096 g) was treated as reported in Tetrahedron Lett., 1475 (1986). to give the title compound (11.201 g) as a yellow oil (yield: quantitative).
$^1$H-NMR (400 MHz, CDCl$_3$)
δ(ppm) 2.86(2H, t, J=6.4 Hz), 3.32(2H, t, J=6.4 Hz), 7.08–7.38(16H, m), 7.53(1H, d, J=8.0 Hz), 8.46(2H, m).
(28-4) 2-(2-Cyanopyridin-5-yl)-1-triphenylmethyloxyethane

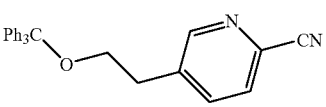

2-Cyano-5-(2-triphenylmethyloxyethyl)pyridine N-oxide (8.0 g) and trimethylsilyl cyanide (11.2 ml) were treated as reported in Synthesis, 314 (1983). to give the title compound (2.831 g) as a pale yellow oil (yield: 30.0%).
$^1$H-NMR (400 MHz, CDCl$_3$):
δ(ppm) 2.91(2H, t, J=6.0 Hz), 3.38(2H, t, J=6.0 Hz), 7.20–7.35(16H, m), 7.60(2H, m), 8.55(1H, s).
(28-5) 2-(2-(Cyanopyridin-5-yl)ethanol

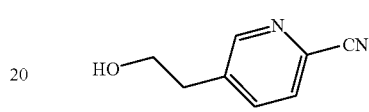

2-(2-Cyanopyridin-5-yl)-1-triphenylmethyloxyethane (2.631 g) and formic acid (38.0 ml) were treated as reported in Tetrahedron Lett., 579 (1986). to give the title compound (0.455 g) as colorless crystals (yield: 45.7%).
$^1$H-NMR (400 MHz, CDCl$_3$)
δ(ppm) 2.95(2H, t, J=5.8 Hz), 3.94(2H, t, J=5.8 Hz), 7.64(1H, d, J=8.0 Hz), 7.75(1H, dd, J=2.0, 8.0 Hz), 8.61(1H, d, J=2.0 Hz)
(28-6) 1-Bromo-2-(2-cyanopyridin-5-yl)ethane

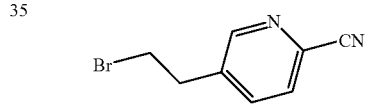

2-(2-Cyanopyridin-5-yl)ethanol (0.423 g) was treated as in the above Production Example 1 to give the title compound (0.406 g) as colorless crystals (yield: 67.3%).
$^1$H-NMR (400 MHz, CDCl$_3$)
δ(ppm) 3.30(2H, t, J=6.8 Hz), 3.94(2H, t, J=6.8 Hz), 7.71(1H, d, J=8.0 Hz), 7.78(1H, dd, J=2.4, 8.0 Hz), 8.62(1H, d, J=2.4 Hz).
Production Example 29 Synthesis of 5-(2-bromoethyl)-3-(t-butyl)dimethylsilyloxymethylpyridine
(29-1) Methyl 5-bromonicotinate

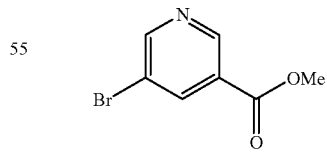

5-Bromonicotinic acid (10 g) and methanol were treated as in the above Production Example 3-3 to give the title compound (10.052 g) as colorless crystals (yield: 94.0%).
$^1$H-NMR (400 MHz, CDCl$_3$):
δ(ppm) 3.97(3H, s), 8.44(1H, dd, J=1.6, 2.4 Hz), 8.85(1H, d, J=2.4 Hz), 9.13(1H, d, J=1.6 Hz).

(29-2) 5-Bromo-3-hydroxymethylpyridine

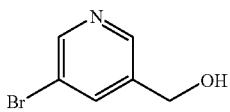

Methyl 5-bromonicotinate (5.0 g) and methanol were treated as in the above Production Example 3-4 to give the title compound (3.410 g) as a yellow oil (yield: 78.4%).

$^1$H-NMR (400 MHz, CDCl$_3$):

δ(ppm) 2.50(1H, m), 3.97(2H, s), 7.90(1H, s), 8.48(1H, s), 8.58(1H, s).

(29-3) 5-Bromo-3-(t-butyldimethylsilyloxymethyl)pyridine

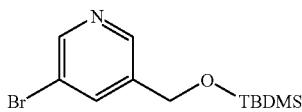

5-Bromo-3-hydroxymethylpyridine (3.41 g), imidazole (13.33 g), t-butyldimethylchlorosilane (13.57 g) and N,N-dimethylformamide (63 ml) were treated as reported in J. Am. Chem. Soc., 6190 (1972) to give the title compound (5.605 g) as a yellow oil (yield: quantitative).

$^1$H-NMR (400 MHz, CDCl$_3$):

δ(ppm) 0.12(6H, s), 0.95(9H, s), 4.74(2H, s), 7.81(1H, s), 8.47(1H, s), 8.56(1H, s).

(29-4) 5-(2-Hydroxyethyl)-3-(t-butyl)dimethylsilyloxymethylpyridine

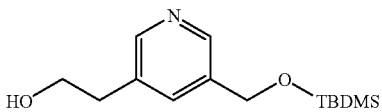

5-Bromo-3-(t-butyl)dimethylsilyloxymethylpyridine (3.41 g) and diethyl ether employed as a solvent were treated as in the above Production Example 16-1 to give the title compound (0.827 g) as a brown oil (yield: 26.0%).

$^1$H-NMR (400 MHz, CDCl$_3$):

δ(ppm) 0.12(6H, s), 0.95(9H, s), 1.61(1H, m), 2.88(2H, t, J=6.4 Hz), 3.89(2H, q, J=6.4 Hz), 4.75(2H, s), 7.54(1H, s), 8.38(1H, s), 8.43(1H, s).

(29-5) 5-(2-Bromoethyl)-3-(t-butyl)dimethylsilyloxymethylpyridine

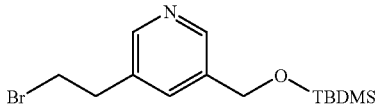

5-(2-Hydroxyethyl)-3-(t-butyl)dimethylsilyloxymethylpyridine (0.4 g) was treated as in the above Production Example 1 to give the title compound (0.248 g) as a yellow oil (yield: 50.0%).

$^1$H-NMR (400 MHz, CDCl$_3$):

δ(ppm) 0.12(6H, s), 0.95(9H, s), 3.18(2H, t, J=7.2 Hz), 3.57(2H, t, J=7.2 Hz), 4.76(2H, s), 7.53(1H, s), 8.38(1H, d, J=2.0 Hz), 8.46(1H, d, J=2.0 Hz).

Production Example 30 Synthesis of 5-(2-bromoethyl)-3-methoxypyridine

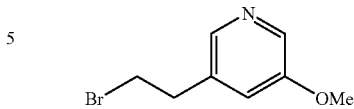

Methoxymethyltriphenylphosphonium chloride (3.0 g) was suspended in tetrahydrofuran (10 ml). Under ice cooling, potassium t-butoxide (0.98 g) was added thereto followed by stirring for 15 min. Next, 5-methoxy-3-pyridinecarboxy-aldehyde (0.4 g) synthesized as reported in Heterocycles, 2159 (1987). and dissolved in tetrahydrofuran (5 ml) was added thereto and the resultant mixture was stirred at room temperature for 2 hr. After adding water and ethyl acetate thereto, the layers were separated and the organic layer was washed with brine, dried over anhydrous magnesium sulfate and concentrated under reduced pressure. The residue was purified by silica gel column chromatography (hexane/ethyl acetate system) to give a yellow oil (0.364 g). This product was dissolved in 1 N hydrochloric acid (44 ml) and stirred at 60° C. for 3 hr. After allowing to cool, the reaction solution was basified with an aqueous solution of sodium hydroxide, extracted with chloroform, washed with brine, dried over anhydrous magnesium sulfate and concentrated under reduced pressure to give a yellow oil (0.220 g). This product was dissolved in ethanol (7.2 ml) and sodium tetrahydroborate (0.054 g) was added thereto under ice cooling. After stirring at room temperature for 30 min, the resultant mixture was diluted with ethyl acetate, washed with brine, dried over anhydrous magnesium sulfate and concentrated under reduced pressure to give a pale yellow oil (0.188 g). This product was treated as in the above Production Example 1 to give the title compound (0.181 g) as a brown oil (yield: 28.4%).

$^1$H-NMR (400 MHz, CDCl$_3$):

δ(ppm) 3.16(2H, t, J=6.4 Hz), 3.57(2H, t, J=6.4 Hz), 3.88(3H, s), 7.08(1H, s), 8.10(1H, s), 8.21(1H, s).

Production Example 31 Synthesis of 2-(2-bromoethyl)thiophene

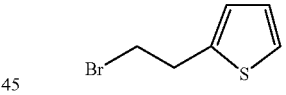

2-Thienylethanol (0.44 ml) was treated as in the above Production Example 1 to give the title compound (0.490 g) as a colorless oil (yield: 64.0%).

$^1$H-NMR (400 MHz, CDCl$_3$):

δ(ppm) 3.38(2H, t, J=7.6 Hz), 3.58(2H, t, J=7.6 Hz), 6.89(1H, d, J=1.2 Hz), 6.96(1H, d, J=4.2 Hz), 7.19(1H, dd, J=1.2, 4.2 Hz).

Production Example 32 Synthesis of 3-(2-bromoethyl)thiophene

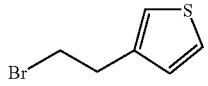

3-Thienylethanol (0.45 ml) was treated as in the above Production Example 1 to give the title compound (0.389 g) as a pale yellow oil (yield: 59.9%).

$^1$H-NMR (400 MHz, CDCl$_3$):

δ(ppm)3.21(2H, t, J=7.6 Hz),3.57(2H,t, J=7.6 Hz), 6.98(1H, d, J=4.8 Hz), 7.09(1H, s), 7.29(1H, d, J=4.8 Hz).

Production Example 33 Synthesis of 2-(2-bromoethyl) thiazole
(33-1) 2-(2-Hydroxyethyl)thiazole

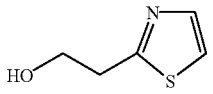

Thiazole (5.0 g) was dissolved in diethyl ether (150 ml) and treated as in the above Production Example 16-1 to give the title compound (1.173 g) as a brown oil (yield: 15.5%).
¹H-NMR (400 MHz, CDCl₃):
δ(ppm) 3.24(2H, t, J=6.0 Hz), 4.02(2H, m), 7.23(1H, d, J=3.4 Hz), 7.69(1H, d, J=3.4 Hz).
(33-2) 2-(2-Bromoethyl)thiazole

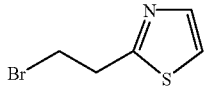

2-(2-Hydroxyethyl)thiazole (1.173 g) was treated as in the above Production Example 1 to give the title compound (0.362 g) as a pale yellow oil (yield: 24.9%).
¹H-NMR (400 MHz, CDCl₃):
δ(ppm)3.57(2H, t, J=7.2 Hz),3.75(2H,t, J=7.2 Hz), 7.26 (1H, d, J=3.4 Hz), 7.74(1H, d, J=3.4 Hz).
Production Example 34 Synthesis of 6-(2-bromoethyl) benzothiazole
(34-1) 2-Amino-6-ethoxycarbonylmethylbenzothiazole

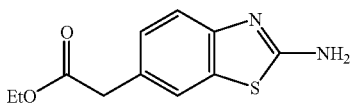

Ethyl 4-aminophenylacetate (18 g) was dissolved in acetic acid (120 ml) and ethyl thiocyanate (29.3 g) was added thereto. Under ice cooling, bromine (6.2 ml) was added dropwise thereinto over 45 minutes while maintaining the reaction temperature at about 10° C. After the completion of the addition, the resultant mixture was stirred at room temperature for 1.5 hr and then at 80° C. for about 2 hr until the reaction was completed. Then the reaction solution was poured into ice water, basified with an 8 N aqueous solution of sodium hydroxide, extracted with chloroform, washed with water, dried over anhydrous magnesium sulfate and then concentrated under reduced pressure to give the title compound (22.23 g) as orange crystals (yield: 93.66%).
¹H-NMR (400 MHz, CDCl₃):
δ(ppm) 1.26(3H, t, J=7.2 Hz), 3.65(2H, s), 4.16(2H, q, J=7.2 Hz), 5.31(2H, br-s), 7.22(1H, dd, J=2.0, 8.4 Hz), 7.48(1H, d, J=8.4 Hz), 7.53(1H, d, J=2.0 Hz).
(34-2) Ethyl (6-benzothiazolyl)acetate

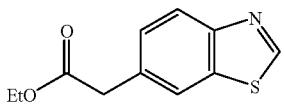

2-Amino-6-ethoxycarbonylmethylbenzothiazole (2.0 g) was dissolved in N,N-dimethylf ormamide (17 ml) and isoamyl nitrite (2.3 ml) was added dropwise into the solution at 65° C. Then the resultant mixture was stirred as such for 15 min. After allowing to cool, the reaction solution was poured into ice water, extracted with ethyl acetate, washed with brine, dried over anhydrous magnesium sulfate and then concentrated under reduced pressure. The residue was purified by silica gel column chromatography (hexane/ethyl acetate system) to give the title compound (1.341 g) as an orange oil (yield: 71.6%).
¹H-NMR (400 MHz, CDCl₃):
δ(ppm) 1.26(3H, t, J=7.2 Hz), 3.77(2H, s), 4.18(2H, q, J=7.2 Hz), 7.45(1H, d, J=8.4 Hz), 7.90(1H, s), 8.09(1H, d, J=8.4 Hz), 8.97(1H, s).
(34-3) 6-(2-Hydroxyethyl)benzothiazole

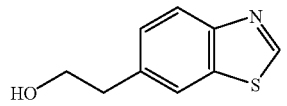

Ethyl (6-benzothiazolyl)acetate (0.22 g) was treated as in the above Production Example 18-2 to give the title compound (0.130 g) as a brown oil (yield: 72.5%).
¹H-NMR (400 MHz, CDCl₃):
δ(ppm) 2.14(1H, m), 3.01(2H, t, J=6.4 Hz), 3.93(2H, t, J=6.4 Hz), 7.36(1H, dd, J=1.6, 8.4 Hz), 7.81(1H, d, J=1.6 Hz), 8.02(1H, d, J=8.4 Hz), 8.97(1H, s).
(34-4) 6-(2-Bromoethyl)benzothiazole

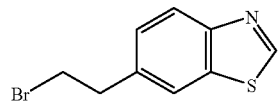

6-(2-Hydroxyethyl)benzothiazole (0.130 g) was treated as in the above Production Example 1. Then the reaction solution was directly purified by silica gel column chromatography (hexane/ethyl acetate system) to give the title compound (0.080 g) as a yellow oil (yield: 45.5%).
¹H-NMR (400 MHz, CDCl₃):
δ(ppm) 3.32(2H, t, J=7.6 Hz), 3.64(2H, t, J=7.6 Hz), 7.37(1H, dd, J=1.6, 8.4 Hz), 7.82(1H, d, J=1.6 Hz), 8.09(1H, d, J=8.4 Hz), 8.97(1H, s).
Production Example 35 Synthesis of (5-methoxy-2-thienyl) ethyl bromide

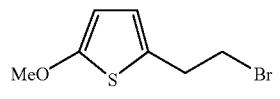

A 2.5 M solution (23 ml) of n-butyllithium in hexane was added dropwise at −78° C. into a solution of 2-methoxythiophene (5.0 g) in ether (50 ml). Then the resultant mixture was warmed to room temperature and stirred. After 10 min, ethylene oxide (2.5 g) was added dropwise thereinto at −78° C. and then the resultant mixture was warmed to room temperature and stirred for 1 hr. After adding a saturated aqueous solution of ammonium chloride and ethyl acetate, the layers were separated and the organic layer was washed with brine, dried over anhydrous magnesium sulfate and purified by silica gel column chromatography (hexane/ethyl acetate system). Then it was diluted with methylene chloride (50 ml) and triphenylphosphine (4.0 g) and N-bromosuccinimide (2.7 g) were added thereto under ice cooling followed by stirring overnight. After concentrating under reduced pressure, the resulting crystalline precipitates were filtered off and the filtrate was concentrated to give the title compound (1.7 g) as a brown oil (yield: 18%).

¹H-NMR (400 MHz, CDCl₃):

δ(ppm) 3.19(2H, t, J=7 Hz), 3.51(2H, t, J=7 Hz), 3.85(3H, s), 6.01(1H, d, J=4 Hz), 6.47(1H, d, J=4 Hz).

Production Example 36 Synthesis of (2-methoxy-5-thiazolyl)ethyl bromide

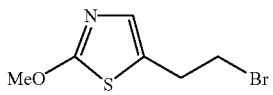

2-Methoxythiazole (3.9 g) was treated as in the above Production Example 35 to give the title compound (1.4 g) as a brown oil (yield: 19%).

¹H-NMR (400 MHz, CDCl₃):

δ(ppm) 3.20(2H, t, J=7 Hz), 3.51(2H, t, J=7 Hz), 4.03(3H, s), 6.89(1H, s).

Production Example 37 Synthesis of (2-cyano-5-thiazolyl)ethyl bromide (37-1) (2-Formyl-5-thiazolyl)ethyl bromide

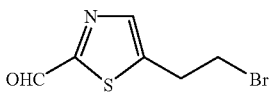

A solution of 2-formylthiazole (5.0 g), trimethylene glycol (6.7 g) and p-toluenesulfonic acid (0.5 g) in toluene (100 ml) was heated under reflux overnight. Then a saturated aqueous solution of sodium bicarbonate was added to the reaction solution and the layers were separated. The organic layer was washed with brine, dried over anhydrous magnesium sulfate and concentrated under reduced pressure. The residue was diluted with ether (200 ml). Then a 2.5 M solution (23 ml) of n-butyllithium in hexane was dropped at −78° C. thereinto followed by warming to room temperature and stirring. After 10 min, ethylene oxide (2.5 g) was added dropwise thereinto at −78° C. and then the resultant mixture was warmed to room temperature and stirred for 1 hr. After adding a saturated aqueous solution of ammonium chloride and ethyl acetate thereto, the layers were separated and the organic layer was washed with brine, dried over anhydrous magnesium sulfate and purified by silica gel column chromatography (hexane/ethyl acetate system). Then it was diluted with methylene chloride (50 ml) and triphenylphosphine (3.9 g) and N-bromosuccinimide (2.7 g) were added thereto under ice cooling followed by stirring overnight. After concentrating under reduced pressure, the resulting crystalline precipitates were filtered off and the filtrate was concentrated. The residue was diluted with tetrahydrofuran (20 ml) and 2 N hydrochloric acid (30 ml) was added thereto. After heating under reflux for 1 day, the reaction solution was basified by adding an aqueous solution of sodium hydroxide. After adding ethyl acetate thereto, the layers were separated and the organic layer was washed with brine, dried over anhydrous magnesium sulfate and concentrated under reduced pressure. The residue was then purified by silica gel column chromatography (hexane/ethyl acetate system) to give the title compound (2.5 g) as a brown oil (yield: 26%).

¹H-NMR (400 MHz, CDCl₃):

δ(ppm) 3.40(2H, t, J=7 Hz), 3.78(2H, t, J=7 Hz), 7.94(1H, s), 9.93(1H, s).

(37-2) (2-Cyano-5-thiazolyl)ethyl bromide

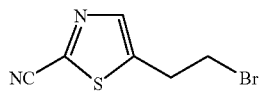

A suspension of the above (2-formyl-5-thiazolyl)ethyl bromide (2.5 g), hydroxylammonium chloride (0.79 g) and anhydrous sodium acetate (1.87 g) in ethanol (50 ml) was stirred at room temperature for a day. The reaction solution was diluted with ethyl acetate and water and then basified with an 8 N aqueous solution of sodium hydroxide followed by separation of an organic layer. The organic layer was washed with brine and dried over anhydrous magnesium sulfate. After evaporating the solvent, the residue was diluted with methylene chloride (50 ml) followed by the addition of triethylamine (2.3 g). Then trifluoromethanesulfonic anhydride (3.2 g) was added dropwise thereinto at −78° C. and the resultant mixture was heated to room temperature. After adding a saturated aqueous solution of sodium bicarbonate and chloroform thereto, the layers were separated and the organic layer was dried over anhydrous magnesium sulfate and purified by silica gel column chromatography (hexane/ethyl acetate system) to give the title compound (0.2 g) as a brown oil (yield: 8.1%).

¹H-NMR (400 MHz, CDCl₃):

δ(ppm) 3.40(2H, t, J=7 Hz), 3.76(2H, t, J=7 Hz), 7.87(1H, s).

Production Example 38 Synthesis of 1-(2-bromoethyl)-4-bromopyrazole (38-1) 1-(2-Hydroxyethyl)-4-bromopyrazole

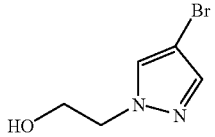

1-(2-Benzyloxyethyl)-4-bromopyrazole (1.078 g) was dissolved in ethanol (20 ml). After adding conc. hydrochloric acid (15 ml), the resultant mixture was stirred at 80° C. for 10 hr. After allowing to cool, it was concentrated under reduced pressure followed by the addition of a saturated aqueous solution of sodium bicarbonate. Then the resultant mixture was extracted with ethyl acetate and the organic layer was washed with water, dried over magnesium sulfate and concentrated under reduced pressure to give the title compound (525 mg) as a colorless oil (yield: 71%).

¹H-NMR (400 MHz, CDCl₃):

δ(ppm) 3.30(1H, br-s), 3.90(2H, t, J=5 Hz), 4.15(2H, t, J=5 Hz ), 7.40(1H, s), 7.45(1H, s).

(38-2) 1-(2-Bromoethyl)-4-bromopyrazole

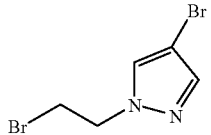

1-(2-Hydroxyethyl)-4-bromopyrazole (525 mg) was treated as in the above Production Example 1 to give the title compound (200 mg) as a colorless oil (yield: 30%).

¹H-NMR (400 MHz, CDCl₃):

δ(ppm) 3.61(2H, t, J=6.2 Hz), 4.62(2H, t, J=6.2 Hz), 7.50(1H, s), 7.51(1H, s).

Production Example 39 Synthesis of 1-(2-benzyloxyethyl)-4-bromopyrazole

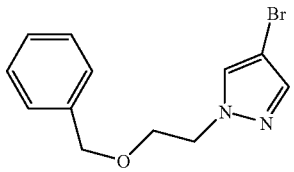

4-Bromopyrazole (2.205 g) was dissolved in tetrahydrofuran (20 ml). Under ice cooling, 60% sodium hydride (625 mg) was added thereto followed by stirring. After 30 min, benzyl 2-bromoethyl ether (3.872 g) obtained from 2-benzyloxyethanol in the same manner as the one of Production Example 1 was added thereto and the resultant mixture was stirred at room temperature overnight. Then the reaction solution was partitioned between ethyl acetate and water and the organic layer was washed with water, dried over magnesium sulfate and concentrated under reduced pressure to give the title compound (2.287 g) as a colorless oil (yield: 53%).

$^1$H-NMR (400 MHz, CDCl$_3$):

δ(ppm) 3. 79 (2H, t, J=5.4 Hz), 4.29 (2H, t, J=5.4 Hz), 4.48 (2H, s), 7.22–7.48(5H, m), 7.46(1H, s), 7.52(1H, s).

Production Example 40 Synthesis of 1-[2-(4-fluorophenyl)-ethyl]-3-methyl-4-piperidone (40-1) Bis(methylpropionyl)-4-fluorophenethylamine

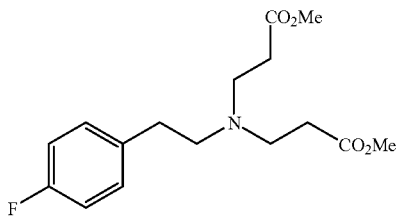

4-Fluorophenethylamine (236.87 g) was dissolved in methanol (360 ml) and ice cooled. Then methyl acrylate (360 ml) was added dropwise thereinto over 30 min followed by heating under reflux for 10 hr. After concentrating under reduced pressure, the title compound (527.04 g) was obtained as a colorless oil (yield: 99.5%).

$^1$H-NMR (400 MHz, CDCl$_3$):

δ(ppm) 2.43(4H, t, J=7.6 Hz), 2.62–2.83(4H, m), 2.83 (4H, t, J=7.6 Hz), 3.66(6H, s), 6.95(2H, t, J=8.8 Hz), 7.12(2H, dd, J=4.8, 8.8 Hz).

(40-2) 1-Fluorophenethyl-3-methoxycarbonyl-4-piperidone (sodium salt)

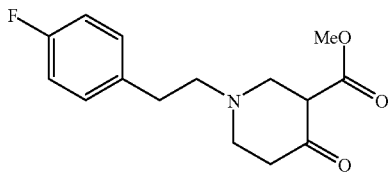

Under ice cooling, 60% sodium hydride (75 g) was suspended in toluene (1400 ml) and heated to a reaction temperature of 110° C. Then a portion (30 ml) of a solution of bis-(methylpropionyl)-4-fluorophenethylamine (263.52 g) in toluene (100 ml) was added dropwise thereinto. Subsequently, methanol (3.2 ml) was added dropwise into the resultant mixture to cause a little evolution of gas and then the mixture was stirred at room temperature until the evolution was ceased. The reaction solution was heated again and a portion (5 ml) of the above solution of bis (methylpropionyl)-4-fluorophenethyl-amine (263.52 g) in toluene (100 ml) was added dropwised thereinto. After the completion of the addition, the resultant mixture was stirred for 30 min and then ice cooled. After adding water (800 ml), the precipitate was collected by filtration, washed with water (700 ml), toluene (500 ml) and hexane (500 ml) and dried to give the title compound (255.0 g) as pale yellow crystals (yield: quantitative).

$^1$H-NMR (400 MHz, DMSO-d$_6$):

δ(ppm) 1.96(2H, t, J=6.0 Hz), 2.51(2H, m), 2.72(2H, t, J=7.6 Hz), 3.15(2H, s), 3.39(3H, s), 7.08(2H, t, J=8.8 Hz), 7.26(2H, dd, J=6.0, 8.8 Hz).

(40-3) 1-Fluorophenethyl-4-piperdone

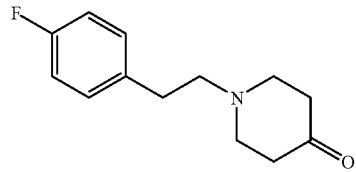

Hydrochloric acid (500 ml) and toluene (500 ml) were added to 1-fluorophenethyl-3-methoxycarbonyl-4-piperidone (sodium salt) and the resultant mixture was heated under reflux at 130° C. for 15.5 hr. Then the reaction solution was ice cooled and basified by adding sodium hydroxide. Next, it was extracted with ethyl acetate, washed with brine, dried over anhydrous magnesium sulfate and filtered through silica gel. After concentrating the filtrate under reduced pressure, the residue was diluted with hexane (500 ml) and isopropyl ether (500 ml) and stirred under ice cooling for 1 hr. The resulting crystalline precipitates were collected by filtration, washed with cold hexane and then dried to give the title compound (133.67 g) as pale yellow crystals (yield: 71.4%).

$^1$H-NMR (400 MHz, CDCl$_3$):

δ(ppm) 2.48(4H, t, J=6.2 Hz), 2.70(2H, m), 2.80(2H, m), 2.82(4H, t, J=6.2 Hz), 6.98(2H, t, J=8.8 Hz), 7.17(2H, dd, J=5.2, 8.8 Hz).

(40-4) Methyl 1-[2-(4-fluorophenyl)ethyl]-3-methyl-4-oxo-3-piperidinecarboxylate

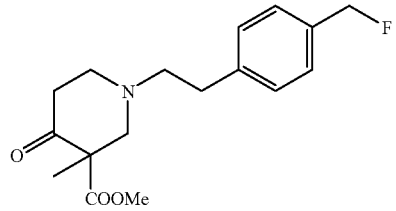

Sodium salt (15.1 g) of methyl 1-[2-(4-fluorophenyl)-ethyl]-4-oxo-3-piperidinecarboxylate was dissolved in dimethylformamide (150 ml). Under ice cooling, methyl iodide (3.1 ml) was added thereto and the resultant mixture was stirred at room temperature overnight. Then ice water (500 ml) was added and the resultant mixture was extracted with ether (200 ml) twice. The organic layer was washed with water (100 ml) and brine (100 ml), dried and concentrated under reduced pressure. The residue was purified by silica gel column chromatography (Fuji Silysia NH-DM2035, hexane/ethyl acetate system) to give the title compound (3.4 g) as a pale yellow liquid (yield: 23%).

$^1$H-NMR (400 MHz, CDCl$_3$):

δ(ppm) 1.26(3H, s), 2.16(1H, d, J=11.5 Hz), 2.45(2H, m), 2.66(2H, m), 2.78(2H, m), 2.87(1H, m), 3.09(1H, m), 3.57 (1H, dd, J=3.0 Hz, 11.5 Hz), 3.70(3H, s), 6.97(2H, br-t), 7.17(2H, br-d).

(40-5) 1-[2-(4-Fluorophenyl)ethyl]-3-methyl-4-piperidone

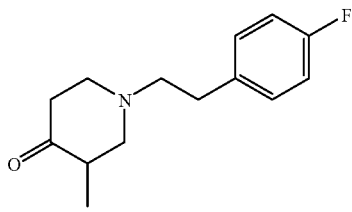

Conc. hydrochloric acid (12 ml) was added to a solution (12 ml) of methyl 1-[2-(4-fluorophenyl)ethyl]-3-methyl-4-oxo-3-piperidinecarboxylate (3.4 g) in toluene followed by heating under reflux for 2.5 hr. The reaction mixture was cooled and added under ice cooling to a 1.5 N aqueous solution (100 ml) of sodium hydroxide. Further, the pH value of the mixture was regulated to 9 with a 5 N aqueous solution of sodium hydroxide. After extracting with ethyl acetate (100 ml) twice, the organic layer was washed with water (100 ml) and brine (100 ml), dried and concentrated under reduced pressure to give the title compound (2.87 g) as a pale yellow liquid (yield: 100%).

$^1$H-NMR (400 MHz, CDCl$_3$):

δ(ppm) 1.02(3H, d, J=7 Hz), 2.16(1H, t, J=10 Hz), 2.37 (2H, m), 2.45(1H, m), 2.58(1H, m), 2.65(2H, m), 2.81(2H, t, J=7 Hz), 3.17(2H, m), 6.97(2H, br-t), 7.16(2H, br-d).

Production Example 41 Synthesis of 1-fluorophenethyl-4-formylpiperidine (41-1) 1-Fluorophenethyl-4-methoxylidenepiperidine

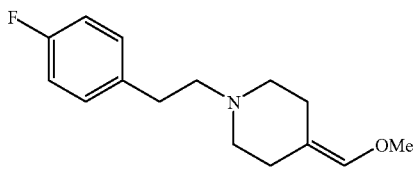

Methoxymethyltriphenylphosphonium chloride (36.3 g) was suspended in tetrahydrofuran (105 ml) and ice cooled. To the resultant suspension were successively added potassium t-butoxide (11.9 g) and 1-fluorophenethyl-4-piperidone (7.8 g) dissolved in tetrahydrofuran (105 ml) and the resultant mixture was stirred at room temperature. After adding water and ethyl acetate to the reaction solution, the layers were separated and the organic layer was washed with brine, dried over anhydrous magnesium sulfate and concentrated under reduced pressure. The residue was purified by silica gel column chromatography (hexane/ethyl acetate system) to give the title compound (7.41 g) as a yellow oil (yield: 84.2%).

$^1$H-NMR (400 MHz, CDCl$_3$):

δ(ppm) 2.12(2H, t, J=5.6 Hz), 2.36(2H, t, J=5.6 Hz), 2.49(4H, m), 2.57(4H, m), 2.79(4H, m), 3.55(3H, m), 5.81 (1H, d, J=1.2 Hz), 6.96(2H, t, J=8.8 Hz), 7.15(2H, dd, J=5.6, 8.8 Hz).

(41-2) 1-Fluorophenethyl-4-formylpiperidine

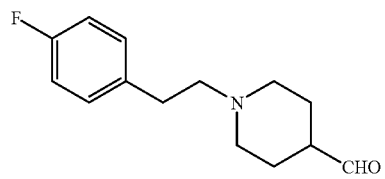

1-Fluorophenethyl-4-methylidenepiperidine (1.0 g) was dissolved in 1 N hydrochloric acid followed by stirring at 70° C. for 4 hr. After allowing to cool, the solution was neutralized with a 5 N aqueous solution of sodium hydroxide, extracted with ethyl acetate, washed with brine, dried over anhydrous magnesium sulfate and concentrated under reduced pressure to give the title compound (0.240 g) as a pale yellow oil (yield: 25.4%).

$^1$H-NMR (400 MHz, CDCl$_3$):

δ(ppm) 0.72–1.82(2H, m), 1.95–2.01(2H, m), 2.23–2.34 (3H, m), 2.59–2.63(2H, m), 2.90–2.95(2H, m), 6.96(2H, t, J=8.4 Hz), 7.15(2H, dd, J=5.6, 8.4 Hz).

Production Example 42 Synthesis of 1-(4-fluorophenethyyl)-4-piperidineethanol

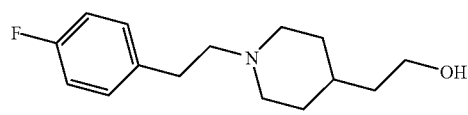

4-Piperidineethanol (3.2 g) and 4-fluorophenethyl bromide (5.0 g) were treated as in Example 2 to give the title compound (4.1 g) as a colorless oil (yield: 65%).

$^1$H-NMR (400 MHz, CDCl$_3$):

δ(ppm) 1.22–1.38(2H, m), 1.40–1.60(3H, m), 1.70–1.79 (2H, m), 1.91–2.02(3H, m), 2.50–2.59(2H, m), 2.78–2.81 (2H, m), 2.95–3.01(2H, m), 3.69–3.75(2H, m), 6.91–7.00 (2H, m), 7.10–7.20(2H, m).

Production Example 43 Synthesis of 1-(4-fluorophenethyl)-4-piperidinacetaldehyde

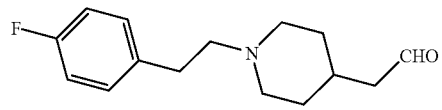

A suspension of 1-(4-fluorophenethyl)-4-piperidineethanol (1.0 g), pyridinium chlorochromate (2.6 g) and molecular sieve (2.0 g) in methylene chloride (60 ml) was stirred at room temperature for 1 hr. Then the reaction mixture was filtered and the filtrate was concentrated under reduced pressure. The obtained residue was purified by silica gel column chromatography (methanol/ethyl acetate system) to give the title compound (360 mg) (yield: 36%).

$^1$H-NMR (400 MHz, CDCl$_3$):

δ(ppm) 1.29–1.43(2H, m), 1.69–1.80(2H, m), 1.81–2.10 (3H, m), 2.33–2.42(2H, m), 2.50–2.60(2H, m), 2.72–2.80 (2H, m), 2.93–3.00(2H, m), 6.93–7.00(2H, m), 7.10–7.20 (2H, m), 9.78–9.80(1H, m).

Production Example 44 Synthesis of 1-(4-fluorophenethyl)-4-aminopiperidine

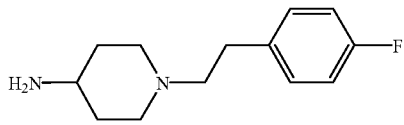

A suspension of 1-(4-fluorophenethyl)-4-piperidone (5.0 g), hydroxylammonium chloride (1.9 g) and anhydrous sodium acetate (4.4 g) in ethanol (50 ml) was heated under reflux for 30 min. The reaction solution was then concentrated under reduced pressure, diluted with a saturated aqueous solution of sodium bicarbonate and ethyl acetate and the layers were separated. The organic layer was washed with brine and dried over magnesium sulfate. After evaporating the solvent, the residue was diluted with tetrahydrofuran (50 ml) and lithium aluminum hydride (1.7 g) was added thereto in portions under ice cooling and stirring followed by heating under reflux for 4 hr. Under cooling with ice water, water (1.7 ml), a 5 N aqueous solution of sodium hydroxide (5.1 ml) and further water (1.7 ml) were carefully added to the reaction solution in this order and the resultant mixture was stirred vigorously. The resulting precipitate was filtered off and the filtrate was concentrated under reduced pressure and purified by NH-silica gel column chromatography (methylene chloride/methanol system) to give the title compound (4.0 g) as a pale yellow oil (yield: 80%).

$^1$H-NMR (400 MHz, CDCl$_3$):

δ(ppm) 1.31–1.60(4H, m), 1.80–1.89(2H, m), 2.01–2.11 (2H, m), 2.50–2.58(2H, m), 2.63–2.81(3H, m), 2.91–3.00 (2H, m), 6.94–7.03(2H, m), 7.14–7.25(2H, m).

Production Example 45 Synthesis of 1-(piperidin-4-yl)-indoline

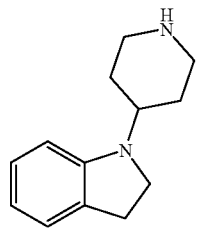

A mixture of indoline (25 g), 1-acetyl-4-piperidone (25 g), platinum oxide (0.5 g), acetic acid (20 ml) and ethanol (200 ml) was catalytically reduced at ordinary temperature under atmospheric pressure overnight. After filtering off the catalyst, the filtrate was concentrated under reduced pressure and diluted with a 2 N aqueous solution of sodium hydroxide and ethyl acetate. The organic layer was washed with brine, dried over anhydrous magnesium sulfate and purified by silica gel column chromatography (methylene chloride/ethanol system). To the obtained residue was added 5 N hydrochloric acid (300 ml) followed by heating the mixture under reflux for 2 hr. Then the reaction solution was basified with a conc. aqueous solution of sodium hydroxide, diluted with ethyl acetate and the layers were separated. The organic layer was washed with a saturated aqueous solution of sodium chloride, dried over anhydrous magnesium sulfate and concentrated under reduced pressure to give the title compound (26 g) as brown crystals (yield: 61%).

$^1$H-NMR (400 MHz, CDCl$_3$):

δ(ppm) 1.51–1.69(3H, m), 1.80–1.85(2H, m), 2.66–2.72 (2H, m), 2.91(2H, t, J=8 Hz), 3.11–3.22(2H, m), 3.39(2H, t, J=8 Hz), 3.40–3.52(1H, m), 6.41(1H, d, J=8 Hz), 6.60(1H, d, J=8 Hz), 7.01–7.10(2H, m).

Production Example 46 Synthesis of 1-(piperidin-4-yl)-6-fluoroindoline

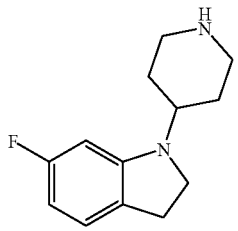

1-Chloroethyl chloroformate (2.8 g) was added dropwise into a solution of 1-(1-benzylpiperidin-4-yl)-6-fluoroindoline (2.0 g) in toluene (50 ml) followed by heating the mixture under reflux for 2 hr. Then the reaction solution was concentrated under reduced pressure and methanol was added thereto followed by heating under reflux again for 2 hr. After concentrating under reduced pressure, a 5 N aqueous solution of sodium hydroxide and chloroform were added thereto, the layers were separated. The organic layer was then washed with brine and dried over anhydrous magnesium sulfate to give the title compound (1.0 g) as a brown oil (yield: 70%).

$^1$H-NMR (400 MHz, CDCl$_3$):

δ(ppm) 1.59–1.71(2H, m), 1.80–1.87(2H, m), 2.06(1H, br-s), 2.68–2.75(2H, m), 2.91(2H, t, J=8 Hz), 3.20–3.29(2H, m), 3.34–3.48(1H, m), 3.45(2H, t, J=8 Hz), 6.08(1H, d, J=8 Hz), 6.23(1H, t, J=8 Hz), 6.91(1H, t, J=8 Hz).

Production Example 47 Synthesis of 6-bromoindoline (47-1) 6-Bromo-2-oxyindole

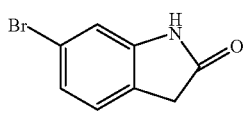

Under ice cooling, diethyl malonate (500 g) was added dropwise into a suspension of sodium hydride (125 g) in dimethyl sulfoxide (800 ml). After the solution became homogeneous, the resultant mixture was heated to 100° C. and a solution of 2,5-dibromonitrobenzene (500 g) in dimethyl sulfoxide (400 ml) was added dropwise thereinto followed by stirring the resultant mixture at 100° C. for 5 hr. Then the reaction solution was diluted with ice water (2 l), mixed with ethyl acetate (8 l), and the layers were separated. The organic layer was washed successively with water (2 l) four times and brine and dried over anhydrous magnesium sulfate. After evaporating the solvent under reduced pressure, the residue was diluted with ethanol (2.5 l) followed by the addition of tin (380 g). Under ice cooling, conc. hydrochloric acid (1.5 l) was added dropwise into the reaction mixture. After the completion of the addition, the resultant mixture was heated under reflux for 3 hr and diluted with ice water (8 l). The resulting crystalline precipitates were collected by filtration, washed with water and hexane, and air dried at 50° C. for 24 hr to give the title compound (321 g) (yield: 84%).

$^1$H-NMR (400 MHz, CDCl$_3$):

δ(ppm) 3.51(2H, s), 7.06(1H, s), 7.10(1H, d, J=8 Hz), 7.17(1H, d, J=8 Hz), 8.27(1H, br-s).

(47-2) 6-Bromoindoline

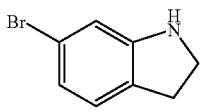

Under ice cooling, a borane/methyl sulfide complex (300 ml) was added dropwise into a suspension of 6-bromo-2-oxyindole (311 g) in toluene (1 l). Then the resultant mixture was slowly heated under reflux. After 2 hr, it was ice cooled followed by the addition thereto of a 5 N aqueous solution of sodium hydroxide (500 ml), an 8 N aqueous solution of sodium hydroxide (500 ml) and ethyl acetate (400 ml). After vigorously stirring for 1 hr, it was diluted with ethyl acetate (1.6 l) and water (1 l) and the layers were separated. The organic layer was washed successively with water (1 l) twice and brine (0.5 l) and dried over anhydrous magnesium sulfate. The residue was purified by NH-silica gel column chromatography (hexane/ethyl acetate system) to give the title compound (169 g) (yield: 58%).

$^1$H-NMR (400 MHz, CDCl$_3$):

δ(ppm) 2.96(2H, t, J=8 Hz), 3.58(2H, t, J=8 Hz), 6.76(1H, s), 6.80(1H, d, J=8 Hz), 6.95(1H, d, J=8 Hz).

Production Example 48 Synthesis of 1-(piperidin-4-yl)-6-bromoindoline

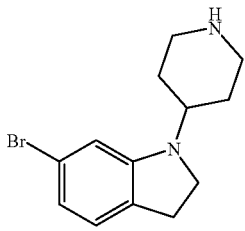

1-Chloroethyl chloroformate (13.7 g) was added dropwise into a solution of 1-(1-benzylpiperidin-4-yl)-bromoindoline (14.3 g) in toluene (250 ml) and the resultant mixture was heated under reflux for 2 hr. Then it was concentrated under reduced pressure and methanol was added thereto followed by heating under reflux for 2 hr. After concentrating under reduced pressure, a 5 N aqueous solution of sodium hydroxide and ethyl acetate were added thereto and the layers were separated. The organic layer was washed with brine and dried over anhydrous magnesium sulfate to give the title compound (8.4 g) as a brown oil (yield: 78%).

$^1$H-NMR (400 MHz, CDCl$_3$):

δ(ppm) 1.51–1.69(2H,m), 1.78–1.83(2H,m), 2.06(1H, br-s), 2.67–2.73(2H, m), 2.90(2H, t, J=8 Hz), 3.19–3.23(2H, m), 3.31–3.43(1H, m), 3.41(2H, t, J=8 Hz), 6.49(1H, s), 6.68(1H, t, J=8 Hz), 6.85(1H, t, J=8 Hz).

Production Example 49 Synthesis of 1-(piperidin-4-yl)-6-nitroindoline

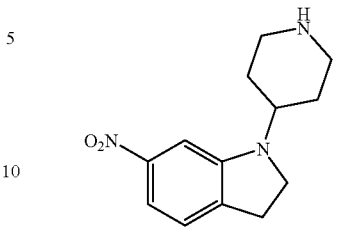

70% nitric acid (2.6 ml) was added dropwise at −15° C. into a solution of 1-(piperidin-4-yl)indoline (6.9 g) in conc. sulfuric acid (50 ml). After 20 min, the reaction mixture was diluted with ice water and basified with a conc. aqueous solution of sodium hydroxide, the reaction solution was mixed with ethyl acetate, and the layers were separated. The organic layer was washed with brine, dried over anhydrous magnesium sulfate and concentrated under reduced pressure to give the title compound (7 g) as a brown oil (yield: 83%).

$^1$H-NMR (400 MHz, CDCl$_3$):

δ(ppm) 1.53–1.69(3H, m), 1.75–1.83(2H, m), 2.69–2.78 (2H, m), 3.03(2H, t, J=8 Hz), 3.16–3.23(2H, m), 3.44–3.51 (1H, m), 3.52(2H, t, J=8 Hz), 7.08(1H, d, J=8 Hz), 7.10(1H, s), 7.48(1H, d, J=8 Hz).

Production Example 50 Synthesis of 6-dimethylaminoindoline (50-1) 1-Acetyl-6-aminoindoline

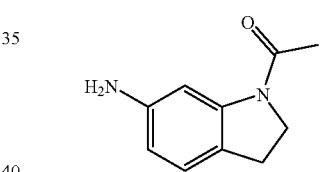

Fuming nitric acid (11 ml) was added dropwise at −15° C. into a solution of indoline (26.5 g) in con. sulfuric acid (250 ml). After 20 min, the resultant mixture was diluted with ice water and washed with ethyl acetate. The aqueous phase was basified with a conc. aqueous solution of sodium hydroxide, extracted with ethyl acetate, washed with brine, dried over anhydrous magnesium sulfate and concentrated under reduced pressure. To the residue were added acetic anhydride (100 ml) and pyridine (100 ml) and the reaction mixture was stirred at room temperature for 4 hr. After adding ice water to the reaction solution, the resulting crystalline precipitates were collected by filtration and mixed with an iron powder (40 g), ammonium chloride (60 g), water (70 ml) and ethanol (300 ml). The resultant mixture was stirred at 60° C. overnight followed by filtration and concentration under reduced pressure. After adding water, the resultant mixture was stirred vigorously. The resulting crystalline precipitates were collected by filtration and air dried at 70° C. overnight to give the title compound (19 g) as a brown powder (yield: 57%).

$^1$H-NMR (400 MHz, CDCl$_3$):

δ(ppm) 2.20(3H, s), 3.08(2H, t, J=8 Hz), 3.63(2H, br-s), 4.01(2H, t, J=8 Hz), 6.33(1H, d, J=8 Hz), 6.91(1H, d, J=8 Hz), 7.67(1H, s).

(50-2) 6-Dimethylaminoindoline

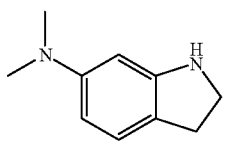

A mixture of 1-acetyl-6-aminoindoline (1.0 g), 37% formaldehyde (5.2 g), acetic acid (1.0 ml), platinum oxide (0.1 g) and methanol (20 ml) was catalytically reduced at ordinary temperature under atmospheric pressure. After a day, the catalyst was filtered off and the filtrate was concentrated under reduced pressure. The residue was diluted with a saturated aqueous solution of sodium bicarbonate and ethyl acetate. The organic layer was washed with brine, dried over anhydrous magnesium sulfate, concentrated under reduced pressure and purified by silica gel column chromatography (methylene chloride/ethanol system). To the obtained residue was added 5 N hydrochloric acid (30 ml) followed by heating the resultant mixture under reflux for 1 hr. Then the reaction solution was basified with a conc. aqueous solution of sodium hydroxide and extracted with chloroform. After purifying by silica gel column chromatography (hexane/ethyl acetate system), the title compound (0.6 g) was obtained as a brown powder (yield: 65%).

$^1$H-NMR (400 MHz, CDCl$_3$):

δ(ppm) 2.89(6H, s), 2.91(2H, t, J=8 Hz), 3.52(2H, t, J=8 Hz), 3.70(1H, br-s), 6.11(1H, d, J=8 Hz), 6.12(1H, s), 6.95(1H, d, J=8 Hz).

Production Example 51 Synthesis of 1-(piperidin-4-yl)-6-methoxyindoline

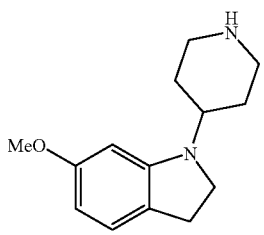

1-Chloroethyl chloroformate (10.5 g) was added dropwise into a solution of 1-(1-benzylpiperidin-4-yl)-6-methoxyindoline (7.9 g) in toluene (200 ml) and the resultant mixture was heated under reflux for 3 hr. Then it was concentrated under reduced pressure and methanol was added thereto followed by heating the resultant mixture under reflux for 2 hr. After concentrating under reduced pressure, a 5 N aqueous solution of sodium hydroxide and chloroform were added thereto, and the layers were separated. The organic layer was washed with brine and dried over anhydrous magnesium sulfate to give the title compound (4.1 g) as a brown oil (yield: 72%).

$^1$H-NMR (400 MHz, CDCl$_3$):

δ(ppm) 1.51–1.62(2H, m), 1.78–1.85(2H,m), 1.92(1H, br-s), 2.62–2.74(2H, m), 2.89(2H, t, J=8 Hz), 3.13–3.22(2H, m), 3.34–3.46(1H, m), 3.40(2H, t, J=8 Hz), 3.76(3H, s), 6.00(1H, s), 6.11(1H, d, J=8 Hz), 6.93(1H, d, J=8 Hz).

Production Example 52 Synthesis of 1-(piperidin-4-yl)-6-acetamidomethylindoline

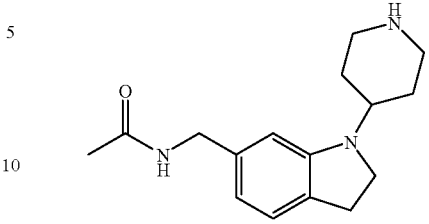

Under ice cooling, acetyl chloride (1.7 ml) was added dropwise into a solution of 1-[1-(4-t-butoxycarbonyl)piperidin-4-yl]-6-aminomethylindoline (8.3 g) and triethylamine (2.4 g) in acetonitrile (150 ml) followed by stirring the resultant mixture at room temperature for 1 hr. To the liquid reaction mixture were added a saturated aqueous solution of sodium bicarbonate and ethyl acetate and the layers were separated. The organic layer was then washed with brine, dried over anhydrous magnesium sulfate and concentrated under reduced pressure. After adding chloroform (100 ml) and trifluoroacetic acid (50 ml), the resultant mixture was stirred at room temperature for 2 hr. After concentrating under reduced pressure, a 2 N aqueous solution of sodium hydroxide (100 ml) and toluene (50 ml) were added thereto followed by vigorous stirring. Then the resultant mixture was purified by NH-silica gel column chromatography (methanol/ethyl acetate system) to give the title compound (3.78 g) as white needles (yield: 58%).

m.p.: 165–167° C.

$^1$H-NMR (400 MHz, CDCl$_3$):

δ(ppm) 1.64–1.86(4H, m), 2.52–2.82(2H, m), 2.93(2H, t, J=8 Hz), 3.24–3.32(2H,m), 3.42(2H, t, J=8 Hz), 3.44–3.52(1H, m), 4.33(2H, d, J=5 Hz), 5.67(1H, br-s), 6.34(1H, s), 6.51(1H, d, J=8 Hz), 7.00(1H, d, J=8 Hz).

FAB-Mass: 274(MH$^+$)

Production Example 53 Synthesis of 6-(N-methylsulfamoylmethyl)indoline (53-1) 1-t-butoxycarbonyl-6-bromoindoline

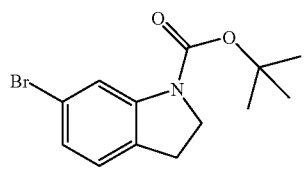

Di-t-butyl carbonate (6.7 g) was added to a solution of 6-bromoindoline (5.1 g) and triethylamine (3.1 g) in tetrahydrofuran (50 ml) followed by stirring the resultant mixture at room temperature overnight. After adding water and ethyl acetate thereto, the layers were separated and the organic layer was washed with brine and dried over anhydrous magnesium sulfate. The residue was then purified by silica gel column chromatography (hexane/ethyl acetate system) to give the title compound (5.5 g) as a colorless oil (yield: 71%).

$^1$H-NMR (400 MHz, CDCl$_3$):

δ(ppm) 1.56(9H, s), 3.04(2H, t, J=8 Hz), 3.99(2H, t, J=8 Hz), 6.98(1H, d, J=8 Hz), 7.03(1H, d, J=8 Hz), 8.04(1H, s).

(53-2) 1-t-Butoxycarbonyl-6-hydroxymethylindoline

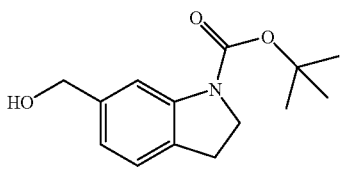

A 2.5 M solution (7 ml) of n-butyllithium in hexane was added dropwise at −78° C. into a solution of 1-t-butoxycarbonyl-6-bromoindoline (3.5 g) in tetrahydrofuran (100 ml) over 5 min. After 10 min, dimethylformamide (1.4 ml) was added thereto and the resultant mixture was heated to room temperature. After adding a saturated aqueous solution of ammonium chloride and ethyl acetate thereto, the layers were separated and the organic layer was washed with brine, dried over anhydrous magnesium sulfate and concentrated under reduced pressure. Then ethanol (20 ml) and sodium borohydride (0.4 g) were added to the residue followed by stirring the resultant mixture at room temperature for 1 hr. After adding ice water and ethyl acetate to the reaction solution, the organic layer was separated, washed with brine, dried over anhydrous magnesium sulfate and concentrated under reduced pressure. The residue was purified by silica gel column chromatography (hexane/ethyl acetate system) to give the title compound (1.9 g) as a colorless oil (yield: 66%).
$^1$H-NMR (400 MHz, CDCl$_3$):
δ(ppm) 1.60(9H, s), 3.08(2H, t, J=8 Hz), 3.99(2H, t, J=8 Hz), 4.68(2H, s), 6.95(1H, d, J=8 Hz), 7.12(1H, d, J=8 Hz), 7.87(1H, s).

(53-3) 1-Acetyl-6-chloromethylindoline

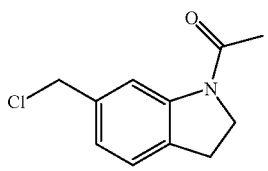

A solution of 1-t-butoxycarbonyl-6-hydroxymethylindoline (1.9 g) in con. hydrochloric acid (20 ml) was stirred at 50° C. overnight. Then it was basified by adding a con. aqueous solution of sodium hydroxide. After adding ethyl acetate (40 ml) and acetyl chloride (0.5 ml), the resultant mixture was stirred at room temperature for 1 hr. The organic layer was separated, washed with brine and dried over anhydrous magnesium sulfate. The residue was purified by silica gel column chromatography (hexane/ethyl acetate system) to give the title compound (0.87 g) as a colorless oil (yield: 54%).
$^1$H-NMR (400 MHz, CDCl$_3$):
δ(ppm) 2.23(3H, s), 3.20(2H, t, J=8 Hz), 4.09(2H, t, J=8 Hz), 4.59(2H, s), 7.06(1H, d, J=8 Hz), 7.16(1H, d, J=8 Hz), 8.25(1H, s).

(53-4) 6-(N-Methylsulfamoylmethyl)indoline

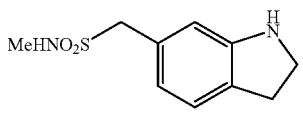

A solution of 1-acetyl-6-chloromethylindoline (470 mg), sodium sulfite (330 mg) and tricaprylylmethylammonium chloride (50 mg) in water (30 ml) was heated under reflux for 1 hr and then concentrated under reduced pressure. To the residue were added phosphorus pentaoxide (500 mg) and phosphorus oxychloride (5 ml) followed by stirring the resultant mixture at room temperature for 3 hr. Next, ice water and ethyl acetate were added to the reaction solution, the layers were separated. The organic layer was washed with brine and dried over anhydrous magnesium sulfate. After concentrating under reduced pressure, a 2 M solution of methylamine in tetrahydrofuran (20 ml) was added to the residue followed by stirring the mixture at room temperature overnight. After adding a saturated aqueous solution of sodium bicarbonate and ethyl acetate to the reaction solution, the layers were separated and the organic layer was washed with brine and dried over anhydrous magnesium sulfate. After concentrating under reduced pressure, the crystalline precipitates were collected, washed with ethanol and dissolved in 5 N hydrochloric acid (5 ml) followed by heating under reflux for 1 hr. Under ice cooling, the pH value of the reaction solution was adjusted to pH 8 with a conc. aqueous solution of sodium hydroxide, chloroform was added and the layers were separated. Then the organic layer was washed with brine, dried over anhydrous magnesium sulfate and concentrated under reduced pressure to give the title compound (100 mg) as white crystals (yield: 20%).
$^1$H-NMR (400 MHz, CDCl$_3$):
δ(ppm) 2.71(3H, s), 3.01(2H, t, J=8 Hz), 3.20(1H, br-s), 3.58(2H, t, J=8 Hz), 4.15(2H, s), 4.25(1H, br-s), 6.65–6.69 (2H, m), 7.08(1H, d, J=8 Hz).

Production Example 54 Synthesis of 3-methylindoline

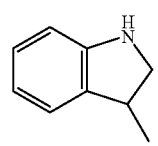

3-Methylindole (1.0 g) was dissolved in trifluoroacetic acid (30 ml). Under ice cooling, triethylsilane (2.4 ml) was added dropwise thereinto followed by stirring for 1 hr. After concentrating under reduced pressure, a saturated aqueous solution of sodium bicarbonate and ethyl acetate were added thereto, the layers were separated. Next, the organic layer was washed with brine, dried over anhydrous magnesium sulfate and concentrated under reduced pressure. The residue was purified by silica gel column chromatography (hexane/ethyl acetate system) to give the title compound (0.673 g) as a pale yellow oil (yield: 66.3%).
$^1$H-NMR (400 MHz, CDCl$_3$):
δ(ppm) 1.32(3H, d, J=6.8 Hz), 3.11(1H, t, J=8.6 Hz), 3.36(1H, m), 3.70(1H, t, J=8.6 Hz), 6.65(1H, d, J=8.0 Hz), 6.73(1H, t, J=8.0 Hz), 7.03(1H, t, J=8.0 Hz), 7.09(1H, d, J=8.0 Hz).

Production Example 55 Synthesis of 3-(4-fluorophenyl)-indoline (55-1) 2-(t-Butoxy)carbonylaminobenzyl alcohol

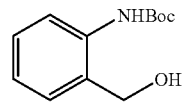

2-Aminobenzyl alcohol (5 g) was treated as reported in Synthesis, 871 (1991). to give the title compound (5.776 g) as a pale yellow oil (yield: 60.4%).

¹H-NMR (400 MHz, DMSO-d₆):

δ(ppm) 1.52(9H, s), 4.69(2H, s), 7.02(1H, t, J=8.0 Hz), 7.17(1H, d, J=8.0 Hz), 7.31(1H, t, J=8.0 Hz), 7.63(1H, m), 7.91(1H, d, J=8.0 Hz).

(55-2) 2-(t-Butoxy)carbonylaminobenzyl bromide

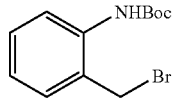

To 2-(t-butoxy)carbonylaminobenzyl alcohol (4.93 g) was added triethylamine (0.58 ml) followed by the same reaction as the one described in the above Production Example 1. Then the reaction solution was concentrated under reduced pressure and purified by silica gel column chromatography (hexane/ethyl acetate system) to give the title compound (5.380 g) as pale yellow crystals (yield: 86.1%).

¹H-NMR (400 MHz, CDCl₃):

δ(ppm) 1.58(9H, s), 4.51(2H, s), 6.68(1H, m), 7.06(1H, t, J=8.0 Hz), 7.28(1H, d, J=8.0 Hz), 7.34(1H, t, J=8.0 Hz), 7.84(1H, d, J=8.0 Hz).

(55-3) 2-(4-Fluorobenzyl)-N-(t-butoxy)carbonylaniline

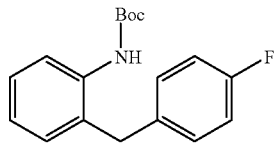

2-(t-Butoxy)carbonylaminobenzyl bromide (2.98 g) and 4-phenylmagnesium bromide were treated as reported in J. Organomet. C. 329, 133–138 (1987). to give the title compound (1.187 g) as pale yellow crystals (yield: 39.4%).

¹H-NMR (400 MHz, CDCl₃):

δ(ppm) 1.46(9H, s), 3.93(2H,s), 6.12(1H,m), 6.91–7.12 (7H, m), 7.82(1H, br-d).

(55-4) 1-(t-Butoxy)carbonyl-3-(4-fluorophenyl)indole

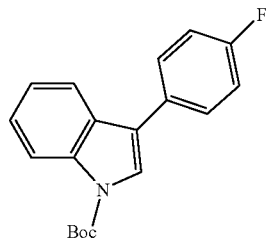

2-(4-Fluorobenzyl)-N-(t-butoxy)carbonylaniline (0.5 g) was treated as reported in Synthesis, 871 (1991). to give the title compound (0.340 g) as a pale yellow oil (yield: 68.2%).

¹H-NMR (400 MHz, CDCl₃):

δ(ppm) 1.69(9H, s), 7.15(2H, t, J=8.8 Hz), 7.29(1H, t, J=8.0 Hz), 7.37(1H, t, J=8.0 Hz), 7.59(2H, dd, J=6.0, 8.8 Hz), 7.67(1H, s), 7.75(1H, d, J=8.0 Hz), 8.22(1H, d, J=8.0 Hz).

(55-5) 3-(4-Fluorophenyl)indoline

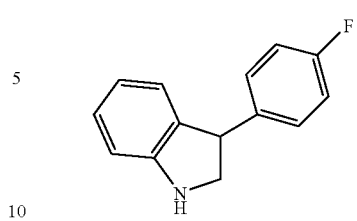

1-(t-Butoxy)carbonyl-3-(4-fluorophenyl)indole (0.340 g) was freed from the protecting group with the use of trifluoroacetic acid and then treated as in the above Production Example 54 to give the title compound (0.184 g) as a pale yellow oil (yield: 79.0%).

¹H-NMR (400 MHz, CDCl₃):

δ(ppm) 3.45(1H, t, J=8.8 Hz), 3.92(1H,t, J=8.8 Hz), 4.48(1H, t, J=8.8 Hz), 6.72(2H, m), 6.89(1H, d, J=8.4 Hz), 6.99(2H, t, J=8.4 Hz), 7.08(1H, t, J=8.4 Hz), 7.23(2H, m).

Production Example 56 Synthesis of 3-(4-fluorobenzyl)indoline (56-1) 3-(4-Fluorobenzyl)indole

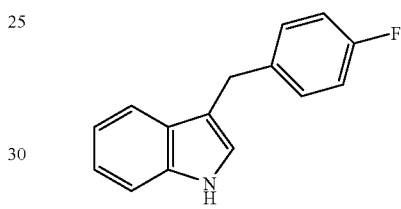

3-Formylindole was treated as reported in Tetrahedron Lett., 1869 (1986). to give the title compound as a yellow oil.

¹H-NMR (400 MHz, CDCl₃):

δ(ppm) 4.05(2H, s), 6.84(1H, s), 6.93(2H, t, J=8.4 Hz), 7.06(1H, t, J=8.0 Hz), 7.15–7.19(3H, m), 7.46(1H, d, J=8.0 Hz), 7.97(1H, m).

(56-2) 3-(4-Fluorobenzyl)indoline

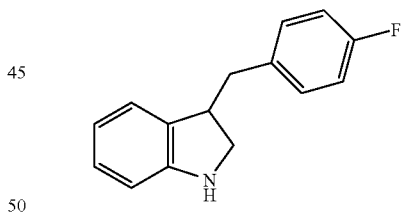

3-(4-Fluorobenzyl)indole (2.119 g) was dissolved in trifluoroacetic acid (3.9 ml). Under ice cooling, a 1.0 M solution (18.7 ml) of a borane/tetrahydrofuran complex in tetrahydrofuran was dropped into the above solution followed by stirring the resultant mixture at room temperature for 1 hr. After adding water, the reaction solution was concentrated under reduced pressure. Then ethanol (20 ml) and a 5 N aqueous solution (46 ml) of sodium hydroxide were added and the resultant mixture was stirred at room temperature for 1 hr. After adding ethyl acetate (200 ml) thereto, the layers were separated and the organic layer was washed with brine, dried over anhydrous magnesium sulfate and concentrated under reduced pressure. The residue was purified by silica gel column chromatography (hexane/ethyl acetate system) to give the title compound (1.163 g) as a yellow oil (yield: 54.4%).

¹H-NMR (400 MHz, CDCl₃):

δ(ppm) 2.80(1H, dd, J=8.0, 13.6 Hz), 3.06(1H, dd, J=4.6, 13.6 Hz), 3.26(1H, m), 3.55(2H, m), 6.48–6.71(2H, m), 6.92(1H, t, J=7.6 Hz), 6.99(2H, t, J=8.8 Hz), 7.05(1H, t, J=7.6 Hz), 7.15(1H, dd, J=5.6, 8.8 Hz).

Production Example 57 Synthesis of 3-(3-pyridylmethyl)-indoline (57-1) 3-(3-Pyridylmethyl)indole

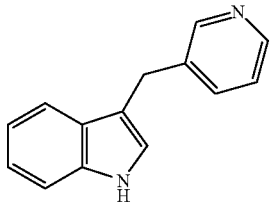

3-Bromopyridine was treated as reported in Tetrahedron Lett., 1869 (1986). to give the title compound as a yellow oil.

¹H-NMR (400 MHz, CDCl₃):

δ(ppm) 4.11(2H, s), 6.92(1H, s), 7.09(1H, t, J=8.0 Hz), 7.18(2H, m), 7.46(1H, d, J=8.0 Hz), 7.48(1H, d, J=8.0 Hz), 7.54(1H, d, J=8.0 Hz), 8.33(1H, m), 8.45(1H, m), 8.60(H, m).

(57-2) 3-(3-Pyridylmethyl)indoline

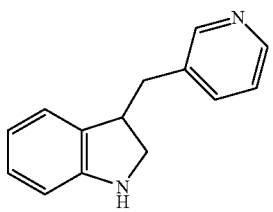

3-(3-Pyridylmethyl)indole (0.212 g) was treated as in the above Production Example 56-2 to give the title compound (0.253 g) as a yellow oil.

¹H-NMR (400 MHz, CDCl₃):

δ(ppm) 2.83(1H, m), 3.06(1H, m), 3.27(1H, d, J=3.2 Hz), 3.56(2H, m), 6.50(1H, d, J=8.0 Hz), 6.69(1H, t, J=8.0 Hz), 6.92(1H, d, J=8.0 Hz), 7.23(1H, m), 7.49(1H, d, J=8.0 Hz), 8.48(1H, m).

Production Example 58 Synthesis of 3-(4-methoxybenzyl)-indoline (58-1) 3-(4-Methoxybenzyl)indole

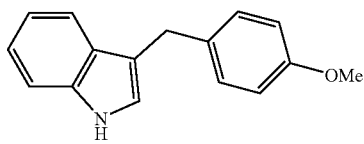

1-Diethylcarbamoyl-3-formylindole (7.33 g), which had been obtained according to the method of Tetrahedron Lett., 1869 (1986)., and 4-methoxyphenylmagnesium bromide were treated as reported in Tetrahedron Lett., 1869 (1986). to give the title compound (5.480 g) as a pale yellow oil (yield: 77.0%).

¹H-NMR (400 MHz, CDCl₃):

δ(ppm) 3.78(3H, s), 4.06(2H, s), 6.82(2H, d, J=6.8 Hz), 6.90(1H, s), 7.07(1H, t, J=8.0 Hz), 7.18(1H, t, J=8.0 Hz), 7.20(2H, d, J=6.8 Hz), 7.36(1H, d, J=8.0 Hz), 7.51(1H, d, J=8.0 Hz), 7.89(1H, m).

(58-2) 3-(4-Methoxybenzyl)indoline

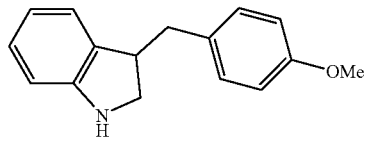

3-(4-Methoxybenzyl)indole (0.5 g) was treated as in Production Example 54 to give the title compound (0.332 g) as a pale yellow oil (yield: 65.7%).

¹H-NMR (400 MHz, CDCl₃):

δ(ppm) 2.76(1H, dd, J=8.4, 14.0 Hz), 3.04(1H, dd, J=5.2, 14.0 Hz), 3.54(2H, m), 3.76(1H, d, J=5.2 Hz), 3.81(3H, s), 6.65(1H, d, J=7.6 Hz), 6.69(1H, t, J=7.6 Hz), 6.85(2H, d, J=8.2 Hz), 6.95(1H, d, J=7.6 Hz), 7.04(1H, t, J=7.6 Hz), 7.12(2H, d, J=8.2 Hz).

Production Example 59 Synthesis of 3-(3-methoxyphenethyl) indoline (59-1) 1-Diethylcarbamoyl-3-[2-(3-methoxyphenyl)vinyl]indole

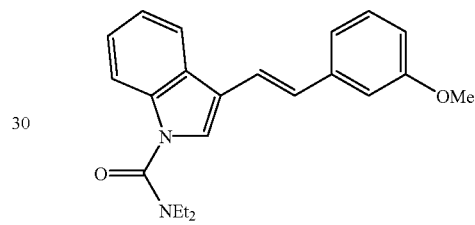

3-Methoxybenzyltriphenylphosphonium chloride (1.71 g) and 1-diethylcarbamoyl-3-formylindole (1.71 g), which had been synthesized according to the method of Tetrahedron Lett., 1869 (1986)., were reacted in tetrahydrofuran (5 ml) as in the above Production Example 41-1 to give the title compound (0.842 g) as a brown oil (yield: 59.1%).

(59-2) 1-Diethylcarbamoyl-3-(3-methoxyphenethyl)indole

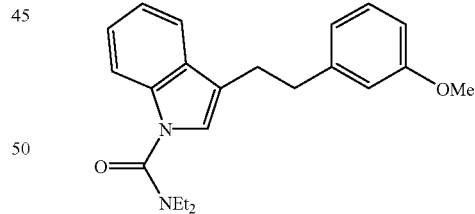

1-Diethylcarbamoyl-3-[2-(3-methoxyphenyl)vinyl]indole (0.842 g) was dissolved in methanol (20 ml) and catalytically reduced with the use of palladium carbon at room temperature under atmospheric pressure for 1 hr. After filtering off the catalyst, the filtrate was concentrated under reduced pressure to give the title compound (0.864 g) as a brown oil (yield: quantitative).

¹H-NMR (400 MHz, CDCl₃):

δ(ppm) 1.19(6H, t, J=7.2 Hz), 3.01(4H, m), 3.42(4H, q, J=7.2 Hz), 3.78(3H, s), 6.72(2H, m), 6.79(1H, d, J=8.4 Hz), 6.95(1H, s), 7.18(2H, t, J=8.4 Hz), 7.27(1H, m), 7.57(1H, d, J=8.4 Hz), 7.63(1H, d, J=8.4 Hz).

(59-3) 3-(3-Methoxyphenethyl)indole

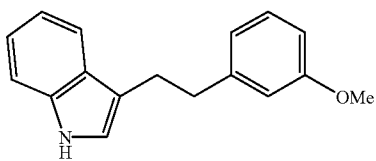

1-Diethylcarbamoyl-3-(3-methoxyphenethyl)indole (0.864 g) was deprotected as reported in Tetrahedron Lett., 7911 (1993). to give the title compound (0.554 g) as a brown oil (yield: 91.1%).
$^1$H-NMR (400 MHz, CDCl$_3$):
δ(ppm) 3.00(2H, m), 3.08(2H, m), 3.78(3H, s), 6.75(2H, m), 6.82(1H, d, J=8.0 Hz), 6.93(1H, s), 7.12(1H, t, J=8.0 Hz), 7.19(2H, q, J=8.0 Hz), 7.36(1H, d, J=8.0 Hz), 7.62(1H, d, J=8.0 Hz), 7.93(1H, m).

(59-4) 3-(3-Methoxyphenethyl)indoline

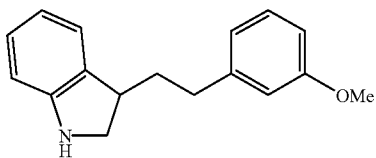

3-(3-Methoxyphenethyl)indole (0.554 g) was treated as in the above Production Example 56-2 to give the title compound (0.133 g) as a pale yellow oil (yield: 23.8%).
$^1$H-NMR (400 MHz, CDCl$_3$):
δ(ppm) 1.83(1H, m), 2.15(1H, m), 2.70(2H, t, J=8.0 Hz), 3.34(1H, m), 3.71(2H, t, J=8.0 Hz), 3.80(3H, s), 6.64(1H, d, J=8.0 Hz), 6.75(3H, m), 6.80(1H, d, J=8.0 Hz), 7.03(1H, t, J=8.0 Hz), 7.10(1H, d, J=8.0 Hz), 7.20(1H, t, J=8.0 Hz).

Production Example 60 Synthesis of 3-(3-fluorophenethyl)-indoline (60-1) 3-[2-(3-Fluorophenyl)vinyl]indole

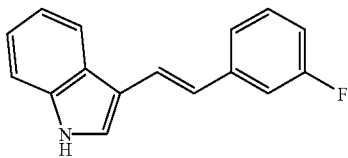

3-Formylindole (1.0 g) and 3-fluorobenzylphosphonium chloride (2.8 g) were treated as in the above Production Example 41-1 to give the title compound (0.598 g) as colorless crystals (yield: 73.1%).
$^1$H-NMR (400 MHz, CDCl$_3$):
δ(ppm) 6.51(1H, d, J=12.0 Hz), 6.80(1H, d, J=12.0 Hz), 6.89(1H, m), 7.06–7.37(7H, m), 7.47(1H, dd, J=0.4, 8.0 Hz), 8.04(1H, m).

(60-2) 3-(3-Fluorophenethyl)indole

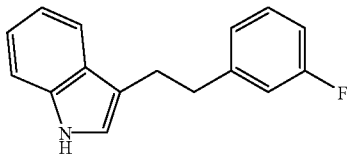

3-[2-(3-Fluorophenyl)vinyl]indole (0.598 g) was treated as in the above Production Example 59-2 to give the title compound (0.541 g) as a brown oil (yield: 89.7%).

$^1$H-NMR (400 MHz, CDCl$_3$):
δ(ppm) 3.04(4H, m), 6.90(2H, m), 6.98(1H, d, J=8.0 Hz), 7.13(1H, dt, J=0.8, 8.0 Hz), 7.23(2H, m), 7.36(1H, d, J=8.0 Hz), 7.61(1H, dd, J=0.8, 8.0 Hz), 7.89(1H, br-s).

(60-3) 3-(3-Fluorophenethyl)indoline

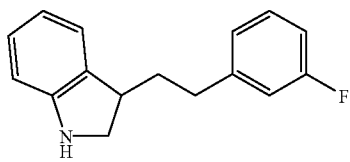

3-(3-Fluorophenethyl)indole (0.541 g) was treated as in the above Production Example 56-2 to give the title compound (0.582 g) as a brown oil (yield: quantitative).

$^1$H-NMR (400 MHz, CDCl$_3$):
δ(ppm) 1.87(1H, m), 2.14(1H, m), 2.72(2H, t, J=8.0 Hz), 3.26(2H, t, J=8.0 Hz), 3.30(1H, m), 3.71(1H, t, J=8.0 Hz), 6.65(1H, d, J=8.0 Hz), 6.73(1H, t, J=8.0 Hz), 6.88(2H, m), 7.03(1H, t, J=8.0 Hz), 7.13(1H, d, J=8.0 Hz), 7.23(1H, m).

Production Example 61 Synthesis of 4-(4-fluorophenyl)-indoline

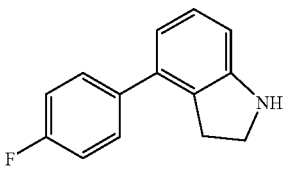

A mixture of 4-bromoindole (1.0 g), which had been synthesized according to the method of J. Org. Chem. (1986, Vol. 5, No. 26, p. 5106.), 4-fluorophenylboronic acid (1.1 g), tetrakis(triphenylphosphine)palladium (0.24 g), a 10% aqueous solution (10 ml) of sodium carbonate and toluene (20 ml) was heated under reflux for 4 hr. Then ethyl acetate was added to the reaction solution and the layers were separated. The organic layer was washed with brine and dried over anhydrous magnesium sulfate. The residue was purified by silica gel column chromatography (hexane/ethyl acetate system). To the resulting residue was added trifluoroacetic acid (10 ml) and a 1 M solution (6.8 ml) of a borane/tetrahydrofuran complex in tetrahydrofuran followed by stirring the mixture at 0° C. for 1 hr. After adding water, the resultant mixture was concentrated under reduced pressure. Then ethanol and an aqueous solution of sodium hydroxide were added thereto and the reaction mixture was stirred for 30 min. After adding ethyl acetate to the reaction solution, the layers were separated and the organic layer was washed with brine, dried over anhydrous magnesium sulfate and concentrated under reduced pressure. The residue was purified by silica gel column chromatography (hexane/ethyl acetate system) to give the title compound (0.5 g) as a colorless oil (yield: 46%).

$^1$H-NMR (400 MHz, CDCl$_3$):
δ(ppm) 3.01(2H, t, J=8 Hz), 3.50(2H, t, J=8 Hz), 3.81(1H, br-s), 6.61(1H, d, J=8 Hz), 6.72(1H, d, J=8 Hz), 7.02–7.10 (3H, m), 7.38–7.41(2H, m).

Production Example 62 Synthesis of thiazolo[5.4-f]indoline

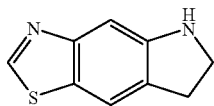

Bromine (2.5 ml) was added dropwise into a solution of 1-acetyl-6-aminoindoline (6.0 g) and potassium thiocyanate (9.3 g) in acetic acid (100 ml) followed by stirring the resultant mixture at room temperature for 5 hr. Under ice cooling, a 5 N aqueous solution of sodium hydroxide was added thereto and the crystalline precipitates were collected by filtration. Then these crystals were air dried at 60° C. overnight and dissolved in dimethylformamide (90 ml). After adding isoamyl nitrite (18 ml) dropwise thereinto, the reaction mixture was stirred at 80° C. for 1 hr followed by concentration under reduced pressure. Then a 5 N aqueous solution of sodium hydroxide and chloroform were added thereto and the layers were separated. The organic layer washed with brine, dried over anhydrous magnesium sulfate and concentrated under reduced pressure. The residue was purified by NH-silica gel column chromatography (hexane/ethyl acetate system). After adding 5 N hydrochloric acid (150 ml), the mixture was heated under reflux for 30 min. Then a 5 N aqueous solution of sodium hydroxide and ethyl acetate were added thereto and the layers were separated. The organic layer was washed with brine and dried over anhydrous magnesium sulfate. The residue was purified by silica gel column chromatography (hexane/ethyl acetate system) to give the title compound (1.2 g) as brown powdery crystals (yield: 21%).

$^1$H-NMR (400 MHz, CDCl$_3$):

δ(ppm) 3.14(2H, t, J=8 Hz), 3.65(2H, t, J=8 Hz), 4.00(1H, br-s), 7.28(1H, s), 7.58(1H, s), 8.83(1H, s).

Production Example 63 Synthesis of 6-(4-fluorobenzenesulfonylamino)indoline

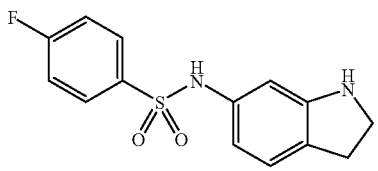

Under ice cooling, 4-fluorobenzenesulfonyl chloride (1.4 g) was added dropwise into a solution (10 ml) of 1-acetyl-6-aminoindoline (1.0 g) in pyridine followed by stirring the resultant mixture for 30 min. After concentrating it under reduced pressure, 5 N hydrochloric acid was added thereto and the resultant mixture was heated under reflux for 5 hr. Then the reaction solution was basified with a conc. aqueous solution of sodium hydroxide and extracted with ethyl acetate. The organic layer was washed with brine, dried over anhydrous magnesium sulfate and purified by NH-silica gel column chromatography (methylene chloride/ethanol system) to give the title compound (1.36 g) as white powdery crystals (yield: 82%).

$^1$H-NMR (400 MHz, CDCl$_3$):

δ(ppm) 2.95(2H, t, J=8 Hz), 3.64(2H, t, J=8 Hz), 3.78(1H, br-s), 6.22(1H,d, J=8 Hz), 6.33(1H, br-s), 6.48(1H, s), 6.90 (1H, d, J=8 Hz), 7.08–7.12(2H, m), 7.71–7.80(2H, m).

Production Example 64 Synthesis of 4-methoxyindoline

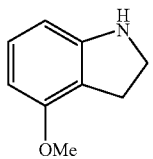

Under ice cooling, a 1 M solution (6.2 ml) of a borane/tetrahydrofuran complex in tetrahydrofuran was added dropwise into a solution of 4-methoxyindole (0.46 g) in trifluoroacetic acid (10 ml) followed by stirring the resultant mixture for 1 hr.

After adding water, the resultant mixture was concentrated under reduced pressure and ethanol and a 5 N aqueous solution of sodium hydroxide were added thereto followed by stirring the mixture overnight. After concentrating it under reduced pressure, the residue was extracted with ethyl acetate. The organic layer was washed with brine, dried over anhydrous magnesium sulfate and concentrated under reduced pressure. The residue was purified by silica gel column chromatography (hexane/ethyl acetate system) to give the title compound (130 mg) as a brown oil (yield: 28%).

$^1$H-NMR (400 MHz, CDCl$_3$):

δ(ppm) 2.95(2H, t, J=8 Hz), 3.52(2H, t, J=8 Hz), 3.80(1H, s), 6.28(1H, d, J=8 Hz), 6.30(1H, d, J=8 Hz), 6.99(1H, t, J=8 Hz).

Production Example 65 Synthesis of 1-(piperidin-4-yl)indan (65-1) 1-Hydroxy-1-(4-pyridyl)indan

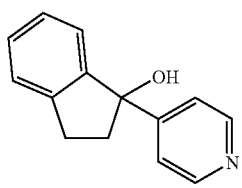

To 4-bromopyridine hydrochloride (19.4 g) were added a 2 N aqueous solution (120 ml) of sodium hydroxide and ether (300 ml) to extract 4-bromopyridine. Then the ether layer was dried over anhydrous potassium carbonate and cooled to −70° C. Into the resultant mixture was added dropwise 2.5 M n-butyllithium (40 ml) with stirring. After the completion of the addition, the reaction solution was stirred for 30 min and a solution (60 ml) of 1-indanone in ether was added thereto at −70° C. Then the reaction solution was allowed to warm to room temperature over 12 hr. Then it was pertitioned between ethyl acetate and a saturated aqueous solution of ammonium chloride. The ethyl acetate layer was washed with water, dried and concentrated under reduced pressure. The residue was purified by silica gel column chromatography (hexane/ethyl acetate system) to give the title compound (7.6 g) as a colorless oil (yield: 35.9%).

$^1$H-NMR (400 MHz, CDCl$_3$):

δ(ppm) 2.40–2.50(2H, m), 2.82(1H, br-s), 2.94–3.04(1H, m) 3.17–3.26(1H, m), 7.02(1H, d, J=8.4 Hz), 7.22(1H, dt, J=8.4, 2.8 Hz), 7.33(2H, d, J=8.0 Hz), 7.30–7.37(2H, m), 8.47(2H, d, J=8.0 Hz).

(65-2) 1-(Piperdin-4-yl)indan

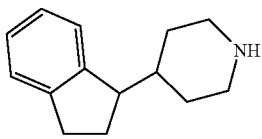

A mixture of 1-hydroxy-1-(4-pyridyl)indan (6.0 g), 6 N hydrochloric acid (20 ml) and ethanol (20 ml) was heated to 100° C for 30 min. Then the reaction solution was concentrated under reduced pressure and ethanol (200 ml) and platinum oxide (0.2 g) were added to the residue followed by hydrogenation under 3 kg/cm². After the completion of the reaction, the reaction solution was filtered through celite and extracted with ethanol. The filtrate was concentrated under reduced pressure and the residue was partitioned between ethyl acetate and a 2 N aqueous solution of sodium hydroxide. The ethyl acetate layer was washed with water, dried, concentrated under reduced pressure and purified by NH-silica gel column chromatography (ethyl acetate) to give the title compound (4.2 g) as pale brown powdery crystals (yield: 73.4%).

$^1$H-NMR (400 MHz, CDCl$_3$):

δ(ppm) 1.13–1.49(3H, m), 1.51(1H, br-s), 1.62–1.70(1H, m), 1.72–1.82(1H, m), 1.90–2.00(1H, m), 2.02–2.18(1H, m), 2.50–2.64(2H, m), 2.75–2.92(2H, m), 3.01–3.13(3H, m), 7.09–7.21(4H, m).

Production Example 66 Synthesis of 1-(piperidin-4-yl)-6-chloro-7-azaindoline

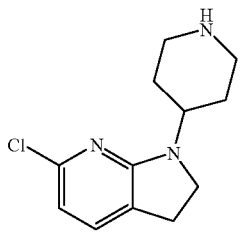

A mixture of 2,6-dichloro-3-formylmethylpyridine (5.6 g), ethyl 4-amino-1-piperidinecarboxylate (7.6 g), platinum oxide (140 mg), acetic acid (1.0 ml) and ethanol (100 ml) was catalytically reduced at ordinary temperature under atmospheric pressure in a stream of hydrogen. After 6 hr, the catalyst was filtered off and the filtrate was concentrated under reduced pressure. The residue was diluted with a saturated aqueous solution of sodium bicarbonate and ethyl acetate and the layers were separated. The organic layer was washed with brine and dried over magnesium sulfate and then the solvent was distilled off. The residue was purified by silica gel column chromatography (methylene chloride/ethanol system). After adding triethylamine (1.5 g) and o-dichlorobenzene (100 ml), the resultant mixture was heated at 180° C. for 2 hr. Then the reaction solution was concentrated under reduced pressure and diluted with a saturated aqueous solution of sodium hydrogencarbonate and ethyl acetate and the layers were separated. The organic layer was washed with brine, dried over magnesium sulfate and purified by silica gel column chromatography (hexane/ethyl acetate system). After adding potassium hydroxide (10 g) and ethylene glycol (200 ml) to the residue, the resultant mixture was heated under reflux for 2 hr. Then the reaction solution was diluted with water and ethyl acetate and the layers were separated. The organic layer was washed with brine and dried over magnesium sulfate. After evaporating the solvent under the title compound (2.3 g) was obtained as a brown oil (yield: 33%).

$^1$H-NMR (400 MHz, CDCl$_3$):

δ(ppm) 1.71–1.89(4H, m), 2.80–2.91(2H, m), 2.94(2H, t, J=8 Hz), 3.25–3.34(2H, m), 3.66(2H, t, J=8 Hz), 4.11–4.23 (1H, m), 6.38(1H, d, J=8 Hz), 7.04(1H, d, J=8 Hz).

Production Example 67 Synthesis of 1-(4-piperidinyl)-7-methoxy-1.2.3.4-tetrahydroquinoline

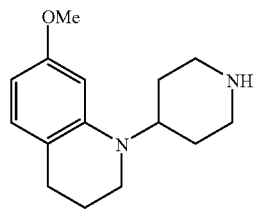

A solution of 1-(4-piperidinyl)-7-methoxy-3,4-dihydrocarbostyryl (1.50 g), which had been obtained by the method described in JP-A 3-173870, in THF (50 ml) was cooled to 0° C. and lithium aluminum hydride (660 mg) was added thereto in five portions. The reaction mixture was stirred at 0° C. for 10 min and then heated under reflux for 4 hr. After the completion of the reaction, the reaction mixture was cooled to 0° C. and water (0.66 ml), a 5 N aqueous solution (0.66 ml) of sodium hydroxide and further water (2 ml) were successively added thereto. After further adding magnesium sulfate, the resultant mixture was stirred for 10 min. The resulting precipitate was filtered off through celite and the filtrate was concentrated to give the title compound (1.27 g) (yield: 89%).

$^1$H-NMR (400 MHz, CDCl$_3$):

δ(ppm) 1.62–1.91(6H, m), 2.02–2.12(1H, m), 2.64–2.75 (3H, m), 3.07–3.22(4H, m), 3.51–3.74(1H, m), 3.77(3H, s), 6.13(1H, dt, J=8.0, 2.0 Hz), 6.24(1H, t, J=2.0 Hz), 6.85(1H, d, J=8.0 Hz).

EXAMPLES

Example 1: Synthesis of 1-[1-(4-fluorophenyl)piperdine-4-yl]indoline

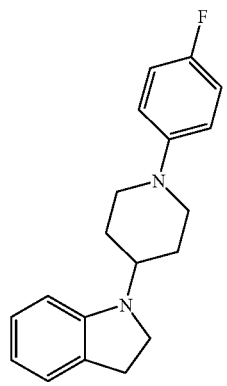

Triacetoxylated sodium borohydride (760 mg) was added to a mixture of indoline (300 mg), 1-(4-fluorophenyl)-4-piperidone (580 mg), acetic acid (650 mg) and dichloroethane (30 ml), and the mixture was stirred for 2 hr. The obtained reaction solution was mixed with ethyl acetate and a saturated aqueous solution of sodium bicarbonate and the layers were separated. The organic layer was washed with brine, dried over anhydrous magnesium sulfate, and concentrated under reduced pressure. The residue was purified by silica gel column chromatography (hexane/ethyl acetate system) to give the title compound (470 mg) as white prismatic crystals (yield: 63%).
m.p.: 120–122° C.
$^1$H-NMR (400 MHz, CDCl$_3$):
δ(ppm) 1.82–1.93(4H, m), 2.71–2.82(2H, m), 2.92–3.01 (2H, m), 3.39–3.43(3H, m), 3.63–3.71(2H, m), 6.42–6.49 (1H, m), 6.60–6.65(1H, m), 6.90–7.10(6H, m).
FAB-Mass: 297(MH+).
Example 2: Synthesis of 1-[1-(4-fluorobenzyl)piperidin-4-yl]indoline

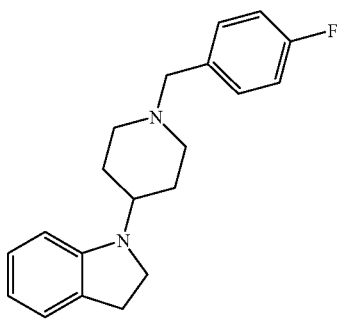

4-Fluorobenzyl bromide (0.067 ml) was dissolved in N,N-dimethylformamide (2.5 ml). After adding 4-fluorobenzyl bromide (0.067 ml) and triethylamine (0.075 ml), the resulting mixture was stirred for 5 hr. Then water and ethyl acetate were added thereto and the layers were separated. The organic layer was washed with brine, dried over anhydrous magnesium sulfate and concentrated under reduced pressure. The residue was purified by silica gel column chromatography (hexane/ethyl acetate system) to give the title compound (0.131 g) as colorless crystals (yield: 86.1%).

Next, hydrochloric acid was added to the product to give a salt followed by recrystallization from ethanol. Thus, the hydrochloride of the title compound was obtained as colorless crystals.
m.p. (hydrochloride): 223° C.
Hydrochloride
$^1$H-NMR (400 MHz, DMSO-d$_6$):
δ(ppm) 1.84(2H, br-d), 2.14(2H, m), 2.90(2H, t, J=8.4 Hz), 3.01(2H, m), 3.33(2H, t, J=8.4 Hz), 3.40(2H, br-d), 3.72(1H, m), 4.27(2H, d, J=4.8 Hz), 6.62(1H, d, J=7.6 Hz), 6.63(1H, t, J=7.6 Hz), 7.02(1H, t, J=7.6 Hz), 7.06(1H, d, J=7.6 Hz), 7.31(2H, t, J=8.8 Hz), 7.70(2H, dd, J=5.6, 8.8 Hz).
ESI-Mass: 311.1(MH+).
Example 3: Synthesis of 1-(1-phenethylpiperidin-4-yl)indoline

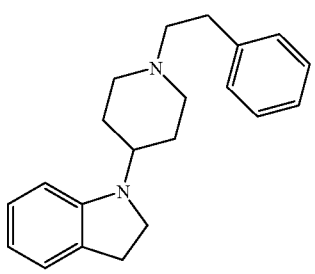

(2-Bromoethyl) benzene (0.19 g) was treated as in Example 2 to give the title compound (0.126 g) as a colorless oil (yield: 77.3%).

Next, hydrochloric acid was added to the product to give a salt followed by recrystallization from ethanol. Thus, the hydrochloride of the title compound was obtained as colorless crystals.
m.p. (hydrochloride): 234° C.
Hydrochloride
$^1$H-NMR (400 MHz, DMSO-d$_6$):
δ(ppm) 1.89(2H, m), 2.10(2H, m), 2.91(2H, t, J=8.2 Hz), 3.09(4H, m), 3.26(2H, m), 3.35(2H, t, J=8.2 Hz), 3.65(2H, m), 3.76(1H, m), 6.60(1H, d, J=7.6 Hz), 6.61(1H, t, J=7.6 Hz), 7.02(1H, t, J=7.6 Hz), 7.06(1H, d, J=7.6 Hz), 7.28(3H, m), 7.35(2H, m).
FAB-Mass: 307(MH+).
Example 4: Synthesis of 1-[1-(4-bromophenethyl)piperidin-4-yl]indoline

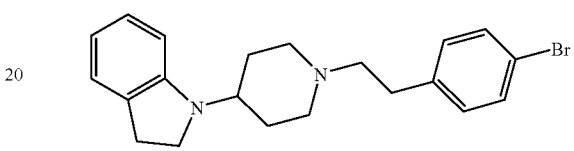

4-Bromophenethyl bromide (0.1 g) was treated as in Example 2 to give the title compound (0.119 g) as a colorless oil (yield: 63.0%).

Next, hydrochloric acid was added to the product to give a salt followed by recrystallization from ethanol. Thus, the hydrochloride (0.110 g) of the title compound was obtained.
m.p. (hydrochloride): 230° C.
Hydrochloride
$^1$H-NMR (400 MHz, DMSO-d$_6$):
δ(ppm) 1.88(2H, br-d), 2.09(2H, m), 2.91(2H, t, J=8.2 Hz), 3.09(4H, m), 3.25(2H,m), 3.36(2H, t, J=8.2 Hz), 3.62 (2H, br-d), 3.75(1H, m), 6.59(1H, d, J=8.0 Hz), 6.60(1H, t, J=8.0 Hz), 7.02(1H, t, J=8.0 Hz), 7.05(1H, d, J=8.0 Hz), 7.27(2H, d, J=8.4 Hz), 7.55(2H, d, J=8.4 Hz).
FAB-Mass: 385(MH+).
Example 5: Synthesis of 1-[1-(3-chlorophenethyl)piperidin-4-yl]indoline

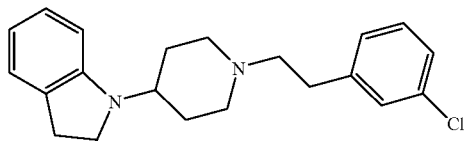

3-Chlorophenethyl bromide (0.1 g) was treated as in Example 2 to give the title compound (0.119 g) as a colorless oil (yield: 63.0%).

Next, hydrochloric acid was added to the product to give a salt followed by recrystallization from ethanol. Thus, the hydrochloride (0.110 g) of the title compound was obtained.
m.p. (hydrochloride): 219° C.
Hydrochloride
$^1$H-NMR (400 MHz, DMSO-d$_6$):
δ(ppm) 1.89(2H, br-d), 2.11(2H, m), 2.91(2H, t, J=8.4 Hz), 3.09(4H, m), 3.27(2H, m), 3.35(2H, t, J=8.4 Hz), 3.63(2H, br-d), 3.77(1H, br-t), 6.62(2H, m), 7.02(1H, t, J=8 Hz), 7.06(1H, d, J=8 Hz), 7.27(1H, d, J=7.2 Hz), 7.32–7.41 (3H, m).
FAB-Mass: 341(MH+).

Example 6 Synthesis of 1-[1-(4-chlorophenethyl)piperidin-4-yl]indoline

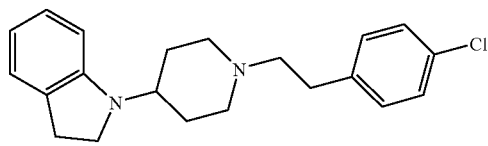

4-Chlorophenethyl bromide (0.1 g) was treated as in Example 2 to give the title compound (0.125 g) as a colorless oil (yield: 74.8%).

Next, hydrochloric acid was added to the product to give a salt followed by recrystallization from ethanol. Thus, the hydrochloride (0.120 g) of the title compound was obtained.

m.p. (hydrochloride): 228° C.

Hydrochloride $^1$H-NMR (400 MHz, DMSO-$d_6$):

δ(ppm) 1.88(2H, br-d), 2.11(2H, m), 2.91(2H, t, J=8.4 Hz), 3.09(4H, m), 3.25(2H, m), 3.35(2H, t, J=8.4 Hz), 3.63(2H, br-d), 3.77(1H, br-t), 6.62(1H, d, J=8.0 Hz), 6.63 (1H, t, J=8.0 Hz), 7.03(1H, t, J=8.0 Hz), 7.06(1H, d, J=8.0 Hz), 7.33(2H, d, J=8.6 Hz), 7.42(2H, d, J=8.6 Hz).

FAB-Mass: 341 (MH+).

Example 7: Synthesis of 1-[1-(2-fluorophenethyl)piperidin-4-yl]indoline

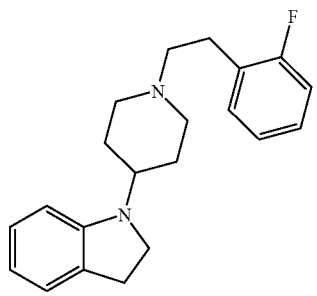

1-(Piperidin-4-yl)indoline (300 mg) and 2-fluorophenethyl bromide (340 mg) obtained in the same manner as the one of Production Example 1 were treated as in Example 2 to give the hydrochloride (290 mg) of the title compound as a white powder (yield: 54%).

m.p. (hydrochloride): 229–231° C.

$^1$H-NMR (400 MHz, DMSO-$d_6$):

δ(ppm) 1.81–1.90(2H, m), 2.00–2.12(2H, m), 2.89(2H, t, J=8 Hz), 3.01–3.16(4H, m), 3.20–3.30(2H, m), 3.33(2H, t, J=8 Hz), 3.60–3.79(3H, m), 6.53–6.60(2H, m), 6.96–7.04 (2H, m) 7.16–7.23(2H, m), 7.29–7.40(2H, m), 10.80(1H, br-s).

FAB-Mass: 325(MH+).

Example 8: Synthesis of 1-[1-(3-fluorophenethyl)piperidin-4-yl]indoline

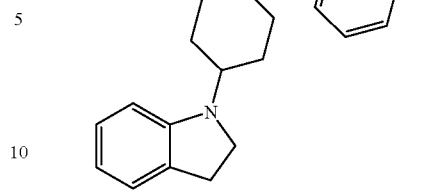

Dicyclohexylcarbodiimide (560 mg) was added to a solution of 1-(piperidin-4-yl)indoline (500 mg) in methylene chloride (30 ml) followed by stirring at 0° C. After 1 hr, 3-fluorophenylacetic acid (420 mg) was added thereto and the resultant mixture was stirred at room temperature for 2 hr. The crystalline precipitates were filtered off and the filtrate was concentrated under reduced pressure and purified by silica gel column chromatography (hexane/ethyl acetate system). The residue was diluted with tetrahydrofuran (30 ml). Next, lithium aluminum hydride (290 mg) was added in portions thereto under ice cooling and stirring and the resultant mixture was stirred at room temperature overnight. Under ice cooling, water (0.29 ml), a 5 N aqueous solution (0.87 ml) of sodium hydroxide and further water (0.29 ml) were carefully added dropwise into the reaction solution followed by vigorous stirring. The resulting precipitate was filtered off and the filtrate was concentrated under reduced pressure and purified by silica gel column chromatography (hexane/ethyl acetate system). Then the obtained product was converted into a hydrochloride in a conventional manner to give the hydrochloride (550 mg) of the title compound as a white powder (yield: 61%).

m.p. (hydrochloride): 231–234° C.

$^1$H-NMR (400 MHz, DMSO-$d_6$):

δ(ppm) 1.81–1.89(2H, m), 1.93–2.07(2H, m), 2.88(2H, t, J=8 Hz), 3.00–3.11(4H, m), 3.23–3.35(4H, m), 3.58–3.75 (3H, m), 6.51–6.57(2H, m), 6.95–7.03(2H, m), 7.06–7.19 (2H, m), 7.35–7.41(2H, m).

FAB-Mass: 325(MH+).

Example 9: Synthesis of 1-[1-(4-fluorophenethyl)piperidin-4-yl]indoline

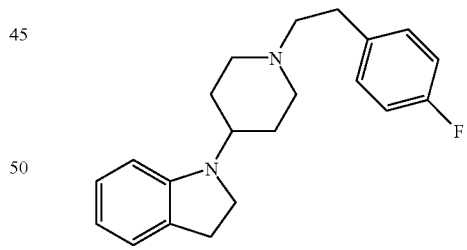

A 2.5 M solution (0.36 ml) of n-butyllithium in hexane was added dropwise over 10 min into a solution of 1-[1-(4-fluorophenethyl)piperidin-4-yl]-6-bromoindoline (300 mg) in tetrahydrofuran (15 ml) at −78° C. After 10 min, the resultant mixture was mixed with a saturated aqueous solution of ammonium chloride and ethyl acetate and the layers were separated. The organic layer was washed with brine, dried over anhydrous magnesium sulfate and purified by silica gel column chromatography (methylene chloride/ethanol system). Then the obtained product was converted into the hydrochloride in a conventional manner to give the hydrochloride (240 mg) of the title compound as white needles (yield: 90%).

m.p. (hydrochloride): 233° C. (decomp.).
¹H-NMR (400 MHz, DMSO-d₆):

δ(ppm) 1.81–1.90(2H, m), 2.00–2.13(2H, m), 2.90(2H, t, J=8 Hz), 3.00–3.14(4H, m), 3.19–3.28(2H, m), 3.30(2H, t, J=8 Hz), 3.58–3.63(2H, m), 3.69–3.79(1H, m), 6.51–6.60 (2H, m), 6.94–7.08(2H, m), 7.12–7.20(2H, m), 7.29–7.39 (2H, m), 10.70(1H, br-s).
FAB-Mass: 325(MH+).

Example 10: Synthesis of 1-[1-(2,4-difluorophenethyl)-piperidin-4-yl]indoline

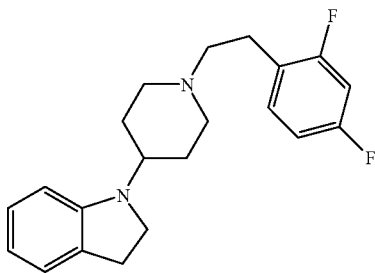

1-(Piperidin-4-yl)indoline (500 mg) and 2,4-difluorophenylacetic acid (470 mg) were treated as in Example 8 to give the hydrochloride (720 mg) of the title compound as a white powder (yield: 76%).
m.p. (hydrochloride): 226–227° C.
¹H-NMR (400 MHz, DMSO-d₆):

δ(ppm) 1.81–2.08(4H, m), 2.89(2H, t, J=8 Hz), 3.00–3.15 (4H, m), 3.20–3.39(4H, m), 3.40–3.75(3H, m), 6.49–6.57 (2H, m), 6.94–7.04(2H, m), 7.07–7.12(1H, m), 7.23–7.30 (1H, m), 7.39–7.46(1H, m).
FAB-Mass: 343(MH+).

Example 11: Synthesis of 1-[1-(3,4-difluorophenethyl)-piperidin-4-yl]indoline

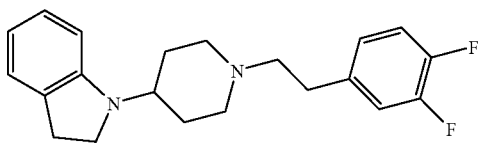

3,4-Difluorophenylacetic acid (0.095 g) was dissolved in tetrahydrofuran (5.0 ml). After adding 1,1-carbonyldiimidazole (0.089 g) to the resultant solution, the resultant mixture was stirred at room temperature for 15 min followedbytheadditionof 1-(piperidin-4-yl)indoline (0.1 g). After stirring at room temperature overnight, the resultant mixture was diluted with ethyl acetate, washed with brine, dried over anhydrous sodium sulfate and concentrated under reduced pressure. The residue was purified by silica gel column chromatography (hexane/ethyl acetate system) to give a colorless oil. Then this product was dissolved in tetrahydrofuran (2.5 ml) and lithium aluminum hydride (0.046 g) was added thereto under ice cooling followed by heating under reflux for 2 hr. After cooling the reaction solution, water (0.05 ml), a 5 N aqueous solution (0.05 ml) of sodium hydroxide and further water (0.15 ml) were added thereto. The precipitated solid was filtered off and the filtrate was concentrated under reduced pressure. The residue was purified by silica gel column chromatography (hexane/ethyl acetate system) to give the title compound (0.190 g) as a colorless oil (yield: quantitative).

Next, hydrochloric acid was added to the product to give a salt followed by recrystallization from ethanol. Thus, the hydrochloride (0.120 g) of the title compound was obtained.

m.p. (hydrochloride): 223° C.
Hydrochloride
¹H-NMR (400 MHz, DMSO-d₆):

δ(ppm) 1.87(2H, br-d), 2.06(2H, m), 2.90(2H, t, J=8.4 Hz), 3.09(4H, m), 3.28(2H, m), 3.33(2H, t, J=8.4 Hz), 3.62(2H, br-d), 3.74(1H, br-t), 6.57(1H, d, J=7.0 Hz), 6.58 (1H, t, J=7.0 Hz), 7.01(1H, t, J=7.0 Hz), 7.04(1H, d, J=7.0 Hz), 7.16(1H, m), 7.39–7.46(2H, m).
FAB-Mass: 343(MH+).

Example 12: Synthesis of 1-[1-(3,5-difluorophenethyl)-piperidin-4-yl]indoline

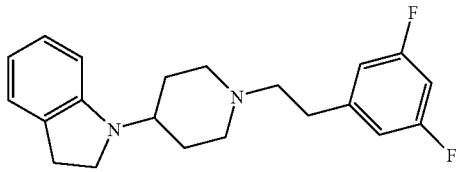

3,5-Difluorophenylacetic acid (0.189 g) was treated as in Example 11 to give the title compound (0.342 g) as a colorless oil (yield: quantitative).

Next, hydrochloric acid was added to the product to give a salt followed by recrystallization from ethanol. Thus, the hydrochloride (0.268 g) of the title compound was obtained.
m.p. (hydrochloride): 208° C.
Hydrochloride
¹H-NMR (400 MHz, DMSO-d₆):

δ(ppm) 1.89(2H, br-d), 2.12(2H, m), 2.92(2H, t, J=8.2 Hz), 3.09(4H, m), 3.27(2H, m), 3.36(2H, t, J=8.2 Hz), 3.61(2H, br-d), 3.78(1H, m), 6.64(1H, d, J=8.0 Hz), 6.64 (1H, t, J=8.0 Hz), 7.04(1H, t, J=8.0 Hz), 7.07(1H, d, J=8.0 Hz), 7.14–7.18(1H, m), 7.38–7.45(2H, m).
FAB-Mass: 343(MH+).

Example 13: Synthesis of 1-[1-(4-fluorophenylpropyl)-piperidin-4-yl]indoline

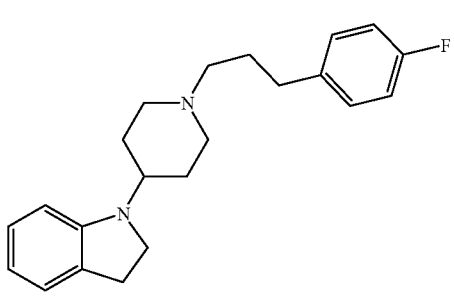

Ethanol (50 ml) was added to 4-fluorocinnamic acid (5 g) and then ethyl acetate was further added thereto to dissolve completely. After adding a palladium carbon catalyst, catalytic reduction was carreid out under atmospheric pressure. Then the reaction mixture was filtered through celite and the filtrate was concentrated under reduced pressure. A portion (0.082 g) of the resulting colorless crystals was dissolved in tetrahydrofuran (5.0 ml), and carbonyldiimidazole (0.079 g) and 1-(4-piperidyl) indoline (0.1 g) were added thereto followed by stirring at room temperature for 14 hr. Then the reaction solution was diluted with ethyl acetate, washed with brine, dried over anhydrous magnesium sulfate and concentrated under reduced pressure to give a pale yellow oily substance (0.171 g). This product was dissolved in tetrahydrofuran (5.0 ml) and lithium aluminum hydride (0.046 g) was added thereto under ice cooling. After heating under reflux for 2 hr, the reaction mixture was ice cooled again and water (0.05 ml), a 5 N aqueous solution (0.05 ml) of sodium hydroxide and further water (0.15 ml) were added thereto. The resulting solid was filtered off and the filtrate was concentrated under reduced pressure. The residue was purified by silica gel column chromatography (hexane/ethyl acetate system) to give the title compound (0.113 g) as a colorless oil (yield: 68.1%).

Next, hydrochloric acid-was added to the product to give a salt followed by recrystallization from ethanol. Thus, the hydrochloride (hygroscopic) of the title compound was obtained.

Hydrochloride $^1$H-NMR (400 MHz, DMSO-$d_6$):

δ(ppm) 1.83(2H, br-d), 1.97–2.14(4H, m), 2.64(2H, t, J=8.0 Hz), 2.90(2H, t, J=8.0 Hz), 3.00(4H, m), 3.33(2H, t, J=8.4 Hz), 3.54(2H, br-d), 3.73(1H, m), 6.58(1H, d, J=7.6 Hz), 6.61(1H, t, J=7.6 Hz), 7.02(1H, t, J=7.6 Hz), 7.05(1H, d, J=7.6 Hz), 7.14(2H, t, J=8.8 Hz), 7.29(2H, dd, J=5.6, 8.8 Hz).

ESI-Mass: 339.2(MH+).

Example 14: Synthesis of 1-{1-[2-(4-fluorophenyl)propyl]piperidin-4-yl}indoline

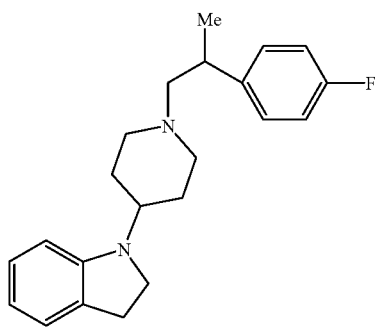

1-(4-Piperazinyl)indoline (0.20 g) was dissolved in dimethylformamide (3 ml) and 4-(2-bromo-1-methylethyl)fluorobenzene (10.0 g) and triethylamine (0.14 ml) were added to the resultant solution followed by stirring at 60° C. overnight. After adding water, the liquid reaction mixture was extracted with ethyl acetate. The organic layer was washed with brine and dried over magnesium sulfate. After evaporating the solvent, the resulting residue was purified by NH-silica gel column chromatography (methanol/methylene chloride system) to give the title compound (178 mg) as an oil.

$^1$H-NMR (400 MHz, CDCl$_3$):

δ(ppm) 1.37(3H, d, J=6.8 Hz), 1.60–2.10(8H, m), 2.85–3.50(8H, m), 6.36(1H, d, J=7.5 Hz), 6.58(1H, t, J=7.5 Hz), 6.97–7.07(4H, m), 7.24–7.30(2H, m).

FAB-Mass: 339(MH+).

Example 15: Synthesis of 1-[1-(4-fluorophenylbutyl)piperidin-4-yl]indoline

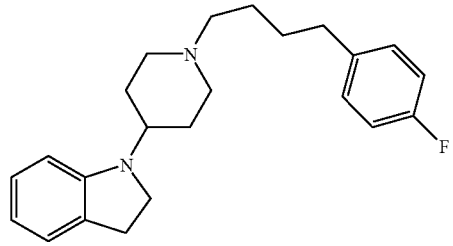

1-(Piperidin-4-yl)indoline (1.0 g) and 4-(4-fluorophenyl)butyric acid (0.9 g) were treated as in Example 8 to give the hydrochloride (0.23 g) of the title compound as a white powder (yield: 12%).

m.p. (hydrochloride): 204–206° C.

$^1$H-NMR (400 MHz, DMSO-$d_6$):

δ(ppm) 1.51–1.71(4H, m), 1.79–1.86(2H, m), 1.89–2.02(2H, m), 2.60(2H, t, J=7 Hz), 2.87(2H, t, J=8 Hz), 2.92–3.07(4H, m), 3.29(2H, t, J=7 Hz), 3.47–3.53(2H, m), 3.62–3.72(1H, m), 6.48–6.56(2H, m), 6.92–7.02(2H, m), 7.06–7.12(2H, m), 7.20–7.28(2H, m), 9.99(1H, br-s).

FAB-Mass: 353(MH+).

Example 16: Synthesis of 1-[1-(4-fluorophenethyl)piperidin-4-yl]methylindoline

1-Fluorophenethyl-4-formylpiperidine (0.240 g) and indoline (0.095 ml) were dissolved in 1,2-dichloroethane (3.5 ml). After successively adding acetic acid (0.29 ml) and triacetoxylated sodium borohydride (0.36 g), the resultant mixture was stirred at room temperature for 2 hr. Then it was mixed with a saturated aqueous solution of sodium bicarbonate and ethyl acetate and the layers were separated. The organic layer was washed with a saturated aqueous solution of sodium chloride, dried over anhydrous magnesium sulfate and concentrated under reduced pressure. The residue was purified by silica gel column chromatography (hexane/ethyl acetate system) to give the title compound (0.211 g) as a yellow oil (yield: 73.3%).

Next, oxalic acid (28 mg) was added to the product to give a salt followed by recrystallization from acetone. Thus, the oxalate of the title compound was obtained as colorless crystals.

m.p. (oxalate): 201–206° C.

Oxalate $^1$H-NMR (400 MHz, DMSO-$d_6$):

δ(ppm) 1.57(2H, m), 1.90(1H, m), 1.95(2H, m), 2.92(6H, m), 3.07(2H, m), 3.23(2H, m), 3.34(2H, t, J=8.4 Hz), 3.57(2H, br-d), 6.52(1H, d, J=7.6 Hz), 6.58(1H, t, J=7.6 Hz), 6.99(1H, t, J=7.6 Hz), 7.03(1H, d, J=7.6 Hz), 7.18(2H, t, J=8.8 Hz), 7.33(2H, dd, J=5.2, 8.8 Hz).

ESI-Mass: 339.1(MH+).

Example 17: Synthesis of 1-{2-[1-(4-fluorophenethyl)piperidin-4-yl]ethyl}indoline

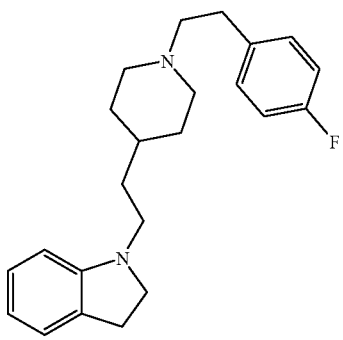

Indoline (170 mg), 1-(4-fluorophenethyl)-4-piperidinacetaldehyde (360 mg), acetic acid (440 mg) and triacetoxylated sodium borohydride (490 mg) were treated as in Example 1 to give the hydrochloride (270 mg) of the title compound as white prisms (yield: 48%).

m.p. (hydrochloride): 159–161° C.

$^1$H-NMR (400 MHz, DMSO-$d_6$):

δ(ppm) 1.45–1.70(5H, m), 1.89–1.98(2H, m), 2.80–3.10 (8H, m), 3.14–3.36(4H, m), 3.50–3.58(2H, m), 6.50–6.58 (2H, m), 6.96–7.03(2H, m), 7.16–7.21(2H, m), 7.30–7.38 (2H, m), 10.16(1H, m).

FAB-Mass: 353(MH+).

Example 18: Synthesis of 1-[1-(4-methoxyphenethyl)piperdin-4-yl]indoline

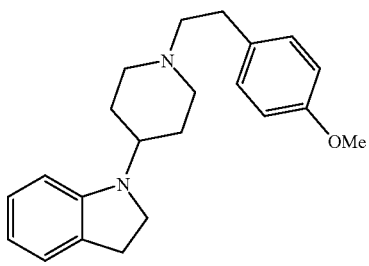

4-Methoxyphenethyl bromide (0.23 g) was treated as in Example 2 to give the title compound (0.131 g) as colorless crystals (yield: 86.1%).

Next, hydrochloric acid was added to the product to give a salt followed by recrystallization from ethanol. Thus, the hydrochloride of the title compound was obtained as colorless crystals.

m.p. (hydrochloride): 244° C.

Hydrochloride $^1$H-NMR (400 MHz, DMSO-$d_6$):

δ(ppm) 1.88(2H, m), 2.02(2H, m), 2.90(2H, t, J=8.4 Hz), 3.00(2H, m), 3.10(2H, m), 3.21(2H, m), 3.33(2H, t, J=8.4 Hz), 3.63(2H, br-d), 3.73(3H, s), 3.74(1H, m), 6.57(1H, d, J=7.6 Hz), 6.59(1H, t, J=7.6 Hz), 6.91(2H, d, J=8.4 Hz), 7.01(1H, t, J=7.6 Hz), 7.04(1H, d, J=7.6 Hz), 7.21(2H, d, J=8.4 Hz).

FAB-Mass: 337(MH+).

Example 19: Synthesis of 1-[1-(3-methoxyphenethyl)piperidin-4-yl]indoline

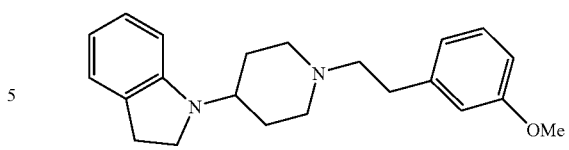

3-Methoxyphenethyl alcohol was treated as in Production Example 1. Then the pale yellow oily substance (0.23 g) thus obtained was treated as in Example 2 to give the title compound (0.150 g) as colorless crystals (yield: 45.4%).

Next, hydrochloric acid was added to the product to give a salt followed by recrystallization from ethanol. Thus, the hydrochloride of the title compound was obtained as colorless crystals.

m.p. (hydrochloride): 229° C.

Hydrochloride $^1$H-NMR (400 MHz, DMSO-$d_6$):

δ(ppm) 1.88(2H, br-d), 2.14(2H, m), 2.92(2H, t, J=8.4 Hz), 3.07(4H, m), 3.25(2H, m), 3.37(2H, t, J=8.4 Hz), 3.63(2H, br-d), 3.75(3H, s), 3.77(1H, m), 6.57(1H, d, J=7.6 Hz), 6.45(1H, m), 6.81–6.88(3H, m), 7.05(2H, m), 7.26(1H, d, J=8.0 Hz).

FAB-Mass: 337(MH+).

Example 20: Synthesis of 1-[1-(4-hydroxyphenethyl)piperidin-4-yl]indoline

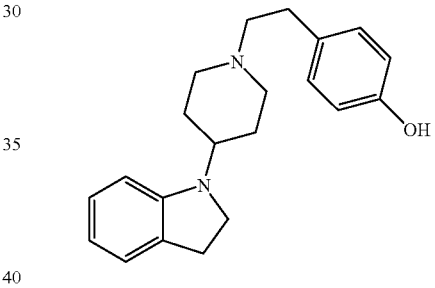

1-[1-(4-Methoxyphenethyl)piperidin-4-yl]indoline (0.23 g) was dissolved in a 47% aqueous solution (5 ml) of hydrobromic acid and the resultant solution was heated under reflux for 90 min. After allowing to cool, the resultant mixture was poured into a saturated aqueous solution of sodium bicarbonate (pH 9–10), extracted with ethyl acetate, washed with brine, dried over anhydrous magnesium sulfate and concentrated under reduced pressure. The residue was purified by NH-silica gel column chromatography (hexane/ethyl acetate system) to give the title compound (0.113 g) as colorless crystals (yield: 75.7%).

Next, hydrochloric acid was added to the product to give a salt followed by recrystallization from ethanol. Thus, the hydrochloride of the title compound was obtained as colorless crystals.

m.p. (hydrochloride): 240° C.

Hydrochloride $^1$H-NMR (400 MHz, DMSO-$d_6$):

δ(ppm) 1.87(2H, m), 2.09(2H, m), 2.91(2H, t, J=8.4 Hz), 2.95(2H, m), 3.07(2H, m), 3.18(2H, m), 3.34(2H, t, J=8.4 Hz), 3.62(2H, br-d), 3.75(1H, m), 6.61(2H, m), 6.73(2H, d, J=8.4 Hz), 7.05(4H, m), 10.69(1H, br-s).

FAB-Mass: 323(MH+).

Example 21: Synthesis of 1-[1-(4-cyanophenethyl)piperidin-4-yl]indoline

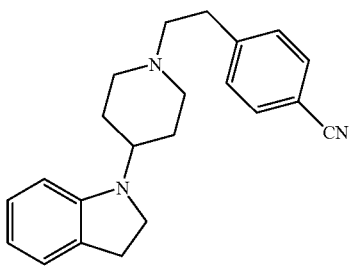
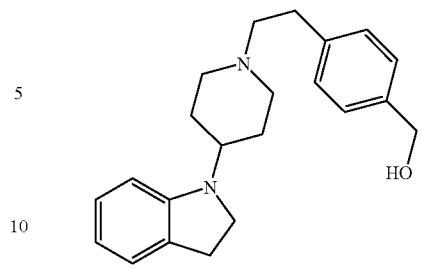

1-[1-(4-Hydroxyiminomethylphenethyl)piperidin-4-yl]indoline (0.466 g) was dissolved in methylene chloride (6.5 ml) and triethylamine (0.35 ml) was added thereto. In a nitrogen atmosphere at −78° C., trifluoroacetic anhydride (0.14 ml) was added dropwise into the resultant solution followed by stirring for 3 hr. After adding a saturated aqueous solution of sodium bicarbonate, the resultant mixture was extracted with ethyl acetate, washed with brine, dried over anhydrous magnesium sulfate and concentrated under reduced pressure. The residue was purified by silica gel column chromatography (ethyl acetate/methylene chloride/methanol system) to give the title compound (0.126 g) as a pale yellow oil (yield: 28.9%).

Next, hydrochloric acid was added to the product to give a salt. Thus, the hydrochloride of the title compound was obtained.

m.p. (hydrochloride): 228° C.
Hydrochloride
$^1$H-NMR (400 MHz, DMSO-d$_6$):
δ(ppm) 1.89(2H, br-d), 2.12(2H, m), 2.91(2H, t, J=8.4 Hz), 3.12(2H, m), 3.21(2H, m), 3.28(2H, m), 3.34(2H, t, J=8.4 Hz), 3.63(2H, br-d), 3.76(1H, m), 6.60(1H, d, J=7.4 Hz), 6.61(1H, t, J=7.4 Hz), 7.02(1H, t, J=7.4 Hz), 7.05(1H, d, J=7.4 Hz), 7.52(2H, d, J=8.0 Hz), 7.84(2H, d, J=8.0 Hz).
FAB-Mass: 332(MH+).

Example 22: Synthesis of 1-[1-(3-hydroxymethylphenethyl)piperidin-4-yl]indoline

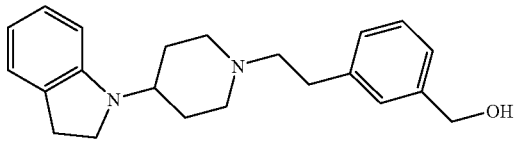

3-(t-Butyl)dimethylsilyloxymethylphenethyl bromide (0.22 g) was treated as in Example 2 to give the title compound (0.116 g) as a pale yellow oil (yield: 31.9%).
Free
$^1$H-NMR (400 MHz, CDCl$_3$):
δ(ppm) 1.75–1.84(4H,m), 2.15(2H,m), 2.63(2H,m), 2.84 (2H, m), 2.95(2H, t, J=8.4 Hz), 3.14(2H, br-t), 3.37(1H, m), 3.39(2H, t, J=8.4 Hz), 4.68(2H, s), 6.39(1H, d), 6.60(1H, t), 7.03(2H, m), 7.12–7.35(4H, m).

Next, hydrochloric acid (0.372 g) was added to the product to give a salt followed by recrystallization from ethanol-acetone mixtures. Thus, the hydrochloride of the title compound was obtained.

m.p.: 218° C.

Example 23: Synthesis of 1-[1-(4-hydroxymethylphenethyl)piperidin-4-yl]indoline 4-(2-Bromoethyl)benzyl alcohol (0.2 g) was treated as in Example 2 to give the title compound (0.177 g) as a pale yellow oil (yield: 53.7%).
Free
$^1$H-NMR (400 MHz, CDCl$_3$):
δ(ppm) 1.79(4H, m), 2.12(2H, dt, J=2.8, 11.6 Hz), 2.59 (2H, m), 2.81(2H, m), 2.94(2H, t, J=8.4 Hz), 3.12(2H,br-d), 3.38(2H, t, J=8.4 Hz), 3.40(1H, m), 4.65(2H, s), 6.42(1H, d, J=8.0 Hz), 6.61(1H, t, J=8.0 Hz), 7.03(1H, t, J=8.0 Hz), 7.05(1H, d, J=8.0 Hz), 7.21(2H, d, J=8.0 Hz), 7.49(2H, d, J=8.0 Hz), 8.11(1H, s).

Next, hydrochloric acid was added to the product to give the hydrochloride of the title compound.
FAB-Mass; 337 (MH+).

Example 24: Synthesis of 1-{1-[4-(2-hydroxyethyl)phenethyl]piperidin-4-yl}indoline

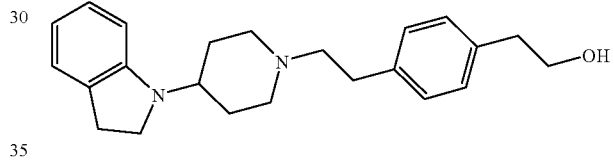

4-[2-(t-Butyldimethylsilyloxy)ethyl]phenethyl bromide (0.2 g) was treated as in Example 2 to give a pale yellow oil (0.113 g). Then this product was dissolved in tetrahydrofuran (1.0 ml). To the resultant solution was added a 2.0 M solution (0.49 ml) of tetrabutylammonium fluoride in tetrahydrofuran and the resultant mixture was stirred at room temperature for 1.5 hr. The liquid reaction mixture was concentrated under reduced pressure to give the title compound (0.086 g) as a yellow oil
(yield: quantitative).
Free
$^1$H-NMR (400 MHz, CDCl$_3$):
δ(ppm) 1.88(4H, m), 2.31(2H, m), 2.75(2H, m), 2.85(2H, t, J=6.4 Hz), 2.95(2H, t, J=8.4 Hz), 3.21(2H, m), 3.24(2H, m), 3.40(2H, t, J=8.4 Hz), 3.85(2H, t, J=6.4 Hz), 6.41(1H, d), 6.60(1H, t), 7.03(2H, m), 7.18(4H, s).

Then oxalic acid (0.372 g) was added to the above product to give the oxalate as a brown oil.
FAB-Mass: 351 (MH+).

Example 25: Synthesis of 1-{4-[(1-hydroxyethyl)phenethyl]piperidin-4-yl}indoline

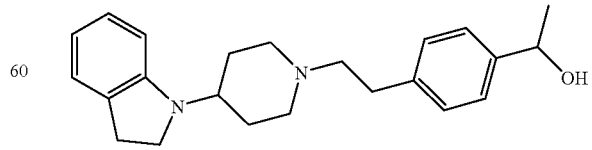

4-(1-Hydroxyethyl)phenethyl bromide (0.2 g) was treated as in Example 2 to give the title compound (0.044 g) as a yellow oil (yield: 12.6%).

Then oxalic acid (11 mg) was added to the above product to give a salt followed by recrystallization from ethanol to give the oxalate.

m.p. (oxalate): 132° C.

Oxalate $^1$H-NMR (400 MHz, DMSO-$d_6$):

δ(ppm) 1.30(3H, d, J=6.4 Hz), 1.86(4H, m), 2.88(2H, t, J=8.0 Hz), 2.92(4H, m), 3.15(2H, m), 3.32(2H, t, J=8.4 Hz), 3.54(2H, m), 3.67(1H, m), 4.69(1H, q, J=6.7 Hz), 6.51(1H, d, J=8.0 Hz), 6.55(1H, t, J=8.0 Hz), 6.99(1H, t, J=8.0 Hz), 7.02(1H, d, J=8.0 Hz), 7.22(2H, d, J=8.0 Hz), 7.30(1H, d, J=8.0 Hz).

FAB-Mass: 351(MH+).

Example 26: Synthesis of 1-{1-[4-(2-hydroxyethoxy)phenethyl]piperidin-4-yl}indoline

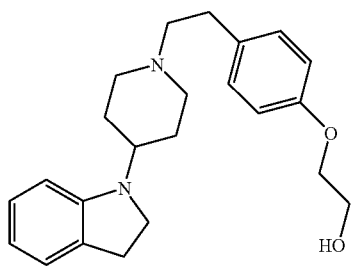

N,N-Dimethylformamide (2.5 ml) was added to 1-[1-(4-hydroxyphenethyl)piperidin-4-yl]indoline (0.1 g), potassium carbonate (0.081 g) and 1-bromo-2-di(t-butyl)dimethylsilyloxyethane (0.20 g) and the resultant mixture was heated and stirred at 80° C. for 28 hr. After allowing to cool, it was extracted with ethyl acetate (200 ml), washed with brine, dried over anhydrous magnesium sulfate and concentrated under reduced pressure. The residue was purified by silica gel column chromatography (hexane/ethyl acetate system) to give a colorless oil. Then this product was dissolved in tetrahydrofuran (1.3 ml) and a 2.0 M solution (0.88 ml) of tetrabutylammonium fluoride in tetrahydrofuran was added thereto followed by stirring the mixture at room temperature for 1 hr. The resultant mixture was extracted with ethyl acetate (200 ml), washed with brine, dried over anhydrous magnesium sulfate and concentrated under reduced pressure. The residue was purified by silica gel column chromatography (hexane/ethyl acetate system) to give the title compound (0.124 g) as a colorless oil (yield: 69.0%).

Free $^1$H-NMR (400 MHz, CDCl$_3$):

δ(ppm) 1.80(4H, m), 2.11(2H, dt, J=3.2, 11.6 Hz), 2.58 (2H, m), 2.76(2H, m), 2.94(2H, t, J=8.4 Hz), 3.12(2H, br-d), 3.39(2H, t, J=8.4 Hz), 3.40(1H, m), 3.94(2H, t, J=8.4 Hz), 4.06(2H, t, J=8.4 Hz), 6.40(1H, d, J=7.6 Hz), 6.60(1H, t, J=7.6 Hz), 6.85(2H, d, J=8.4 Hz), 7.04(2H, m), 7.13(2H, d, J=8.4 Hz).

ESI-Mass: 367.2(MH+).

Next, hydrochloric acid was added to the above product to give the hydrochloride of the title compound as colorless crystals.

m.p. (hydrochloride): 229° C.

Example 27: Synthesis of 1-[1-(4-trifluoromethylphenethyl)piperidin-4-yl]indoline

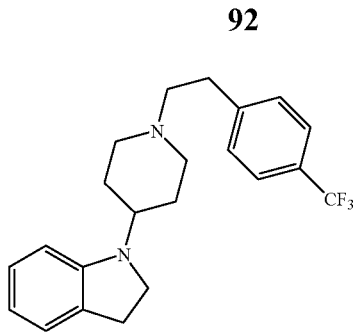

1-(Piperidin-4-yl)indoline (1.0 g) and 4-trifluoromethylphenylacetic acid (1.0 g) were treated as in Example 8 to give the hydrochloride (0.98 g) of the title compound as a white powder (yield: 48%).

m.p. (hydrochloride): 212° C. (decomp.).

$^1$H-NMR (400 MHz, DMSO-$d_6$):

δ(ppm) 1.81–1.89(2H, m), 1.94–2.09(2H, m), 2.88(2H, t, J=8 Hz), 3.02–3.20(4H, m), 3.28–3.36(4H, m), 3.60–3.79 (3H, m), 6.52–6.58(2H, m), 6.96–7.04(2H,m), 7.53(2H, d, J=8 Hz), 7.72(2H, d, J=8 Hz).

FAB-Mass: 375(MH+).

Example 28: Synthesis of 1-[1-(4-methanesulfonylphenethyl)piperidin-4-yl]indoline

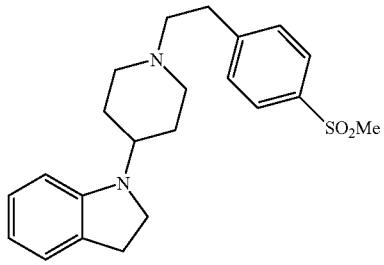

1-(Piperidin-4-yl)indoline (200 mg) and 4-methanesulfonylphenethyl bromide (290 mg) were treated as in Example 2 to give the title compound (180 mg) as a white powder (yield: 43%).

m.p. (hydrochloride): 208–210° C.

$^1$H-NMR (400 MHz, CDCl$_3$):

δ(ppm) 1.69–1.86(4H, m), 2.10–2.18(2H, m), 2.61–2.67 (2H, m), 2.87–2.98(4H, m), 3.04(3H, s), 3.06–3.14(2H, m), 3.35–3.44(3H, m), 6.41(1H, d, J=8 Hz), 6.60(1H, t, J=8 Hz), 7.01–7.06(2H, m), 7.41(2H, d, J=8 Hz), 7.85(2H, d, J=8 Hz).

FAB-Mass: 385(MH+).

Example 29: Synthesis of 1-[1-(4-nitrophenethyl)piperidin-4-yl]indoline

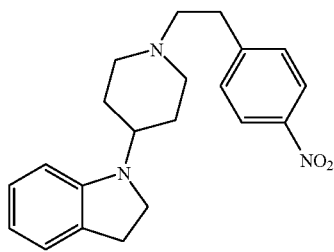

1-(Piperazin-4-yl)indoline (2.00 g) was dissolved in dimethylformamide (20 ml) and 4-(2-bromoethyl)nitrobenzene (10.0 g) and triethylamine (2.9 ml) were added thereto followed by stirring the resultant mixture at 100° C. overnight. After adding water to the reaction solution, extracted with ethyl acetate, the organic layer was washed with brine and dried over magnesium sulfate. After distilling off the solvent, the obtained residue was purified by silica gel column chromatography (hexane/ethyl acetate system) to give the title compound (1.05 g) as a slightly yellow solid.

$^1$H-NMR (400 MHz, CDCl$_3$):

δ(ppm) 1.70–1.90(4H, m), 2.14–2.22(2H, m), 2.64–2.72 (4H, m), 2.90–3.00(2H, m), 3.08–3.16(2H, m), 3.36–3.46 (3H, m), 6.41(1H, d, J=7.6 Hz), 6.61(1H, d, J=7.6 Hz), 7.02–7.08(2H, m), 7.35–7.40(2H, m), 8.13–8.18(2H, m).

FAB-Mass: 352(MH+).

m.p.: 95–97° C.

Example 30: Synthesis of 1-[1-(4-aminophenethyl)piperidin-4-yl]indoline

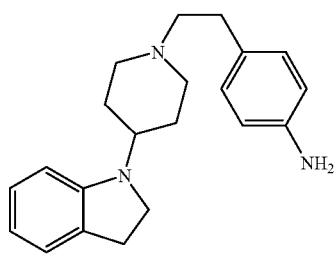

1-[1-(4-Nitrophenethyl)piperidin-4-yl]indoline (780 g) was dissolved in methanol (7 ml) and conc. hydrochloric acid (0.5 ml) was added dropwise into the resultant solution. Subsequently, the resultant mixture was catalytically reduced under atmospheric pressure in the presence of a palladium catalyst. After filtering off the catalyst, a 1 N aqueous solution of sodium hydroxide was added to the filtrate followed by extraction with chloroform. The organic layer was washed with brine and dried over magnesium sulfate. After evaporating the solvent, the title compound (620 mg) was obtained as an oil.

$^1$H-NMR (400 MHz, CDCl$_3$):

δ(ppm) 1.70–1.85(4H, m), 2.06–2.15(2H, m), 2.52–2.60 (2H, m), 2.67–2.75(2H, m), 2.94(2H, t, J=8.2 Hz), 3.08–3.16 (2H, m), 3.35–3.45(3H, m), 3.57(2H, br-s), 6.41(1H, d, J=8.0 Hz), 6.57–6.67(3H, m), 6.97–7.02(2H, m), 7.05(1H, d, J=8.0 Hz).

FAB-Mass: 322(MH+).

Example 31: Synthesis of 1-[1-(4-methylsulfonylaminophenethyl)piperidin-4-yl]-indoline and 1-{1-[4-bis(methyl-sulfonyl)aminophenethyl]piperidin-4-yl)indoline

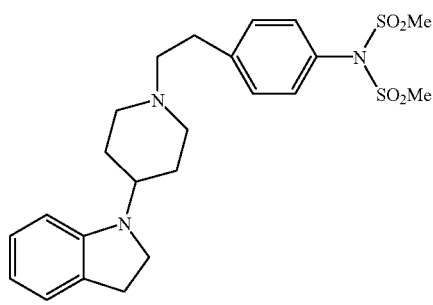

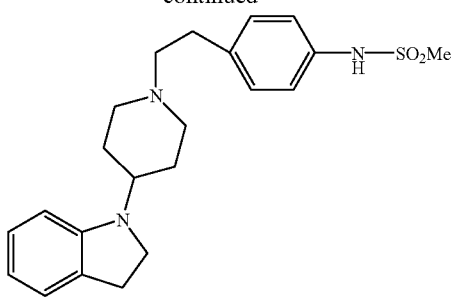

1-[1-(4-Aminophenethyl)piperidin-4-yl]indoline (140 mg) was dissolved in methylene chloride (2 ml). Under ice cooling, methanesulfonyl chloride (0.12 ml) and triethylamine (0.1 ml) were added to the resultant solution followed by stirring for 45 min. After adding a 10% aqueous solution of potassium carbonate, the reaction solution was extracted with ethyl acetate. The organic layer was washed with brine and dried over magnesium sulfate. After evaporating the solvent, the resulting residue (150 mg) was purified by NH-silica gel column chromatography (hexane/ethyl acetate system) to successively give 1-{1-[4-bis(methylsulfonyl)aminophenethyl]piperidin-4-yl}indoline (50 mg) and 1-[1-(4-methylsulfonylaminophenethyl)piperidin-4-yl]indoline (35 mg) each as an oil.

(1) 1-{1-[4-bis(methylsulfonyl)aminophenethyl]piperidin-4-yl}indoline $^1$H-NMR (400 MHz, CDCl$_3$):

δ(ppm) 1.71–1.87(4H, m), 2.09–2.18(2H, m), 2.60–2.66 (2H, m), 2.83–2.89(2H, m), 2.95(2H, t, J=8.4 Hz), 3.08–3.15 (2H, m), 3.35–3.45(3H, m), 3.39(6H, s), 6.41(1H, d, J=7.5 Hz), 6.60(1H, t, J=7.5 Hz), 7.01–7.07(2H, m), 7.25–7.33 (4H, m).

FAB-Mass: 478(MH+).

(2) 1-[1-(4-methylsulfonylaminophenethyl)piperidin-4-yl]indoline $^1$H-NMR (400 MHz, DMSO-d$_6$):

δ(ppm) 1.52–1.66(4H, m), 2.00–2.08(2H, m), 2.64–2.70 (2H, m), 2.80–2.86(2H, m), 2.96–3.02(2H, m), 3.25–3.40 (3H, m), 3.32(3H, s), 6.41(1H, d, J=7.4 Hz), 6.48(1H, t, J=7.4 Hz), 6.91–6.99(2H, m), 7.07–7.19(4H, m).

FAB-Mass: 400(MH+).

Example 32: Synthesis of 1-[1-(4-acetamidophenethyl)piperidin-4-yl]indoline

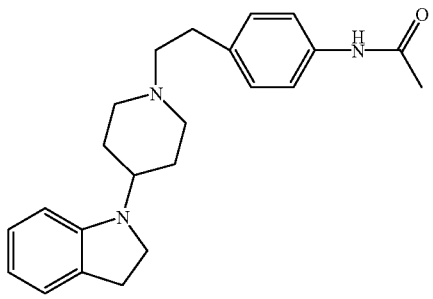

1-[1-(4-Aminophenethyl)piperidin-4-yl]indoline (310 mg) was dissolved in methylene chloride (3 ml). Under ice cooling, acetyl chloride (0.103 ml) was added to the resultant solution followed by stirring the obtained mixture for 45 min. After adding a 10% aqueous solution of potassium carbonate, the reaction solution was extracted with ethyl acetate. Then the organic layer was washed with brine and dried over magnesium sulfate. After evaporating the solvent, the resulting residue was purified by NH-silica gel column chromatography (hexane/ethyl acetate system) to give the title compound (200 mg) as an oil.
¹H-NMR (400 MHz, CDCl₃):
δ(ppm) 1.70–1.86(4H, m), 2.08–2.16(2H, m), 2.17(3H, s), 2.56–2.62(2H, m), 2.76–2.82(2H, m), 2.95(2H, t, J=8.4 Hz), 3.08–3.14(2H, m), 3.35–3.44(3H, m), 6.41(1H, d, J=7.5 Hz), 6.60(1H, t, J=7.5 Hz), 7.04(1H, t, J=7.5 Hz), 7.10(1H, br-s), 7.16(2H, d, J=8.4 Hz), 7.40(2H, d, J=8.4 Hz).
FAB-Mass: 364(MH+).
Example 33: Synthesis of 1-[1-(4-ethylaminophenethyl)piperidin-4-yl]indoline

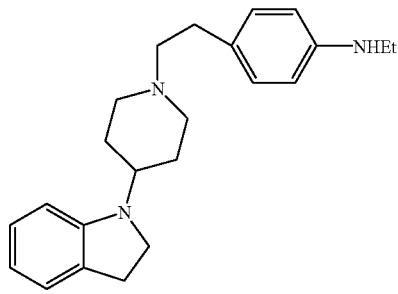

1-[1-(4-Acetaminophenethyl)piperidin-4-yl]indoline (135 mg) was dissolved in tetrahydrofuran (5 ml). After adding lithium aluminum hydride (28 mg) at room temperature, the resultant mixture was heated under reflux for 2 hr. After adding water, the reaction solution was extracted with ethyl acetate. Then the organic layer was washed with brine and dried over magnesium sulfate. After evaporating the solvent, the obtained residue was purified by NH-silica gel column chromatography (hexane/ethyl acetate system) to give the title compound (40 mg) as an oil.
¹H-NMR (400 MHz, CDCl₃):
δ(ppm) 1.25(3H, t, J=7.1 Hz), 1.72–1.86(4H, m), 2.06–2.14(2H, m), 2.54–2.60(2H,m), 2.68–2.76(2H,m), 2.91–2.98(2H, m), 3.09–3.16(3H, m), 3.35–3.44(4H, m), 6.41(1H, d, J=8.0 Hz), 6.54–6.70(3H, m), 7.00–7.07(4H, m).
Example 34: Synthesis of 1-[1-(4-hydroxyiminomethylphenethyl piperidin-4-yl]indoline

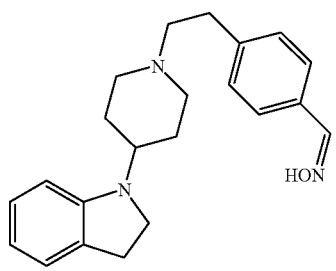

4-(2-Bromoethyl)benzaldoxime (0.49 g) was treated as in Example 2 to give the title compound (0.480 g) as pale yellow crystals (yield: 70.1%).
Free
¹H-NMR (400 MHz, CDCl₃):
δ(ppm) 1.87(4H, m), 2.19(2H, dt, J=3.0, 11.2 Hz), 2.68 (2H, m), 2.89(2H, m), 2.93(2H, t, J=8.4 Hz), 3.20(2H, br-d), 3.40(2H, t, J=8.4 Hz), 3.43(1H, m), 6.42(1H, d, J=8.0 Hz), 6.61(1H, t, J=8.0 Hz), 7.03(1H, t, J=8.0 Hz), 7.05(1H, d, J=8.0 Hz), 7.21(2H, d, J=8.0 Hz), 7.49(2H, d, J=8.0 Hz), 8.11(1H, s).

Next, hydrochloric acid was added to the product to give the hygroscopic and amorphous hydrochloride of the title compound was obtained.
FAB-Mass: 350(MH+).
Example 35: Synthesis of 1-[1-(4-aminomethylphenethyl)piperidin-4-yl]indoline

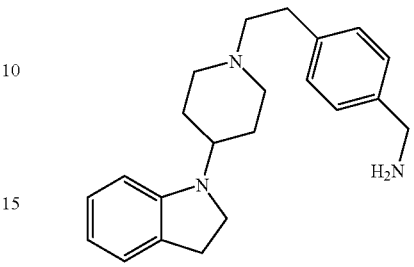

1-[1-(4-Hydroxyiminomethylphenethyl)piperidin-4-yl]indoline (2.71 g) was dissolved in tetrahydrofuran (40 ml). Under ice cooling, lithium aluminum hydride (0.59 g) was added thereto and the resultant mixture was heated under reflux for 2 hr. Then the reaction mixture was ice cooled again followed by the addition of water (0.6 ml), a 5 N aqueous solution (0.6 ml) of sodium hydroxide and further water (1.8 ml) thereto. The resulting precipitate was filtered off and the filtrate was washed with ethyl acetate and concentrated under reduced pressure to give the title compound (1.462 g) as a pale yellow oil (yield: 56.2%).
Free
¹H-NMR (400 MHz, CDCl₃):
δ(ppm) 1.58(2H, m), 1.79(4H, m), 2.12(2H, dt, J=3.0, 11.6 Hz), 2.61(2H, m), 2.81(2H, m), 2.95(2H, t, J=8.4 Hz), 3.13(2H, br-d), 3.39(2H, t, J=8.4 Hz), 3.40(1H, m), 3.84(2H, s), 6.42(1H, d, J=7.6 Hz), 6.60(1H, t, J=7.6 Hz), 7.04(1H, t, J=7.6 Hz), 7.05(1H, d, J=7.6 Hz), 7.18(2H, d, J=8.4 Hz), 7.24(2H, d, J=8.4 Hz).
Next, hydrochloric acid was added to the product to give the hygroscopic and amorphous hydrochloride of the title compound was obtained.
FAB-Mass: 336(MH+).
Example 36: Synthesis of 1-[1-(4-acetamidomethylphenethyl)piperidin-4-yl]indoline

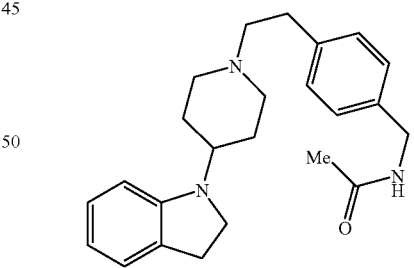

1-[1-(4-Aminomethylphenethyl)piperidin-4-yl]indoline (0.6 g) was dissolved in tetrahydrofuran (9.0 ml). Under ice cooling, acetyl chloride (0.14 ml) was added dropwise thereinto and the resultant mixture was stirred for 2 hr. After adding a saturated aqueous solution of sodium bicarbonate, the mixture was extracted with ethyl acetate, washed with brine, dried over anhydrous magnesium sulfate and concentrated under reduced pressure. The residue was purified by Cromatorex NH silica gel column chromatography (hexane/ethyl acetate system) to give the title compound (0.518 g) as a pale yellow oil (yield: 79.2%).

Next, hydrochloric acid was added to the product to give the pale yellow, hygroscopic and amorphous hydrochloride of the title compound.
Hydrochloride
$^1$H-NMR (400 MHz, DMSO-$d_6$):
δ(ppm) 1.86(3H, s), 1.90(2H, m), 2.08(2H, m), 2.90(2H, t, J=8.2 Hz), 3.08(4H, m), 3.23(2H, m), 3.33(2H, t, J=8.2 Hz), 3.63(2H, br-d), 3.74(1H, m), 4.22(2H, d, J=6.0 Hz), 6.58(1H, d, J=7.6 Hz), 6.59(1H, t, J=7.6 Hz), 7.01(1H, t, J=7.6 Hz), 7.05(1H, d, J=7.6 Hz), 7.23(4H, s), 8.36(1H, t, J=6.0 Hz).
FAB-Mass: 378(MH+).

Example 37: Synthesis of 1-[1-(4-chloroacetamidomethylphenethyl)piperidin-4-yl]indoline

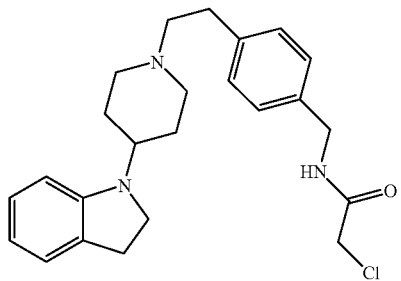

1-[1-(4-Aminomethylphenethyl)piperidin-4-yl]indoline (0.1 g) and chloroacetyl chloride (0.026 ml) were treated as in Example 36 to give the title compound (0.074 g) as a pale yellow oil (yield: 62.1%).
Free
$^1$H-NMR (400 MHz, CDCl$_3$):
δ(ppm) 1.79(4H, m), 2.12(2H, m), 2.61(2H, m), 2.82(2H, m), 2.94(2H, t, J=8.4 Hz), 3.12(2H, br-d), 3.39(2H, t, J=8.4 Hz), 3.40(1H, m), 4.13(2H, s), 4.46(2H, d, J=5.6 Hz), 6.41(1H, d, J=7.6 Hz), 6.60(1H, t, J=7.6 Hz), 6.83(1H, br-s), 7.04(2H, t, J=8.0 Hz), 7.20(4H, m).

Next, oxalic acid (8 mg) was added to the above free compound to give a salt followed by recrystallization from a solvent mixture of ethanol with isopropyl ether. Thus, the oxalate (0.054 g) of the title compound was obtained as colorless crystals.
m.p. (oxalate): 138° C.
FAB-Mass: 412(MH+).

Example 38: Synthesis of 1-[1-(4-methanesulfonylaminomethylphenethyl)piperidin-4-yl]indoline

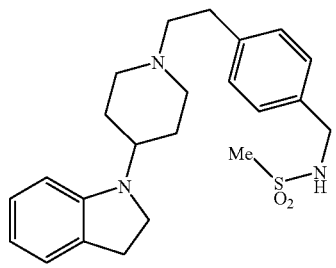

1-[1-(4-Aminomethylphenethyl)piperidin-4-yl]indoline (0.120 g) and methanesulfonyl chloride (0.030 ml) were treated as in Example 36 to give the title compound (0.078 g) as a pale yel low oil (yield: 54.5%).
Free
$^1$H-NMR (400 MHz, CDCl$_3$):
δ(ppm) 1.85(4H, m), 2.20(2H, m), 2.66(2H, m), 2.86(2H, m), 2.89(3H, s), 2.95(2H, t, J=8.7 Hz), 3.28(2H, m), 3.39(2H, t, J=8.7 Hz), 3.42(1H, m), 4.30(2H, d, J=5.8 Hz), 4.63(1H, m), 6.41(1H, d, J=8 Hz), 6.61(1H, t, J=8 Hz), 7.03(1H, t, J=8 Hz), 7.05(1H, d, J=8 Hz), 7.21(2H, d, J=8 Hz), 7.28(2H, d, J=8 Hz).

Next, oxalic acid (18 mg) was added to the above free compound followed by recrystallization from a solvent mixture of acetone with water to give the oxalate of the title compound.
m.p. (oxalate): 199° C.
FAB-Mass: 414(MH+).

Example 39: Synthesis of 1-[1-(4-propionylaminomethylphenethyl)piperidin-4-yl]-3-methylindoline

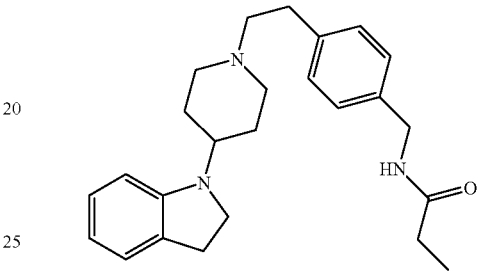

1-[1-(4-Aminomethylphenethyl)piperidin-4-yl]-3-methylindoline (0.1 g) and propionyl chloride (0.028 ml) were treated as in Example 36 to give the title compound (0.122 g) as a pale yellow oil (yield: quantitative).

Next, oxalic acid (13 mg) was added thereto followed by recrystallization from ethyl acetate to give the oxalate (0.064 g) of the title compound as colorless crystals.
m.p. (oxalate): 96–105° C
Oxalate
$^1$H-NMR (400 MHz, DMSO-$d_6$):
δ(ppm) 1.02(3H, t, J=8.4 Hz), 1.86(2H, m), 2.10(2H, m), 2.13(2H, q, J=8.4 Hz), 2.81(2H, m), 2.88(2H, t, J=8.4 Hz), 2.91(2H, m), 3.07(2H, m), 3.10(2H, t, J=8.4 Hz), 3.49(2H, br-d), 3.64(1H, m), 4.22(2H, s), 6.52(2H, m), 7.01(2H, m), 7.20(4H, m).
FAB-Mass: 392(MH+).

Example 40: Synthesis of 1-[1-(4-carbamoylphenethyl)piperidin-4-yl]indoline

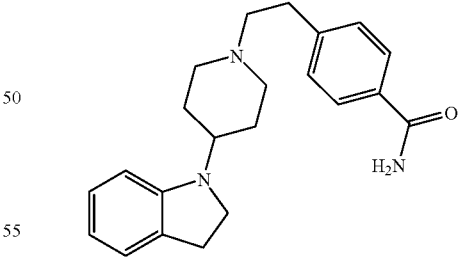

4-Carbamoylphenethyl bromide (0.135 g) was treated as in Example 2 to give the title compound (0.097 g) as pale yellow crystals (yield: 56.6%).
Next, oxalic acid (13 mg) was added thereto to give the amorphous oxalate of the title compound.
m.p. (oxalate): 178–193° C.
Oxalate
$^1$H-NMR (400 MHz, DMSO-$d_6$):
δ(ppm) 1.78(4H, m), 2.61(2H, m), 2.87(2H, t, J=8.4 Hz), 2.94(4H, m), 3.31(2H, t, J=8.4 Hz), 3.34(2H, m), 3.55(1H, m), 6.48(1H, d, J=7.6 Hz), 6.53(1H, t, J=7.6 Hz), 6.98(1H, t, J=7.6 Hz), 7.01(1H, d, J=7.6 Hz), 7.31(1H, m), 7.34(2H, d, J=8.4 Hz), 7.82(2H, d, J=8.4 Hz), 7.93(1H, m).

ESI-Mass: 350.1(MH+).

Example 41: Synthesis of 1-[1-(4-N-isopropylcarbamoylmethylphenethyl)piperidin-4-yl]indoline

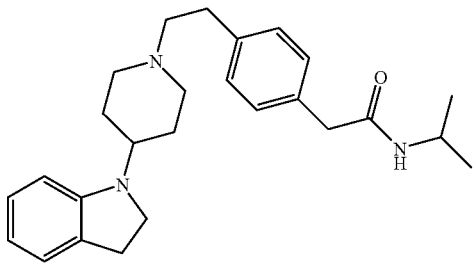

N-Isopropyl-4-(2-bromoethyl)phenylacetamide (0.029 g) was treated as in Example 2 to give the title compound (0.040 g) as colorless crystals (yield: 92.1%).

Next, oxalic acid (5 mg) was added thereto to give the amorphous oxalate of the title compound.

m.p. (oxalate): 88–96° C.

Oxalate $^1$H-NMR (400 MHz, DMSO-$d_6$):

δ(ppm) 1.64(6H, d, J=6.8 Hz), 1.82(4H, m), 2.82–2.92 (6H, m), 3.06(2H, m), 3.31(2H, m), 3.33(2H, s), 3.46(2H, m), 3.63(1H, m), 9.79(1H, q, J=6.8 Hz), 6.50(1H, d, J=8 Hz), 6.54(1H, t, J=8 Hz), 6.98(1H, t, J=8 Hz), 7.01(1H, d, J=8 Hz), 7.19(4H, s), 7.93(1H, d, J=8 Hz).

ESI-Mass: 406.25(MH+).

Example 42: Synthesis of 1-[1-(4-sulfamoylphenethyl)piperidin-4-yl]indoline

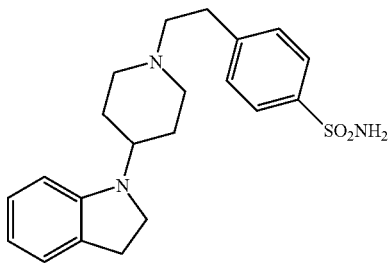

1-(Piperidin-4-yl)indoline (300 mg) and 4-sulfamoylphenethyl bromide (400 mg) were treated as in Example 2 to give the title compound (60 mg) as a pale yellow powder (yield: 10%).

m.p.: 207–210° C.

$^1$H-NMR (400 MHz, CDCl$_3$):

δ(ppm) 1.70–1.87(4H, m), 2.11–2.20(2H, m), 2.60–2.66 (2H, m), 2.86–2.98(4H, m), 3.08–3.15(2H, m), 3.34–3.45 (3H, m), 6.41(1H, d, J=8 Hz), 6.61(1H, d, J=8 Hz), 7.01–7.08(2H, m), 7.36(2H, d, J=8 Hz), 7.85(2H, d, J=8 Hz).

FAB-Mass: 386(MH+).

Example 43: Synthesis of 1-{1-[(3-(2-hydroxyethoxy)phenethyl]piperidin-4-yl}indoline

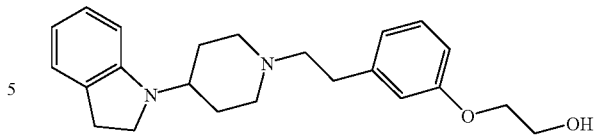

3-[2-(t-Budyldimethylsilyloxy)ethoxy]phenethyl bromide (0.33 g) was treated as in Example 24 to give the title compound (0.197 g) as a yellow oil (yield: 53.8%)

Next, oxalic acid (48 mg) was added thereto to give the oxalate of the title compound.

m.p. (oxalate): 118° C.

$^1$H-NMR (400 MHz, DMSO-$d_6$):

δ(ppm) 1.86(4H, m), 2.88(2H, t, J=8.2 Hz), 2.92(4H, m), 3.17(2H, m), 3.31(2H, t, J=8.2 Hz), 3.53(2H, br-d), 3.67(1H, m), 3.71(2H, t, J=9.0 Hz), 3.08(2H, t, J=9.0 Hz), 6.52(1H, d, J=7.6 Hz), 6.55(1H, t, J=7.6 Hz), 6.83(2H, m), 6.87(1H, br-s), 6.99(1H, t, J=7.6 Hz), 7.02(1H, d, J=7.6 Hz), 7.24(1H, t, J=8.4 Hz).

FAB-Mass: 367(MH+).

Example 44: Synthesis of 1-{1-[4-(2-dimethylaminoethoxy)phenethyl]piperidin-4-yl}indoline

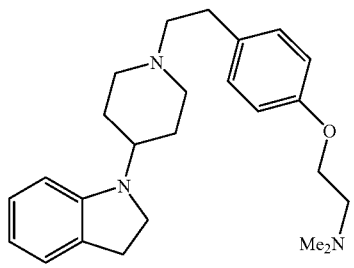

N,N-Dimethylformamide (2.5 ml) was added to 1-[1-(4-hydroxyphenethyl)piperidin-4-yl]indoline (0.1 g), potassium carbonate (0.081 g) and 2-dimethylaminoethyl chloride hydrochloride (0.078 g) followed by stirring at 80° C. overnight (12 hr). After allowing to cool, the resultant mixture was mixed with ethyl acetate (200 ml) and the layers were separated. The organic layer was washed with brine, dried over anhydrous magnesium sulfate and concentrated under reduced pressure. The residue was purified by silica gel column chromatography (hexane/ethyl acetate system) to give the title compound (0.052 g) as a brown oil (yield: 27.0%).

Next, hydrochloric acid was added thereto to give the hydrochloride of the title compound.

m.p. (hydrochloride): 258–259° C.

Hydrochloride $^1$H-NMR (400 MHz, DMSO-$d_6$):

δ(ppm) 1.87(2H, m), 2.12(2H, m), 2.82(6H, m), 2.91(2H, t, J=8.4 Hz), 3.06(4H, m), 3.21(2H, m), 3.34(2H, t, J=8.4 Hz), 3.48(2H, m), 3.63(2H, br-d), 3.75(1H, m), 4.37(2H, t, J=4.8 Hz), 6.59(1H, d, J=8.0 Hz), 6.60(1H, t, J=8.0 Hz), 6.98(2H, d, J=8.6 Hz), 7.01(1H, t, J=8.0 Hz), 7.05(1H, d, J=8.0 Hz), 7.24(2H, d, J=8.6 Hz).

ESI-Mass: 394.2(MH+).

Example 45: Synthesis of 1-{1-[3,4-di(hydroxymethyl)phenethyl]piperidin-4-yl}indoline

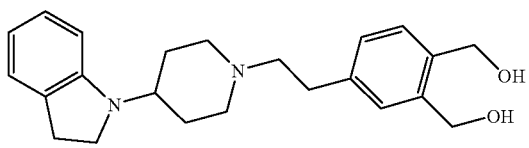

3,4-Di[(t-butyl)dimethylsilyloxymethyl]phenethyl bromide (0.421 g) was treated as in Example 24 to give the title compound (0.318 g) as a pale yellow oil (yield: 98.6%).

Next, hydrochloric acid was added thereto to give a salt followed by recrystallization from ethanol to give the hydrochloride (0.617 g) of the title compound as colorless crystals (yield: 47.1%).

m.p. (hydrochloride): 178° C.

Hydrochloride $^1$H-NMR (400 MHz, DMSO-$d_6$):

δ(ppm) 1.89(2H, m), 1.04(2H, m), 2.90(2H, t, J=8.0 Hz), 3.08(4H, m), 3.25(2H, m), 3.33(2H, t, J=8.0 Hz), 3.66(2H, br-d), 3.73(1H, m), 4.50(2H, s), 4.53(2H, s), 6.55(1H, d, J=7.6 Hz), 6.58(1H, t, J=7.6 Hz), 7.01(1H, t, J=7.6 Hz), 7.04(1H, d, J=7.6 Hz), 7.14(1H, dd, J=1.6, 8.0 Hz), 7.32(1H, d, J=1.6 Hz), 7.34(1H, d, J=8.0 Hz).

FAB-Mass: 367(MH+).

Example 46: Synthesis of 1-{1-[3,4-(methylenedioxy)phenethyl]piperidin-4-yl}indoline

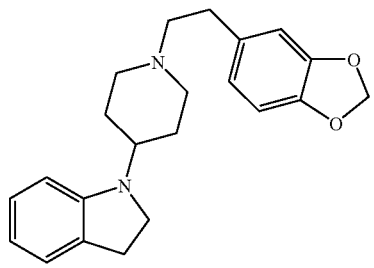

3,4-(Methylenedioxy)phenylacetic acid (0.198 g) was treated as in Example 11 to give the title compound (0.304 g) as a colorless oil (yield: 89.8%).

Next, hydrochloric acid was added thereto to give a salt followed by recrystallization from ethanol to give the hydrochloride of the title compound as colorless crystals.

m.p. (hydrochloride): 236° C.

Hydrochloride $^1$H-NMR (400 MHz, DMSO-$d_6$):

δ(ppm) 1.88(2H, br-d), 2.12(2H, m), 2.93(2H, t, J=8.0 Hz), 3.03(4H, m), 3.20(2H, m), 3.37(2H, t, J=8.0 Hz), 3.61(2H, br-d), 3.78(1H, m), 5.99(2H, s), 6.74(1H, d, J=8.0 Hz), 6.88(2H, m), 7.06(2H, m).

FAB-Mass: 361(MH+).

Example 47: Synthesis of 1-{1-[2-(4-chlorophenylsulfonylamino)ethyl]piperidin-4-yl}indoline

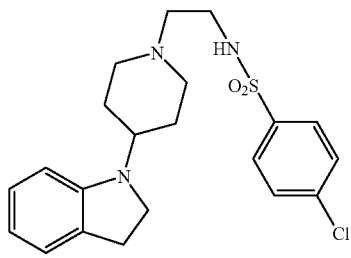

1-[1-(2-Aminoethyl)piperidin-4-yl]indoline (113 mg) was dissolved in chloroform (3 ml). Under ice cooling, 4-chlorobenzenesulfonyl chloride (97 mg) was added thereto and the resultant mixture was stirred for 6 hr. After adding water, the reaction solution was extracted with chloroform. The organic layer was washed with brine and dried over magnesium sulfate. After evaporating the solvent, the resulting residue (205 mg) was purified by NH-silica gel column chromatography (methanol/methylene chloride system) to give the title compound (134 mg) as an oil.

$^1$H-NMR (400 MHz, CDCl$_3$):

δ(ppm) 1.54–1.66(2H, m), 1.71–1.78(2H, m), 1.99–2.07 (2H, m), 2.42(2H, t, J=5.8 Hz), 2.70–2.76(2H, m), 2.94–3.02 (4H, m), 3.28–3.40(3H, m), 5.30(1H, br-s), 6.36(1H, d, J=8.0 Hz), 6.59–6.63(1H, m), 7.00–7.08(2H, m), 7.47–7.52 (2H, m), 7.80–7.84(2H, m).

FAB-Mass: 420(MH+).

Example 48: Synthesis of 1-{1-[2-(4-methoxyphenylsulfonylamino)ethyl]piperidin-4-yl}indoline

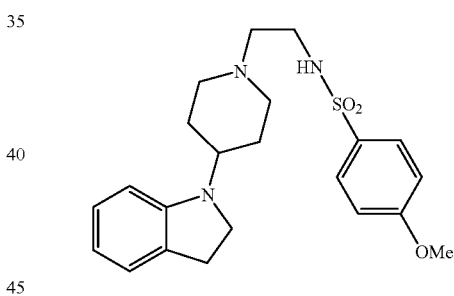

1-[1-(2-Aminoethyl)piperidin-4-yl]indoline (113 mg) was dissolved in chloroform (3 ml). Under ice cooling, 4-methoxybenzenesulfonyl chloride (95 mg) was added thereto and the resultant mixture was stirred at room temperature overnight. After adding water, the reaction solution was extracted with chloroform. The organic layer was washed with brine and dried over magnesium sulfate. After evaporating the solvent, the resulting residue (80 mg) was purified by NH-silica gel column chromatography (methanol/methylene chloride system) to give the title compound (45 mg) as an oil.

$^1$H-NMR (400 MHz, CDCl$_3$):

δ(ppm) 1.54–1.76(4H, m), 1.96–2.04(2H, m), 2.40(2H, t, J=5.8 Hz), 2.67–2.74(2H, m), 2.93–3.00(4H, m), 3.27–3.36 (1H, m), 3.37(2H, t, J=8.4 Hz), 3.86(3H, s), 5.19(1H, br-s), 6.36(1H, d, J=8.0 Hz), 6.58–6.62(1H, m), 6.95–7.08(4H, m), 7.78–7.83(2H, m).

FAB-Mass: 416(MH+).

Example 49: Synthesis of 1-{1-[2-(4-pyridyl)ethyl]piperidin-4-yl}indoline

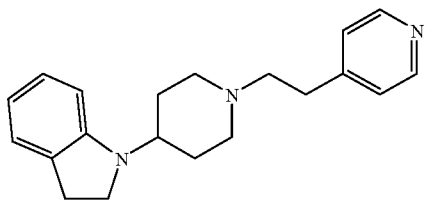

1-(4-Piperidyl)indoline (0.1 g) was dissolved in ethanol (5 ml). After adding 4-vinylpyridine (0.16 ml), the resultant mixture was heated under reflux in a nitrogen atmosphere for 12 hr. Then the reaction solution was concentrated under reduced pressure and purified by silica gel column chromatography (toluene/acetone system) to give the title compound (0.064 g) as a colorless oil (yield: 42.5%).

Free $^1$H-NMR (400 MHz, CDCl$_3$):

δ(ppm) 1.74–1.85(4H, m), 2.15(2H, dt, J=2.8, 12.0 Hz), 2.64(2H, m), 2.82(2H, m), 2.95(2H, t, J=8.4 Hz), 3.10(2H, br-d), 3.39(2H, t, J=8.4 Hz), 3.40(1H, m), 6.41(1H, d, J=8.0 Hz), 6.61(1H, t, J=8.0 Hz), 7.04(1H, t, J=8.0 Hz), 7.05(1H, d, J=8.0 Hz), 7.14(2H, dd, J=2.0, 4.8 Hz), 8.50(2H, dd, J=2.0, 4.8 Hz).

Next, hydrochloric acid was added to the above product to give the hydrochloride of the title compound as a hygroscopic pale yellow amorphous solid.

FAB-Mass: 308(MH+).

Example 50: Synthesis of 1-{1-[2-(2-pyridyl)ethyl]piperidin-4-yl}indoline

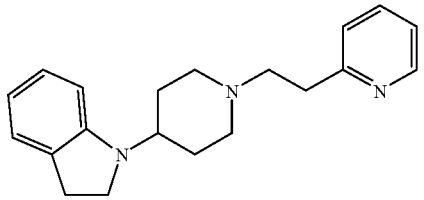

2-Vinylpyridine (0.16 ml) was treated as in Example 49 to give the title compound (0.041 g) as a colorless oil (yield: 27.2%).

Next, hydrochloric acid was added thereto to give a salt followed by recrystallization from ethanol-isopropyl-ether mixtures to give the hydrochloride (0.036 g) of the title compound.

m.p. (hydrochloride): 258–260° C.

Hydrochloride $^1$H-NMR (400 MHz, DMSO-d$_6$):

δ(ppm) 1.89(2H, br-d), 2.16(2H, m), 2.93(2H, t, J=8.0 Hz), 3.20(2H, m), 3.38(2H, t, J=8.0 Hz), 3.61(6H, m), 3.83(1H, br-t), 6.66(2H, m), 7.05(1H, t, J=8 Hz), 7.08(1H, d, J=8 Hz), 7.89(1H, m), 8.00(1H, d, J=7.6 Hz), 8.47(1H, m), 8.82(1H, d, J=5.2 Hz).

FAB-Mass: 308(MH+).

Example 51: Synthesis of 1-{1-[2-(3-pyridyl)ethyl]piperidin-4-yl}indoline

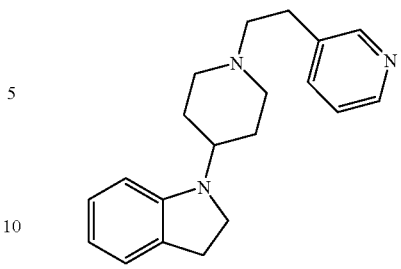

3-(2-Bromoethyl)pyridine (0.481 g) was treated as in Example 2 to give the title compound (0.601 g) as a pale yellow oil (yield: 75.5%).

Next, oxalic acid was added thereto to give a salt followed by recrystallization from ethanol to give the oxalate of the title compound.

m.p. (oxalate): 174° C.

Oxalate $^1$H-NMR (400 MHz, DMSO-d$_6$):

δ(ppm) 1.92(4H, m), 2.87(2H, t, J=8.4 Hz), 3.04(4H, m), 3.10(2H, m), 3.31(2H, t, J=8.4 Hz), 3.61(2H, br-d), 3.72(1H, m), 6.53(1H, d, J=7.6 Hz), 6.56(1H, t, J=7.6 Hz), 7.00(1H, t, J=7.6 Hz), 7.03(1H, d, J=7.6 Hz), 7.39(1H, dd, J=4.8, 7.6 Hz), 7.74(1H, ddd, J=1.6, 1.6, 7.6 Hz), 8.48(1H, dd, J=1.6, 4.8 Hz), 8.53(1H, J=1.6 Hz).

ESI-Mass: 308(MH+).

Example 52: Synthesis of 1-{1-[2-(2-methoxy-5-pyridyl)ethyl]piperidin-4-yl}indoline

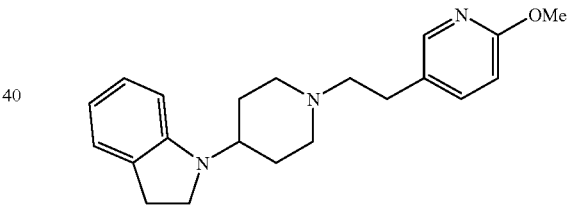

1-Bromo-2-(2-methoxypyridin-5-yl)ethane (1.221 g) was treated as in Example 2 to give the title compound (1.394 g) as a pale yellow oil (yield: 82.6%).

Next, oxalic acid (0.372 g) was added thereto to give a salt followed by recrystallization from ethanol to give the oxalate of the title compound.

m.p. (oxalate): 173° C.

Oxalate $^1$H-NMR (400 MHz, DMSO-d$_6$):

δ(ppm) 1.83–1.95(4H, br-d), 2.88(2H, t, J=8.4 Hz), 2.94 (4H, m), 3.15(2H, m), 3.31(2H, t, J=8.4 Hz), 3.53(2H, br-d), 3.68(1H, m), 3.83(3H, s), 6.52(1H, d, J=8.0 Hz), 6.55(1H, t, J=8.0 Hz), 6.81(1H, d, J=8.4 Hz), 6.99(1H, t, J=8.0 Hz), 7.02(1H, d, J=8.0 Hz), 7.64(1H, dd, J=2.4, 8.4 Hz), 8.08(1H, d, J=2.4 Hz).

FAB-Mass; 338(MH+).

Example 53: Synthesis of 1-{1-[2-(3-methoxypyridin-5-yl)-ethyl]piperidin-4-yl}indoline

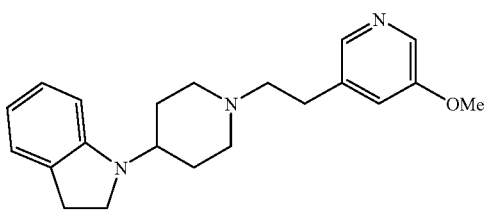

5-(2-Bromoethyl)-3-methoxypyridine (0.181 g) was treated as in Example 2 to give the title compound (1.104 g) as a yellow oil (yield: 37.1%).

Next, oxalic acid (28 mg) was added thereto to give a salt followed by recrystallization from ethanol to give the oxalate (0.077 g) of the title compound.
m.p. (oxalate): 220° C.
Oxalate
$^1$H-NMR (400 MHz, DMSO-d$_6$):
δ(ppm) 1.89(4H, m), 2.88(2H, t, J=8.4 Hz), 3.99(2H, m), 3.22(2H, m), 3.31(2H, t, J=8.4 Hz), 3.54(2H, br-d), 3.68(1H, m), 3.83(3H, s), 6.52(1H, d, J=7.6 Hz), 6.55(1H, t, J=7.6 Hz), 6.99(1H, t, J=7.6 Hz), 7.02(1H, d, J=7.6 Hz), 7.35(1H, t, J=2.0 Hz), 8.11(1H, t, J=2.0 Hz), 8.19(1H, t, J=2.0 Hz).
FAB-Mass: 338(MH+).

Example 54: Synthesis of 1-{1-[2-(2-cyanopyridin-5-yl)ethyl]piperidin-4-yl}indoline

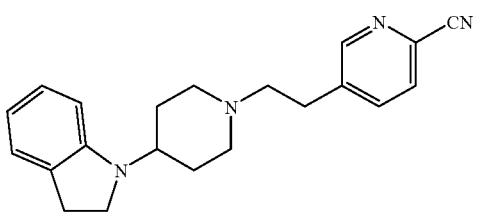

1-Bromo-2-(2-cyanopyridin-5-yl)ethane (0.406 g) was treated as in Example 2 to give the title compound (0.068 g) as a pale yellow oil (yield: 9.7%).

Next, oxalic acid (18 mg) was added thereto to give a salt followed by recrystallization from ethanol to give the oxalate of the title compound.
m.p. (oxalate): 136° C.
Oxalate
$^1$H-NMR (400 MHz, DMSO-d$_6$):
δ(ppm) 1.82(4H, m), 2.81(2H, m), 2.87(2H, t, J=8.2 Hz), 3.07(2H, m), 3.14(2H, m), 3.31(2H, t, J=8.2 Hz), 3.44(2H, br-d), 3.63(1H, m), 6.51(1H, d, J=7.6 Hz), 6.54(1H, t, J=7.6 Hz), 6.99(1H, t, J=7.6 Hz), 7.01(1H, d, J=7.6 Hz), 8.01(2H, m), 8.71(1H, d, J=1.6 Hz).
FAB-Mass: 333(MH+).

Example 55: Synthesis of 1-{1-[2-(2-hydroxymethylpyridin5-yl)ethyl]piperidin-4-yl}indoline

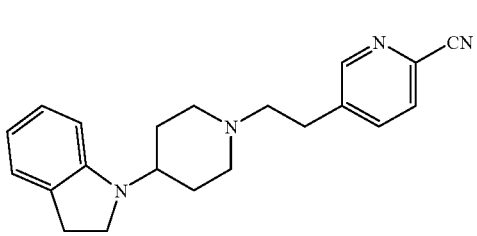

1-{1-[2-(2-Cyanopyridin-5-yl)ethyl]piperidin-4-yl}indoline (0.103 g) was dissolved in toluene (1.5 ml). In a nitrogen atmosphere at −78° C., a 1.5 M solution (0.44 ml) of diisobutylaluminum hydride in toluene was added thereto and the resultant mixture was stirred under the same conditions for 1 hr. Then the reaction solution was poured into a 5% aqueous solution of sulfuric acid and basified with an aqueous solution of sodium hydroxide. Next, diethyl ether was added and the layers were separated. The organic layer was washed with brine, dried over anhydrous magnesium sulfate and concentrated under reduced pressure to give the title compound (0.066 g) as a yellow oil (yield: 64.5%).
Free
$^1$H-NMR (400 MHz, CDCl$_3$)
δ(ppm) 1.79(4H, m), 2.13(2H, dt, J=2.8, 8.0 Hz), 2.60 (2H, m), 2.80(2H, m), 2.97(2H, d, J=8.4 Hz), 3.10(2H, br-d), 3.39(2H, t, J=8.4 Hz), 3.40(1H, m), 3.95(2H, s), 6.41(1H, d, J=7.6 Hz), 6.60 (1H, t, J=7.6 Hz), 7.04 (1H, t, J=7. 6 Hz), 7.05 (1H, d, J=7.6 Hz), 7.21(1H, d, J=8.0 Hz), 7.50(1H, dd, J=2.0, 8.0 Hz), 8.42(1H, d, J=2.0 Hz).
ESI-Mass: 338.3(MH+).

Next, oxalic acid (18 mg) was added to the above product to give the oxalate of the title compound as a hygroscopic amorphous solid.

Example 56 Synthesis of 1-{1-[2-(3-hydroxymethylpyridin-5-yl)ethyl]piperidin-4-yl}indoline

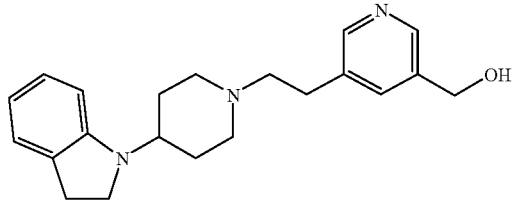

5-(2-Bromoethyl)-3-(t-butyl)dimethylsilyloxymethyl-pyridine (0.248g) was treated as in Example 24 to give the title compound (0.150 g) as a pale yellow oil (yield: 61.4%).

Next, oxalic acid (40 mg) was added thereto to give a salt followed by recrystallization from ethanol to give the oxalate (0.143 g) of the title compound.
m.p. (oxalate): 177° C.
Oxalate
$^1$H-NMR (400 MHz, DMSO-d$_6$):
δ(ppm) 1.89(4H, m), 2.88(2H, t, J=8.4 Hz), 3.01(2H, m), 3.22(2H, m), 3.32(2H, t, J=8.4 Hz), 3.57(2H, br-d), 3.69(1H, m), 4.53(2H, s), 6.53(1H, d, J=7.6 Hz), 6.56(1H, t, J=7.6 Hz), 6.99(1H, t, J=7.6 Hz), 7.02(1H, d, J=7.6 Hz), 7.66(1H, s), 8.39(1H, d, J=1.8 Hz), 8.41(1H, d, J=1.8 Hz).
FAB-Mass: 338(MH+).

Example 57: Synthesis of 1-[1-(2,6-difluoro-3-pyridylethyl)piperidin-4-yl]indoline

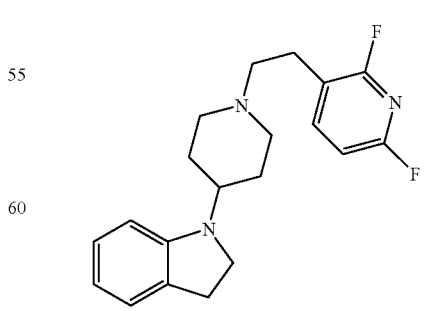

1-(Piperidin-4-yl)indoline (300 mg) and 2,6-difluoro-3-bromoethylpyridine (330 mg) were treated as in Example 2 to give the hydrochloride (270 mg) of the title compound as a white powder (yield: 47%).
m.p. (hydrochloride): 202–204° C.
$^1$H-NMR (400 MHz, DMSO-$d_6$):
δ(ppm) 1.82–1.91(2H, m), 2.00–2.13(2H, m), 2.88(2H, t, J=8 Hz), 3.03–3.16(4H, m), 3.24–3.34(4H, m), 3.58–3.66 (2H, m), 3.68–3.78(1H, m), 6.54–6.61(2H, m), 6.96–7.05 (2H, m), 7.17–7.22(1H, m), 8.10–8.18(1H, m).
FAB-Mass: 344(MH+).

Example 58: Synthesis of 1-{1-[2-(2-thienyl)ethyl]piperidin-4-yl}indoline

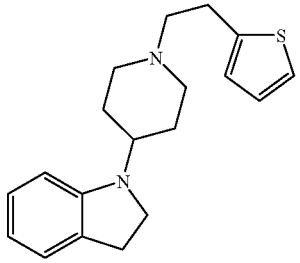

1-(4-Piperidyl) indoline (0.1 g) was treated as in Example 2 to give the title compound (0.057 g) as colorless crystals (yield: 37.2%).
Next, hydrochloric acid was added thereto to give a salt followed by recrystallization from ethanol-isopropyl ether mixtures to give the hydrochloride of the title compound as colorless crystals.
m.p. (hydrochloride): 243° C.
Hydrochloride
$^1$H-NMR (400 MHz, DMSO-$d_6$):
δ(ppm) 1.88(2H, br-d), 2.15(2H, m), 2.93(2H, t, J=8.4 Hz), 3.09 (2H, m), 3.34 (6H, m), 3.64 (2H, br-d), 3.78 (1H, tt, J=3.6, 12 Hz), 6.66(2H, m), 7.00(2H, m), 7.06(2H, m)), 7.42(1H, dd, J=1.2, 4.8 Hz).
FAB-Mass: 313(MH+).

Example 59: Synthesis of 1-{1-[2-(3-thienyl)ethyl]piperidin-4-yl}indoline

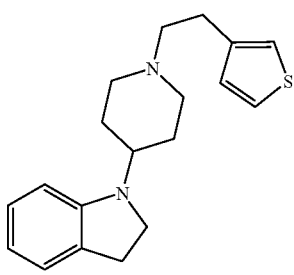

3-(2-Bromoethyl)thiophene (0.19 g) was treated as in Example 2 to give the title compound (0.105 g) as a colorless oil (yield: 68.6%).
Next, hydrochloric acid was added thereto to give a salt followed by recrystallization from ethanol-isopropyl ether mixtures to give the hydrochloride of the title compound as colorless crystals.
m.p. (hydrochloride): 248° C.
Hydrochloride
$^1$H-NMR (400 MHz, DMSO-$d_6$):
δ(ppm) 1.88 (2H, br-d), 2.04 (2H, m), 2.90 (2H, t, J=8.4 Hz), 3.08 (4H, m), 3.30 (2H, m), 3.32 (2H, t, J=8.4 Hz), 3.63 (2H, br-d), 3.74(1H, m), 6.56(1H, d, J=7.6 Hz), 6.58(1H, t, J=7.6 Hz), 7.00 (H, t, J=7.6 Hz), 7.04 (1H, d, J=7.6 Hz), 7.08 (1H, dd, J=1.2, 4.8 Hz), 7.34(1H, m), 7.55 (1H, dd, J=2.8, 4.8 Hz).
FAB-Mass: 313(MH+).

Example 60: Synthesis of 1-[1-(2-thiazolylethyl)piperidin-4-yl]indoline

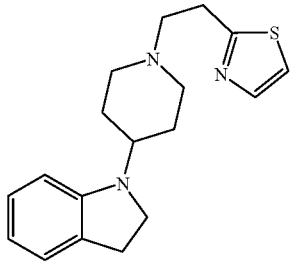

2-(2-Bromoethyl)thiazole (0.46 g) was treated as in Example 2 to give the title compound (0.102 g) as colorless crystals (yield: 14.4%).
Next, oxalic acid (15 mg) was added thereto to give a salt followed by recrystallization from ethanol-acetone mixtures to give the oxalate of the title compound as colorless crystals.
m.p. (oxalate): 149° C.
Oxalate
$^1$H-NMR (400 MHz, DMSO-$d_6$):
δ(ppm) 1.85(2H, m), 2.86(2H, m), 2.87(2H, t, J=8.4 Hz), 3.30(2H, m), 3.31(2H, t, J=8.4 Hz), 3.40(4H, m), 3.47(2H, br-d), 3.63(1H, m), 6.50(1H, d, J=7.6 Hz), 6.55(1H, t, J=7.6 Hz), 6.99(1H, t, J=7.6 Hz), 7.02(1H, d, J=7.6 Hz), 7.65(1H, d, J=3.6 Hz), 7.75(1H, d, J=3.6 Hz).
FAB-Mass: 314(MH+).

Example 61: Synthesis of 1-[1-(4-methyl-5-thiazolethyl)piperidin-4-yl]indoline

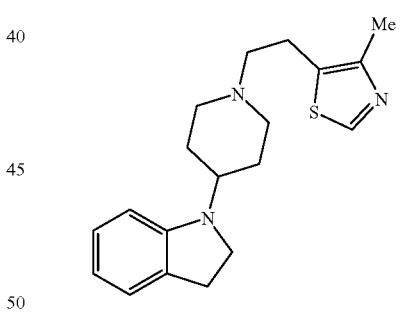

1-(Piperidin-4-yl)indoline (300 mg) and 4-methyl-5-thiazolethyl bromide (310 mg) obtained in the same manner as the one of Production Example 1 were treated as in Example 2 to give the hydrochloride (140 mg) of the title compound as a gray powder (yield: 26%).
m.p. (hydrochloride): 222–225° C.
$^1$H-NMR (400 MHz, DMSO-$d_6$):
δ(ppm) 1.82–1.89(2H, m), 1.95–2.10(2H, m), 2.37(3H, s), 2.87(2H, t, J=8 Hz), 3.01–3.12(2H, m), 3.15–3.33(6H, m), 3.60–3.76(3H, m), 6.51–6.60(2H, m), 6.95–7.03(2H, m), 8.93(1H, s).
FAB-Mass: 328(MH+).

Example 62: Synthesis of 1-{1-[(indol-3-yl)ethyl]-piperidin-4-yl}indoline

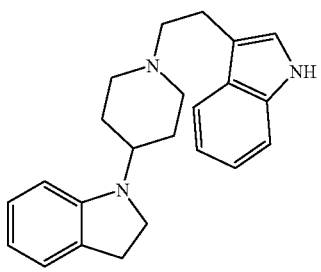

1-(Piperidin-4-yl)indoline (300 mg) and 3-(2-bromoethyl)indole (340 mg) obtained in the same manner as the one of Production Example 1 were treated as in Example 2 to give the hydrochloride (410 mg) of the title compound as a brown powder (yield: 72%).

m.p. (hydrochloride): 240° C. (decomp.).

$^1$H-NMR (400 MHz, DMSO-$d_6$):

δ(ppm) 1.82–1.91(2H, m), 1.93–2.08(2H, m), 2.89(2H, t, J=8 Hz), 3.07–3.20(4H, m), 3.27–3.36(4H, m), 3.65–3.76 (3H, m), 6.51–6.58(2H, m), 6.96–7.04(3H,m), 7.06–7.11 (1H, m), 7.24(1H, s), 7.35(1H, d, J=8 Hz), 7.61(1H, d, J=8 Hz).

FAB-Mass: 346(MH+).

Example 63: Synthesis of 1-{1-[2-(6-benzothiazolyl)-ethyl]piperidin-4-yl}indoline

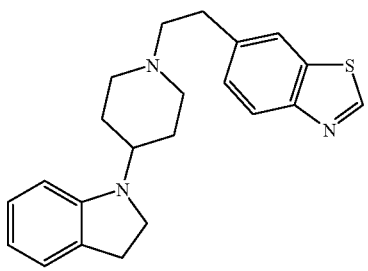

6-(2-Bromoethyl)benzothiazole (0.073 g) was treated as in Example 2 to give the title compound (0.084 g) as a pale yellow oil (yield: 70.0%).

Next, oxalic acid (21 mg) was added thereto to give a salt followed by recrystallization from ethanol to give the oxalate of the title compound.

m.p. (oxalate): 197° C.

Oxalate $^1$H-NMR (400 MHz, DMSO-$d_6$):

δ(ppm) 1.87(4H, m), 2.88(2H, t, J=8.4 Hz), 2.95(2H, m), 3.13(2H, m), 3.25(2H, m), 3.32(2H, t, J=8.4 Hz), 3.56(2H, m), 3.68(1H, m), 6.52(1H, d, J=8.0 Hz), 6.55(1H, t, J=8.0 Hz), 6.99(1H, t, J=8.0 Hz), 7.02(1H, d, J=8.0 Hz), 7.48(1H, dd, J=1.6, 8.4 Hz), 8.06(1H, d, J=8.4 Hz), 8.09(1H, d, J=1.6 Hz), 9.37(1H, s).

FAB-Mass: 364(MH+).

Example 64: Synthesis of 1-[1-(5-methoxy-2-thienyl)ethylpiperidin-4-yl]indoline

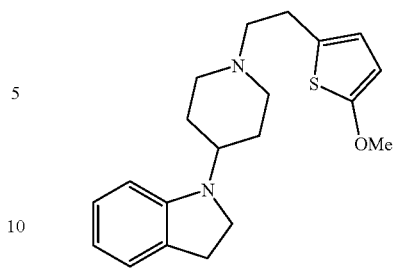

1-(Piperidin-4-yl)indoline (300 mg) and (5-methoxy-2-thienyl)ethyl bromide (400 mg) were treated as in Example 2 to give the hydrochloride (260 mg) of the title compound as a white powder (yield: 46%).

m.p. (hydrochloride): 204° C. (decomp.).

$^1$H-NMR (400 MHz, DMSO-$d_6$):

δ(ppm) 1.80–1.89(2H, m), 2.00–2.11(2H, m), 2.90(2H, t, J=8 Hz), 3.00–3.28(6H, m), 3.32(2H, t, J=8 Hz), 3.55–3.62 (2H, m), 3.67–3.78(1H,m), 3.80(3H, s), 6.13(1H,d, J=4 Hz), 6.56–6.60(3H, m), 6.97–7.04(2H, m), 10.79(1H, br-s).

FAB-Mass: 343(MH+).

Example 65: Synthesis of 1-[1-(2-methoxy-5-thiazolyl)ethylpiperidin-4-yl]indoline

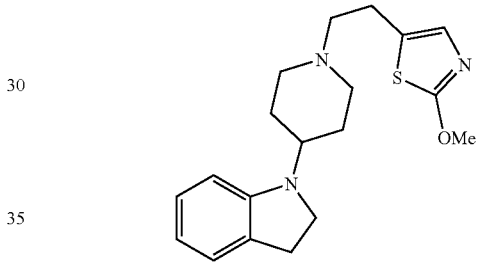

1-(Piperidin-4-yl)indoline (300 mg) and (2-methoxy-5-thiazolyl)ethyl bromide (380 mg) were treated as in Example 2 to give the hydrochloride (340 mg) of the title compound as a white powder (yield: 60%).

m.p. (hydrochloride): 207° C. (decomp.).

$^1$H-NMR (400 MHz, DMSO-$d_6$):

δ(ppm) 1.80–1.86(2H, m), 1.92–2.03(2H, m), 2.89(2H, t, J=8 Hz), 3.00–3.12(2H, m), 3.15–3.32(6H, m), 3.67–3.75 (3H, m), 3.95(3H, s), 6.50–6.59(2H, m), 6.94–7.07(3H, m), 10.36(1H, br-s).

FAB-Mass: 344(MH+).

Example 66: Synthesis of 1-[1-(2-cyano-5-thiazolyl)ethylpiperidin-4-yl]indoline

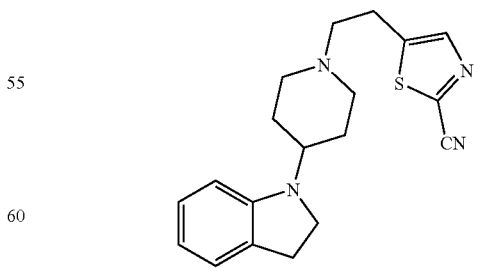

1-(Piperidin-4-yl)indoline (190 mg) and (2-cyano-5-thiazolyl)ethyl bromide (200 mg) were treated as in Example 2 to give the hydrochloride (21 mg) of the title compound as a gray powder (yield: 6.1%).

m.p. (hydrochloride): 209–211° C.

$^1$H-NMR (400 MHz, DMSO-$d_6$):

δ(ppm) 1.81–2.00(4H, m), 2.89(2H, t, J=8 Hz),3.01–3.15 (2H, m), 3.30(2H, t, J=8 Hz), 3.36–3.78(7H, m), 6.49–6.55 (2H, m), 6.92–7.03(2H, m), 8.02(1H, s).

FAB-Mass: 339(MH+).

Example 67: Synthesis of 1-(1-pyrazinylethylpiperidin-4-yl)indoline

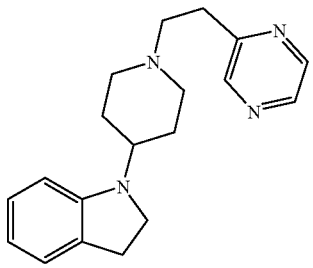

A solution of 1-(piperidin-4-yl)indoline (500 mg) and vinylpyrazine (260 mg) in o-dichlorobenzene (5 ml) was heated at 180° C. for 3 hr. Next, the reaction solution was purified by silica gel column chromatography (methylene chloride/ethanol system) and treated in a conventional manner so as to give the oxalate (90 mg) of the title compound as a white powder (yield: 9.0%).

m.p. (oxalate): 168–170° C.

$^1$H-NMR (400 MHz, DMSO-$d_6$):

δ(ppm) 1.75–1.83(4H, m), 2.80–2.91(4H, m), 3.11–3.20 (2H, m), 3.21–3.33(4H, m), 3.41–3.52(2H, m), 3.55–3.69 (1H, m), 6.48(1H, d, J=8 Hz), 6.53(1H, t, J=8 Hz), 6.95–7.00 (2H, m), 8.53(1H, s), 8.57–8.59(1H, m), 8.63(1H, s).

FAB-Mass: 309(MH+).

Example 68: Synthesis of 1-{1-[2-(4-bromopyrazol-1-yl)ethyl]piperidin-4-yl}indoline

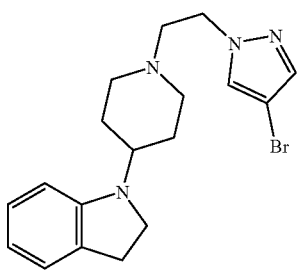

1-(4-Piperidyl)indoline (162 mg) and 1-(2-bromoethyl)-4-bromopyrazole (200 mg) were treated as in Example 2 to give the hydrochloride (372 mg) of the title compound as beige crystals (yield: 67%).

m.p. (hydrochloride): 210–212° C.

$^1$H-NMR (400 MHz, DMSO-$d_6$):

δ(ppm) 1.83(2H, d, J=11.6 Hz), 2.00–2.12(2H, m), 2.88 (2H, t, J=8.4 Hz), 3.07(2H, q, J=11.2 Hz), 3.31(2H, t, J=8.4 Hz), 3.46–3.54(4H, m), 3.66–3.76(1H, m), 4.63(2H, t, J=6.8 Hz), 6.56–6.64(2H, m), 6.97–7.06(2H, m), 7.64(1H, s), 8.11(1H, s), 11.10(1H, br-s).

ESI-Mass: 351(MH+).

Example 69: Synthesis of 1-{1-[3-(4-fluorophenoxy)propyl]piperidin-4-yl}indoline

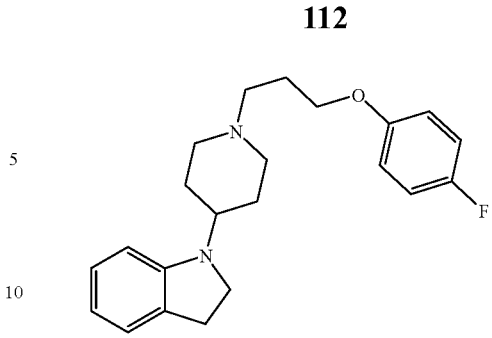

1-(Piperidin-4-yl)indoline (300 mg) and 1-bromo-3-(4-fluorophenoxy)propane (420 mg) were treated as in Example 2 to give the hydrochloride (330 mg) of the title compound as white needles (yield: 56%).

m.p. (hydrochloride): 207–210° C.

$^1$H-NMR (400 MHz, DMSO-$d_6$):

δ(ppm) 1.80–1.87(2H, m), 1.91–2.20(4H, m), 2.88(2H, t, J=8 Hz), 3.00–3.11(2H, m), 3.13–3.21(2H, m), 3.30(2H, t, J=8 Hz), 3.52–3.61(2H, m), 3.66–3.77(1H, m), 4.04(2H, t, J=6 Hz), 6.49–6.70(2H, m), 6.92–7.03(4H, m), 7.08–7.15 (2H, m).

FAB-Mass: 355(MH+).

Example 70: Synthesis of 1-{1-[3-(4-hydroxymethylphenoxy)propyl]piperidin-4-yl}indoline

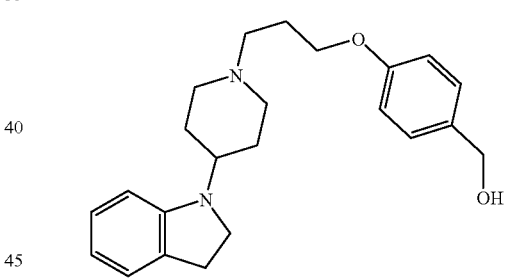

1-(4-Piperidyl)indoline (263 mg) and 4-(3-bromopropoxy)benzyl alcohol (389 mg) were treated as in Example 2 to give the title compound (422 mg) as a pale orange amorphous solid (yield: 92%).

$^1$H-NMR (400 MHz, CDCl$_3$):

δ(ppm) 2.20–2.35(4H, m), 2.47–2.73(4H, m), 2.55(2H, t, J=7.4 Hz), 2.94(2H, t, J=8.4 Hz), 3.07(2H, d, J=11.2 Hz), 3.35–3.43(1H, m), 3.38(2H, t, J=8.4 Hz), 4.02(2H, t, J=6.4 Hz), 4.62(2H, s), 6.41(1H, d, J=8 Hz), 6.60(1H, dt, J=7.4 Hz, 0.8 Hz), 6.89(2H, d, J=8.8 Hz), 7.04(1H, ddd, J=8 Hz, 7.4 Hz, 0.8 Hz), 7.05(1H, d, J=7.4 Hz), 7.29(2H, d, J=8.8 Hz).

ESI-Mass: 367(MH+).

Example 71: Synthesis of 1-{1-[3-(4-hydroxyethylphenoxy)propyl]piperidin-4-yl}indoline

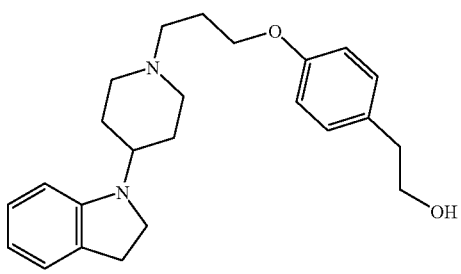

1-(4-Piperidyl)indoline (303 mg) and 4-(3-bromopropoxy)phenethyl alcohol (389 mg) were treated as in Example 2 to give the hydrochloride (500 mg) of the title compound as a beige amorphous solid (yield: 80%).

$^1$H-NMR (400 MHz, DMSO-$d_6$):

δ(ppm) 1.84(2H, d, J=13.2 Hz), 2.40–2.22(4H, m), 2.63 (2H, t, J=7.2 Hz), 2.90(2H, t, J=8.4 Hz), 3.05(2H, q, J=10.4 Hz), 3.12–3.19(2H, m), 3.33(2H, t, J=8.4 Hz), 3.52(2H, t, J=7.2 Hz), 3.52–3.60(2H, m), 3.70–3.80(1H, m), 4.01(2H, t, J=6 Hz), 6.58–6.68(2H, br-t), 6.83(2H, d, J=8.8 Hz), 7.01 (1H, d, J=8 Hz), 7.05(1H, d, J=8 Hz), 7.11(2H, d, J=8.8 Hz), 10.80(1H, br-s).

ESI-Mass: 381(MH+).

Example 72: Synthesis of 1-{1-[4-(4-fluorophenyl)-4-oxobutyl]piperidin-4-yl}indoline

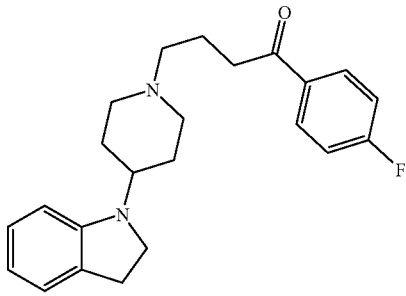

1-(Piperidin-4-yl)indoline (1.0 g) and 4-chloro-1-(4-fluorophenyl)-1-butanone (1.1 g) were treated as in Example 2 to give the title compound (0.5 g) (yield: 27%).

A portion of this product was then treated in a conventional manner so as to give the hydrochloride of the title compound as a white powder.

m.p. (hydrochloride): 213° C. (decomp.).

$^1$H-NMR (400 MHz, DMSO-$d_6$):

δ(ppm) 1.80–1.88(2H, m), 1.94–2.10(4H, m), 2.88(2H, t, J=8 Hz), 3.00–3.10(4H, m), 3.19(2H, t, J=8 Hz), 3.30(2H, t, J=8 Hz), 3.50–3.60(2H, m), 3.67–3.78(1H, m), 6.52–6.58 (2H, m), 6.96–7.03(2H, m), 7.34–7.39(2H, m), 8.03–8.07 (2H, m).

FAB-Mass: 367(MH+).

Example 73: Synthesis of 1-{1-[4-(4-fluorophenyl)-4-hydroxybutyl]piperidin-4-yl}indoline

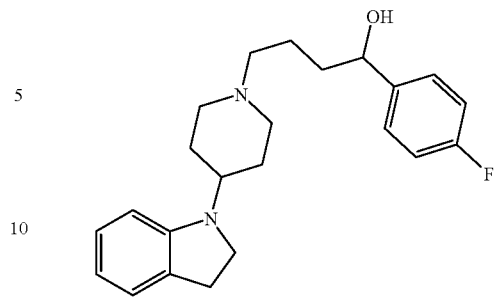

Sodium borohydride (38 mg) was added to a solution of 1-{1-[4-(4-fluorophenyl)-4-oxobutyl]piperidin-4-yl}indoline (320 mg) in ethanol (20 ml) and the resultant mixture was stirred for 5 hr. After concentrating under reduced pressure, water and ethyl acetate were added thereto and the layers were separated. The organic layer was washed with brine, dried over anhydrous magnesium sulfate and concentrated under reduced pressure. Then the residue was purified by silica gel column chromatography (hexane/ethyl acetate system) and treated in a conventional manner so as to give the hydrochloride (250 mg) of the title compound as a gray powder (yield: 71%).

m.p. (hydrochloride): 174–175° C.

$^1$H-NMR (400 MHz, DMSO-$d_6$):

δ(ppm) 1.55–2.00(6H, m), 2.87(2H, t, J=8 Hz), 2.95–3.05 (4H, m), 3.28(2H, t, J=8 Hz), 3.46–3.54(2H, m), 3.62–3.71 (1H, m), 4.57(1H, t, J=6 Hz), 6.49–6.56(2H, m), 6.95–7.02 (2H, m), 7.11–7.16(2H, m), 7.34–7.38(2H, m), 9.71(1H, br-s).

FAB-Mass: 369(MH+).

Example 74: Synthesis of 1-[1-(phthalimido-1-yl)ethylpiperidin-4-yl}indoline

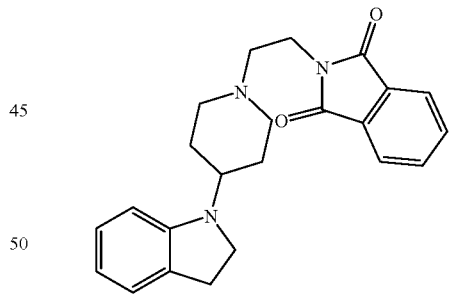

1-(Piperidin-4-yl)indoline (500 mg) and N-(2-bromoethyl)phthalimide (750 mg) were treated as in Example 2 to give the title compound (520 mg) as a colorless oil (yield: 55%).

$^1$H-NMR (400 MHz, CDCl$_3$):

δ(ppm) 1.59–1.81(4H, m), 2.09–2.20(2H, m), 2.68(2H, t, J=7 Hz), 2.90(2H, t, J=8 Hz), 3.08–3.15(2H, m), 3.30–3.41 (1H, m), 3.32(2H, t, J=8 Hz), 3.83(2H, t, J=7 Hz), 6.38(1H, d, J=8 Hz), 6.59(1H, t, J=8 Hz), 7.00–7.08(2H, m), 7.68–7.73(2H, m), 7.80–7.87(2H, m).

Example 75: Synthesis of 1-[1-(4-fluorobenzamido)ethylpiperidin-4-yl]indoline

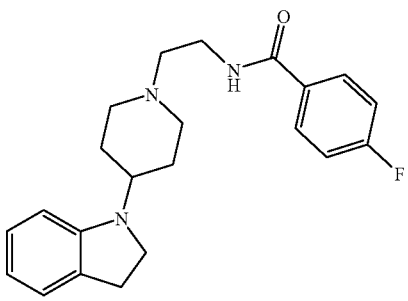

A solution of 1-[1-(phthalimido-1-yl)ethylpiperidin-4-yl]indoline (520 mg) and hydrazine (100 mg) in ethanol (20 ml) was heated under reflux for 5 hr. After cooling to room temperature, the resulting crystalline precipitates were filtered off and the filtrate was concentrated. The resulting residue was mixed with methylene chloride (30 ml), a 2 N aqueous solution (5 ml) of sodium hydroxide and 4-fluorobenzoyl chloride (250 mg) followed by vigorously stirring the resultant mixture at room temperature. After 1 hr, the reaction solution was diluted with methylene chloride and the layers were separated. The organic layer was washed with brine, dried over anhydrous magnesium sulfate and purified by silica gel column chromatography (methylene chloride/ethanol system) followed by conversion into a hydrochloride. Thus the hydrochloride (160 mg) of the title compound was obtained as a white powder (yield: 28%).
m.p. (hydrochloride): 221° C. (decomp.).
$^1$H-NMR (400 MHz, DMSO-$d_6$):
δ(ppm) 1.81–2.02(4H, m), 2.88(2H, t, J=8 Hz),3.02–3.15 (2H, m), 3.20–3.31(4H, m), 3.60–3.75(5H, m), 6.49–6.56 (2H, m), 6.95–7.02(2H, m), 7.29–7.34(2H, m), 7.94–7.99 (2H, m), 8.86(1H, t, J=6 Hz).
FAB-Mass: 368(MH+).
Example 76: Synthesis of 1-{1-[1-(3,4-dimethoxyphenyl)propan-2-yl]piperidin-4-yl}indoline

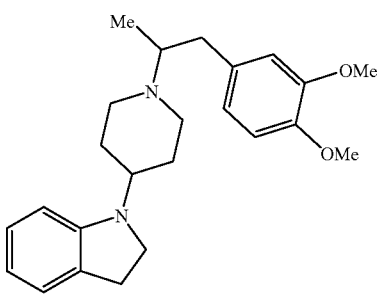

A mixture of 1-(piperidin-4-yl)indoline (300 mg), 3,4-dimethoxyphenylacetone (870 mg), sodium cyanoborohydride (280 mg) and molecular sieve (1.0 g) in methanol (20 ml) was stirred at room temperature for 3 days. Then the reaction solution was filtered and concentrated under reduced pressure, water and ethyl acetate were added thereto and the layers were separated. The organic layer was washed with brine, dried over anhydrous magnesium sulfate and purified by silica gel column chromatography (methylene chloride/ethanol system) followed by conversion into a hydrochloride in a conventional manner. Thus the hydrochloride (220 mg) of the title compound was obtained as a white powder (yield: 35%).
m.p. (hydrochloride): 245° C. (decomp.).
$^1$H-NMR (400 MHz, DMSO-$d_6$):
δ(ppm) 1.00(3H, d, J=7 Hz), 1.82–1.91(2H, m), 2.01–2.13 (2H, m), 2.55–2.63(1H, m), 2.88(2H, t, J=8 Hz), 3.17–3.28 (4H, m), 3.43–3.61(4H, m), 3.71(3H, s), 3.74(3H, s), 3.76–3.83(1H, m), 6.52–6.56(2H, m), 6.75–6.78(1H, m), 6.87–6.90(2H, m), 6.98–7.03(2H, m), 9.90(1H, br-s).
FAB-Mass: 381(MH+).
Example 77: Synthesis of 1-{1-[(1,4-benzodioxan-2-yl)methyl]piperidin-4-yl}indoline

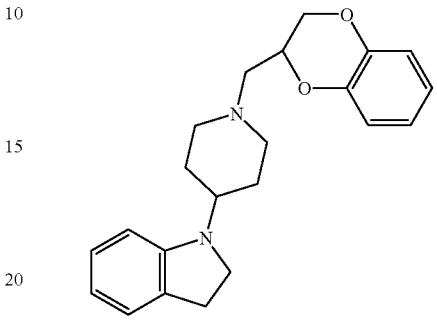

1-(4-Piperidyl)indoline (303 mg) and 2-bromoethyl-1,4-benzodioxane (344 mg) were treated as in Example 2 to give the hydrochloride (372 mg) of the title compound as beige crystals (yield: 67%).
m.p. (hydrochloride): 200–205° C.
$^1$H-NMR (400 MHz, DMSO-$d_6$):
δ(ppm) 1.88(2H, d, J=12.4 Hz), 2.10–2.25(2H, m), 2.92 (2H, t, J=8.4 Hz), 3.13–3.58(7H, m), 3.72–3.82(2H, m), 4.05(1H, dd, J=11.4 Hz, 6.8 Hz), 4.34(1H, dd, J=11.4 Hz, 2 Hz), 4.90–4.95(1H, m), 6.67(1H, d, J=6.8 Hz), 6.68(1H, dd, J=6.8 Hz, 6.6 Hz), 6.84–6.96(4H, m), 7.04(1H, dd, J=9 Hz, 7.6 Hz), 7.08(1H, d, J=7.6 Hz), 11.40(1H, br-s).
ESI-Mass: 351(MH+).
Example 78: Synthesis of 1-{1-[3-(3,4-methylenedioxypheoxy)propyl]piperidin-4-yl}indoline

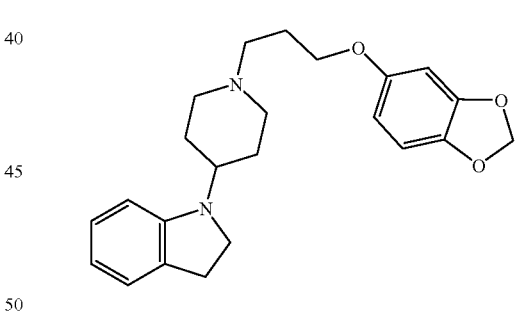

1-(4-Piperidyl)indoline (303 mg) and 3-bromopropoxy-1,2-methylenedioxybenzene (389 mg) were treated as in Example 2 to give the hydrochloride (443 mg) of the title compound as pale blue crystals (yield: 73%).
m.p. (hydrochloride): 210–212° C.
$^1$H-NMR (400 MHz, DMSO-$d_6$):
δ(ppm) 1.84(2H, d, J=11.6 Hz), 1.98–2.18(4H, m), 2.88 (2H, t, J=8.4 Hz), 3.05(2H, q, J=11.6 Hz), 3.11–3.20(2H, m), 3.30(2H, t, J=8.4 Hz), 3.57(2H, d, J=11.6 Hz), 3.72(1H, m), 3.97(2H, t, J=6 Hz), 5.94(2H, s), 6.37(1H, dd, J=8.4 Hz, 2.8 Hz), 6.54(1H, d, J=7.6 Hz), 6.57(1H, t, J=7.6 Hz), 6.63(1H, d, J=2.8 Hz), 6.80(1H, d, J=8.4 Hz), 6.99(1H, t, J=7.6 Hz), 7.02(1H, d, J=7.6 Hz), 10.45(1H, br-s).
ESI-Mass: 381(MH+).
Example 79: Synthesis of cis-1-[1-(4-fluorophenethyl)-3-methylpiperidin-4-yl]indoline

117

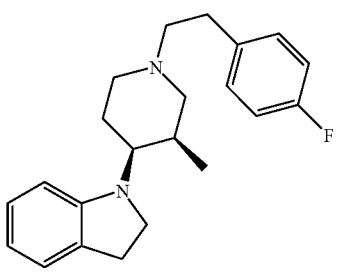

Indoline (238 mg), 1-[2-(4-fluorophenyl)ethyl]-3-methyl-4-piperidone (588 mg) obtained in Production Example 40-5 and triacetoxylated sodium borohydride (1.19 g) were treated as in Example 101 to give the title compound (100 mg) as a yellow oil (yield: 15%).

m.p. (oxalate): 229–230° C.

$^1$H-NMR (400 MHz, CDCl$_3$):

δ(ppm) 1.09(3H, d, J=6.5 Hz), 1.69(1H, m), 2.10(2H, m), 2.26(1H, br-d), 2.30(1H, m), 2.47(1H, m), 2.56(1H, m), 2.74(2H, m), 2.81(1H, br-d), 2.98(3H, m), 3.42(1H, m), 3.56(1H, q, J=9.0 Hz), 3.64(1H, m),6.31(1H, br-d), 6.54(1H, br-t),6.96(2H, br-d), 7.03(2H, m), 7.17(2H, m).

FAB-Mass: 339(MH+).

Example 80-1: Synthesis of 1-benzyl-3-hydroxymethyl-4-piperidone (80-1-1) Ethyl 1-benzyl-4,4-ethylenedioxy-3-piperidinecarboxylate

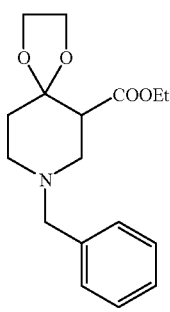

p-Toluenesulfonic acid monohydrate (1.5 g) was added to a solution (600 ml) of ethyl 1-benzyl-4-oxo-3-piperidinecarboxylate (CAS Registry No. 1454-53-1, 44.7 g) and ethylene glycol (100 ml) in toluene and the resultant mixture was heated under reflux overnight. After cooling the mixture to room temperature, ice water (500 ml) and a saturated aqueous solution (300 ml) of sodium bicarbonate were added thereto followed by extraction with ethyl acetate (400 ml) for three times. The organic phase was washed successively with water (200 ml) twice and brine (300 ml) and dried over anhydrous magnesium sulfate. The residue was purified by silica gel column chromatography (hexane/ethyl acetate system) to give the title compound (30.4 g) as a yellow oil (yield: 66%).

$^1$H-NMR (400 MHz, CDCl$_3$):

δ(ppm) 1.22(3H, t, J=6.0 Hz), 1.74(1H, m), 1.98(1H, m), 2.48(1H, m), 2.68(2H, m), 2.82(2H, m), 3.49(1H, d, J=11.0 Hz), 3.57(1H, d, J=11.0 Hz), 3.89(1H, d, J=7.0 Hz), 3.96 (3H, m), 4.13(2H, q, J=6.0 Hz), 7.22–7.32(5H, m).

(80-1-2) 1-Benzyl-4,4-ethylenedioxy-3-piperidinemethanol

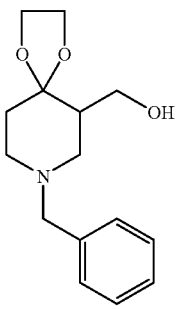

In a stream of nitrogen, lithium aluminum hydride (702 mg) was carefully added to ice cooled dry tetrahydrofuran (100 ml). Into the resultant mixture was slowly added dropwise a solution of ethyl 1-benzyl-4,4-ethylenedioxy-3-piperidinecarboxylate (4.58 g) obtained above in tetrahydrofuran (30 ml). The resultant mixture was gradually heated and further stirred at room temperature overnight. Under ice cooling, water (0.7 ml), a 5 N aqueous solution (2.1 ml) of sodium hydroxide and further water (2.1 ml) were successively added to the reaction mixture carefully. Next, the resulting mixture was dried over anhydrous sodium sulfate and filtered through celite followed by concentration under reduced pressure. Thus the title compound (4.03 g) was obtained as a colorless oil (yield: 100%).

$^1$H-NMR (400 MHz, CDCl$_3$):

δ(ppm) 1.67(1H, m), 1.92(1H, m), 2.01(1H, m), 2.43–2.66(3H, m), 2.70(1H, br-d), 3.49(2H, s), 3.77(1H, d, J=11.0 Hz), 3.83(1H, d, J=11.0 Hz), 3.96(4H, br-s), 7.23–7.33(5H, m).

(80-1-3) 1-Benzyl-3-hydroxymethyl-4-piperidone

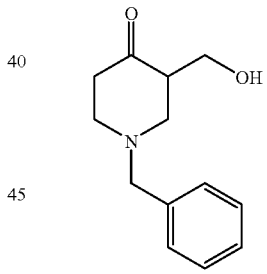

1-Benzyl-4,4-ethylenedioxy-3-piperidinemethanol (960 mg) was dissolved under ice cooling in a mixed solvent of water (10 ml) and conc. sulfuric acid (6 ml). The resultant mixture was gradually heated to room temperature and further stirred for a day. Under ice cooling, a 5 N aqueous solution of sodium hydroxide was added to the mixture to adjust to ca. pH 8. After extracting with chloroform (50 ml) twice, the mixture was washed successively with water and brine, dried over anhydrous magnesium sulfate and concentrated under reduced pressure to give the title compound (710 mg) as a colorless oil (yield: 89%).

$^1$H-NMR (400 MHz, CDCl$_3$):

δ(ppm) 2.47(2H, m), 2.60(2H, m), 2.70(1H, m), 3.01(2H, m), 3.62(2H, s), 3.71(1H, dd, J=7.5 Hz, 13.5 Hz), 3.76(1H, br-d), 7.25–7.37(5H, m).

Example 80-2: Synthesis of cis-1-(1-benzyl-3-hydroxymethylpiperidin-4-yl)indoline

119

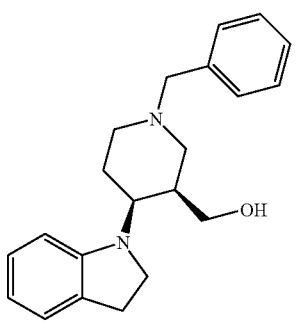

Indoline (238 mg), 1-benzyl-3-hydroxymethyl-4-piperidone (548 mg) and triacetoxylated sodium borohydride (1.19 g) were treated as in Example 1 to give the title compound (140 mg) as a yellow powder (yield: 22%).

$^1$H-NMR (400 MHz, CDCl$_3$):

δ(ppm) 1.79(1H, br-d), 2.08(1H, br-s), 2.14(1H, dt, J=2.8 Hz, 12.0 Hz), 2.49(1H, br-d), 2.54(1H, dt, J=4.5 Hz, 12.0 Hz), 3.02(3H, m), 3.14(1H, br-d), 3.49(1H, d, J=12.0 Hz), 3.55(1H, d, J=12.0 Hz), 3.56(1H, t, J=12.5 Hz), 3.64(1H, q, J=9.0 Hz), 3.82(2H, m), 3.97(1H, br-d), 6.28(1H, d, J=7.5 Hz), 6.56(1H, t, J=7.5 Hz), 7.00(1H, t, J=7.5 Hz), 7.04(1H, d, J=7.5 Hz), 7.27–7.37(5H, m).

Example 81-1: Synthesis of cis-1-(3-acetoxymethylpiperidin-4-yl)indoline (81-1-1) cis-1-(1-Benzyl-3-acetoxymethylpiperidin-4-yl)indoloine

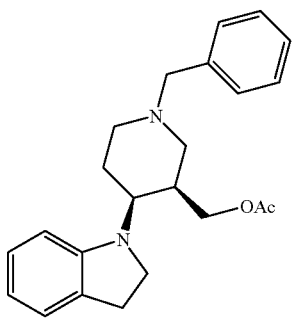

Under ice cooling, triethylamine (111 mg) and acetyl chloride (86 mg) were added to a solution of cis-1-(1-benzyl-3-hydroxymethylpiperidin-4-yl)indoline (322 mg) in tetrahydrofuran (3 ml). The resultant mixture was stirred under ice cooling for 30 min and then at room temperature for additional 1 hr. Then ethyl acetate (15 ml) was added thereto followed by filtration through celite. After removing the solvent under reduced pressure, the residue was purified by silica gel column chromatography (hexane/ethyl acetate system) to give the title compound (340 mg) as a yellow oil (yield: 93%).

$^1$H-NMR (400 MHz, CDCl$_3$):

δ(ppm) 1.76(1H, br-d), 1.83(3H, s), 1.99–2.20(3H, m), 2.44(1H, m), 2.92–3.03(4H, m), 3.40(1H, d, J=13.0 Hz), 3.48–3.56(3H, m), 3.58(1H, d, J=13.0 Hz), 4.13(1H, dd, J=4.2 Hz, 10.0 Hz), 4.63(1H, t, J=10.0 Hz), 6.31(1H, d, J=7.5 Hz), 6.57(1H, t, J=7.5 Hz), 7.02(2H, m), 7.21–7.31 (5H, m).

120

(81-1-2) cis-1-(3-Acetoxymethylpiperidin-4-yl)indoline

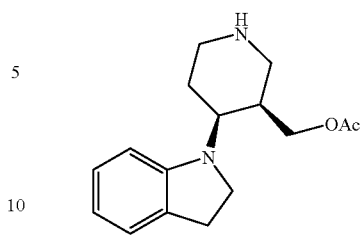

Under ice cooling, a solution of 1-chloroethyl chloroformate (135 mg) in dichloroethane (1 ml) was added to a solution of cis-1-(1-benzyl-3-acetoxymethylpiperidin-4-yl) indoline (340 mg) in dichloroethane (5 ml). After stirring for 30 min, the mixture was heated under reflux for 1 hr. Then, it was cooled and concentrated under reduced pressure. After adding methanol (10 ml) thereto, the mixture was stirred at 50° C. for 10 min and heated under reflux for 30 min. Then it was cooled to room temperature again and concentrated under reduced pressure. After adding a saturated aqueous solution (10 ml) of sodium bicarbonate, the mixture was extracted with chloroform (15 ml) for three times. The organic phase was dried over anhydrous magnesium sulfate and concentrated under reduced pressure to give the title compound (290 mg) as a yellow powder (yield: 100%).

$^1$H-NMR (400 MHz, CDCl$_3$):

δ(ppm) 1.94(1H, dd, J=4.5 Hz, 13.0 Hz), 1.99(3H, s), 2.45(1H, m), 2.79(1H, dt, J=3.0 Hz, 12.0 Hz), 2.87(1H, dd, J=3.0 Hz, 12.5 Hz), 2.97(3H, m), 3.19(1H, br-d), 3.26(1H, br-d, J=13.5 Hz), 3.55(2H, t, J=9.0 Hz), 3.64(1H, td, J=5.0 Hz, 12.5 Hz), 4.20(1H, dd, J=4.5 Hz, 11.5 Hz), 4.56(1H, t, J=10.5 Hz), 6.34(1H, d, J=7.5 Hz), 6.58(1H, t, J=7.5 Hz), 7.03(2H, m).

Example 81-2 Synthesis of cis-1-[1-(4-fluorophenethyl)-3-hydroxymethylpiperidin-4-yl]indoline (81-2-1) cis-1-[1-(4-Fluorophenethyl)-3-acetoxymethyl-piperidin-4-yl]indoline

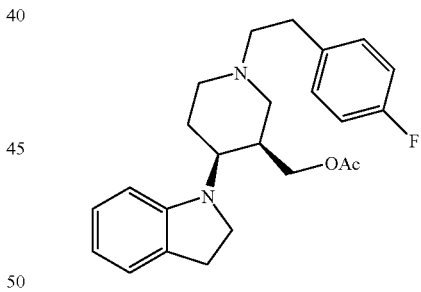

cis-1-(3-Acetoxymethylpiperidin-4-yl)indoline (280 mg) was dissolved in dimethylformamide (4 ml) and methanol (1 ml). To the resultant solution were added triethylamine (222 mg) and 4-fluorophenethyl bromide (285 mg) followed by stirring at 50° C. for 2 hr. Then the reaction mixture was cooled and water (50 ml) was added thereto. After extracting with ether (50 ml) twice, the organic phase was washed with water (20 ml) twice and a 2 N aqueous solution (50 ml) of sodium hydroxide once and dried over anhydrous magnesium sulfate. Then the solvent was evaporated under reduced pressure and the residue was purified by silica gel column chromatography (hexane/ethyl acetate system) to give the title compound (100 mg) as a colorless oil (yield: 28%).

$^1$H-NMR (400 MHz, CDCl$_3$):

δ(ppm) 1.77(1H, br-d), 1.93(3H, s), 1.98(1H, dd, J=4.0 Hz, 12.0 Hz), 2.12–2.21(2H, m), 2.42–2.63(4H, m), 2.73

(2H, m), 2.98(2H, m), 3.06(1H, br-d), 3.46–3.58(3H, m), 4.20(1H, dd, J=3.5 Hz, 10.0 Hz), 4.46(1H, t, J=9.5 Hz), 6.33(1H, d, J=7.5 Hz), 6.58(1H, t, J=7.5 Hz), 6.96(2H, br-t), 7.04(2H, br-d), 7.15(2H, m).

(81-2-2) cis-1-[1-(4-Fluorophenethyl)-3-hydroxymethylpiperidin-4-yl]indoline

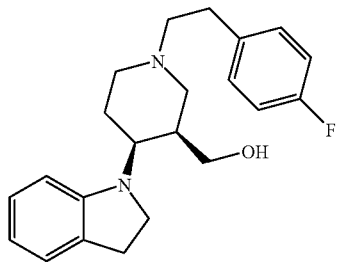

Potassium carbonate (130 mg) was added to a solution of cis-1-[1-(4-fluorophenethyl)-3-acetoxymethylpiperidin-4-yl]indoline (100 mg) obtained above in methanol (6 ml) and the resultant mixture was stirred at room temperature for 4 hr. After adding ether (20 ml), the mixture was filtered through celite and the filtrate was concentrated under reduced pressure. Ethyl acetate (20 ml) was added to the residue followed by filtration again. Then the filtrate was concentrated under reduced pressure and the residue was purified by silica gel column chromatography (hexane/ethyl acetate system) to give the title compound (40 mg) as a pale yellow powder (yield: 45%).
m.p. (oxalate): 173–174° C.
$^1$H-NMR (400 MHz, CDCl$_3$):
1.82(1H, br-d), 2.08(1H, br-s), 2.18(1H, t, J=11.0 Hz), 2.50(2H, m), 2.59(2H, t, J=7.5 Hz), 2.80(2H, br-t), 3.01(2H, m), 3.16(2H, m), 3.57(1H, m), 3.64(1H, q, J=9.0 Hz), 3.82(2H, m), 3.94(1H, d, J=10.5 Hz), 6.27(1H, d, J=7.5 Hz), 6.55(1H, t, J=7.5 Hz), 6.96–7.06(4H, m), 7.14(2H, m).
FAB-Mass: 355(MH+).

Example 82: Synthesis of trans-1-(4-fluorophenethyl)-3-hydroxymethylpiperidin-4-yl]indoline (82-1) trans-1-(1-Acetyl-3-hydroxymethylpiperidin-4-yl) indoline

To a solution of trans-1-(1-acetyl-3-ethoxycarbonyl-piperidin-4-yl)indoline (780 mg) in ethanol (40 ml) was added sodium borohydride (5.7 g) in 3 portions at 30 min. intervals. After stirring at room temperature overnight, sodium borohydride (3.3 g) was added thereto and the resultant mixture was stirred for additional 4 hr. Then ethyl acetate (20 ml) and water (50 ml) were successively added carefully to the reaction mixture followed by extraction with ethyl acetate (50 ml) for three times. The organic phase was washed with water (100 ml) twice and brine once, dried over anhydrous magnesium sulfate and concentrated under reduced pressure. The residue was purified by silica gel column chromatography (methylene chloride/methanol system) to give the title compound (250 mg) as a yellow powder (yield: 39%).
$^1$H-NMR (400 MHz, CDCl$_3$):
δ(ppm) 1.60(1H, m), 1.72(1H, m), 1.97(1H, m), 2.11(3H of 1tautomer, s), 2.14(3H of 1tautomer, s), 2.51(2H, m), 2.92–3.15(3H, m), 3.28(1H, m), 3.38–3.81(4H, m), 3.89(1H of 1tautomer, br-d), 3.99(1H of 1tautomer, br-d), 4.75(1H, br-d), 6.50(1H, m), 6.67(1H, m), 7.05(2H, m).

(82-2) trans-1-(3-Hydroxymethylpiperidin-4-yl) indoline

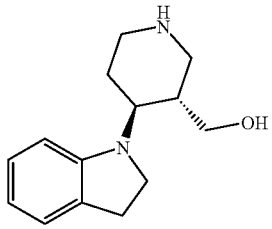

Sodium hydroxide (220 mg) was added to a solution of trans-1-(1-acetyl-3-hydroxymethylpiperidin-4-yl)indoline (250 mg) in ethanol (10 ml)-water (0.5 ml) mixtures and the resultant mixture was heated under reflux for 20 hr. After cooling and adding water (50 ml), the resultant mixture was extracted with chloroform (30 ml) for three times. The organic phase was washed successively with water (50 ml) and brine (50 ml), dried over anhydrous magnesium sulfate and concentrated under reduced pressure to give the title compound (190 mg) as a colorless oil (yield: 85%).
$^1$H-NMR (400 MHz, CDCl$_3$):
δ(ppm) 1.56–1.69(2H, m), 1.95–2.07(1H, m), 2.46(1H, t, J=11.5 Hz), 2.64(1H, dt, J=2.5 Hz, 11.5 Hz), 2.95(2H, m), 3–17(2H, m), 3.34(1H, br-q), 3.42(1H, dt, J=4.5 Hz, 10.5 Hz), 3.50(1H, dt, J=5.0 Hz, 8.5 Hz), 3.61(1H, dd, J=5.0 Hz, 11.0 Hz), 3.67(1H, dd, J=5.0 Hz, 11.0 Hz), 6.53(1H, d, J=7.5 Hz), 6.66(1H, t, J=7.5 Hz), 7.06(2H, m).

(82-3) trans-1-[1-(4-Fluorophenethyl)-3-hydroxymethylpiperidin-4-yl]indoline

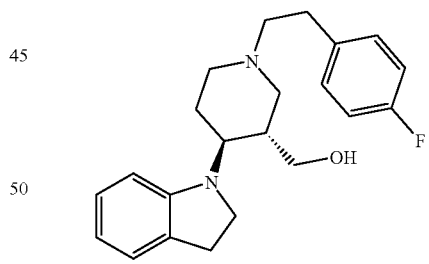

trans-1-(3-Hydroxymethylpiperidin-4-yl)indoline (190 mg) was reacted with triethylamine (152 mg) and 4-fluorophenethyl bromide (406 mg) as in Example 2 to give the title compound (210 mg) as a brown oil (yield: 72%).
m.p. (oxalate): 113–116° C.
$^1$H-NMR (400 MHz, CDCl$_3$):
δ(ppm) 1.69(1H, m), 1.79(1H, m), 1.92(1H, t, J=11.0 Hz), 2.07(1H, br-t), 2.17(1H, m), 2.58(2H, br-t), 2.79(2H, br-t), 2.95(2H, m), 3.06(1H, br-d), 3.13(1H, br-d), 3.35(2H, m), 3.49(1H, m), 3.64(1H, dd, J=4.5 Hz, 11.0 Hz), 3.71(1H, dd, J=6.0 Hz, 11.0 Hz), 6.52(1H, d, J=7.5 Hz), 6.67(1H, t, J=7.5 Hz), 6.97(2H, t, J=8.0 Hz), 7.07(2H, br-t), 7.15(2H, m).
FAB-Mass: 355(MH+).

Example 83: Synthesis of 1-[2-(4-acetamidomethylphenyl)ethyl]-4-(indan-1-yl)piperidin-1-oxide

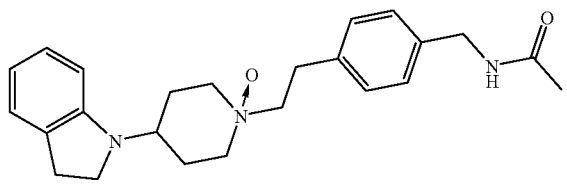

1-[1-(4-Acetoamidomethylphenethyl)piperidin-4-yl]-indoline (0.50 g) obtained in Example 36 was dissolved in methylene chloride (20 ml) and 70% m-chloroperbenzoic acid (0.37 g) was added thereto at 0° C. The reaction solution was stirred at room temperature for 30 min followed by the addition of sodium carbonate (5.0 g). The reaction mixture was filtered through alumina and washed with a mixture of methylene chloride and methanol (10:1). After concentrating the filtrate under reduced pressure, the resulting residue was purified by silica gel column chromatography (methylene chloride/methanol system) to give the title compound (0.15 g) as a white powder (yield: 28.8%).
m.p.: 130–131° C.
$^1$H-NMR (400 MHz, CDCl$_3$):
δ(ppm) 1.77(2H, br-d), 2.03(3H, s), 2.50–2.73(5H, m), 2.97(2H, t, J=8.0 Hz), 3.16–3.26(3H, m), 3.36–3.60(5H, m), 4.40(2H, d, J=9.6 Hz), 6.32(1H, m), 6.41(1H, d, J=8.0 Hz), 6.65(1H, t, J=7.6 Hz), 7.04(1H, t, J=7.6 Hz), 7.08(1H, d, J=7.2 Hz), 7.19(2H, d, J=8.0 Hz), 7.23(2H, d, J=8.0 Hz).
FAB-Mass: 394(MH+).

Example 84: Synthesis of cis-1-[1-ethyl-3-(4-fluorophenoxymethyl)piperidin-4-yl]indoline

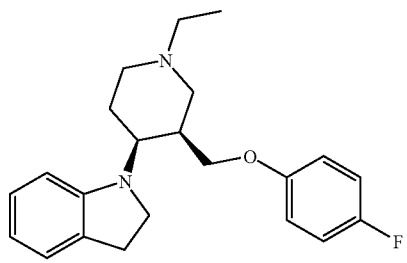

Under a nitrogen gas stream, 4-fluorophenol (168 mg) and triphenylphosphine (420 mg) were added to a solution of cis-1-(1-ethyl-3-hydroxymethylpiperidin-4-yl)indoline (300 mg) in tetrahydrofuran (4 ml). After cooling the resultant mixture to −10° C., diethyl azodicarboxylate (278 mg) was gradually added dropwise thereinto. Then the resultant mixture was gradually warmed to room temperature and stirred at the same temperature overnight. After adding water (40 ml), the reaction mixture was extracted with ether (40 ml) for three times. The organic phase was washed successively with a saturated aqueous solution (40 ml) of sodium bicarbonate and a 1 N aqueous solution (40 ml) of sodium hydroxide, dried over anhydrous magnesium sulfate and concentrated under reduced pressure. The residue was purified by silica gel column chromatography (Fuji Silysia Chemical Ltd. NH-DM2035, hexane/ethyl acetate system) to give the title compound (100 mg) as a colorless oil (yield: 25%).
m.p. (oxalate): 97–98° C.
$^1$H-NMR (400 MHz, CDCl$_3$):
δ(ppm) 1.04(3H, t, J=7.0 Hz), 1.82(1H, m), 2.00(1H, dq, J=3.5 Hz, 11.5 Hz), 2.11(2H, m), 2.35(1H, m), 2.44(1H, m), 2.62(1H, m), 2.98(3H, m), 3.17(1H, br-d, JJ=10.5 Hz), 3.54(3H, m), 4.10(1H, dd, J=3.5 Hz, 8.0 Hz), 4.34(1H, t, J=8.5 Hz), 6.38(1H, d, J=7.5 Hz), 6.59(1H, t, J=7.5 Hz), 6.77(2H, m), 6.88(2H, br-t), 7.01–7.06(2H, m).
FAB-Mass: 355(MH+).

Example 85-1: Synthesis of ethyl 1-acetyl-4-oxo-3-piperidinecarboxylate (85-1-1) Ethyl 4-oxo-3-piperidinecarboxylate hydrochloride

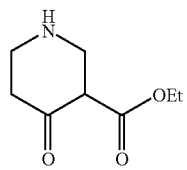

10% palladium/active carbon (2 g) was added to a solution of ethyl 1-benzyl-4-oxo-3-piperidinecarboxylate hydrochloride (30 g) in methanol (500 ml) and the resultant mixture was stirred at room temperature under hydrogen atmosphere for a day. After filtering the reaction mixture through celite, the filtrate was concentrated under reduced pressure to give the title compound (20.0 g) as a white powder (yield: 97%).
$^1$H-NMR (400 MHz, CDCl$_3$):
δ(ppm) 1.30(3H, t, J=6.0 Hz), 2.66(2H, t, J=5.5 Hz), 3.42(2H, t, J=5.5 Hz), 3.84(2H, s), 4.29(2H, q, J=6.0 Hz).

(85-1-2) Ethyl 1-acetyl-4-oxo-3-piperidinecarboxylate

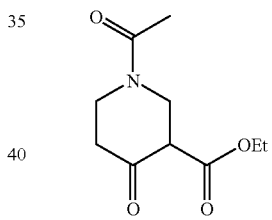

Ethyl 1-benzyl-4-oxo-3-piperidinecarboxylate hydrochloride (20.0 g) obtained above was dissolved in pyridine (150 ml). To the resultant solution was added acetic anhydride (10.2 g) at room temperature over 5 min or longer and the resultant mixture was stirred at room temperature for 2 hr. After adding ethyl acetate (500 ml), the reaction mixture was filtered. The filtrate was concentrated under reduced pressure and the residue was purified by silica gel column chromatography (ethyl acetate/methanol system) to give the title compound (19.9 g) as a white powder (yield: 97%).
$^1$H-NMR (400 MHz, CDCl$_3$):
δ(ppm) mixture of tautomers
major: 1.34(3H, t, J=6.0 Hz), 2.16(3H,s), 2.39(2H, t, J=5.5 Hz), 3.75(2H, t, J=5.5 Hz), 4.10(2H, s), 4.28(2H, q, J=6.0 Hz), 12.08(1H,s).
minor: 1.32(3H, t, J=6.0 Hz), 2.15(3H, s), 2.44(2H, t, J=5.5 Hz), 3.60(2H, t, J=5.5 Hz), 4.23(2H, s), 4.26(2H, q, J=6.0 Hz), 12.06(1H, s).

Example 85-2: Synthesis of cis-1-(1-acetyl-3-ethoxycarbonylpiperidin-4-yl)indoline

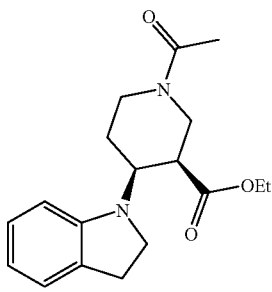

Indoline (12.5 g), ethyl 1-acetyl-4-oxo-3-piperidinecarboxylate (22.3 g) and triacetoxylated sodium borohydride (48.7 g) were treated as in Example 1 to give the title compound (7.12 g) as a pale yellow powder (yield: 22%).

$^1$H-NMR (400 MHz, CDCl$_3$):

δ(ppm) mixture of tautomers 1.19(3H of 1tautomer, t, J=6.0 Hz), 1.21(3H of 1tautomer, t, J=6.0 Hz), 2.07(3H of 1tautomer, s), 2.14(3H of 1tautomer, s), 2.36–3.07(5H, m), 3.19–3.62(3H, m), 3.75(1H of 1tautomer, m), 3.93–4.13(3H, m), 4.66(1H of 1tautomer, br-d), 4.82(1H of 1tautomer, br-d), 6.34(1H, d, J=7.5 Hz), 6.61(1H, t, J=7.5 Hz), 7.05(2H, m).

Example 85-3: Synthesis of trans-1-(1-acetyl-3-ethoxycarbonylpiperidin-4-yl)indoline

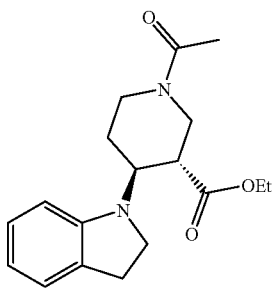

Potassium carbonate (138 mg) was added to a solution (150 ml) of cis -1-(1-acetyl-3-ethoxycarbonylpiperidin-4-yl)indoline (4.35 g) in ethanol and the resultant mixture was stirred at 60° C. for a day followed by concentration under reduced pressure. Ethyl acetate (200 ml) was added to the residue, which was then washed successively with water (50 ml) once and brine (50 ml) once, dried over anhydrous magnesium sulfate and concentrated under reduced pressure. Thus the title compound (4.22 g) was obtained as a yellow oil (yield: 97%).

$^1$H-NMR (400 MHz, CDCl$_3$):

δ(ppm) mixture of tautomers 1.11(3H, t, J=6.0 Hz), 1.59 (1H, m), 1.71(1H, m), 2.13(3H of 1tautomer, s), 2.14(3H of 1tautomer, s), 2.61–2.82(2H, m), 2.95(2H, m), 3.22(1H, m), 3.34(1H, m), 3.54(1H, m), 3.93(2H, m), 3.99(2H, m), 4.77 (1H of 1 tautomer, br-d), 4.88(1H of 1 tautomer, br-d), 6.45(1H, m), 6.61(1H, br-t), 7.03(2H, br-t).

Example 85-4: Synthesis of trans-1-[1-ethyl-3-(4-fluorobenzyloxymethyl)piperidin-4-yl]indoline (85-4-1) trans-1-(1-Ethyl-3-hydroxymethylpiperidin-4-yl)indoline

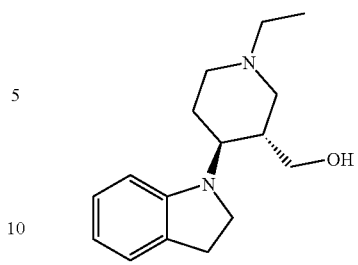

In a stream of nitrogen, lithium aluminum hydride (133 mg) was carefully added to dry tetrahydrofuran (5 ml) under ice cooling. To the resultant mixture was gradually added a solution of trans-1-(1-acetyl-3-ethoxycarbonylpiperidin-4-yl)indoline (850 mg) in dry tetrahydrofuran (5 ml) and the resulting mixture was stirred at 0° C. overnight. Under ice cooling and vigorous stirring, water (0.13 ml), a 5 N aqueous solution (0.13 ml) of sodium hydroxide and further water (0.4 ml) were successively added thereto. After allowing to warm the resultant mixture to room temperature, ethyl acetate (30 ml) was added thereto followed by drying over anhydrous sodium sulfate. After filtering and concentrating under reduced pressure, the resulting residue was purified by silica gel column chromatography (methylene chloride/methanol system) to give the title compound (340 mg) as a pale yellow powder (yield: 49%).

$^1$H-NMR (400 MHz, CDCl$_3$):

δ(ppm) 1.11(3H, t, J=6.0 Hz), 1.68(1H, m), 1.79(2H, m), 1.96(1H, dt, J=2.5 Hz, 11.0 Hz), 2.17(1H, m), 2.44(2H, q, J=6.0 Hz), 2.95(2H, m), 3.05(2H, m), 3.34(2H, m), 3.48(1H, dt, J=5.0 Hz, 8.0 Hz), 3.63(1H, dd, J=5.0 Hz, 10.0 Hz), 3.69(1H, dd, J=5.5 Hz, 10.5 Hz), 6.51(1H, d, J=7.5 Hz), 6.65(1H, t, J=7.5 Hz), 7.06(2H, m).

(85-4-2) trans-1-[1-Ethyl-3-(4-fluorobenzyloxymethyl)piperidin-4-yl]indoline

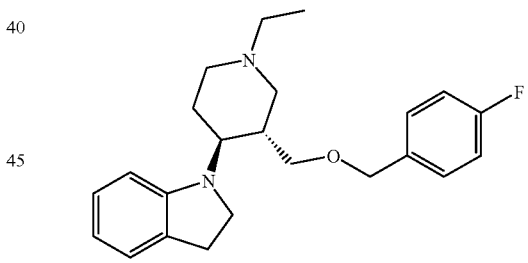

To a suspension of 55% sodium hydride (83 mg) in dimethylformamide (3 ml) were added under ice cooling a solution of trans-1-(1-ethyl-3-hydroxymethylpiperidin-4-yl) indoline (340 mg) in dimethylformamide (2 ml) and 4-fluorobenzyl bromide (378 mg). The resulting mixture was gradually warmed to room temperature and then stirred at the same temperature overnight. After adding water (50 ml), it was extracted with ethyl acetate (50 ml) thrice. The organic phase was washed with water (50 ml) once and then with brine (50 ml) once, dried over anhydrous magnesium sulfate and concentrated under reduced pressure. Next, the residue was purified by silica gel column-chromatography (Fuji Silysia Chemical Ltd. NH-DM2035, hexane/ethyl acetate system) to give the title compound (50 mg) as a colorless oil (yield: 10%).

m.p. (oxalate): 177–178° C.

$^1$H-NMR (400 MHz, CDCl$_3$):

δ(ppm) 1.11(3H, t, J=6.0 Hz), 1.73(1H, m), 1.96(2H, m), 2.15(1H, m), 2.45(2H, q, J=6.0 Hz), 2.83–2.97(2H, m), 3.04(1H, m), 3.23(1H, br-d), 3.32(3H, m), 3.57(1H, dd, J=2.5 Hz, 9.0 Hz), 4.35(1H, d, J=11.5 Hz), 4.41(1H, d, J=11.5 Hz), 4.50(2H, s), 6.37(1H, d, J=7.5 Hz), 6.57(1H, t, J=7.5 Hz), 6.95(2H, br-t), 7.02(2H, m), 7.22(2H, dd, J=6.0 Hz, 9.0 Hz).
FAB-Mass: 369(MH+).

Example 86: Synthesis of cis-1-[1-ethyl-3-(4-fluorobenzyloxymethyl)piperidin-4-yl]indoline (86-1) cis-1-1(-Ethyl-3-acetoxymethylpiperidin-4-yl)indoline

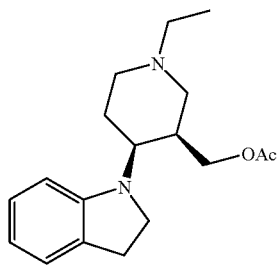

Triethylamine (1.21 g) and ethyl iodide (1.72 g) were added to a solution of cis-1-(3-acetoxymethylpiperidin-4-yl)indoline (3.53 g) in dimethylformamide (40 ml) followed by stirring the mixture at 50° C. for 4 hr. Under ice cooling, water (150 ml) was added to the reaction mixture, which was then extracted with ethyl acetate (100 ml) for three times. The organic phase was washed with water (50 ml) twice and brine (100 ml) once, dried over anhydrous magnesium sulfate and concentrated under reduced pressure. The residue was purified by silica gel column chromatography (ethyl acetate/methanol system) to give the title compound (2.06 g) as a pale yellow oil (yield: 63%).

$^1$H-NMR (400 MHz, CDCl$_3$):
δ(ppm) 1.04(3H, t, J=7.0 Hz), 1.77(1H, m), 1.92(3H, s), 1.96–2.11(3H, m), 2.31–2.48(3H, m), 2.93–3.03(4H, m), 3.49(1H, m), 3.56(2H, m), 4.22(1H, dd, J=4.5 Hz, 10.5 Hz), 4.47(1H, dd, J=9.0 Hz, 10.0 Hz), 6.32(1H, d, J=7.5 Hz), 6.56(1H, t, J=7.5 Hz), 7.02(2H, m).

(86-2) cis-1-(1-Ethyl-3-hydroxymethylpiperidin-4-yl)indoline

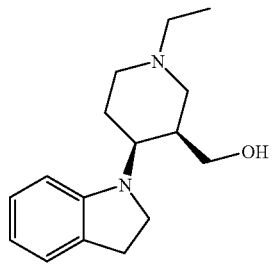

Potassium carbonate (3.0 g) was added to a solution of cis-1-(1-ethyl-3-acetoxymethylpiperidin-4-yl)indoline-(2.06 g) in methanol (120 ml) and the resultant mixture was stirred at room temperature for 4 hr. After adding ether (80 ml), the mixture was filtered through celite and the filtrate was concentrated under reduced pressure. The residue was purified by silica gel column chromatography (Fuji Silysia Chemical Ltd. NH-DM2035, hexane/ethyl acetate system) to give the title compound (1.19 g) as a pale yellow powder (yield: 67%).

$^1$H-NMR (400 MHz, CDCl$_3$):
δ(ppm) 1.11(3H, t, J=7.0 Hz), 1.82(1H, br-d), 2.06(1H, m), 2.11(1H, dd, J=3.0 Hz, 11.5 Hz), 2.40(2H, q, J=7.0 Hz), 2.41(1H, m), 2.52(1H, m), 3.01(2H, m), 3.10(1H, m), 3.16(1H, td, J=2.0 Hz, 11.5 Hz), 3.56(1H, td, J=5.0 Hz, 12.0 Hz), 3.66(1H, q, J=9.0 Hz), 3.82(1H, dd, J=6.0 Hz, 9.0 Hz), 3.87(1H, br-d), 3.98(1H, td, J=2.0 Hz, 11.5 Hz), 6.27(1H, d, J=7.5 Hz), 6.55(1H, t, J=7.5 Hz), 7.00(1H, br-t), 7.04(1H, br-d).

(86-3) cis-1-[1-Ethyl-3-(4-fluorobenzyloxymethyl)piperidin-4-yl]indoline

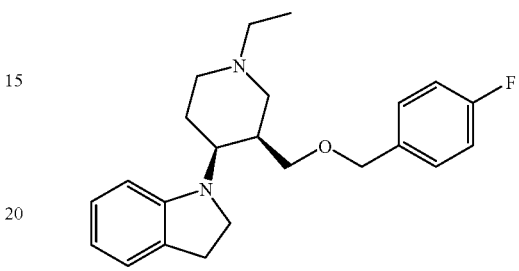

To a suspension of 65% sodium hydride (42 mg) in dimethylformamide (3 ml) were added under ice cooling a solution of cis-1-(1-ethyl-3-hydroxymethylpiperidin-4-yl)indoline (250 mg) in dimethylformamide (1 ml) and 4-fluorobenzyl bromide (264 mg). Then the reaction mixture was gradually warmed to room temperature and stirred at the same temperature overnight. After adding ice water (30 ml), the resultant mixture was extracted with ethyl acetate (30 ml) for three times. The organic phase was washed with water (50 ml) once and then with brine (50 ml) once, dried over anhydrous magnesium sulfate and concentrated under reduced pressure. The residue was purified by silica gel column chromatography (Fuji Silysia Chemical Ltd. NH-DM2035, hexane/ethyl acetate system) to give the title compound (100 mg) as a pale brown amorphous solid (yield: 28%).

$^1$H-NMR (400 MHz, CDCl$_3$):
δ(ppm) 1.07(3H, t, J=7.0 Hz), 1.75(1H, m), 1.94(1H, m), 2.07(1H, m), 2.31–2.54(3H, m), 2.94(3H, m), 3.15(1H, br-d), 3.48(2H, m), 3.62(1H, dd, J=4.0 Hz, 8.0 Hz), 3.86(1H, m), 4.18(1H, d, J=4.0 Hz), 4.41(1H, d, J=4.0 Hz), 6.36(1H, d, J=7.5 Hz), 6.57(1H, t, J=7.5 Hz), 6.95(2H, br-t), 7.00–7.06(2H, m), 7.20(2H, dd, J=6.0 Hz, 9.0 Hz).
FAB-Mass: 369(MH+).

Example 87: Synthesis of 1-(1-acetylpiperidin-4-yl)indoline-7-carbaldehyde (87-1) 1-(1-Acetylpiperidin-4-yl)indoline

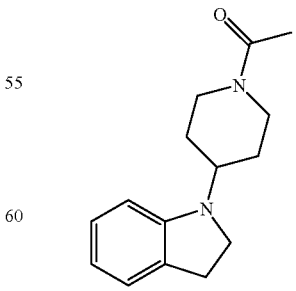

Indoline (25 ml), 1-acetyl-4-piperidone (25 g) and glacial acetic acid (20 ml) were dissolved in methanol (300 ml). After adding 10% palladium carbon (1.0 g) thereto, catalytic reduction was carried out under atmospheric pressure. After the completion of the reaction, the reaction solution was filtered through celite, washed with methanol and concentrated under reduced pressure. The residue was partitioned between water and ethyl acetate and basified with a 5 N aqueous solution of sodium hydroxide followed by extraction with ethyl acetate. The ethyl acetate layer was washed with water and brine, dried and concentrated under reduced pressure. The resulting residue was purified by silica gel column chromatography (ethyl acetate/hexane system) to give the title compound (35.6 g) as a pale yellow wax (yield: 82.2%).

$^1$H-NMR (400 MHz, CDCl$_3$):

δ(ppm) 1.50–1.62(2H, m), 1.81–1.93(2H, m), 2.12(3H, s), 2.59(1H, br-t), 2.96(2H, t, J=7.2 Hz), 3.15(1H, br-t), 3.31–3.39(2H, m), 3.57–3.64(1H, m), 3.93(1H, br-d), 4.78 (1H, br-d), 6.42(1H, d, J=8.0 Hz), 6.62(1H, t, J=8.0 Hz), 7.02–7.09(2H, m).

(87-2) 1-(4-Piperidin-1-yl)indoline

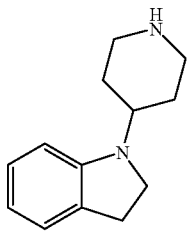

1-(1-Acetylpiperidin-4-yl)indoline (24.4 g) obtained in the above (87-1) was dissolved in ethanol (500 ml). To the resultant solution was added a 5 N aqueous solution (80 ml) of sodium hydroxide followed by heating under reflux for 5 hr. Then the reaction solution was concentrated under reduced pressure and the residue was partitioned between water and ethyl acetate. The ethyl acetate layer was washed with brine, dried and concentrated under reduced pressure. The residue was purified by NH-silica gel column chromatography (ethyl acetate) to give the title compound (15.9 g) as a flesh-colored wax (yield: 78.7%).

$^1$H-NMR (400 MHz, CDCl$_3$):

δ(ppm) 1.53–1.65(2H, m),1.77–1.85(2H, m), 2.68(2H, br-t), 2.95(2H, t, J=7.2 Hz), 3.16–3.22(1H, m), 3.39(2H, t, J=7.2 Hz), 3.40–3.50(1H, m), 6.41(1H, d, J=8.0 Hz), 6.59 (1H, t, J=8.0 Hz), 7.01–7.07(2H, m).

(87-3) 1-(1-Acetylpiperidin-4-yl)indoline-7-carbaldehyde

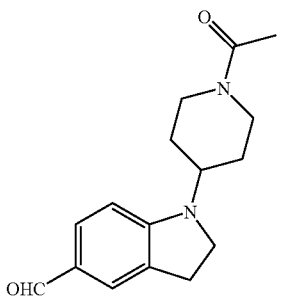

Phosphorus oxychloride (4.60 g) was added dropwise into ice cooled DMF (40 ml) followed by stirring for 15 min. Next, 1-(1-acetylpiperidin-4-yl)indoline (7.32 g) obtained in the above (87-1) was added thereto. The reaction solution was heated at 80° C. for 3 hr with vigorous stirring. After cooling, the reaction solution was partitioned between ethyl acetate and water. The ethyl acetate layer was washed with water and brine, dried and concentrated under reduced pressure. The resulting residue was purified by silica gel column chromatography (ethyl acetate) to give the title compound (3.2 g) as a pale yellow oil (yield: 39.0%).

$^1$H-NMR (400 MHz, CDCl$_3$):

δ(ppm) 1.62(2H, br-q), 1.81–1.92(2H, m), 2.12(3H, s), 2.61(1H, br-t), 3.04(2H, t, J=7.2 Hz), 3.16(1H, br-t), 3.50–3.60(2H, m), 3.66–3.75(1H, m), 3.95(1H, br-d), 4.81 (1H, br-d), 6.40(1H, d, J=8.0 Hz), 7.53–7.59(2H, m), 9.66 (1H, s).

Example 88: Synthesis of 1-[1-(t-butoxycarbonyl) piperidin-4-yl]-6-bromoindoline

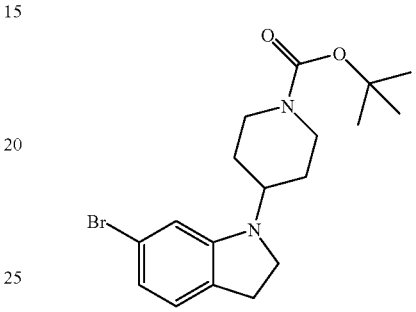

Triacetoxylated sodium borohydride (11.7 g) was added to a mixture of 6- bromoindoline (8.3 g), 1-(t-butoxycarbonyl)-4-piperidone (10 g, [CAS Registry No. 7909-07-3]), acetic acid (14.9 g) and dichloroethane (200 ml) followed by stirring overnight. Then the reaction solution was concentrated under reduced pressure, and the pH value thereof was adjusted to 9 with ethyl acetate, an 8 N aqueous solution of sodium hydroxide and water and the layers were separated. The organic layer was washed with brine, dried over anhydrous magnesium sulfate and concentrated under reduced pressure. The resulting residue was purified by silica gel column chromatography (hexane/ethyl acetate system) to give the title compound (10.3 g) (yield: 64%).

δ(ppm) 1.48(9H, s), 1.50–1.62(2H, m), 1.75–1.82(2H, m), 2.71–2.82(2H, m), 2.90(2H, t, J=8 Hz), 3.40–3.50(1H, m), 3.42(2H, t, J=8 Hz), 4.17–4.32(2H, m), 6.52(1H, br-s), 6.75(1H, d, J=8 Hz), 6.90(1H, d, J=8 Hz).

Example 89: Synthesis of 1-[1-(t-butoxycarbonyl)-piperidin-4-yl]-6-hydroxymethylindoline

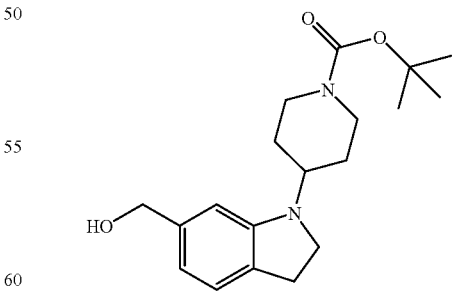

A 2.5 M solution (16 ml) of n-butyllithium in hexane was added dropwise at ±78° C. into a solution of 1-[1-(t-butoxycarbonyl)piperidin-4-yl]-6-bromoindoline (10 g) in tetrahydrofuran (250 ml) over 5 mm. After 10 mm, dimethylformamide (3.0 ml) was added and the resultant mixture was allowed to warm to room temperature. Next, a saturated aqueous solution of ammonium chloride and ethyl acetate were added thereto and the layers were separated. The organic layer was washed with brine, dried over anhydrous magnesium sulfate and concentrated under reduced pressure. To the residue were added ethanol (50 ml) and sodium borohydride (1.0 g) and the resultant mixture was stirred at room temperature for 30 mm. Then ice water and ethyl acetate were added to the reaction solution and the layers were separated. The organic layer was washed with brine, dried over anhydrous magnesium sulfate and concentrated under reduced pressure. The resulting residue was purified by silica gel column chromatography (hexane/ethyl acetate system) to give the title compound (7.9 g) (yield: 91%).

$^1$H-NMR (400 MHz, CDCl$_3$):

δ(ppm) 1.48(9H, s), 1.50–1.63(2H, m), 1.75–1.83(2H, m), 2.71–2.83(2H, m), 2.91(2H, t, J=8 Hz), 3.39(2H, t, J=8 Hz), 3.50–3.60(1H, m), 4.10–4.29(2H, m), 4.31(2H, d, J=6 Hz), 6.49(1H, br-s), 6.61(1H, d, J=8 Hz), 7.03(1H, d, J=8 Hz).

Example 90: Synthesis of 1-[1-(t-butoxycarbonyl)piperidin-4-yl]-6- aminomethylindoline

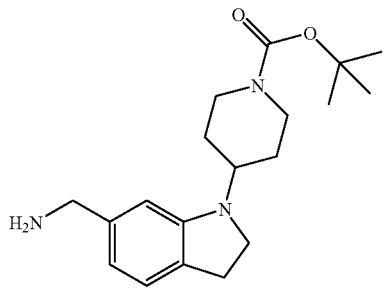

Under ice cooling, a solution of diethyl azodicarboxylate (4.6 g) in tetrahydrofuran (20 ml) was added dropwise into a solution of 1-[1-(t-butoxycarbonyl)piperidin-4-yl]-6-hydroxymethylindoline (7.9 g), triphenylphosphine (6.9 g) and phthalimide (3.9 g) in tetrahydrofuran (250 ml) and the resultant mixture was stirred at room temperature for 3 hr. After concentrating under reduced pressure, the resulting residue was purified by silica gel column chromatography (ethyl acetate/hexane system). Then hydrazine hydrate (3.6 g) and ethanol (150 ml) were added thereto followed by healing under reflux for 2 hr. After ice cooling, the resulting crystalline precipitates were filtered off and the filtrate was concentrated under reduced pressure to give the title compound (8.3 g).

$^1$H-NMR (400 MHz, CDCl$_3$):

δ(ppm) 1.48(9H, s), 1.50–1.60(2H, m), 1.71–1.81(2H, m), 2.72–2.89(2H, m), 2.91(2H, t, J=8 Hz), 3.35(2H, t, J=8 Hz), 3.49–3.60(1H, m), 3.83(2H, s), 4.13–4.29(2H, m), 6.42(1H, br-s), 6.58(1H, d, J=8 Hz), 7.00(1H, d, J=8 Hz).

Example 91: Synthesis of 1-(1-benzylpiperidin-4-yl)-6-bromoindoline

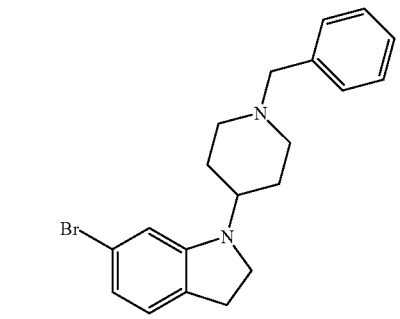

Triacetoxylated sodium borohydride (14.6 g) was added to amixture of 6-bromoindoline (10 g), 1-benzyl-4-piperidone (9.5 g), acetic acid (12 g) and dichloroethane (200 ml) over 5 min followed by stirring overnight. Then the reaction solution was concentrated under reduced pressure, the pH value thereof was adjusted to 10 by dilution with ethyl acetate, an 8 N aqueous solution of sodium hydroxide and water and the organic layer was separated. The organic layer was washed successively with water and brine, dried over anhydrous magnesium sulfate and concentrated under reduced pressure. The resulting residue was purified by NH-silica gel column chromatography (hexane/ethyl acetate system) to give the title compound (16.3 g) as a brown oil (yield: 87%).

$^1$H-NMR (400 MHz, CDCl$_3$):

δ(ppm) 1.51–1.60(2H, m), 1.69–1.79(2H, m), 2.01–2.13 (2H, m), 2.89(2H, t, J=8 Hz), 2.95–3.03(2H, m), 3.22–3.32 (1H, m), 3.40(2H, t, J=8 Hz), 3.53(2H, s), 6.44(1H, s), 6.65(1H, t, J=8 Hz), 6.84(1H, t, J=8 Hz), 7.22–7.36(5H, m).

Example 92-1: Synthesis of 1-(1-benzylpiperidin-4-yl)-6-fluoroindole

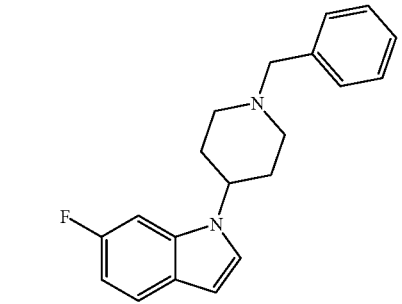

A solution of 1-benzyl-4-(3-fluorophenyl)-aminopiperidine (11.7 g) synthesized in accordance with the method of Referential Example 1 of JP-B 40-6347 and oxalyl chloride (10.5 g) in ether (300 ml) was heated under reflux for 2 hr. After concentrating under reduced pressure, the residue was diluted with methylene chloride (120 ml) and the resultant solution was added dropwise at 0° C. into a solution of anhydrous aluminum chloride (27 g) in methylene chloride (100 ml). After stirring for 1 hr, the reaction solution was carefully added to a saturated aqueous solution of sodium bicarbonate. The resulting crystalline precipitates were filtered off and washed with methylene chloride. Next, the filtrate was pertitioned between two liquid layers. The organic layer was washed with brine and dried over anhydrous magnesium sulfate. The resulting residue was purified by silica gel column chromatography (hexane/ethyl acetate system) followed by dilution with tetrahydrofuran (200 ml). Into the resultant solution was added dropwise under ice cooling a 1 M solution (120 ml) of a borane/tetrahydrofuran complex in tetrahydrofuran and the resultant mixture was stirred at room temperature overnight followed by heating under reflux for 3 hr. A saturated aqueous solution of sodium bicarbonate was carefully added dropwise into the reaction solution, then ethyl acetate was added thereto and the layers were separated. The organic layer was washed with brine, dried over anhydrous magnesium sulfate and concentrated under reduced pressure. The residue was diluted with pyridine (100 ml) and stirred at room temperature for 4 hr. Then a saturated aqueous solution of sodium bicarbonate and ethyl acetate were added thereto and the layers were separated. The organic layer was washed with brine and dried over anhydrous magnesium sulfate. The resulting residue was then purified by silica gel column chromatography (hexane/ethyl acetate system) to give the title compound (3.5 g) as a yellow oil (yield: 35%).

$^1$H-NMR (400 MHz, CDCl$_3$):

δ(ppm) 2.00–2.30(6H, m), 3.02–3.18(2H, m), 3.55–3.67 (2H, m), 4.09–4.19(1H, m), 6.49(1H, s), 6.81–6.89(1H, m), 7.00–7.04(1H, m), 7.20(1H, s), 7.22–7.40(5H, m), 7.49–7.56(1H, m).

Example 92-2: Synthesis of 1-(1-benzylpiperidin-4-yl)-6-fluoroindoline

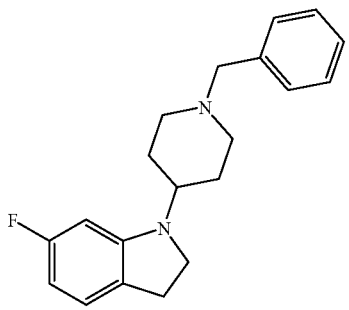

Under ice cooling, a 1 M solution (23 ml) of a borane/tetrahydrofuran complex in tetrahydrofuran was added dropwise into a solution of 1-(1-benzylpiperidin-4-yl)-6-fluoroindole (3.5 g) in trifluoroacetic acid (50 ml) followed by stirring for 2 hr. After adding water thereto, the resultant mixture was concentrated under reduced pressure and then basified by adding ethanol and a 5 N aqueous solution of sodium hydroxide followed by stirring for 2 hr. Then a saturated aqueous solution of sodium bicarbonate and ethyl acetate were added thereto and the layers were separated. The organic layer was washed with brine and dried over anhydrous magnesium sulfate. The residue was then purified by silica gel column chromatography (hexane/ethyl acetate system) to give the title compound (2.0 g) as a brown oil (yield: 57%).

$^1$H-NMR (400 MHz, CDCl$_3$):

δ(ppm) 1.72–1.83(4H, m), 2.89(2H, t, J=8 Hz), 3.00–3.09 (2H, m), 3.23–3.44(3H, m), 3.42(2H, t, J=8 Hz), 3.52–3.61 (2H, m), 6.02–6.09(1H, m), 6.20–6.28(1H, m), 6.89–6.93 (1H, m), 7.23–7.40(5H, m).

Example 93: Synthesis of 1-(1-benzylpiperidin-4-yl)-6-formylindoline

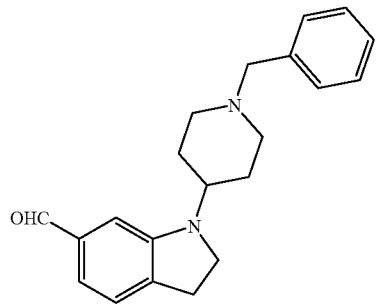

1-(1-Benzylpiperidin-4-yl)-6-bromoindoline (8.54 g) was dissolved in tetrahydrofuran (125 ml). Into the resultant mixture were successively added dropwise in a nitrogen atmosphere a 2.5 M solution (11.5 ml) of n-butyllithium in n-hexane and N,N-dimethylformamide (6.1 ml) followed by stirring for 2 hr. Then water and ethyl acetate were added thereto and the layers were separated. The organic layer was washed with brine, dried over anhydrous magnesium sulfate and concentrated under reduced pressure. The resulting residue was purified by silica gel column chromatography (hexane/ethyl acetate system) to give the title compound (6.360 g) as a yellow oil (yield: 86.1%).

$^1$H-NMR (400 MHz, CDCl$_3$):

δ(ppm) 1.74–1.80(4H, m), 2.11(2H, m), 2.99–3.03(2H, m), 3.01(2H, t, J=8.4 Hz), 3.43(1H, m), 3.47(2H, t, J=8.4 Hz), 3.55(2H, s), 6.82(1H, d, J=1.6 Hz), 7.06(1H, dd, J=1.6, 7.2 Hz), 7.15(1H, d, J=7.2 Hz), 7.28(1H, t, J=4.4 Hz), 7.33(1H, d, J=4.4 Hz), 9.85(1H, s).

Example 94: Synthesis of 1-(1-benzylpiperidin-4-yl)-6-hydroxyiminomethylindoline

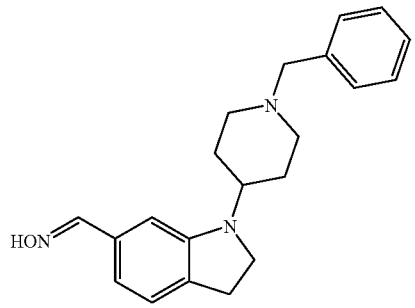

1-(1-Benzylpiperidin-4-yl)-6-formylindoline (6.36 g) was treated as in Example 46 to give the title compound (6.200 g) as a yellow oil (yield: 89.4%).

$^1$H-NMR (400 MHz, CDCl$_3$):

δ(ppm) 1.74–1.89(4H, m), 2.09(2H, dt, J=2.4, 11.6 Hz), 2.91(2H, t, J=8.4 Hz), 3.02(2H, br-d), 3.40(1H, m), 3.41(2H, t, J=8.4 Hz), 3.55(2H, s), 6.66(1H, s), 6.70(1H, dd, J=1.4, 7.2 Hz), 7.01(1H, d, J=7.2 Hz), 7.27(1H, m), 7.32(4H, m), 8.06(1H, s).

Example 95: Synthesis of 1-(1-benzylpiperidin-4-yl)-6-aminomethylindoline

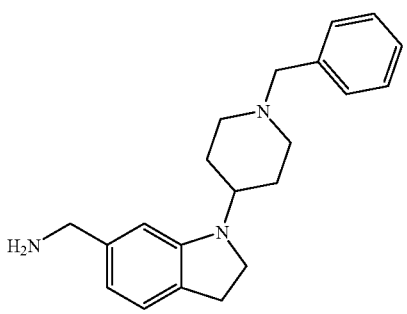

1-(1Benzylpiperidin-4-yl)-6-hydroxyiminomethylindoline (5.5 g) was treated as in Example 35 to give the title compound (5.598 g) as a brown oil.

$^1$H-NMR (400 MHz, CDCl$_3$):
δ(ppm) 1.75(4H, m), 2.09(2H, m), 2.10(2H, t, J=8.4 Hz), 3.00(2H, m), 3.39(2H, t, J=8.4 Hz), 3.55(2H, s), 3.76(2H, s), 6.36(1H, t, J=0.6 Hz), 6.51(1H, dd, J=0.6, 7.2 Hz), 6.99(1H, d, J=7.2 Hz), 7.27(1H, m), 7.32(4H, m).

Example 96: Synthesis of 1-(1-benzylpiperidin-4-yl-6-acetamidomethylindoline

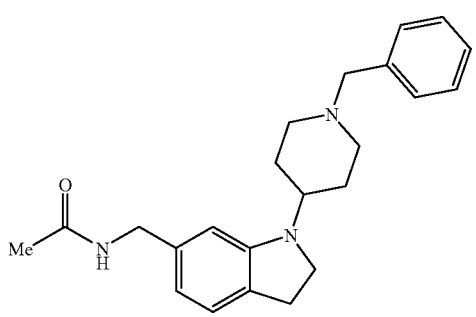

1-(1-Benzylpiperidin-4-yl)-6-aminomethylindoline (5.598 g) and acetyl chloride (1.3 ml) were treated as in Example 36 to give the title compound (5.598 g) as a brown oil.
Free
$^1$H-NMR (400 MHz, CDCl$_3$):
δ(ppm) 1.76(4H, m), 1.99(3H, s), 2.12(2H, m), 2.91(2H, t, J=8.4 Hz), 3.02(2H, br-d), 3.36(1H, m), 3.40(2H, t, J=8.4 Hz), 3.57(2H, br-s), 4.31(2H, d, J=5.6 Hz), 5.65(1H, m), 6.30(1H, br-d), 6.49(1H, dd, J=1.2, 7.4 Hz), 6.98(1H, d, J=7.4 Hz), 7.28(1H, m), 7.35(4H, d, J=8.4 Hz).
ESI-Mass: 364.1.

Example 97: Synthesis of 1-[1-(4-methoxyphenethyl)piperidin-4-yl]-6-acetamidomethylindoline

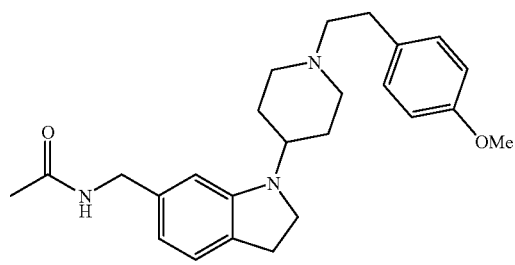

1-(Piperidin-4-yl)-6-acetamidomethylindoline (250 mg) and 4-methoxyphenethyl bromide (240 mg) were treated as in Example 2 to give the title compound (200 mg) as a white powder (yield: 53%).
m.p.: 151–152° C.
$^1$H-NMR (400 MHz, CDCl$_3$):
δ(ppm) 1.50–1.63(2H, m), 1.79–1.81(2H, m), 2.01(3H, s), 2.10–2.30(2H, m), 2.75–2.96(4H, m), 2.93(2H, t, J=8 Hz), 3.10–3.30(2H, m), 3.36–3.50(1H, m), 3.44(2H, t, J=8 Hz), 3.79(3H, s), 4.33(2H, d, J=6 Hz), 6.47(1H, s), 6.52(1H, d, J=8 Hz), 6.83–6.87(2H, m), 7.00(1H, d, J=8 Hz), 7.13–7.16 (2H, m).
FAB-Mass: 408(MH+).

Example 98: Synthesis of 1-[1-(4-chlorophenethyl)piperidin-4-yl]-6-acetamidomethylindoline

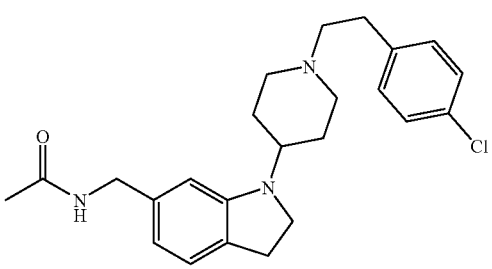

1-(Piperidin-4-yl)-6-acetamidomethylindoline (250 mg) and 4-chlorophenethyl bromide (240 mg) were treated as in Example 2 to give the title compound (240 mg) as white scaly crystals (yield: 63%).
m.p.: 151–152° C.
$^1$H-NMR (400 MHz, CDCl$_3$):
δ(ppm) 1.50–1.64(2H, m), 1.54–1.90(2H, m), 2.01(3H, s), 2.04–2.34(2H, m), 2.60–3.00(4H, m), 2.93(2H, t, J=8 Hz), 3.06–3.26(2H, m), 3.36–3.48(1H, m), 3.43(2H, t, J=8 Hz), 4.33(2H, d, J=6 Hz), 6.38(1H, s), 6.51(1H, d, J=8 Hz), 7.00(1H, d, J=8 Hz), 7.11–7.20(2H, m), 7.23–7.29(2H, m).
FAB-Mass: 412(MH+).

Example 99: Synthesis of 1-[1-(4-fluorophenethyl)piperidin-4-yl]-5-methoxyindoline

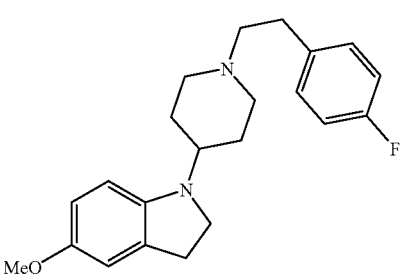

1-(4-Fluorophenethyl)-4-(4-methoxyphenyl)aminopiperidine (10 g) synthesized in accordance with the method of Referential Example 1 of JP-B 40-6347 was treated as in Example 106 to give the hydrochloride (180 mg) of the title compound as a white powder (yield: 1.4%).
m.p. (hydrochloride): 209–211° C.
$^1$H-NMR (400 MHz, DMSO-d$_6$):
δ(ppm) 1.83–2.09(4H, m), 2.83–2.96(2H, m), 2.98–3.10 (4H, m), 3.20–3.29(2H, m), 3.31–3.45(2H, m), 3.60–3.80 (3H, m), 3.69(3H, s), 4.24–4.34(1H, m), 6.58–6.70(2H, m), 6.75–6.80(1H, m), 7.11–7.20(2H, m), 7.29–7.40(2H, m).
FAB-Mass: 355(MH+).

Example 100-1: Synthesis of 1-(4-fluorophenethyl)-4-(3-bromophenyl)aminopiperidine

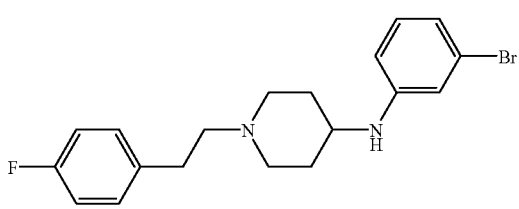

A solution of o-bromoaniline (17.2 g) and 4-fluorophenethylpiperidone (22 g) in toluene (200 ml) was heated under reflux overnight by using a Dean-Starke reflux condenser. After concentrating under reduced pressure, the residue was diluted with 1,2-dichloroethane (200 ml) and sodium borohydride (7.6 g) and acetic acid (8.0 g) were added thereto followed by stirring the resultant mixture at 0° C. for 4 hr. Next, a saturated aqueous solution of sodium bicarbonate and ethyl acetate were added to the reaction solution and the layers were separated. The organic layer was washed with brine and dried over anhydrous magnesium sulfate. The residue was purified by silica gel column chromatography (methylene chloride/ethanol system) to give the title compound (10 g) as a brown oil (yield: 27%).
$^1$H-NMR (400 MHz, CDCl$_3$):
δ(ppm) 1.42–1.60(2H, m), 2.02–2.10(2H, m), 2.18–2.25 (2H, m), 2.55–2.63(2H, m), 2.78–2.84(2H, m), 2.90–3.00 (2H, m), 3.23–3.32(1H, m), 3.60(1H, d, J=8 Hz), 6.50(1H, d, J=8 Hz), 6.72(1H, s), 6.79(1H, d, J=8 Hz), 6.94–7.02(3H, m), 7.12–7.20(2H, m).

Example 100-2: Synthesis of 1-[1-(4-fluorophenethyl) piperidin-4-yl]-2,3-dioxo-6-bromoindoline

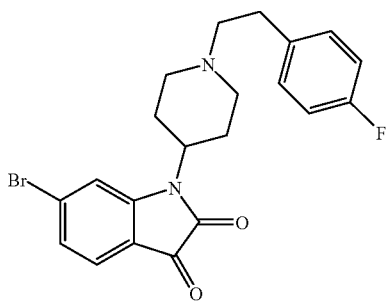

A solution of 1-(4-fluorophenethyl)-4-(3-bromophenyl) aminopiperidine (10 g) and oxalyl chloride (6.7 g) in ether (200 ml) was heated under reflux for 2 hr. After concentrating under reduced pressure, the residue was diluted with methylene chloride (200 ml) and the resultant solution was added dropwise at 0° C. into a solution of anhydrous aluminum chloride (24.7 g) in methylene chloride (60 ml). After stirring for 1 hr, the reaction solution was carefully added to a saturated aqueous solution of sodium bicarbonate. The resulting crystalline precipitates were filtered off and washed with methylene chloride and the filtrate was partitioned between two liquid layers. The organic layer was washed with brine and dried over anhydrous magnesium sulfate. The resulting residue was purified by silica gel column chromatography (hexane/ethyl acetate system) to give the title compound (7.4 g) as a yellow powder (yield: 65%).
$^1$H-NMR (400 MHz, CDCl$_3$):
δ(ppm) 1.75–1.83(2H, m), 2.15–2.25(2H, m), 2.35–2.50 (2H, m), 2.60–2.69(2H, m), 2.78–2.87(2H, m), 3.11–3.20 (2H, m), 4.12–4.28(1H, m), 6.95–7.03(2H, m), 7.15–7.20 (2H, m), 7.28(1H, d, J=8 Hz), 7.36(1H, s), 7.49(1H, d, J=8 Hz).

Example 100-3: Synthesis of 1-[1-(4-fluorophenethyl) piperidin-4-yl]-6-bromoindole

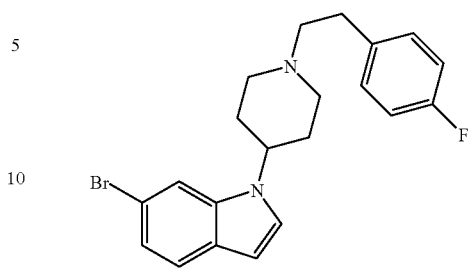

Under ice cooling, a 1 M solution (69 ml) of a borane/tetrahydrofuran complex in tetrahydrofuran was added dropwise into a solution of 1-[1-(4-fluorophenethyl)-piperidin-4-yl]-2,3-dioxo-6-bromoindoline (7.4 g) in tetrahydrofuran (150 ml) followed by stirring at room temperature overnight and heating under reflux for 3 hr. Into the reaction solution was carefully added dropwise a saturated aqueous solution of sodium bicarbonate. Then ethyl acetate was added to the resultant mixture and the organic layer was separated. The organic layer was washed with brine, dried over anhydrous magnesium sulfate and concentrated under reduced pressure. The residue was then diluted with pyridine (50 ml) and stirred at room temperature for 4 hr. Next, a saturated aqueous solution of sodium bicarbonate and ethyl acetate were added thereto and the layers were separated. The organic layer was washed with brine and dried over anhydrous magnesium sulfate. The residue was purified by silica gel column chromatography (hexane/ethyl acetate system) to give the title compound (3.9 g) as a yellow oil (yield: 57%).
$^1$H-NMR (400 MHz, CDCl$_3$):
δ(ppm) 2.01–2.12(4H, m), 2.20–2.32(2H, m), 2.61–2.69 (2H, m), 2.79–2.86(2H, m), 3.13–3.21(2H, m), 4.10–4.21 (1H, m), 6.48(1H, d, J=2 Hz), 6.95–7.02(2H, m), 7.12–7.23 (2H, m), 7.45–7.55(3H, m), 7.91(1H, t, J=6 Hz).

Example 100-4: Synthesis of 1-[1-(4-fluorophenethyl) piperidin-4-yl]-6-bromoindoline

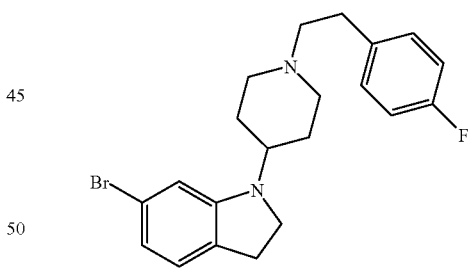

Under ice cooling, a 1 M solution (20 ml) of a borane/tetrahydrofuran complex in tetrahydrofuran was added dropwise into a solution of 1-[1-(4-fluorophenethyl)-piperidin-4-yl]-6-bromoindole (3.9 g) in trifluoroacetic acid (50 ml) followed by stirring for 3 hr. After adding water thereto and concentrating under reduced pressure, the reaction mixture was basified by adding ethanol and a 5 N aqueous solution of sodium hydroxide and then stirred for 30 min. Next, a saturated aqueous solution of sodium bicarbonate and ethyl acetate were added thereto and the layers were separated. The organic layer was washed with brine and dried over anhydrous magnesium sulfate. The residue was then purified by silica gel column chromatography (toluene/acetone system) to give the title compound (2.0 g) as a white powder (yield: 51%).

m.p.: 99–101° C.
¹H-NMR (400 MHz, CDCl₃):
δ(ppm) 1.74–1.84(4H, m), 2.10–2.19(2H, m), 2.58–2.64 (2H, m), 2.78–2.84(2H, m), 2.89(2H, t, J=8 Hz), 3.10–3.17 (2H, m), 3.28–3.38(1H, m), 3.43(2H, t, J=8 Hz), 6.47(1H, d, J=2 Hz), 6.69(1H, dd, J=2.8 Hz), 6.87(1H, d, J=8 Hz), 6.96–7.00(2H, m), 7.15–7.18(2H, m).
FAB-Mass: 404(MH+).

Example 101: Synthesis of 1-[1-(4-fluorophenethyl) piperidin-4-yl]-6-bromoindoline

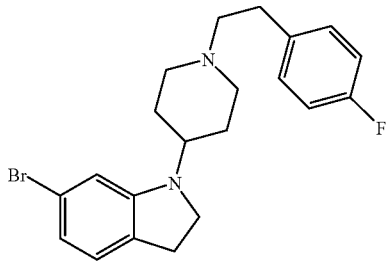

Triacetoxylated sodium borohydride (298 g) was added over 30 min to a mixture of 6-bromoindoline (175 g), 1-(4-fluorophenethyl)-4-piperidone (194 g), acetic acid (250 ml) and dichloroethane (2.5 l) followed by stirring 2 hr. Then the reaction solution was concentrated under reduced pressure, diluted with ethyl acetate (2 l), an 8 N aqueous solution of sodium hydroxide (1 l) and water (500 ml) and the layers were separated. The organic layer was washed successively with water (0.5 l) and brine (0.5 l), dried over anhydrous magnesium sulfate and concentrated under reduced pressure. The resulting residue was dissolved in hot ethyl acetate (500 ml) and then cooled with ice water. The resulting crystalline precipitates were collected by filtration to give the title compound (205 g) (yield: 58%).

These crude crystals were recrystallized from hexane-ethyl acetate mixtures to give the title compound as white prisms.
m.p.: 99–101° C.
¹H-NMR (400 MHz, CDCl₃):
δ(ppm) 1.74–1.84(4H, m), 2.10–2.19(2H, m), 2.58–2.64 (2H, m), 2.78–2.84(2H, m), 2.89(2H, t, J=8 Hz), 3.10–3.17 (2H, m), 3.28–3.38(1H, m), 3.43(2H, t, J=8 Hz), 6.47(1H, d, J=2 Hz), 6.69(1H, dd, J=2.8 Hz), 6.87(1H, d, J=8 Hz), 6.96–7.00(2H, m), 7.15–7.18(2H, m).
FAB-Mass: 404(MH+).

Example 102: Synthesis of 1-[1-(4-fluorophenethyl) piperidin-4-yl]-6-chloroindoline

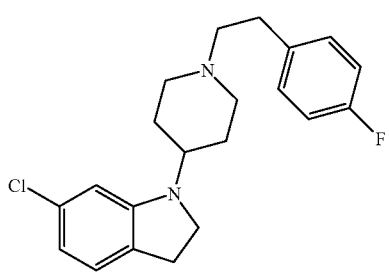

1-(4-Fluorophenethyl)-4-(3-chlorophenyl)-aminopiperidine (1.4 g) synthesized in accordance with the method of Referential Example 1 of JP-B 40-6347 was treated as in Example 101 to give the hydrochloride (380 mg) of the title compound as a white powder (yield: 25%).

m.p. (hydrochloride): 236–240° C.
¹H-NMR (400 MHz, DMSO-d₆):
δ(ppm) 1.79–1.90(2H, m), 1.99–2.12(2H, m), 2.87(2H, t, J=8 Hz), 3.00–3.13(4H, m), 3.20–3.29(2H, m), 3.36(2H, t, J=8 Hz), 3.55–3.63(2H, m), 3.70–3.80(1H, m), 6.52(1H, d, J=8 Hz), 6.57(1H, s), 6.97(1H, d, J=8 Hz), 7.13–7.20(2H, m), 7.29–7.35(2H, m).
FAB-Mass: 359(MH+).

Example 103: Synthesis of 1-[1-(4-fluorophenethyl) piperidin-4-yl]-6-fluoroindoline

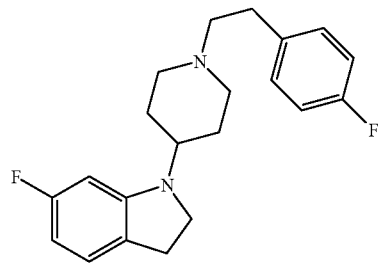

1-(Piperidin-4-yl)-6-fluoroindoline (200 mg) and 4-fluorophenethyl bromide (220 mg) were treated as in Example 2 to give the hydrochloride (220 mg) of the title compound as a white powder (yield: 65%).
m.p. (hydrochloride): 214–216° C.
¹H-NMR (400 MHz, DMSO-d₆):
δ(ppm) 1.81–1.90(2H, m), 1.95–2.08(2H, m), 2.85(2H, t, J=8 Hz), 2.99–3.10(4H, m), 3.20–3.29(2H, m), 3.38(2H, t, J=8 Hz), 3.67–3.75(3H, m), 6.26(1H, t, J=8 Hz), 6.39(1H, d, J=8 Hz), 6.95(1H, t, J=8 Hz), 7.14–7.19(2H, m), 7.30–7.34 (2H, m).
FAB-Mass: 343(MH+).

Example 104: Synthesis of 1-[1-(4-fluorophenethyl) piperidin-4-yl]-6-hydroxyindoline

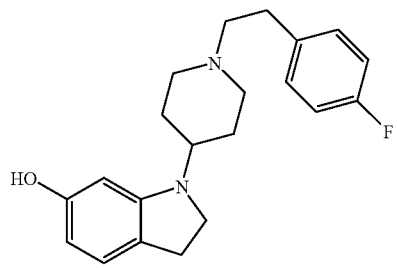

A solution of 1-[1-(4-fluorophenethyl)piperidin-4-yl]-6-methoxyindoline (1.6 g) in conc. hydrogen bromide (40 ml) was heated at 100° C. for 2 hr. Next, it was basified with a conc. aqueous solution of sodium hydroxide and extracted with ethyl acetate. The organic layer was washed with brine, dried over anhydrous magnesium sulfate and concentrated under reduced pressure. The resulting residue was purified by silica gel column chromatography (methylene chloride/ethanol system) followed by conversion into a hydrochloride in a conventional manner. Thus the hydrochloride (1.2 g) of the title compound was obtained as brown prisms (yield: 68%).
m.p. (hydrochloride): 232° C. (decomp.).
¹H-NMR (400 MHz, DMSO-d₆):
δ(ppm) 1.81–2.00(4H, m), 2.73(2H, t, J=8 Hz), 2.97–3.12 (4H, m), 3.21–3.33(4H, m), 3.59–3.69(3H, m), 5.93(1H, s), 5.97(1H, d, J=8 Hz), 6.75(1H, d, J=8 Hz), 7.12–7.21(2H, m), 7.30–7.38(2H, m), 8.89(1H, s).

FAB-Mass: 341(MH+).

Example 105: Synthesis of 1-[1-(4-fluorophenethyl)piperidin-4-yl]-4-methoxyindoline

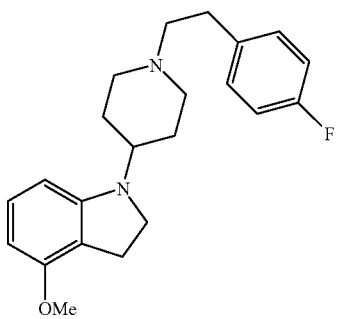

A mixture of 4-methoxyindoline (0.25 g), 1-(4-fluorophenethyl)-4-piperidone, platinum oxide (50 mg), -acetic acid (1.0 ml) and ethanol (20 ml) was catalytically reduced under hydrogen atmosphere at ordinary temperature under atmospheric pressure. After stirring the reaction mixture overnight, the catalyst was filtered off and the filtrate was concentrated under reduced pressure. Then it was diluted with a saturated aqueous solution of sodium bicarbonate and ethyl acetate and the layers were separated. The organic layer was washed with brine and dried over anhydrous magnesium sulfate. The resulting residue was purified by silica gel column chromatography (hexane/ethyl acetate system) followed by conversion into a hydrochloride in a conventional manner. Thus the hydrochloride (92 mg) of the title compound was obtained as a white powder (yield: 27%).

m.p. (hydrochloride): 195–198° C.

$^1$H-NMR (400 MHz, DMSO-d$_6$):

δ(ppm) 1.81–2.04(4H,m), 2.79(2H, t, J=8 Hz), 3.00–3.13 (4H, m), 3.21–3.36(4H, m), 3.59–3.71(3H, m), 3.72(3H, s), 6.22(1H, d, J=8 Hz), 6.27(1H, d, J=8 Hz), 6.98(1H, t, J=8 Hz), 7.15–7.20(2H, m), 7.31–7.35(2H, m).

FAB-Mass: 355(MH+).

Example 106-1: Synthesis of 1-(1-benzylpiperidin-4-yl)-6-methoxyindoline-2,3-dione

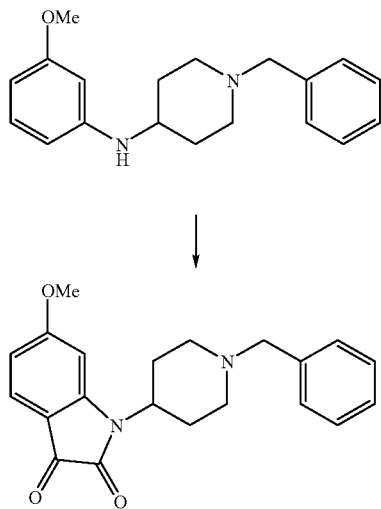

1-Benzyl-4-(3-methoxyphenyl)aminopiperidine (1.88 g) synthesized in accordance with the method of Referential Example 1 of JP-B 40-6347 was dissolved in ether (38 ml). Into the resultant solution was added dropwise oxalyl chloride (1.62 g) over 30 min at room temperature followed by heating under reflux for 3.5 hr. After cooling to room temperature, the reaction solution was concentrated under reduced pressure. Into a suspension of aluminum chloride (5.9 g) in methylene chloride (20 ml) was added dropwise a solution of the resulting residue in methylene chloride (100 ml) at 0° C. over 30 min. After the completion of the addition, the resultant mixture was stirred at room temperature for additional 1.5 hr. After the completion of the reaction, the reaction solution was poured into ice and neutralized by adding an aqueous solution of sodium bicarbonate thereto. The resulting precipitate was filtered off and the filtrate was extracted with methylene chloride. After removing the solvent, the resulting residue was purified by silica gel column chromatography (hexane/ethyl acetate system) to give 1-(1-benzylpiperidin-4-yl)-6-methoxyindoline-2,3-dione (1.63 g) (yield: 73%).

$^1$H-NMR (400 MHz, CDCl$_3$):

δ(ppm) 1.69–1.76(2H, m), 2.12(2H, br-t), 2.42(2H, dq, J=12.0, 4.0 Hz), 3.03(2H, br-d), 3.55(2H, s), 3.93(3H, s), 4.08–4.18(1H, m), 6.54(1H, dd, J=8.4, 1.6 Hz), 6.66(1H, d, J=1.6 Hz), 7.24–7.36(5H, m), 7.59(1H, d, J=8.4 Hz).

Example 106-2: Synthesis of 1-(1-benzylpiperidin-4-yl)-6-methoxyindole

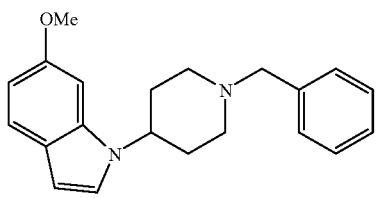

A 2 M solution (0.47 ml) of a diborane/dimethyl sulfide complex in tetrahydrofuran was added to a solution of 1-(1-benzylpiperidin-4-yl)-6-methoxyindoline-2,3-dione (110 mg) in tetrahydrofuran (2 ml) followed by stirring for 1 hr and then heating under reflux for 4.5 hr. After the completion of the reaction, an aqueous solution of sodium bicarbonate was added to the reaction solution, which was then extracted with ethyl acetate. The ethyl acetate layer was dried over magnesium sulfate andthe solvent was removed. The residue was dissolved in pyridine and stirred for 4.5 hr. After evaporating off pyridine, ethyl acetate and an aqueous solution of sodium bicarbonate were added thereto. The ethyl acetate layer was separated and dried over magnesium sulfate. After distilling off the solvent, the resulting residue was purified by silica gel column chromatography (hexane/ethyl acetate system) to give 1-(1-benzylpiperidin-4-yl)-6-methoxyindole (28 mg) (yield: 28%).

$^1$H-NMR (400 MHz, CDCl$_3$):

δ(ppm) 2.02–2.12(4H, m), 2.17–2.27(2H, m), 3.07(2H, br-d), 3.60(2H, s), 3.87(3H, s), 4.09–4.18(1H, m), 6.44(1H, d, J=3.2 Hz), 6.78(1H, dd, J=8.8, 2.0 Hz), 6.82(1H, br-d), 7.13(1H, d, J=3.2 Hz), 7.25–7.37(5H, m), 7.49(1H, d, J=8.8 Hz).

Example 106-3: Synthesis of 1-[1-(4-fluorophenethyl)piperidin-4-yl]-6-methoxyindole

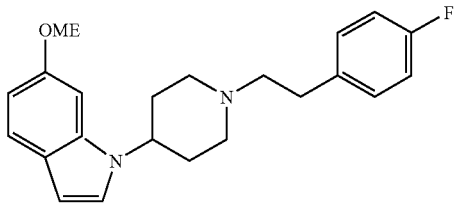

1-Chloroethyl chloroformate (32 mg) was added to a solution of 1-(1-benzylpiperidin-4-yl)-6-methoxyindole (24 mg) in toluene (2 ml) followed by heating under reflux for 3 hr. The reaction solution was concentrated under reduced pressure and the resulting residue was dissolved in methanol followed by heating under reflux for 9 hr. After the completion of the reaction, methanol was evaporated and the residue was dissolved in dimethylformamide (1 ml). Next, 2-(4-fluorophenyl)ethyl bromide (19 mg) was added thereto and the resultant mixture was stirred at 60° C. for 11 hr. After the completion of the reaction, brine was added to the mixture. Then it was extracted with ethyl acetate and dried over magnesium sulfate. After removing the solvent, the resulting residue was purified by silica gel column chromatography (toluene/acetone system) to give the title compound (7 mg) (yield: 27%).

m.p.: 230° C. (decomp.).

$^1$H-NMR (400 MHz, CDCl$_3$):

δ(ppm) 2.06–2.14(4H, m), 2.25–2.33(2H, m), 2.67(2H, dd, J=9.2, 10.8 Hz), 2.83(2H, dd, J=10.8, 9.2 Hz), 3.20(2H, br-d, J=11.6 Hz), 3.88(3H, s), 4.12–4.21(1H, m), 6.45(1H, d, J=3.2 Hz), 6.79(1H, dd, J=8.4, 2.0 Hz), 6.83(1H, d, J=2.0 Hz), 6.99(2H, t, J=12.4 Hz), 7.14(1H, d, J=3.2 Hz), 7.18(2H, dd, J=8.4, 5.6 Hz), 7.50(1H, d, J=8.4 Hz).

MS; [M+H]+: m/z=353.

Example 106-4: Synthesis of 1-[1-(4-flourophenethyl) piperidin-4-yl]-6-methoxyindoline

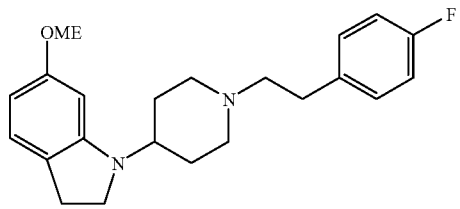

A 1 M solution (0.18 ml) of a borane/tetrahydrofuran complex was added dropwise at 0° C. into a solution of 1-[1-(4-fluorophenethyl)piperidin-4-yl]-6-methoxyindole (24 mg) in trifluoroacetic acid (1 ml) over 2 min followed by stirring at 0° C. for 30 min. Af ter the completion of the reaction, water (0.1 ml) was added thereto and the resulting reaction solution was concentrated under reduced pressure. The resulting residue was dissolved in a 2 N aqueous solution of sodium hydroxide and stirred at room temperature for 10 min. The mixture was extracted with methylene chloride. The organic layer was separated and dried over magnesium sulfate. After concentrating the solvent under reduced pressure, the resulting residue was purified by preparative TLC to give 1-[1-(4-fluorophenethyl)piperidin-4-yl)]-6-methoxyindoline (10 mg) (yield: 35%).

m.p.: 242° C. (decomp.).

$^1$H-NMR (400 MHz, CDCl$_3$):

δ(ppm) 1.75–1.90(4H, m), 2.10–2.22(2H, m), 2.58–2.70 (2H, m), 2.80(2H, dd, J=11.6, 7.2 Hz), 2.88(2H, t, J=8.8 Hz), 3.14(2H, br-d, J=10.8 Hz), 3.31–3.82(1H, m), 3.41(2H, t, J=8.4 Hz), 3.77(3H, s), 6.00(1H, d, J=2.0 Hz), 6.13(1H, dd, J=8.0, 2.0 Hz), 6.93(1H, 2H, t, J=8.8 Hz), 6.97(2H, t, J=8.8 Hz), 7.16(2H, dd, J=8.4, 5.6 Hz).

MS; [M+H]+: m/z=355.

Example 107: Synthesis of 1-[1-(4-fluorophenethyl) piperdin-4-yl]7-methoxyindoline

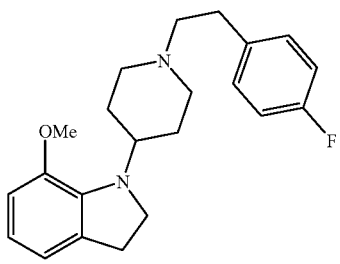

1-(4-Fluorophenethyl)-4-(2-methoxyphenyl)-aminopiperidine (3.9 g) synthesized in accordance with the method of Referential Example 1 of JP-B 40-6347 was treated as in Example 106 to give the hydrochloride (530 mg) of the title compound as a white powder (yield: 11%).

m.p. (hydrochloride): 204–206° C.

$^1$H-NMR (400 MHz, DMSO-d$_6$):

δ(ppm) 1.72–1.80(2H, m), 1.90–2.40(2H, m), 2.86(2H, t, J=8 Hz), 2.95–3.08(4H, m), 3.21–3.34(4H, m), 3.55–3.63 (2H, m), 3.73(3H, s), 4.24–4.34(1H, m), 6.60–6.64(1H, m), 6.69–6.74(2H, m), 7.14–7.19(2H, m), 7.28–7.32(2H, m).

FAB-Mass: 355(MH+).

Example 108: Synthesis of 1-[1-(4-fluorophenethyl) piperdin-4-yl]-6,7-dimethoxyindoline

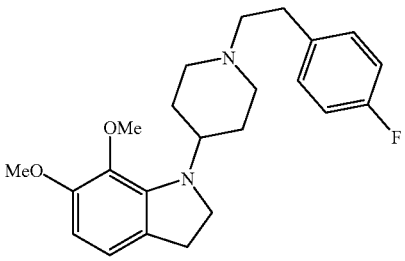

1-(4-Fluorophenethyl)-4-(2,3-dimethoxyphenyl) aminopiperidine (8.1 g) synthesized in accordance with the method of Referential Example 1 of JP-B 40-6347 was treated as in Example 106 to give the oxalate (34 mg) of the title compound as a white powder (yield: 1.7%).

m.p. (oxalate): 179–181° C.

$^1$H-NMR (400 MHz, DMSO-d$_6$):

δ(ppm) 1.72–1.86(4H, m), 2.79(2H, t, J=8 Hz), 2.86–2.97 (2H, m), 3.04–3.18(2H, m), 3.29(2H, t, J=8 Hz), 3.40–3.58 (4H, m), 3.64 (3H, S), 3.69 (3H, s), 4.05–4.17 (1H, m), 6.25 (1H, d, J=8 Hz) 6.69(1H, d, J=8 Hz), 7.13–7.18(2H, m), 7.28–7.32(2H, m).

FAB-Mass: 385(MH+)

Example 109: Synthesis of 1-[1-(4-fluorophenethyl) piperdin-4-yl]-6-nitroindoline

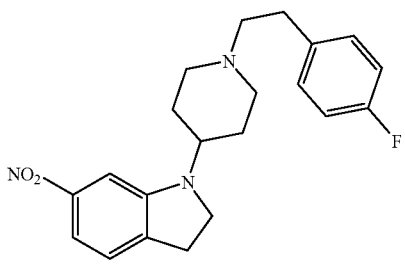

1-(Piperidin-4-yl)-6-nitroindoline (3.5 g) and 4-fluorophenethyl bromide (4.1 g) were treated as in Example 2 to give the title compound (5.1 g) as a paleyellow powder (yield: 81%).

¹H-NMR (400 MHz, CDCl₃)

δ(ppm) 1.71–2.89(4H, m), 2.09–2.20(2H, m), 2.55–2.66 (2H, m), 2.76–2.83(2H, m), 3.03(2H, t, J=8 Hz), 3.10–3.19 (2H, m), 3.39–3.49(1H, m), 3.56(2H, t, J=8 Hz), 6.95–7.00 (2H, m), 7.09(1H, d, J=8 Hz), 7.10(1H, s), 7.12–7.21(2H, m), 7.50(1H, d, J=8 Hz)

Example 110: Synthesis of 1-[1-(4-fluorophenethyl) piperdin-4-yl]-6aminoindoline

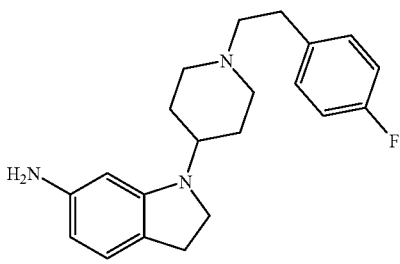

A mixture of 1-[1-(4-fluorophenethyl)piperidin-4-yl]-6-nitroindoline (5.1 g), powdery iron (5.0 g), ammonium chloride (10 g), water (20 ml) and ethanol (100 ml) was stirred at 60° C. for 4 hr. Next, the reaction solution was filtered and the filtrate was concentrated under reduced pressure. Then a 5 N aqueous solution of sodium hydroxide and ethyl acetate were added thereto and the layers were separated. The organic layer was washed with brine, dried over anhydrous magnesium sulfate and concentrated under reduced pressure. Then the resulting residue was purified by silica gel column chromatography (methylene chloride/ethanol system) to give the title compound (3.4 g) as a brown powder (yield: 73%).

m.p. 104–106° C.

¹H-NMR (400 MHz, CDCl₃)

δ(ppm) 1.69–1.88(4H, m), 2.05–2.13(2H, m), 2.53–2.60 (2H, m), 2.71–2.81(2H, m), 2.83(2H, t, J=8 Hz), 3.09–3.13 (2H, m), 3.29–3.35(1H, m), 3.36(2H, t, J=8 Hz), 3.50(2H, br-s), 5.82(1H, s), 5.98(1H, d, J-=8 Hz), 6.81(1H, d, J=8 Hz), 6.91–7.00(2H, m), 7.12–7.20(2H, m).

FAB-Mass: 340(MH+).

Example 111: Synthesis of 1-[1-(4-fluorophenethyl) piperdin-4yl]-6-methylaminoindoline

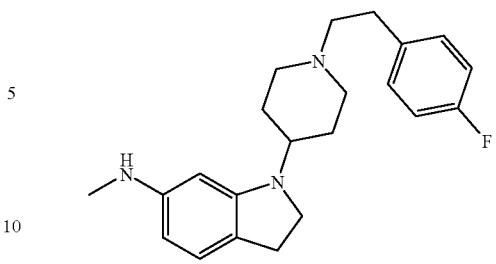

Ethyl chlorocarbonate (100 mg) was added dropwise at room temperature into a solution of 1-[1-(4-fluorophenethyl)-piperidin-4-yl]-6-aminoindoline (0.3 g) and triethylamine (100 mg) in methylene chloride (5 ml). Then the resultant mixture was stirred for 30 min and concentrated under reduced pressure. The resulting residue was partitioned between water and ethyl acetate. The organic layer was washed with brine, dried over anhydrous magnesium sulfate and concentrated under reduced pressure. The residue was added to a suspension of lithium aluminum hydride (67 mg) in tetrahydrofuran (5 ml) and heated under reflux for 1 hr. Under ice cooling, water (0.14 ml), a 5 N aqueous solution (0.42 ml) of sodium hydroxide and further water (0.14 ml) were carefully added dropwise into the reaction solution followed by vigorous stirring. The resulting precipitate was filtered off and the filtrate was concentrated under reduced pressure. Next, the obtained residue was purified by NH-silica gel column chromatography (hexane/ethyl acetate system) followed by conversion into a hydrochloride in a conventional manner. Thus the hydrochloride (220 mg) of the title compound was obtained as a brown hygroscopic amorphous solid (yield: 64%).

¹H-NMR (400 MHz, DMSO-d₆):

δ(ppm) 1.81–1.90(2H, m), 1.99–2.13(2H, m), 2.82(3H, s), 2.90(2H, t, J=8 Hz), 3.00–3.12(4H, m), 3.20–3.33(2H, m), 3.41(2H, t, J=8 Hz), 3.59–3.69(2H, m), 3.80–3.90(1H, m), 6.56–6.62(2H, m), 7.09(1H, d, J=8 Hz), 7.12–7.20(2H, m), 7.29–7.35(2H, m).

FAB-Mass: 354(MH+).

Example 112: Synthesis of 1-[1-(4-fluorophenethyl) piperidin-4-yl]-6-ethylaminoindoline

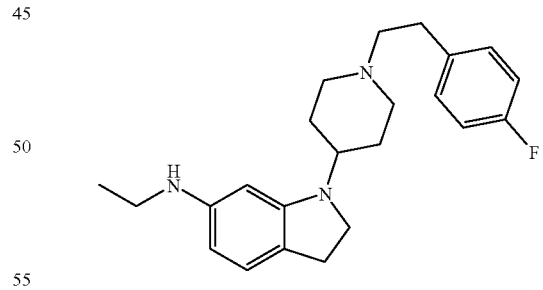

A mixture of 1-1-(4-fluorophenethyl)piperidin-4-yl]-6-aminoindoline (0.3 g), pyridine (5 ml) and acetic anhydride (3 ml) was stirred at room temperature for 30 min. After concentrating the resultant mixture under reduced pressure, water and ethyl acetate were added thereto and the layers were separated. The organic layer was washed with brine, dried over anhydrous magnesium sulfate and concentrated under reduced pressure. The residue was added to a suspension of lithium aluminum hydride (127 mg) in tetrahydrofuran (5 ml) and heated under reflux for 1 hr. Under ice cooling, water (0.14 ml), a 5 N aqueous solution (0.42 ml)

of sodium hydroxide and further water (0.14 ml) were carefully added dropwise into the reaction solution followed by vigorous stirring. The resulting precipitate was filtered off and the filtrate was concentrated under reduced pressure. Next, the resulting residue was purified by NH-silica gel column chromatography (hexane/ethyl acetate system) followed by conversion into a hydrochloride in a conventional manner. Thus the hydrochloride (210 mg) of the title compound was obtained as a pale brown hygroscopic amorphous solid (yield: 59%).

$^1$H-NMR (400 MHz, DMSO-$d_6$):

δ(ppm) 1.20(3H, t, J=7 Hz), 1.82–1.91(2H, m), 2.01–2.10 (2H, m), 2.89(2H, t, J=8 Hz), 3.00–3.09(4H, m), 3.21–3.32 (4H, m), 3.39(2H, t, J=8 Hz) 3.60–3.72(3H, m ), 6.55–6.62 (2H, m ), 7.09(1H, d, J=8 Hz), 7.10–7.21(2H, m), 7.28–7.33 (2H, m).

FAB-Mass: 368(MH+).

Example 113: Synthesis of 1-[1-(4-fluorophenethyl) piperdin-4-yl]-6-isopropylaminoindioline

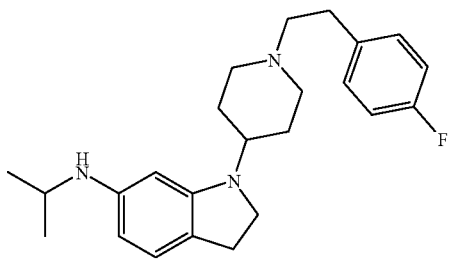

1-[1-(4-Fluorophenethyl)piperidin-4-yl]-6-aminoindoline (0.3 g), acetone (0.075 g), acetic acid (0.23 g) and triacetoxylated sodium borohydride (0.36 g) were treated as in Example 101 to give the hydrochloride (240 mg) of the title compound as a pale brown, hygroscopic and amorphous solid (yield: 65%).

$^1$H-NMR (400 MHz, DMSO-$d_6$):

δ(ppm) 1.23(6H, d, J=7 Hz),1.80–1.91(2H, m), 2.02–2.20 (2H, m), 2.91(2H, t, J=8 Hz), 3.00–3.13(4H, m), 3.20–3.29 (2H, m), 3.40(2H, t, J=8 Hz), 3.60–3.71(4H, m), 6.61–6.69 (2H, m), 7.09(1H, d, J=8 Hz), 7.11–7.20(2H, m), 7.31–7.39 (2H, m).

FAB-Mass: 382(MH+).

Example 114: Synthesis of 1-[1-(4-fluorophenethyl) piperdin-4-yl]-6-dimethylaminoindoline

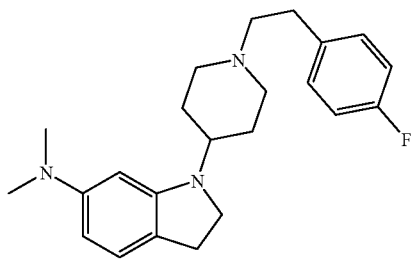

6-Dimethylaminoindoline (0.6 g), 1-(4-fluorophenethyl-4-piperidone (0.98 g), acetic acid (1.1 g) and triacetoxylated sodium borohydride (1.2 g) were treated as in Example 101 to give the hydrochloride (0.77 g) of the title compound as a white powder (yield: 52%).

m.p. (hydrochloride): 205–208° C.

$^1$H-NMR (400 MHz, DMSO-$d_6$):

δ(ppm) 1.81–2.03(4H, m), 2.71(2H, t, J=8 Hz),2.80(6H, s) 2.99–3.13(4H, m), 3.20–3.31(4H, m), 3.53–3.67(2H, m), 3.70–3.80(1H, m), 5.89–5.99(2H, m), 6.80(1H, d, J=8 Hz), 7.11–7.19(2H, m), 7.29–7.36(2H, m).

FAB-Mass: 367(MH+).

Example 115: Synthesis of 1-[1-(4-fluorophenethyl) piperdin-4-yl]-6-acetamidoindoline

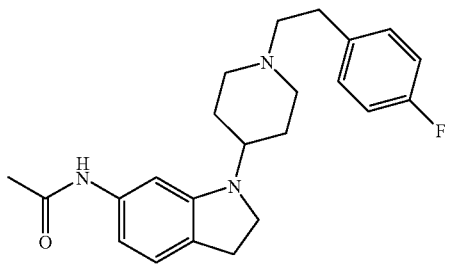

1-[1-(4-Fluorophenethyl)piperidin-4-yl]-6-aminoindoline (1.0 g) and acetic anhydride (1 ml) were treated as in Example 133 to give the title compound (450 mg) as a pale yellow powder (yield: 41%).

m.p.: 148–150° C.

$^1$H-NMR (400 MHz, CDCl$_3$)

δ(ppm) 1.80–1.91(4H, m), 2.15(3H, s), 2.20–2.35(2H, m), 2.62–2.75 (2H, m), 2.81–2.97 (2H, m), 2.90 (2H, t, J=8 Hz), 3.13–3.29 (2H, m), 3.39–3.48 (1H, m), 3.42 (2H, t, J=8 Hz), 6.44 (1H, d, J=8 Hz), 6.93–7.01(4H, m), 7.16–7.20(3H, m).

FAB-Mass: 382(MH+)

Example 116: Synthesis of 1-[1-(4-fluorophenethyl)-piperdin-4-yl]-6-methanesulfonylaminoindoline

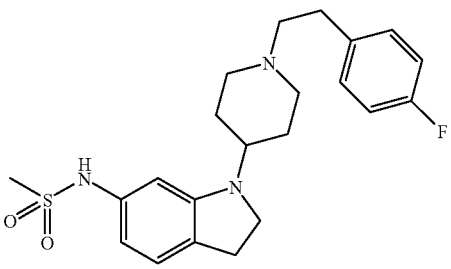

Methanesulfonyl chloride (0.4 g) was added dropwise at 0° C. into a mixture of 1-[1-(4-fluorophenethyl)piperidin-4-yl]-6-aminoindoline (0.3 g), 4-dimethylaminopyridine (0.1 g) and pyridine (10 ml) followed by stirring for 2 hr. Then water and ethyl acetate were added to the reaction solution and the layers were separated. The organic layer was washed with water and brine and dried over anhydrous magnesium sulfate. The residue was purified by NH-silica gel column chromatography (hexane/ethyl acetate system) followed by conversion into a hydrochloride in a conventional manner. Thus the hydrochloride (160 mg) of the title compound was obtained as a pale yellow hygroscopic amorphous solid (yield: 40%).

$^1$H-NMR (400 MHz, DMSO-$d_6$):

δ(ppm) 1.80–2.03 (4H, m), 2.85 (2H, t, J=8 Hz), 2.89 (3H, s), 2.99–3.17(4H, m), 3.20–3.43(5H, m), 3.58–3.69(2H, m), 6.37–6.40 (2H, m), 6.94 (1H, d, J=8 Hz), 7.15–7.20 (2H, m), 7.30–7.34 (2H, m), 9.33(1H, s).

FAB-Mass: 418(MH+).

Example 117: Synthesis of of 1-[1-(4-fluorophenethyl)-piperidin-4-yl]-6-ethanesulfonylaminoindoline

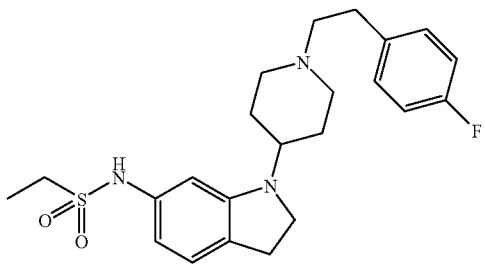

1-[1-(4-Fluorophenethyl)piperidin-4-yl]-6-aminoindoline (0.4 g) and ethanesulfonyl chloride (0.61 g) were treated as in Example 116 to give the hydrochloride (160 mg) of the title compound as a brown hygroscopic amorphous solid (yield: 29%).
$^1$H-NMR (400 MHz, DMSO-d$_6$):
δ(ppm) 1.16(3H, t, J=7 Hz), 1.81–1.89(2H, m), 1.94–2.05 (2H, m), 2.82(2H, t, J=8 Hz), 2.98(2H, q, J=7 Hz), 2.99–3.16 (4H, m), 3.20–3.29(2H, m), 3.31(2H, t, J=8 Hz), 3.35–3.44 (1H, m), 3.55–3.68(2H, m), 6.37–6.39(2H, m), 6.93(1H, d, J=8 Hz), 7.13–7.19(2H, m), 7.29–7.33(2H, m), 9.42(1H, s).
FAB-Mass: 432(MH+).

Example 118: Synthesis of 1-[1-(4-fluorophenethyl)-piperdin-4-yl]-6-propanesulfonylaminoindoline

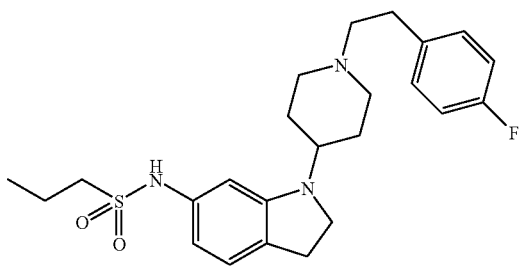

1-[1-(4-Fluorophenethyl)piperidin-4-yl]-6-aminoindoline (0.4 g) and propanesulfonyl chloride (0.67 g) were treated as in Example 116 to give the hydrochloride (210 mg) of the title compound as a white powder (yield: 37%).
m.p. (hydrochloride): 166–169° C.
$^1$H-NMR (400 MHz, DMSO-d$_6$)
δ(ppm) 0.91(3H, t, J=7 Hz), 1.65(2H, sextet, J=7 Hz), 1.82–2.04(4H, m), 2.84(2H, t, J=8 Hz), 2.94(2H, q, J=7 Hz), 3.00–3.16(4H, m), 3.22–3.43(5H, m), 3.59–3.68(2H, m), 6.38–6.40(2H, m), 6.91(1H, d, J=8 Hz), 7.11–7.20(2H, m), 7.30–7.38(2H, m), 9.41(1H, s).
FAB-Mass: 446(MH+).

Example119: Synthesis of 1-[1-(4-fluorophenethyl)-piperdin-4-yl]-6-(4-fluorobenzenesulfonylamino)indoline

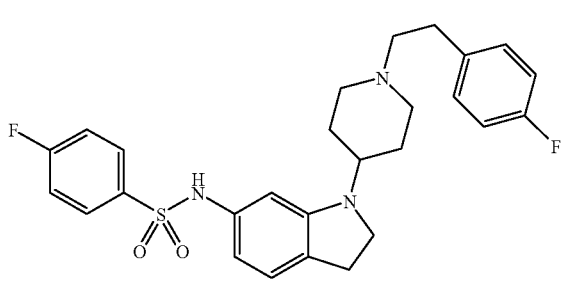

6-(4-Fluorobenzenesulfonylamino)indoline (0.23 g), 1-(4-fluorophenethyl)-4-piperidone (0.33 g), acetic acid (0.36 g) and triacetoxylated sodium borohydride (0.42 g) were treated as in Example 101 to give the hydrochloride (0.29 g) of the title compound as a white powder (yield: 68%).
m.p. (hydrochloride): 140–143° C.
$^1$H-NMR (400 MHz, DMSO-d$_6$):
δ(ppm) 1.69–1.73(2H, m), 1.83–1.99(2H, m), 2.75(2H, t, J=8 Hz), 3.01–3.19(4H, m), 3.20–3.31(4H, m), 3.51–3.63 (3H, m) 6.12(1H, d, J=8 Hz), 6.28(1H, s), 6.81(1H, d, J=8 Hz), 7.13–7.21(2H, m), 7.30–7.41(4H, m), 7.74–7.79(2H, m).
FAB-Mass: 498(MH+)

Example 120: Synthesis of 1-[1-(4-fluorophenethyl)-piperdin-4-yl]-6-(N-methylmethanesulfonylamino)indoline

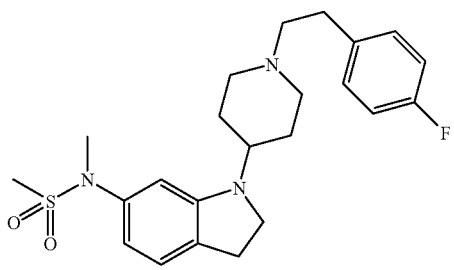

1-[1-(4-Fluorophenethyl)piperidin-4-yl]-6-methylaminoindoline (150 mg) and methanesulfonyl chloride (54 mg) were treated as in Example 116 to give the hydrochloride (100 mg) of the title compound as white prisms (yield: 55%).
m.p. (hydrochloride): 136–139° C.
$^1$H-NMR (400 MHz, DMSO-d$_6$):
δ(ppm) 1.82–1.89(2H, m), 1.98–2.10(2H, m), 2.83–2.90 (2H, m), 2.90(3H, s), 3.01–3.14(4H, m), 3.17(3H, s), 3.20–3.28(2H, m), 3.32–3.40(2H, m), 3.58–3.76(3H, m), 6.54–6.59(2H, m), 7.01(1H, d, J=8 Hz), 7.14–7.19(2H, m), 7.30–7.34(2H, m).
FAB-Mass: 432(MH+).

Example 121: Synthesis of 1-[1-(4-fluorophenethyl) piperdin-4-yl]-6-hydroxyethoxyindoline

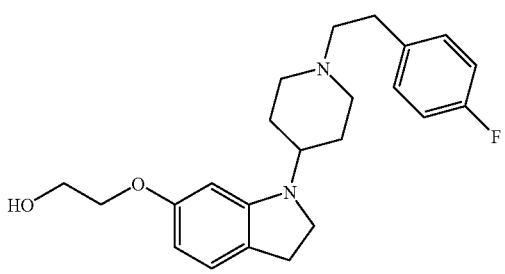

60% sodium hydride (0.11 g) was added to a solution of 1-[1-(4-fluorophenethyl)pipe ridin-4-yl]-6-hydroxyindoline (0.8 g) in dimethylf ormamide (30 ml) and the resultant mixture was stirred at 50° C. After 10 min, (t-butyl) dimethyl-siloxyethyl bromide (0.67 g) was added to the reaction solution followed by stirring for additional 2 hr. Then the mixture was concentrated under reduced pressure, diluted with a 2 N aqueous solution of sodium hydroxide and ethyl acetate and the layers were separated. The organic layer was washed with brine, dried over anhydrous magnesium sulf ate and concentrated under reduced pressure. The residue was purified by silica gel column chromatography (methylene chloride/ethanol system). To the residue were added a 1 M solution (2.4 ml) of tetrabutylammonium fluoride in tetrahydrofuran and tetrahydrofuran (20 ml) and the resultant mixture was stirred at room temperature for 3 hr. Next, the mixture was diluted with a 2 N aqueous solution of sodium hydroxide and ethyl acetate and the layers were separated. The organic layer was washed with brine, dried over anhydrous magnesium sulfate and concentrated under reduced pressure. The residue was purified by silica gel column chromatography (methylene chloride/ethanol system) followed by conversion into a hydrochloride in a conventional manner to give the hydrochloride (300 mg) of the title compound as a white powder (yield: 25%).

m.p. (hydrochloride): 235–238° C.

$^1$H-NMR (400 MHz, DMSO-$d_6$):

δ(ppm) 1.84–1.99(2H, m), 2.79(2H, t, J=8 Hz), 2.97–3.14 (4H, m), 3.22–3.34(4H, m), 3.60–3.77(5H, m), 3.88(2H, t, J=5 Hz), 4.79(1H, br-s), 6.09(1H, d, J=8 Hz), 6.12(1H, s), 6.88(1H, d, J=8 Hz), 7.12–7.20(2H, m), 7.30–7.38(2H, m).

FAB-Mass: 385(MH+).

Example 122: Synthesis of 1-[1-(4-fluorophenethyl)-piperdin-4-yl]-6methanesulfonyloxyindoline

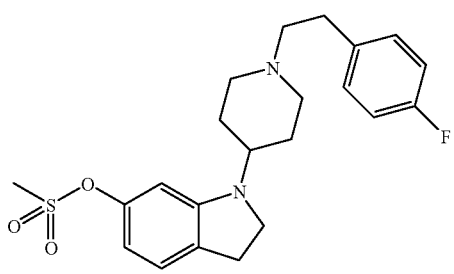

A solution of 1-[1-(4-fluorophenethyl)piperidin-4-yl]-6-methoxyindoline (1.0 g) in conc. hydrogen bromide (20 ml) was heated at 100° C. for 2 hr. Next, the mixture was basified with a conc. aqueous solution of sodium hydroxide and extracted with ethyl acetate. The organic layer was washed with brine, dried over anhydrous magnesium sulfate and concentrated under reduced pressure. The residue was dissolved in pyridine (10 ml) and methanesulfonyl chloride (0.46 g) was added dropwise thereinto under ice cooling. After stirring overnight, the resultant mixture was concentrated under reduced pressure, diluted with a 2 N aqueous solution of sodium hydroxide and ethyl acetate and the layers were separated. The organic layer was washed with brine, dried over anhydrous magnesium sulfate and concentrated under reduced pressure. Then the residue was purified by NH-silica gel column chromatography (ethyl acetate/hexane system) followed by conversion into a hydrochloride in a conventional manner to give the hydrochloride (300 mg) of the title compound as a pale brown powder (yield: 15%).

m.p. (hydrochloride): 220–223° C.

$^1$H-NMR (400 MHz, DMSO-$d_6$):

δ(ppm) 1.83–1.92(2H, m), 1.94–2.06(2H, m), 2.90(2H, t, J=8 Hz), 3.00–3.14(4H, m), 3.21–3.28(2H, m), 3.30(3H, s), 3.34–3.44(2H, m), 3.59–3.66(2H, m), 3.68–3.78(1H, m), 6.46–6.48(2H, m), 7.04(1H, d, J=8 Hz), 7.15–7.19(2H, m), 7.30–7.34(2H, m).

FAB-Mass: 419(MH+).

Example 123: Synthesis of 1-[1-(4-fluorophenethyl) piperdin-4-yl]-7-hydroxyethoxyindoline

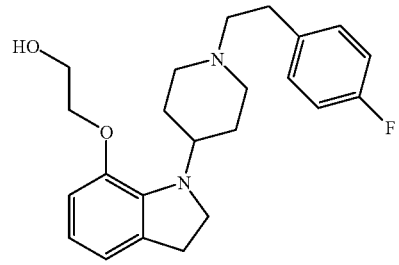

A solution of 1-[1-(4-fluorophenethyl)piperidin-4-yl]-7-methoxyindoline (0.3 g) in conc. hydrogen bromide (6 ml) was heated at 100° C. for 2 hr. Then the solution was basified with a conc. aqueous solution of sodium hydroxide and extracted with ethyl acetate. The organic layer was washed with brine, dried over anhydrous magnesium sulfate and concentrated under reduced pressure. The resulting residue was dissolved in dimethylformamide (10 ml) and 60% sodium hydride (32 mg) was added thereto followed by stirring at 50° C. After 30 min, (t-butyl)dimethylsiloxyethyl bromide (0.19 g) was added to the reaction solution and the resultant mixture was stirred for additional 30 min. After concentrating underreduced pressure, it was diluted with a 2 N aqueous solution of sodium hydroxide and ethyl acetate and the layers were separated. The organic layer was washed with brine, dried over anhydrous magnesium sulfate and concentrated under reduced pressure. The residue was purified by silica gel column chromatography (ethyl acetate/methanol system). To the residue were added a 1 M solution (0.45 ml) of tetrabutylammonium fluoride in tetrahydrofuran and tetrahydrofuran (10 ml) and the resultant mixture was stirred at room temperature overnight. Then it was diluted with a 2 Naqueous solution of sodium hydroxide and ethyl acetate and the layers were separated. The organic layer was washed with brine, dried over anhydrous magnesium sulfate and concentrated under reduced pressure. The residue was purified by silica gel column chromatography (ethyl acetate/methanol system) followed by conversion into a hydrochloride in a conventional manner to give the hydrochloride (80 mg) of the title compound as a white, hygroscopic and amorphous solid (yield: 25%).

$^1$H-NMR (400 MHz, DMSO-$d_6$):

δ(ppm) 1.79–1.86(2H, m), 1.95–2.07(2H, m), 2.91(2H, t, J=8 Hz), 2.95–3.07(4H, m), 3.20–3.27(2H, m), 3.30–3.41 (2H, m), 3.56–3.63(2H, m), 3.74(2H, t, J=5 Hz), 3.96(2H, t, J=5 Hz), 4.38–4.47(1H, m), 6.69–6.80(3H, m), 7.11–7.21 (2H, m), 7.29–7.35(2H, m).

FAB-Mass: 385(MH+).

Example 124: Synthesis of 1-[1-(4-fluorophenethyl) piperidin-4-yl]-6-cyanoindoline

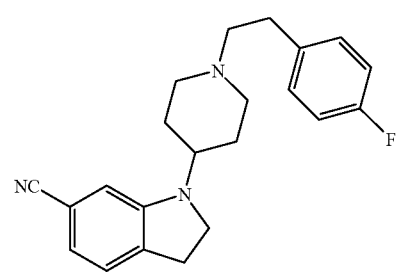

Trifluoromethanesulfonic anhydride (0.72 ml) was added dropwise at −78° C. into a solution of 1-[1-(4- fluorophenethyl)piperidin-4-yl]-6-hydroxyiminomethylindoline (1.5 g) and triethylamine (1.2 ml) in methylene chloride (1 l) and the resultant mixture was warmed to room temperature. Next, a saturated aqueous solution of sodium bicarbonate and chloroform were added thereto and the layers were separated. The organic layer was dried over anhydrous magnesium sulfate and the residue was purified by NH-silica gel column chromatography (hexane/ethyl acetate system) to give the title compound (1.0 g) as a white powder (yield: 67%).

A portion of these crystals were converted into a hydrochloride in a conventional manner to give the hydrochloride of the title compound as white powdery crystals.

m.p. (hydrochloride): 230° C. (decomp.).

$^1$H-NMR (400 MHz, DMSO-$d_6$):

δ(ppm) 1.82–1.91(2H, m), 1.95–2.09(2H, m), 2.98(2H, t, J=8 Hz), 3.00–3.13 (4H, m),3.21–3.30 (2H, m),3.41 (2H, t, J=8 Hz), 3.59–3.68(2H, m), 3.74–3.83(1H, m), 6.90(1H, s), 6.96(1H, d, J=8 Hz), 7.11–7.20(3H, m), 7.30–7.39(2H, m), 10.51(1H, br-s).

FAB-Mass: 350(MH+).

Example 125: Synthesis of 1-[1-(4-fluorophenethyl)piperdin-4-yl]-6-carbamoylindoline

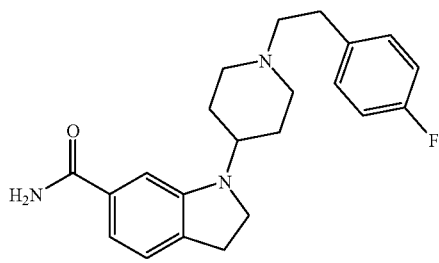

A solution of 1-[1-(4-fluorophenethyl)piperidin-4-yl]-6-cyanoindoline (1.0 g) in conc. sulfuric acid (1 l) was heated at 50° C. for 2 hr. After diluting with ice water, the reaction solution was basified with a conc. aqueous solution of sodium hydroxide. Then ethyl acetate was added thereto and the layers were separated. The organic layer was washed with brine, dried over anhydrous magnesium sulfate and concentrated under reduced pressure to give the title compound (0.81 g) as a white powder (yield: 77%).

A portion of these crystals were converted into a hydrochloride in a conventional manner to give the hydrochloride of the title compound as a white powder.

m.p. (hydrochloride): 160–162° C.

$^1$H-NMR (400 MHz, DMSO-$d_6$):

δ(ppm) 1.87–1.95(2H, m), 1.99–2.13(2H, m), 2.94(2H, t, J=8 Hz), 3.04–3.17(4H, m), 3.24–3.31(2H, m), 3.38(2H, t, J=8 Hz) 3.60–3.68(2H, m), 3.73–3.83(1H, m), 7.01(1H, s), 7.07(1H, d, J=8 Hz),7.12(1H, d, J=8 Hz),7.16–7.21(3H, m),7.32–7.36(2H, m), 7.79(1H, br-s).

FAB-Mass: 368(MH+).

Example 126: Synthesis of 1-[1-(4-fluorophenethyl)-piperdine-4-yl]-6-(1-pyrrolylcarhonyl)indoline

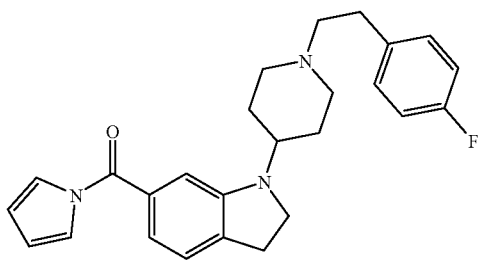

A mixture of 1-[1-(4-fluorophenethyl)piperidin-4-yl]-6-carbamoylindoline (0.3 g), 1,4-dichloro-1,4-dimethoxybutane (0.7 g), Amberlyst A-21 (0.5 g) and acetonitrile (10 ml) was heated at 60° C. for 10 hr. After filtering, the reaction solution was basified with a saturated aqueous solution of sodium bicarbonate and then ethyl acetate was added thereto and the layers were separated. The organic layer was washed with brine, dried over anhydrous magnesium sulfate and concentrated under reduced pressure. The residue was purified by silica gel column chromatography (hexane/ethyl acetate system) followed by conversion into an oxalate in a conventional manner to give the oxalate (0.13 g) of the title compound as a pale yellow powder (yield: 31%).

m.p. (oxalate): 169–171° C.

$^1$H-NMR (400 MHz, DMSO-$d_6$):

δ(ppm) 1.83–1.94(4H, m), 2.90–2.97(4H, m), 3.02 (2H, t, J=8 Hz), 3.08–3.19(2H, m), 3.41–3.55(4H, m), 3.72–3.83 (1H, m) 6.37(2H, s), 6.80(1H, s), 6.89(1H, d, J=8 Hz), 7.14–7.21(3H, m), 7.28–7.34(4H, m).

FAB-Mass: 418(MH+).

Example 127: Synthesis of 1-[1-(4-fluorophenethyl)piperdin-4-yl]-6-acetylindoline

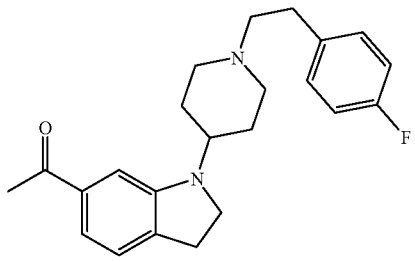

A 2.5 M solution (1.5 ml) of n-butyllithium in hexane was added dropwise at −78° C. into a solution (30 ml) of 1-[1-(4-fluorophenethyl)piperidin-4-yl]-6-bromoindoline (1.0 g) in tetrahydrofuran over 5 min. After 10 min, dimethylacetamide (0.34 ml) was added thereto and the resultant mixture was warmed to room temperature. Next, a saturated aqueous solution of ammonium chloride and ethyl acetate were added thereto to and the layers were separated. The organic layer was washed with brine, dried over anhydrous magnesium sulfate and concentrated under reduced pressure. The residue was purified by NH-silica gel column chromatography (hexane/ethyl acetate system) to give the title compound (250 mg) as a yellow powder (yield: 27%).

m.p. 90–92° C.

$^1$H-NMR (400 MHz, CDCl$_3$)

δ(ppm) 1.71–1.86(4H, m), 2.12–2.22(2H, m), 2.56(3H, s), 2.57–2.64(2H, m), 2.77–2.84(2H, m), 2.99(2H, t, J=8 Hz), 3.07–3.16(2H, m), 3.42–3.56(1H, m), 3.46(2H, t, J=8 Hz), 6.94–6.99(3H, m), 7.08(1H, d, J=8 Hz), 7.14–7.23(3H, m).

FAB-Mass: 367(MH+).

Example 128: Synthesis of 1-[1-(4-fluorophenethyl)piperdin-4-yl]-6-methanesulfonylindoline

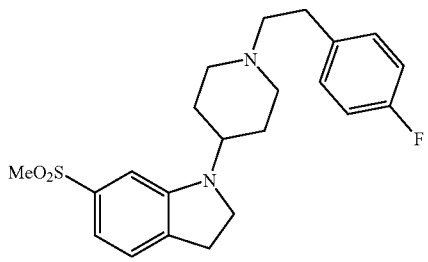

A 2.5 M solution (0.6 ml) of n-butyllithium in hexane was added dropwise at −78° C. into a solution of 1-[1-(4-fluorophenethyl)piperidin-4-yl]-6-bromoindoline (470 mg) in tetrahydrofuran (20 ml) over 10 min. After 10 min, a saturated solution of sulfur dioxide in tetrahydrofuran (50 ml) was added thereto and the resultant mixture was warmed to room temperature. After concentrating the reaction solution under reduced pressure, dimethylformamide (10 ml) and methyl iodide (100 mg) were added to the residue and the resultant mixture was stirred at room temperature overnight. Then the reaction solution was concentrated under reduced pressure, a saturated aqueous solution of sodium bicarbonate and ethyl acetate were added thereto and the layers were separated. The organic layer was washed with brine and dried over anhydrous magnesium sulfate. The residue was purified by NH-silica gel column chromatography (hexane/ethyl acetate system) followed by conversion into a hydrochloride in a conventional manner to give the hydrochloride (20 mg) of the title compound as brown prisms (yield: 3.8%).

m.p. (hydrochloride): 228° C. (decomp.).

$^1$H-NMR (400 MHz, DMSO-$d_6$):
δ(ppm) 1.83–2.09(4H, m), 2.98–3.18(6H, m), 3.10(3H, s), 3.20–3.31(2H, m), 3.44(2H, t, J=8 Hz), 3.59–3.68(2H, m), 3.80–3.93 (1H, m), 6.91(1H, s), 7.06(1H, d, J=8 Hz), 7.14–7.23 (3H, m), 7.30–7.35(2H, m)

FAB-Mass: 403(MH+).

Example 129: Synthesis of 1-[1-(4-fluorophenethyl)-piperidin-4-yl]-6-thiocarbamoylmethylindoline

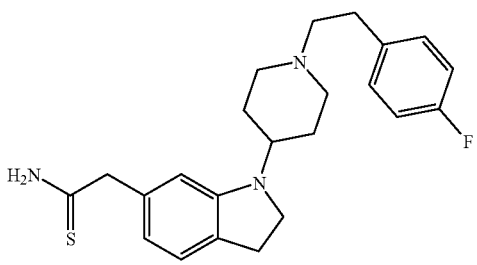

A mixture of 1-[1-(4-fluorophenethyl)piperidin-4-yl]-6-carbamoylmethylindoline (720 mg), phosphorus pentasulfide (250 mg) and pyridine (20 ml) was heated under reflux for 1 hr. Then the mixture was diluted with a 5 N aqueous solution of sodium hydroxide and ethyl acetate. The organic layer was washed with brine and dried over anhydrous magnesium sulfate. The residue was purified by NH-silica gel column chromatography (hexane/ethyl acetate system) followed by conversion into a hydrochloride in a conventional manner to give the hydrochloride (170 mg) of the title compound as a white hygroscopic amorphous solid (yield: 21%).

$^1$H-NMR (400 MHz, DMSO-$d_6$):
δ(ppm) 1.86–1.94(2H, m), 2.02–2.15(2H, m), 2.86(2H, t, J=8 Hz), 3.03–3.16(4H, m), 3.22–3.30(2H, m), 3.33(2H, t, J=8 Hz), 3.60–3.74(3H, m), 3.70(2H, s), 6.57(1H, d, J=8 Hz), 6.61(1H, s), 6.95(1H, d, J=8 Hz), 7.16–7.21(2H, m), 7.32–7.36(2H, m), 9.26(1H, br-s), 9.42(1H, br-s), 10.60(1H, br-s).

FAB-Mass: 398(MH+).

Example 130: Synthesis of 1-[1-(4-fluorophenethyl)piperdin-4-yl]-6-formylindoline

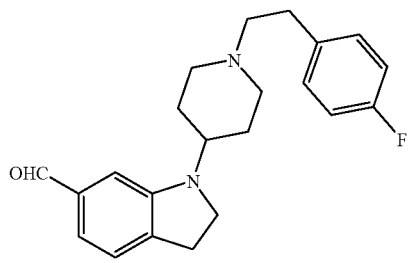

A 2.5 M solution (50 ml) of n-butyllithium in hexane was added dropwise at −78° C. into a solution of 1-[1-(4-fluorophenethyl)piperidin-4-yl]-6-bromoindoline (40 g) in tetrahydrofuran (1 l) over 10 min. After 10 min, dimethylformamide (11.6 ml) was added thereto and the resultant mixture was warmed to room temperature. Next, a saturated aqueous solution of ammonium chloride (200 ml) and ethyl acetate (500 ml) were added thereto and the layers were separated. The organic layer was washed with brine, dried over anhydrous magnesium sulfate and concentrated under reduced pressure to give the crude title compound (37.5 g). A portion of this crude product was purified by silica gel column chromatography (ethyl acetate/ethanol system) to give the title compound as a yellow powder.

m.p.: 109–111° C.

$^1$H-NMR (400 MHz, CDCl$_3$)
δ(ppm) 1.78–1.80(4H, m), 2.10–2.29(2H, m), 2.59–2.68 (2H, m), 2.79–2.90(2H, m), 3.03(2H, t, J=8 Hz), 3.10–3.19 (2H, m), 3.42–3.53 (1H, m), 3.50 (2H, t, J=8 Hz), 6.82 (1H, s), 6.91–7.00 (2H, m), 7.09(1H, d, J=8 Hz), 7.13–7.19(3H, m), 9.85(1H, s).

FAB-Mass: 353(MH+).

Example 131: Synthesis of 1-[1-(4-fluorophenethyl)-piperdin-4-yl]-6-hydroxyiminomethylindoline

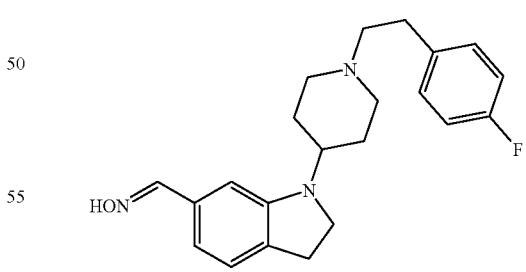

A suspension of crude 1-[1-(4-fluorophenethyl)-piperidin-4-yl]-6-formylindoline (35 g), hydroxylammonium chloride (10.4 g) and anhydrous sodium acetate (12.3 g) in ethanol (400 ml) was stirred at room temperature for a day. Then the reaction solution was concentrated under reduced pressure, diluted with ethyl acetate (500 ml), an 8 N aqueous solution (30 ml) of sodium hydroxide and water (100 ml) and the layers were separated. The organic layer was washed with brine and dried over magnesium sulfate. After removing the solvent, the residue was dissolved in a hot toluene (100 ml)-isopropyl ether (100 ml) mixtures and allowed to cool at room temperature. The resulting crystals were collected by filtration and dried at 50° C. to give the title compound (31 g) as a pale yellow powder (yield: 85%).
m.p.: 152–154° C.
¹H-NMR (400 MHz, CDCl₃):
δ(ppm) 1.78–1.85(4H, m), 2.08–2.20(2H, m), 2.56–2.64 (2H, m), 2.78–2.84(2H, m), 2.92(2H, t, J=8 Hz), 3.10–3.19 (2H, m), 3.40–3.50(1H, m), 3.46(2H, t, J=8 Hz), 6.69(1H, s), 6.70(1H, d, J=8 Hz), 6.92–7.00(2H, m), 7.03(1H, d, J=8 Hz), 7.15–7.20(2H, m), 8.06(1H, s).
FAB-Mass: 368(MH+).
Example 132: Synthesis of 1-[1-(4-fluorophenethyl)piperidin-4-yl]-6-aminomethylindoline

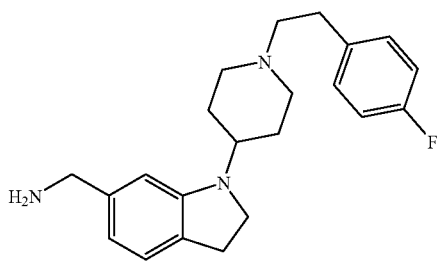

Under ice cooling and stirring, 1-[1-(4-fluorophenethyl)piperidin-4-yl]-6-hydroxyiminomethylindoline (31 g) was added in portions to a suspension of lithium aluminum hydride (8.0 g) in tetrahydrofuran (500 ml) and then the resultant mixture was heated under reflux for 3 hr. Under cooling with ice water, water (8 ml), a 5 N aqueous solution (24 ml) of sodium hydroxide and further water (8 ml) were carefully added dropwise to the reaction solution followed by vigorous stirring. The resulting precipitate was filtered off and the filtrate was concentrated under reduced pressure to give the crude title compound (about 30 g). A portion of this crude product was purified by NH-silica gel column chromatography (ethyl acetate) and recrystallized from ethyl acetate-isopropyl ether mixtures to give the title compound as a pale yellow powder.
m.p.: 83–85° C.
¹H-NMR (400 MHz, CDCl₃)
δ(ppm) 1.52–2.02 (6H, m), 2.10–2.20 (2H, m), 2.56–2.63 (2H, m), 2.78–2.83(2H, m), 2.91(2H, t, J=8 Hz), 3.10–3.18 (2H, m), 3.37–3.50 (1H, m), 3.41 (2H, t, J=8 Hz), 3.69 (2H, s), 6.39 (1H, s) 6.51(1H, d, J=8 Hz), 6.93–7.01(3H, m), 7.12–7.20(2H, m).
FAB-Mass: 354(MH+).
Example 133: Synthesis of 1-[1-(4-fluorophenethylpiperdin-4-yl]-6-acetamidomethylindoline

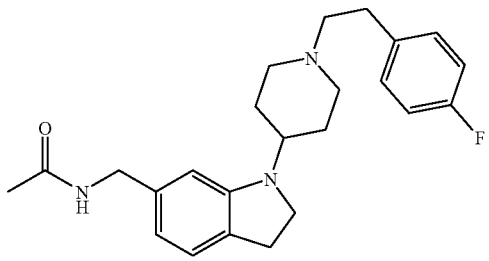

Under ice cooling, acetyl chloride (6.6 ml) was added dropwise into a solution of 1-[1-(4-fluorophenethyl)piperidin-4-yl]-6-aminomethylindoline (30 g) obtained above and triethylamine (9.4 g) in acetonitrile (500 ml) and the resultant mixture was stirred at room temperature for 1 hr. After adding a 5 N aqueous solution (40 ml) of sodium hydroxide and water (500 ml) to the reaction solution, the resulting crystalline precipitates were collected by filtration, washed successively with water and ethyl acetate and then dried at 50° C. overnight to give the crude title compound (22.8 g). This crude product was recrystallized successively from ethyl acetate and ethanol to give the title compound (17.9 g) as white needles (yield: 54%).
m.p.: 160 162° C.
¹H-NMR (400 MHz, CDCl₃)
δ(ppm) 1.78–1.86(4H, m), 2.01(3H, s), 2.12–2.28(2H, m) 2.58–2.72(2H, m), 2.76–2.89(2H, m), 2.93(2H, t, J=8 Hz), 3.08–3.26(2H,m), 3.35–3.46(1H, m), 3.42(2H, t, J=8 Hz) 4.33(2H, d, J=6 Hz), 5.69(1H, br-s), 6.34(1H, s), 6.51(1H, d, J=8 Hz), 6.95–7.02(3H, m), 7.14–7.20(2H, m).
FAB-Mass: 396(MH+).
Example 134: Synthesis of 1-[1-(2-fluorophenethyl)piperdin-4-yl]-6-acetamidomethylindoline

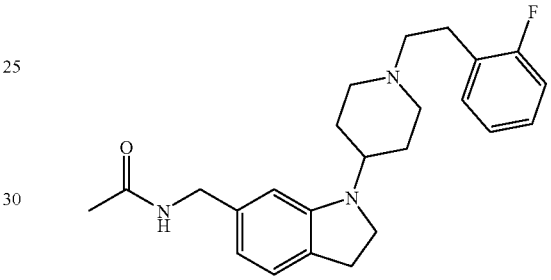

1-(Piperidin-4-yl)-6-acetamidomethylindoline (250 mg) and 2-fluorophenethyl bromide (220 mg) were treated as in Example 2 to give the title compound (190 mg) as a whitepowder (yield: 52%).
m.p.: 160–161° C.
¹H-NMR (400 MHz, CDCl₃)
δ(ppm) 1.51–1.68(2H, m), 1.81–1.92(2H, m), 2.00(3H, s), 2.20–2.40(2H, m), 2.70–2.89(4H, m), 2.91(2H, t, J=8 Hz), 3.01–3.10(2H, m), 3.40–3.48(3H, m), 4.32(2H, d, J=6 Hz), 6.39(1H, s), 6.51(1H, d, J=8 Hz), 6.98–7.10(3H, m), 7.18–7.30(2H, m).
FAB-Mass: 396(MH+).
Example 139: Synthesis of 1-[1-(3-fluorophenethyl)piperdin-4-yl]-6-acetamidomethylindoline

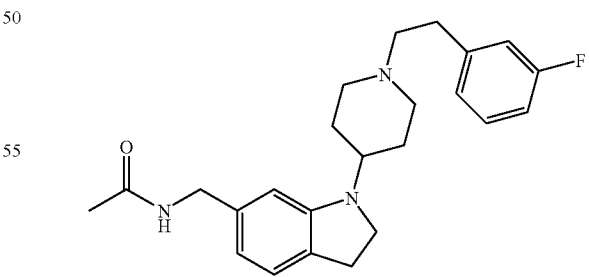

1-(Piperidin-4-yl)-6-acetamidomethylindoline (250 mg) and 3-fluorophenethyl bromide (220 mg) were treated as in Example 2 to give the title compound (210 mg) as white needles (yield: 58%).
m.p.: 161–162° C.
¹H-NMR (400 MHz, CDCl₃)

δ(ppm) 1.51–1.68(2H, m), 1.80–1.89(2H, m), 2.00(3H, s), 2.11–2.37(4H, m), 2.65–2.75(2H, m), 2.91(2H, t, J=8 Hz), 3.12–3.29(2H, m), 3.40–3.48(3H, m), 4.32 (2H, d, J=6 Hz), 6.38(1H, s), 6.51(1H, d, J=8 Hz), 6.98–6.98(2H, m), 7.00–7.05(2H, m), 7.21–7.30(1H, m).
FAB-Mass: 396(MH+).

Example 136: Synthesis of 1-[1-(4-fluorophenethyl) piperdin-4-yl]-6-hydroxymethylindoline

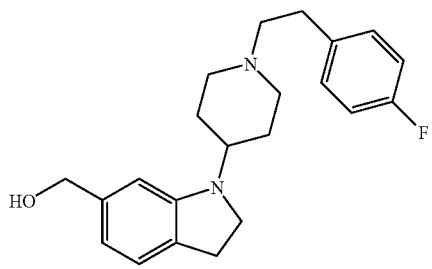

A 2.5 M solution (100 ml) of n-butyllithium in hexane was added dropwise at −78° C. into a solution (2 l) of 1-[1-(4-fluorophenethyl)piperidin-4-yl]-6-bromoindoline (80 g) in tetrahydrofuran over 15 min. After 10 min, dimethylformamide (23.2 ml) was added thereto and the resultant mixture was warmed to room temperature. Next, a saturated aqueous solution of ammonium chloride (400 ml) and ethyl acetate (1 l) were added thereto and the layers were separated. The organic layer was washed with brine, dried over anhydrous magnesium sulfate and concentrated under reduced pressure. To the resulting reside were added ethanol (240 ml) and sodium borohydride (7.6 g) and the resultant mixture was stirred at room temperature for 1 hr. After adding ice water (480 ml) to the reaction solution, the resulting crystals were collected by filtration, washed with water and air-dried at 50° C. over day and night to give the title compound (about 71 g) as a yellow powder. A portion of this crude product was purified by silica gel column chromatography (ethyl acetate/methanol system) followed by conversion into a hydrochloride in a conventional manner to give the hydrochloride of the title compound as a pale purple powder.

m.p. (hydrochloride): 190° C. (decomp.).
$^1$H-NMR (400 MHz, DMSO-$d_6$):
δ(ppm) 1.81–1.90(2H, m), 1.99–2.11(2H, m), 2.81–2.90 (2H, m), 3.02–3.13(4H, m), 3.20–3.29(2H, m), 3.31(2H, t, J=8 Hz), 3.68–3.63(2H, m) 3.70–3.80(1H, m), 4.38(2H, s), 6.30–6.37(2H, m), 6.96(1H, d, J=8 Hz), 7.12–7.20(2H, m), 7.30–7.36(2H, m), 10.60(1H, br-s).
FAB-Mass: 355(MH+).

Example 137: Synthesis of 1-[1-(4-fluorophenethyl) piperdin-4-yl]-6-(1-hydroxyethyl)indoline

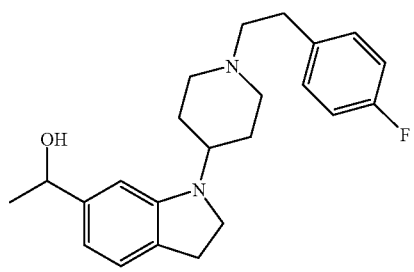

Sodium borohydride (0.03 g) was added to a solution (5 ml) of 1-[1-(4-fluorophenethyl)piperidin-4-yl]-6-acetylindoline (0.17 g) in ethanol and the resultant mixture was stirred at room temperature overnight. Then ethyl acetate and water were added to the reaction solution and the layers were separated. The organic layer was washed with brine and dried over anhydrous magnesium sulfate. Then the residue was purified by silica gel column chromatography (hexane/ethyl acetate system) to give the title compound (150 mg) as a colorless oil (yield: 89%).

To a solution of this oily substance in acetone, oxalic acid (37 mg) was added to give the oxalate (140 mg) of the title compound as a gray powder.

m.p. (oxalate): 113–116° C.
$^1$H-NMR (400 MHz, DMSO-$d_6$):
δ(ppm) 1.28(3H, d, J=6 Hz), 1.84–2.05(4H, m), 2.84(2H, t, J=8 Hz), 3.00–3.35(8H, m), 3.55–3.68(2H, m), 3.70–3.80 (1H, m) 4.61(1H, q, J=6 Hz), 6.52–6.54(2H, m), 6.94(1H, d, J=8 Hz), 7.16–7.21(2H, m), 7.32–7.36(2H, m).
FAB-Mass: 369(MH+).

Example 138: Synthesis of 1-[1-(4-fluorophenethyl)-piperdin-4-yl]-6-(1-hydroxypropyl)indoline

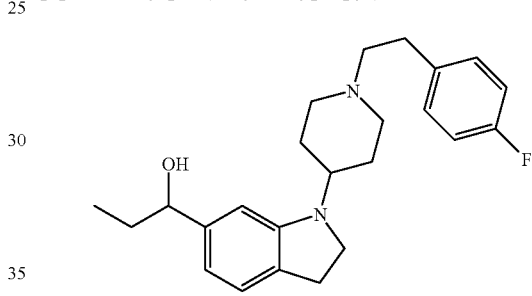

A 3 M solution (1.4 ml) of ethylmagnesium in ether was added dropwise at −78° C. into a solution of 1-[1-(4-fluorophenethyl)piperidin-4-yl]-6-formylindoline (1.0 g) in tetrahydrofuran (30 ml) and the resultant mixture was allowed to warm to room temperature. Then a saturated aqueous solution of ammonium chloride and ethyl acetate were added to the reaction solution and the layers were separated. The organic layer was washed with brine and dried over magnesium sulfate. After removing the solvent, the residue was purified by NH-silica gel column chromatography (hexane/ethyl acetate system) to give the title compound (710 mg) as a colorless oil (yield: 66%).

To a solution of this oil (200 mg) in acetone, oxalic acid (47 mg) was added to give the oxalate (150 mg) of the title compound as a pale brown powder.

m.p. (oxalate): 106–108° C.
$^1$H-NMR (400 MHz, DMSO-$d_6$):
δ(ppm) 0.80(3H, t, J=7 Hz), 1.50–1.61(2H, m), 1.80–1.95 (4H, m), 2.85(2H, t, J=8 Hz), 2.95–3.25(6H, m), 3.31(2H, t, J=8 Hz), 3.51–3.62(2H, m), 3.66–3.78(1H, m), 4.32(1H, t, J=6 Hz), 6.49–6.51(2H, m), 6.94(1H, d, J=8 Hz), 7.16–7.21 (2H, m), 7.31–7.35(2H, m).
FAB-Mass: 383(MH+).

Example 139: Synthesis of 1-[1-(4-fluorophenethyl)-piperdin-4-yl]-6-(1-hydroxy-1-methylethyl)indoline

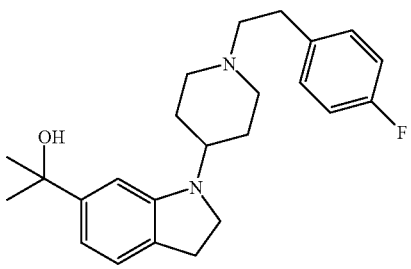

1-[1-(4-Fluorophenethyl)piperidin-4-yl]-6-bromoindoline (0.75 g), a 2.5 M solution (1.1 ml) of n-butyllithium in hexane and acetone (0.16 g) were treated as in Example 130 to give the oxalate (250 mg) of the title compound as a pale yellow powder (yield: 35%).

m.p. (oxalate): 179–182° C.

$^1$H-NMR (400 MHz, DMSO-$d_6$)

δ(ppm) 1.38(6H, s), 1.81–1.90(4H, m), 2.83 (2H, t, J=8 Hz), 2.91–3.04(4H, m), 3.11–3.20(2H, m), 3.30(2H, t, J=8 Hz), 3.50–3.59 (2H, m), 3.66–3.74 (1H, m), 6.63–6.65(2H, m), 6.92 (1H, d, J=8 Hz), 7.15–7.20(2H, m), 7.31–7.35(2H, m).

FAB-Mass: 383(MH+).

Example 140: Synthesis of 1-[1-(4-fluorophenethyl)-piperdin-4-yl]-6-(1-hydroxycyclobutyl)indoline

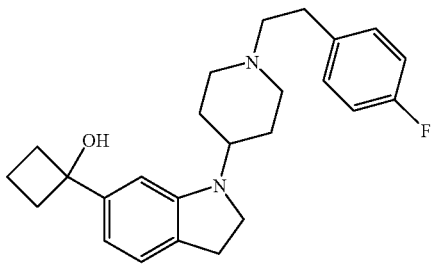

1-[1-(4-Fluorophenethyl)piperidin-4-yl]-6-bromoindoline (0.5 g), a 2.5 M solution (0.8 ml) of n-butyllithium in hexane and cyclobutanone (0.14 ml) were treated as in Example 130 to give the hydrochloride (150 mg) of the title compound as a white powder (yield: 29%).

m.p. (hydrochloride): 172–175° C.

$^1$H-NMR (400 MHz, DMSO-$d_6$):

δ(ppm) 1.53–1.64(1H, m), 1.82–1.94(3H, m), 1.96–2.09 (2H, m), 2.16–2.26(2H, m), 2.31–2.40(2H, m), 2.87(2H, t, J=8 Hz), 3.00–3.44(9H, m), 3.60–3.70(2H, m), 6.64(1H, s), 6.72(1H, d, J=8 Hz), 6.99 (1H, d, J=8 Hz), 7.16–7.22 (2H, m), 7. 32–7.36 (2H, m)

FAB-Mass: 395(MH+).

Example 141: Synthesis of 1-[1-(4-fluorophenethyl)-piperdin-4-yl]-6-(1hydroxycyclopentyl)indoline

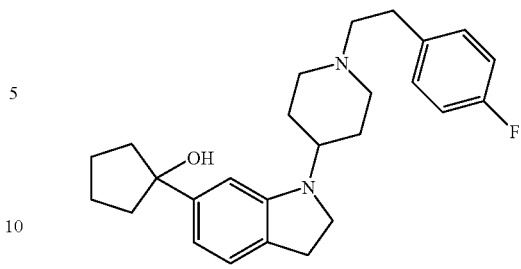

1-[1-(4-Fluorophenethyl)piperidin-4-yl]-6-bromoindoline (0.5 g), a 2.5 M solution (0.8 ml) of n-butyllithium in hexane and cyclopentanone (0.17 ml) were treated as in Example 130 to give the hydrochloride (240 mg) of the title compound as a white powder (yield: 45%).

m.p. (hydrochloride): 191–194° C.

$^1$H-NMR (400 MHz, DMSO-$d_6$):

δ(ppm) 1.64–2.00(12H, m), 2.81(2H, t, J=8 Hz), 2.96–3.04(2H, m), 3.06–3.16(2H, m)3.20–3.31(2H, m), 3.34–3.78(5H, m), 6.59(1H, s), 6.64(1H, d, J=8 Hz), 6.90 (1H, d, J=8 Hz), 7.11–7.19(2H, m), 7.30–7.38(2H, m).

FAB-Mass: 409(MH+).

Example 142: Synthesis of 1-[1-(4-fluorophenethyl) piperdin-4-yl]-6chloromethylindoline

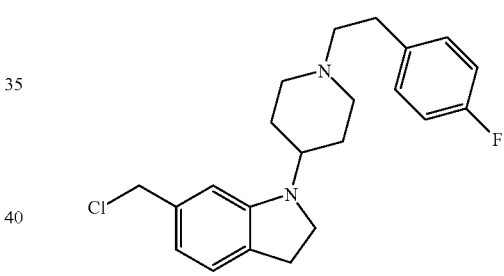

Conc. hydrochloric acid (280 ml) was added to 1-[1-(4-fluorophenethyl)piperidin-4-yl]-6-hydroxymethylindoline (about 70 g) and the resultant mixture was stirred at 80° C. for a day. Under ice cooling, the reaction solution was neutralized with a conc. aqueous solution of sodium hydroxide followed by addition of ethyl acetate (200 ml). The resulting crystals were collected by filtration and dissolved in ethyl acetate (500 ml) and a 5 N aqueous solution (500 ml) of sodium hydroxide and the layers were separated. The organic layer was washed with brine, dried over anhydrous magnesium sulfate and concentrated under reduced pressure to give the title compound (70 g) as a pale yellow powder (yield: 94%).

$^1$H-NMR (400 MHz, CDCl$_3$)

δ(ppm) 1.76–1.90(4H, m), 2.10–2.26(2H, m), 2.58–2.70 (2H, m), 2.78–2.90(2H, m), 2.94(2H, t, J=8 Hz), 3.10–3.24 (2H, m), 3.36–3.51(1H, m), 3.43(2H, t, J=8 Hz), 4.53(2H, s), 6.40(1H, s), 6.60(1H, d, J=8 Hz), 6.95–7.02(3H, m), 7.14–7.19(2H, m).

Example 143: Synthesis of 1-[1-(4-fluorophenethyl) piperdin-4-yl]-6-fluoromethylindoline

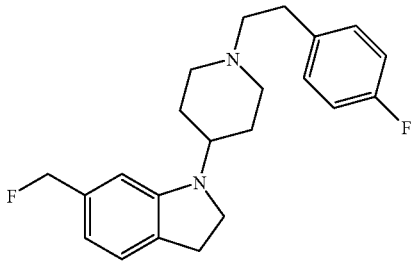

Diethylaminosulfatrifluoride (DAST, 160 mg) was added dropwise at −78° C. into a solution of 1-[1-(4-fluorophenethyl)piperidin-4-yl]-6-hydroxymethylindoline (300 mg) inmethylene chloride (10 ml) and the resultant mixture was stirred for 1 hr. Then a saturated aqueous solution of sodium bicarbonate and ethyl acetate were added thereto and the layers were separated. The organic layer was dried over anhydrous magnesium sulfate and the obtained residue was purified by NH-silica gel column chromatography (hexane/ethyl acetate system) followed by conversion into a hydrochloride in a conventional manner to give the hydrochloride (100 mg) of the title compound as a white powder (yield: 30%).

m.p. (hydrochloride) 190° C. (decomp.)

$^1$H-NMR (400 MHz, DMSO-$d_6$):

δ(ppm) 1.84–1.93 (2H, m), 2.01–2.14 (2H, m), 2.87–2.95 (2H, m), 3.00–3.16(4H, m), 3.21–3.30(4H, m), 3.37(2H, t, J=8 Hz), 3.59–3.68(2H, m), 3.73–3.83(1H, m), 5.28(2H, d, J=22 Hz), 6.60–6.63(2H, m), 7.05(1H, d, J=8 Hz), 7.16–7.21 (2H, m), 7.33–7.36(2H, m), 10.70(1H, br-s).

FAB-Mass: 357 (MH+).

Example 144: Synthesis of 1-[1-(4-fluoropheneyl)piperdin-4-yl]-6-(1-fluoroethyl)indoline

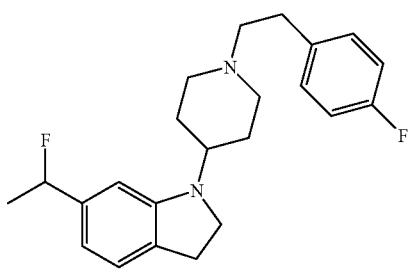

Diethylaminosulfatrifluoride (DAST, 220 mg) was added dropwise at −78° C. into a solution (20 ml) of 1-[1-(4-fluorophenethyl)piperidin-4-yl]-6-(1-hydroxyethyl)indoline (400 mg) in methylene chloride and the resultant mixture was stirred for 1 hr. Then a saturated aqueous solution of sodium bicarbonate and chloroform were added thereto and the layers were separated. The organic layer was dried over anhydrous magnesium sulfate and the resulting residue was purified by silica gel column chromatography (hexane/ethyl acetate system) followed by conversion into a hydrochloride in a conventional manner to give the hydrochloride (100 mg) of the title compound as a white hygroscopic amorphous solid (yield: 23%).

$^1$H-NMR (400 MHz, DMSO-$d_6$):

δ(ppm) 1.55(3H, dd, J=24, 6 Hz), 1.82–1.92(2H, m), 1.96–2.10(2H, m), 2.81–2.93(2H, m), 3.01–3.18(4H, m), 3.22–3.49(4H, m), 3.59–3.69(2H, m), 3.71–3.85(1H, m), 5.57(1H, dq, J=48, 6 Hz), 6.54–6.61(2H, m), 6.98–7.04(1H, m), 7.18–7.21(2H, m), 7.32–7.40(2H, m).

FAB-Mass: 371(MH+).

Example 145: Synthesis of 1-[1-(4-fluorophenethyl)piperdin-4-yl]-6-cyanomethylindoline

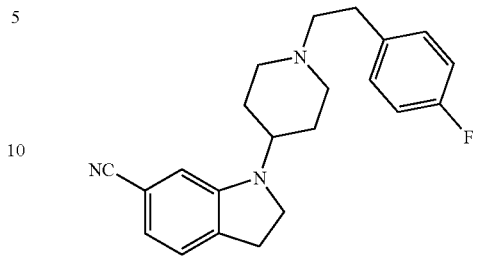

Dimethyl sulfoxide (500 ml) and sodium cyanide (9.8 g) were added to 1-[1-(4-fluorophenethyl)piperidin-4-yl]-6-chloromethylindoline (about 70 g) and the resultant mixture was stirred at 50° C. for 2 hr. Next, ice water (500 ml) was added to the reaction solution followed by vigorously stirring. The resulting crystals were collected by filtration, washed with water and air-dried at 80° C. to give the title compound (67 g) as a pale yellow powder (yield: 93%).

A portion of this product was purified by silica gel column chromatography (ethyl acetate/hexane system) followed by conversion into a hydrochloride in a conventional manner to give the hydrochloride of the title compound as a white powder.

m.p. (hydrochloride): 211–214° C.

$^1$H-NMR (400 MHz, DMSO-$d_6$):

δ(ppm) 1.83–1.91(2H, m), 1.99–2.12(2H, m), 2.90(2H, t, J=8 Hz), 3.00–3.19(4H, m), 3.21–3.32(2H, m), 3.35(2H, t, J=8 Hz) 3.60–3.80(3H, m), 3.90(2H, s), 6.49(1H, s), 6.51 (1H, d, J=8 Hz) 7.01(1H, d, J=8 Hz), 7.13–7.21(2H, m), 7.30–7.40(2H, m).

FAB-Mass: 364(MH+)

Example 146: Synthesis of 1-[1-(4-fluoropenethyl)piperdin-4yl]-6-carboxymethylindoline

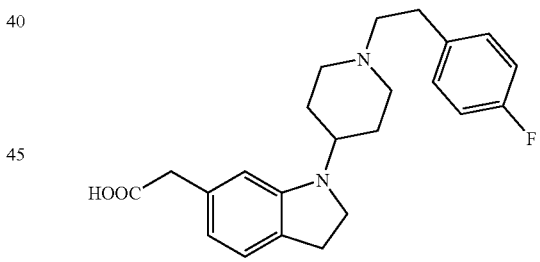

1-[1-(4-Fluorophenethyl)piperidin-4-yl]-6-cyanomethylindoline (about 67 g) was dissolved in water (134 ml) and conc. sulfuric acid (134 ml) and the resultant solution was heated under reflux for 7 hr. Under ice cooling, the pH value of the reaction mixture was adjusted to 10 with a conc. aqueous solution of sodium hydroxide. Then ethyl acetate (300 ml) was added thereto followed by vigorous stirring. After adjusting the pH value of the resultant mixture to about 6 with conc. hydrochloric acid, the resulting crystalline precipitates were collected by filtration, washed with water and air-dried at 50° C. over day and night to give the title compound (58 g) as a white powder (yield: 76%).

m.p.: 130–132° C.

$^1$H-NMR (400 MHz, DMSO-$d_6$)

δ(ppm) 1.53–1.73(4H, m) 2.70–2.90(4H, m), 3.00–3.53 (12H, m), 6.31 (1H, s), 6.39 (1H, d, J=8 Hz), 6.90 (1H, d, J=8 Hz) 7.04–7.15(2H, m), 7.22–7.30(2H, m).

FAB-Mass: 383 (MH+).
Example 147: Synthesis of 1-[1-(4-fluorophenethyl) piperdin-4-yl]-6-carbamoylmethylindoline

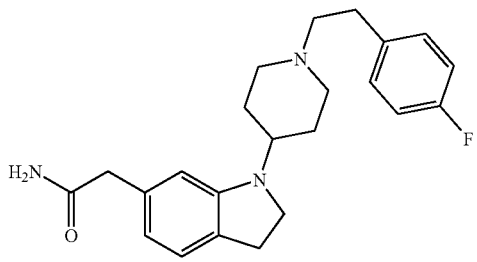

Crude 1-[1-(4-fluorophenethyl)piperidin-4-yl]-6-cyanomethylindoline (230 mg) was dissolved in conc. sulfuric acid (5 ml) and the resultant solution was stirred overnight. The reaction solution was diluted with ice water and the pH value thereof was adjusted to 10 under ice cooling with a conc. aqueous solution of sodium hydroxide. After extracting the reaction solution with ethyl acetate, the organic layer was washed with brine, dried over anhydrous magnesium sulfate and concentrated under reduced pressure. The residue was purified by silica gel column chromatography (ethyl acetate/ethanol system) followed by conversion into a hydrochloride in a conventional manner to give the hydrochloride (200 mg) of the title compound as a white hygroscopic amorphous solid (yield: 76%).

$^1$H-NMR (400 MHz, DMSO-$d_6$):
δ(ppm) 1.83–1.92(2H, m), 2.02–2.17(2H, m), 2.86(2H, t, J=8 Hz), 3.00–3.16(4H, m), 3.21–3.29(2H, m), 3.34(2H, t, J=8 Hz), 3.60–4.10 (5H, m), 6.43–6.51 (2H, m), 6.81 (1H, br-s), 6.95 (1H, d, J=8 Hz), 7.16–7.21(2H, m), 7.32–7.39 (3H, m).
FAB-Mass: 382(MH+).
Example 148: Synthesis of 1-[1-(4-fluorophenethyl)-piperdin-4-yl]-6-(methylcarbamoylmethyl)indoline

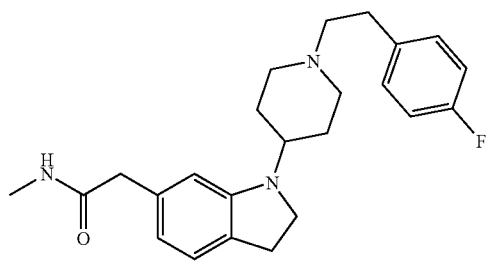

Ethyl chlorocarbonate (87 mg) was added at −78° C. to a mixture of 1-[1-(4-fluorophenethyl)piperidin-4-yl]-6-carboxymethylindoline (250 mg), triethylamine (81 mg), dimethylformamide (6 ml) and tetrahydrofuran (8 ml). After heating the resultant mixture to −30° C., a 2 N solution (0.4 ml) of methylamine in tetrahydrofuran was added thereto. The resultant mixture was further warmed to room temperature and stirred for additional 30 min. Ice water and ethyl acetate were added to the liquid reaction mixture and the layers were separated. The organic layer was washed successively with water, a saturated aqueous solution of sodium bicarbonate and brine, dried over anhydrous magnesium sulfate and concentrated under reduced pressure. The residue was purified by silica gel column chromatography (ethyl acetate/ethanol system) followed by conversion into a hydrochloride in a conventional manner to give the hydrochloride (120 mg) of the title compound as a white hygroscopic amorphous substance (yield: 45%).

$^1$H-NMR (400 MHz, DMSO-$d_6$):
δ(ppm) 1.83–1.92(2H, m), 2.00–2.13(2H, m), 2.55(3H, d, J=4 Hz), 2.86(2H, t, J=8 Hz), 2.99–3.16 (4H, m), 3.22–3.30 (4H, m) 3.33 (2H, t, J=8 Hz) 3.60–3.76 (3H, m), 6.45–6.50 (2H, m) 6.94 (1H, d, J=8 Hz), 7.16–7.22(2H, m), 7.32–7.40 (2H, m), 7.84(1H, d, J=4 Hz), 10.53(1H, br-s).
FAB-Mass: 396(MH+).
Example 149: Synthesis of 1-[1-(4-fluorophenethyl)-piperdin-4-yl]-6-(ethylcarbamoylmethyl)indoline

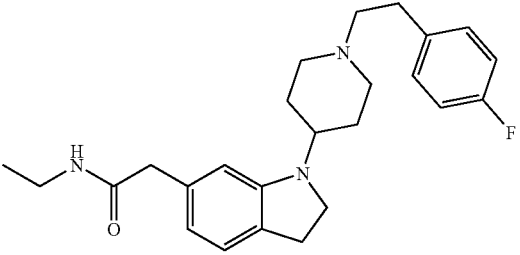

Under ice cooling, 1,1'-carbonyldiimidazole (1.0 g) was added to a solution of 1-[1-(4-fluorophenethyl)piperidin-4-yl]-6-carboxymethylindoline (2.0 g) in dimethylformamide (40 ml). After stirring the mixture for 2 hr, ethylamine hydrochloride (0.51 g) was added thereto. Then the resultant mixture was allowed to warm to room temperature and stirred for additional 5 hr. A saturated aqueous solution of sodium bicarbonate and ethyl acetate were added to the reaction solution and the layers were separated. The organic layer was washed with brine, dried over anhydrous magnesium sulfate and concentrated under reduced pressure. Then the residue was dissolved in hot toluene (10 ml). After allowing to cool to room temperature, the resulting crystals were collected by filtration to give the title compound (1.3 g) as a white powder (yield: 56%).

Next, the product was converted into a hydrochloride in a conventional manner followed by recrystallization from acetone to give the hydrochloride of the title compound as a white powder.
m.p. (hydrochloride): 161–164° C.
$^1$H-NMR (400 MHz, DMSO-$d_6$):
δ(ppm) 0.99(3H, t, J=7 Hz), 1.83–1.93(2H, m), 1.96–2.11 (2H, m), 2.85(2H, t, J=8 Hz), 2.98–3.17(6H, m), 3.23–3.39 (6H, m), 3.61–3.75(3H, m), 6.41–6.48(2H, m), 6.93(1H, d, J=8 Hz), 7.15–7.23(2H, m), 7.30–7.37(2H, m), 7.92(1H, br-s).
FAB-Mass: 410(MH+).
Example 150: Synthesis of 1-[1-(4-fluorophenethyl)-piperdin-4-yl]-6-(n-propylcarbamolymethyl)indoline

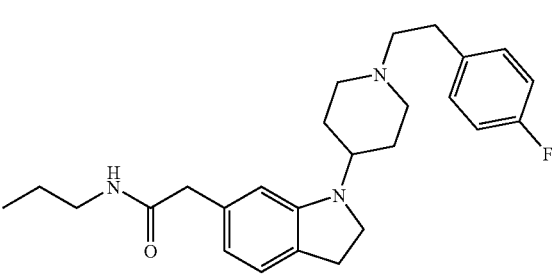

1-[1-(4-Fluorophenethyl)piperidin-4-yl]-6-carboxymethylindoline (220 mg), 1,1'-carbonyldiimidazole (110 mg) and n-propylamine (41 mg) were treated as in Example 149 to give the title compound (90 mg) as white needles (yield: 37%).

m.p.: 143–145° C.
¹H-NMR (400 MHz, CDCl₃)

δ(ppm) 0.83(3H, t, J=7 Hz), 1.42(2H, sextet, J=7 Hz), 1.75–1.79(4H, m), 2.10–2.30(2H, m), 2.53–2.71(2H, m), 2.78–2.90(2H, m), 2.95(2H, t, J=8 Hz), 3.09–3.21(4H,m), 3.37–3.49(1H, m), 3.42(2H, t, J=8 Hz), 3.50(2H, s), 5.51 (1H, br-s), 6.29(1H, s), 6.48(1H, d, J=8 Hz), 6.92–7.01(3H, m), 7.12–7.20(2H, m).
FAB-Mass: 424(MH+).

Example 151: Synthesis of 1-[1-(4-fluorophenethyl)-piperdin-4-yl]-6-(isopropylcarbamoylmethyl)indoline

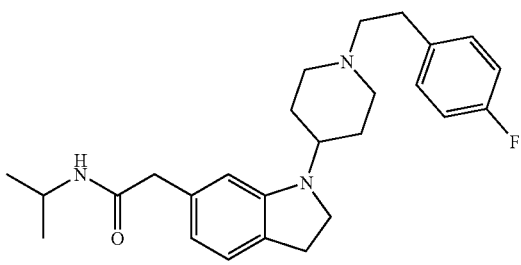

Under ice cooling, 1,1'-carbonyldimidazole (15 g) was added to a solution of 1-[1-(4-fluorophenethyl)piperidin-4-yl]-6-carboxymethylindoline (30 g) in dimethylformamide (240 ml) and the resultant mixture was stirred for 2 hr. After adding isopropylamine (5.6 g), the mixture was warmed to room temperature and then stirred for additional 2 hr. Next, ice water (240 ml) and ethyl acetate (300 ml) were added to the reaction solution and the layers were separated. The organic layer was washed successively with water, a saturated aqueous solution of sodium bicarbonate and brine, dried over anhydrous magnesium sulfate and concentrated under reduced pressure. The residue was dissolved in hot ethyl acetate (80 ml). After allowing to cool to room temperature, the resulting crystals were collected by filtration to give the title compound (17.2 g) as a white powder (yield: 52%).

Next, the product was converted into a hydrochloride in a conventional manner followed by recrystallization from ethanol to give the hydrochloride of the title compound as a white powder.

m.p. (hydrochloride): 153–155° C.
¹H-NMR (400 MHz, DMSO-d₆):

δ(ppm) 1.03(6H, d, J=7 Hz), 1.84–1.92(2H, m), 1.96–2.10 (2H, m), 2.85(2H, t, J=8 Hz), 3.01–3.16(4H, m), 3.20–3.38 (6H, m), 3.61–3.83(4H, m), 6.42–6.46(2H, m), 6.93(1H, d, J=8 Hz), 7.16–7.23(2H, m), 7.31–7.38(2H, m), 7.83(1H, d, J=8 Hz).
FAB-Mass: 424(MH+).

Example 152: Synthesis of 1-[1-(4-fluorophenethyl)-piperidin-4-yl]-6-(isobutylcarbamoylmethyl)indoline

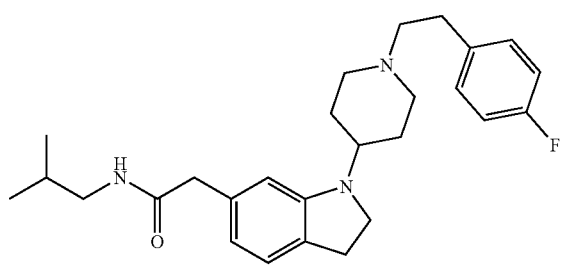

1-[1-(4-Fluorophenethyl)piperidin-4-yl]-6-carboxymethylindoline (300 mg), 1,1'-carbonyldiimidazole (150 mg) and isobutylamine (69 mg) were treated as in Example 151 to give the hydrochloride (270 mg) of the title compound as white needles (yield: 72%).

m.p. (hydrochloride): 122–124° C.
¹H-NMR (400 MHz, DMSO-d₆):

δ(ppm) 0.81(6H, d, J=7 Hz), 1.66(1H, septet, J=7 Hz), 1.84–1.92(2H, m), 2.00–2.15(4H, m), 2.81–2.90(4H, m), 3.02–3.15(2H, m), 3.23–3.38(4H, m), 3.44–3.73(5H, m), 6.48–6.53(2H, m), 6.95(1H, d, J=8 Hz), 7.17–7.22(2H, m), 7.29–7.40(2H, m), 7.94(1H, br-s).
FAB-Mass: 438(MH+).

Example 153: Synthesis of 1-[1-(4-fluorophenethyl)-piperidin-4-yl]-6-(t-butylcarbamoylmethyl)indoline

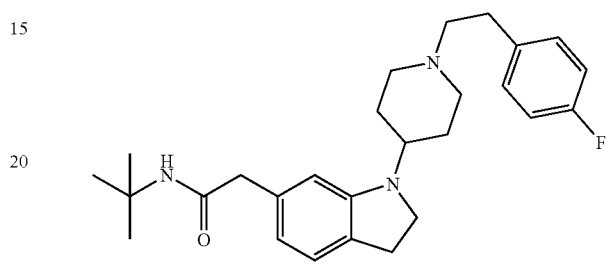

1-[1-(4-Fluorophenethyl)piperidin-4-yl]-6-carboxymethylindoline (250 mg), 1,1'-carbonyldiimidazole (130 mg) and t-butylamine (58 mg) were treated as in Example 151 to give the hydrochloride (140 mg) of the title compound as a pale brown powder (yield: 45%).

m.p. (hydrochloride): 189–192° C.
¹H-NMR (400 MHz, DMSO-d₆):

δ(ppm) 1.24(9H, s), 1.84–1.92(2H, m), 2.03–2.16(2H, m), 2.87(2H, t, J=8 Hz), 3.03–3.15(4H, m), 3.22–3.30(4H, m), 3.34(2H, t, J=8 Hz), 3.58–3.77(3H, m), 6.47–6.50(2H, m), 6.95(1H, d, J=8 Hz), 7.16–7.21(2H, m), 7.32–7.36(2H, m), 7.58(1H, br-s), 10.69(1H, br-s).
FAB-Mass: 438(MH+).

Example 154: Synthesis of 1-[1-(4-fluorophenethyl)-piperidin-4-yl]-6-(cyclopropylcarbamoylmethyl)indoline

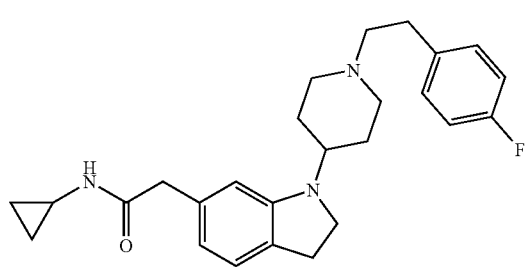

1-[1-(4-Fluorophenethyl)piperidin-4-yl]-6-carboxymethylindoline (250 mg), 1,1'-carbonyldiimidazole (130 mg) and cyclopropylamine (45 mg) were treated as in Example 151 to give the title compound (110 mg) as a white powder (yield: 40%).

m.p.: 182–184° C.
¹H-NMR (400 MHz, CDCl₃):

δ(ppm) 0.36–0.41(2H, m), 0.69–0.74(2H, m), 1.75–1.90 (4H, m), 2.10–2.30(2H, m), 2.60–2.71(3H, m), 2.75–2.90 (2H, m), 2.94(2H, t, J=8 Hz), 3.10–3.25(2H, m), 3.35–3.48 (5H, m), 5.60(1H, br-s), 6.26(1H, s), 6.42(1H, d, J=8 Hz), 6.96–7.01(3H, m), 7.15–7.20(2H, m).
FAB-Mass: 422(MH+).

Example 155: Synthesis of 1-[1-(4-fluorophenethyl)-piperidin-4-yl]-6-(tetramethylenecarbamoylmethyl)indoline

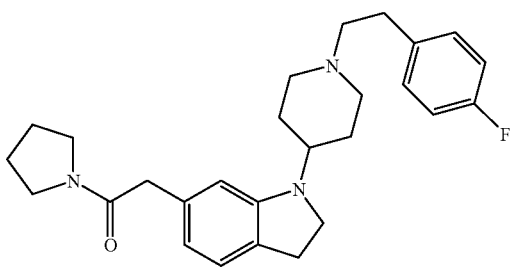

1-[1-(4-Fluorophenethyl)piperidin-4-yl]-6-carboxymethylindoline (360 mg), 1,1'-carbonyldiimidazole (160 mg) and pyrrolidine (70 mg) were treated as in Example 151 to give the hydrochloride (280 mg) of the title compound as a white powder (yield: 60%).

m.p. (hydrochloride): 159–161° C.

$^1$H-NMR (400 MHz, DMSO-d$_6$):

δ(ppm) 1.90–2.04(8H, m), 2.86(2H, t, J=8 Hz), 3.00–3.19 (4H, m), 3.21–3.39(6H, m), 3.42(2H, t, J=8 Hz), 3.61–3.76 (3H, m), 6.41(1H, s), 6.43(1H, d, J=8 Hz), 6.94(1H, d, J=8 Hz), 7.17–7.22(2H, m), 7.30–7.37(2H, m).

FAB-Mass: 436(MH+).

Example 156: Synthesis of 1-[1-(4-fluorophenethyl)-piperidin-4-yl]-1-6-propionylaminomethylindoline

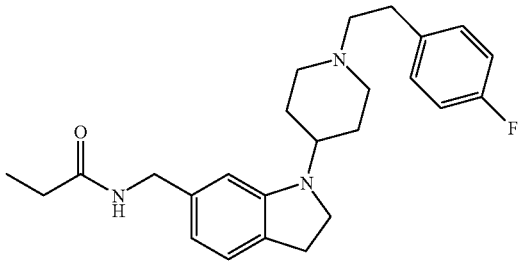

1-[1-(4-Fluorophenethyl)piperidin-4-yl]-6-aminomethylindoline (200 mg), triethylamine (69 mg) and propionyl chloride (63 mg) were treated as in Example 133 to give the hydrochloride (88 mg) of the title compound as a pale brown powder (yield: 35%).

m.p. (hydrochloride): 157° C. (decomp.).

$^1$H-NMR (400 MHz, DMSO-d$_6$):

δ(ppm) 0.99(3H, t, J=7 Hz), 1.82–2.10(4H, m), 2.10(2H, q, J=7 Hz), 2.84(2H, t, J=8 Hz), 2.92–3.14(4H, m), 3.21–3.35(4H, m), 3.59–3.73(3H, m), 4.12(2H, d, J=6 Hz), 6.41(1H, s), 6.44(1H, d, J=8 Hz), 6.94(1H, d, J=8 Hz), 7.15–7.20(2H, m), 7.30–7.35(2H, m), 8.12(1H, t, J=6 Hz).

FAB-Mass: 410(MH+).

Example 157: Synthesis of 1-[1-(4-fluorophenethyl)-piperidin-4-yl]-6-(n-butyryl)aminomethylindoline

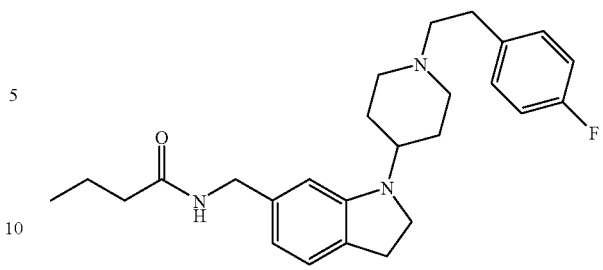

1-[1-(4-Fluorophenethyl)piperidin-4-yl]-6-aminomethylindoline (200 mg), triethylamine (69 mg) and n-butyryl chloride (72 mg) were treated as in Example 133 to give the title compound (110 mg) as pale yellow needles (yield: 46%).

m.p.: 153–155° C.

$^1$H-NMR (400 MHz, CDCl$_3$):

δ(ppm) 0.96(3H, t, J=7 Hz), 1.68(2H, sextet, J=7 Hz), 1.75–1.83(4H, m), 2.10–2.22(2H, m), 2.17(2H, q, J=7 Hz), 2.55–2.70(2H, m), 2.74–2.90(2H, m), 2.93(2H, t, J=8 Hz), 3.05–3.20(2H, m), 3.35–3.45(1H, m), 3.42(2H, t, J=8 Hz), 4.34(2H, d, J=6 Hz), 6.33(1H, s), 6.50(1H, d, J=8 Hz), 6.95–7.00(3H, m), 7.10–7.19(2H, m).

FAB-Mass: 424(MH+).

Example 158: Synthesis of 1-[1-(4-fluorophenethyl)-piperidin-4-yl]-6-isobutyrylaminomethylindoline

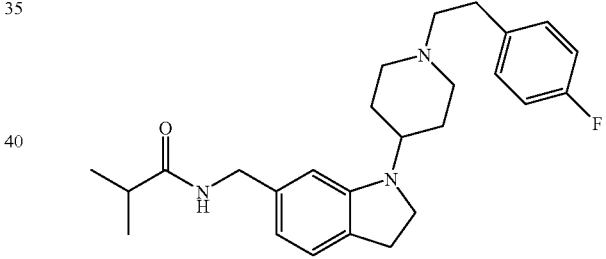

1-[1-(4-Fluorophenethyl)piperidin-4-yl]-6-aminomethylindoline (300 mg), triethylamine (80 mg) and isobutyryl chloride (90 mg) were treated as in Example 133 to give the title compound (200 mg) as white needles (yield: 58%).

m.p.: 163–165° C.

$^1$H-NMR (400 MHz, CDCl$_3$):

δ(ppm) 1.17(6H, d, J=7 Hz), 1.51–1.66(2H, m), 1.75–1.87 (2H, m), 2.10–2.25(2H, m), 2.36(1H, septet, J=7 Hz), 2.56–2.72(2H, m), 2.75–2.95(2H, m), 2.93(2H, t, J=8 Hz), 3.08–3.25(2H, m), 3.35–3.45(1H, m), 3.42(2H, t, J=8 Hz), 4.34(2H, d, J=6 Hz), 6.33(1H, s), 6.50(1H, d, J=8 Hz), 6.96–7.01(3H, m), 7.15–7.19(2H, m).

FAB-Mass: 424(MH+).

Example 159: Synthesis of 1-[1-(4-fluorophenethyl)-piperidin-4-yl]-6-cyclopropanecarboxamindomethylindoline

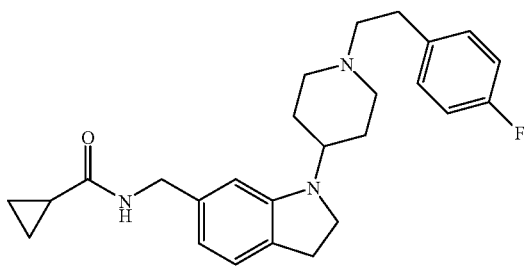

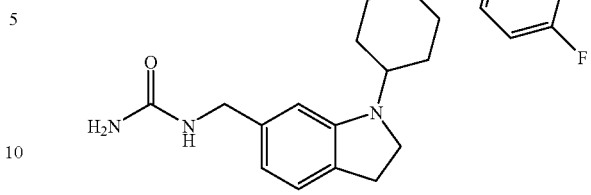

1-[-(4-Fluorophenethyl)piperidin-4-yl]-6-aminomethylindoline (250 mg) and cyclopropanecarbonyl chloride (81 mg) were treated as in Example 133 to give the hydrochloride (100 mg) of the title compound as a white powder (yield: 31%).

m.p.: 143–146° C.

$^1$H-NMR (400 MHz, DMSO-$d_6$):

δ(ppm) 0.60–0.69(4H, m), 1.55–1.63(1H, m), 1.83–1.90 (2H, m), 1.99–2.09(2H, m), 2.86(2H, t, J=8 Hz), 3.02–3.16 (4H, m), 3.22–3.30(2H, m), 3.31(2H, t, J=8 Hz), 3.60–3.79 (3H, m), 4.16(2H, d, J=6 Hz), 6.47(1H, s), 6.48(1H, d, J=8 Hz), 6.98(1H, d, J=8 Hz), 7.16–7.21(2H, m), 7.32–7.38(2H, m), 8.43(1H, d, J=6 Hz).

FAB-Mass: 422(MH+).

Example 160: Synthesis of 1-[1-(4-fluorophenethyl)-piperidin-4-yl]-6-methylsulfonylaminomethylindoline

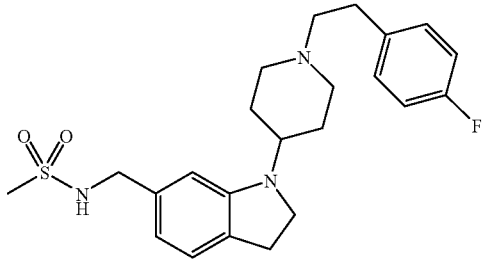

Under ice cooling, methanesulfonyl chloride (78 mg) was added dropwise into a solution of 1-[1-(4-fluorophenethyl)-piperidin-4-yl]-6-aminomethylindoline (200 mg) in pyridine (20 ml) and the resultant mixture was stirred for 30 min. After concentrating under reduced pressure, the residue was partitioned between ethyl acetate and water. The organic layer was washed with brine, dried over anhydrous magnesium sulfate and concentrated under reduced pressure. Then the residue was purified by silica gel column chromatography (ethyl acetate/ethanol system) followed by conversion into a hydrochloride in a conventional manner to give the hydrochloride (160 mg) of the title compound as a white hygroscopic amorphous solid (yield: 60%).

$^1$H-NMR (400 MHz, DMSO-$d_6$):

δ(ppm) 1.81–1.91(2H, m), 2.00–2.12(2H, m), 2.78(3H, s), 2.82–2.90(2H, m), 2.97–3.15(4H, m), 3.19–3.30(2H, m), 3.33(2H, t, J=8 Hz), 3.58–3.75(3H, m), 4.02(2H, s), 6.53 (1H, s), 6.55(1H, d, J=8 Hz), 6.98(1H, d, J=8 Hz), 7.14–7.19 (2H, m), 7.30–7.34(2H, m), 7.42(1H, br-s), 10.70(1H, br-s).

FAB-Mass: 432(MH+).

Example 161: Synthesis of 1-[1-(4-fluorophenethyl)-piperidin-4-yl]-6-ureidomethylindoline A solution of 1-[1-(4-fluorophenethyl)piperidin-4-yl]-6-aminomethylindoline (300 mg) and nitrourea (90 mg) in methanol (10 ml) was heated under reflux for 3 hr. After concentrating under reduced pressure, the residue was crystallized from ethyl acetate. The resulting crystals were dissolved in ethanol followed by conversion into a hydrochloride to give the hydrochloride (260 mg) of the title compound as a gray hygroscopic amorphous solid (yield: 71%).

$^1$H-NMR (400 MHz, DMSO-$d_6$):

δ(ppm) 1.83–2.02(4H, m), 2.84(2H, t, J=8 Hz), 2.98–3.16 (4H, m), 3.20–3.74(7H, m), 4.04(2H, br-s), 6.42(1H, s), 6.45(1H, d, J=8 Hz), 6.94(1H, d, J=8 Hz), 7.15–7.20(2H, m), 7.31–7.34(2H, m)

FAB-Mass: 397(MH+).

Example 162: Synthesis of 1-[1-(4-fluorophenethyl)-piperidin-4-yl]-6-N-methylaminomethylindoline

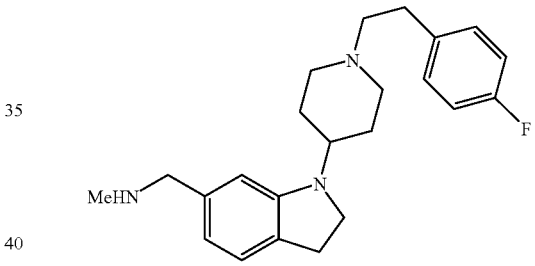

Ethyl chlorocarbonate (300 mg) was added dropwise at room temperature into a solution of 1-[1-(4-fluorophenethyl)-piperidin-4-yl]-6-aminomethylindoline (800 mg) and triethylamine (290 mg) in methylene chloride (20 ml) and the resultant mixture was stirred for 90 min. After concentrating under reduced pressure, the residue was partitioned between ethyl acetate and water. The organic layer was washed with brine, dried over anhydrous magnesium sulfate and concentrated under reduced pressure. The resulting residue was then added to a suspension of lithium aluminum hydride (260 mg) in tetrahydrofuran (20 ml) and the resultant mixture was heated under reflux for 1 hr. Under ice water cooling, water (0.26 ml), a 5 N aqueous solution (0.78 ml) of sodium hydroxide and further water (0.26 ml) were carefully added dropwise to the reaction solution followed by vigorous stirring. The resulting precipitate was filtered off and the filtrate was concentrated under reduced pressure. The residue was purified by NH-silica gel column chromatography (ethyl acetate/ethanol system) to give the title compound (700 mg) as an oil (yield: 83%).

A portion of this product was converted into a hydrochloride in a conventional manner to give the hydrochloride of the title compound as a dark red hygroscopic amorphous solid.

$^1$H-NMR (400 MHz, DMSO-$d_6$):

δ(ppm) 1.90–1.98(2H, m), 2.06–2.20(2H, m), 2.48(3H, s), 2.89(2H, t, J=8 Hz), 2.99–3.12(4H, m), 3.22–3.31(2H, m), 3.35(2H, t, J=8 Hz), 3.58–3.68(3H, m), 3.95(2H, br-s), 6.64(1H, d, J=8 Hz), 6.87(1H, s), 7.03(1H, d, J=8 Hz), 7.10–7.19(2H, m), 7.30–7.34(2H, m), 9.22(2H, br-s), 10.79 (1H, br-s).

FAB-Mass: 368(MH+).

Example 163: Synthesis of 1-[1-(4-fluorophenethyl)-piperidin-4-yl]-6-N-methylacetamidomethylindoline

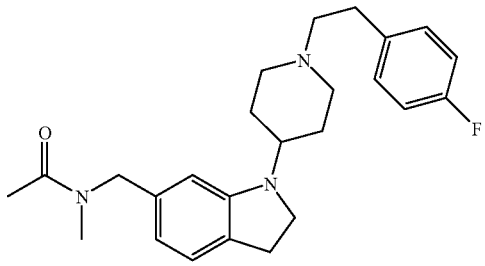

1-[1-(4-Fluorophenethyl)piperidin-4-yl]-6-N-methylaminomethylindoline (540 mg), triethylamine (200 mg) and acetyl chloride (150 mg) were treated as in Example 133 to give the hydrochloride (330 mg) of the title compound as a white hygroscopic amorphous solid (yield: 50%).

¹H-NMR (400 MHz, DMSO-d₆):

δ(ppm) 1.81–1.89(2H, m), 1.92–2.06(2H, m), 2.02(3H, s), 2.75(1.5H, s), 2.85(1.5H, s), 2.80–2.90(2H, m), 3.00–3.14 (4H, m), 3.21–3.36(4H, m), 3.58–3.73(3H, m), 4.35(1H, s), 4.40(1H, s), 6.32(0.5H, s), 6.36(0.5H, s), 6.37(0.5H, d, J=8 Hz), 6.40(0.5H, d, J=8 Hz), 6.95(0.5H, d, J=8 Hz), 6.99 (0.5H, d, J=8 Hz), 7.14–7.19(2H, m), 7.30–7.34(2H, m).

FAB-Mass: 410(MH+).

Example 164: Synthesis of 1-[1-(4-fluorophenethyl)-piperidin-4-yl]-6-(N-methylsulfamoylmethyl)indoline

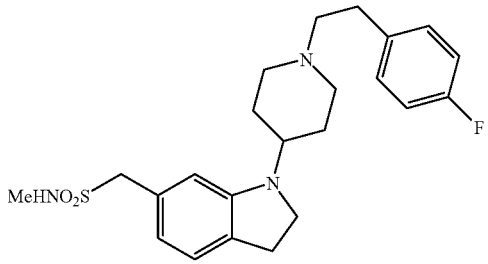

6-(N-Methylsulfamoylmethyl)indoline (100 mg), 1-(4-fluorophenethyl)-4-piperidone (150 mg), acetic acid (120 mg) and triacetoxylated sodium borohydride (140 mg) were treated as in Example 1 to give the title compound (100 mg) as white prisms (yield: 53%).

m.p.: 162–164° C.

¹H-NMR (400 MHz, CDCl₃):

δ(ppm) 1.70–1.89(4H, m), 2.07–2.20(2H, m), 2.55–2.64 (2H, m), 2.71(3H, d, J=6 Hz), 2.75–2.86(2H, m), 2.95(2H, t, J=8 Hz), 3.08–3.15(2H, m), 3.37–3.50(3H, m), 4.10–4.30 (1H, m), 4.18(2H, s), 6.43(1H, s), 6.54(1H, d, J=8 Hz), 6.91–7.03(3H, m), 7.11–7.20(2H, m).

FAB-Mass: 432(MH+).

Example 165: Synthesis of 1-[1-(4-fluorophenethyl)-piperidin-4-yl]-6-(1-acetamidoethlyl)indoline

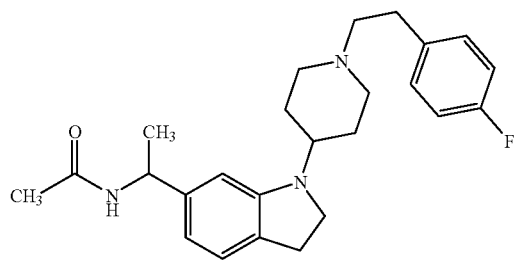

1-[1-(4-Fluorophenethyl)piperidin-4-yl]-6-(1-hydroxyethyl)indoline (300 mg) was treated as in Example 90 to give the hydrochloride (80 mg) of the title compound as a pale yellow hygroscopic amorphous solid (yield: 22%).

¹H-NMR (400 MHz, DMSO-d₆):

δ(ppm) 1.29(3H, d, J=7 Hz), 1.82(3H, s), 1.83–1.93(2H, m), 2.00–2.15(2H, m), 2.84(2H, t, J=8 Hz), 3.01–3.15(4H, m), 3.20–3.35(2H, m), 3.32(2H, t, J=8 Hz), 3.60–3.77(3H, m), 4.80(1H, quintet, J=7 Hz), 6.51–6.53(2H, m), 6.95(1H, d, J=8 Hz), 7.17–7.21(2H, m), 7.32–7.37(2H, m), 8.19(1H, d, J=8 Hz).

FAB-Mass: 410(MH+).

Example 166: Synthesis of 1-[1-(4-fluorophenethyl) piperidin-4-yl]-6-acetamidoethylindoline

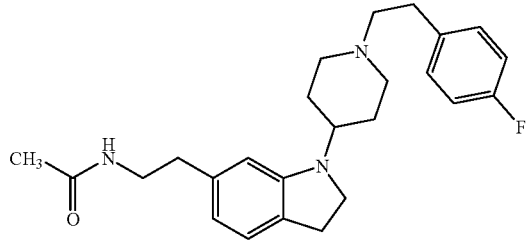

A mixture of 1-[1-(4-fluorophenethyl)piperidin-4-yl]-6-cyanomethylindoline (0.25 g), platinum oxide (50 mg), 5 N hydrochloric acid (1.0 ml) and methanol (20 ml) was catalytically reduced under hydrogen atmosphere of 3 atm. After 4 hr, the catalyst was filtered off and the filtrate was concentrated under reduced pressure. To the resulting residue were added a 5 N aqueous solution (10 ml) of sodium hydroxide, acetyl chloride (0.2 ml) and methylene chloride (20 ml) and the resultant mixture was stirred vigorously for 1 hr. Next, it was diluted with water and chloroform and the layers were separatetd. The organic layer was washed with brine and dried over anhydrous magnesium sulfate. The residue was purified by NH-silica gel column chromatography (hexane/ethyl acetate system) followed by conversion into an oxalate in a conventional manner to give the oxalate (90 mg) of the title compound as a brown hygroscopic amorphous solid (yield: 26%).

¹H-NMR (400 MHz, DMSO-d₆):

δ(ppm) 1.80–1.94(4H, m), 2.08(3H, s), 2.58(2H, t, J=7 Hz), 2.84(2H, t, J=8 Hz), 2.93–3.07(4H, m), 3.15–3.24(4H, m), 3.31(2H, t, J=8 Hz), 3.51–3.59(2H, m), 3.64–3.74(1H, m), 6.36(1H, s), 6.39(1H, d, J=8 Hz), 7.15–7.21(2H, m), 7.31–7.39(2H, m), 7.88(1H, t, J=6 Hz).

FAB-Mass: 410(MH+).

Example 167: Synthesis of 1-[1-(4-fluorophenethyl)-piperidin-4-yl]-6-[(piperidin-4-yl)methyl]indoline

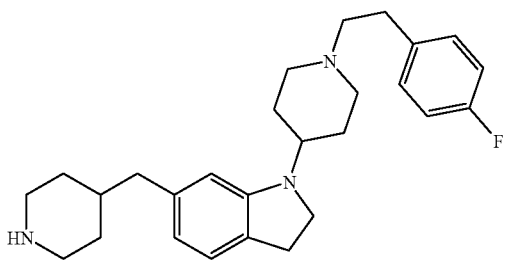

A mixture of 1-[1-(4-fluorophenethyl)piperidin-4-yl]-6-(1-hydroxy-4-pyridylmethyl)indoline (1.2 g), 10% palladium-carbon (600 mg), 5 N hydrochloric acid (2.9 ml) and ethanol (30 ml) was catalytically reduced under hydrogen atmosphere of 3 atm. After 7 hr, platinum oxide (150 mg) was added thereto and the catalytic reduction was continued for additional 2 hr. Then the catalyst was filtered off and the filtrate was concentrated under reduced pressure. The resulting residue was diluted with a saturated aqueous solution of sodium bicarbonate and ethyl acetate and the layers were separated. The organic layer was washed with brine and dried over anhydrous magnesium sulfate. The residue was purified by NH-silica gel column chromatography (ethanol/ethyl acetate system) followed by conversion into a hydrochloride in a conventional manner to give the hydrochloride (510 mg) of the title compound as a white powder (yield: 33%).

m.p. (hydrochloride): 162–165° C.

$^1$H-NMR (400 MHz, DMSO-$d_6$):

δ(ppm) 1.27–1.40(2H, m), 1.65–1.91(5H, m), 2.03–2.17 (2H, m), 2.38–2.44(2H, m), 2.51–2.84(2H, m), 2.84(2H, t, J=8 Hz), 3.01–3.45(10H, m), 3.59–3.76(3H, m), 3.36–3.39 (2H, m), 6.93(1H, d, J=8 Hz), 7.16–7.21(2H, m), 7.32–7.36 (2H, m), 8.68(1H, br-s), 8.85(1H, br-s), 10.79(1H, br-s).

FAB-Mass: 422(MH+).

Example 168: Synthesis of 1-[1-(4-fluorophenethyl)-piperidin-4-yl]-6-(1-acetylpiperidin-4-yl)methyllindoline

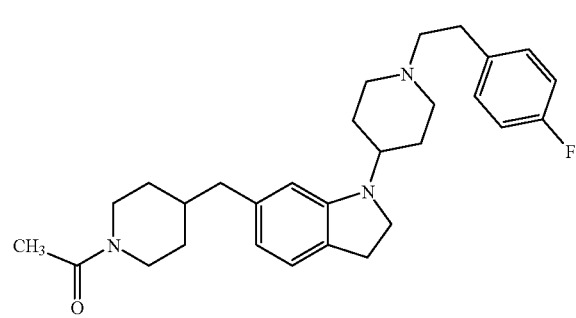

1-[1-(4-Fluorophenethyl)piperidin-4-yl]-6-[(piperidin-4-yl)methyl]indoline (100 mg) and acetyl chloride (0.1 ml) were treated as in Example 133 to give the hydrochloride (50 mg) of the title compound as a pale yellow hygroscopic amorphous solid (yield: 45%).

$^1$H-NMR (400 MHz, DMSO-$d_6$):

δ(ppm) 0.87–1.12(2H, m), 1.50–1.78(3H, m), 1.82–1.91 (2H, m), 1.96(3H, s), 2.00–2.16(2H, m), 2.36–2.45(2H, m), 2.81–2.98(4H, m), 3.00–3.16(4H, m), 3.20–3.38(4H, m), 3.57–3.80(4H, m), 4.26–4.36(1H, m), 6.40–6.42(2H, m), 6.94(1H, d, J=8 Hz), 7.16–7.21(2H, m), 7.32–7.36(2H, m).

FAB-Mass: 464(MH+).

Example 169: Synthesis of 1-[1-(4-fluorophenethyl)-piperidin-4-yl]-6-[(1-ethylpiperidin-4-yl)methyl]indoline

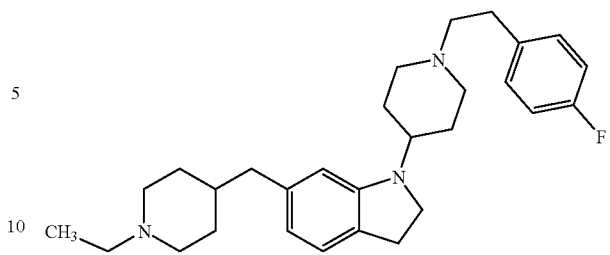

1-[1-(4-Fluorophenethyl)piperidin-4-yl]-6-[(piperidin-4-yl)methyl]indoline (190 mg) and ethyl iodide (84 mg) were treated as in Example 2 to give the hydrochloride (50 mg) of the title compound as a pale brown hygroscopic amorphous solid (yield: 21%).

$^1$H-NMR (400 MHz, DMSO-$d_6$):

δ(ppm) 1.22(3H, t, J=7 Hz), 1.43–1.56(2H, m), 1.68–1.70 (5H, m), 2.04–2.19(2H, m), 2.38–2.45(2H, m), 2.69–2.83 (2H, m), 2.85(2H, t, J=8 Hz), 2.95–3.18(6H, m), 3.20–3.31 (2H, m), 3.32(2H, t, J=8 Hz), 3.35–3.43(2H, m), 3.57–3.70 (3H, m), 6.37–6.41 (2H, m), 6.94(1H, d, J=8 Hz), 7.16–7.22 (2H, m), 7.30–7.37(2H, m), 10.17(1H, br-s), 10.80(1H, br-s).

FAB-Mass: 450(MH+).

Example 170: Synthesis of 1-[1-(4-fluorophenethyl)-piperidin-4-yl]-6-[(1-methylpiperidin-4-yl)methyl]indoline

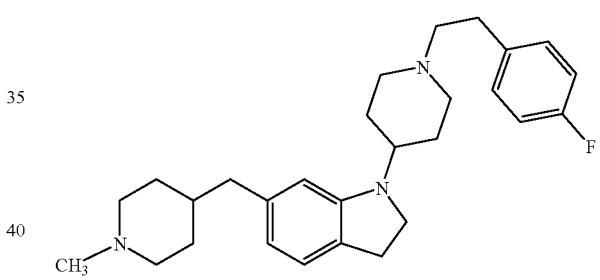

A mixture of 1-[1-(4-fluorophenethyl)piperidin-4-yl]-6-[(piperidin-4-yl)methyl]indoline (200 mg), formamide (40 mg), formic acid (44 mg), water (5 ml) and methanol (5 ml) was heated under reflux overnight. Then, a saturated aqueous solution of sodium bicarbonate and ethyl acetate were added thereto and the layers were separated. The organic layer was washed with brine and dried over anhydrous magnesium sulfate. Then the residue was purified by NH-silica gel column chromatography (hexane/ethyl acetate system) followed by conversion into a hydrochloride in a conventional manner to give the hydrochloride (60 mg) of the title compound as a pale yellow hygroscopic amorphous solid (yield: 25%).

$^1$H-NMR (400 MHz, DMSO-$d_6$):

δ(ppm) 1.40–1.54(2H, m), 1.63–1.76(3H, m), 1.82–1.90 (2H, m), 2.05–2.18(2H, m), 2.38–2.44(2H, m), 2.51(3H, s), 2.64–2.65(2H, m), 2.80–2.90(2H, m), 3.01–3.17(4H, m), 3.20–3.39(6H, m), 3.58–3.70(3H, m), 6.38–6.42(2H, m), 6.94(1H, d, J=8 Hz), 7.16–7.21(2H, m), 7.32–7.36(2H, m), 10.34(1H, br-s), 10.85(1H, br-s).

FAB-Mass: 436(MH+).

Example 171: Synthesis of 1-[1-(4-fluorophenethyl) piperidin-4-yl]-6-(2-pyridyl)indoline

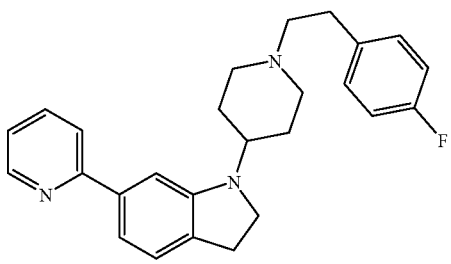

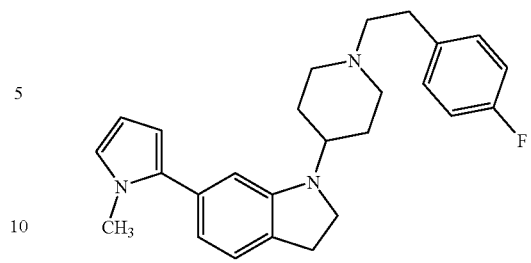

1-[1-(4-Fluorophenethyl)piperidin-4-yl]-6-bromoindoline (0.405 g) and 2-tributylstannylpyridine (1.85 g) synthesized in accordance with the method described in Tetrahedron Lett., 4407 (1986). were treated as in Production Example 13-2 to give the title compound (0.234 g) as a pale yellow oil (yield: 46.6%).

Next, oxalic acid (52 mg) was added to the above product to give an oxalate followed by recrystallization from acetone to give the oxalate (0.254 g) of the title compound as orange crystals.

m.p. (oxalate): 182° C.
Oxalate
$^1$H-NMR (400 MHz, DMSO-$d_6$):
δ(ppm) 1.92(4H, m), 2.95(2H, t, J=8.4 Hz), 2.99(2H, m), 3.04(2H, m), 3.17(2H, m), 3.40(2H, t, J=8.4 Hz), 3.56(2H, br-d), 3.86(1H, m), 7.17(4H, m), 7.32(4H, m), 7.85(2H, m), 8.62(1H, d, J=4.4 Hz).
FAB-Mass: 402(MH+).

Example 172: Synthesis of 1-[1-(4-fluorophenethyl)piperidin-4-yl]-6-(2-thiazolyl)indoline

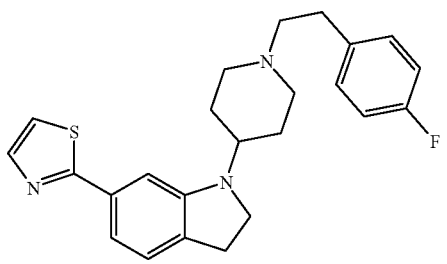

1-[1-(4-Fluorophenethyl)piperidin-4-yl]-6-bromoindoline (0.56 g) and 2-tributylstannylthiazole (2.778 g) synthesized in accordance with the method described in Synthesis, 757 (1986). were treated as in Production Example 13-2 to give the title compound (0.017 g) as pale yellow crystals (yield: 3.0%).

Next, oxalic acid (2 mg) was added to the above product to give an oxalate followed by recrystallization from acetone to give the oxalate of the title compound as yellow crystals.

m.p. (oxalate): 170° C.
Oxalate
$^1$H-NMR (400 MHz, DMSO-$d_6$):
δ(ppm) 1.90(4H, m), 2.95(2H, t, J=8.4 Hz), 2.98(2H, m), 3.04(2H, m), 3.16(2H, m), 3.42(2H, t, J=8.4 Hz), 3.56(2H, m), 3.85(1H, m), 7.06(1H, s), 7.13(2H, m), 7.33(2H, m), 7.71(1H, d, J=3.2 Hz), 7.86(1H, d, J=3.2 Hz).
FAB-Mass: 408(MH+).

Example 173: Synthesis of 1-[1-(4-fluorophenethyl)-piperidin-4-yl]-6-(1-methylpyrrol-2-yl)indoline 1-[1-(4-Fluorophenethyl)piperidin-4-yl]-6-bromoindoline (0.1 g) and 1-methyl-2-tributylstannylpyrrole (0.37 g) synthesized in accordance with the method described in Tetrahedron Lett., 4407 (1986). were treated as in Production Example 13-2 to give the title compound (0.016 g) as a yellow oil (yield: 15.8%).

Next, oxalic acid (2 mg) was added to the above product to give an oxalate followed by recrystallization from acetone to give the oxalate of the title compound as yellow crystals.

m.p. (oxalate): 118° C.
Oxalate
$^1$H-NMR (400 MHz, DMSO-$d_6$):
δ(ppm) 1.83(4H, m), 2.79(2H, m), 2.90(2H, t, J=8.4 Hz), 2.92(2H, m), 3.02(2H, m), 3.37(2H, t, J=8.4 Hz), 3.41(2H, m), 3.60(3H, s), 3.68(1H, m), 6.01(1H, dd, J=2.4, 3.6 Hz), 6.05(1H, dd, J=2.0, 3.6 Hz), 6.51(1H, d, J=1.2 Hz), 6.58(1H, dd, J=1.2, 7.6 Hz), 6.78(1H, dd, J=2.0, 2.4 Hz), 7.04(1H, d, J=7.6 Hz), 7.15(2H, m), 7.31(2H, m).
ESI-Mass: 404.2(MH+).

Example 174: Synthesis of 1-[1-(4-fluorophenethyl)-piperidin-4-yl]-6-[1-hydroxy-1-(2-pyridyl)methyl]indoline

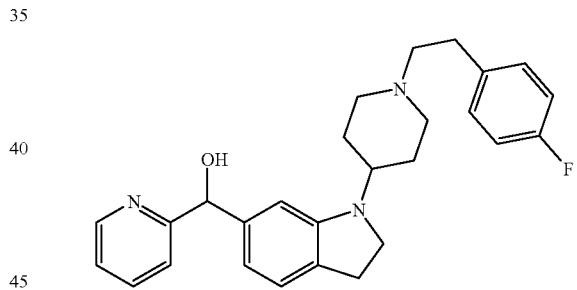

2-Bromopyridine (0.16 ml), 1-[1-(4-fluorophenethyl)-piperidin-4-yl]-6-formylindoline (0.5 g) and diethyl ether employed as the solvent were treated as in Example 93 to give the title compound (0.344 g) as a yellow oil (yield: 56.1%).

To a 50 mg portion of the above product was added oxalic acid (10 mg) to give the oxalate of the title compound.
m.p. (oxalate): 105° C.
Free
$^1$H-NMR (400 MHz, CDCl$_3$):
δ(ppm) 1.72–1.81(4H, m), 2.08–2.19(2H, m), 2.57–5.61 (2H, m), 2.78–2.82(2H, m), 2.91(1H, t, J=8.4 Hz), 3.10(2H, br-t), 3.38(2H, t, J=8.4 Hz), 3.40(1H, m), 5.21(1H, d, J=4.0 Hz), 5.66(1H, d, J=4.0 Hz), 6.43(1H, d, J=1.2 Hz), 6.56(1H, dd, J=1.2, 7.2 Hz), 6.95–6.99(3H, m), 7.13–7.26(4H, m), 7.60(1H, ddd, J=1.6, 7.2, 8.8 Hz), 8.54(1H, ddd, J=0.8, 1.6, 4.0 Hz).
ESI-Mass: 432.2(MH+).

Example 175: Synthesis of 1-[1-(4-fluorophenethyl)-piperidin-4-yl]-6-[1-(2-pyridyl)methyl]indoline

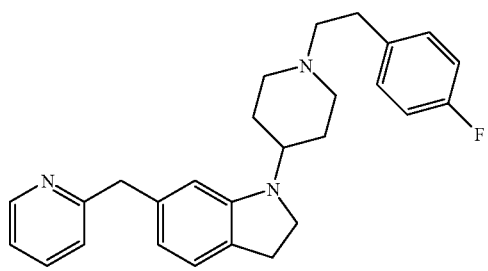

1-[1-(4-Fluorophenethyl)piperidin-4-yl]-6-[1-hydroxy-1-(2-pyridyl)methyl]indoline (0.321 g) was dissolved in ethanol (86.4 ml) followed by the addition of 1 N hydrochloric acid (3.7 ml) and palladium carbon. Then the resultant mixture was catalytically reduced under atmospheric pressure for 3 hr. After filtering off the catalyst, the filtrate was concentrated under reduced pressure. To the residue were added a saturated aqueous solution of sodium bicarbonate and ethyl acetate and the layers were separated. The organic layer was washed with brine, dried over anhydrous sodium sulfate and concentrated under reduced pressure. Then the residue was purified by NH-silica gel column chromatography (hexane/ethyl acetate-methanol system) to give the title compound (0.076 g) as a yellow oil (yield: 24.6%).

Then oxalic acid (16.5 mg) was added to the above product to give the oxalate of the title compound as a yellow hygroscopic amorphous solid.

Oxalate $^1$H-NMR (400 MHz, DMSO-$d_6$):

δ(ppm) 1.77(4H, m), 2.67(2H, m), 2.81(2H, t, J=8.2 Hz), 2.87–2.93(4H, m), 3.30(2H, t, J=8.2 Hz), 3.36(2H, br-d), 3.95(1H, m), 4.17(2H, s), 6.42–6.44(2H, m), 6.91(1H, d, J=7.5 Hz), 7.12–7.21(4H, m), 7.29–7.32(2H, m), 7.67(1H, ddd, J=1.8, 6.0, 6.0 Hz), 8.46(1H, dd, J=0.8, 4.8 Hz).

FAB-Mass: 416(MH+).

Example 176: Synthesis of 1-[1-(4-fluorophenethyl)-piperidin-4-yl]-6-[1-hydroxy-1-(3-pyridyl)methyl]indoline

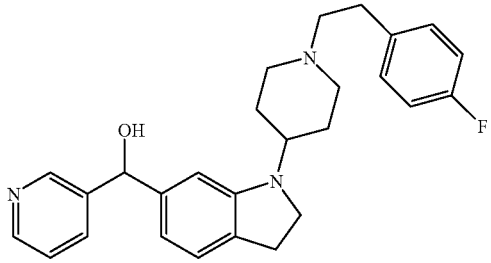

3-Bromopyridine (0.44 ml), 1-[1-(4-fluorophenethyl)-piperidin-4-yl]-6-formylindoline (0.4 g) and diethyl ether employed as the solvent were treated as in Example 93 to give the title compound (0.337 g) as a yellow oil (yield: 68.8%).

Then oxalic acid was added to the above product to give the oxalate of the title compound as an amorphous solid.

m.p. (oxalate): 110–113° C.

Oxalate $^1$H-NMR (400 MHz, DMSO-$d_6$):

δ(ppm) 1.88(4H, m), 2.83(2H, t, J=8.5 Hz), 3.01(4H, m), 3.19(2H, m), 3.30(2H, t, J=8.5 Hz), 3.57(2H, m), 3.71(1H, m), 5.65(1H, s), 6.56(1H, d, J=7.6 Hz), 6.59(1H, s), 6.95(1H, d, J=7.6 Hz), 7.18(2H, m), 7.32(3H, m), 7.70(1H, ddd, J=1.6, 2.0, 6.0 Hz), 8.40(1H, dd, J=1.6, 5.2 Hz), 8.57(1H, d, J=2.0 Hz).

ESI-Mass: 432.2(MH+).

Example 177: Synthesis of 1-[1-(4-fluorophenethyl)-piperidin-4-yl]-6-[1-(3-pyridyl)methyl]indoline

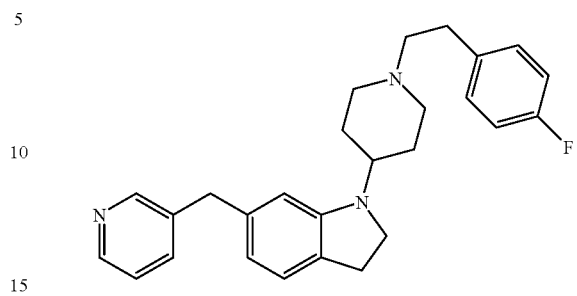

1-[1-(4-Fluorophenethyl)piperidin-4-yl]-6-[1-hydroxy-1-(3-pyridyl)methyl]indoline (0.1 g) was treated as in Example 175 to give the title compound (0.018 g) as a colorless oil (yield: 18.7%).

Free $^1$H-NMR (400 MHz, CDCl$_3$):

δ(ppm) 1.79(4H, m), 2.14(2H, m), 2.61(2H, m), 2.81(2H, m), 2.91(2H, t, J=8.4 Hz), 3.13(2H, br-d), 3.25(1H, m), 3.40(2H, t, J=8.4 Hz), 3.88(2H, s), 6.19(1H, d, J=1.2 Hz), 6.41(1H, dd, J=1.2, 7.4 Hz), 6.97(3H, m), 7.17(3H, m), 7.47(1H, m), 8.44(1H, dd, J=1.2, 4.8 Hz), 8.51(1H, d, J=1.2 Hz).

ESI-Mass: 416.2(MH+).

Next, oxalic acid (5 mg) was added to the above product to give the oxalate of the title compound as an amorphous solid.

Example 178: Synthesis of 1-[1-(4-fluorophenethyl)-piperidin-4-yl]-6-(1-hydroxy-4-pyridylmethyl)indoline

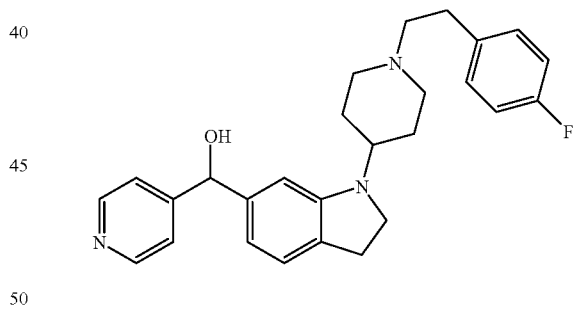

1-[1-(4-Fluorophenethyl)piperidin-4-yl]-6-bromoindoline (700 mg), a 2.5 M solution (1.0 ml) of n-butyllithium in hexane and 4-pyridinecarbaldehyde (280 mg) were treated as in Example 130 to give the oxalate (130 mg) of the title compound as a brown hygroscopic amorphous substance (yield: 15%).

$^1$H-NMR (400 MHz, DMSO-$d_6$):

δ(ppm) 1.75–1.93(4H, m), 2.83(2H, t, J=8 Hz), 2.91–3.02 (4H, m), 3.11–3.19(2H, m), 3.30(2H, t, J=8 Hz), 3.48–3.57 (2H, m), 3.61–3.71(1H, m), 5.57(1H, s), 6.55–6.57(2H, m), 6.94(1H, d, J=8 Hz), 7.15–7.20(2H, m), 7.31–7.36(4H, m), 8.45–8.47(2H, m).

FAB-Mass: 432(MH+).

Example 179: Synthesis of 1-[1-(4-fluorophenethyl)-piperidin-4-yl]-6-(4-pyridylmethyl)indoline

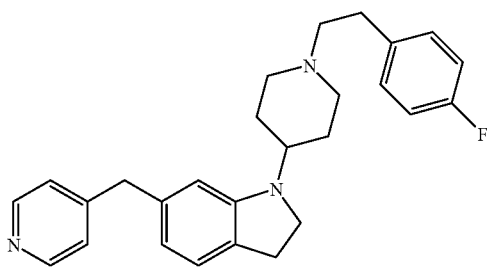

A mixture of 1-[1-(4-fluorophenethyl)piperidin-4-yl]-6-(1-hydroxy-4-pyridylmethyl)indoline (350 mg), 10% palladium carbon (200 mg), 5 N hydrochloric acid (0.8 ml) and ethanol (20 ml) was catalytically reduced under hydrogen atmosphere of 3 atm. After 5 hr, the catalyst was filtered off and the filtrate was concentrated under reduced pressure. Then the residue was diluted with a saturated aqueous solution of sodium bicarbonate and ethyl acetate and the layers were separated. The organic layer was washed with brine and dried over anhydrous magnesium sulfate. Then the residue was purified by NH-silica gel column chromatography (hexane/ethyl acetate system) followed by conversion into an oxalate in a conventional manner to give the oxalate (190 mg) of the title compound as a white powder (yield: 46%).

m.p. (oxalate): 195–197° C.
$^1$H-NMR (400 MHz, DMSO-$d_6$):

δ(ppm) 1.79–1.94(4H, m), 2.84(2H, t, J=8 Hz), 2.92–2.90 (4H, m), 3.11–3.19(2H, m), 3.32(2H, t, J=8 Hz), 3.48–3.56 (2H, m), 3.59–3.69(1H, m), 3.83(2H, s), 6.41–6.43(2H, m), 6.94(1H, d, J=8 Hz), 7.15–7.22(4H, m), 7.30–7.34(2H, m), 8.42–8.44(2H, m).

FAB-Mass: 416(MH+).

Example 180: Synthesis of 1-[1-(4-fluorophenethyl)-piperidin-4-yl]-6-(2-pyridylcarbonyl)indoline

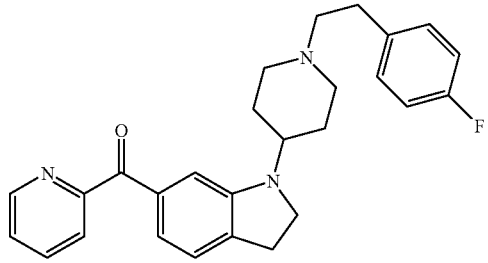

1-[1-(4-Fluorophenethyl)piperidin-4-yl]-6-[1-hydroxy-1-(2-pyridyl)methyl]indoline (0.895 g) was treated in accordance with the method described in J. Org. Chem., 2899 (1993). to give the title compound (0.357 g) as a yellow oil (yield: 40.1%).

$^1$H-NMR (400 MHz, CDCl$_3$):

δ(ppm) 1.81(4H, m), 2.18(2H, m), 2.60(2H, m), 2.80(2H, m), 3.01(2H, t, J=8.4 Hz), 3.11(2H, m), 3.47(2H, t, J=8.4 Hz), 3.51(1H, m), 6.97(2H, m), 7.02(1H, d, J=0.6 Hz), 7.09(1H, d, J=7.2 Hz), 7.17(3H, m), 7.45(1H, ddd, J=1.4, 5.0, 7.6 Hz), 7.87(1H, ddd, J=1.8, 7.6, 7.6 Hz), 7.93(1H, ddd, J=0.8, 1.4, 7.6 Hz), 8.71(1H, ddd, J=0.8, 1.8, 5.0 Hz).

Example 181: Synthesis of 1-[1-(4-fluorophenethyl)-piperidin-4-yl]-6-[1-hydroxy-1-(2-pyridyl)ethyl]indoline

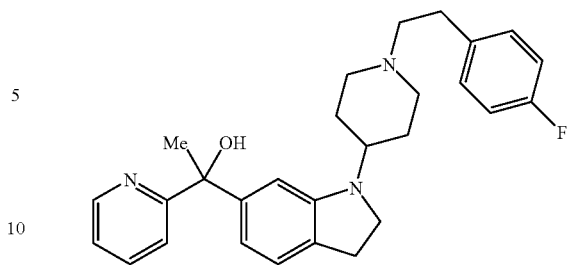

1-[1-(4-Fluorophenethyl)piperidin-4-yl]-6-(2-pyridylcarbonyl)indoline (0.074 g) was dissolved in tetrahydrofuran (1.0 ml). To the resultant solution was added at −78° C. a 3.0 M solution of methylmagnesium bromide in diethyl ether and the resultant mixture was stirred for 1 hr. Next, water and ethyl acetate were added thereto and the layers were separated. The organic layer was washed with brine, dried over anhydrous sodium sulfate and concentrated under reduced pressure. The residue was purified by NH-silica gel column chromatography (hexane/ethyl acetate-methanol system) to give the title compound (0.029 g) as a yellow oil (yield: 37.8%).

Next, oxalic acid (6 mg) was added to the above product to give the oxalate of the title compound as a yellow amorphous solid.

m.p. (oxalate): 98–108° C.
Oxalate
$^1$H-NMR (400 MHz, DMSO-$d_6$):

δ(ppm) 1.84(4H, m), 2.80(2H, t, J=8.4 Hz), 2.99(2H, m), 3.11(2H, m), 3.24(2H, m), 3.28(2H, t, J=8.4 Hz), 3.59(2H, m), 3.70(1H, m), 6.61(1H, d, J=7.4 Hz), 6.69(1H, s), 6.88 (1H, d, J=7.4 Hz), 7.19(3H, m), 7.36(2H, m), 7.58(1H, m), 7.71(1H, m), 8.46(1H, m).

ESI-Mass: 446.3(MH+).

Example 182-1: Synthesis of 1-[1-(4-fluorophenethyl)-piperidin-4-yl]-6-[1-hydroxy-1-(2-pyridyl)-2-trimethylsilylethyl]indoline

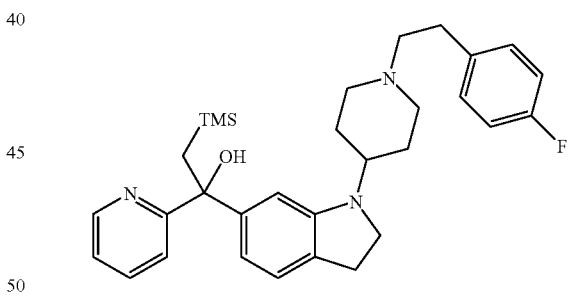

(wherein TMS means trimethylsilyl.)

1-[1-(4-Fluorophenethyl)piperidin-4-yl]-6-[1-hydroxy-1-(2-pyridyl)ethyl]indoline (0.357 g) was treated in accordance with the method described in Synthesis, 384 (1984). to give the title compound (0.250 g) as a yellow oil (yield: 58.3%).

$^1$H-NMR (400 MHz, CDCl$_3$):

δ(ppm) −0.75(9H, s), 1.75(4H, m), 2.13(2H, m), 2.58(2H, m), 2.78(2H, m), 2.87(3H, t, J=8.4 Hz), 3.09(2H, m), 3.36 (2H, t, J=8.4 Hz), 3.43(1H, m), 5.99(2H, s), 6.64(1H, d, J=1.2 Hz), 6.76(1H, dd, J=1.2, 7.6 Hz), 6.94(1H, d, J=7.6 Hz), 6.97(2H, m), 7.11(1H, ddd, J=0.8, 4.8, 7.6 Hz), 7.15 (2H, m), 7.39(1H, ddd, J=0.8, 0.8, 8.0 Hz), 7.59(1H, ddd, J=1.6, 7.6, 8.0 Hz), 8.45(1H, ddd, J=0.8, 1.6, 4.8 Hz).

Example 182-2: Synthesis of 1-[1-(4-fluorophenethyl)-piperidin-4-yl]-6-[1-(2-pyridyl)vinyl]indoline

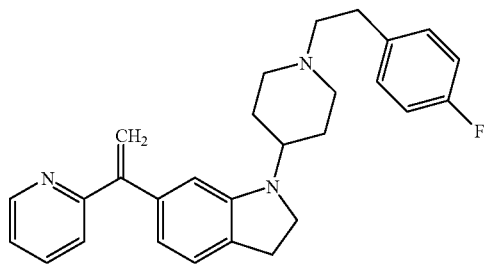

1-[1-(4-Fluorophenethyl)piperidin-4-yl]-6-[1-hydroxy-1-(2-pyridyl)-2-trimethylsilylethylindoline (0.250 g) was treated in accordance with the method described in J. Am. Chem. Soc., 1464 (1975). to give the title compound (0.138 g) as a yellow oil (yield: 66.6%).

$^1$H-NMR (400 MHz, CDCl$_3$):

δ(ppm) 1.80(4H, m), 2.07(2H, m), 2.56(2H, m), 2.77(2H, m), 2.97(2H, t, J=8.4 Hz), 3.08(2H, br-d), 3.36(1H, m), 3.43(2H, t, J=8.4 Hz), 5.40(1H, d, J=1.8 Hz), 5.98(1H, d, J=1.8 Hz), 6.37(1H, d, J=1.2 Hz), 6.57(1H, dd, J=1.2, 7.6 Hz), 6.96(2H, m), 7.03(1H, d, J=7.6 Hz), 7.14(2H, m), 7.20(1H, ddd, 0.6, 5.0, 7.6 Hz), 7.27(1H, ddd, 0.4, 0.6, 7.2 Hz), 7.60(1H, ddd, 2.0, 7.2, 7.6 Hz), 8.64(1H, ddd, 0.4, 2.0, 5.0 Hz).

Example 182-3: Synthesis of 1-[1-(4-fluorophenethyl)-piperidin-4-yl]-6-[1-(2-pyridyl)ethyl]indoline

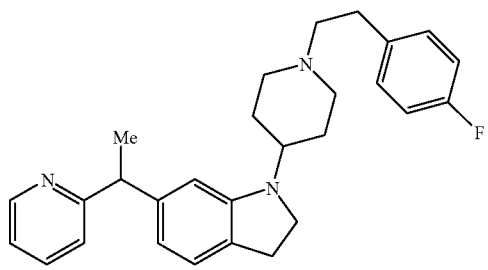

1-[1-(4-Fluorophenethyl)piperidin-4-yl]-6-[1-(2-pyridyl)vinyl]indoline (0.138 g) was treated as in Production Example 59-2 to give the title compound (0.110 g) as a yellow oil (yield: 79.3%).

Next, oxalic acid (23 mg) was added to the above product to give the oxalate of the title compound as an amorphous solid.

m.p. (oxalate): 95–102° C.

Oxalate $^1$H-NMR (400 MHz, DMSO-d$_6$):

δ(ppm) 1.58(3H, d, J=7.2 Hz), 1.83(4H, m), 2.81(2H, t, J=8.0 Hz), 2.96(2H, m), 3.16(2H, m), 3.29(2H, t, J=8.0 Hz), 3.53(2H, m), 3.67(1H, m), 4.14(1H, q, J=7.2 Hz), 6.48(2H, m), 6.91(1H, d, J=7.6 Hz), 7.18(4H, m), 7.33(2H, m), 7.66(1H, ddd, J=1.6, 7.6, 7.6 Hz), 8.48(1H, m).

ESI-Mass: 430.3(MH+).

Example 183: Synthesis of 1-[1-(4-fluorophenethyl)-piperidin-4-yl]-6-(3-pyridylcarbonyl)indoline

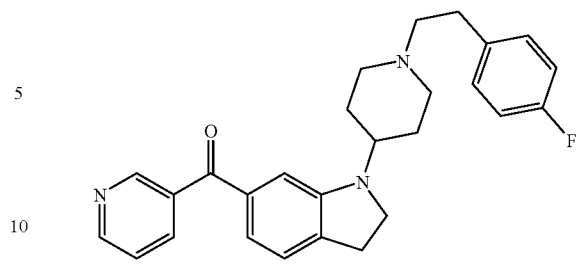

1-[1-(4-Fluorophenethyl)piperidin-4-yl]-6-[1-hydroxy-1-(3-pyridyl)methyl]indoline (0.121 g) was treated in accordance with the method described in J. Org. Chem., 2899 (1993). to give the title compound (0.009 g) as a yellow oil (yield: 7.5%).

Free $^1$H-NMR (400 MHz, CDCl$_3$):

δ(ppm) 1.84(4H, m), 2.17(2H, m), 2.61(2H, m), 2.80(2H, m), 3.04(2H, t, J=8.4 Hz), 3.14(2H, m), 3.49(1H, m), 3.51(2H, t, J=8.4 Hz), 6.87(1H, t, J=1.6 Hz), 6.93(1H, dd, J=1.6, 7.2 Hz), 6.98(2H, m), 7.10(1H, d, J=7.2 Hz), 7.16(2H, m), 7.43(1H, ddd, J=0.8, 4.8, 7.2 Hz), 8.10(1H, ddd, J=1.6, 2.0, 7.2 Hz), 8.78(1H, dd, J=0.8, 4.8 Hz), 8.97(1H, dd, J=0.8, 2.0 Hz).

ESI-Mass: 430.2(MH+).

Next, oxalic acid (2 mg) was added to the above product to give the oxalate of the title compound.

m.p. (oxalate): 115° C.

Example 184: Synthesis of 1-[1-(4-fluorophenethyl)-piperidin-4-yl]-6-[1-hydroxy-1-(2-methoxypyridin-3-yl)-methyl]indoline

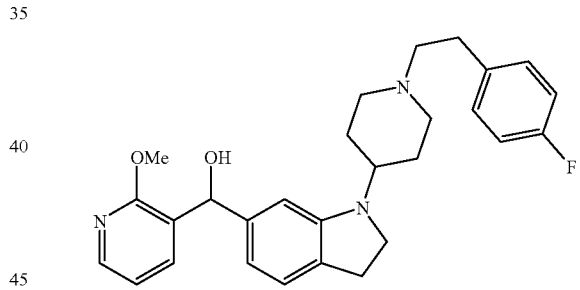

2-Methoxypyridine (0.3 ml) and 1-[1-(4-fluorophenethyl)piperidin-4-yl]-6-formylindoline (0.5 g) were treated in accordance with the method described in J. Org. Chem., 1367 (1988). to give the title compound (0.493 g) as a pale yellow oil (yield: 75.2%).

Next, oxalic acid was added thereto to give the oxalate of the title compound as an amorphous solid.

m.p. (oxalate): 101° C.

Oxalate $^1$H-NMR (400 MHz, DMSO-d$_6$):

δ(ppm) 1.82(4H, m), 2.81(2H, t, J=8.4 Hz), 2.96(4H, m), 3.14(2H, m), 3.31(2H, t, J=8.4 Hz), 3.53(2H, m), 3.67(1H, m), 3.84(3H, s), 5.75(1H, s), 6.49(1H, dd, J=0.8, 7.4 Hz), 6.55(1H, d, J=0.8 Hz), 6.91(1H, d, J=7.4 Hz), 6.98(1H, dd, J=5.2, 7.6 Hz), 7.16(2H, m), 7.33(2H, m), 7.79(1H, dd, J=2.0, 7.6 Hz), 8.02(1H, dd, J=2.0, 5.2 Hz).

ESI-Mass: 462.3(MH+).

Example 185: Synthesis of 1-[1-(4-fluorophenethyl)-piperidin-4-yl]-6-[1-(2-methoxypyridin-3-yl)methyl]indoline

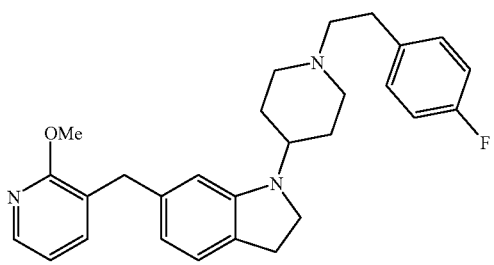

1-[1-(4-Fluorophenethyl)piperidin-4-yl]-6-[1-hydroxy-1-(2-methoxypyridin-3-yl)methyl]indoline (0.418 g) was treated as in Example 175 to give the title compound (0.040 g) as a pale yellow oil (yield: 9.9%).

Next, oxalic acid (8 mg) was added thereto to give the oxalate of the title compound as an amorphous solid.
m.p. (oxalate): 182° C.
Oxalate
$^1$H-NMR (400 MHz, DMSO-d$_6$):
δ(ppm) 1.85(4H, m), 2.83(2H, t, J=8.4 Hz), 2.96(4H, m), 3.17(2H, m), 3.31(2H, t, J=8.4 Hz), 3.54(2H, m), 3.65(1H, m), 3.75(2H, s), 3.87(3H, s), 6.39(1H, d, J=7.6 Hz), 6.41 (1H, s), 6.90(1H, dd, J=5.2, 7.6 Hz), 6.92(1H, d, J=7.6 Hz), 7.18(2H, m), 7.33(2H, m), 7.39(1H, dd, J=2.0, 7.6 Hz), 8.01(1H, dd, J=2.0, 5.2 Hz).
ESI-Mass: 446.3(MH+).

Example 186: Synthesis of 1-[1-(4-fluorophenethyl)-piperidin-4-yl]-6-[1-hydroxy-1-(2-methoxypyridin-6-yl)-methyl]indoline

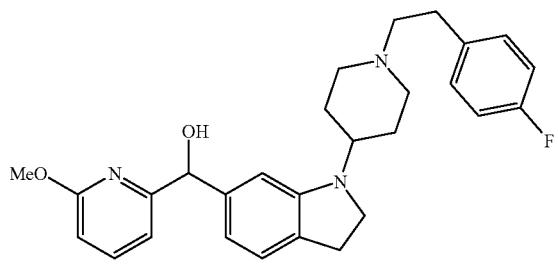

Tetramethylethylenediamine (0.26 ml) was added to 6-bromo-2-methoxypyridine (0.32 g) synthesized in accordance with the method described in Tetrahedron, 1373 (1985). and 1-[1-(4-fluorophenethyl)piperidin-4-yl]-6-formylindoline (0.4 g) and diethyl ether was employed as the solvent. The resultant mixture was treated as in Example 93 to give the title compound (0.401 g) as colorless crystals (yield: 76.5%).

Next, oxalic acid was added thereto to give the oxalate of the title compound as an amorphous solid.
m.p. (oxalate): 95° C.
Oxalate
$^1$H-NMR (400 MHz, DMSO-d$_6$):
δ(ppm) 1.84(2H, m), 2.16(2H, m), 2.82(2H, t, J=8.4 Hz), 2.99(4H, m), 3.16(2H, t), 3.30(2H, t, J=8.4 Hz), 3.54(2H, m), 3.68(1H, m), 3.81(3H, s), 5.48(1H, s), 6.52(3H, m), 6.92(1H, d, J=7.9 Hz), 7.09(1H, d, J=7.1 Hz), 7.16(3H, m), 7.34(2H, m), 7.65(1H, d, J=7.6 Hz).
FAB-Mass: 462(MH+).

Example 187: Synthesis of 1-[1-(4-fluorophenethyl)-piperidin-4-yl]-1-6-[1-(2-methoxypyridin-6-yl)methyl]indoline

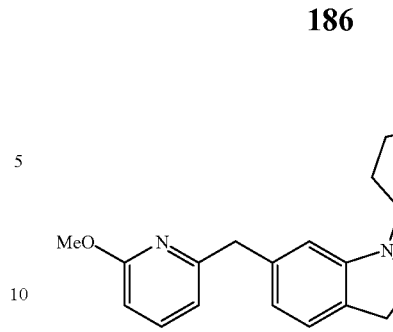

1-[1-(4-Fluorophenethyl)piperidin-4-yl]-6-[1-hydroxy-1-(2-methoxypyridin-6-yl)methyl]indoline (0.363 g) was treated as in Example 175 to give the title compound (0.127 g) as a pale yellow oil (yield: 39.2%).

Next, oxalic acid (26 mg) was added thereto to give the oxalate of the title compound as an amorphous solid.
m.p. (oxalate): 139° C.
Oxalate
$^1$H-NMR (400 MHz, DMSO-d$_6$):
δ(ppm) 1.83(4H, m), 2.84(2H, t, J=8.4 Hz), 2.87(2H, m), 2.93(2H, m), 3.06(2H, m), 3.31(2H, t, J=8.4 Hz), 3.45(2H, m), 3.64(1H, m), 3.83(3H, s), 3.85(2H, s), 6.47(2H, m), 6.60(1H, d, J=8.2 Hz), 6.75(1H, d, J=7.3 Hz), 6.93(1H, d, J=8.0 Hz), 7.16(2H, m), 7.32(2H, m), 7.57(1H, dd, J=7.3, 8.2 Hz).
FAB-Mass: 446(MH+).

Example 188: Synthesis of 1-[1-(4-fluorophenethyl)-piperidin-4-yl]-6-1-hydroxy-1-(2-methoxypyridin-5-yl)-methyl]indoline

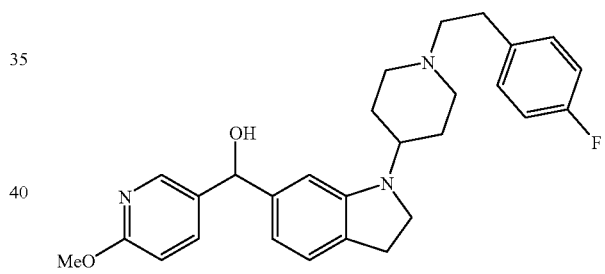

A mixture of 5-bromo-2-methoxypyridine (0.32 g) synthesized in accordance with the method described in Tetrahedron, 1373 (1985). and 1-[1-(4-fluorophenethyl)-piperidin-4-yl]-6-formylindoline (0.4 g) and diethyl ether employed as a solvent was treated as in Example 93 to give the title compound (0.461 g) as a pale yellow oil (yield: 88.0%).
Free
$^1$H-NMR (400 MHz, CDCl$_3$):
δ(ppm) 1.79(4H, m), 2.13(2H, m), 2.48(1H, br-d), 2.60 (2H, m), 2.80(2H, m), 2.92(2H, t, J=8.4 Hz), 3.11(2H, br-d), 3.38(1H, m), 3.41(2H, t, J=8.4 Hz), 3.91(1H, ddd, J=0.4, 0.4, 2.8 Hz), 5.72(1H, d, J=2.4 Hz), 6.42(1H, d, J=0.8 Hz), 6.55(1H, dd, J=0.8 Hz), 6.68(1H, dd, J=0.4, 8.8 Hz), 6.97 (3H, m), 7.15(2H, m), 7.56(1H, ddd, J=0.4, 2.4, 8.8 Hz), 8.17(1H, ddd, J=0.4, 0.4, 2.4 Hz).
ESI-Mass: 462.2(MH+).

Next, oxalic acid or hydrochloric acid was added thereto to give the oxalate or the hydrochloride as a hygroscopic amorphous solid of the title compound.
Oxalate
M.p. (oxalate): 108° C.
$^1$H-NMR (400 MHz, DMSO-d$_6$):

δ(ppm) 1.76(4H, m), 2.63(4H, m), 2.86(2H, t, J=8.2 Hz), 3.89(4H, m), 3.31(2H, t, J=8.2 Hz), 3.33(2H, m), 3.55(1H, m), 3.80(3H, s), 5.58(1H, s), 6.54(1H, s), 6.72(1H, d, J=8.6 Hz), 6.92(1H, d, J=7.6 Hz), 7.14(2H, t, J=8.2 Hz), 7.30(2H, dd, J=5.6, 8.2 Hz), 7.57(1H, dd, J=2.2, 8.6 Hz), 8.13(1H, d, J=2.2 Hz).
Oxalate
FAB-Mass: 462(MH+).
Hydrochloride
¹H-NMR (400 MHz, DMSO-d₆):
δ(ppm) 1.86(2H, m), 2.10(2H, m), 2.86(2H, t, J=8.4 Hz), 3.11(4H, m), 3.24(2H, m), 3.34(2H, t, J=8.4 Hz), 3.64(2H, m), 3.75(1H, m), 3.82(3H, s), 5.61(1H, s), 6.55(1H, s), 6.58(1H, d, J=7.6 Hz), 6.67(1H, br-s), 6.78(1H, d, J=8.4 Hz), 6.97(1H, d, J=7.6 Hz), 7.19(2H, m), 7.34(2H, m), 7.63(1H, dd, J=2.4, 8.4 Hz), 8.16(1H, d, J=2.4 Hz).
FAB-Mass: 462(MH+).

Example 189: Synthesis of 1-[1-(4-fluorophenethyl)-piperidin-4-yl]-6-[1-(2-methoxypyridin-5-yl)methyl]indoline

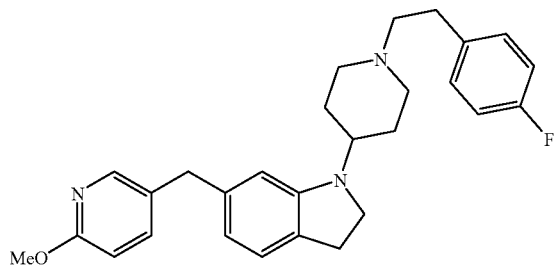

1-[1-(4-Fluorophenethyl)piperidin-4-yl]-6-[1-hydroxy-1-(2-methoxypyridin-5-yl)methyl]indoline (0.335 g) was treated as in Example 175 to give the title compound (0.046 g) as a pale yellow oil (yield: 14.2%).

Next, oxalic acid (10 mg) was added thereto to give the oxalate of the title compound.
m.p. (oxalate): 166° C.
Oxalate
¹H-NMR (400 MHz, DMSO-d₆):
δ(ppm) 1.57(4H, m), 1.85(2H, m), 2.30(2H, m), 2.80(2H, m), 2.93(2H, t, J=8.4 Hz), 3.21(2H, m), 3.42(2H, t, J=8.4 Hz), 3.46(1H, m), 4.0(3H, s), 4.89(1H, d, J=4.2 Hz), 5.59 (1H, d, J=4.2 Hz), 6.45(1H, d, J=1.1 Hz), 6.60(1H, d, J=7.3 Hz), 6.62(1H, d, J=8.2 Hz), 6.71(1H, d, J=7.3 Hz), 6.99(2H, m), 7.00(1H, d, J=7.3 Hz), 7.18(2H, m), 7.50(1H, dd, J=7.3, 8.2 Hz).
FAB-Mass: 446(MH+).

Example 190: Synthesis of 1-[1-(4-fluorophenethyl)-piperidin-4-yl]-6-[1-hydroxy-1-(2-pyridon-5-yl)methyl]-indoline

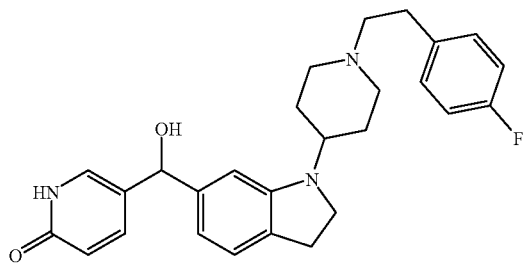

The hydrochloride (0.101 g) of 1-[1-(4-fluorophenethyl)piperidin-4-yl]-6-[1-hydroxy-1-(2-methoxypyridin-5-yl)methyl]indoline which had been prepared about one month before was allowed to stand at room temperature for 2 months. Then, it was dissolved in ethyl acetate and mixed with a saturated aqueous solution of sodium bicarbonate and the layers were separated. The organic layer was washed with brine, dried over anhydrous magnesium sulfate and concentrated under reduced pressure. Next, the residue was purified by NH-silica gel column chromatography (hexane/ethyl acetate system) to give the title compound (0.033 g) as pale yellow crystals.
m.p. (free): 202° C.
Free
¹H-NMR (400 MHz, CDCl₃):
δ(ppm) 1.82(4H, m), 2.31(2H, m),2.68(2H,m), 2.86(2H, m), 2.92(2H, t, J=8.4 Hz), 3.19(2H, m), 3.38(1H, m), 3.42 (2H, t, J=8.4 Hz), 5.53(1H, s), 6.38(1H, br-s), 6.47(1H, d, J=932 Hz), 6.54(1H, dd, J=0.8, 7.2 Hz), 6.95–7.01(3H, m), 7.14–7.17(2H, m), 7.32(1H, d, J=2.4 Hz), 7.44(1H, dd, J=2.4, 9.2 Hz).
FAB-Mass: 448(MH+).

Example 191-1: Synthesis of 5-bromo-2-dimethylaminopyridine

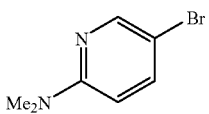

2-Dimethylaminopyridine (1.0 ml) was dissolved in chloroform (60 ml). After adding tributylammonium bromide (3.88 g) thereto, the resultant mixture was stirred for 7 min. Then the reaction solution was washed with an aqueous solution of sodium thiosulfate and water, dried over anhydrous sodium sulfate and concentrated under reduced pressure. The residue was purified by silica gel column chromatography (hexane/ethyl acetate-methanol system) to give the title compound (1.097 g) as yellow crystals (yield: 72.0%).
¹H-NMR (400 MHz, CDCl₃):
δ(ppm) 3.05(6H, s), 6.40(1H, dd, J=0.8, 8.8 Hz), 7.48(1H, dd, J=2.8, 8.8 Hz), 8.16(1H, dd, J=0.8, 2.8 Hz).

Example 191-2: Synthesis of 2-dimethylamino-5-formylpyridine

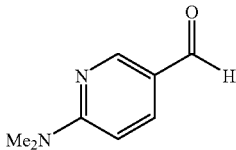

Tetramethylethylenediamine (8.0 ml) was added to the mixture of 5-bromo-2-dimethylaminopyridine (5.0 g), N,N-dimethylformamide (6.1 ml) and diethyl ether employed as the solvent. The resultant mixture was treated in as in Example 93 to give the title compound (3.273 g) as pale yellow crystals (yield: 89.6%).
¹H-NMR (400 MHz, CDCl₃):
δ(ppm) 3.21(6H, s), 6.56(1H, dd, J=0.4, 9.2 Hz), 7.91(1H, dd, J=2.4, 9.2 Hz), 8.55(1H, dd, J=0.4, 2.4 Hz), 9.77(1H, s).

Example 191-3: Synthesis of 1-[1-(4-fluorophenethyl)-piperidin-4-yl]-6-[1-hydroxy-1-(2-dimethylaminopyridin-5-yl)methyl]indoline

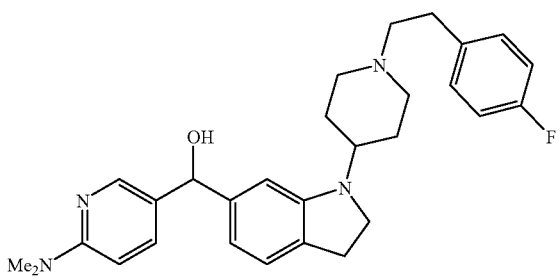

1-[1-(4-Fluorophenethyl)piperidin-4-yl]-6-bromoindoline (0.5 g) and 2-dimethylamino-5-formylpyridine (0.345 g) were treated as in Example 130 to give the title compound (0.376 g) as a colorless oil (yield: 65.3%).

Next, hydrochloric acid was added thereto to give the hydrochloride of the title compound as an amorphous solid.
m.p. (hydrochloride): 185–196° C.
Hydrochloride
$^1$H-NMR (400 MHz, DMSO-$d_6$):

δ(ppm) 1.86(2H, m), 2.08–2.18(2H, m), 2.86(2H, t, J=8.4 Hz), 3.07–3.15(4H, m), 3.21(6H, s), 3.71(2H, m), 3.34(2H, t, J=8.4 Hz), 3.64(2H, br-d), 3.73(1H, m), 5.63(1H, s), 6.56(1H, d, J=7.4 Hz), 6.69(1H, s), 6.98(1H, t, J=7.4 Hz), 7.18(3H, m), 7.34(2H, m), 7.85(1H, dd, J=2.0, 9.6 Hz), 7.90(1H, d, J=2.0 Hz).
ESI-Mass: 475.2(MH+).

Example 192-1: Synthesis of 5-bromo-2-chloropyridine

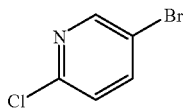

5-Bromo-2-methoxypyridine (1.88 g) was treated in accordance with the method described in Synth. Commun., 2971 (1990). to give the title compound (0.046 g) as a pale yellow oil (yield: 14.2%).
$^1$H-NMR (400 MHz, CDCl$_3$):

δ(ppm) 7.24(1H, dd, J=0.4, 8.1 Hz), 7.77(1H, dd, J=2.4, 8.1 Hz), 8.47(1H, dd, J=0.4, 2.4 Hz).

Example 192-2: Synthesis of 1-[1-(4-fluorophenethyl)-piperidin-4-yl]-6-[1hydroxy-1-(2-chloropyridin-5-yl)-methyl]indoline

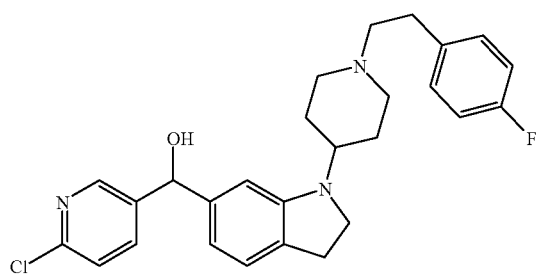

5-Bromo-2-chloropyridine (0.151 g) and 1-[1-(4-fluorophenethyl)piperidin-4-yl]-6-formylindoline (0.2 g) were treated as in Example 93 to give the title compound (0.130 g) as a colorless oil (yield: 49.7%).

Next, hydrochloric acid was added thereto to give the hydrochloride of the title compound as an amorphous solid.
m.p. (hydrochloride): 136° C.
Hydrochloride
$^1$H-NMR (400 MHz, DMSO-$d_6$):

δ(ppm) 1.84(2H, m), 2.12(2H, m), 2.84(2H, t, J=8.4 Hz), 3.04–3.17(4H, m), 3.16(2H, t, J=8.4 Hz), 3.65(2H, br-d), 3.74(1H, m), 5.68(1H, s), 6.58(1H, d, J=7.6 Hz), 6.64(1H, s), 6.97(1H, d, J=7.6 Hz), 7.19(2H, m), 7.34(2H, m), 7.43 (1H, d, J=8.4 Hz), 7.76(1H, dd, J=2.4, 8.4 Hz), 8.42(1H, d, J=2.4 Hz).

ESI-Mass: 466.1(MH+).

Example 193: Synthesis of 1-[1-(4-fluorophenethyl)-piperidin-4-yl]-6-[1-(2-thiazolyl)-1-hydroxymethyl]indoline

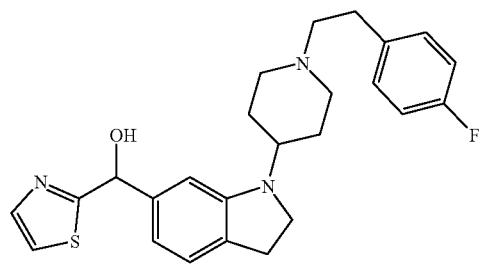

Thiazole (0.12 ml) was dissolved in tetrahydrofuran (5 ml). In a nitrogen atmosphere at −78° C., a 1.66 M solution (1.0 ml) of n-butyllithium in n-hexane was added dropwise into the solution obtained above and the resultant mixture was stirred under the same conditions for 10 min. Next, 1-[1-(4-fluorophenethyl)piperidin-4-yl]-6-formylindoline (0.5 g) dissolved in tetrahydrofuran (7 ml) was added thereto and the resultant mixture was stirred at −78° C. for 3 hr. To the reaction solution were successively added a saturated aqueous solution of ammonium chloride and ethyl acetate (200 ml) and the layers were separated. The organic layer was washed with brine, dried over anhydrous sodium sulfate and concentrated under reduced pressure. The resulting residue was purified by NH-silica gel column chromatography (hexane/ethyl acetate/methanol system) to give the title compound (0.134 g) as a pale yellow oil (yield: 32.6%).

Next, oxalic acid (3 mg) was added to 40 mg of the above product to give the oxalate of the title compound as a colorless amorphous solid.

m.p. (oxalate): 118° C.

Oxalate $^1$H-NMR (400 MHz, DMSO-$d_6$):

δ(ppm) 1.78(4H, m), 2.84(2H, t, J=8.6 Hz), 2.89(4H, m), 2.95(2H, m), 3.32(2H, t, J=8.6 Hz), 3.37(2H, m), 3.58(1H, m), 4.81(1H, s), 5.56(1H, s), 6.00(1H, d, J=7.2 Hz), 6.95 (1H, d, J=7.2 Hz), 7.15(2H, m), 7.31(2H, m), 7.59(1H, d, J=3.0 Hz), 7.66(1H, d, J=3.0 Hz).

ESI-Mass: 438.2(MH+).

Example 194: Synthesis of 1-[1-(4-fluorophenethyl)-piperidin-4-yl]-6-(2-thiazolylcarbonyl)indoline

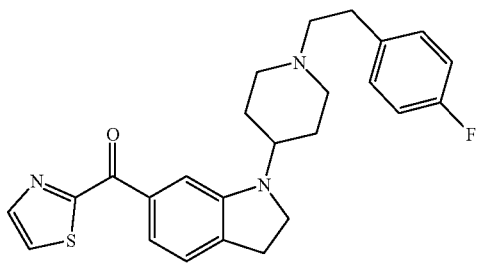

1-[1-(4-Fluorophenethyl)piperidin-4-yl]-6-[1-(2-thiazolyl)-1-hydroxymethyl]indoline (0.1 g) was treated in accordance with the method described in J. Org. Chem., 2480 (1978). to give the title compound (0.022 g) as a yellow oil (yield: 22.1%).

Next, oxalic acid (5 mg) was added thereto to give the oxalate of the title compound as a colorless amorphous solid.
m.p. (oxalate): 132° C.
Free
$^1$H-NMR (400 MHz, CDCl$_3$):
δ(ppm) 1.51(4H, m), 1.82(2H, m), 2.62(2H, m), 2.80(2H, m), 2.97(2H, t, J=8.4 Hz), 3.14(2H, m), 3.43(2H, t, J=8.4 Hz), 3.49(1H, m), 6.20(2H, m), 7.11(3H, m), 7.17(1H, br-s), 7.61(1H, d, J=3.2 Hz), 7.89(1H, d, J=7.6 Hz), 7.99(1H, d, J=3.2 Hz).
FAB-Mass: 436(MH+).

Example 195-Synthesis of 1-1-(4-fluorophenethyl)-piperidin-4-yl]-6-[1-(4-thiazolyl)-1-hydroxymethyl]indoline

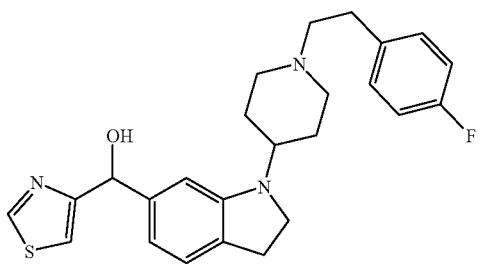

4-Bromo-2-trimethylsilylthiazole (0.2 g) synthesized in accordance with the method described in J. Org. Chem., 1749 (1988). and 1-[1-(4-fluorophenethyl)piperidin-4-yl]-6-formylindoline (0.2 g) were treated as in Example 193 to give the title compound (0.039 g) as apale yellow oil (yield: 15.7%).

Next, oxalic acid (4 mg) was added thereto to give the oxalate of the title compound as an amorphous solid.
m.p. (oxalate): 115° C.
Oxalate
$^1$H-NMR (400 MHz, DMSO-d$_6$):
δ(ppm) 1.78(4H, m), 2.74(2H, m), 2.83(2H, t, J=8.4 Hz), 2.89(2H, m), 2.97(2H, m), 3.31(2H, t, J=8.4 Hz), 3.38(2H, m), 3.57(1H, m), 5.72(1H, s), 6.55(2H, m), 6.92(1H, d, J=7.2 Hz), 7.15(2H, m), 7.31(2H, m), 7.44(1H, dd, J=0.4, 2.0 Hz), 8.96(1H, d, J=2.0 Hz).
FAB-Mass: 438(MH+).

Example 196; Synthesis of 1-[1-(4-fluorophenethyl)-piperidin-4-yl]-6-[1-(5-thiazolyl)-1-hydroxymethyl]indoline

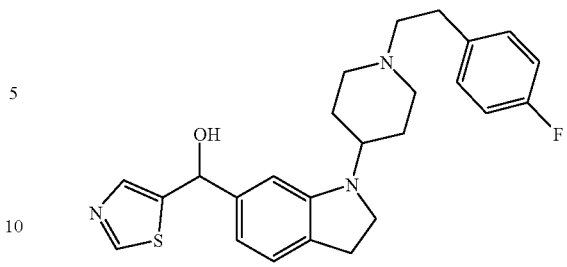

2-Trimethylsilylthiazole (0.134 g) and 1-[1-(4-fluorophenethyl)piperidin-4-yl]-6-formylindoline (0.2 g) were treated as in Example 193 to give the title compound (0.145 g) as a pale yellow oil (yield: 58.4%).

Next, oxalic acid (15 mg) was added thereto to give the oxalate of the title compound as an amorphous solid.
m.p. (oxalate): 112° C.
Oxalate
$^1$H-NMR (400 MHz, DMSO-d$_6$):
δ(ppm) 1.80(4H, m), 2.86(2H, t, J=8.4 Hz), 2.91(4H, m), 3.04(2H, m), 3.33(2H, t, J=8.4 Hz), 3.46(2H, m), 3.62(1H, m), 5.90(1H, s), 6.58(2H, m), 6.97(1H, d, J=7.2 Hz), 7.16(2H, m), 7.31(2H, m), 7.66(1H, s), 8.93(1H, s).
FAB-Mass: 438(MH+).

Example 197: Synthesis of 1-[1-(4-fluorophenethyl)-piperidin-4-yl]-6-[1-hydroxy-1-(pyrimidin-2-yl)methyl]indoline

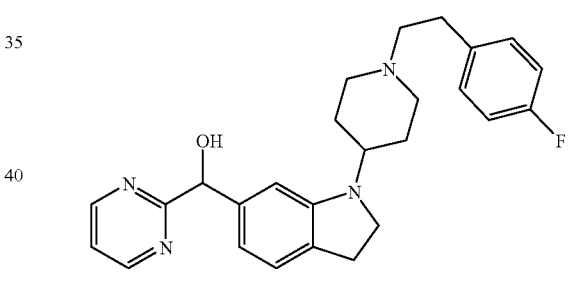

2-Tributylstannylpyridine (0.2 g) synthesized in accordance with the method described in J. Am. Chem. Soc. 1481 (1978). and 1-[1-(4-fluorophenethyl)piperidin-4-yl]-6-formylindoline (0.21 g) were treated in accordance with the method described in Tetrahedron Lett., 275 (1994). to give the title compound (0.038 g) as a yellow oil (yield: 16.2%).

Next, oxalic acid (8 mg) was added thereto to give the oxalate of the title compound as an amorphous solid.
m.p. (oxalate): 123° C.
Oxalate
$^1$H-NMR (400 MHz, DMSO-d$_6$):
δ(ppm) 1.84(4H, m), 2.82(2H, t, J=8.2 Hz), 2.98(2H, m), 3.04(2H, m), 3.19(2H, m), 3.29(2H, t, J=8.2 Hz), 3.58(2H, m), 3.68(1H, m), 5.65(1H, s), 6.60(1H, d, J=7.2 Hz), 6.65 (1H, s), 6.91(1H, d, J=7.2 Hz), 7.18(2H, m), 7.33(2H, m), 7.36(1H, t, J=4.8 Hz), 8.76(2H, d, J=4.8 Hz).
ESI-Mass: 433.3(MH+).

Fxample 198: Synthesis of 1-[1-(4-fluorophenethyl)-piperdin-4-yl]-6-[1-hydroxy-1-(pyrimidin-5-yl)methyl]indoline

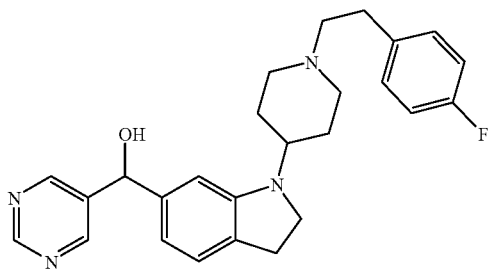

5-Bromopyridine (1.27 g) and 1-[1-(4-fluorophenethyl)piperidin-4-yl]-6-formylindoline (0.21 g) were treated in accordance with the method described in Synth. Commun., 253 (1994). to give the title compound (0.624 g) as a pale yellow oil (yield: 36.1%).

Next, oxalic acid (32 mg) was added to 0.156 g of the above product to give the oxalate of the title compound as a hygroscopic amorphous solid.

Oxalate $^1$H-NMR (400 MHz, DMSO-$d_6$):

δ(ppm) 1.78–1.92(4H, m), 2.84(2H, t, J=8.4 Hz), 2.95 (4H, m), 3.13(2H, m), 3.23(2H, t, J=8.2 Hz), 3.51(2H, m), 3.68(1H, m), 5.71(1H, s), 6.59(1H, d, J=7.0 Hz), 6.60(1H, s), 6.97(1H, d, J=7.0 Hz), 7.17(2H, m), 7.33(2H, m), 8.75 (2H, s), 9.04(1H, s).

FAB-Mass: 433(MH+).

Example 199: Synthesis of 1-[1-(4-fluorophenethyl)-piperdin-4-yl]-6-[1-hydroxy-1-(2-pyrrolyl)methyl]indoline

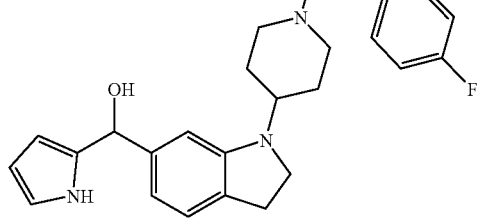

1-[1-(4-Fluorophenethyl)piperidin-4-yl]-6-bromoindoline (0.2 g) and 2-pyrrolecarboxyaldehyde (0.44 ml) were treated as in Example 193 to give the title compound (0.044 g) as a colorless oil (yield: 21.0%).

Free $^1$H-NMR (400 MHz, CDCl$_3$):

δ(ppm) 1.80(4H, m), 2.14(2H, m), 2.60(2H, m), 2.81(2H, m), 2.94(2H, t, J=8.4 Hz), 3.12(2H, br-d), 3.38(1H, m), 3.42(2H, t, J=8.4 Hz), 5.79(1H, s), 6.03(1H, m), 6.13(1H, m), 6.50(1H, d, J=1.2 Hz), 6.62 (1H, dd, J=1.2, 7.2 Hz), 6.71(1H, m), 6.97 (2H, m), 7.02(1H, d, J=7.2 Hz), 7.15(2H, m), 8.33(1H, m).

Fab-Mass: 420(MH+).

Example 200: Synthesis of 1-[1-(4-fluorophenethyl)-piperidin-4-yl]-6-N,N-dimethylaminomethylindoline

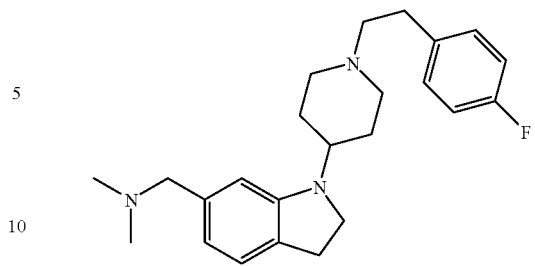

1-[1-(4-Fluorophenethyl)piperidin-4-yl]-6-aminomethylindoline (500 mg), formaldehyde (290 mg) and formic acid (180 mg) were treated as in Example 170 to give the hydrochloride (60 mg) of the title compound as a pale brown hygroscopic amorphous solid (yield: 9.3%).

$^1$H-NMR (400 MHz, DMSO-$d_6$):

δ(ppm) 1.94–2.03(2H, m), 2.04–2.17(2H, m), 2.66(3H, s), 2.67(3H, s), 2.92(2H, t, J=8 Hz), 3.00–3.12(4H, m), 3.26–3.35(2H, m), 3.39(2H, t, J=8 Hz), 3.58–3.70(3H, m), 4.12(2H, s), 6.65(1H, d, J=8 Hz), 6.93(1H, s), 7.08(1H, d, J=8 Hz), 7.16–7.21(2H, m), 7.32–7.36(2H, m), 10.52(1H, br-s), 10.62(1H, br-s).

FAB-Mass: 382(MH+).

Example 201-1: Synthesis of 1-[1-(4-fluorophenethyl)-piperdin-4-yl]-6-bromoindole

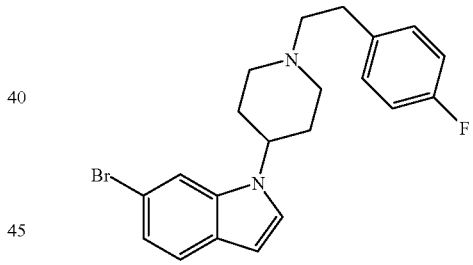

1-[1-(4-Fluorophenethyl)piperidin-4-yl]-6-bromoindoline (0.1 g) was dissolved in chloroform (27 ml). After adding manganese dioxide (2.75 g), the resultant mixture was heated under reflux for 4 hr. Then manganese dioxide was filtered off and the filtrate was concentrated under reduced pressure to give the title compound (0.480 g) as a yellow oil (yield: 96.5%).

$^1$H-NMR (400 MHz, CDCl$_3$)

δ(ppm) 2.09(4H, m) 2.25(2H, m), 2.50(2H, m), 2.82(2H, m) 3.17 (2H, br-d), 4.17 (1H, m), 6.49(1H, d, J=2.8 Hz), 6.99(2H, m) 7.18(2H, m), 7.20(1H, d, J=8.4 Hz), 7.21(1H, d, J=2.8 Hz), 7.48(1H, d, J=8.4 Hz), 7.53(1H, br-s).

Example 201-2: Synthesis of 1-[1-(4-fluorophenethyl)-piperidin-4-yl]-6-(4-fluorophenyl)indole

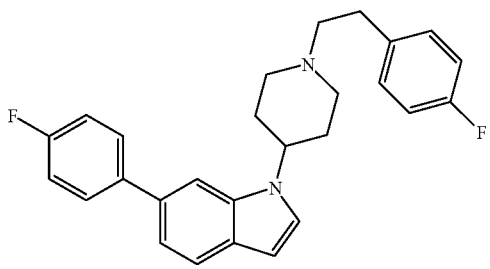

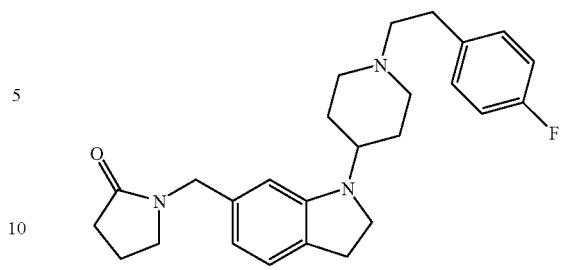

1-[1-(4-Fluorophenethyl)piperidin-4-yl]-6-bromoindole (0.1 g), 4-fluorophenylboronic acid (0.067 g), tetraquistriphenylphosphine palladium (0.014 g) and sodium carbonate (0.12 g) were dissolved in toluene (5 ml) and water (1.2 ml) and the resultant solution was stirred at 90° C. for 12 hr. After filtering the reaction mixture, ethyl acetate and a saturated aqueous solution of sodium bicarbonate were added to the filtrate and the layers were separated. The organic layer was washed with brine, dried over anhydrous magnesium sulfate and concentrated under reduced pressure. Then the residue was purified by silica gel column chromatography (hexane/ethyl acetate system) to give the title compound (0.075 g) as pale yellow crystals (yield: 71.6%).

$^{1}$H-NMR (400 MHz, CDCl$_{3}$)

δ(ppm) 2.19(4H, m), 2.42(2H, m), 2.75(2H, m), 2.89(2H, m) 3.27(2H, m), 4.33(1H, m), 6.51(1H, d, J=2.4 Hz), 6.98 (2H, m), 7.14(6H, m), 7.30(1H, dd, J=1.4, 8.0 Hz), 7.44(1H, s), 7.59(2H, m), 7.67(1H, d, J=8.0 Hz)

Example 201-3: Synthesis of 1-[1-(4-fluorophenethyl)-piperdin-4-yl]-6-(4-fluorophenyl)indoline

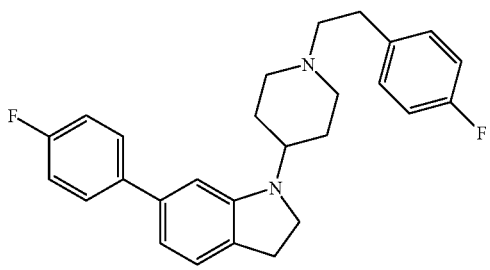

1-[1-(4-Fluorophenethyl)piperidin-4-yl]-6-(4-fluorophenyl)indole (0.075 g) was treated as in Production Example 56-2 to give the title compound (0.020 g) as a yellow oil (yield: 26.6%).

Next, oxalic acid was added thereto to give the oxalate of the title compound.

m.p. (oxalate): 130–145° C.

Oxalate $^{1}$H-NMR (400 MHz, DMSO-d$_{6}$)

δ(ppm) 1.93(2H, m), 2.08(2H, m), 2.93(2H, t, J=8.2 Hz), 3.10(4H, m), 3.25(2H, m), 3.39(2H, t, J=8.2 Hz), 3.64(2H, m), 3.89(1H, m), 6.77(1H, s), 6.82(1H, d, J=7.4 Hz), 7.00 (1H, d, J=7.4 Hz) 7.19 (2H, m), 7.25(2H, m), 7.34 (2H, m), 7.65 (2H, m)

FAB-Mass: 417(MH+).

Example 202: Synthesis of 1-[1-(4-fluorophenethyl)-piperdin-4-yl]-6-(2-pyrrolidon-1-yl)methylindoline 60% Sodium hydride (40 mg) was added to a solution of 2-pyrrolidone (85 mg) in dimethylformamide (10 ml) and the resultant mixture was stirred at 50° C. for 2 hr. Next, 1-[1-(4-fluorophenethyl)piperidin-4-yl]-6-chloromethylindoline (200 mg) was added thereto and the resultant mixture was stirred for additional 2 hr. Then ethyl acetate and water were added to the reaction solution and the layers were separated. The organic layer was washed with brine, dried over anhydrous magnesium sulfate and concentrated under reduced pressure. The residue was purified by silica gel column chromatography (ethyl acetate/ethanol system) followed by conversion into a hydrochloride in a conventional manner to give the hydrochloride (170 mg) of the title compound as a purple powder (yield: 69%).

m.p. (hydrochloride): 140–142° C.

$^{1}$H-NMR (400 MHz, DMSO-d$_{6}$):

δ(ppm) 1.81–1.92(4H, m), 1.94–2.08(2H, m), 2.25(2H, t, J=8 Hz), 2.81–2.87(2H, m), 3.00–3.35(10H, m), 3.57–3.74 (3H, m) 4.22(2H, s) 6.35(1H, s), 6.40(1H, d, J=8 Hz),6.96 (1H, d, J=8 Hz) 7.14–7.19(2H, m), 7.30–7.34(2H, m).

FAB-Mass: 422(MH+).

Example 203: Synthesis of 1-[1-(4-fluorophenethyl)-piperdin-4-yl]-6-(2-piperdin-1-yl)methylindoline

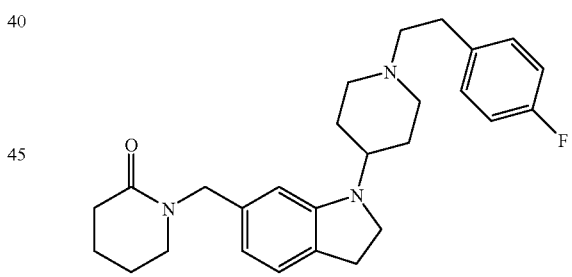

2-Piperidone (64 mg), 60% sodium hydride (26 mg) and 1-[1-(4-fluorophenethyl)piperidin-4-yl]-6-chloromethylindoline (200 mg) were treated as in Example 202 to give the hydrochloride (130 mg) of the title compound as a dark red hygroscopic amorphous solid (yield: 51%).

$^{1}$H-NMR (400 MHz, DMSO-d$_{6}$):

δ(ppm) 1.60–1.73(4H, m), 1.82–1.89(2H, m), 2.02–2.15 (2H, m), 2.26–2.32(2H, m), 2.87(2H, t, J=8 Hz), 3.04–3.16 (6H, m), 3.21–3.28(2H, m), 3.34(2H, t, J=8 Hz), 3.60–3.70 (2H, m), 4.40(2H, s), 6.41(1H, s), 6.45(1H, d, J=8 Hz), 6.98(1H, d, J=8 Hz), 7.16–7.21(2H, m), 7.32–7.36(2H, m).

FAB-Mass: 4$^{3}$6(MH+).

Example 204: Synthesis of 1-[1-(4-fluorophenethyl)-piperdin-4-yl]-6-(succinimido-1-yl)methylindoline

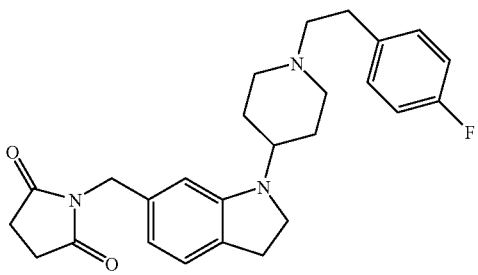

Succinimide (64 mg), 60% sodium hydride (26 mg) and 1-[1-(4-fluorophenethyl)piperidin-4-yl]-6-chloromethylindoline (200 mg) were treated as in Example 202 to give the hydrochloride (140 mg) of the title compound as a dark purple hygroscopic amorphous solid (yield: 55%).

$^1$H-NMR (400 MHz, DMSO-$d_6$)

δ(ppm) 1.84–2.05(4H, m), 2.67(4H, s), 2.85(2H, t, J=8 Hz) 3.02–3.20(4H, m), 3.24–3.35(4H, m), 3.60–3.75(3H, m), 4.43(2H, s), 6.41–6.44(2H, m), 6.94(1H, d, J=8 Hz), 7.17–7.22(2H, m), 7.32–7.37(2H, m).

FAB-Mass: 436(MH+).

Example 205: Synthesis of 1-[1-(4-fluorophenethyl)-piperdin-4-yl]-6-(glutarimido-1-yl)methylindoline

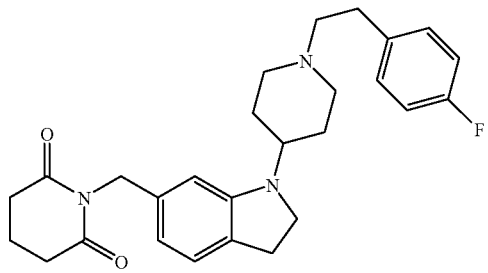

Glutarimide (73 mg), 60% sodium hydride (26 mg) and 1-[1-(4-fluorophenethyl)piperidin-4-yl]-6-chloromethylindoline (200 mg) were treated as in Example 202 to give the oxalate (240 mg) of the title compound as a pale brown powder (yield: 82%).

m.p. (oxalate): 109–111° C.

$^1$H-NMR (400 MHz, DMSO-d6):

δ(ppm) 1.80–1.91(6H, m), 2.65(4H, t, J=6 Hz), 2.83(2H, t, J=8 Hz), 2.92–3.04(4H, m), 3.12–3.22(2H, m), 3.31(2H, t, J=8 Hz), 3.49–3.71(3H, m), 4.72(2H, s), 6.35–6.37(2H, m), 6.91(1H, d, J=8 Hz), 7.15–7.20(2H, m), 7.31–7.35(2H, m).

FAB-Mass: 450(MH+).

Example 206: Synthesis of 1-[1-(4-fluorophenethyl)-piperdin-4-yl]-6-(2-imidazolidonyl)methylindoline

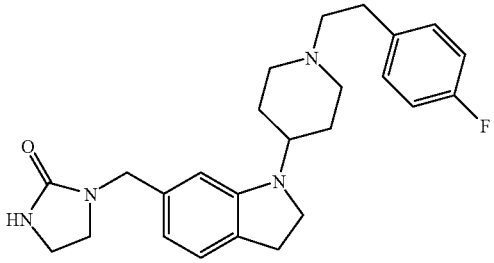

2-Imidazolidone (60 mg), 60% sodium hydride (28 mg) and 1-[1-(4-fluorophenethyl)piperidin-4-yl]-6-chloromethylindoline (260 mg) were treated as in Example 202 to give the oxalate (120 mg) of the title compound as white prisms (yield: 33%).

m.p. (oxalate): 184–186° C.

$^1$H-NMR (400 MHz, DMSO-$d_6$):

δ(ppm) 1.80–1.89 (4H, m), 2.86 (2H, t, J=8 Hz) 2.90–2.99 (4H, m), 3.08–3.24(6H, m), 3.33(2H, t, J=8 Hz), 3.47–3.55 (2H, m), 3.60–3.68(1H, m), 4.10(2H, s), 6.34–6.37(2H, m), 6.43(1H, d, J=8 Hz), 6.97 (1H, d, J=8 Hz), 7.15–7.19 (2H, m), 7.31–7.34 (2H, m)

FAB-Mass: 423(MH+).

Example 207: Synthesis of 1-[1-(4-fluorophenethyl)-piperdin-4-yl]-6-(2,4-imidazolidinedion-3-yl) methylindoline

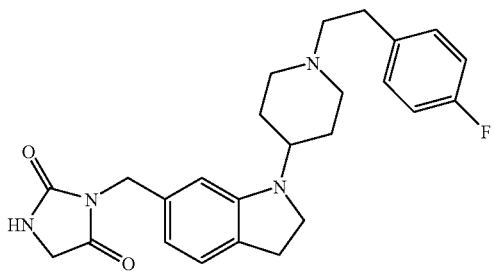

Hydantoin (130 mg), 60% sodium hydride (54 mg) and 1-[1-(4-fluorophenethyl)piperidin-4-yl]-6-chloromethylindoline (400 mg) were treated as in Example 202 to give the title compound (230 mg) as a white powder (yield: 49%).

m.p.: 191–193° C.

$^1$H-NMR (400 MHz, CDCl$_3$):

δ(ppm) 1.68–1.84 (4H, m), 2.11–2.21(2H, m) 2.56–2.63 (2H, m), 2.76–2.83(2H, m), 2.90(2H, t, J=8 Hz), 3.06–3.15 (2H, m), 3.39(2H, t, J=8 Hz), 3.35–3.46(1H, m), 3.92(2H, s), 4.57(2H, s), 5.90 (1H, s), 6.47 (1H, s), 6.65 (1H, d, J=8 Hz), 6.94–7.00(3H, m), 7.13–7.19(2H, m)

FAB-Mass: 436(MH+).

Example 208: Synthesis of 1-[1-(4-fluorophenethyl)-piperdin-4-yl]-6-(2-oxazolidon-3-yl)methylindoline

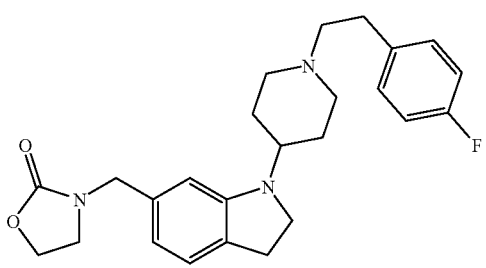

2-Oxazolidone (120 mg), 60% sodium hydride (54 mg) and 1-[1-(4-fluorophenethyl)piperidin-4-yl]-6-chloromethylindoline (400 mg) were treated as in Example 202 to give the hydrochloride (450 mg) of the title compound as a pale red hygroscopic amorphous solid (yield: 92%).

$^1$H-NMR (400 MHz, DMSO-$d_6$)

δ(ppm) 1.82–1.90(2H, m), 2.05–2.18(2H, m), 2.89(2H, t, J=8 Hz), 3.03–3.15(4H, m), 3.19–3.28(2H, m), 3.31–3.80 (7H, m) 4.21–4.29(4H, m), 6.44–6.50(2H, m), 7.01(1H, d, J=8 Hz), 7.16–7.21(2H, m), 7.32–7.36(2H, m).

FAB-Mass: 424(MH+).

Example 209: Synthesis of 1-[1-(4-fluorophenethyl)-piperdin-4-yl]-6-(2,4-thiazolidinedion-3-yl)methylindoline

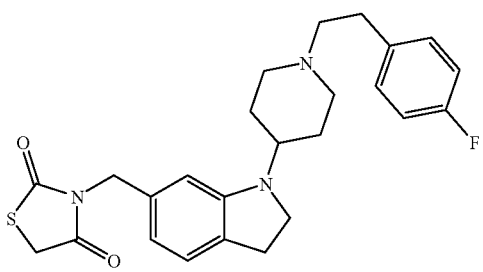

2,4-Thiazolidinedione (110 mg), 60% sodium hydride (40 mg) and 1-[1-(4-fluorophenethyl)piperidin-4-yl]-6-chloromethylindoline (300 mg) were treated as in Example 202 to give the hydrochloride (120 mg) of the title compound as a red hygroscopic amorphous solid (yield: 30%).

$^1$H-NMR (400 MHz, DMSO-$d_6$):

δ(ppm) 1.83–2.06(4H, m), 2.86(2H, t, J=8 Hz), 3.10–3.19 (4H, m), 3.24–3.35(4H, m), 3.60–3.76(3H, m), 4.27(2H, s), 4.56(2H, s), 6.43–6.45(2H, m), 6.97(1H, d, J=8 Hz), 7.17–7.22(2H, m) 7.32–7.36(2H, m)

FAB-Mass: 454(MH+).

Example 210: Synthesis of 1-[1-(4-fluorophenethyl)-piperdin-4-yl]-6-(pyrrol-1-yl)methylindoline

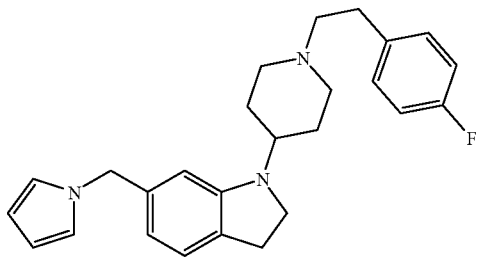

Pyrrole (50 mg), 60% sodium hydride (30 mg) and 1-[1-(4-fluorophenethyl)piperidin-4-yl]-6-chloromethylindoline (250 mg) were treated as in Example 202 to give the hydrochloride (240 mg) of the title compound as a brown powder (yield: 82%).

m.p. (hydrochloride): 162° C. (decomp.).

$^1$H-NMR (400 MHz, DMSO-d):

δ(ppm) 1.80–1.87 (2H m), 2.06–2.19(2H, m), 2.84(2H, t, J=8 Hz), 2.99–3.12 (4H, m), 3.18–3.25(2H, m), 3.33 (2H, t, J=8 Hz), 3.56–3.70(3H, m), 4.92(2H, s), 5.94–5.96(2H, m), 6.41(1H, d, J=8 Hz), 6.52(1H, s), 6.75–6.77 (2H, m), 6.95 (1H, d, J=8 Hz) 7.14–7.19(2H, m), 7.29–7.34(2H, m), 11.06(1H, br-s).

FAB-Mass: 405(MH+).

Example 211: Synthesis of 1-[1-(4-fluorophenethyl)-piperdin-4-yl]-6-(imidazol-1-yl)methylindoline

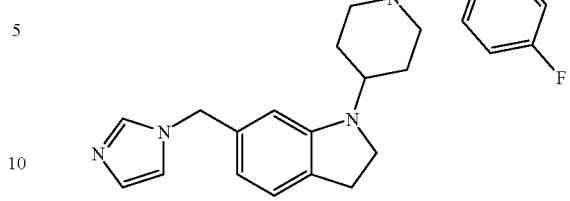

Imidazole (50 mg), 60% sodium hydride (30 mg) and 1-[1-(4-fluorophenethylpiperidin-4-yl]-6-chloromethylindoline (250 mg) were treated as in Example 202 to give the hydrochloride (260 mg) of the title compound as a red hygroscopic amorphous solid (yield: 88%).

$^1$H-NMR (400 MHz, DMSO-$d_6$):

δ(ppm) 1.81–1.90(2H, m), 2.15–2.28(2H, m), 2.86(2H, t, J=8 Hz), 2.99–3.14 (4H, m), 3.21–3.29 (2H, m), 3. 36 (2H, t, J=8 Hz) 3.58–3.68 (3H, m), 5.25 (2H, s), 6.59 (1H, d, J=8 Hz), 6. 81 (1H, s), 7.01 (1H, d, J=8 Hz), 7.14–7.19 (2H, m), 7.30–7.34 (2H, m),7.66(1H, s), 7.82 (1H, s), 11.07 (1H, br-s) FAB-Mass: 405(MH+).

Example 212: Synthesis of 1-[1-(4-fluorophenethyl)-piperdin-4-yl]-6-(1,2,3-triazol-1-yl)methylindoline and 1-[1-(4-fluorophenethyl)piperdin-4-yl]-6-(1,2,3-triazol-2-yl)methylindoline

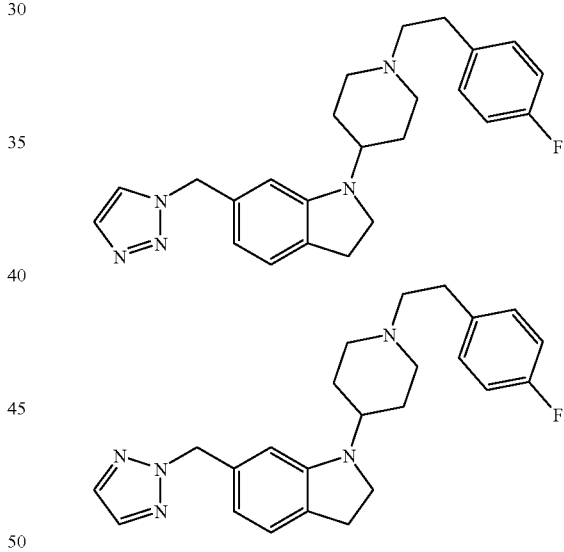

1,2,3-Triazole (51 mg), 60% sodium hydride (30 mg) and 1-[1-(4-fluorophenethyl)piperidin-4-yl]-6-chloromethylindoline (250 mg) were treated as in Example 202 to give the hydrochloride (180 mg) of highly polar 1-[1-(4-fluorophenethyl)piperidin-4-yl]-6-(1,2,3-triazol-1-yl) methylindoline as a dark red hygroscopic amorphous solid (yield: 61%), and also the hydrochloride (40 mg) of lowly polar 1-[1-(4-fluorophenethyl)piperidin-4yl]-6-(1,2,3-triazol-2-yl)methylindoline as a pale red hygroscopic amorphous solid (yield: 14%).

(1) 1-[1-(4-Fluorophenethyl)piperdin-4-yl]-6-(1,2,3-triazol-1-yl)methylindoline (highly polar)

$^1$H-NMR (400 MHz, DMSO-$d_6$):

δ(ppm) 1.80–1.88(2H, m), 2.05–2.18(2H, m), 2.87(2H, t, J=8 Hz), 3.02–3.14(4H, m), 3.21–3.30(2H, m),3.34(2H, t, J=8 Hz) 3.60–3.75(3H, m), 5.46(2H, s), 6.51(1H, d, J=8 Hz), 6.57(1H, s), 7.00(1H, d, J=8 Hz), 7.16–7.21(2H, m), 7.32–7.40(2H, m), 7.73(1H, s), 8.17(1H, S), 10.88(1H, br-s).
FAB-Mass: 406(MH+).
(2) 1-1[-(4-Fluorophenethyl)piperdin-4-yl]-6-(1,2,3-triazol-2-yl)methylindoline (lowly polar)
¹H-NMR (400 MHz, DMSO-d₆):
δ(ppm) 1.81–1.90(2H, m), 1.94–2.10(2H, m), 2.86(2H, t, J=8 Hz), 3.01–3.18(4H, m), 3.22–3.30(2H, m), 3.33(2H, t, J=8 Hz) 3.60–3.75(3H, m), 5.49(2H, s), 6.45(1H, d, J=8 Hz), 6.48(1H, s) 6.98(1H, d, J=8 Hz), 7.17–7.22(2H, m), 7.32–7.36(2H, m), 7.78(2H, s).
FAB-Mass: 406(MH+)
Example 213: Synthesis of 1-[1-(4-fluorophenethyl)-piperdin-4-yl]-6-(1,2,4-triazol -2-yl)methylindoline

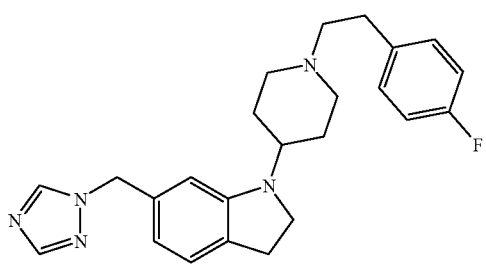

1,2,4-Triazole (51 mg), 60% sodium hydride (30 mg) and 1-[1-(4-fluorophenethylpiperidin-4-yl]-6-chloromethylindoline (250 mg) were treated as in Example 202 to give the hydrochloride (210 mg) of the title compound as a brown hygroscopic amorphous substance (yield: 71%).
¹H-NMR (400 MHz, DMSO-d₆):
δ(ppm) 1.81–1.90 (2H, m), 1.95–2.14 (2H, m), 2.87 (2H, t, J=8 Hz), 3.01–3.15(4H, m), 3.21–3.32(2H, m), 3.34(2H, t, J=8 Hz) 3.60–3.74 (3H, m), 5.27 (2H, s), 6.48 (1H, d, J=8 Hz), 6.50–6.59 (1H, m), 6.99(1H, d, J=8 Hz), 7.17–7.22(2H, m), 7.32–7.40(2H, m) 7.97–8.00(1H, m), 8.64–8.72(1H, m).
FAB-Mass: 406(MH+).
Example 214: Synthesis of 1-[1-(4-fluorophenethyl)-piperdin-4-yl]-6-(2-tiazolyl)methylindoline

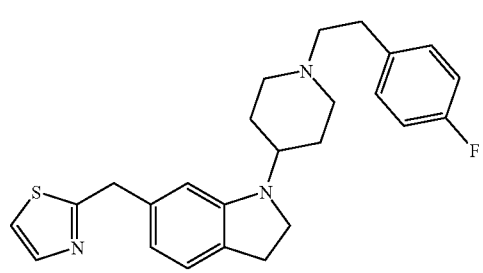

A mixture of 1-[1-(4-fluorophenethyl)piperidin-4-yl]-6-thiocarbamoylmethylindoline (150 mg), 40% chloroacetaldehyde (300 mg), potassium carbonate (79 mg) and dimethoxyethane (32 ml) was stirred overnight. Then the liquid reaction mixture was filtered and the filtrate was concentrated under reduced pressure. To the residue were added trifluoroacetic anhydride (240 mg), pyridine (210 mg) and dimethoxyethane (4 ml) and the resultant mixture was stirred for 30 min. Then the reaction solution was concentrated under reduced pressure and diluted with a saturated aqueous solution of sodium bicarbonate and ethyl acetate. The organic layer was washed with a saturated aqueous solution of sodium chloride and dried over anhydrous magnesium sulfate. The residue was purified by NH-silica gel column chromatography (hexane/ethyl acetate system) followed by conversion into a hydrochloride in a conventional manner to give the hydrochloride (40 mg) of the title compound as a brown hygroscopic amorphous solid (yield: 23%).
¹H-NMR (400 MHz, DMSO-d₆):
δ(ppm) 1.82–1.90(2H, m), 2.03–2.15(2H, m), 2.88(2H, t, J=8 Hz), 3.03–3.15(4H, m), 3.20–3.28(2H, m), 3.35(2H, t, J=8 Hz), 3.58–3.66(2H, m), 3.68–3.80(1H, m), 4.23(2H, s), 6.55(1H, d, J=8 Hz), 6.57 (1H, s), 6.99 (1H, d, J=8 Hz), 7.16–7.21 (2H, m), 7.31–7.35 (2H, m), 7.60 (1H, s), 7.75 (1H, s) 10.82 (1H, br-s).
FAB-Mass: 422(MH+).
Example 215: Syntesis of 1-[1-(4-fluorophenethyl)-piperdin-4-yl]-3-(4-methoxybenzyl)indoline

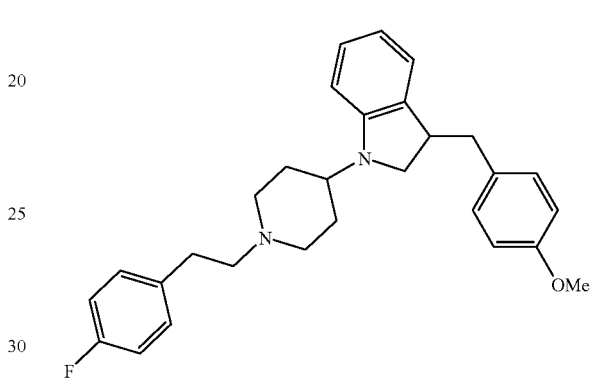

3-(4-Methoxybenzyl)indoline (0.2 g) and 1-(4-fluorophenethyl)-4-piperidone (0.262 g) were treated as in Example 16 to give the title compound (0.343 g) as a colorless oil (yield: 94.9%).
Next, oxalic acid (36 mg) was added thereto to give the oxalate (0.101 g) of the title compound as colorless crystals.
m.p. (oxalate): 187° C.
Oxalate
¹H-NMR (400 MHz, DMSO-d₆):
δ(ppm) 1.80(4H, m), 2.63(1H, dd, J=9.0, 13.6 Hz), 2.96 (4H, m), 3.15 (4H, m), 3.27 (1H, t, J=8.6 Hz), 3.43 (1H, m), 3.52 (2H, m), 3.67(1H, m), 3.74(3H, s), 6.52(1H, d, J=7.6 Hz), 6.55(1H, t, J=7.6 Hz), 6.87 (2H, d, J=8.4 Hz), 6.92 (1H, d, J=7.6 Hz) 7.01(1H, t, J=7.6 Hz), 7.16(2H, d, J=8.4 Hz), 7.18(2H, d, J=8.4 Hz), 7.32(2H, dd, J=6.0, 8.4 Hz).
ESI-Mass: 445.3(MH+).
Example 216: Synthesis of 1-[1-(4-fluorophenethyl)-piperdin-4-yl]-3-methylindoline

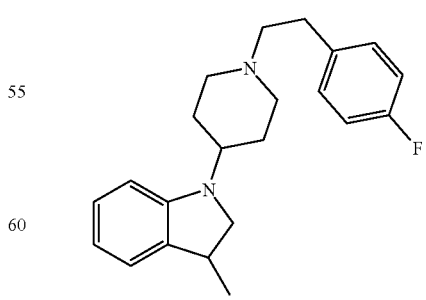

3-Methylindoline (0.2 g) and 1-(4-fluorophenethyl)-4-piperidone (0.50 g) were treated as in Example 16 to give the title compound (0.384 g) as a pale yellow oil (yield: 7.0.7%)

Next, hydrochloric acid was added thereto to give a salt followed by recrystallization from ethanol. Thus the hydrochloride (0.314 g) of the title compound was obtained as colorless crystals.
m.p. (hydrochloride): 232° C.
Hydrochloride
$^1$H-NMR (400 MHz, DMSO-$d_6$):
δ(ppm) 1.25(3H, d, J=6.8 Hz), 1.89(2H, m), 2.33(2H, m), 2.88(1H, t, J=8.0 Hz), 3.10(4H, m), 3.23(3H, m), 3.55(1H, t, J=8.0 Hz), 3.61 (2H, m), 3.78 (1H, m), 6.67 (2H, m), 7.06 (2H, m) 7.18 (2H, t, J=8.8 Hz), 7.33 (2H, m).
ESI-Mass: 339.2(MH+).
Example 217: 1-[1-(4-fluorophenethyl)piperdin-4-yl]-5-chloro-6-aminoindoline

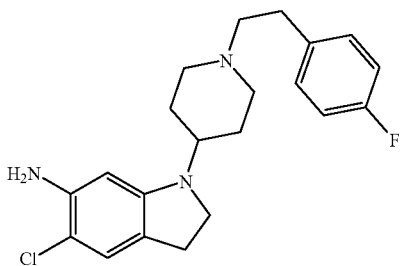

N-Chlorosuccinimide (0.24 g) was added at room temperature to a solution of 1-[1-(4-fluorophenethyl)piperidin-4-yl]-6-aminoindoline (0.5 g) in acetonitrile (50 ml) and the resultant mixture was stirred for 1 hr. Then the reaction mixture was filtered and concentrated under reduced pressure. Next, a 5 N aqueous solution of sodium hydroxide and ethyl acetate were added thereto and the layers were separated. The organic layer was washed with brine and dried over anhydrous magnesium sulfate. The resulting residue was purified by silica gel column chromatography (methylene chloride/ethanol system) to give the title compound (0.19 g) as a brown oil (yield: 34%).
$^1$H-NMR (400 MHz, CDCl$_3$)
δ(ppm) 1.69–1.83 (4H, m), 2.03–2.11 (2H, m), 2.51–2.60 (2H, m), 2.75–2.82(2H, m), 2.83(2H, t, J=8 Hz), 3.08–3.15 (2H, m), 3.20–3.32(1H, m), 3.38(2H, t, J=8 Hz), 3.85(2H, br-s), 5.89(1H, s), 6.89(1H, s), 6.92–7.00(2H, m), 7.11–7.21 (2H, m).
Example 218: Synthesis of 1-[1-(4-fluorophenethyl)-piperdin-4yl]-5-chloro-6-methanesulfonylaminoindoline

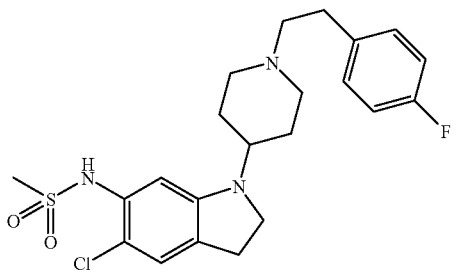

1-[1-(4-Fluorophenethyl)piperidin-4-yl]-5-chloro-6-aminoindoline (0.19 g) and methanesulfonyl chloride (0.058 g) were treated as in Example 116 to give the oxalate (160 mg) of the title compound as a pale red powder (yield: 58%).
m.p. (oxalate): 193–196° C.
$^1$H-NMR (400 MHz, DMSO-$d_6$):
δ(ppm) 1.73–1.83(4H, m), 2.81–3.00(6H, m), 2.91(3H, s), 3.09–3.15(2H, m), 3.37(2H, t, J=8 Hz), 3.42–3.56(2H, m), 3.58–3.65(1H, m), 6.49(1H, s), 7.10(1H, s), 7.12–7.20(2H, m), 7.23–7.31(2H, m)
FAB-Mass: 452(MH+).
Example 219: Synthesis of 1-[1-(4-fluorophenethyl)-piperdin-4-yl]-5-chloro-6-methoxyindoline

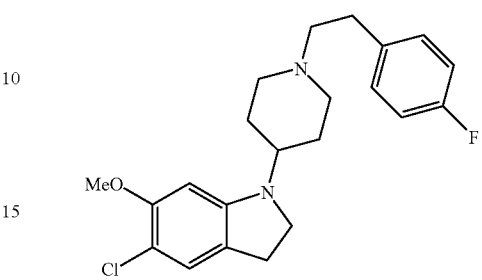

N-Chlorosuccinimide (0.15 g) was added at room temperature to a solution of 1-[1-(4-fluorophenethyl)piperidin-4-yl]-6-methoxyindoline (0.39 g) in methylene chloride (5 ml) and the resultant mixture was stirred for 20 min. Then a 5 N aqueous solution of sodium hydroxide and ethyl acetate were added to the reaction solution and the layers were separated. The organic layer was washed with brine and dried over anhydrous magnesium sulfate. The resulting residue was purified by silica gel column chromatography (methylene chloride/ethanol system) followed by conversion into a hydrochloride to give the hydrochloride (0.10 g) of the title compound as a pale red powder (yield: 21%).
m.p. (hydrochloride) 135–138° C.
$^1$H-NMR (400 MHz, DMSO-$d_6$):
δ(ppm) 1.83–2.08(4H, m),2.82(2H, t, J=8 Hz),3.00–3.12 (4H, m), 3.21–3.29(2H, m), 3.34(2H, t, J=8 Hz), 3.60–3.67 (2H, m), 3.72–3.84(1H, m), 3.79(3H, s), 6.34(1H, s), 6.99 (1H, s), 7.15–7.20(2H, m), 7.30–7.34(2H, m).
FAB-Mass: 399(MH+).
Example 220: Synthesis of 1-[1-(1-(2,4-diffluorophenethyl)-piperdin-4-yl]-6-aminodoline

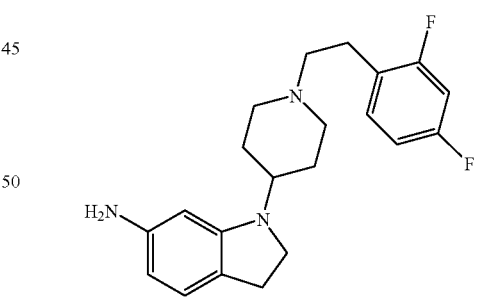

1-(Piperidin-4-yl)-6-nitroindoline (3.5 g) was treated as in Example 2 or Example 110 to give the title compound (2.4 g) as a pale yellow powder (yield: 40%).
$^1$H-NMR (400 MHz, CDCl$_3$):
δ(ppm) 1.69–1.88(4H, m), 2.09–2.15(2H, m), 2.52–2.60 (2H, m), 2.78–2.89(2H, m), 3.07–3.11(2H, m), 3.14–3.21 (1H, m), 3.22(2H, t, J=8 Hz), 3.50(2H, br-s), 5.81(1H, s), 5.98(1H, d, J=8 Hz), 6.72–6.83(3H, m), 7.10–7.20(1H, m).
Example 221: Synthesis of 1-[1-(2,4-difluorophenethyl)-piperdin-4-yl]-6-methanesulfonylaminoindoline

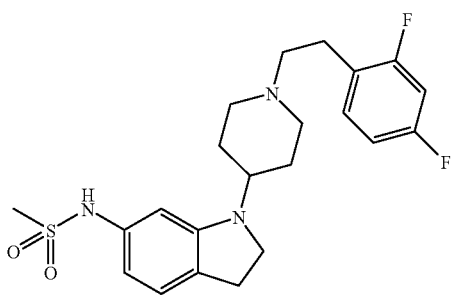

1-[1-(2,4-Difluorophenethyl)piperidin-4-yl]-6-aminoindoline (0.4 g) and methanesulfonyl chloride (0.51 g) were treated as in Example 116 to give the hydrochloride (240 mg) of the title compound as a pale yellow hygroscopic amorphous solid (yield: 45%).

¹H-NMR (400 MHz, DMSO-d6):

δ(ppm) 1.83–1.89(2H, m), 1.99–2.10(2H, m), 2.84(2H, t, J=8 Hz), 2.89(3H, s), 3.05–3.27(6H, m), 3.33(2H, t, J=8 Hz), 3.35–3.43(1H, m), 3.59–3.68(2H, m), 6.38–6.41(2H, m), 6.94(1H, d, J=8 Hz), 7.06–7.11(1H, m), 7.22–7.28(1H, m), 7.39–7.45(1H, m), 9.34(1H, br-s), 10.76(1H, br-s).

FAB-Mass: 436(MH+)

Example 222: Synthesis of 1-[1-(2,4-difluorophenethyl)-piperdin-4-yl]-6-acetamidoindoline

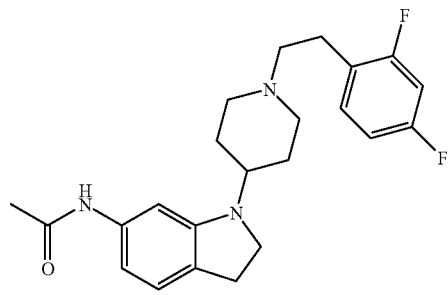

1-[1-(2,4-Difluorophenethyl)piperidin-4-yl]-6-aminoindoline (0.6 g) and acetic anhydride (5 ml) were treated as in Example 133 to give the hydrochloride (640 mg) of the title compound as a white powder (yield: 87%).

¹H-NMR (400 MHz, DMSO-d₆):

δ(ppm) 1.83–1.98 (4H, m), 1.99 (3H, s), 2.81 (2H, t, J=8 Hz) 3.00–3.13 (4H, m), 3.22–3.33 (4H, m), 3.55–3.69 (3H, m), 6.58 (1H, d, J=8 Hz), 6.90 (1H, d, J=8 Hz), 6.95 (1H, s), 7.07–7.12 (1H, m) 7.24–7.30(1H, m) 7.39–7.45(1H, m), 9.69(1H, br-s).

FAB-Mass: 400(MH+).

Example 223: Synthesis of 1-[1-(2,4-difluorophenethyl)-piperdin-4-yl]-6-bromoindoline

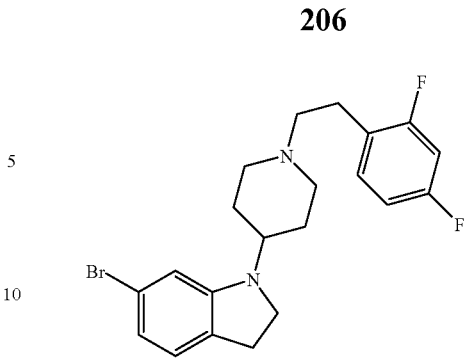

1-(Piperidin-4-yl)-6-bromoindoline (3.0 g) and 2,4-difluorophenethyl bromide (3.1 g) were treated as in Example 2 to give the title compound (2.7 g) as a white powder (yield: 60%).

¹H-NMR (400 MHz, CDCl₃):

δ(ppm) 1.70–1.85(4H, m), 2.10–2.21(2H, m), 2.51–2.63 (2H, m), 2.79–2.89(2H, m), 2.90(2H, t, J=8 Hz), 3.08–3.17 (2H, m), 3.28–3.37(1H, m), 3.41(2H, t, J=8 Hz), 6.48(1H, s), 6.69(1H, d, J=8 Hz), 6.72–6.84(2H, m), 6.90(1H, d, J=8 Hz), 7.11–7.20(1H, m)

Example 224: Synthesis of 1-[1-(2,4-difluorophenethyl)-piperdin-4-yl]-6-acetamidomethylindoline

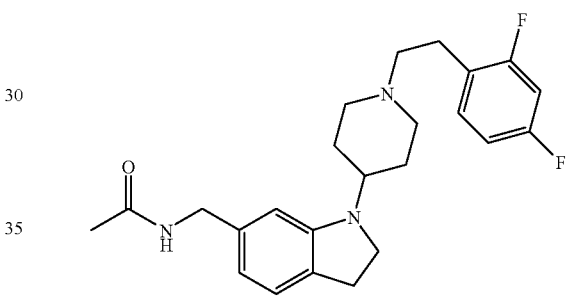

1-[1-(2,4-Difluorophenethyl)piperidin-4-yl]-6-bromoindoline (3.5 g) was treated as in Examples 130 to 133 to give the hydrochloride (0.26 g) of the title compound as a gray powder (yield: 7.3%).

m.p. (hydrochloride): 179° C. (decomp.)

¹H-NMR (400 MHz, DMSO-d₆):

δ(ppm) 1.80(3H, s), 1.85–2.05(4H, m), 2.90(2H, t, J=8 Hz) 3.03–3.28(4H, m), 3.21–3.39(4H, m), 3.64–3.78(3H, m), 4.30(2H, s), 6.51–6.60(2H, m), 6.98–7.08(2H, m), 7.11–7.19(1H, m), 7.32–7.40(1H, m), 8.25(1H, br-s).

FAB-Mass: 414(MH+).

Example 225: Synthesis of 1-[1-(2,4-difluorophenethyl)-piperdin-4-yl]-6-carbamoylmethylindoline

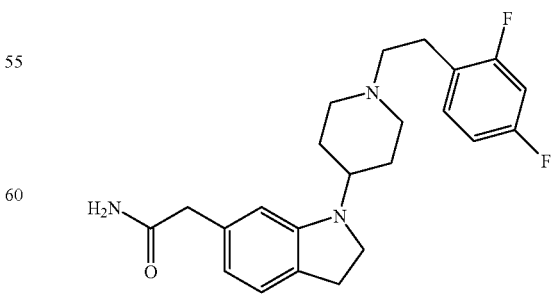

1-[1-(2,4-Difluorophenethyl)piperidin-4-yl]-6-bromoindoline (1.8 g) was treated as in Examples 136, 142, 145 and 147 to give the hydrochloride (0.12 g) of the title compound as a pale green powder (yield: 6.6%).
m.p. (hydrochloride): 241–243° C.
¹H-NMR (400 MHz, DMSO-d₆):
δ(ppm) 1.85–2.05(4H, m), 2.89 (2H, t, J=8 Hz),3.03–3.18 (4H, m), 3.21–3.43(4H, m), 3.49(2H, s), 3.64–3.77(3H, m), 6.52–6.59 (2H, m), 6.98–7.10 (4H, m), 7.29–7.35 (1H, m), 7.59 (1H, br-s).
FAB-Mass: 400(MH+).
Fxample 226: Synthesis of 1-{1-[3-(4-fluorophenyl)-propyl] piperdin-4-yl}-6-acetamidomethylindoline

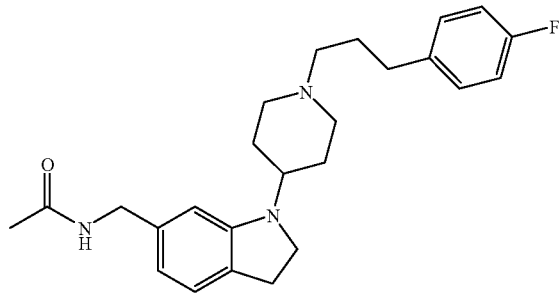

1-(Piperidin-4-yl)-6-acetamidomethylindoline (250 mg) and 3-(4-fluorophenyl) propyl bromide (24 0 mg) were treated as in Example 2 to give the title compound (220 mg) as pale yellow prisms (yield: 58%).
m.p.: 128–130° C.
¹H-NMR (400 MHz, CDCl₃):
δ(ppm) 1.73–1.99(6H, m), 2.00(3H, s), 2.02–2.20(2H, m), 2.39–2.67(4H, m), 2.92(2H, t, J=8 Hz), 3.02–3.20(2H, m) 3.34–3.44(1H, m), 3.41(2H, t, J=8 Hz), 4.32(2H, d, J=6 Hz), 5.71 (1H, br-s), 6.33 (1H, s) 6.45 (1H, d, J=8 Hz), 6.94–7.00 (3H, m), 7.12–7.16(2H, m)
FAB-Mass: 410(MH+).
Example 227: Synthesis of 1-{1-[4-4-fluorophenyl)butyl]-piperdin-4-yl}-6-acetamidomethylindoline

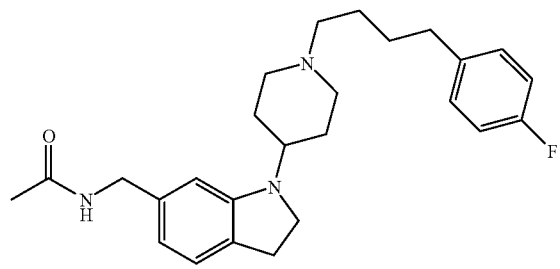

1-(Piperidin-4-yl)-6-acetamidomethylindoline (250 mg) and 4-(4-fluorophenyl)butyl bromide (250 mg) were treated as in Example 2 to give the title compound (280 mg) as white needles (yield: 70%).
m.p.: 119–121° C.
¹H-NMR (400 MHz, CDCl₃):
δ(ppm) 1.50–1.68(4H, m), 1.70–1.84(4H, m) 1.99–2.12 (2H, m), 2.00(3H, s), 2.34–2.45(2H, m), 2.57–2.64(2H, m), 2.91(2H, t, J=8 Hz), 3.00–3.10(2H, m), 3.32–3.44(1H, m), 3.40(2H, t, J=8 Hz), 4.32(2H, d, J=6 Hz), 5.70(1H, br-s), 6.31(1H, s), 6.59 (1H, d, J=8 Hz), 6.93–7.00(3H, m), 7.10–7.14(2H, m).
FAB-Mass: 424(MH+).
Example 228: Synthesis of 1-[1-(4-methoxyphenethyl)-piperdin-4-yl]-6-methoxyindoline

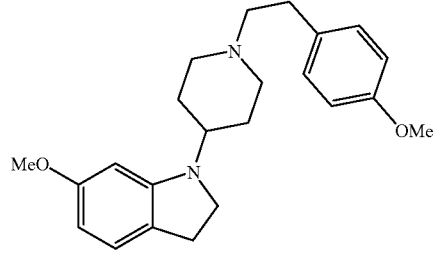

1-(Piperidin-4-yl)-6-methoxyindoline (320 mg) and 4-methoxyphenethyl bromide (360 mg) were treated as in Example 2 to give the oxalate (220 mg) of the title compound as a white powder (yield: 34%).
m.p. (oxalate): 165–167° C.
¹H-NMR (400 MHz, DMSO-d₆):
δ(ppm) 1.74–1.88(4H, m), 2.79(2H, t, J=8 Hz), 2.84–2.90 (4H, m), 3.03–3.12(2H, m), 3.30(2H, t, J=8 Hz), 3.47–3.69 (3H, m), 3.67 (3H, s) 3.71 (3H, s), 6.07–6.15 (2H, m), 6.84–6.93 (3H, m) 7.16–7.21(2H, m).
FAB-Mass: 367(MH+).
Example 229: Synthesis of 1-[1-(4-methoxyphenethyl)-piperdin-4-yl]-6-fluoroindoline

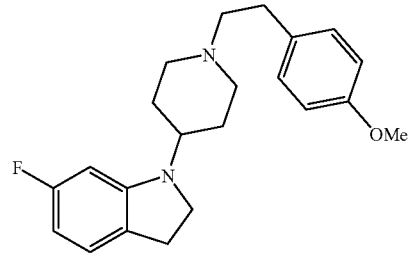

1-(Piperidin-4-yl)-6-fluoroindoline (250 mg) and 4-methoxyphenethyl bromide (290 mg) were treated as in Example 2 to give the hydrochloride (120 mg) of the title compound as a white powder (yield: 27%).
m.p. (hydrochloride): 212–214° C.
¹H-NMR (400 MHz, DMSO-d₆):
δ(ppm) 1.83–1.92 (4H, m), 2.83 (2H, t, J=8 Hz), 2.90–2.97 (2H, m), 3.00–3.10(2H, m), 3.17–3.26(2H, m), 3.38(2H, t, J=8 Hz), 3.60–3.73(3H, m), 3.72(3H, s), 6.24–6.29(1H, m), 6.36–6.40(1H, m), 6.87–6.97(3H, m), 7.17–7.21(2H, m).
FAB-Mass: 355(MH+).
Example 230: Synthesis of 1-[1-(4-sulfamoylphenethyl)-piperdin-4-yl]-6-methoxyindoline

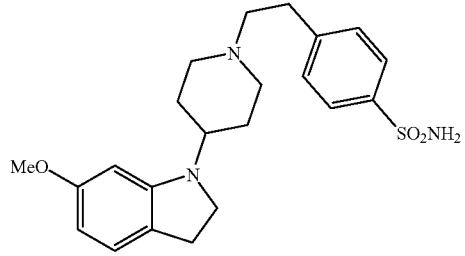

1-(Piperidin-4-yl)-6-methoxyindoline (350 mg) and 4-sulfamoylphenethyl bromide (340 mg) were treated as in Example 2 to give the title compound (70 mg) as a brown powder (yield: 13%).

m.p.: 179–182° C.

$^1$H-NMR (400 MHz, CDCL$_3$):

δ(ppm) 1.71–1.90(4H, m), 2.11–2.29(2H, m), 2.61–2.70 (2H, m), 2.82–2.98(4H, m), 3.10–3.21(2H, m), 3.31–3.41 (3H, m), 3.78(3H, s), 4.98(2H, br-s), 6.00(1H, s), 6.12(1H, d, J=8 Hz), 6.94(1H, d, J=8 Hz), 7.35(1H, d, J=8 Hz), 7.85(1H, d, J=8 Hz).

FAB-Mass: 416(MH+).

Example 231: Synthesis of 1-[1-(4-fluorophenoxypropyl)-piperdin-4-yl]-6-bromoindoline

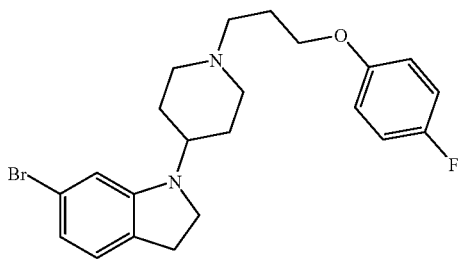

1-(Piperidin-4-yl)-6-bromoindoline (1.6 g) and 4-fluorophenoxypropyl bromide (1.6 g) were treated as in Example 2 to give the title compound (2.2 g) as a white powder (yield: 90%).

$^1$H-NMR (400 MHz, CDCl$_3$):

δ(ppm) 1.51–1.85(2H, m), 1.87–1.89(2H, m), 1.92–2.19 (4H, m), 2.52–2.62(2H, m), 2.90(2H, t, J=8 Hz), 3.03–3.14 (2H, m), 3.28–3.33(1H, m), 3.42(2H, t, J=8 Hz), 3.97(2H, t, J=6 Hz), 6.45(1H, s), 6.68(1H, d, J=8 Hz), 6.80–6.89(3H, m), 6.92–7.00(2H, m).

Example 232: Synthesis of 1-[1-(4-fluorophenoxypropyl)-piperdin-4-yl]-6-acetamidomethylindoline

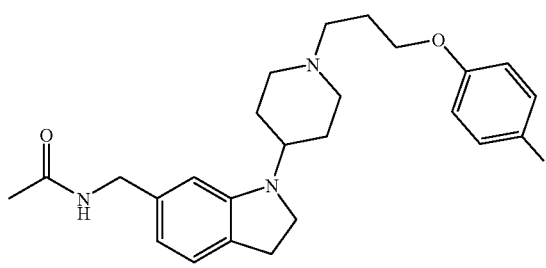

1-[1-(4-Fluorophenoxypropyl)piperidin-4-yl]-6-bromoindoline (1.2 g) was treated as in Examples 130, 131 and 133 to give the oxalate (46 mg) of the title compound as a brown hygroscopic amorphous solid (yield: 3.2%).

$^1$H-NMR (400 MHz, DMSO-d$_6$):

δ(ppm) 1.77–1.93(4H, m), 2.03–2.13(2H, m), 2.08(3H, s), 2.84(2H, t, J=8 Hz), 2.85–2.99(2H, m), 3.04–3.12(2H, m), 3.31(2H, t, J=8 Hz), 3.44–3.53(2H, m), 3.60–3.69(1H, m), 4.03(2H, t, J=6 Hz), 4.13(2H, d, J=6 Hz), 6.39(1H, s), 6.45(1H, d, J=8 Hz), 6.93–6.98(3H, m), 7.11–7.16(2H, m), 8.21(1H, t, J=6 Hz).

FAB-Mass: 426(MH+).

Example 233: Synthesis of 1-{1-[2-(6-benzothiazolyl)ethyl]-piperdin-4-yl}-6-methoxyindoline

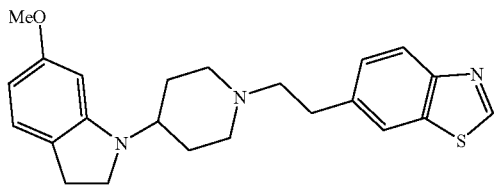

6-(2-Bromoethyl)benzothiazole (0.108 g) and 1-(piperidin-4-yl)-6-methoxyindoline (0.105 g) were treated as in Example 2 to give the title compound (0.145 g) as a yellow oil (yield: 81.9%).

Next, oxalic acid (37 mg) was added thereto to give a salt followed by recrystallization from ethanol. Thus the oxalate (0.097 g) of the title compound was obtained.

m.p.: 188° C.

Oxalate $^1$H-NMR (400 MHz, DMSO-d$_6$):

δ(ppm) 1.87(4H, m), 2.82(2H, t, J=7.6 Hz), 3.21(2H, br-t), 3.18(2H, m), 3.28(2H, m), 3.34(2H, t, J=7.6 Hz), 3.58(2H, m), 3.70(3H, s), 3.72(1H, m), 6.12(1H, d, J=7.6 Hz), 6.15(1H, s) 6.91(1H, d, J=7.6 Hz), 7.50(1H, d, J=8.4 Hz), 8.08(1H, d, J=8.4 Hz), 8.10(1H, s), 9.39(1H, s).

ESI-Mass: 394.2(MH+).

Example 234: Synthesis of 1-[1-(4-fluorophenethyl)-piperdin-4-yl]thiazolo[5,4-f]indoline

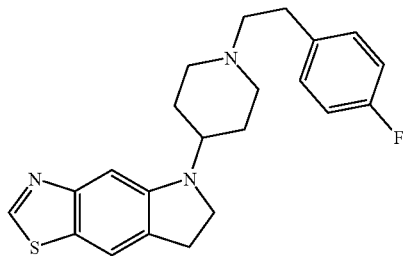

Thiazolo[5,4-f]indoline (0.2 g), 1-(4-fluorophenethyl)-4-piperidone (0.6 g), acetic acid (0.66 g) and triacetoxylated sodium borohydride (0.79 g) were treated as in Example 101 to give the hydrochloride (0.34 g) of the title compound as a yellow powder (yield: 71%).

m.p. (hydrochloride): 165° C. (decomp.).

$^1$H-NMR (400 MHz, DMSO-d$_6$):

δ(ppm) 1.93–2.06 (4H, m), 2.98–3.06 (4H, m), 3.08–3.19 (2H, m), 3.24–3.32 (2H, m), 3.43 (2H, t, J=8 Hz), 3.60–3.70 (2H, m), 3.81–3.90 (1H, m), 7.16–7.20 (3H, m), 7.31–7.36 (2H, m), 7.70 (1H, S), 9.14 (1H, s).

FAB-Mass: 382(MH+)

Example 235: Synthesis of 1-[1-(4-fluorophenethyl)-piperdin-4-yl]-6-aminothiazolo[5,4]indoline

211

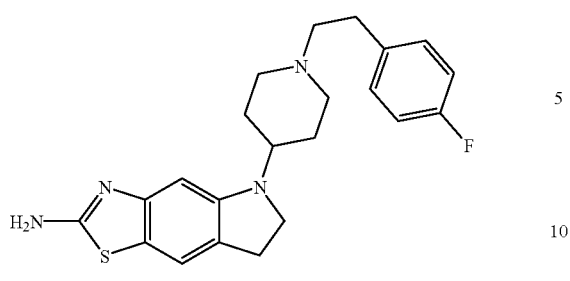

Bromine (0.22 ml) was added dropwise into a solution of 1-[1-(4-fluorophenethyl)piperidin-4-yl]-6-aminoindoline (1.2 g) and potassium thiocyanate (1.0 g) in acetic acid (12 ml) and the resultant mixture was heated at 100° C. for 1 hr. Under ice cooling, a 5 N aqueous solution of sodium hydroxide and chloroform were added to the reaction solution and the layers were separated. The organic layer was washed with brine and dried over anhydrous magnesium sulfate. Then the residue was purified by silica gel column chromatography (methylene chloride/ethanol system) to give the title compound (0.20 g) as a brown powder (yield: 14%).
m.p.: 173° C. (decomp.).
$^1$H-NMR (400 MHz, CDCl$_3$):
  δ(ppm) 1.68–1.90(2H, m), 2.07–2.16(2H, m), 2.55–2.61 (2H, m), 2.75–2.82(2H, m), 2.97(2H, t, J=8 Hz), 3.07–3.14 (2H, m), 3.36–3.45(1H, m), 3.41(2H, t, J=8 Hz), 5.25(2H, br-s), 6.62(1H, s), 6.94–6.99(2H, m), 7.14–7.19(3H, m).
FAB-Mass: 397(MH+).
Example 236: Synthesis of 1-[1-(4-fluorophenethyl)-piperdin-4-yl]-7-hydroxy-(4a,7a)-cyclohexanoindoline and 1-[1-(4-fluorophenethyl)piperidin-4-yl]-4-hydroxy-(3b,6a)-cyclohexanoindoline and oxalates thereof

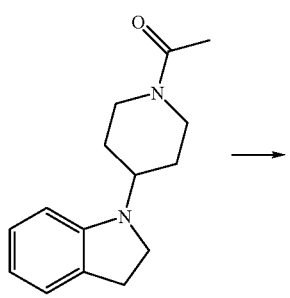

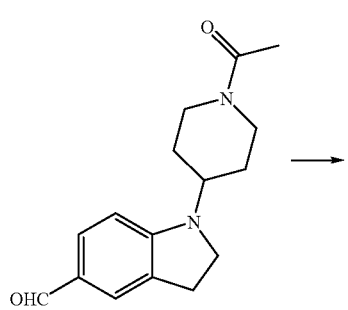

212
-continued

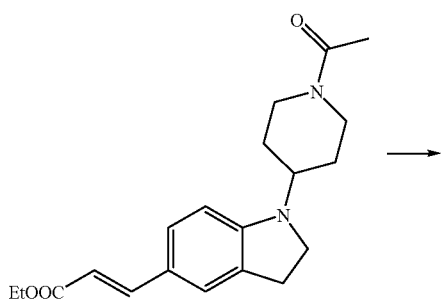

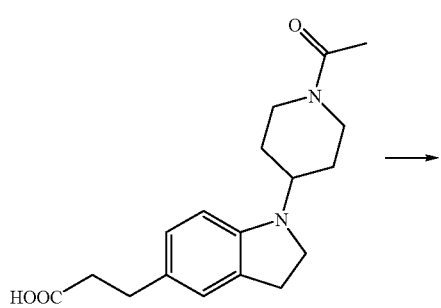

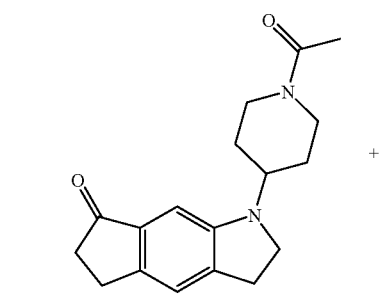

+

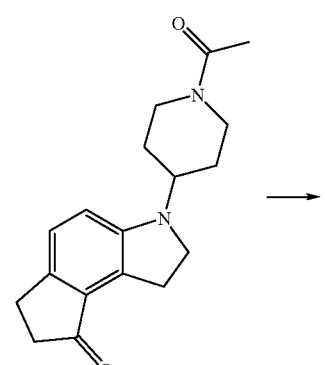

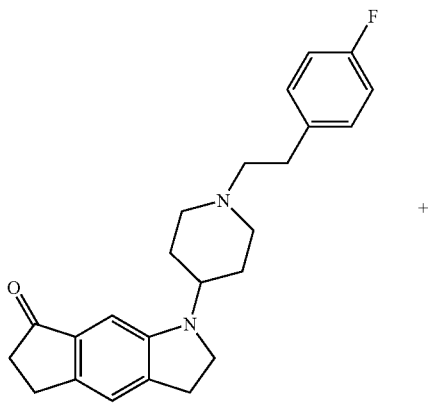

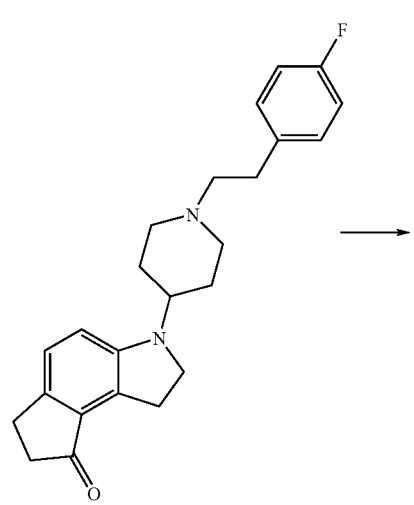

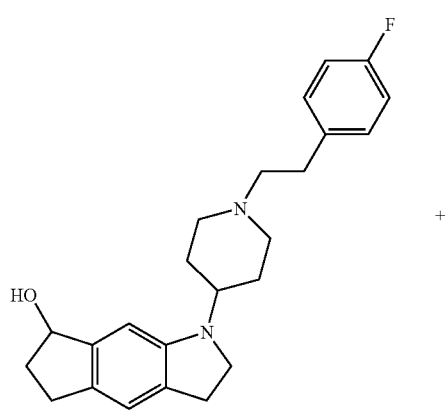

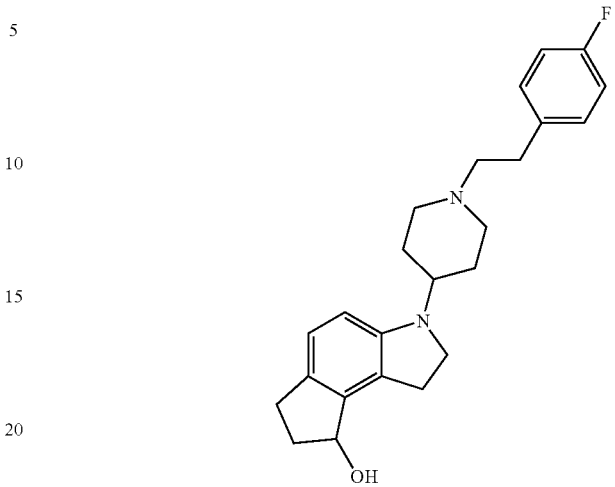

Under ice cooling, triethyl phosphonoacetate (2.24 g) was added dropwise into a suspension of 60% sodium hydride (0.4 g) in THF (30 ml). After the completion of the evolution of hydrogen, a solution of 1-(1-acetylpiperidin-4-yl)-indoline-7-carboxaldehyde (2.4 g) in THF (20 ml) was added dropwise into the reaction solution and the resultant mixture was reacted at room temperature for 3 hr. Then the reaction solution was partitioned between ethyl acetate and water followed by washing with water, drying and concentration under reduced pressure.

The resulting residue was dissolved in ethanol (50 ml). After adding 10% palladium carbon (0.3 g) thereto, hydrogenation was carried out under atmospheric pressure. After the completion of the reaction, the reaction solution was filtered through celite and washed with ethanol. A 5 N aqueous solution (5 ml) of sodium hydroxide was added to the filtrate and the resultant mixture was reacted at 50° C. for 1 hr. After cooling the reaction solution, a 5 N aqueous solution (5 ml) of hydrochloric acid was added thereto followed by concentration under reduced pressure. Then methylene chloride (100 ml) was added to the residue and the resultant mixture was filtered through celite. The filtrate was concentrated.

To the resulting crude carboxylic acid (1.8 g) thus obtained was added polyphosphoric acid (30 g) and the resultant mixture was reacted at 120° C. for 2 hr. Next, the reaction solution was cooled to 50° C. and water (200 ml) was added thereto followed by extraction with ethyl acetate. The ethyl acetate layer was washed successively with water, a 10% aqueous solution of potassium carbonate, water and brine, dried and concentrated under reduced pressure. The residue was purified by silica gel column chromatography (ethyl acetate/n-hexane system) to give a mixture (0.31 g) of cyclopentanone derivatives as a colorless oil.

This mixture was dissolved in ethanol (15 ml). After adding an 8 N aqueous solution (5 ml) of sodium hydroxide thereto, the resultant mixture was heated under reflux for 6 hr. Then the reaction solution was concentrated under reduced pressure and the residue was partitioned between ethyl acetate and an aqueous solution of ammonium chloride. The ethyl acetate layer was washed with water, dried and concentrated under reduced pressure. The resulting residue was purified by silica gel short column chromatography (methylene chloride/methanol system) to give a pale brown oil (0.21 g).

This oily mixture (0.20 g), 4-fluorophenethyl bromide (0.18 g) and potassium carbonate (0.43 g) were suspended in DMF (15 ml) and then reacted at 60° C. for 12 hr. The reaction solution was partitioned between ethyl acetate and water. The ethyl acetate layer was washed with water and brine, dried and concentrated under reduced pressure. The resulting residue was purified by silica gel column chromatography (methylene chloride/methanol system) to give a mixture (0.12 g) of ketone derivatives as a colorless oil.

This mixture was dissolved in methanol and sodium borohydride was added thereto at room temperature. After reacting for 30 min, the solvent was evaporated under reduced pressure. Then the residue was partitioned between ethyl acetate and water. The ethyl acetate layer was washed with water, dried and concentrated under reduced pressure. The resulting residue was purified by silica gel column chromatography (methylene chloride/methanol system) to give 1-[1-(4-fluorophenethyl)piperidin-4-yl]-7-hydroxy-(4a,7a)-cyclohexanoindoline (0.04 g) and 1-[1-(4-fluorophenethyl)-piperidin-4-yl]-4-hydroxy-(3b,6a)-cyclohexanoindoline (0.03 g) each as a colorless oil. These compounds were each dissolved in methanol and reacted with oxalic acid. After removing the solvent, ether was added to the residue. The resulting precipitate was collected by filtration and dried. Thus the oxalates of the title compounds were obtained each as an amorphous solid.

(1) 1-[1-(4-Fluorophenethyl)piperidin-4-yl]-7-hydroxy-(4a,7a)-cyclohexanoindoline Oxalate $^1$H-NMR (400 MHz, CD$_3$OD):

δ(ppm) 1.87(1H, m), 2.04(4H, m), 2.39(1H, m), 2.63(1H, m), 2.86(3H, m), 3.02–3.25(4H, m), 3.30–3.40(4H, m), 3.70–3.85(3H, m), 5.06(1H, br-t), 6.56(1H, s), 6.92(1H, s), 7.05(2H, t, J=8.0 Hz), 7.31(2H, br).

FAB-Mass: 381(MH+).

(2) 1-[1-(4-Fluorophenethyl)piperidin-4-yl]-4-hydroxy-(3b,6a)-cyclohexanoindoline Oxalate $^1$H-NMR (400 MHz, CD$_3$OD):

δ(ppm) 1.87–2.06 (5H, m), 2.37 (1H, m), 2.65 (1H, m), 2.93 (2H, m), 3.02–3.23(5H, m), 3.30–3.40(4H, m), 3.70–3.84(3H, m), 5.15(1H, br-t), 6.48(1H, d, J=8.0 Hz), 6.92(1H, d, J=8.0 Hz), 7.05(2H, t, J=8.0 Hz), 7.32(2H, br-t).

FAB-Mass: 381(MH+).

Example 237: Synthesis of 1-(1-methylpiperdin-4-yl)-6-(4-fluorobenzenesulfonylamino)indoline

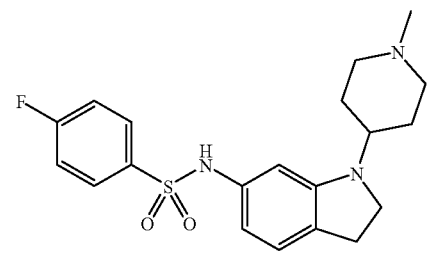

6-(4-Fluorobenzenesulfonylamino) indoline (0.3 g), 1-methyl-4-piperidone (0.17 g), acetic acid (0.36 g) and triacetoxylated sodium borohydride (0.41 g) were treated as in Example 101 to give the hydrochloride (0.08 g) of the title compound as a pale yellow powder (yield: 19%).

m.p. (hydrochloride): 170–172° C.

$^1$H-NMR (400 MHz, DMSO-d$_6$):

δ(ppm) 1.63–1.71(2H, m), 1.80–1.94(2H, m), 2.71(3H, s), 2.76(2H, t, J=8 Hz), 3.03–3.14(2H, m), 3.24(2H, t, J=8 Hz) 3.40–3.56 (3H, m) 6.18 (1H, d, J=8 Hz), 6.22 (1H, s), 6.81 (1H, d, J=8 Hz), 7.35–7.39(2H, m), 7.69–7.78(2H, m).

FAB-Mass: 390(MH+).

Example 238: Synthesis of 1-(1-ethylpiperdin-4-yl)6-(4-fluorobenzenesulfonylamino)indoline

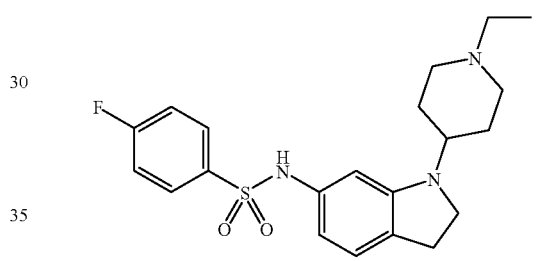

6-(4-Fluorobenzenesulfonylamino)indoline (0.3 g), 1-ethyl-4-piperidone (0.19 g), acetic acid (0.36 g) and tri-acetoxylated sodium borohydride (0.41 g) were treated as in Example 101 to give the hydrochloride (0.34 g) of the title compound as a pale yellow hygroscopic amorphous solid (yield: 77%).

$^1$H-NMR (400 MHz, DMSO-d$_6$):

δ(ppm) 1.22(3H, t, J=7 Hz),1.62–1.71(2H, m),1.80–1.99 (2H, m), 2.76(2H, t, J=8 Hz), 2.95–3.19(4H, m), 3.22(2H, t, J=8 Hz), 3.48–3.80(3H, m), 6.16(1H, d, J=8 Hz), 6.23(1H, s), 6.81(1H, d, J=8 Hz), 7.31–7.40(2H, m), 7.70–7.80(2H, m).

FAB-Mass: 390(MH+).

Example 239: Synthesis of 1-(1-ethylpiperdinyl)-4-(4-fluorophenyl)indoline

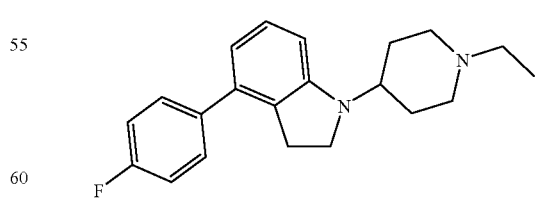

4-(4-Fluorophenyl)indoline (250 mg), 1-ethyl-4-piperidone (230 mg), acetic acid (430 mg) and triacetoxylated sodium borohydride (510 mg) were treated as in Example 1 to give the hydrochloride (200 mg) of the title compound as a white powder (yield: 46%).

m.p. (hydrochloride): 270° C. (decomp.).
¹H-NMR (400 MHz, DMSO-d₆):
δ(ppm) 1.23 (3H, t, J=7 Hz), 1.83–2.04 (4H, m),2.91–3.12 (6H, m), 3.24–3.34(2H, m), 3.50–3.57(2H, m), 3.70–3.80 (1H, m), 6.54(1H, d, J=8 Hz), 6.60(1H, d, J=8 Hz), 7.09(1H, t, J=8 Hz), 7.21–7.26(2H, m), 7.45–7.48(2H, m), 9.89(1H, br-s).
FAB-Mass: 325(MH+).
Example 240: Synthesis of 1-(1-ehtylpiperdin-4-yl)-3-(4-fluorophenyl)indoline

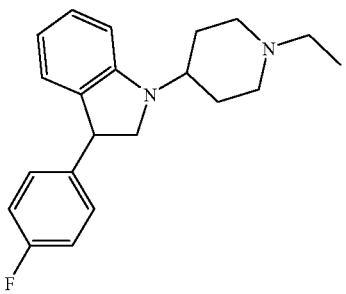

3-(4-Fluorophenyl)indoline (0.184 g) was treated as in Example 16 to give the title compound (0.102 g) as a yellow oil (yield: 38.0%).

Next, oxalic acid (14 mg) was added thereto to give a salt followed by recrystallization from ethanol. Thus the oxalate (0.063 g) of the title compound was obtained.
m.p. (oxalate): 216° C.
Oxalate
¹H-NMR (400 MHz, DMSO-d₆):
δ(ppm) 1.20(3H, t, J=6.8 Hz), 1.90(4H, m), 2.96(2H, m), 3.04(2H, m), 3.23(1H, t, J=8.2 Hz), 3.48(2H, m), 3.75(2H, m), 4.42(1H, t, J=8.2 Hz), 6.58(1H, t, J=7.6 Hz), 6.64(1H, d, J=7.6 Hz), 6.78(1H, d, J=7.6 Hz), 7.06(1H, t, J=7.6 Hz), 7.14(2H, t, J=8.4 Hz), 7.28(1H, dd, J=5.6, 8.4 Hz).
FAB-Mass: 325(MH+).
Example 241: Synthesis of 1-(1-ethylpiperdin-4-yl)-3-(4-methoxyphenyl)indoline

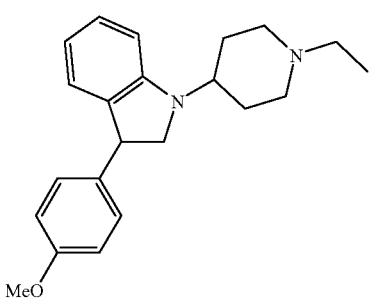

Methoxymethyltriphenylphosphonium bromide (7.113 g) and 4-anisaldehyde (2.6 ml) were treated as in Production Example 41-1 to give a pale yellow, oil (2.235 g). Then this product was dissolved in isopropanol (25 ml) and 2 N hydrochloric acid (25 ml). After adding phenylhydrazine (1.0 ml), the resultant mixture was heated under reflux for 1 hr. Then the reaction solution was allowed to cool and concentrated under reduced pressure. Next, ethyl acetate was added thereto and the layers were separated. The organic layer was washed with saturated aqueous solution of sodium bicarbonate and brine, dried over anhydrous sodium sulfate and concentrated under reduced pressure. The resulting residue was purified by silica gel column chromatography (hexane/ethyl acetate system) to give a yellow oil (1.249 g) The resulting product was treated as in Production Example 54 to give a yellow oil (0.534 g). Subsequently, this product and 1-ethyl-4-piperidone were treated as in Example 16 to give the title compound (0.307 g) as a yellow oil (yield: 4.4%).

Next, oxalic acid (41 mg) was added thereto to give a salt followed by recrystallization from ethanol. Thus the oxalate (0.151 g) of the title compound was obtained as pale yellow crystals.
m.p. (oxalate): 143° C.
Oxalate
¹H-NMR (400 MHz, DMSO-d₆):
δ(ppm) 1.20(3H, t, J=7.2 Hz), 1.89(4H, m), 2.95(2H, m), 3.04(2H, m), 3.19(1H, t, J=8.4 Hz), 3.48(2H, m), 3.72(3H, s), 3.75(2H, m), 4.34(1H, t, J=8.4 Hz), 6.57(1H, t, J=7.6 Hz), 6.62(1H, d, J=7.6 Hz), 6.75(1H, d, J=7.6 Hz), 6.88(2H, d, J=8.8 Hz), 7.05(1H, t, J=7.6 Hz), 7 16(2H, t, J=8.8 Hz).
ESI-Mass: 337.1(MH+).
Example 242: Synthesis of 1-(1-ethyl)piperdin-4-yl)-3-(4-methoxybenzyl)indoline

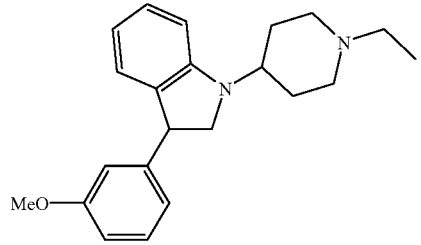

3-(4-Methoxybenzyl)indoline (0.332 g) and 1-ethyl-4-piperidone (0.28 ml) were treated as in Example 16 to give the title compound (0.380 g) as a pale yellow oil (yield: 78.0%).

Next, oxalic acid (49 mg) was added thereto to give a salt followed by recrystallization from acetone. Thus the oxalate (0.150 g) of the title compound was obtained.
m.p. (oxalate): 136° C.
Oxalate
¹H-NMR (400 MHz, DMSO-d₆):
δ(ppm) 1.18(3H, t, J=7.6 Hz), 1.80(4H, m), 2.63(1H, dd, J=9.2, 13.6 Hz), 2.89 (2H, m), 2.99 (4H, m), 3.23 (1H, t, J=8.6 Hz) 3.44(3H, m), 3.67(1H, m), 3.73(3H, s), 6.51(1H, d, J=7.6 Hz), 6.55(1H, t, J=7.6 Hz), 6.87(2H, d, J=8.4 Hz), 6.92(1H, d, J=7.6 Hz), 7.01(1H, t, J=7.6 Hz), 7.15(2H, d, J=8.4 Hz).
ESI-Mass: 351.3(MH+).
Example 243-1: Synthesis of 1-(4-pyridylmethyl)-3-(4-methoxybenzyl)indoline

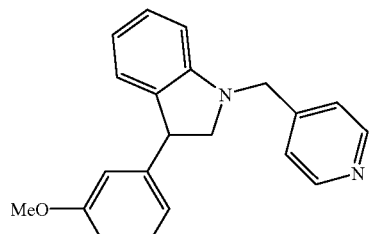

3-(4-Methoxybenzyl)indoline (2.0 g) and 4-pyridinecarboxyaldehyde (1.2 ml) were treated as in Example 16 to give the title compound (1.474 g) as apaleyellowoil (yield: 53.44%).

¹H-NMR (400 MHz, CDCl₃):
δ(ppm) 2.27(1H, d, J=8.8, 14.0 Hz), 3.08(2H, m), 3.36 (1H, t, J=8.8 Hz), 3.55(1H, m), 3.79(3H, s), 4.20(2H, d, J=7.6 Hz), 7.00(1H, d, J=7.6 Hz), 7.06(3H, m), 7.20(2H, m), 8.53(2H, dd, J=1.6, 4.8 Hz).

Example 243-2: Synthesis of 1-[(1-ethylpiperdin-3-en-4-yl)methyl]-3-(4-methoxybenzyl)indoline

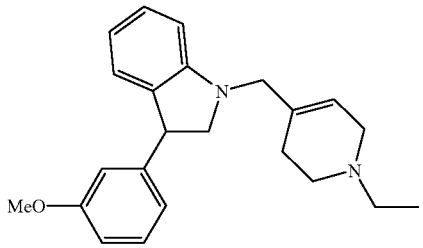

1-(4-Pyridylmethyl)-3-(4-methoxybenzyl)indoline (0.7 g) was dissolved in acetonitrile (10 ml). After adding ethyl iodide (0.29 ml), the mixture was heated in a sealed tube at 70 to 90° C. for 9 hr. After allowing to cool, the reaction solution was concentrated under reduced pressure. Then ethanol (20 ml) and sodium borohydride (0.40 g) were added to the residue followed by stirring at room temperature for 1 hr. The reaction solution was concentrated under reduced pressure, diluted with ethyl acetate (200 ml), washed with brine, dried over anhydrous magnesium sulfate and concentrated under reduced pressure. The resulting residue was purified by silica gel column chromatography (hexane/ethyl acetate system) to give the title compound (0.115 g) as a pale yellow oil (yield: 15.0%).

¹H-NMR (400 MHz, CDCl₃):
δ(ppm) 1.12(3H, t, J=7.2 Hz), 2.14(2H, m), 2.48(2H, q, J=7.2 Hz), 2.56 (2H, m), 2.73 (1H, dd, J=9.2, 14.4 Hz), 2.96 (2H, br-d), 3.01(2H, m), 3.40(2H, t, J=9.2 Hz), 3.53(2H, br-s), 3.79 (3H, s),5.58 (1H, br-s), 6.47 (1H, d, J=9.1 Hz), 6.61 (1H, d, J=9.1 Hz), 6.83 (2H, m), 6.83 (2H, m), 6.91 (1H, d, J=8.0 Hz), 6.47(1H, d, J=9.1 Hz), 7.07(3H, m).

Example 243-1: Synthesis of 1-[(1-ehtyl)piperdin-4-yl)methyl]-3-(4-methoxybenzyl)indoline

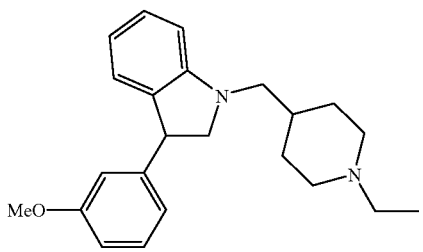

1-[(1-Ethylpiperidin-3-en-4-yl)methyl]-3-(4-methoxybenzyl)indoline (0.115 g) was dissolved in ethanol (3.2 ml). After adding a palladium carbon catalyst thereto, catalytic reduction was carried out under atmospheric pressure at room temperature for 54 hr. Then the catalyst was filtered off and the filtrate was concentrated under reduced pressure. The resulting residue was purified by NH-silica gel column chromatography (hexane/ethyl acetate system) to give the title compound (0.053 g) as a pale yellow oil (yield: 45.8%).

Next, oxalic acid (6 mg) was added thereto to give a salt followed by recrystallization from a solvent mixture of ethyl acetate with isopropyl ether. Thus the oxalate (0.313 g) of the title compound was obtained as colorless crystals.

m.p. (oxalate): 78° C.
Oxalate
¹H-NMR (400 MHz, DMSO-d₆):
δ(ppm) 1.17(3H, t, J=7.2 Hz), 1.38(2H, m), 1.82(2H, br-t), 2.64(1H, dd, J=8.6, 14.0 Hz), 2.75(2H, br-t), 2.83(1H, m), 2.97(4H, m), 3.29(1H, t, J=8.6 Hz), 3.34(2H, br-d), 3.45(1H, m), 3.73(3H, s), 6.48(1H, d, J=7.6 Hz), 6.55(1H, t, J=7.6 Hz), 6.86(2H, d, J=8.4 Hz), 6.94(1H, d, J=7.6 Hz), 6.99(1H, t, J=7.6 Hz), 7.14(2H, d, J=8.4 Hz).
FAB-Mass: 365(MH+).

Example 244: Synthesis of 1-(1-wthylpiperdin-4-yl)-3-(4-fluorobenzyl)indoline

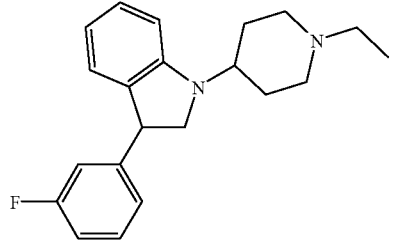

3-(4-Fluorobenzyl)indoline (1.163 g) and 1-ethyl-4-piperidone (1.0 ml) were treated as in Example 16 to give the title compound (1.614 g) as a yellow oil (yield: 93.7%).

Next, oxalic acid (21 mg) was added thereto to give a salt followed by recrystallization from ethanol. Thus the oxalate of the title compound was obtained.

m.p. (oxalate): 203° C.
Oxalate
¹H-NMR (400 MHz, DMSO-d6):
δ(ppm) 1.20(3H, t, J=7.2 Hz), 1.82(4H, m), 2.70(1H, dd, J=8.8, 13.2 Hz), 2.90–3.07(6H, m), 3.26(1H, t, J=8.8 Hz), 3.41–3.50(3H, m), 3.68(1H, m), 6.54(2H, m), 6.91(1H, d, J=7.6 Hz), 7.02(1H, t, J=7.6 Hz), 7.12(2H, t, J=8.8 Hz), 7.27(1H, dd, J=5.6, 8.8 Hz).
ESI-Mass: 339.2(MH+).

Example 245: Synthesis of 1-(1-ethylpiperidin-4-yl)-3-(3-pyridylmethyl)indoline

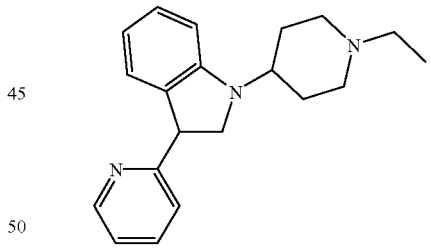

3-(3-Pyridylmethyl)indoline (0.253 g) was treated as in Example 16 to give the title compound (0.233 g) as a yellow oil (yield: 71.0%).

Next, oxalic acid (65 mg) was added thereto to give a salt followed by recrystallization from ethanol. Thus the oxalate (0.191 g) of the title compound was obtained (yield: 45.5%).

m.p. (oxalate): 149° C.
Oxalate
¹H-NMR (400 MHz, DMSO-d₆):
δ(ppm) 1.20(3H, t, J=7.6 Hz), 1.83(4H, m), 2.76(1H, dd, J=8.8, 11.6 Hz), 3.04(6H, m), 3.29(1H, t, J=8.8 Hz), 3.50 (3H, m), 3.68(1H, m), 6.52(1H, d, J=7.6 Hz), 6.56(1H, t, J=7.6 Hz), 6.92(1H, d, J=7.6 Hz), 7.02(1H, t, J=7.6 Hz), 7.32(1H, dd, J=4.8, 8.0 Hz), 7.65(1H, dt, J=2.0, 8.0 Hz), 8.43(2H, m).

Example 246: Synthesis of 1-(1-ethylpiperidin-4-yl)-3-(3-methoxyphenethyl)indoline

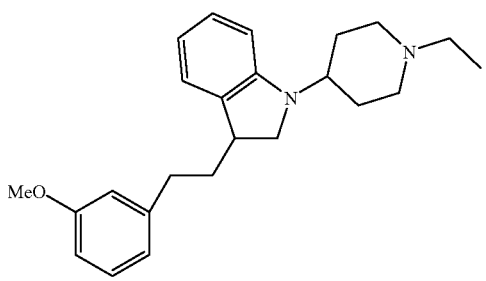

3-(3-Methoxyphenethyl)indoline (0.133 g) was treated as in Example 16 to give the title compound (0.132 g) as a yellow oil (yield: 52.3%).

Next, hydrochloric acid was added thereto to give the hydrochloride of the title compound as a hygroscopic amorphous solid.

Hydrochloride
$^1$H-NMR (400 MHz, DMSO-$d_6$):
δ(ppm) 1.26(3H, t, J=8.0 Hz), 1.74(1H, m), 1.86(2H, m), 2.07(3H, m), 2.63(2H, t, J=8.0 Hz), 2.99–3.07(5H, m), 3.14(1H, m), 3.52(3H, t, J=8.0 Hz), 3.72(1H, m), 3.74(3H, s), 6.59(2H, m), 7.02(1H, t, J=8.0 Hz), 7.08(1H, d, J=8.0 Hz), 7.20(1H, d, J=8.0 Hz).
ESI-Mass: 365.2(MH+).

Example 247: Synthesis of 1-(1-ethylpiperidin-4-yl)-3-(3-fluorophenethyl)indoline

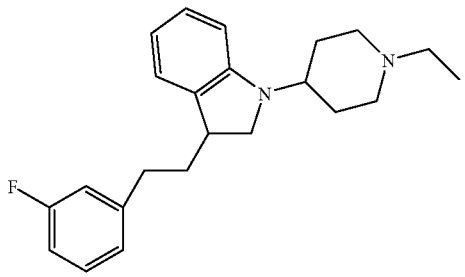

3-(3-Fluorophenethyl)indoline (0.582 g) was treated as in Example 16 to give the title compound (0.641 g) as a yellow oil (yield: 66.2%).

Next, oxalic acid (68 mg) was added thereto to give a salt followed by recrystallization from ethyl acetate. Thus the oxalate (0.313 g) of the title compound was obtained as colorless crystals.
m.p. (oxalate): 138° C.
Oxalate
$^1$H-NMR (400 MHz, DMSO-$d_6$):
δ(ppm) 1.22(3H, t, J=7.2 Hz), 1.72(1H, m), 1.89(4H, m), 2.07(1H, m), 2.67(2H, t, J=8.4 Hz), 2.97(2H, br-t), 3.12(1H, m), 3.50(3H, t, J=8.4 Hz), 3.70(1H, m), 6.53(1H, d, J=7.6 Hz), 6.58(1H, d, J=7.6 Hz), 7.00(2H, m), 7.06(1H, d, J=7.6 Hz), 7.09(2H, m), 7.32(1H, q, J=7.6 Hz).
ESI-Mass: 353.1(MH+).

Example 248: Synthesis of 1-[1-(4-fluorophenethyl)-piperidin-4-yl]indan

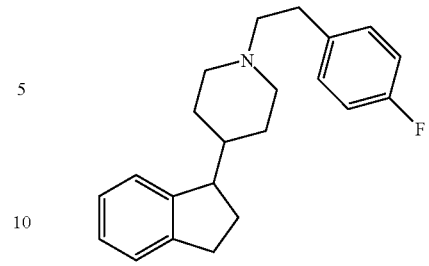

1-(Piperidin-4-yl)indan (300 mg) and 4-fluorophenethyl bromide (370 mg) were treated as in Example 2 to give the hydrochloride (250 mg) of the title compound as a white powder (yield: 46%).
m.p. (hydrochloride): 222–224° C.
$^1$H-NMR (400 MHz, DMSO-$d_6$):
δ(ppm) 1.50–1.98(6H, m), 2.01–2.12(1H, m), 2.72–2.94 (4H, m), 2.98–3.04(2H, m), 3.08–3.22(3H, m), 3.46–3.57 (2H, m), 7.11–7.22(6H, m), 7.28–7.31(2H, m), 10.33(1H, br-s).
FAB-Mass: 324(MH+).

Example 249: Synthesis of 1-1-(4-methoxyphenethyl)-piperidin-4-yl]indan

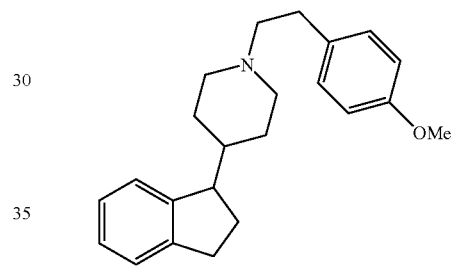

1-(Piperidin-4-yl)indan (300 mg) and 4-methoxyphenethyl bromide (390 mg) were treated as in Example 2 to give the hydrochloride (260 mg) of the title compound as a white powder (yield: 47%).
m.p. (hydrochloride): 191° C. (decomp.).
$^1$H-NMR (400 MHz, DMSO-$d_6$):
δ(ppm) 1.48–1.57(1H, m), 1.60–1.97(5H, m), 2.01–2.11 (1H, m), 2.71–3.00(6H, m), 3.08–3.18(3H, m), 3.45–3.56 (2H, m), 3.70(3H, s), 6.87(2H, d, J=8 Hz), 7.11–7.23(6H, m), 10.43(1H, br-s).
FAB-Mass: 336(MH+).

Example 250: Synthesis of 1-{4-[2-(4-fluorophenyl)ethyl]-piperazin-1-yl}-6-methoxyindan hydrochloride (250-1) 1-(Piperazin-1-yl)-6-mehoxyindan

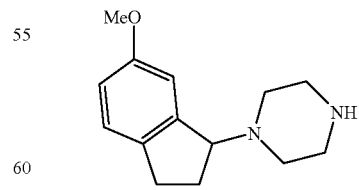

1-(4-Acetylpiperazin-1-yl)-6-methoxyindan (2.20 g) obtained as an intermediate in the above Example and an 8 N aqueous solution (8.0 ml) of sodium hydroxide were heated under reflux in ethanol. Then the reaction mixture was concentrated under reduced pressure, extracted with methylene chloride, dried and concentrated under reduced pressure again. The resulting residue was purified by silica gel column chromatography (methylene chloride/methanol system) to give the title compound (1.48 g) as a wax (yield: 73%).

(250-2) 1-[4-(4-Fluorophenacyl)piperazin-1-yl]-6-methoxyindan

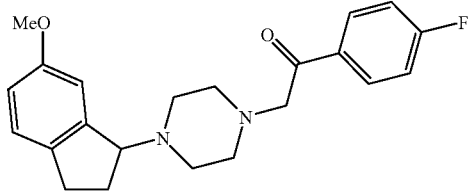

In the presence of a 5 N aqueous solution (2.0 ml) of sodium hydroxide, 1-(piperazin-1-yl)-6-methoxyindan (0.41 g) and 4-fluorophenacyl chloride (0.46 g) were reacted in methylene chloride at 0° C. Then, the reaction mixture was extracted with methylene chloride. The methylene chloride layer was washed with water, dried and concentrated under reduced pressure. The resulting residue was purified by silica gel column chromatography (toluene/acetone system) to give the title compound (0.60 g).

(250-3) 1-(4-[2-(4-Fluorophenyl)ethyl]piperazin-1-yl]-6-methoxyindan hydrochloride

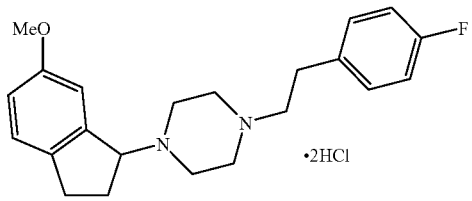

Lithium aluminum hydride (0.13 g) was suspended in THF. Into the resultant suspension was added dropwise a solution of 1-[4-(4-fluorophenacyl)piperazin-1-yl]-6-methoxyindan (0.60 g) in THF and the reaction mixture was heated under reflux while monitoring the reaction by TLC. Then the reaction solution was ice cooled and water (0.13 ml), a 5 N aqueous solution (0.13 ml) of sodium hydroxide and water (0.39 ml) were successively added thereto followed by stirring at room temperature for 1 hr. The resulting precipitate was filtered off and washed with THF. The filtrate was concentrated under reduced pressure and the resulting residue was purified by silica gel column chromatography (methylene chloride/methanol system) to give an oil (0.48 g) (yield: 83%).

This oily product was converted into a hydrochloride in a conventional manner to give the title compound as a white powder.

m.p.: 213° C. (decomp.).

$^1$H-NMR (400 MHz, CDCl$_3$):

δ(ppm) 2.03–2.19(2H, m), 2.49–2.66(10H, m), 2.69–2.90 (4H, m), 3.80(3H, s), 4.32(1H, t, J=7.2 Hz), 6.77(1H, dd, J=8.4, 2.8 Hz), 6.90(1H, d, J=2.8 Hz), 6.93–6.99(2H, m), 7.11(1H, d, J=8.4 Hz), 7.12–7.17(2H, m).

FAB-Mass: 355(MH+).

Example 251; Synthesis of 1-(4-ethylpiperazin-1-yl)-6-methoxyindan hydrochloride (251-1) 1-Chloro-6-mehtoxyindan

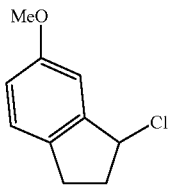

6-Methoxyindan-1-one (5.0 g) was dissolved in methanol (50 ml). Next, sodium tetrahydroborate (1.41 g) was added thereto at 0° C., and the resultant mixture was reacted at room temperature for 5 hr. The reaction solution was concentrated under reduced pressure and the residue was partitioned between ethyl acetate and water. The ethyl acetate layer was washed with water, dried and concentrated under reduced pressure to give 6-methoxyindan-1-ol (5.1 g) as an oil. This alcohol was not purified but reacted as such with thionyl chloride (4.5 ml) in ether at room temperature for 6 hr. The reaction solution was poured into ice water and extracted with ether. The ether layer was washed with water, dried and concentrated under reduced pressure to give the title compound (2.76 g).

(251-2) 1-(4-Acetylpiperazin-1-yl)-6-methoxyindan

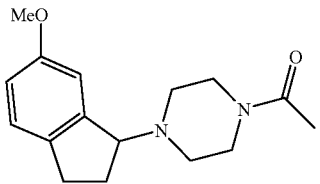

1-Chloro-6-methoxyindan (2.76 g), 1-acetylpiperazine (2.30 g) and potassium carbonate (2.90 g) were heated under reflux in acetone overnight. Then the reaction solution was cooled, filtered and washed with acetone. The filtrate was concentrated under reduced pressure and the residue was partitioned between ethyl acetate and water. The ethyl acetate layer was washed with water, dried and concentrated under reduced pressure. The resulting residue was purified by silica gel column chromatography (toluene/acetone system) to give the title compound (2.70 g) as an oil.

(251-3) 1-(4-Ethylpiperazin-1-yl)-6-methoxyindan hydrochloride

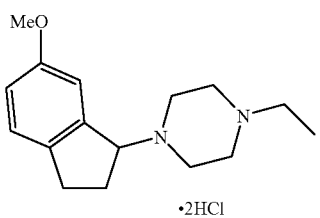

Lithium aluminum hydride (0.14 g) was suspended in THF. Into the resultant suspension was added dropwise a solution of 1-(4-acetylpiperazin-1-yl)-6-methoxyindan (0.50 g) in THF and the reaction mixture was heated under reflux while monitoring the reaction by TLC. Then the reaction solution was ice cooled and water (0.14 ml), a 5 N aqueous solution (0.14 ml) of sodium hydroxide and further water (0.42 ml) were successively added thereto followed by stirring at room temperature for 1 hr. The resulting precipitate was filtered off and washed with THF. The filtrate was concentrated under reduced pressure and the obtained residue was purified by silica gel column chromatography (methylene chloride/methanol system) to give 1-(4-ethylpiperazin-1-yl)-6-methoxyindan (0.30 g) as an oil (yield: 63%).

This oily product was converted into a hydrochloride in a conventional manner to give the title compound as a white powder.

¹H-NMR (400 MHz, CDCl₃):

δ(ppm) 1.08(3H, t, J=7.2 Hz), 2.02–2.19(2H, m), 2.41 (2H, q, J=7.2 Hz), 2.43–2.65(8H, m), 2.69–2.90(2H, m), 3.80(3H, s), 4.92(1H, t, J=7.2 Hz), 6.77(1H, dd, J=8.4, 2.8 Hz), 6.90(1H, d, J=2.8 Hz), 7.09(1H, d, J=8.4 Hz).

FAB-Mass: 261(MH+).

Example 252: Synthesis of trans-1-(4-ethylpiperazin-1-yl)-2-ethoxycarboxyaminoindan

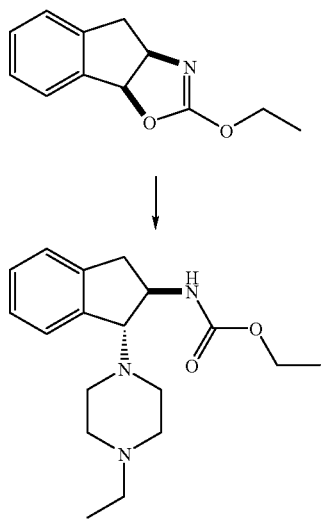

A mixture of (±)-(Z)-2-ethoxy-3a,8b-dihydro-4H-indeno [2,1-d]oxazole (1.4 g) synthesized in accordance with the method described in WO95/04028, ethylpiperazine (1.3 ml), scandium trifluoromethanesulfonate (50 mg) and toluene (40 ml) was stirred under nitrogen atmosphere at 70° C. for 17 hr as in Example 13 of WO95/04028 and Tetrahedron Lett., 1627-1628, 35(1994). After allowing to cool to room temperature again, ethyl acetate and water were added to the reaction solution and the layers were separated. The organic layer was washed with brine, dried over anhydrous magnesium sulfate and concentrated under reduced pressure. The resulting residue was purified by Chromatorex NH-silica gel column chromatography (hexane/ethyl acetate system) to give the title compound (675 mg) (yield: 31%).

¹H-NMR (400 MHz, CDCl₃):

δ(ppm) 1.07(3H, t, J=7.2 Hz), 1.23(3H, m), 2.40(2H, q, J=7.2 Hz), 2.45(4H, br-s), 2.68(6H, m), 3.37(1H, dd, J=16.2, 7.4 Hz), 4.02(1H, d, J=4.8 Hz), 4.12(2H, m), 7.16–7.23(3H, m), 7.33(1H, m).

Example 253: Synthesis of trans-1-(4-ethylpiperazin-1-yl)-2-methylaminoindan

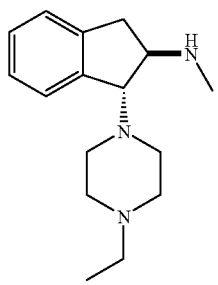

trans-1-(4-Ethylpiperazin-1-yl)-2-ethoxycarboxyaminoindan (670 mg) was dissolved in dry ether (20 ml) and lithium aluminum hydride (401 mg) was added thereto at room temperature. Under nitrogen atmosphere, the mixture was stirred for 21 hr. Then water (0.4 ml), a 5 N aqueous solution (0.4 ml) of sodium hydroxide and further water (1.2 ml) were successively added thereto followed by stirring. The reaction solution was filtered through celite and the filtrate was concentrated under reduced pressure to give the title compound (503 mg).

¹H-NMR (400 MHz, CDCl₃):

δ(ppm) 1.08(3H, t, J=7.2 Hz), 2.42(2H, q, J=7.2 Hz), 2.47(4H, m), 2.69(5H, m), 3.18(1H, dd, J=16.2, 7.4 Hz), 3.48(1H, dt, J=7.4, 4.8 Hz), 4.03(1H, d, J=4.8 Hz), 7.14–7.21(3H, m), 7.36(1H, m).

Example 254: Synthesis of trans-1-(4-ethylpiperazin-1-yl)-2-[methyl-(4-trifluorobenzyl)amino]indan

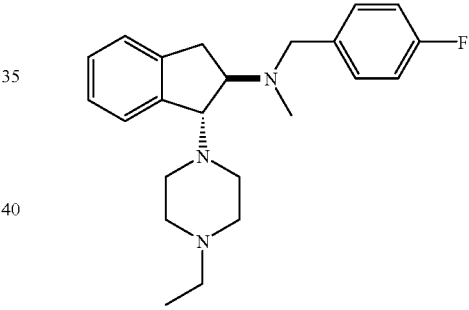

N-Methylamine (500 mg), 4-fluorobenzaldehyde (0.52 ml), acetic acid (0.6 ml) and methylene chloride (20 ml) were treated as in Example 101 to give the title compound (670 mg) (yield: 95%).

Next, this product was dissolved in ethyl acetate (10 ml) and a solution (2 ml) of 4 NHCl in ethyl acetate was added thereto. After concentrating the solvent under reduced pressure, ether was added to the residue followed by concentration. Then, it was dried in vacuo to give the hydrochloride (821 mg) of the title compound as white crystals.

Free

¹H-NMR (400 MHz, CDCl₃):

δ(ppm) 1.08(3H, t, J=7.2 Hz), 2.10(3H, s), 2.41(2H, q, J=7.2 Hz), 2.45(4H, br-s), 2.64(4H, br-s), 2.95(2H, m), 3.48(3H, s), 3.73(1H, ddd, J=7.4, 7.2, 4.4 Hz), 4.33(1H, d, J=4.4 Hz), 6.98(2H, m), 7.19(3H, m), 7.29(3H, m), 7.36(1H, m).

HCl salt m.p.: 196–198° C.

FAB-Mass: 368 (MH+).

Example 255: Synthesis of 7-[4-hydroxy-1-(4-fluorophenethyl piperidin-4-yl]-5,6-dihydro-7H-pyrindine

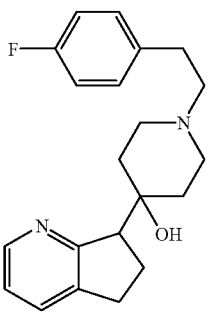

6,7-Dihydro-5H-cyclopenta[B]pyridine (1.00 g, CAS Registry No. 533-37-9) was dissolved in tetrahydrofuran (15 ml). Under a stream of nitrogen, a 1.6 M solution (5.8 ml) of n-butyllithium in hexane was added dropwise into the resultant solution while cooling to −55° C. or below. After stirring for 5 min, a solution of 1-(4-fluorophenethyl)-4-piperidone (2.04 g) in tetrahydrofuran (10 ml) was added dropwise thereinto at the same temperature over 20 min. After stirring for 30 min, the reaction solution was allowed to warm to room temperature again and water was added thereto. Then it was extracted with ethyl acetate and the organic layer was washed with brine and dried over magnesium sulfate. After evaporating the solvent, the resulting residue (3.17 g) was purified by silica gel column chromatography (methanol/methylene chloride system) to give the title compound (600 mg) as a slight brown oil.

$^1$H-NMR (400 MHz, CDCl$_3$):

δ(ppm) 1.72–2.08(4H, m), 2.22–3.10(12H, m), 3.37(1H, d, J=9.5 Hz), 5.81(1H, br-s), 6.93–7.01(2H,m), 7.08(1H, dd, J=8.0, 5.5 Hz), 7.12–7.20(2H, m), 7.33(1H, d, J=8.0 Hz), 8.28(1H, d, J=5.5 Hz).

FAB-Mass: 341(MH+).

Example 256: Synthesis of 7-[1-(4-fluorophenethyl)piperidin-4-ylidene]-5,6-dihydropyrindine

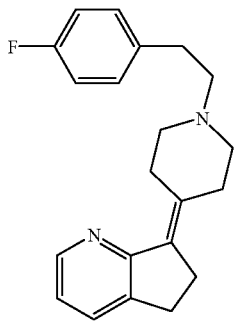

7-[4-Hydroxy-1-(4-fluorophenethyl)piperidin-4-yl]-5,6-dihydro-7H-pyrindine (350 mg) was dissolved in tetrahydrofuran (3 ml). Under ice cooling, thionyl chloride (0.11 ml) and triethylamine (0.50 ml) were added dropwise thereinto. Then the resultant mixture was stirred at room temperature for 15 minutes followed by addition of water. Next, the mixture was extracted with ethyl acetate and the organic layer was washed with brine and dried over magnesium sulfate. After removing the solvent, the resulting residue (250 mg) was purified by silica gel column chromatography (hexane/ethyl acetate system) to give the title compound (45 mg) as an oil.

$^1$H-NMR (400 MHz, CDCl$_3$):

δ(ppm) 2.45–2.50(2H, m), 2.58–2.68(6H, m), 2.75–2.95 (6H, m), 3.48(2H, br-s), 6.93–7.00(3H, m), 7.14–7.20(2H, m), 7.48(1H, d, J=7.6 Hz), 8.40(1H, d, J=4.4 Hz).

FAB-Mass: 323(MH+).

Example 257: Synthesis of 7-[1-(4-fluorophenethyl)piperidin-4-yl]-5,6-dihydro-7H-pyrindine

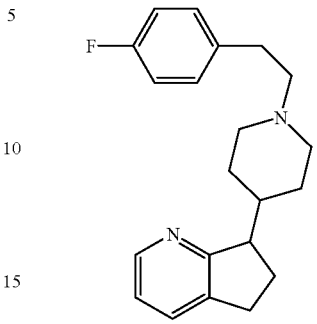

7-[1-(4-Fluorophenethyl)piperidin-4-ylidene]-5,6-dihydropyrindine (100 mg) was dissolved in methanol (5 ml). After adding two drops of acetic acid thereinto, the resultant mixture was vigorously shaken in the presence of a palladium catalyst under a hydrogen gas pressure of 3 kg/cm$^2$ for 12 hr. After filtering off the catalyst, water was added to the reaction mixture followed by extraction with ethyl acetate. The organic layer was washed with brine a and dried over magnesium sulfate. Then the solvent was distilled away to give the title compound (45 mg) as an oil.

$^1$H-NMR (400 MHz, CDCl$_3$):

δ(ppm) 1.22–1.52(2H, m), 1.94–2.40(4H, m), 2.55–2.96 (4H, m), 3.00–3.30(6H, m), 3.45–3.70(2H, m), 6.97–7.02 (2H, m), 7.07(1H, dd, J=5.2, 7.6 Hz), 7.19–7.25(2H, m), 7.52(1H, d, J=7.6 Hz), 8.34(1H, d, J=5.2 Hz).

FAB-Mass: 325(MH+).

Example 258: Synthesis of 7-[4-(4-fluorophenethyl)piperazin-1-yl]-5,6-dihydro-7H-pyrindine

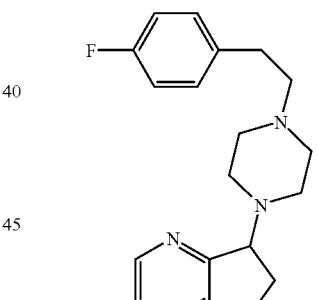

7-Hydroxy-6,7-dihydro-5H-cyclopenta[B]pyridine (247 mg) synthesized in accordance with the method described in JP-A 1-211581 was dissolved in methylene chloride (5 ml). Under ice cooling, thionyl chloride (0.147 ml) was added to the resultant solution and the resultant mixture was stirred for 25 min. Then the reaction solution was evaporated to dryness under reduced pressure. To the residue were added a solution of 1-(4-fluorophenethyl)piperazine (570 mg) synthesized in accordance with the method described in JP-A 54-92979 in dimethylformamide (5 ml) and triethylamine (0.38 ml) followed by heating at 60° C. for 5 hr. After adding water, the reaction solution was extracted with ethylacetate. The organic layer was washed with brine and dried over magnesium sulfate. After evaporating the solvent, the resulting residue was purified by NH-silica gel column chromatography (hexane/methylene chloride system) to give the title compound (200 mg) as an oil.

¹H-NMR (400 MHz, CDCl₃):

δ(ppm) 2.15–2.25(2H, m), 2.50–3.00(14H, m), 4.28(1H, t, J=7.0 Hz), 6.92–7.00(2H, m), 7.08(1H, dd, J=5.0, 7.4 Hz), 7.12–7.18(2H, m), 7.50(1H, d, J=7.4 Hz), 8.46(1H, d, J=5.0 Hz)

FAB-Mass: 326(MH+).

Example 259-1: Synthesis of cis- and trans-2,6-dichloro-3-methoxyethylenylpyridines

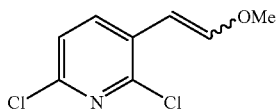

Potassium t-butoxide (22.2 g) was added to a solution of methoxymethyltriphenylphosphonium chloride (62.5 g) in tetrahydrofuran (250 ml) and the resultant mixture was stirred at 0° C. for 20 min. Into the resultant solution was added dropwise a solution of 2,6-dichloro-3-formylpyridine (24.7 g) synthesized in accordance with the method described in J. CHEM. SOC. PERKIN TRANS. 1 (1990, No. 9, p. 2409.) in tetrahydrofuran (100 ml) followed by stirring for 2 hr. Then water and ethyl acetate were added to the reaction solution and the layers were separated. The organic layer was washed with a saturated aqueous solution of sodium chloride and dried over anhydrous magnesium sulfate. The resulting residue was purified by silica gel column chromatography (hexane/ethyl acetate system) to give a mixture (21.5 g) of the geometrical isomers of the title compound as a pale yellow oil (yield: 75%).

¹H-NMR (400 MHz, CDCl₃):

δ(ppm) 3.71(3H, s), 3.82(3H, s), 5.53(1H, d, J=7 Hz), 5.93(1H, d, J=12 Hz), 6.38(1H, d, J=7 Hz), 7.03(1H, d, J=12 Hz), 7.17(1H, d, J=8 Hz), 7.19(1H, d, J=8 Hz), 7.60(1H, d, J=8 Hz), 8.36(1H, d, J=8 Hz).

Example 259-2: Synthesis of 2.6-dichloro-3-formylmethylpyridine

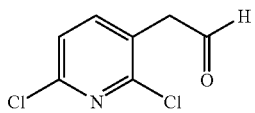

A solution of cis- and trans-2,6-dichloro-3-methoxyethylenylpyridines (21.5 g) and 35% perchloric acid (100 ml) in ether (200 ml) was stirred at room temperature for a day. Then the reaction solution was basified by adding a conc. aqueous solution of sodium hydroxide and ethyl acetate was added thereto and the layers were separated. The organic layer was washed with brine and dried over magnesium sulfate. After evaporating the solvent, the resulting residue was purified by silica gel column chromatography (hexane/ethyl acetate system) to give the title compound (15 g) as a pale yellow oil (yield: 56%).

¹H-NMR (400 MHz, CDCl₃):

δ(ppm) 3.90(2H, s), 7.31(1H, d, J=8 Hz), 7.55(1H, d, J=8 Hz), 9.81(1H, s).

Example 259-3: Synthesis of 2,6-dichloro-3-hydroxyethylpyridine

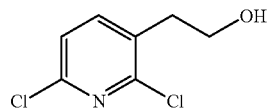

A solution of cis- and trans-2,6-dichloro-3-methoxyethylenylpyridines (2.0 g) and 35% perchloric acid (10 ml) in ether (30 ml) was stirred at room temperature for a day. Then the reaction solution was basified by adding a conc. aqueous solution of sodium hydroxide and ethyl acetate was added thereto and the layers were separated. The organic layer was washed with brine and dried over magnesium sulfate. After evaporating the solvent, ethanol (20 ml) and sodium borohydride (0.076 g) were added to the residue and the resultant mixture was stirred at room temperature for 1 hr. Then the reaction solution was concentrated under reduced pressure, diluted with a saturated aqueous solution of sodium hydrogencarbonate and ethyl acetate and the layers were separated. The organic layer was washed with brine and dried over magnesium sulfate. After evaporating the solvent, the obtained residue was purified by silica gel column chromatography (hexane/ethyl acetate system) to give the title compound (1.3 g) as a pale yellow oil (yield: 69%).

¹H-NMR (400 MHz, CDCl₃):

δ(ppm) 1.50(1H, t, J=6 Hz), 2.99(2H, t, J=6 Hz), 3.95(1H, q, J=6 Hz), 7.23(1H, d, J=8 Hz), 7.62(1H, d, J=8 Hz).

Example 259-4: Synthesis of 1-[1-(4-fluorophenethyl) piperidin-4-yl]-6-chloro-7-azaindoline

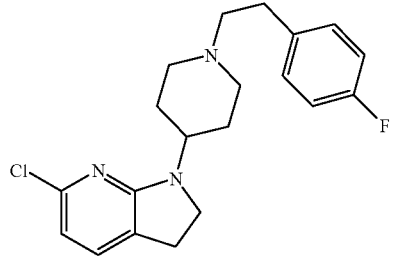

Under ice cooling, methanesulfonyl chloride (0.45 g) was added dropwise into a solution of 2,6-dichloro-3-hydroxyethylpyridine (0.65 g) in pyridine (10 ml) and the resultant mixture was stirred for 3 hr. Then the reaction solution was concentrated under reduced pressure, diluted with a saturated aqueous solution of sodium bicarbonate and ethyl acetate and the layers were separated. The organic layer was washed with brine and dried over magnesium sulfate. After evaporating the solvent, 1-(4-fluorophenethyl)-4-aminopiperidine (0.75 g) and dichlorobenzene (20 ml) were added to the residue and the resultant mixture was heated at 180° C. for 2 hr. The reaction solution was concentrated under reduced pressure, diluted with a saturated aqueous solution of sodium bicarbonate and ethyl acetate and the layers were separated. The organic layer was washed with brine and dried over magnesium sulfate. After evaporating the solvent, the resulting residue was purified by NH-silica gel column chromatography (hexane/ethyl acetate system) to give the title compound (0.43 g) as a colorless oil (yield: 35%).

A portion of this product was converted into a hydrochloride in a conventional manner to give the title compound as a white powder.

m.p. (hydrochloride): 225° C. (decomp.).

¹H-NMR (400 MHz, DMSO-d₆):

δ(ppm) 1.81–1.90(2H, m), 1.99–2.10(2H, m), 2.93(2H, t, J=8 Hz), 3.00–3.08(2H, m), 3.10–3.27(4H, m), 3.52(2H, t, J=8 Hz), 3.55–3.64(2H, m), 4.00–4.12(1H, m), 6.44(1H, d, J=8 Hz), 7.12–7.20(2H, m), 7.23(1H, d, J=8 Hz), 7.29–7.34 (2H, m).

FAB-Mass: 360(MH+).

Example 260: Synthesis of 1-[1-(4-fluorophenethyl) piperidin-4-yl]-7-azaindoline

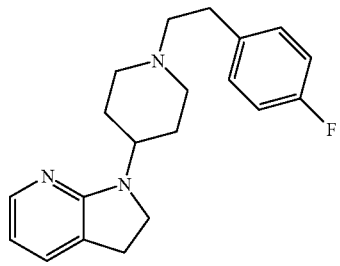

2-Chloro-3-formylpyridine (1.5 g) synthesized in accordance with the method described in J. CHEM. SOC. PERKIN TRANS. 1 (1990, No. 9, P. 2409.) was treated as in Examples 259-1, 259-3 and 259-4 to give the hydrochloride (0.21 g) of the title compound as a white powder (yield: 4.9%).

m.p. (hydrochloride): 223° C. (decomp.)

¹H-NMR (400 MHz, DMSO-d₆):

δ(ppm) 1.79–2.00(2H, m), 2.03–2.21(2H, m), 2.95–3.10 (4H, m), 3.22–3.36(4H, m), 3.60–3.69(4H, m), 4.15–4.24 (1H, m), 6.51–6.60(1H, m), 7.12–7.20(2H, m), 7.29–7.37 (3H, m), 7.67–7.73(1H, m).

FAB-Mass: 326(MH+).

Example 261-1: Synthesis of 2,6-(difluoro-3-bromoethylpyridine

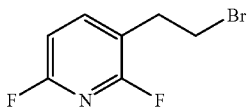

Under ice cooling, triphenylphosphine (3.1 g) and N-bromosuccinimide (1.9 g) were added to a solution of 2,6-difluoro-3-hydroxyethylpyridine (1.58 g) obtained as in Example 259-3 in methylene chloride (100 ml) and the resultant mixture was stirred for 2 hr. After concentrating the resultant mixture under reduced pressure, the residue was purified by silica gel column chromatography (hexane/ethyl acetate system) to give the title compound (1.6 g) as a colorless oil (yield: 73%).

¹H-NMR (400 MHz, CDCl₃):

δ(ppm) 3.20(1H, t, J=6 Hz), 3.59(2H, t, J=6 Hz), 6.80–6.85(1H, m), 7.75–7.83(1H, m).

Example 261-2: Synthesis of 1-[1-(4-fluorophenethyl) piperidin-4-yl]-6-fluoro-7-azaindoline

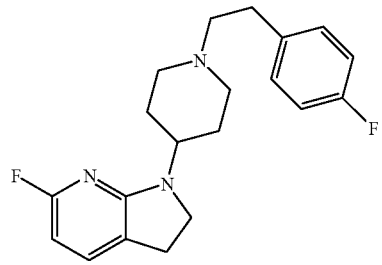

A mixture of 2,6-difluoro-3-bromoethylpyridine (0.3 g), 1-(4-fluorophenethyl)-4-aminopiperidine (0.3 g), triethylamine (0.27 g) ando-dichlorobenzene (20 ml) was heated at 180° C. for 2 hr. Then the reaction solution was concentrated under reduced pressure, diluted with a saturated aqueous solution of sodium hydrogencarbonate and ethyl acetate and the layers were separated. The organic layer was washed with brine and dried over magnesium sulfate. After evaporating the solvent, the resulting residue was purified by silica gel column chromatography (hexane/ethyl acetate system) followed by conversion into a hydrochloride in a conventional manner to give the hydrochloride (0.14 g) of the title compound as a white powder (yield: 30%).

m.p. (hydrochloride): 202–204° C.

¹H-NMR (400 MHz, DMSO-d₆):

δ(ppm) 1.81–1.90(2H, m), 1.99–2.11(2H, m), 2.91(2H, t, J=8 Hz), 3.00–3.19(4H, m), 3.20–3.30(2H, m), 3.51(2H, t, J=8 Hz), 3.58–3.65(2H, m), 3.93–4.03(1H, m), 6.03(1H, d, J=8 Hz), 7.14–7.21(2H, m), 7.29–7.35(3H, m).

FAB-Mass: 344(MH+).

Example 262: Synthesis of 1-[1-(2,4-difluorophenethyl)-piperidin-4-yl]-6-chloro-7-azaindoline

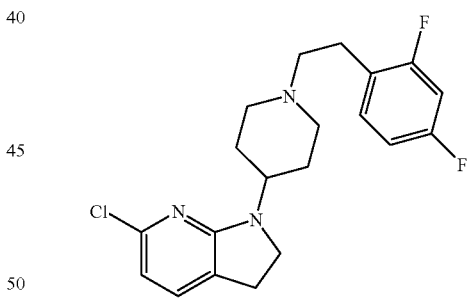

1-(Piperidin-4-yl)-6-chloro-7-azaindoline (0.5 g) and 2,4-difluorophenethyl bromide (0.43 g) were treated as in Example 2 to give the hydrochloride (74 mg) of the title compound as a brown powder (yield: 7.8%).

m.p. (hydrochloride): 221° C. (decomp.).

¹H-NMR (400 MHz, DMSO-d₆):

δ(ppm) 1.81–1.91(2H, m), 2.00–2.15(2H, m), 2.91(2H, t, J=8 Hz),3.03–3.39(6H, m),3.53(2H, t, J=8 Hz),3.60–3.68 (2H, m), 4.01–4.12(1H, m), 6.46(1H, d, J=8 Hz), 7.08–7.17 (1H, m), 7.21–7.31(2H, m), 7.40–7.48(1H, m).

FAB-Mass: 378(MH+).

Example 263: Synthesis of 1-[1-(4-methoxyphenethyl) piperidin-4-yl]-6-chloro-7-azaindoline

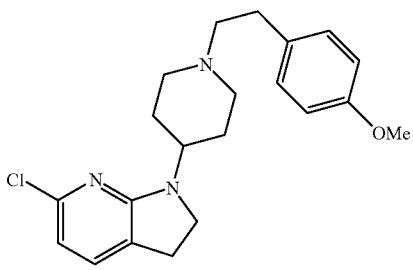

1-(Piperidin-4-yl)-6-chloro-7-azaindoline (0.8 g) and 4-methoxyphenethyl bromide (0.72 g) were treated as in Example 2 to give the hydrochloride (220 mg) of the title compound as a pale yellow powder (yield: 16%).
m.p. (hydrochloride): 199° C. (decomp.).
$^1$H-NMR (400 MHz, DMSO-d$_6$):
δ(ppm) 1.82–1.91(2H, m), 1.97–2.09(2H, m), 2.89–2.98 (4H, m), 3.08–3.24(4H, m), 3.52(2H, t, J=8 Hz), 3.56–3.64 (2H, m), 4.00–4.10(1H, m), 6.44(1H, d, J=7 Hz), 6.90(1H, d, J=9 Hz), 7.18(1H, d, J=9 Hz), 7.22(1H, d, J=7 Hz).
FAB-Mass: 372(MH+).

Example 264: Synthesis of 1-[1-(4-fluorophenethyl)-piperdin-4-yl]-6-azaindoline

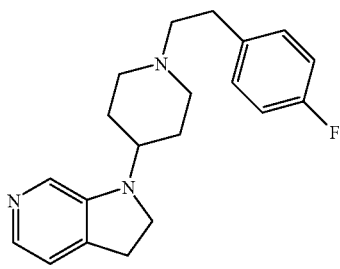

Under a stream of hydrogen, a mixture of 6-azaindoline (180 mg) synthesized in accordance with the method described in Tetrahedron, (1988, vol. 44, No. 10, p. 2977.), 1-(4-fluorophenethyl)-4-piperidone (530 mg), platinumoxide (20 mg), acetic acid (0.5 ml) and ethanol (10 ml) was catalytically reduced at ordinary temperature under atmospheric pressure. After stirring the reaction mixture overnight, the catalyst was filtered off and the filtrate was concentrated under reduced pressure. The resulting residue was diluted with a saturated aqueous solution of sodium hydrogencarbonate and ethyl acetate and the layers were separated. The organic layer was washed with brine and dried over anhydrous magnesium sulfate and the resulting residue was purified by NH-silica gel column chromatography (hexane/ethyl acetate system) followed by conversion into an oxalate in a conventional manner to give the oxalate (35 mg) of the title compound as a pale yellow powder (yield: 5.2%).
m.p. (oxalate): 196–198° C.
$^1$H-NMR (400 MHz, DMSO-d$_6$):
δ(ppm) 1.83–1.91(4H, m), 2.90–3.05(6H, m), 3.18–3.27 (2H, m), 3.38(2H, t, J=8 Hz), 3.51–3.60(2H, m), 3.69–3.79 (1H, m), 7.10(1H, d, J=5 Hz), 7.14–7.19(2H, m), 7.30–7.34 (2H, m), 7.83(1H, d, J=5 Hz), 7.86(1H, s).
FAB-Mass: 326(MH+).

Example 265: Synthesis of 5-[1-(4-fluorophenethyl) piperidin-4-ylidene1-7-methyl-5,6-dihydrocyclopentapyrazine

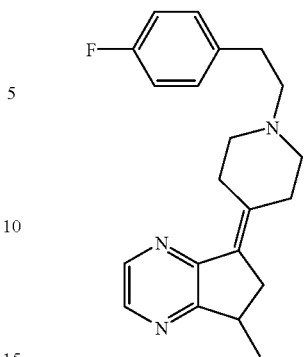

5-Methyl-6,7-dihydro-5(H)-cyclopenta[B]pyrazine (2.82 g, CAS Registry No. 23747-48-0) was dissolved in tetrahydrofuran (30 ml). Under a stream of nitrogen, a 1.6 M solution (13.4 ml) of n-butyllithium in hexane was added dropwise into the resultant solution while cooling to −55° C. or below. After stirring for 5 min, a solution of 1-(4-fluorophenethyl)-4-piperidone (3.72 g) in tetrahydrofuran (10 ml) was added dropwise thereinto at the same temperature over 5 min. After stirring for 5 min, the reaction solution was allowed to warm to room temperature and water was added thereto. Then it was extracted with ethyl acetate and the organic layer was washed with brine and dried over magnesium sulfate. After evaporating the solvent, the resulting residue (6.5 g) was purified by NH-silica gel column chromatography (hexane/ethyl acetate system) to give an isomer A (1.48 g) and another isomer B (2.94 g) of 5-[4-hydroxy-1-(4-fluorophenethyl)piperidin-4-yl]-7-methyl-5,6-dihdyro-5H-cyclopentapyrazine each as an oil.
Isomer A:
$^1$H-NMR (400 MHz, CDCl$_3$):
δ(ppm) 1.40(3H, d, J=6.8 Hz), 1.48–1.85(5H, m), 2.47–2.65(5H, m), 2.72–2.85(4H, m), 3.14–3.24(1H, m), 3.32–3.38(1H, m), 4.48(1H, s), 6.93–7.00(2H, m), 7.12–7.19(2H, m), 8.24(1H, dd, J=1.2, 2.8 Hz), 8.36(1H, dd, J=1.2, 2.8 Hz).
Isomer B:
$^1$H-NMR (400 MHz, CDCl$_3$):
δ(ppm) 1.33(3H, d, J=7.2 Hz), 1.65–1.97(5H, m), 2.27–2.86(9H, m), 3.25–3.36(1H, m), 3.38–3.44(1H, m), 4.11(1H, s), 6.93–7.01(2H, m), 7.12–7.20(2H, m), 8.27(1H, dd, J=0.8, 2.8 Hz), 8.36(1H, dd, J=0.8, 2.8 Hz).

The above isomer A (1.48 g) was dissolved in acetic acid (10 ml). Then conc. sulfuric acid (2.0 ml) was added thereto while cooling in a water bath and the resultant mixture was stirred at room temperature for 2 hr. The reaction solution was basified with 10% potassium carbonate and extracted with ethyl acetate. The organic layer was washed with brine and dried over magnesium sulfate. After evaporating the solvent, the resulting residue was purified by NH-silica gel column chromatography (hexane/ethyl acetate system) to give the title compound (680 mg) as an oil.
$^1$H-NMR (400 MHz, CDCl$_3$):
δ(ppm) 1.38(3H, d, J=6.8 Hz), 2.12–2.40(1H, m), 2.45–2.50(2H, m), 2.56–2.69(6H, m), 2.79–2.86(2H,m), 3.06–3.14(1H, m), 3.20–3.30(1H, m), 3.33–3.39(1H, m), 6.94–7.00(2H, m), 7.15–7.19(2H, m), 8.18(1H, d, J=2.7 Hz), 8.36(1H, dd, J=0.8, 2.7 Hz).
FAB-Mass: 338(MH+).

Example 266: Synthesis of 5-[1-(4-fluorophenethyl)-piperidin-4-yl]-7-methyl-5,6-dihydro-5H-cyclopentapyrazine

235

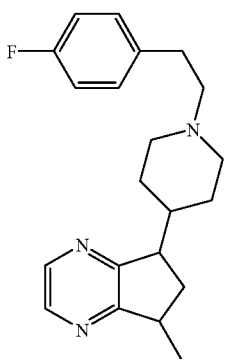

5-[1-(4-Fluorophenethyl)piperidin-4-ylidene]-7-methyl-5,6-dihydrocyclopentapyrazine (300 mg) was dissolved in methanol (10 ml). After adding five drops of acetic acid thereinto, the resultant mixture was vigorously shaken in the presence of a palladium catalyst under a hydrogen gas pressure of 4.2 kg/cm$^2$ for 13 hr. After filtering off the catalyst, water was added to the reaction mixture followed by extraction with ethyl acetate. The organic layer was washed with brine and dried over magnesium sulfate. Then the solvent was evaporated to give the oily title compound (200 mg) as a mixture of stereoisomers (about 5:1).

$^1$H-NMR (400 MHz, CDCl$_3$):

δ(ppm) 1.34(d, J=7.2 Hz) and 1.40(d, J=6.8 Hz)1:5 corresponding to 3H in total, 1.44–1.56(3H, m), 1.62–1.90(2H, m), 2.00–2.20(3H, m), 2.43–2.51(1H, m), 2.54–2.66(2H, m), 2.76–2.88(2H, m), 3.04–3.20(4H, m), 6.93–7.00(2H, m), 7.13–7.19(2H, m), 8.30(s) and 8.31(s)5:1 corresponding to 2H in total.

FAB-Mass: 340(MH+).

Example 267: Synthesis of 1-{1-[2-(4-methoxyphenyl)ethyl]piperidin-4-yl}-7-methoxy-1,2,3,4-tetrahydroquinoline hydrochloride

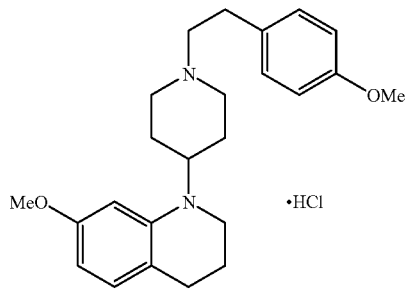

A solution of 1-(4-piperidinyl)-7-methoxy-1,2,3,4-tetrahydroquinoline (250 mg), 2-(4-methoxyphenyl)ethyl bromide (260 mg) and diisopropylethylamine (270 mg) in DMF (5 ml) was heated at 60° C. for 12 hr under stirring. After the completion of the reaction, the reaction solution was cooled to room temperature and water was added thereto followed by extraction with ethyl acetate. The ethyl acetate layer was washed with brine and dried over magnesium sulfate. After evaporating the solvent, the resulting obtained residue was purified by silica gel column chromatography (toluene/acetone system) to give 1-{1-[2-(4-methoxyphenyl)ethyl]piperidin-4-yl}-7-methoxy-1,2,3,4-tetrahydroquinoline as an oil. This free compound was dissolved in ethyl acetate and 8.5% HCl/ethyl acetate was added thereto. The resulting hydrochloride was recrystallized from ethanol/ether to give the title compound (225 mg) (yield: 53%).

236 m.p.: 232–235° C.

$^1$H-NMR (400 MHz, DMSO-d$_6$):

δ(ppm) 1.72–1.84(4H, m), 2.10–2.24(2H, m), 2.57(2H, t, J=6.0 Hz), 2.96–3.03(2H, m), 3.09(2H, t, J=5.6 Hz), 3.11–3.21(4H, m), 3.58(2H, br-d), 3.66(3H, s), 3.71(3H, s), 3.90–4.00(1H, m), 6.11(1H, dd, J=8.4, 2.4 Hz), 6.28(1H, d, J=2.4 Hz), 6.78(1H, d, J=8.4 Hz), 6.89(2H, d, J=8.4 Hz), 7.18(2H, d, J=8.4 Hz), 10.68–10.81(1H, br-s).

MS: 381(M+H)+.

Next, the procedure of Example 267 was repeated to give the products of Examples 268 to 274.

Example 268: 1-{1-[2-(4-Fluorophenyl)ethyl]piperidin-4-yl}-7-methoxy-1,2,3,4-tetrahydroquinoline hydrochloride

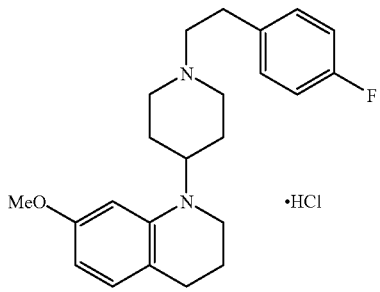

(Yield: 75%).

m.p.: 258° C. (decomp.).

$^1$H-NMR (400 MHz, DMSO-d$_6$):

δ(ppm) 1.74–1.84(4H, m), 2.23(2H, qd, J=12, 2 Hz), 2.569(2H, t, J=6.4 Hz), 3.04–3.23(6H, m), 3.57(2H, d, J=11.6 Hz), 3.66(3H, s), 3.93–4.03(1H, m), 6.14(1H, dd, J=8, 1.6 Hz), 6.32(1H, d, J=1.6 Hz), 6.79(1H, d, J=7.6 Hz), 7.16(2H, t, J=9.2 Hz), 7.32(2H, dd, J=8.8, 5.6 Hz), 11.05–11.20(1H, br-s).

MS: 369(M+H)+.

Example 269: 1-[1-(4-Cyanopropyl)piperidin-4-yl]-7-methoxy-1,2,3,4-tetrahydroquinoline hydrochloride

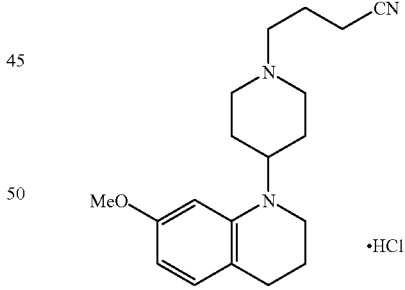

(Yield: 55%).

m.p.: 180–183° C. (decomp.).

$^1$H-NMR (400 MHz, DMSO-d$_6$):

δ(ppm) 1.71–1.82(4H, m), 1.97–2.12(2H, m), 2.15–2.28 (2H, m), 2.56(2H, t, J=6.4 Hz), 2.67(2H, t, J=7.2 Hz), 2.99–3.18(6H, m), 3.51(2H, br-d, J=11.6 Hz), 3.66(3H, s), 3.90–4.01(1H, m), 6.12(1H, dd, J=8.4, 1.0 Hz), 6.29(1H, d, J=1.0 Hz), 6.78(1H, d, J=8.4 Hz), 10.94–11.12(1H, br-s).

MS: 314(M+H)+.

Example 270: 1-{1-[2-(2-Thienyl)ethyl]piperidin-4-yl}-7-methoxy-1,2,3,4-tetrahydroquinoline hydrochloride

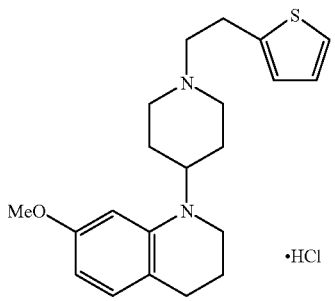

(Yield: 35%).
m.p.: 232–235° C.
¹H-NMR (400 MHz, DMSO-d₆):
δ(ppm) 1.73–1.84(4H, m), 2.16–2.29(2H, m), 2.57(2H, t, J=6.4 Hz), 3.10(2H, t, J=5.2 Hz), 3.13–3.40(6H, m), 3.58 (2H, br-d), 3.66(3H, s), 3.91–4.02(1H, m), 6.15(1H, br-d), 6.32(1H, br-s), 6.80(1H, d, J=8.0 Hz), 6.97(1H, d, J=1.6 Hz), 6.99(1H, d, J=5.2 Hz), 7.40(1H, dd, J=5.2, 1.6 Hz), 11.21–11.33(1H, br-s).
MS: 357(M+H)+.
Example 271: 1-{1-[2-(4-Fluorophenyl)ethyl]piperidin-4-yl}-7,8-dimethoxy-1,2,3,4-tetrahydroquinoline hydrochloride

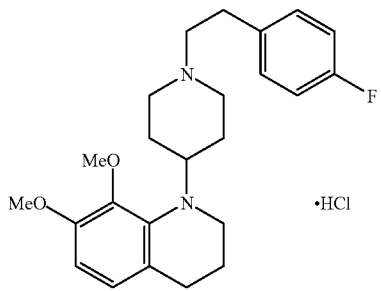

(Yield: 82%).
m.p.: 213–215° C.
¹H-NMR (400 MHz, DMSO-d₆):
δ(ppm) 1.62–1.89(4H, m), 2.11–2.31(2H, m), 2.57–2.69 (2H, m), 2.88–3.23(8H, m), 3.51–3.69(2H, m), 3.62(3H, s), 3.71(3H, s), 6.40–6.62(1H, br-d), 6.63–6.75(1H, br-d), 7.15 (2H, t, J=8.8 Hz), 7.29(2H, dd, J=7.6, 5.2 Hz), 10.50–10.77 (1H, br-s).
MS: 399(M+H)+.
Example 272: 1-{1-[2-(4-Fluorophenyl)ethyl]piperidin-4-yl}-7,8-methylenedioxy-1,2,3,4-tetrahydroquinoline hydrochloride

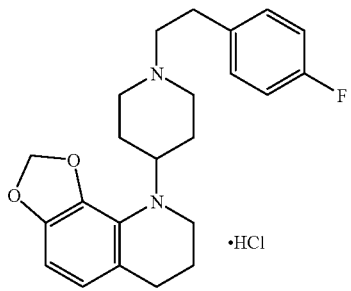

(Yield: 55%).
m.p.: 225–227° C.
¹H-NMR (400 MHz, DMSO-d₆):
δ(ppm) 1.71–1.83(4H, m), 2.24(2H, qd, J=12.4, 3.2 Hz), 2.58(2H, t, J=6.0 Hz), 2.92–3.10(6H, m), 3.18–3.25(2H, m), 3.58(2H, br-d), 4.14–4.23(1H, m), 5.83(2H, s), 6.23(1H, d, J=8.0 Hz), 6.46(1H, d, J=8.0 Hz), 7.16(2H, t, J=8.8 Hz), 7.29(2H, dd, J=8.8, 5.6 Hz), 10.84–10.91(1H, m).
MS: 383(M+H)+.
Example 273: 1-{1-[2-(4-Fluorophenyl)ethyl]piperidin-4-yl}-7-methoxy-8-methyl-1,2,3,4-tetrahydroquinoline oxalate

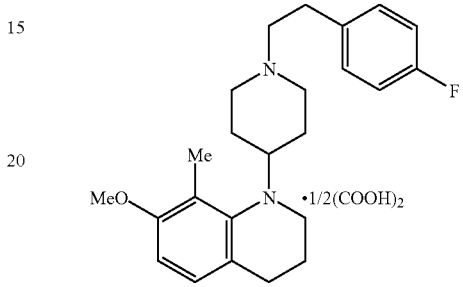

(Yield: 68%).
m.p.: 176–178° C.
¹H-NMR (400 MHz, DMSO-d₆):
δ(ppm) 1.66–1.75(4H, m), 1.97–2.09(2H, m), 2.02(3H, s), 2.58(2H, t, J=6.8 Hz), 2.79–3.22(9H, m), 3.40–3.51(2H, m), 3.71(3H, s), 6.47(1H, d, J=8.4 Hz), 6.76(1H, d, J=8.4 Hz), 7.13(2H, t, J=8.8 Hz), 7.29(2H, dd, J=11.2, 8.8 Hz).
MS: 383(M+H)+.
Example 274: 1-{1-[2-(4-Fluorophenyl)-2-oxoethyl]piperidin-4-yl}-7-methoxy-1,2,3,4-tetrahydroauinoline hydrochloride

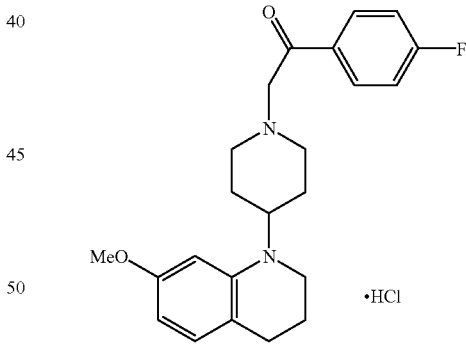

(Yield: 60%).
m.p.: 153–155° C. (decomp.)
¹H-NMR (400 MHz, DMSO-d₆):
δ(ppm) 1.70–1.83(4H, m), 2.15–2.29(2H, m), 2.54(2H, t, J=6.4 Hz), 3.08(2H, t, J=6.0 Hz), 3.17–3.32(2H, m), 3.56 (2H, br-d, J=12.0 Hz), 3.62 (3H, s), 3.92–4.03 (1H, m), 4.98 (2H, d, J=4.4 Hz) 6.11 (H, dd, J=7.2, 1.0 Hz), 6.32 (1H, d, J=1.0 Hz), 6.76 (1H, d, J=7.2 Hz), 7.41(2H, t, J=8.8 Hz), 8.04(2H, dd, J=8.8, 5.6 Hz), 10.22–10.39(1H, m).
MS: 383(M+H)+.
Example 275: 1-{1-[2-(4-Fluorophenyl)-2-hydroxyethyl]piperidin-4-yl}-7-methoxy-1,2,3,4-tetrahydroquinoline oxalate

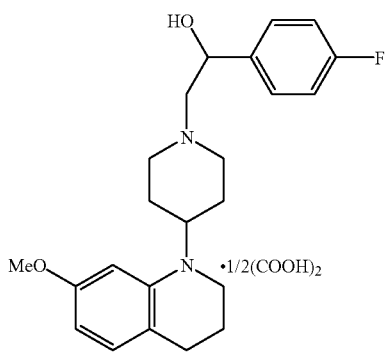

Sodium borohydride (73 mg) was added at 0° C. to a solution of 1-{1-[2-(4-fluorophenyl)-2-oxoethyl]piperidin-4-yl}-7-methoxy-1,2,3,4-tetrahydroquinoline (400 mg) in methanol (10 ml). The resultant mixture was stirred at the same temperature for 1 hr and then at room temperature for 1 hr. After the completion of the reaction, water was added to the reaction solution followed by extraction with ethyl acetate. The resulting residue was purified by column chromatography (hexane/ethyl acetate system) to give 1-{1-[2-(4-fluorophenyl)-2-hydroxyethyl]piperidin-4-yl}-7-methoxy-1,2,3,4-tetrahydroquinoline as an oil. This product was dissolved in ethanol and oxalic acid was added thereto. The resulting precipitate of salt was recrystallized form ethanol/ether to give the title compound (280 mg) (yield: 68%).

m.p.: 170–172° C.

$^1$H-NMR (400 MHz, DMSO-$d_6$):

δ(ppm) 1.62–2.01(6H, m), 2.55(2H, t, J=6.4 Hz), 2.58–2.90(4H, m), 3.09(2H, t, J=5.6 Hz), 3.21–3.39(2H, m), 3.64(3H, s), 3.65–3.78(1H, m), 4.82–4.91(1H, m), 6.06(1H, dd, J=8.4, 2.4 Hz), 6.20(1H, d, J=2.4 Hz), 6.75(1H, d, J=8.4 Hz), 7.17(2H, t, J=8.8 Hz), 7.42(2H, dd, J=8.8, 6.0 Hz).

MS: 385(M+H)+.

Example 276: 1-{1-[2-(4-Fluorophenyl)-2-fluoroethyl]piperidin-4-yl}-7-methoxy-1,2,3,4-tetrahydroguinoline hydrochloride

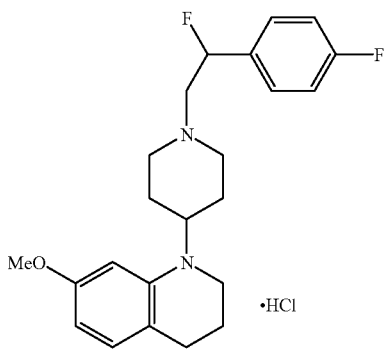

A solution of 1-{1-[2-(4-fluorophenyl)-2-hydroxyethyl]piperidin-4-yl}-7-methoxy-1,2,3,4-tetrahydroquinoline (250 mg) in methylene chloride (5 ml) was cooled to –78° C. and diethylaminosulfur trifluoride (DAST, 0.1 ml) was added thereto. Then the reaction solution was stirred at the same temperature for 45 min. After the completion of the reaction, saturated sodium bicarbonate was added to the reaction solution, which was then allowed to warm to room temperature under stirring. The reaction solution was extracted with ethyl acetate and the organic layer was dried over magnesium sulfate. After evaporating the solvent, the resulting residue was purified by silica gel column chromatography (hexane/hexane system) to give 1-{1-[2-(4-fluorophenyl)-2-fluoroethyl]piperidin-4-yl}-7-methoxy-1,2,3,4-tetrahydroquinoline as an oil. This product was dissolved in ethyl acetate. After adding hydrochloric acid, the resulting salt was recrystallized from ethanol/ether to give the title compound (60 mg) (yield: 24%).

m.p.; 227–229° C.

m.p.: 227–229 C.

$^1$H-NMR (400 MHz, DMSO-$d_6$):

δ(ppm) 1.72–1.88(4H, m), 2.10–2.34(2H, m), 2.57(2H, t, J=6.0 Hz), 3.11(2H, t, J=5.2 Hz), 3.17–3.80(6H, m), 3.66 (3H, s), 3.93–4.03(1H, m), 6.13(1H, dd, J=8.0 Hz), 6.31(1H, dd, J=50, 8.6 Hz), 6.32(1H, s), 6.79(1H, d, J=8.0 Hz), 7.31(2H, t, J=8.8, 6.0 Hz), 7.53(2H, dd, J=8, 5.6 Hz), 11.46–11.72(1H, m).

MS: 387(M+H)+.

Example 277-Synthesis of 1-[2-(4-fluorophenyl)ethyl]-4-(6-methoxy-1,2,3,4-tetrahydronaphthalen-1-yl)piperidin (277-1) 4-(1-Hydroxy-6-1,2,3,4-tetrahydronaphthalen-1-yl)pyridine

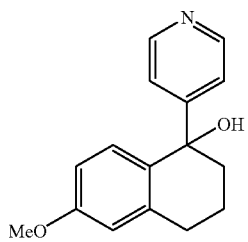

4-Bromopyridine hydrochloride 7.04g (1.0 equivalent) was partitioned between an aqueous solution of sodium hydroxide and diethyl ether. The organic layer was separated and dried over magnesium sulfate. Under nitrogen atmosphere, this solution was cooled to –78° C. Then a 1.6 M solution (25.0 ml, 1.0 equivalent) of n-butyllithium in hexane was added dropwise thereinto and the resultant mixture was stirred for additional 30 mm. Next, 6-methoxytetralone (7.049 g, 4.0 mmol) dissolved in tetrahydrofuran (50 ml) was added thereto and the resultant mixture was gradually warmed to room temperature while stirring continuously. After adding a saturated aqueous solution of ammonium chloride, the mixture was extracted with ethyl acetate. The organic layer was washed with brine and dried over magnesium sulfate. After evaporating the solvent under reduced pressure, the residue was reprecipatated from chloroform/n-hexane to give the title compound (4.019 g) as a pale yellowish brown powder (yield: 39.4%).

δ(ppm) 1.58–1.68(1H, m), 1.91–2.00(3H, m), 2.81(2H, br-s), 3.72(3H, s), 5.69(1H, s), 6.65–6.70(2H, m), 6.77(1H, d, J=8.8 Hz), 7.22(2H, d, J=6.0 Hz), 8.45(2H, d, J =6.0 Hz).

(277-2) 1-[2-(4-Fluorophenyl)ethyl]-4-(6-methoxy-3,4-dihydronaphthalen-1-yl)pyridinium bromide

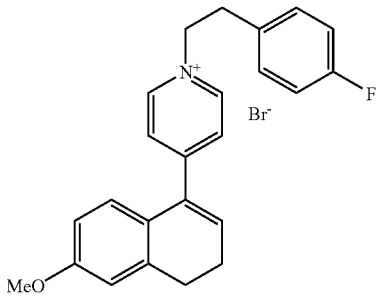

Under a nitrogen atmosphere, a mixture of 4-(1-hydroxy-6-methoxy-1,2,3,4-tetrahydronaphthalen-1-yl)pyridine (compound 1-1) (3.978 g, 15.6 mmol), 4-fluorophenethyl bromide (3.322 g, 1.05 equivalents) and acetonitrile (100 ml) was stirred at 80° C. for 26 hr. Then 6.327 g (2.0 equivalents) of 4-fluorophenethyl bromide was further added thereto and the resultant mixture was stirred for additional 12 hr. After adding ethyl acetate and water, an insoluble precipitate was collected by filtration and air-dried at 50° C. to give the title compound (5.785 g) as a pale brown powder (yield: 84.3%).

$^1$H-NMR (400 MHz, DMSO-$d_6$):

δ(ppm) 2.42–2.47(2H, m), 2.79(2H, br-t), 3.28(2H, br-t), 3.79(3H, s), 4.83(2H, t, J=7.4 Hz), 6.54(1H, t, J=4.8 Hz), 6.78(1H, dd, J=2.8, 8.4 Hz), 6.86(1H, d, J=8.4 Hz), 6.90(1H, d, J=2.8 Hz), 7.15–7.20(2H, m), 7.30–7.33(2H, m), 8.06(2H, d, J=6.8 Hz), 8.96(2H, d, J=6.8 Hz).

(277-3) 1-[2-(4-Fluorophenyl)ethyl]-4-(6-methoxy-3,4-dihydronaphthalen-1-yl)-1,2,3,6-tetrahydropyridine

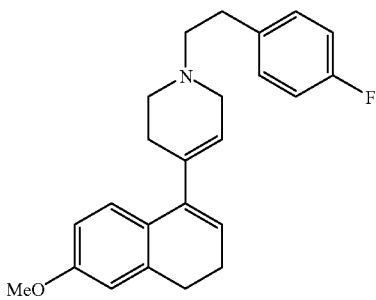

1-[2-(4-Fluorophenyl)ethyl]-4-(6-methoxy-3,4-dihydronaphthalen-1-yl)pyridinium bromide (compound 1-2) (5.710 g, 13 mmol) was dissolved in methanol (50 ml) and stirred under ice cooling. After adding 0.49 g of sodium borohydride thereto, the resultant mixture was stirred at room temperature for 2 hr. After removing the solvent under reduced pressure, water was added to the residue followed by extraction with ethyl acetate. The organic layer was washed with water and a saturated aqueous solution of sodium chloride and dried over magnesium sulfate. After evaporating the solvent under reduced pressure, the resulting residue was purified by silica gel column chromatography (n-hexane/ethyl acetate system) to give the title compound (4.169 g) as a pale brown viscous oil (yield: 88.5%).

$^1$H-NMR (400 MHz, CDCl3):

δ(ppm) 2.21–2.27(2H, m), 2.33–2.38(2H, m), 2.66–2.74 (6H, m), 2.84–2.88(2H, m), 3.19(2H, br-q), 3.80(1H, s), 5.71(1H, br-quintet), 5.84(1H, t, J=4.8 Hz), 6.69(1H, dd, J=2.4, 8.4 Hz), 6.73(1H, d, J=2.4 Hz), 6.96–7.00(2H, m), 7.11(1H, d, J=8.4 Hz), 7.17–7.20(2H, m).

(277-4) 1-[2-(4-Fluorophenyl)ethyl]-4-(6-methoxy-1,2,3,4-tetrahydrofuran-1-yl)piperidine

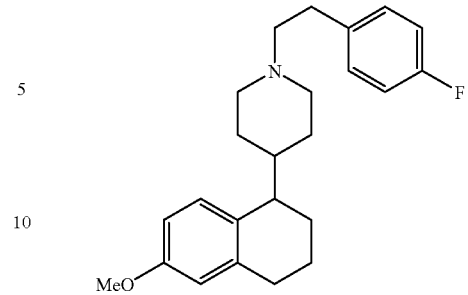

1-[2-(4-Fluorophenyl)ethyl]-4-(6-methoxy-3,4-dihydronaphthalen-1-yl)-1,2,3,6-tetrahydropyridine (compound 1-3) (1.035 g, 2.85 mmol) was dissolved in methanol (100 ml). After adding 10% palladium-carbon (0.11 g), the mixture was catalytically reduced under atmospheric pressure for 12 hr. After filtering off the catalyst, 10% palladium-carbon (0.11 g) was added thereto again and catalytic reduction was carried out under atmospheric pressure for 6 hr. Then the catalyst was filtered off and the solvent was removed under reduced pressure to give the title compound (0.910 g) as a pale brown amorphous solid (yield: 93.9%).

This product was converted into a hydrochloride in a conventional manner followed by recrystallization from ethanol/diisopropyl ether to give the title compound as a colorless powder.

Free:

m.p.: 190–191° C. (decomp.).

$^1$H-NMR (400 MHz, CDCl$_3$):

δ(ppm) 1.58–1.90(8H, m), 2.27(2H, br-s), 2.66–2.64(4H, m), 2.84(2H, br-s), 3.01(2H, br-s), 3.33(2H, br-s), 3.77(3H, s), 6.62(1H, d, J=2.8 Hz), 6.68(1H, dd, J=2.8, 8.4 Hz), 6.96–6.70(2H, m), 7.03(1H, d, J=8.4 Hz), 7.16–7.20(2H, m).

FAB-MS: [M+H]+: m/z=368.

Example 278: Synthesis of 1-[2-(4-fluorophenyl)ethyl]-4-] 6-(2-hydroxy)ethoxy-1,2,3,4-tetrahydronaphthalen-1-yl] piperidine (278-1) 1-[2-(4-Fluorophenyl)ethyl]-4-[6-hydroxy-1,2,3,4-tetrahydronaphthalen-1-yl]piperidine

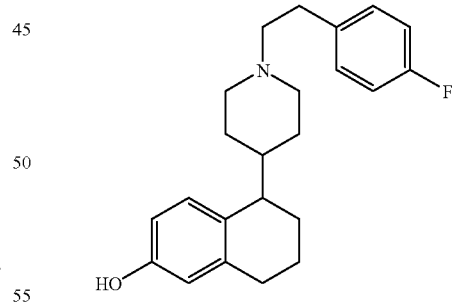

47% hydrobromic acid (45 ml) was added to 1-[2-(4-fluorophenyl)ethyl]-4-(6-methoxy-1,2,3,4-tetrahydronaphthalen-1-yl)piperidine (2.718 g, 7.57 mmol) and the resultant mixture was heated under reflux for 1 hr. After adding glacial acetic acid (20 ml), the resultant mixture was heated under reflux for additional 1.5 hr. Then the mixture was allowed to cool followed by addition of water thereto. The resulting precipitate was collected by filtration, chloroform and a saturated aqueous solution of sodium bicarbonate were added thereto and the layers were separated. The resulting solution was dried over magnesium sulfate and the solvent was evaporated under reduced pressure to give the title compound (2.043 g) as a brown amorphous substance (yield: 76.4%).

¹H-NMR (400 MHz, CDCl₃):

δ(ppm) 1.35–2.04(10H, m), 2.52–2.70(6H, m), 2.77–2.82 (2H, m), 3.08(2H, br-t), 6.45(1H, d, J=2.8 Hz), 6.59(1H, dd, J=2.8, 8.0 Hz), 6.93–6.97(2H, m), 7.00(1H, d, J=8.0 Hz), 7.11–7.14(2H, m).

(278-2) 1-[2-(4-Fluorophenyl)ethyl]-4-[6-(2-t-butyldimethylsilyloxy)ethoxy-1,2,3,4-tetrahydronaphthalen-1-yl]piperidine

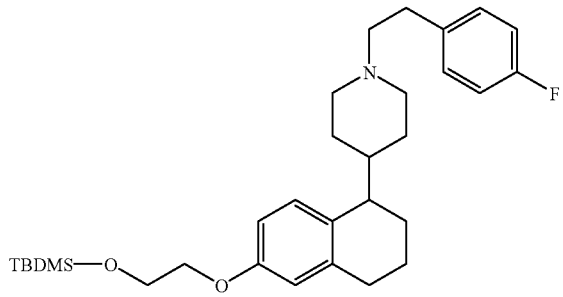

55% sodium hydride (0.055 g, 1.1 equivalents) was washed with n-hexane and suspended in N,N-dimethylformamide (3 ml) followed by stirring under ice cooling. To the resultant solution was added 1-[2-(4-fluorophenyl)ethyl]-4-[6-hydroxy-1,2,3,4-tetrahydronaphthalen-1-yl]piperidine (compound 2-1) (2.718 g, 7.57 mmol) dissolved in N,N-dimethylformamide (1 ml) and the resultant mixture was stirred at room temperature for 30 min. Then the resultant mixture was ice cooled again followed by addition of (2-t-butyldimethylsilyloxy)ethanol (0.410 g, 1.5 equivalents) dissolved in N,N-dimethylformamide (1 ml). Under a nitrogen atmosphere, the resulting mixture was stirred at 50° C. for 25 hr. After adding water, the reaction solution was extracted with ethyl acetate. The extract was washed successively with water and brine and dried over magnesium sulfate. After removing the solvent under reduced pressure, the resulting residue was purified by silica gel column chromatography (n-hexane/ethyl acetate system) to give the title compound (0.371 g) as a colorless viscous oil (yield: 63.4%).

¹H-NMR (400 MHz, CDCl₃):

δ(ppm) 0.10(6H, s), 0.91(9H, s), 1.36–1.98(12H, m), 2.40–2.54(2H, m), 2.60–2.79(4H, m), 2.99–3.06(2H, m), 3.93–3.96(2H, m), 3.98–4.01(2H, m), 6.61(1H, d, J=2.4 Hz), 6.68(1H, dd, J=2.4, 8.4 Hz), 6.93–6.97(2H, m), 7.04(1H, d, J=8.4 Hz), 7.12–7.16(2H, m).

(278-3) 1-[2-(4-Fluorophenyl)ethyl]-4-[6-(2-hydroxy)-ethoxy-1,2,3,4-tetrahydronaphthalen-1-yl]piperidine

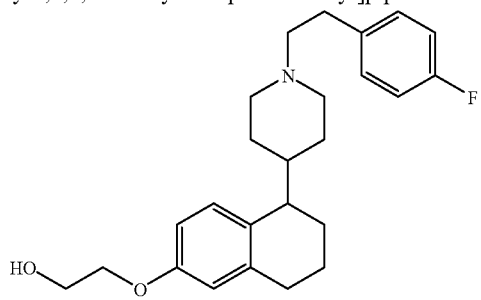

1-[2-(4-Fluorophenyl)ethyl]-4-[6-(2-t-butyldimethylsilyloxy)ethoxy-1,2,3,4-tetrahydronaphthalen-1-yl]piperidine (compound 2-2) (0.350 g, 0.684 mmol) was dissolved in tetrahydrofuran (5 ml). After adding a 1.0 M solution (821 ml, 1.2 equivalents) of tetra-n-butylammonium fluoride in tetrahydrofuran thereto, the resultant mixture was stirred at room temperature for 9.5 hr. After adding water, the reaction solution was extracted with ethyl acetate. The extract was washed successively with water (for three times) and brine and dried over magnesium sulfate. After evaporating the solvent, the resulting residue was purified by silica gel column chromatography (chloroform/methanol system) to give the title compound (0.242 g) as a colorless viscous oil (yield: 89.0%).

This product was converted into a hydrochloride in a conventional manner and recrystallized from ethanol/diisopropyl ether to give the title compound as a colorless powder.

Free:

¹H-NMR (400 MHz, CDCl₃):

δ(ppm) 1.21–1.88(12H,m), 2.41–2.45(2H,m), 2.51–2.70 (4H, m), 2.90–2.97(2H, m), 3.83(2H, t, J=9.2 Hz), 3.95(2H, t, J=9.2 Hz), 6.53(1H, d, J=2.8 Hz), 6.60(1H, dd, J=2.8, 8.8 Hz), 6.83–6.87(2H, m), 6.96(1H, d, J=8.8 Hz), 7.02–7.05 (2H, m).

FAB-MS: [M+H]+: m/z=398.

m.p.: 213–215° C. (decomp.).

Example 279: Synthesis of trans-1-(4-ethylpiperazin-1-yl)-7-methoxy-2-(4-trifluoromethylphenoxy)-1,2,3,4-tetrahydronaphthalene (279-1) trans-1-(4-Ethylpiperazin-1-yl)-2-hydroxy-7-methoxy-1,2,3,4-tetrahydronaphthalene

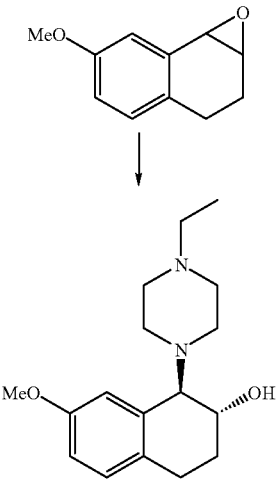

7-Methoxy-3,4-dihydronaphthalene-1,2-oxide (5.28 g) synthesized in accordance with the method described in Tetrahedron, 33, 85–94. was dissolved in n-butanol (100 ml). After adding ethylpiperazine (3.42 g), the resultant mixture was heated under reflux for 12 hr. After removing the solvent under reduced pressure, the residue was recrystallized from ethyl acetate (5 ml) and ether (80 ml). The crystals were collected by filtration and washed with ether to give the title compound (6.88 g) as pale yellow crystals (yield: 79%).

¹H-NMR (400 MHz, CDCl₃):

δ(ppm) 1.73–1.85(1H, m), 2.09–2.16(1H, m), 2.48(4H, br-s), 2.77(2H, m), 2.91(4H, br-s), 3.16(1H, br-s), 3.68(1H, d, J=8.5 Hz), 3.78(3H, s), 3.95(1H, ddd, J=3.0 Hz, 8.5 Hz, 10.5 Hz), 6.71(1H, br-d), 6.99(1H, d, J=10.0 Hz), 7.12(1H, br-s).

(279-2) trans-1-(4-Ethylpiperazin-1-yl)-7-methoxy-2-(4-trifluoromethylphenoxy)-1,2,3,4-tetrahydronaphthalene

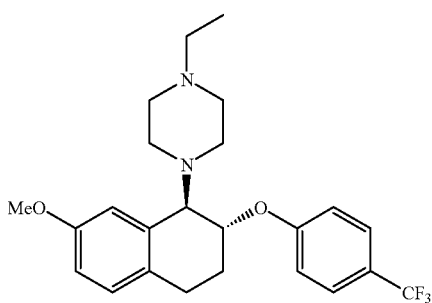

A solution of potassium t-butoxide (247 mg) and 4-fluorobenzotrifluoride (492 mg) in dimethylformamide (1 ml) was added slowly at room temperature to a solution of trans-1-(4-ethylpiperazin-1-yl)-2-hydroxy-7-methoxy-1,2,3,4-tetrahydronaphthalene (435 mg) in dimethylformamide (3 ml) and the resultant mixture was stirred for 4 hr. After adding water (50 ml), the reaction mixture was extracted with ethyl acetate (50 ml) for three times. The organic phase was washed with water (50 ml) twice and brine (50 ml) once and dried over anhydrous magnesium sulfate followed by concentration under reduced pressure. The resulting residue was purified by silica gel column chromatography (NH-DM2035, Fuji Silysia Chemical Ltd., hexane/ethyl acetate system) to give the title compound (190 mg) as a colorless oil (yield: 29%).

m.p. (oxalate): 207–210° C.

$^1$H-NMR (400 MHz, CDCl$_3$):

δ(ppm) 1.03(3H, t, J=7.0 Hz), 1.85–1.96(1H, m), 2.15–2.22(1H, m), 2.39(2H, q, J=7.0 Hz), 2.42(4H, br-s), 2.70(2H, br-s), 2.77(2H, br-s), 2.80(2H, t, J=6.0 Hz), 3.81 (3H, s), 4.05(1H, d, J=7.5 Hz), 4.79(1H, m), 6.76(1H, dd, J=3.0 Hz, 8.0 Hz), 6.97(2H, d, J=8.5 Hz), 7.02(1H, d, J=8.0 Hz), 7.33(1H, d, J=3.0 Hz), 7.53(2H, d, J=8.5 Hz).

FAB-Mass:435(MH+).

Example 280: Synthesis of 1-{4-[2-(4-fluorophenyl)ethyl]piperazin-1-yl}-7-methoxy-1,2,3,4-tetrahydronaphthalene hydrochloride (280-1) 1-Hydroxy-7-methoxy-1,2,3,4-tetrahydronaphthalene

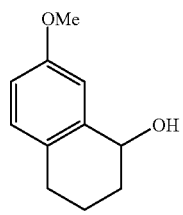

7-Methoxy-1,2,3,4-tetrahydronaphthalen-1-one (5 g) was dissolved in methanol and sodium tetrahydroborate (1.3 g) was added thereto at 0° C. After reacting at room temperature for 2 hr, the reaction solution was partitioned between ethyl acetate and water. The ethyl acetate layer was washed with water, dried and concentrated under reduced pressure to give the title compound (5.19 g) as a colorless oil.

(280-2) 1-(4-Acetylpiperazin-1-yl)-7-methoxy-1,2,3,4-tetrahydronaphthalene

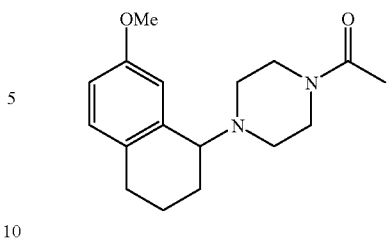

1-Hydroxy-7-methoxy-1,2,3,4-tetrahydronaphthalene (5.19 g) was reacted with thionyl chloride (4.3 ml) in ether at room temperature for 3 hr. Then the reaction solution was partitioned between ether and water. The ether layer was washed successively with water, a saturated aqueous solution of sodium bicarbonate and brine, dried and concentrated under reduced pressure. The resulting residue, 1-acetylpiperazine and potassium carbonate were heated under reflux in acetone for 10 hr. Then the reaction solution was filtered and insolubles were washed with methylene chloride. After concentrating the filtrate under reduced pressure, the resulting residue was purified by silica gel column chromatography (methylene chloride/methanol system) to give the title compound (3.0 g) as a pale yellow oil.

(280-3) 7-Methoxy-1-(Diperazin-1-yl)-1,2,3,4-tetrahydronaphthalene

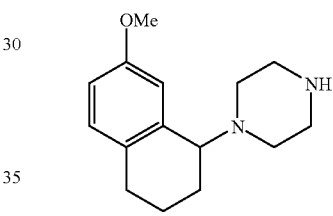

1-(4-Acetylpiperazin-1-yl)-7-methoxy-1,2,3,4-tetrahydronaphthalene (0.85 g) was dissolved in ethanol (10 ml). After adding an 8 N aqueous solution (3 ml) of sodium hydroxide, the resultant mixture was heated under reflux for 3 hr. Then the liquid reaction mixture was concentrated under reduced pressure and the residue was purified by NH-silica gel column chromatography (ethyl acetate) to give the title compound (0.6 g) as a pale brown oil.

(280-4) 1-[4-(4-Fluorophenylacetyl)piperazin-1-yl]-7-methoxy-1,2,3,4-tetrahydronaphthalene

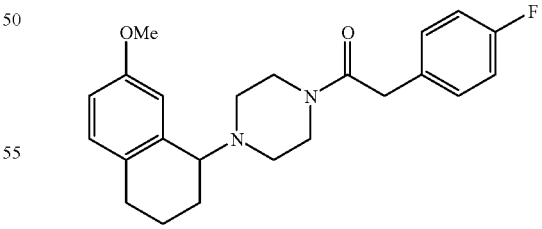

7-Methoxy-1-(piperazin-1-yl)-1,2,3,4-tetrahydronaphthalene (0.6 g) was reacted in methylene chloride for 2 hr with an acid chloride prepared from 4-fluorophenylacetic acid (0.44 g) and thionyl chloride (0.21 ml) Then the liquid reaction mixture was partitioned between methylene chloride and water, extracted with methylene chloride, dried and concentrated under reduced pressure. The resulting residue was purified by silica gel column chromatography (toluene/acetone system) to give the title compound (0.56 g) as an oil.

(280-5) 1-{4-[2-(4-Fluorophenyl)ethyl]piperdin-1-yl}-7-methoxy-1,2,3,4-tetrahydronaphthalene

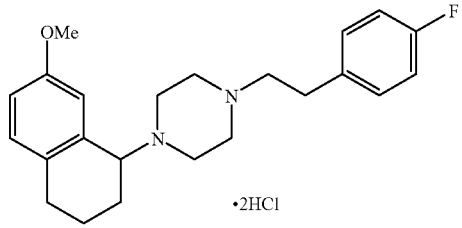

1-[4-(4-Fluorophenylacetyl)piperazin-1-yl]-7-methoxy-1,2,3,4-tetrahydronaphthalene (0.41 g) and lithium aluminum hydride (0.05 g) were heated under reflux in THF (15 ml) for 6 hr. Next, the reaction solution was cooled and water (50 ml) a 5 N aqueous solution (50 ml) of sodium hydroxide and further water (150 ml) were successively added thereto. After stirring the resultant mixture at room temperature for 1 hr, the resulting precipitate was filtered through celite and washed with THF. The filtrate was concentrated under reduced pressure and the resulting residue was purified by silica gel column chromatography (toluene/acetone system) to give the title compound (0.38 g) as an oil.

m.p.: 205° C. (decomp.).

$^1$H-NMR (400 MHz, CDCl$_3$):

δ(ppm) 1.60–1.70(2H, m), 1.93–2.02(2H, m), 2.48–2.81 (14H, m), 3.76–3.83(1H, m), 3.79(3H, s), 6.71(1H, dd, J=8.4, 2.8 Hz), 6.96(2H, t, J=8.4 Hz), 7.12–7.19(3H, m), 7.32(1H, d, J=2.8 Hz).

FAB-Mass: 269(MH+).

Example 281: Synthesis of 1-{4-[2-(4-fluorophenyl)-2-oxoethyl]piperazin-1-yl}-7-methoxy-1,2,3,4-tetrahydronaphthalene hydrochloride

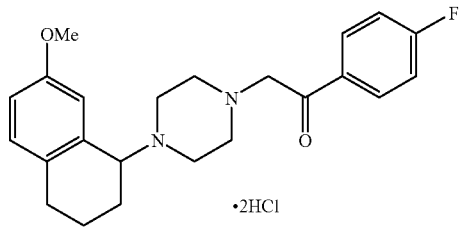

7-Methoxy-1-(piperazin-1-yl)-1,2,3,4-tetrahydronaphthalene (0.27 g), 4-fluorophenacyl bromide (0.24 g) and diisopropylethylamine (0.43 g) were dissolved in DMF (15 ml) and reacted at room temperature for 12 hr. Then the liquid reaction mixture was distributed between ethyl acetate and water. The ethyl acetate layer was washed with water, dried and concentrated under reduced pressure. The resulting residue was purified by silica gel column chromatography (ethyl acetate/n-hexane system) to give an oil (0.34 g). This product was converted into a hydrochloride in a conventional manner to give the title compound as a white powder.

m.p.: 194° C. (decomp.).

$^1$H-NMR (400 MHz, CDCl$_3$):

δ(ppm) 1.60–1.69(2H, m), 1.92–2.01(2H, m), 2.53–2.68 (8H, m), 3.76(2H, s), 3.79(3H, s), 6.70(1H, dd, J=8.4, 2.8 Hz), 6.97(1H, d, J=8.4 Hz), 7.09–7.15(2H, m), 7.31(1H, d, J=2.8 Hz), 8.04–8.10(2H, m).

FAB-Mass: 383(MH+).

Example 282-1: Synthesis of 8-aminobenzosuberone

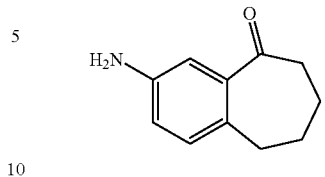

Ammonium nitrate (24 g) was added in portions at –10° C. to a solution of benzosuberone (40 g) and trifluoroacetic anhydride (85 ml) in chloroform (400 ml) and the resultant mixture was stirred at room temperature overnight. The reaction solution was concentrated under reduced pressure, then a saturated aqueous solution of sodium bicarbonate and ethyl acetate were added thereto and the layers were separated. The organic layer was washed with brine and dried over anhydrous magnesium sulfate followed by purifying by silica gel column chromatography (hexane/ethyl acetate system). Then palladium carbon (5 g) and ethanol (300 ml) were added thereto and catalytic reduction was carried out under hydrogen atmosphere at 50° C. After stirring overnight, the catalyst was filtered off and the residue was concentrated under reduced pressure and purified by silica gel column chromatography (hexane/ethyl acetate system) to give the title compound (10 g) (yield: 24%).

$^1$H-NMR (400 MHz, CDCl$_3$):

δ(ppm) 1.71–1.89(4H, m), 2.67–2.72(2H, m), 2.80–2.85 (2H, m), 3.70(2H, br-s), 6.76(1H, dd, J=8, 3 Hz), 6.97(1H, d, J=8 Hz), 7.04(1H, t, J=3 Hz).

Example 282-2: Synthesis of 8-methoxybenzosuberone

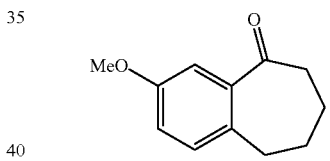

An aqueous solution (15 ml) of sodium nitrite (9.0 g) was added dropwise into a mixture of 8-aminobenzosuberone (4.0 g), conc. sulfuric acid (3 ml) and water (47 ml) at 5° C. or below. After 30 min, the reaction solution was added dropwise into a saturated aqueous solution (25 ml) of copper sulfate heated to 90° C. and stirred for 30 min. After cooling the reaction solution to room temperature, ethyl acetate was added thereto and the layers were separated. The organic layer was washed with brine, dried over anhydrous magnesium sulfate and concentrated under reduced pressure. To the residue were added methyl iodide, potassium carbonate and dimethylformamide and the resultant mixture was stirred at room temperature for 7 hr. After concentrating the reaction solution under reduced pressure, water and ethyl acetate were added thereto and the layers were separated. The organic layer was washed with brine and dried over anhydrous magnesium sulfate followed by purifying by silica gel column chromatography (hexane/ethyl acetate system) to give the title compound (3.5 g) (yield: 80%).

$^1$H-NMR (400 MHz, CDCl$_3$):

δ(ppm) 1.78–1.90(4H, m), 2.70–2.75(2H, m), 2.87–2.92 (2H, m), 3.81(3H, s), 6.99(1H, dd, J=8, 3 Hz), 7.11(1H, d, J=8 Hz), 7.29(1H, t, J=3 Hz).

Example 282-3: Synthesis of 1-(4-fluorophenethyl)-4-(2-methoxybenzocycloheptan-9-yl)piperazine

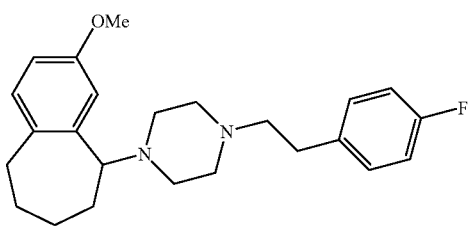

Sodium borohydride (0.7 g) was added to a solution of 8-methoxybenzosuberone (3.5 g) in ethanol (40 ml) and the resultant mixture was stirred at room temperature for 1 hr. Then the reaction solution was concentrated under reduced pressure and diluted with a saturated aqueous solution of sodium bicarbonate and ethyl acetate and the layers were separated. The organic layer was washed with brine and dried over magnesium sulfate. After evaporating the solvent, toluene (50 ml) and thionyl chloride (2.4 g) were added to the residue. The resultant mixture was stirred for 2 hr and then concentrated under reduced pressure. To the residue were added dimethylformamide (50 ml), 1-(4-fluorophenethyl)piperazine (2.1 g) synthesized in accordance with the method described in JP-A 54-92979 and triethylamine (0.7 g) and the resultant mixture was stirred at 100° C. for 3 hr. After concentrating the liquid reaction mixture under reduced pressure, a saturated aqueous solution of sodium bicarbonate and ethyl acetate were added thereto and the layers were separated. The organic layer was washed with brine and dried over anhydrous magnesium sulfate. The resulting residue was purified by silica gel column chromatography (methylene chloride/ethanol system) followed by conversion into a hydrochloride in a conventional manner to give the hydrochloride (230 mg) of the title compound as a white powder (yield: 11%).

m.p (hydrochloride): 188–190° C.

$^1$H-NMR (400 MHz, DMSO-d$_6$):

δ(ppm) 1.20–1.35(1H, m), 1.50–1.65(2H, m), 1.74–1.98 (4H, m), 2.06–2.19(2H, m), 2.21–2.67(4H, m), 2.96–3.06 (3H, m), 3.20–3.35(3H, m), 3.49–3.80(2H, m), 3.74(3H, s), 6.69–6.89(2H, m), 7.00–7.09(1H, m), 7.12–7.20(2H, m), 7.28–7.40(2H, m).

FAB-Mass: 383(MH+).

Example 283: Synthesis of 5-{4-[2-(4-fluorophenyl)-ethyl]piperazin-1-yl}-5,6,7,8-tetrahydroisoquinoline hydrochloride (283-1) 5,6,7,8-Tetrahydroisoquinoline-2-oxide

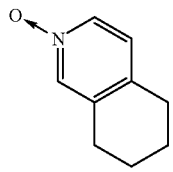

5,6,7,8-Tetrahydroisoquinoline (10 g) was added to methylene chloride (100 ml) and a 10% aqueous solution (100 ml) of sodium carbonate. Under vigorous stirring, a 70% solution of m-chloroperbenzoic acid (20 g) in methylene chloride (100 ml) was dropped thereinto at 0° C. Then the reaction solution was extracted with methylene chloride. The methylene chloride layer was washed with brine, dried and concentrated under reduced pressure. The resulting residue was purified by silica gel column chromatography (methylene chloride/methanol system) to give the title compound (7.50 g) as a colorless oil.

(283-2) 5,6,7,8-Tetrahydroisoquinolin-5-ol

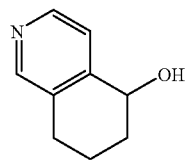

5,6,7,8-Tetrahydroisoquinoline-2-oxide (7.50 g) was dissolved in acetic anhydride (30 ml). After reacting at 120° C. for 6 hr, the reaction solution was concentrated under reduced pressure. Next, a 10% aqueous solution (30 ml) of hydrochloric acid was added to the residue followed by heating at 100° C. for 2 hr. The reaction solution was cooled, basified with 5N sodium hydroxide and extracted with ethyl acetate. The ethyl acetate layer was washed with water and dried. After evaporating the solvent under reduced pressure, the resulting residue was purified by silica gel column chromatography (ethyl acetate) to give the title compound (1.90 g).

(283-3) 5-{4-[2-(4-Fluorophenyl)ethyl]piperazin-1-yl}-5,6,7,8-tetrahydroisoquinoline hydrochloride

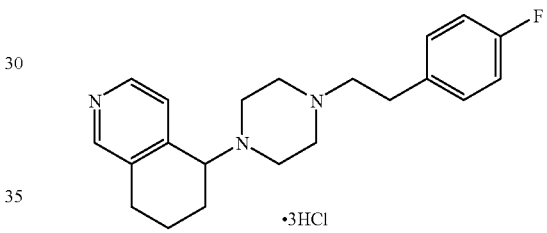

5,6,7,8-Tetrahydroisoquinolin-5-ol (1.90 g), methanesulfonyl chloride (1.48 g) and triethylamine (5.0 ml) were reacted in THF (50 ml) at 0° C. for 6 hr. The reaction solution was partitioned between ethyl acetate and a saturated aqueous solution of sodium bicarbonate. The ethyl acetate layer was washed with water, dried and concentrated under reduced pressure to give a pale yellow oil. This product was dissolved in DMF followed by addition of 4-[2-(4-fluorophenyl)ethyl]piperazine (2.0 g) and potassium carbonate (2.0 g). After reacting for 12 hr, the reaction solution was concentrated under reduced pressure and the obtained residue was purified by silica gel column chromatography (methylene chloride/methanol system) to give a pale yellow oil (0.71 g). Next, this product was converted into a hydrochloride in a conventional manner to give the title compound (0.52 g) as a white powder.

m.p.: 174–176° C.

$^1$H-NMR (400 MHz, D$_2$O)

δ(ppm) 1.77(2H, m), 1.99–2.16(2H, m), 2.87(2H, m), 3.03(4H, m), 3.38(4H, m), 4.19(1H, m), 7.05(2H, t, J=8.4 Hz), 7.26(2H, dd, J=8.4, 7.2 Hz), 8.28(1H, d, J=8.0 Hz), 8.43(1H, d, J=8.0 Hz), 8.45(1H, s).

FAB-Mass: 340(MH+).

Example 284: Synthesis of 1-[1-(4-fluorophenethyl)pieridin-4-yl]-5,6-methylenedioxyindoline

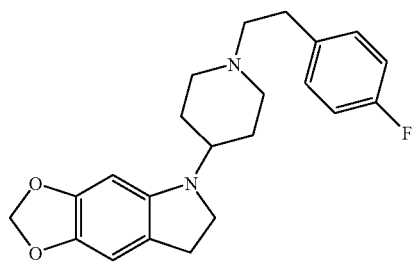

1-(4-Fluorophenethyl)-4-(3,4-methylenedioxyphenyl)-aminopiperidine (10 g) synthesized in accordance with the method described in Referential Example 1 of JP-B 40-6347 was treated as in Example 106 to give the hydrochloride (330 mg) of the title compound as dark red prismatic crystals (yield: 2.8%).

m.p. (hydrochloride): 229° C. (decomp.)

$^1$H-NMR (400 MHz, DMSO-$d_6$):

δ(ppm) 1.80–2.09(4H, m), 2.72–2.85(2H, m), 2.99–3.19 (4H, m), 3.19–3.35(4H, m), 3.55–3.61(3H, m), 5.82(2H, s), 6.44(1H, s), 6.71(1H, s), 7.12–7.20(2H, m), 7.29–7.38(2H, m).

FAB-Mass: 369(MH+).

Example 285: Synthesis of 1-[1-(4-fluorophenethyl) piperidin-4-yl]-6-acetamidomethylindole

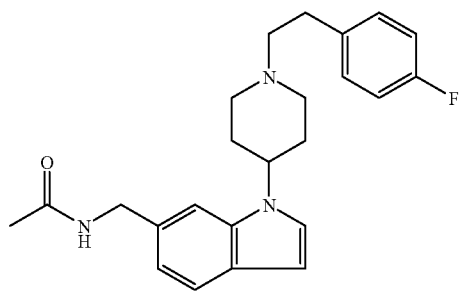

1-[1-(4-Fluorophenethyl)piperidin-4-yl]-6-acetamidomethylindoline (7.5 g) obtained in Example 133 was dissolved in acetone (500 ml) at 50° C. To the resultant solution was added active manganese dioxide (35.6 g) in portions under stirring. The resulting suspension was heated under reflux for 1.5 hr, then filtered through celite and washed with acetone. The filtrate was concentrated under reduced pressure and the resulting pale yellow solid was recrystallized from ethyl acetate to give the title compound (4.2 g) as awhite powder (yield: 56%).

$^1$H-NMR (400 MHz, DMSO-$d_6$):

δ(ppm) 1.86(s, 3H), 1.88–2.04(m, 4H), 2.23(dt, J=11.2, 2.4 Hz, 2H), 2.55–2.62(m, 2H), 2.74–2.81(m, 2H), 3.09(br-d, 2H), 4.26–4.36(m, 1H), 4.33(d, J=5.6 Hz, 2H), 6.41(d, J=3.2 Hz, 1H), 6.94(d, J=7.2 Hz, 1H), 7.08–7.15(m, 2H), 7.26–7.33(m, 2H), 7.41(br-s, 1H), 7.45–7.49(m, 2H), 8.26–8.32(m, 1H).

m.p.: 127–128° C.

Mass: FAB+394(M+H).

Example 286: Synthesis of 1-[1-(4-fluorophenethyl) piperidin-4-yl]-6-(N-isopropylcarbamoylmethyl)indole

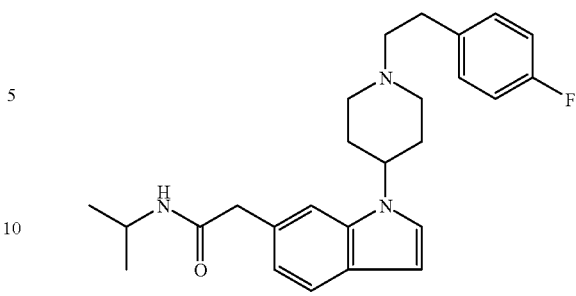

A suspension of 1-[1-(4-fluorophenethyl)piperidin-4-yl]-6-(isopropylcarbamoylmethyl)indoline (1 g) obtained in Example 151 and active manganese dioxide (4 g) in 1,2-dichloroethane (100 ml) was heated under reflux for 1.5 hr, then filtered through celite and concentrated under reduced pressure. The resulting pale yellow solid was recrystallized from ethyl acetate to give the title compound (0.4 g) as a white powder (yield: 40%).

$^1$H-NMR (400 MHz, CDCl$_3$):

δ(ppm) 1.04(d, J=6.0 Hz, 6H), 2.04–2.18(m, 4H), 2.25–2.40(m, 2H), 2.63–2.74(m, 2H), 2.80–2.91(m, 2H), 3.15–3.28(m, 2H), 3.68(s, 2H), 4.02–4.12(m, 1H), 4.20–4.31(m, 1H), 5.20–5.32(m, 1H), 6.53(d, J=3 Hz, 1H), 6.95–7.02(m, 3H), 7.18–7.21(m, 2H), 7.26–7.28(m, 2H), 7.61(d, J=8 Hz, 1H).

m.p.: 146–148° C.

Mass: ESI 422(M+).

Example 287: Synthesis of 1-[1-(4-fluorophenethyl) piperidin-4-yl]-6-(1-methylpyrrol-2-yl)indole

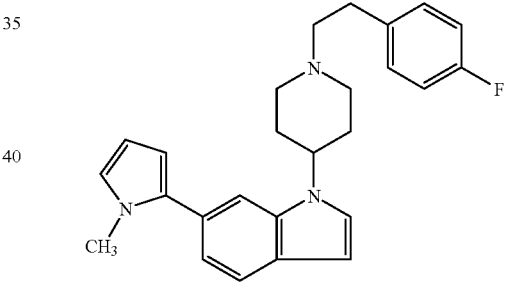

1-[1-(4-Fluorophenethyl)piperidin-4-yl]-6-bromoindole (0.2 g) was dissolved in toluene (2.50 ml). Next, 1-methyl-2-tributylstannylpyrrole (1.44 g) synthesized in accordance with the method described in Tetrahedron Lett., 4407 (1986). with the use of 1-methylpyrrole and tributylthin chloride was added thereto and the resultant mixture was heated under reflux for 3 hr under nitrogen atmosphere. After adding ethyl acetate, the mixture was washed with brine, dried over anhydrous magnesium sulfate and concentrated under reduced pressure. The resulting residue was purified by silica gel column chromatography (hexane/ethyl acetate system) to give the title compound (0.115 g) as a yellow oil (yield: 57.28%).

$^1$H-NMR (400 MHz, CDCl$_3$):

δ(ppm) 1.92–1.99(4H, m), 2.05–2.13(2H, m), 2.47–2.51 (2H, m), 2.64–2.68(2H, m), 3.32(2H, br-d), 3.50(3H, s) 4.05–4.13(1H, m), 6.16–6.19(2H, m), 6.38(1H, d, J=3.6 Hz), 6.57(1H, t, J=2.2 Hz), 6.82(2H, t, J=8.6 Hz), 6.98–7.03(3H, m), 7.11(1H, d, J=3.6 Hz), 7.23(1H, s), 7.48(1H, d, J=8.8 Hz).

ESI-Mass: 402.

Example 288: Synthesis of 1-[1-(4-acetamidomethylphenethyl)piperidin-4-yl]indole

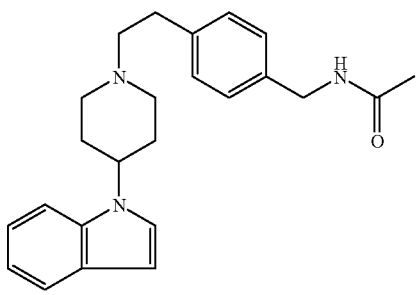

A suspension of 1-[1-(4-acetamidomethylphenethyl) piperidin-4-yl]indoline (0.80 g) obtained in Example 36 and active manganese dioxide (1.32 g) in chloroform (30 ml) was heated under reflux for 6 hr with vigorous stirring. Then the reaction mixtures were filtered through celite and the residue was washed with chloroform. The filtrate was concentrated under reduced pressure and the obtained residue was crystallized from a solvent mixture of ethyl acetate with hexane to give the title compound (0.64 g) as a white powder (yield: 80.4%).
m.p.: 133–134° C.
$^1$H-NMR (400 MHz, CDCl$_3$):
δ(ppm) 2.02(3H, s), 2.06–2.35(5H, m), 2.64–2.73(2H, m), 2.82–2.90(2H, m), 3.15–3.25(2H, br-d), 4.22–4.32(1H, m), 4.41(2H, d, J=5.6 Hz), 6.53(1H, d, J=3.6 Hz), 7.07–7.13(1H, m), 7.18–7.26(5H, m), 7.38(1H, d, J=8.0 Hz), 7.63(2H, d, J=8.0 Hz).
FAB-Mass: 376(MH+).

Example 289: Synthesis of 1-[1-(4-fluorophenethyl)piperidin-4-yl]-6-cyanoindole

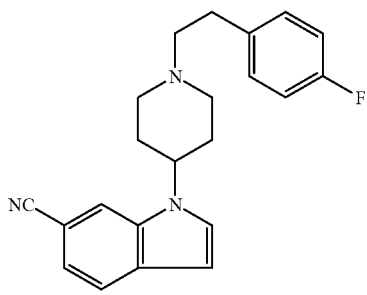

1-[1-(4-Fluorophenethyl)piperidin-4-yl]-6-cyanoindoline (0.50 g) obtained in Example 124 and active manganese dioxide (1.00 g) were treated as in Example 288 to give the title compound (0.42 g) as a white powder (yield: 83.8%).
m.p.: 131–132° C.
$^1$H-NMR (400 MHz, CDCl$_3$):
δ(ppm) 2.06–2.16(3H, m), 2.25–2.34(2H, m), 2.64–2.70(2H, m), 2.79–2.87(2H, m), 3.16–3.24(2H, m), 4.21–4.31(1H, m), 4.41(2H, d, J=5.6 Hz), 6.60(1H, d, J=3.2 Hz), 6.97–7.03(2H, m), 7.16–7.22(2H, m), 7.33(1H, dd, J=8.0, 1.2 Hz), 7.44(1H, d, J=3.2 Hz), 7.67(2H, d, J=8.0 Hz), 7.73(1H, br-s).
FAB-Mass: 378(MH+).

Example 290: Synthesis of cis-1-[1-(4-fluorophenethyl)-3-methylpiperidin-4-yl]indole

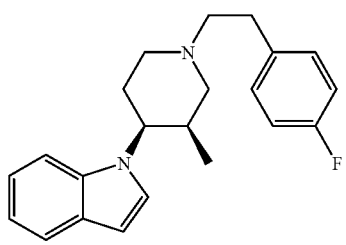

cis-1-[1-(4-Fluorophenethyl-3-methylpiperidin-4-yl]indoline was synthesized in a similar manner to the one of Example 79-4 by starting with indoline (560 mg), 1-[2-(4-fluorophenyl)ethyl]-3-methyl-4-piperidone (1.19 mg) and sodium triacetoxyborohydride (2.40 g). As the by-product in this reaction, the title compound (30 mg) was obtained as a white amorphous substance (yield: 3%).
$^1$H-NMR (400 MHz, CDCl$_3$):
δ(ppm) 0.80(3H, d, J=6.5 Hz), 1.88(1H, br-d), 2.26(1H, dt, J=12.0, 3.5 Hz), 2.35–2.67(5H, m), 2.74–2.82(2H, m), 2.89(1H, br-d), 3.14(1H, br-d), 4.46(1H, dt, J=120.5, 4.0 Hz), 6.49(1H, d, J=3.1 Hz), 6.98(2H, br-t), 7.10(1H, br-d), 7.16–7.22(4H, m), 7.36(2H, d, J=8.0 Hz), 7.64(2H, d, J=8.0 Hz).
FAB-Mass: 337(MH+).

Example 291: Synthesis of 1-[1-(4-fluorophenethyl)homopiperidin-4-yl]-6-methoxyindoline (291-1) 1-(4-Fluorophenethyl)-4-(3-methoxyphenylamino)-homopiperidine

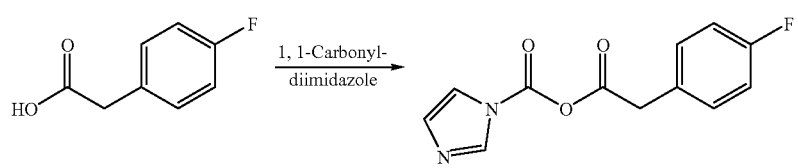

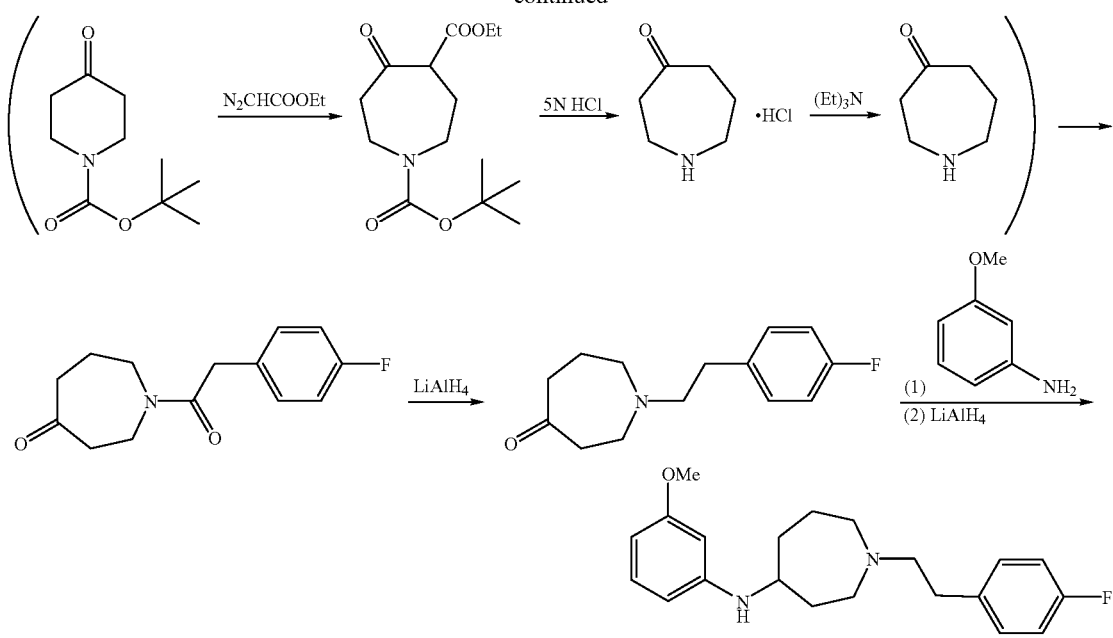

4-Fluorophenylacetic acid (1.5 g) was dissolved in tetrahydrofuran (44 ml). To the resultant solution was added N,N-carbonyldimidazole (1.6 g) and the resultant mixture was stirred at room temperature for 15 min. Next, 4-homopiperidone hydrochloride (1.0 g) synthesized in accordance with the method described in Synth. Commun., 1249(1992). and triethylamine (1.2 ml) were successively added thereto followed by stirring at room temperature for 12 hr. After adding water, the reaction solution was partitioned between water and ethyl acetate. The organic layer was washed with brine, dried over anhydrous magnesium sulfate and concentrated under reduced pressure. The residue was dissolved in tetrahydrofuran and lithium aluminum hydride was added thereto under ice cooling. Next, the resultant mixture was heated under reflux and treated in a conventional manner. The resulting product was purified by silica gel column chromatography (hexane/ethyl acetate system) to give a brown oil.

The above product and m-anisidine (0.39 ml) were treated as in Example 1 to give a yellow oil. This product was dissolved in tetrahydrofuran (30 ml). Under ice cooling, lithium aluminum hydride (0.72 g) was added thereto and the resultant mixture was heated under reflux for 2.5 hr. Under ice cooling, water (0.72 ml), a 5 N aqueous solution (0.72 ml) of sodium hydroxide and further water (2.2 ml) were successively added thereto and the resulting solid was filtered off. The filtrate was concentrated under reduced pressure and the obtained residue was purified by silica gel column chromatography (ethyl acetate/methanol system) to give the title compound (1.348 g) as a brown oil (yield: 44.6%).

$^1$H-NMR (400 MHz, CDCl$_3$):

δ(ppm) 1.62–1.79(5H, m), 1.95–2.04(1H, m), 2.59–2.67 (2H, m), 2.70–2.85(6H, m), 3.66(1H, m), 3.76(3H, s), 4.02 (1H, br-s), 6.00(1H, t, J=2.4 Hz), 6.12(1H, ddd, J=0.8, 2.4, 8.0 Hz), 6.23(1H, ddd, J=0.8, 2.4, 8.0 Hz), 6.98(2H, t, J=8.8 Hz), 7.05(1H, t, J=8.0 Hz), 7.16(2H, dd, J=4.2, 8.8 Hz).

(291-2) 1-(4-Fluorophenethyl)-4-(6-methoxyisatin-1-yl) homopiperidine

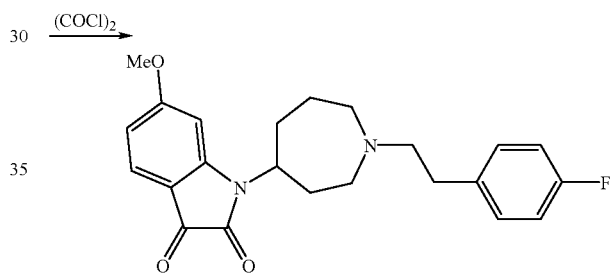

1-(4-Fluorophenethyl)-4-(3-methoxyphenylamino) homopiperidine (1.148 g) was treated in accordance with the method described in J. Prakt. Chem., 137 (1922). to give the title compound (1.203 g) as an orange oil (yield: 90.6%).

$^1$H-NMR (400 MHz, CDCl$_3$):

δ(ppm) 1.83–2.00(3H, m), 2.10(2H, m), 2.78(7H, br-s), 2.87(2H, br-s), 3.93(3H, s), 3.43(1H, m), 4.40(1H, br-s), 6.52(1H, s), 6.53(1H, d, J=8.8 Hz), 6.99(1H, t, J=8.8 Hz), 7.18(1H, dd, J=5.6, 8.8 Hz), 7.59(1H, d, J=8.8 Hz).

(291-3) 1-[1-(4-Fluorophenethyl)homopiperidin-4-yl]-6-methoxyindoline

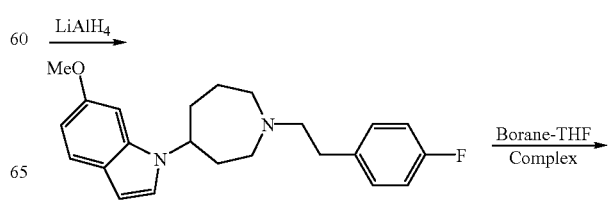

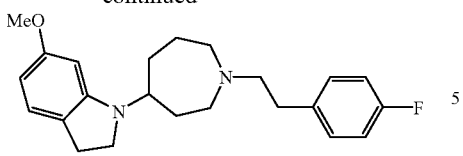

1-(4-Fluorophenethyl)-4-(6-methoxyisatin-1-yl) homopiperidine (0.4 g) was dissolved in tetrahydrofuran (1.0 ml). Under nitrogen atmosphere, a 2.0 M solution (4.0 ml) of borane-tetrahydrofuran complex in tetrahydrofuran was added dropwise thereinto in a water bath followed by heating under reflux for 3 hr. The reaction solution was ice cooled and water was added thereto. Next, the reaction solution was partitioned between water and ethyl acetate and the organic layer was washed with brine, dried over anhydrous magnesium sulfate and concentrated under reduced pressure. The residue was dissolved in pyridine (5.0 ml) and stirred at room temperature for 11 hr. After adding water, the reaction solution was partitioned between water and ethyl acetate. The organic layer was washed with brine, dried over anhydrous magnesium sulfate and concentrated under reduced pressure. Then the resulting residue was purified by NH-silica gel column chromatography (hexane/ethyl acetate system) to give 1-(4-florophenethyl)-4-(6-methoxyindol-1-yl)homopiperidine as a yellow oil. Then this product was treated as in Production Example 64 to give the free title compound (0.095g) asayellowoil (yield: 27.2%).

Next, this product was treated with oxalic acid in a conventional manner to give the oxalate of the title compound as a hygroscopic solid.

Free:

$^1$H-NMR (400 MHz, CDCl$_3$):

δ(ppm) 1.61–1.99(6H, m), 2.66–2.90(10H, m), 3.38(2H, dt, J=1.6, 8.6 Hz), 3.63(1H, m), 3.76(3H, s), 6.00(1H, d, J=2.4 Hz), 6.12(1H, dd, J=2.4, 7.6 Hz), 6.92(1H, d, J=7.6 Hz), 6.97(2H, t, J=8.4 Hz), 7.15(2H, dd, J=5.6, 8.4 Hz).

ESI-Mass: 369.1

Example 292: Synthesis of 1-[1-(4-fluorophenethyl)-pyrrolidin-3-yl]-6-methoxyindoline (292-1) 1-Benzyl-3-(6-methoxyindolin-1-yl)pyrrolidine

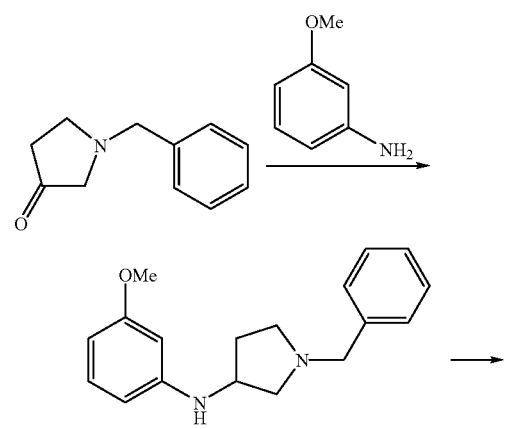

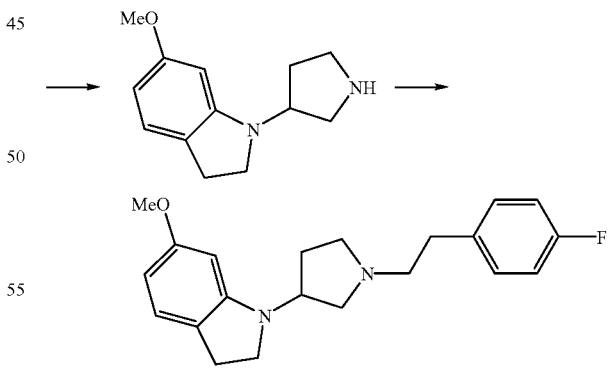

1-Benzyl-3-pyrrolidone (10.0 g) and m-anisidine (0.39 ml) were treated as in Example 1 to give a brown oil. Then this product was treated as in the above (291-2) to give red crystals. Subsequently, these crystals were treated as in the above (291-3) to give the title compound (2.301 g) as a pale yellow oil (yield: 13.1%).

$^1$H-NMR (400 MHz, CDCl$_3$):

δ(ppm) 2.00(1H, br-s), 2.21(1H, br-s), 2.68–2.98(4H, br-s), 2.86 (1H, t, J=8.0 Hz), 3.42 (1H, q, J=8.0 Hz), 3.60–3.90 (2H, br-s), 3.75(3H, s), 4.24(1H, br-s), 6.09(1H, d, J=2.4 Hz), 6.16(1H, dd, J=2.4, 8.0 Hz), 6.92(1H, d, J=8.0 Hz), 7.27–7.42(5H, m).

(292-2) 1-[1-(4-Fluorophenethyl)pyrrolidin-3-yl]-6-methoxyindoline

1-Benzyl-3-(6-methoxyindolin-1-yl)pyrrolidine (0.5 g) was treated as in Tetrahedron Lett., 1567 (1977). to give a yellow oil. Then this product and 4-fluorophenethyl bromide (0.15 g) were treated as in Example 2 to give the free title compound (2.301 g) as a pale yellow oil (yield: 13.1%).

Next, this free compound was treated with oxalic acid in acetone in a conventional manner to give the oxalate of the title compound as a hygroscopic amorphous solid.

Oxalate:

¹H-NMR (400 MHz, DMSO-d₆):

δ(ppm) 1.89(1H, m), 2.08(1H, m), 2.62–3.06(10H, m), 3.32(2H, t, J=8.2 Hz), 3.65(3H, s), 4.30(1H, m), 6.10(1H, dd, J=2.0, 8.0 Hz), 6.15(1H, d, J=2.0 Hz), 6.87(1H, d, J=8.0 Hz), 7.10(2H, t, J=8.4 Hz), 7.27(2H, dd, J=5.4, 8.4 Hz).

ESI-Mass: 341.1.

Example 293: Synthesis of 3,3-dimethyl-1-[1-(4-fluorophenethyl)piperidin-4-yl]-6-bromoindoline (293-1) 3,3-Dimethyl-6-bromoindolin-2-one

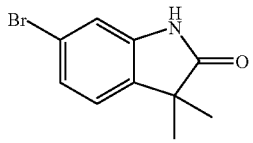

A solution (50 ml) of 6-bromoindolin-2-one (3.18 g) in THF was cooled to −78° C. and 1.5 M lithium diisopropylamide (20 ml) was added dropwise thereinto followed by stirring for 15 min. After adding methyl iodide (0.92 ml), the reaction mixture was brought to room temperature and stirred for 1 hr. Then the reaction solution was cooled to −78° C. again and 1.5 M lithium diisopropylamide (10 ml) was added dropwise thereinto followed by stirring for 15 min. After adding methyl iodide (0.92 ml), the reaction solution was brought to room temperature with stirring. Then a saturated aqueous solution of ammonium chloride was added thereto and the resultant mixture was extracted with ethyl acetate. The residue was washed with hexane to give the title compound (3.35 g) as a white amorphous solid (yield: 93.0%).

¹H-NMR (400 MHz, CDCl₃):

δ(ppm) 1.38(6H, s), 7.05(1H, d, J=8.0 Hz), 7.096(1H, d, J=1.6 Hz), 7.169(1H, d, J=1.6 Hz), 8.41(1H, m).

(293-2) 3.3-Dimethyl-6-bromoindoline

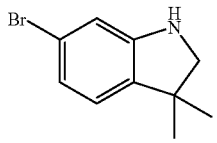

A borane-dimethylsulfide complex (3 ml) was added dropwise into a solution (80 ml) of 3,3-dimethyl-6-bromoindolin-2-one (3.35 g) in toluene under stirring at 60° C. Then the reaction mixtures were heated under reflux for 3 hr. Under ice cooling, a 5 N aqueous solution (20 ml) of sodium hydroxide was added thereto and the resultant mixture was stirred at room temperature for 30 min. Then the reaction mixtures were extracted with ethyl acetate, washed with water and brine and dried. The extract was concentrated under reduced pressure to give the title compound (3.10 g) as a yellow oil (yield: 98.3%).

¹H-NMR (400 MHz, CDCl₃):

δ(ppm) 1.28(6H, s), 3.35(2H, s), 6.83–6.91(3H, m).

(293-3) 3,3-Dimethyl-1-[1-(4-fluorophenethyl)piperidin-4-yl]-6-bromoindoline

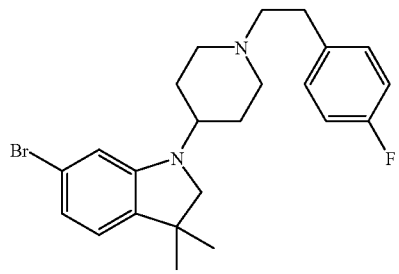

3,3-Dimethyl-6-bromoindoline (3.10 g), 1-[2-(4-fluorophenyl)ethyl]-4-piperidone (2.81 g) and triacetoxylated sodium borohydride (5.70 g) were treated as in Example 16 to give the title compound (2.72 g) as a white amorphous solid (yield: 49.8%).

¹H-NMR (400 MHz, CDCl₃):

δ(ppm) 1.24(6H, s), 1.80(4H, br-s), 2.13–2.24(2H, m), 2.58–2.67(2H, m), 2.79–2.86(2H, m), 3.11–3.21(2H, m), 3.17(2H, s), 3.28–3.40(1H, m), 6.44(1H, s), 6.72(1H, d, J=8.0 Hz), 6.80(1H, d, J=8.0 Hz), 6.93–7.01(2H, m), 7.13–7.20(2H, m).

FAB-Mass: 432(MH+).

Example 294: Synthesis of 1-[1-(4-fluorophenethyl)piperidin-4-yl]-6-(ethylcarbamoylmethyl)indole A suspension of 1-[1-(4-fluorophenethyl)piperidin-4-yl]-6-(ethylcarbamoylmethyl)indoline (0.41 g) obtained in Example 149 and active manganese dioxide (0.40 g) in chloroform (30 ml) was vigorously stirred at 50° C. for 6 hr. Then the reaction mixtures were filtered through celite and the residue was washed with chloroform. After concentrating the filtrate under reduced pressure, the residue was recrystallized from chloroform/hexane to give the title compound (0.33 g) as white needles (yield: 89.5%).

m.p.: 159.6–160.1° C.

¹H-NMR(400 MHz,CDCl₃); δ(ppm) 1.02(3H,t,J=7.2 Hz), 2.07–2.13(4H, m), 2.25–2.32(2H, m), 2.64–2.68(2H, m), 2.81–2.85(2H, m), 3.17–3.26(4H, m), 3.70(2H,s), 4.21–4.29 (1H, m), 5.40(1H, br-t), 6.53(1H, d, J=3.2 Hz), 6.95–7.01 (3H, m), 7.17–7.21(2H, m), 7.26–7.28(2H, m), 7.61(1H, d, J=8.0 Hz).

ESI-Mass; 408(MH+).

Example 295: Synthesis of 1-[1-(4-fluorophenethyl)piperidin-4-yl]-6-[N-(cyclopropylcarbamoyl)methyl]indole A suspension of 1-[1-(4-fluorophenethyl)piperidin-4-yl]-6-[(cyclopropylcarbamoyl)methyl]indoline (0.04 g) obtained in Example 154 and active manganese dioxide (0.04 g) in chloroform (30 ml) was vigorously stirred at 50° C. for 10 hr. Then the reaction mixtures were filtered through celite and the residue was washed with chloroform. After concentrating the filtrate under reduced pressure, the residue was recrystallized from chloroform/hexane to give the title compound (0.03 g) as a white powder (yield: 81.9%).

m.p.: 156.4–156.8° C.

¹H-NMR(400 MHz, CDCl₃); δ(ppm) 0.34–0.38(2H, m), 0.68–0.73(2H, m), 2.06–2.14(4H, m), 2.25–2.32(2H, m), 2.62–2.68(3H, m), 2.81–2.85(2H, m), 3.18(2H, br-d), 3.68 (2H, s), 4.20–4.28(1H, m), 5.50(1H, br-s), 6.52(1H, d, J=3.2 Hz), 6.93(1H, dd, J=1.4, 8.2 Hz), 6.97–7.01(2H, m), 7.17–7.20(2H, m), 7.25–7.27(2H, m), 7.60(1H, d, J=8.2 Hz).

ESI-Mass; 420(MH+).

Example 296: Synthesis of 1-[1-(4-fluorophenethyl)piperidin-4-yl]-6-[N-(isobutylcarbamoyl)methyl]indole A suspension of 1-[1-(4-fluorophenethyl)piperidin-4-yl]-6-[(isobutylcarbamoyl)methyl]indoline (0.07 g) obtained in Example 152 and active manganese dioxide (0.07 g) in chloroform (30 ml) was vigorously stirred at 50° C. overnight. Then the reaction mixtures were filtered through celite and the residue was washed with chloroform. After concentrating the filtrate under reduced pressure, the residue was recrystallized from chloroform/hexane to give the title compound (0.05 g) as a white powder (yield: 70.0%).
m.p.: 131.8–132.2° C.
$^1$H-NMR(400MHz, CDCl$_3$); δ(ppm) 0.79(6H, d, J=6.8 Hz), 1.61–1.71(1H, m), 2.07–2.13(4H, m), 2.24–2.31(2H, m), 2.64–2.68(2H, m), 2.81–2.85(2H, m), 3.01(2H, t, J=6.4 Hz), 3.18(2H, br-d), 3.72(2H, s), 4.20–4.28(1H, m), 5.46(1H, br-t), 6.53(1H, d, J=2.8 Hz), 6.96–7.01(3H, m), 7.17–7.20(2H, m), 7.26–7.27(2H, m), 7.61(1H, d, J=8.0 Hz).
ESI-Mass; 436(MH+).

Example 297: Synthesis of 1-[1-(4-fluorophenethyl)piperidin-4-yl]-6-(n-propylcarbamoylmethyl)indole A suspension of 1-[1-(4-fluorophenethyl)piperidin-4-yl]-6-[(n-propylcarbamoyl)methyl]indoline (0.04 g) obtained in Example 150 and active manganese dioxide (0.08 g) in chloroform (30 ml) was vigorously stirred at 50° C. overnight. Then the reaction mixtures were filtered through celite and the residue was washed with chloroform. After concentrating the filtrate under reduced pressure, the residue was recrystallized from chloroform/hexane to give the title compound (0.03 g) as white needles (yield: 84.6%).
m.p.: 131.1–131.9° C.
$^1$H-NMR(400 MHz,CDCl$_3$); δ(ppm) 0.81(3H,t,J=7.4 Hz), 1.41(2H,tq,J=7.4,7.4 Hz), 2.07–2.12(4H,m), 2.25–2.31(2H, m), 2.64–2.68(2H,m), 2.81–2.85(2H,m), 3.71(2H,s), 4.20–4.28(1H,m), 5.43(1H,br-t), 6.53(1H,d,J=3.2 Hz), 6.96–7.01(3H,m), 7.17–7.21(2H,m), 7.25–7.27(2H,m), 7.61 (1H,d,J=8.0 Hz).
ESI-Mass; 422(MH+).

Example 298: Synthesis of 1-[1-(4-fluorophenethyl)piperidin-4-yl]-6-(tetramethylenecarbamoylmethyl)indole oxalate A suspension of 1-[1-(4-fluorophenethyl)piperidin-4-yl]-6-(tetramethylenecarbamoylmethyl)indoline (0.08 g) obtained in Example 155 and active manganese dioxide (0.07 g) in chloroform (30 ml) was vigorously stirred at 50° C. overnight. Then the reaction mixtures were filtered through celite and the residue was washed with chloroform. After concentrating the filtrate under reduced pressure, the free compound (0.06 g) of the title compound was obtained as a pale brown viscous compound (yield: 87.0%).

Next, this free compound was converted into an oxalate in a conventional manner, which was then reprecipitated from methanol/diethyl ether to give the title compound as a colorless powder.
Free compound:
$^1$H-NMR(400 MHz,CDCl$_3$); δ(ppm) 1.78–1.93(4H,m), 2.09 (4H,br-s), 2.25–2.33(2H,m), 2.64–2.68(2H,m), 2.81–2.85 (2H,m), 3.17(2H,br-d), 3.45–3.51(4H,m), 3.78(2H,s), 4.24–4.32(1H,m), 6.49(1H,d,J=3.0 Hz), 6.97–7.01(3H,m), 7.17–7.20(2H,m), 7.22(1H,d,J=3.0 Hz), 7.38(1H,s), 7.55 (1H,d,J=8.0 Hz).
Oxalate:
m.p.: 171.5–172.1° C.
$^1$H-NMR(400 MHz,CDCl$_3$); δ(ppm) 1.72–1.79(2H,m), 1.83–1.90(2H,m), 2.09–2.21(4H,m), 2.92–3.18(6H,m), 3.29 (2H,t,J=7.0 Hz), 3.49(2H,t,J=7.0 Hz), 3.49–3.56(2H,m), 3.70(2H,s), 4.58(1H,br-s), 6.45(1H,d,J=3.2 Hz), 6.93(1H, dd,J=1.2,8.4 Hz), 7.16–7.20(2H,m), 7.33–7.37(2H,m), 7.39–7.42(2H,m), 7.46(1H,d,J=8.4 Hz).
ESI-Mass; 434(MH+).

Example 299: Synthesis of 1-[1-(2,4-difluorophenethyl)piperidin-4-yl]-6-carbamoylmethylindole A suspension of 1-[1-(2,4-difluorophenethyl)-piperidin-4-yl]-6-carbamoylmethylindoline (0.05 g) obtained in Example 225 and active manganese dioxide (0.10 g) in chloroform (30 ml) was vigorously stirred at 50° C. overnight. Then the reaction mixtures were filtered through celite and the residue was washed with chloroform. After concentrating the filtrate under reduced pressure, the residue was recrystallized from chloroform/hexane to give the title compound (0.02 g) as a white powder (yield: 41.7%).
m.p.: 156.9–157.8° C.
$^1$H-NMR(400 MHz,CDCl$_3$); δ(ppm) 2.03–2.12(4H,m), 2.25–2.31(2H,m), 2.63–2.67(2H,m), 2.84–2.88(2H,m), 3.17 (2H,br-d), 4.22–4.30(1H,m), 5.54(2H,br-s), 6.52(1H,dd,J= 0.8,3.2 Hz), 6.88(1H,dt,J=1.2,8.6 Hz), 7.10(1H,ddd,J=0.8, 7.0,8.0 Hz), 7.13–7.22(2H,m), 7.24(1H,d,J=3.6 Hz), 7.38 (1H,dd,J=0.4,8.4 Hz), 7.62–7.65(1H,m).
ESI-Mass; 398(MH+).

Example 300: Synthesis of 1-[1-(4-fluorophenethyl)piperidin-4-yl]-6-(2-hydroxyethyl)carbamoylmethylindole 1-[1-(4-Fluorophenethyl)piperidin-4-yl]-6-carboxymethylindoline (0.20 g) obtained in Example 146 was dissolved in N,N-dimethylformamide (5 ml). To the resultant solution was added 1,1-carbonyldiimidazole (0.104 g) and the resultant mixture was stirred under nitrogen atmosphere at room temperature for 15 min. Next, ethanolamine (320 ml) was added thereto and the mixture was further stirred overnight. After evaporating the solvent under reduced pressure, water and ethyl acetate were added to the residue. The organic layer was separated, washed successively with water and brine and dried over magnesium sulfate. Then the solvent was evaporated under reduced pressure to give a pale brown viscous oil (0.15 g).

This residue was dissolved in chloroform (30 ml) and manganese dioxide (0.31 g) was added thereto. After stirring the resultant mixture at 50° C. overnight, the manganese dioxide was filtered off and the solvent was evaporated under reduced pressure. Then the residue was recrystallized from chloroform/n-hexane to give the title compound (0.13 g) as a pale yellow powder.
m.p.: 140.0–141.2° C.
$^1$H-NMR(400 MHz,CDCl$_3$); δ(ppm) 2.08–2.21(4H,m), 2.28 (2H,br-t), 2.64–2.68(2H,m), 2.81–2.85(2H,m), 3.19(2H,br-d), 3.35–3.39(2H,m), 3.67(2H,t,J=5.0 Hz), 3.74(2H,s), 4.19–4.28(1H,m), 5.90(1H,br-t), 6.51(1H,br-d), 6.96–7.02 (3H,m), 7.17–7.21(2H,m), 7.25(1H,d,J=3.2 Hz), 7.31(1H, br-s), 7.61(1H,d,J=8.4 Hz).
ESI-Mass; 424(MH+).

Example 301: Synthesis of 1-[1-(4-fluorophenethyl)piperidin-4-yl]-6-dimethylcarbamoylmethylindole oxalate 1-[1-(4-Fluorophenethyl)piperidin-4-yl]-6-carboxymethylindoline (0.19 g) obtained in Example 146 was dissolved in N,N-dimethylformamide (5 ml). To the resultant solution was added 1,1-carbonyldiimidazole (0.10 g) and the resultant mixture was stirred under nitrogen atmosphere at room temperature for 15 min. Next, a 2 M solution (2.50 ml) of dimethylamine in tetrahydrofuran was added thereto and the mixture was further stirred overnight. After evaporating the solvent under reduced pressure, water and ethyl acetate were added to the residue. The organic layer was separated, washed successively with water and brine and dried over magnesium sulfate. Then the solvent was evaporated under reduced pressure to give a pale brown viscous oil (0.13 g).

This substance was dissolved in chloroform (30 ml) and manganese dioxide (0.28 g) was added thereto. After stirring the resultant mixture at 50° C. overnight, additional manganese dioxide (0.14 g) was added thereto and the mixture was stirred for 5 hr. Then the manganese dioxide was filtered off and the solvent was evaporated under reduced pressure to give a free compound (0.15 g) of the title compound as a pale brown viscous oil, which was then converted into an oxalate in a conventional manner.

m.p.: 170.1–170.6° C.

$^1$H-NMR(400 MHz,DMSO-d$_6$); δ(ppm) 2.14–2.24(4H,m), 2.83(3H,s), 2.95–3.10(4H,m), 3.03(3H,s), 3.15(2H,br-s), 3.53(2H,br-d), 3.76(2H,s), 4.58(1H,br-s), 6.45(1H,d,J=3.2 Hz), 6.91(1H,d,J=8.2 Hz), 7.15–7.20(2H,m), 7.33–7.37(2H,m), 7.40(2H,br-s), 7.47(1H,d,J=8.2 Hz).

ESI-Mass; 408(MH+).

Example 302: Synthesis of 1-[1-(4-fluorophenethyl)piperidin-4-yl]-6-(4-hydroxypiperidin-1-yl)carbonylmethyl)indole 1-[1-(4-Fluorophenethyl)piperidin-4-yl]-6-carboxymethylindoline (0.21 g) obtained in Example 146 was dissolved in N,N-dimethylformamide (5 ml). To the resultant solution was added 1,1-carbonyldiimidazole (0.11 g) and the resultant mixture was stirred in a nitrogen atmosphere at room temperature for 15 min. Next, 4-hydroxypiperidine (0.56 g) was added thereto and the mixture was further stirred overnight. After evaporating the solvent under reduced pressure, water and ethyl acetate were added to the residue. The organic layer was separated, washed successively with water and brine and dried over magnesium sulfate. Then the solvent was evaporated under reduced pressure to give a pale brown viscous oil (0.18 g).

This residue (0.13 g) was dissolved in chloroform (30 ml) and manganese dioxide (0.33 g) was added thereto. After stirring the resultant mixture at 50° C. for 10 hr, the manganese dioxide was filtered off and the solvent was removed under reduced pressure. Then the residue was recrystallized from chloroform/n-hexane to give the title compound (0.16 g) as colorless micaceous flakes.

m.p.: 190.5–192.2° C. (decomp.).

$^1$H-NMR(400 MHz,CDCl$_3$); δ(ppm) 1.22–1.50(2H,m), 1.62–1.69(1H,m), 1.82–1.89(1H,m), 2.05–2.11(4H,m), 2.24–2.31(2H,m), 2.63–2.67(2H,m), 2.80–2.84(2H,m), 3.15–3.24(4H,m), 3.76–3.88(2H,m), 3.88(2H,s), 4.11–4.17(2H,m), 4.21–4.29(1H,m), 6.49(1H,d,J=3.6 Hz), 6.95–7.01(3H,m), 7.17–7.20(2H,m), 7.22(1H,d,J=3.6 Hz), 7.30(1H,s), 7.56(1H,d,J=8.4 Hz).

ESI-Mass: 464(MH+).

Example 303: Synthesis of 1-[1-(4-fluorophenethyl)piperidin-4-yl]-6-[bis(2-hydroxyethyl)]carbamoylmethylindole oxalate 1-[1-(4-Fluorophenethyl)piperidin-4-yl]-6-carboxymethylindoline (0.20 g) obtained in Example 146 was dissolved in N,N-dimethylformamide (5 ml). To the resultant solution was added 1,1-carbonyldiimidazole (0.10 g) and the resultant mixture was stirred under nitrogen atmosphere at room temperature for 15 min. Next, diethanolamine (0.56 g) dissolved in N,N-dimethylformamide (1 ml) was added thereto and the mixture was further stirred overnight. After evaporating the solvent under reduced pressure, water and ethyl acetate were added to the residue. The organic layer was separated, washed successively with water and brine and dried over magnesium sulfate. Then the solvent was evaporated under reduced pressure to give a pale brown viscous oil (0.16 g).

This residue was dissolved in chloroform (30 ml) and manganese dioxide (0.30 g) was added thereto. After stirring the resultant mixture at 50° C. overnight, the manganese dioxide was filtered off and the solvent was removed under reduced pressure. The residue was purified by silica gel column chromatography (chloroform/methanol system) to give a free compound (0.10 g) of the title compound as a pale brown viscous oil, which was then converted into an oxalate in a conventional manner.

$^1$H-NMR(400 MHz,DMSO-d$_6$); δ(ppm) 2.10(2H,br-d), 2.29(2H,br-q), 3.98–3.08(4H,m), 3.16–3.21(2H,m), 3.39(2H,br-t), 3.45–3.58(8H,m), 3.83(2H,s), 4.57–4.65(1H,m), 6.45(1H,d,J=3.2 Hz), 6.91(1H,d,J=8.0 Hz), 7.17(2H,br-t), 7.33–7.37(2H,m), 7.40(2H,br-s), 7.47(1H,d,J=8.0 Hz).

ESI-Mass; 468(MH+).

Example 304: Synthesis of 1-[1-(4-fluorophenethyl)piperidin-4-yl]-6-(1,3-dihydroxypropan-2-yl)carbamoylmethylindole oxalate 1-[1-(4-Fluorophenethyl)piperidin-4-yl]-6-carboxymethylindoline (0.23 g) obtained in Example 146 was dissolved in N,N-dimethylformamide (5 ml). To the resultant solution was added 1,1-carbonyldiimidazole (0.11 g) and the resultant mixture was stirred under nitrogen atmosphere at room temperature for 15 min. Next, 2-amino-1,3-propanediol (Serinol, 0.27 g) was added thereto and the mixture was further stirred overnight. After evaporating the solvent under reduced pressure, water and ethyl acetate were added to the residue. The organic layer was separated, washed successively with water and brine and dried over magnesium sulfate. Then the solvent was evaporated under reduced pressure to give a pale brown viscous oil (0.20 g).

This residue was dissolved in chloroform (30 ml) and manganese dioxide (0.27 g) was added thereto. After stirring the resultant mixture at 50° C. overnight, additional manganese dioxide (0.19 g) was added thereto followed by stirring for 6 hr. Then the manganese dioxide was filtered off and the solvent was removed under reduced pressure. The residue was purified by silica gel column chromatography (chloroform/methanol system) to give a free compound (0.09 g) of the title compound as a pale brown viscous oil, which was then converted into an oxalate in a conventional manner.

m.p.: 213.1–214.5° C. (decomp.).

$^1$H-NMR(400 MHz,DMSO-d$_6$); δ(ppm) 2.06–2.23(4H,m), 2.81–3.09(6H,m), 3.41–3.47(6H,m), 3.52(2H,s), 3.67–3.75(1H,m), 4.49–4.57(1H,m), 6.43(1H,d,J=3.2 Hz), 6.95(1H,d,J=8.4 Hz), 7.17(2H,br-t), 7.32–7.36(2H,m), 7.41–7.46(3H,m), 7.72(1H,d,J=8.4 Hz).

ESI-Mass: 454(MH+).

Example 305: Synthesis of 1-[1-(4-fluorophenethyl)piperidin-4-yl]-6-carbamoylmethylindole 1-[1-(4-Fluorophenethyl)piperidin-4-yl]-6-carboxymethyl-indoline (0.22 g) obtained in Example 146 was dissolved in N,N-dimethylformamide (5 ml). To the resultant solution was added 1,1-carbonyldiimidazole (0.11 g) and the resultant mixture was stirred under nitrogen atmosphere at room temperature for 15 min. Next, a saturated solution (2 ml) of ammonia in methanol was added thereto and the mixture was further stirred overnight. After evaporating the solvent under reduced pressure, water and ethyl acetate were added to the residue. The organic layer was separated, washed successively with water and brine and dried over magnesium sulfate. Then the solvent was evaporated under reduced pressure to give a pale brown viscous oil (0.11 g).

This residue was dissolved in chloroform (30 ml) and manganese dioxide (0.24 g) was added thereto. After stirring the resultant mixture at 50° C. for 4 hr, additional manganese dioxide (0.12 g) was added thereto followed by stirring overnight. Then the manganese dioxide was filtered off and the solvent was evaporated under reduced pressure. The residue was recrystallized from chloroform/n-hexane to give the title compound (0.08 g) as a pale yellow powder.

m.p.: 159.1–160.8° C.
¹H-NMR(400 MHz,CDCl₃); δ(ppm) 2.07–2.13(4H,m), 2.25–2.31(2H,m), 2.64–2.68(2H,m), 2.81–2.85(2H,m), 3.18(2H,br-d), 3.73(2H,s), 4.21–4.29(1H,m), 5.33(1H,br-s), 4.43(1H,br-s), 6.52(1H,dd,J=3.2 Hz), 6.97–7.01(3H,m), 7.17–7.20(2H,m), 7.26(1H,d,J=3.2 Hz), 7.29(1H,s), 7.62(1H,d,J=8.0 Hz).
ESI-Mass; 380(MH+).

Example 306: Synthesis of 1-[1-(4-fluorophenethyl)piperidin-4-yl]-6-(carbamoylmethyl)carbamoylmethylindole oxalate 1-[1-(4-Fluorophenethyl)piperidin-4-yl]-6-carboxymethyl-indoline (0.22 g) obtained in Example 146 was dissolved in N,N-dimethylformamide (5 ml). To the resultant solution was added 1,1-carbonyldiimidazole (0.11 g) and the resultant mixture was stirred under nitrogen atmosphere at room temperature for 15 min. Next, a suspension of glycinamide hydrochloride (0.31 g) and triethylamine (395 ml) in N,N-dimethylformamide (10 ml) was added thereto and the mixture was further stirred overnight. After evaporating the solvent under reduced pressure, water and ethyl acetate were added to the residue. The organic layer was separated, washed successively with water and brine and dried over magnesium sulfate. Then the solvent was evaporated under reduced pressure to give a pale brown viscous oil (0.10 g).

This residue was dissolved in chloroform (30 ml) and manganese dioxide (0.14 g) was added thereto. After stirring the resultant mixture at 50° C. overnight, additional manganese dioxide (0.10 g) was added thereto followed by stirring for 3.5 hr. Then the manganese dioxide was filtered off and the solvent was evaporated under reduced pressure. The residue was purified by silica gel column chromatography (chloroform/methanol system) to give a free compound (0.06 g) of the title compound as a pale brown amorphous substance, which was then converted into an oxalate in a conventional manner.
¹H-NMR(400 MHz,DMSO-d₆); δ(ppm) 2.06–2.22(4H,m), 2.86–3.07(6H,m), 3.57(2H,s), 3.65(2H,d,J=5.6 Hz), 4.56(1H,br-s), 7.44(1H,d,J=2.8 Hz), 6.96(1H,d,J=7.8 Hz), 7.04(1H,br-s), 7.17(1H,br-t), 7.33–7.36(3H,m), 7.41(1H,br-s), 7.46(1H,d,J=7.8 Hz), 7.50(1H,s), 8.13(1H,br-t).
ESI-Mass; 437(MH+).

Example 307: Synthesis of 1-[1-(4-fluorophenethyl)piperidin-4-yl]-6-(2-dimethylaminoethyl)carbamoylmethylindole 1-[1-(4-Fluorophenethyl)piperidin-4-yl]-6-carboxymethylindoline (0.22 g) obtained in Example 146 was dissolved in N,N-dimethylformamide (5 ml). To the resultant solution was added 1,1-carbonyldiimidazole (0.11 g) and the resultant mixture was stirred under nitrogen atmosphere at room temperature for 15 min. Next, N,N-dimethylethylenediamine (310 ml) was added thereto and the mixture was further stirred overnight. After evaporating the solvent under reduced pressure, water and ethyl acetate were added to the residue. The organic layer was separated, washed successively with water and brine and dried over magnesium sulfate. Then the solvent was distilled off under reduced pressure to give a pale brown viscous oil (0.18 g).

This residue was dissolved in chloroform (30 ml) and manganese dioxide (0.24 g) was added thereto. After stirring the resultant mixture at 50° C. for 9 hr, additional manganese dioxide (0.28 g) was added thereto followed by stirring overnight. Then the manganese dioxide was filtered off and the solvent was evaporated under reduced pressure. The residue was recrystallized from chloroform/n-hexane to give the title compound (0.12 g) as a pale brown powder.

m.p.: 111.8–112.9° C.
¹H-NMR(400 MHz,CDCl₃); δ(ppm) 2.07–2.14(4H,m), 2.13(6H,s), 2.24–2.32(2H,m), 2.32(2H,t,J=6.0 Hz), 2.64–2.68(2H,m), 2.81–2.85(2H,m), 3.18(2H,br-d), 3.28(2H,dt,J=6.0, 6.0 Hz), 3.69(2H,s), 4.21–4.29(1H,m), 5.98(1H,br-t), 6.51(1H,d,J=3.4 Hz), 6.97–7.01(3H,m), 7.17–7.20(2H,m), 7.24(1H,d,J=3.4 Hz), 7.30(1H,s), 7.59(1H,d,J=8.0 Hz).
ESI-Mass; 451(MH+).

Example 308: Synthesis of 1-[1-(4-fluorophenethyl)piperidin-4-yl]-6-cyanomethylcarbamoylmethylindole oxalate 1-[1-(4-Fluorophenethyl)piperidin-4-yl]-6-carboxymethylindoline (0.22 g) obtained in Example 146 was dissolved in N,N-dimethylformamide (5 ml). To the resultant solution was added 1,1-carbonyldiimidazole (0.11 g) and the resultant mixture was stirred under nitrogen atmosphere at room temperature for 15 min. Next, aminoacetonitrile hydrochloride (0.26 g) dissolved in N,N-dimethylformamide (10 ml) was added thereto. After further adding triethylamine (394 ml), the resultant mixture was stirred overnight. After evaporating the solvent under reduced pressure, water and ethyl acetate were added to the residue. The organic layer was separated, washed successively with water and brine and dried over magnesium sulfate. Then the solvent was evaporated under reduced pressure to give a pale brown viscous oil (0.17 g).

This residue was dissolved in chloroform (30 ml) and manganese dioxide (0.25 g) was added thereto. After stirring the resultant mixture at 50° C. 8 hr, additional manganese dioxide (0.28 g) was added thereto followed by stirring overnight. Then the manganese dioxide was filtered off and the solvent was evaporated under reduced pressure. The residue was purified successively by silica gel column chromatography (chloroform/methanol system) and NH silica gel column chromatography (chloroform/ethyl acetate system) to give a free compound (0.04 g) of the title compound as a pale brown viscous oil, which was then converted into an oxalate in a conventional manner.
¹H-NMR(400 MHz,DMSO-d₆); δ(ppm) 2.04–2.21(4H,m), 2.77–3.06(6H,m), 3.41–3.46(2H,m), 3.58(2H,s), 4.13(2H,d,J=5.6 Hz), 4.53(1H,br-s), 6.45(1H,d,J=3.2 Hz), 6.94(1H,d,J=8.6 Hz), 7.16(2H,br-t), 7.32–7.36(2H,m), 7.44(2H,br-s), 7.48(1H,d,J=8.6 Hz), 8.69(1H,br-t).
ESI-Mass; 419(MH+).

Example 309: Synthesis of 1-[1-(4-fluorophenethyl)piperidin-4-yl]-6-(2-methoxyethyl)carbamoylmethylindole 1-[1-(4-Fluorophenethyl)piperidin-4-yl]-6-carboxymethylindoline (0.22 g) obtained in Example 146 was dissolved in N,N-dimethylformamide (5 ml). To the resultant solution was added 1,1-carbonyldiimidazole (0.11 g) and the resultant mixture was stirred under nitrogen atmosphere at room temperature for 15 min. Next, 2-methoxyethylamine (245 ml) was added thereto and the mixture was further stirred for 4 hr. After evaporateing solvent under reduced pressure, water and ethyl acetate were added to the residue. The organic layer was separated, washed successively with water and brine and dried over magnesium sulfate. Then the solvent was evaporated under reduced pressure to give a pale brown viscous oil (0.19 g).

This residue was dissolved in chloroform (30 ml) and manganese dioxide (0.31 g) was added thereto. After stirring the resultant mixture at 50° C. overnight, additional manganese dioxide (0.27 g) was added thereto followed by stirring for 5 hr. Then manganese dioxide (0.19 g) was further added thereto and the resultant mixture was stirred for additional 1 hr. Then the manganese dioxide was filtered off and the solvent was evaporated under reduced pressure.

The residue was recrystallized from chloroform/n-hexane to give the title compound (0.13 g) as a colorless powder.
m.p.: 113.2–114.4° C.
$^1$H-NMR(400 MHz,CDCl$_3$); δ(ppm) 2.07–2.13(4H,m), 2.25–2.31(2H,m), 2.64–2.68(2H,m), 2.81–2.85(2H,m), 3.18 (2H,br-d), 3.26(3H,s), 3.39(4H,br-d), 3.71(2H,s), 4.21–4.29 (1H,m), 5.81(1H,br-s), 6.52(1H,d,J=3.4 Hz), 6.96–7.01(3H, m), 7.17–7.21(2H,m), 7.26(1H,d,J=3.4 Hz), 7.28(1H,s), 7.60(1H,d,J=8.0 Hz).
ESI-Mass; 438(MH+).

Example 310: Synthesis of 1-[1-(4-fluorophenethyl) piperidin-4-yl]-6-(2-fluoroethyl)carbamoylmethylindole 1-[1-(4-Fluorophenethyl)piperidin-4-yl]-6-carboxymethylindoline (0.22 g) obtained in Example 146 was dissolved in N,N-dimethylformamide (5 ml). To the resultant solution was added 1,1-carbonyldiimidazole (0.11 g) and the resultant mixture was stirred under nitrogen atmosphere at room temperature for 15 min. Next, 2-fluoroethylamine hydrochloride (0.30 g) dissolved in N,N-dimethylformamide (5 ml) was added thereto. Afterfurther addingtriethylamine (397 ml), the mixture was stirred for 4 hr. After evaporating the solvent under reduced pressure, water and ethyl acetate were added to the residue. The organic layer was separated, washed successively with water and brine and dried over magnesium sulfate. Then the solvent was evaporated under reduced pressure to give pale brown crystals (0.19 g).

These crystals were dissolved in chloroform (30 ml) and manganese dioxide (0.30 g) was added thereto. After stirring the resultant mixture at 50° C. overnight, additional manganese dioxide (0.26 g) was added thereto followed by stirring for 5 hr. Then manganese oxide (0.19 g) was furthermore added and the resultant mixture was stirred for additional 2 hr. Next, the manganese dioxide was filtered off and the solvent was evaporated under reduced pressure. The residue was recrystallized from chloroform/n-hexane to give the title compound (0.15 g) as a colorless powder.
m.p.: 163.3–163.8° C.
$^1$H-NMR(400 MHz,CDCl$_3$); δ(ppm) 2.05–2.13(4H,m), 2.25–2.31(2H,m), 2.64–2.68(2H,m), 2.81–2.85(2H,m), 3.18 (2H,br-d), 3.50(2H,ddt,J=4.8,28.0,4.8 Hz), 3.74(2H,s), 4.21–4.29(1H,m), 4.43(2H,dt,J=47.2,4,8 Hz), 5.80(1H,br-t), 6.53(1H,d,J=3.2 Hz), 6.97–7.01(3H,m), 7.17–7.20(2H,m), 7.26–7.28(2H,m), 7.62(1H,d,J=8.0 Hz).
ESI-Mass; 426(MH+).

Example 311: Synthesis of 1-[1-(4-fluorophenethyl) piperidin-4-yl]-6-[2-(ethylcarbamoyl)ethyl]indole oxalate 311-1) 1-[1-(4-Fluorophenethyl)piperidin-4-yl]-6-[2-(ethoxycarbonyl)vinyl]indole 55% oily sodium hydride (0.46 g) was washed with n-hexane and suspended in tetrahydrofuran (1 ml) followed by stirring under ice-cooling. Then ethyl diethylphosphonoacetate (2.37 g) dissolved in tetrahydrofuran (7 ml) was added thereto and the resultant mixture was stirred at room temperature for 30 min. Next, 1-[1-(4-fluorophenethyl) piperidin-4-yl]-6-formylindole (3.53 g) obtained in Example 130 dissolved in tetrahydrofuran (10 ml) was added thereto and the resultant mixture was stirred under nitrogen atmosphere at room temperature for 2 days. After evaporating the solvent under reduced pressure, water and ethyl acetate were added to the residue. The organic layer was separated, washed successively with water and brine and dried over magnesium sulfate. Then the solvent was evaporated under reduced pressure and the residue was purified by silica gel column chromatography (ethyl acetate/n-hexane system) to give the title compound (3.59 g) as yellow crystals.
$^1$H-NMR(400 MHz,CDCl$_3$); δ(ppm) 1.36(3H,t,J=7.2 Hz), 2.08–2.14(4H,m), 2.26–2.33(2H,m), 2.65–2.69(2H,m), 2.81–2.85(2H,m), 3.20(2H,br-d), 4.28(2H,q,J=7.2 Hz), 4.23–4.32(1H,m), 6.47(1H,d,J=16.0 Hz), 6.53(1H,d,J=3.2 Hz), 6.97–7.02(2H,m), 7.17–7.21(2H,m), 7.32(1H,d,J=3.2 Hz), 7.34(1H,d,J=8.4 Hz), 7.52(1H,s), 7.61(1H,d,J=8.4 Hz), 7.84(1H,d,J=16.0 Hz).

311-2) 1-[1-(4-Fluorophenethyl)piperidin-4-yl]-6-[2-(ethoxy-carbonyl)ethyl]indole The above 1-[1-(4-fluorophenethyl)piperidin-4-yl]-6-[2-(ethoxycarbonyl)vinyl]indole (1.89 g) was dissolved in a mixture of ethanol (40 ml) and ethyl acetate (20 ml). Then 10% Pd/C (0.10 g) was added thereto and catalytic reduction was carried out under atmospheric pressure overnight. After filtering off the catalyst, the solvent was evaporated under reduced pressure to give the title compound (1.87 g) as a colorless viscous oil.
$^1$H-NMR(400 MHz,CDCl$_3$); δ(ppm) 1.25(3H,t,J=7.2 Hz), 2.06–2.12(4H,m), 2.24–2.31(2H,m), 2.64–2.70(4H,m), 2.81–2.85(2H,m), 3.08(2H,t,J=8.0 Hz), 3.18(2H,br-d), 4.14 (2H,q,J=7.2 Hz), 4.19–4.27(1H,m), 6.48(1H,d,J=3.2 Hz), 6.95–7.01(3H,m), 7.17–7.20(4H,m), 7.54(1H,d,J=8.0 Hz).

311-3) 1-[1-(4-Fluorophenethyl)piperidin-4-yl]-6-(2-carboxyethyl)indole

The above 1-[1-(4-fluorophenethyl)piperidin-4-yl]-6-[2-(ethoxycarbonyl)ethyl]indole (1.85 g) was dissolved in methanol (25 ml). Then a 5 N aqueous solution (1.75 ml) of sodium hydroxide was added thereto and the resultant mixture was stirred at room temperature overnight. After removing the solvent under reduced pressure, the residue was neutralized with 5 N hydrochloric acid and extracted with ethyl acetate. The organic layer was washed successively with water and brine and dried over magnesium sulfate. After evaporating the solvent under reduced pressure, the title compound (1.70 g) was obtained as a pale brown amorphous substance.
$^1$H-NMR(400 MHz,CDCl$_3$); δ(ppm) 1.79–1.82(2H,m), 2.32–2.43(4H,m), 2.78–2.84(4H,m), 2.92–2.97(2H,m), 3.13 (2H,t,J=7.4 Hz), 3.20(2H,br-d), 4.14–4.22(1H,m), 6.40(1H, d,J=3.2 Hz), 6.96–7.03(3H,m), 7.05(1H,d,J=3.2 Hz), 7.16–7.20(2H,m), 7.33(1H,s), 7.49(1H,d,J=8.0 Hz).

311-4) 1-[1-(4-Fluorophenethyl)piperidin-4-yl]-6-(2-ethylcarbamoyl)ethyl]indole oxalate The above 1-[1-(4-fluorophenethyl)piperidin-4-yl]-6-(2-carboxyethyl)indole (0.10 g) was dissolved in N,N-dimethylformamide (2 ml). To the resultant solution was added 1,1-carbonyldiimidazole (0.05 g) and the resultant mixture was stirred under nitrogen atmosphere at room temperature for 15 min. Next, a 70% aqueous solution (106 ml) of ethylamine was added thereto and the mixture was stirred overnight. After evaporating the solvent under reduced pressure, water and ethyl acetate were added to the residue. The organic layer was separated, washed successively with water and brine and dried over magnesium sulfate. Then the solvent was evaporated under reduced pressure and the residue was purified by NH-silica gel column chromatography (ethyl acetate/n-hexane system) to give a free compound (0.05 g) of the title compound as a colorless viscous oil, which was then converted into an oxalate in a conventional manner.
$^1$H-NMR(400 MHz,DMSO-d$_6$); δ(ppm) 2.05(2H,br-d), 2.13–2.22(2H,m), 2.39(2H,t,J=7.8 Hz), 2.81(2H,br-t), 2.89–2.95(4H,m), 3.01–3.09(4H,m), 3.42(2H,br-d), 4.48–4.56(1H,m), 6.41(1H,d,J=3.2 Hz), 6.89(1H,d,J=8.0 Hz), 7.16(2H,br-t), 7.32–7.37(3H,m), 7.39(1H,d,J=3.2 Hz), 7.43(1H,d,J=8.0 Hz), 7.82(1H,t,J=5.4 Hz).
ESI-Mass; 422(MH+).

Example 312: Synthesis of 1-[1-(4-fluorophenethyl) piperidin-4-yl]-6-[2-(pyrrolidin-1-yl)ethyl] carbamoylmethylindole oxalate 1-[1-(4-Fluorophenethyl)piperidin-4-yl]-6-carboxymethylindoline (0.21 g) obtained in Example 146 was dissolved in N,N-dimethylformamide (5 ml). To the resultant solution was added 1,1-carbonyldiimidazole (0.11 g) and the resultant mixture was stirred under nitrogen atmosphere at room temperature for 15 min. Next, 1-(2-aminoethyl)pyrrolidine (353 ml) was added thereto and the mixture was stirred for additional 4.5 hr. After evaporating the solvent under reduced pressure, water and ethyl acetate were added to the residue. The organic layer was separated, washed successively with water and brine and dried over magnesium sulfate. Then the solvent was evaporated under reduced pressure to give a pale brown viscous oil (0.19 g).

This residue was dissolved in chloroform (30 ml) and manganese dioxide (0.17 g) was added thereto. After stirring the resultant mixture at 50° C. overnight, additional manganese dioxide (0.17 g) was added thereto followed by stirring for 7 hr. Then manganese oxide (0.17 g) was furthermore added and the resultant mixture was stirred for additional 5 hr. Next, the manganese dioxide was filtered off and the solvent was removed under reduced pressure to give a free compound (0.19 g) of the title compound as a pale brown viscous oil, which was then converted into an oxalate in a conventional manner.

$^1$H-NMR(400 MHz,DMSO-d$_6$); δ(ppm) 1.78–1.82(4H,m), 1.95(2H,br-d), 2.06–2.16(2H,m), 2.41(2H,br-t), 2.70–2.74 (2H,m), 2.81–2.85(2H,m), 2.93–2.98(6H,m), 3.20(2H,br-d), 3.28–3.34(2H,m), 3.50(2H,s), 4.32–4.40(1H,m), 6.40(1H,d, J=3.2 Hz), 6.94(1H,d,J=9.2 Hz), 7.12(2H,br-t), 7.28–7.32 (2H,m), 7.42–7.45(3H,m), 8.30(1H,br-t).
ESI-Mass; 477(MH+).

Example 313: Synthesis of 1-[1-(4-fluorophenethyl)piperidin-4-yl]-6-[2-(morpholin-4-yl)ethyl]carbamoylmethylindole oxalate 1-[1-(4-Fluorophenethyl)piperidin-4-yl]-6-carboxymethylindoline (0.22 g) obtained in Example 146 was dissolved in N,N-dimethylformamide (5 ml). To the resultant solution was added 1,1-carbonyldiimidazole (0.11 g) and the resultant mixture was stirred under nitrogen atmosphere at room temperature for 15 min. Next, 4-(2-aminoethyl)morpholine (379 ml) was added thereto and the mixture was stirred for additional 4 hr. After evaporating the solvent under reduced pressure, water and ethyl acetate were added to the residue. The organic layer was separated, washed successively with water and brine and dried over magnesium sulfate. Then the solvent was evaporated under reduced pressure to give a pale brown viscous oil (0.19 g).

This residue was dissolved in chloroform (30 ml) and manganese dioxide (0.17 g) was added thereto. After stirring the resultant mixture at 50° C. overnight, additional manganese dioxide (0.17 g) was added thereto followed by stirring for 8 hr. Then manganese oxide (0.17 g) was furthermore added and the resultant mixture was stirred for additional 3 hr. Then manganese dioxide (0.08) g was further added and the mixture was stirred for 1.5 hr. Then manganese dioxide (0.08) g was furthermore added and the mixture was stirred for additional 5 hr. Next, the manganese dioxide was filtered off and the solvent was distilled off under reduced pressure to give a free compound (0.20 g) of the title compound as a pale brown viscous oil, which was then converted into an oxalate in a conventional manner.

$^1$H-NMR(400 MHz,DMSO-d$_6$); δ(ppm) 2.04(2H,br-d), 2.17–2.27(4H,m), 2.40–2.44(6H,m), 2.79(2H,br-t), 2.91–2.95(2H,m), 2.98–3.03(2H,m), 3.19(2H,br-q), 3.42 (2H,br-d), 3.50(2H,s), 3.53(4H,br-t), 4.47–4.55(1H,m), 6.43 (1H,d,J=3.2 Hz), 6.96(1H,dd,J=0.8,8.0 Hz), 7.13–7.18(2H, m), 7.32–7.35(2H,m), 7.42(1H,d,J=3.2 Hz), 7.45–7.47(2H, m), 7.93(1H,t,J=5.6 Hz).
ESI-Mass; 493(MH+).

Example 314: Synthesis of 1-[1-(4-fluorophenethyl)piperidin-4-yl]-6-(pyridin-4-yl)methylcarbamoylmethylindole 1-[1-(4-Fluorophenethyl)piperidin-4-yl]-6-carboxymethylindoline (0.21 g) obtained in Example 146 was dissolved in N,N-dimethylformamide (5 ml). To the resultant solution was added 1,1-carbonyldiimidazole (0.11 g) and the resultant mixture was stirred under nitrogen atmosphere at room temperature for 15 min. Next, 4-aminomethylpyridine (283 ml) was added thereto and the mixture was stirred for additional 6 hr. After evaporating the solvent under reduced pressure, water and ethyl acetate were added to the residue. The organic layer was separated, washed successively with water and brine and dried over magnesium sulfate. Then the solvent was evaporated under reduced pressure to give a pale brown viscous oil (0.20 g).

This residue was dissolved in chloroform (30 ml) and manganese dioxide (0.37 g) was added thereto. After stirring the resultant mixture at 50° C. overnight, additional manganese dioxide (0.18 g) was added thereto followed by stirring for 3 hr. Next, the manganese dioxide was filtered off and the solvent was evaporated under reduced pressure to give the title compound (0.16 g) as a pale yellow amorphous solid.

$^1$H-NMR(400 MHz,CDCl$_3$); δ(ppm) 2.07–2.16(4H,m), 2.24–2.31(2H,m), 2.64–2.68(2H,m), 2.81–2.85(2H,m), 3.18 (2H,br-d), 3.81(2H,s), 4.19–4.27(1H,m), 4.39(2H,d,J=6.0 Hz), 5.89(1H,t,J=6.0 Hz), 6.53(1H,d,J=3.2 Hz), 6.97–7.01 (3H,m), 7.06(2H,d,J=5.8 Hz), 7.17–7.20(2H,m), 7.27(1H,d, J=3.2 Hz), 7.29(1H,s), 7.63(1H,d,J=8.0 Hz), 8.48(2H,d,J=5.8 Hz).
ESI-Mass; 471(MH+).

Example 315: Synthesis of 1-[1-(4-fluorophenethyl)piperidin-4-yl]-6-[2-(pyridin-2-yl)ethyl]carbamoylmethylindole oxalate 1-[1-(4-Fluorophenethyl)piperidin-4-yl]-6-carboxymethyl-indoline (0.23 g) obtained in Example 146 was dissolved in N,N-dimethylformamide (5 ml). To the resultant solution was added 1,1-carbonyldiimidazole (0.11 g) and the resultant mixture was stirred under nitrogen atmosphere at room temperature for 15 min. Next, 2-(2-aminoethyl)pyridine (352 ml) was added thereto and the mixture was stirred for additional 6 hr. After evaporating the solvent under reduced pressure, water and ethyl acetate were added to the residue. The organic layer was separated, washed successively with water and brine and dried over magnesium sulfate. Then the solvent was evaporated under reduced pressure to give a pale brown viscous oil (0.23 g).

This residue was dissolved in chloroform (30 ml) and manganese dioxide (0.42 g) was added thereto. After stirring the resultant mixture at 50° C. overnight, additional manganese dioxide (0.21 g) was added thereto followed by stirring for 7.5 hr. Next, the manganese dioxide was filtered off and the solvent was evaporated under reduced pressure to give a free compound (0.23 g) of the title compound as a pale brown viscous oil, which was then converted into an oxalate in a conventional manner.

$^1$H-NMR(400 MHz,CDCl$_3$); δ(ppm) 2.08(2H,br-d), 2.23–2.34(2H,m), 2.06(2H,t,J=7.2 Hz), 2.93–3.00(4H,m), 3.11–3.15(2H,m), 3.41(2H,br-q), 3.48(2H,s), 3.52(2H,br-d), 4.54–4.62(1H,m), 6.44(1H,d,J=3.0 Hz), 6.91(1H,d,J=9.2 Hz), 7.15–7.20(4H,m), 7.33–7.36(2H,m), 7.42(1H,d,J=3.0 Hz), 7.44–7.46(2H,m), 7.61(1H,dt,J=2.0,8.6 Hz), 8.07(1H, t,J=5.6 Hz), 8.44(1H,br-d).
ESI-Mass; 485(MH+).

Example 316: Synthesis of 1-[1-(4-fluorophenethyl)piperidin-4-yl]-6-methylcarbamoylmethylindole 1-[1-(4-Fluorophenethyl)piperidin-4-yl]-6-carboxymethylindoline (0.29 g) obtained in Example 146 was dissolved in N,N-dimethylformamide (5 ml). To the resultant solution was added 1,1-carbonyldiimidazole (0.15 g) and the resultant mixture was stirred under nitrogen atmosphere at room temperature for 15 min. Next, a 40% aqueous solution (662 ml) of methylamine was added thereto and the mixture was stirred overnight. After evaporating the solvent under reduced pressure, water and ethyl acetate were added to the residue. The organic layer was separated, washed successively with water and brine and dried over magnesium sulfate. Then the solvent was evaporated under reduced pressure to give pale brown crystals (0.22 g).

These crystals were dissolved in chloroform (30 ml) and manganese dioxide (0.49 g) was added thereto. After stirring the resultant mixture at 50° C. overnight, additional manganese dioxide (0.24 g) was added thereto followed by stirring for 2 hr. Then manganese dioxide (0.19 g) was further added and the resultant mixture was stirred for 2 hr. Next, the manganese dioxide was filtered off and the solvent was evaporated under reduced pressure. The residue was recrystallized from chloroform/n-hexane to give the title compound (0.18 g) as a pale brown powder.
m.p.: 149.4–150.5° C.
$^1$H-NMR(400 MHz,CDCl$_3$); δ(ppm) 2.05–2.13(4H,m), 2.25–2.31(2H,m), 2.64–2.68(2H,m), 2.73(3H,d,J=4.8 Hz), 2.81–2.85(2H,m), 3.18(2H,br-d), 3.72(2H,s), 4.20–4.28(1H,m), 5.40(1H,br-s), 6.53(1H,d,J=3.2 Hz), 6.95–7.01(3H,m), 7.17–7.20(2H,m), 7.26–7.27(2H,m), 7.61(1H,d,J=7.6 Hz).
ESI-Mass; 394(MH+).

Example 317: Synthesis of 1-[1-(4-fluorophenethyl)piperidin-4-yl]-6-(2-methoxypyridin-5-yl)carbonylindole 1-[1-(4-Fluorophenethyl)piperidin-4-yl]-6-[(2-methoxypyridin-5-yl)hydroxymethyl]indoline (0.16 g) obtained in Example 189 was dissolved in chloroform (30 ml). To the resultant solution was added manganese dioxide (0.30 g) and the resultant mixture was stirred at 50° C. overnight. Next, the manganese dioxide was filtered off and the solvent was evaporated under reduced pressure. The residue was purified by silica gel column chromatography (ethyl acetate/n-hexane system) to give a free compound (0.07 g) of the title compound as a pale brown viscous oil, which was then converted into an oxalate in a conventional manner.
$^1$H-NMR(400 MHz,DMSO-d$_6$); δ(ppm) 2.04–2.11(2H,m), 2.16–2.25(2H,m), 2.75(2H,br-t), 2.89–2.97(4H,m), 3.98 (3H,s), 4.68–4.76(1H,m), 6.65(1H,d,J=3.2 Hz), 7.00(1H,d,J=8.8 Hz), 7.15(2H,br-t), 7.31–7.34(2H,m), 7.44(1H,d,J=8.4 Hz), 7.70(1H,d,J=8.4 Hz), 7.80(1H,d,J=3.2 Hz), 8.07(1H,s), 8.11(1H,dd,J=2.4,8.8 Hz), 8.60(1H,d,J=2.4 Hz).
ESI-Mass; 458(MH+).

Example 318: Synthesis of 1-[1-(4-fluorophenethyl)piperidin-4-yl]-6-[(2-methoxypyridin-5-yl)hydroxymethyl]indole oxalate 1-[1-(4-Fluorophenethyl)piperidin-4-yl]-6-(2-methoxypyridin-5-ylcarbonyl)indole (0.07 g) obtained in Example 317 was dissolved in methanol (10 ml). To the resultant solution was added sodium borohydride in portions. After confirming the disappearance of the starting compound by thin layer chromatography, the solvent was evaporated under reduced pressure. Then water was added to the residue followed by extraction with ethyl acetate. The organic layer was washed successively with water and brine and dried over magnesium sulfate. Then the solvent was evaporated under reduced pressure to give a free compound (0.11 g) of the title compound as a colorless viscous oil, which was then converted into an oxalate in a conventional manner.

$^1$H-NMR(400 MHz,DMSO-d$_6$); δ(ppm) 2.03–2.08(2H,m), 2.13–2.21(2H,m), 2.75–3.00(6H,m), 3.40(2H,br-d), 3.80 (2H,s), 4.52–4.60(1H,m), 6.42(1H,d,J=3.2 Hz), 6.72(1H,d,J=8.6 Hz), 6.96(1H,d,J=8.6 Hz), 7.16(2H,br-t), 7.32–7.35 (2H,m), 7.44–7.46(2H,m), 7.62(1H,dd,J=2.2,8.6 Hz), 7.65 (1H,s), 8.19(1H,d,J=2.2 Hz).
ESI-Mass; 460(MH+).

Example 319: Synthesis of 1-[1-(4-fluorophenethyl)piperidin-4-yl]-6-(1-hydroxyproyl)indole oxalate 1-[1-[(4-Fluorophenethyl)piperidin-4-yl]-6-formylindoline (0.10 g) obtained in Example 130 was dissolved in tetrahydrofuran (5 ml) and stirred under ice cooling. To the resultant solution was added a 1.0 M solution (0.5 ml) of ethylmagnesium bromide in tetrahydrofuran and the resultant mixture was stirred for 25 min. Next, a 1.0 M solution (0.5 ml) of ethyl magnesium bromide in tetrahydrofuran was further added thereto and the resultant mixture was stirred for additional 15 min. To the reaction mixtures were successively added a saturated aqueous solution of ammonium chloride, water and ethyl acetate. The organic layer was separated, washed successively with water and brine and dried over magnesium sulfate. Then the solvent was evaporated under reduced pressure to give a free compound (0.10 g) of the title compound as a pale brown viscous oil, which was then converted into an oxalate in a conventional manner.
$^1$H-NMR(400 MHz,DMSO-d$_6$); δ(ppm) 0.85(3H,t,J=7.4 Hz), 1.62–1.75(2H,m), 2.08(2H,br-d), 2.19–2.29(2H,m), 2.93–2.99(4H,m), 3.08–3.12(2H,m), 3.49(2H,br-d), 4.54 (1H,t,J=6.4 Hz), 4.59–4.65(1H,m), 6.43(1H,d,J=3.0 Hz), 7.00(1H,d,J=8.0 Hz), 7.17(2H,br-t), 7.33–7.36(2H,m), 7.41 (1H,d,J=3.0 Hz), 7.47(1H,d,J=8.0 Hz), 7.49(1H,s).
ESI-Mass; 381(MH+).

Example 320: Synthesis of 1-[1-(4-fluorophenethyl)piperidin-4-yl]-6-(1-hydroxy-1-methylethyl)indoline 1-[1-(4-Fluorophenethyl)piperidin-4-yl]-6-(1-hydroxy-1-methylethyl)indoline (0.1 g) obtained in Example 139 and activated manganese dioxide (0.5 g) were treated as in Example 288 to give the title compound (0.07 g) as a pale yellow oil (yield: 70.3%).

Next, this product was converted into an oxalate in a conventional manner.
Oxalate:
m.p.: 97–99° C.
$^1$H-NMR(400 MHz,DMSO-d$_6$); δ(ppm) 1.49(6H,s), 2.04–2.15(2H,m), 2.16–2.30(2H,m), 2.92–3.06(4H,m), 3.08–3.19(2H,m), 3.47–3.56(2H,m), 4.58–4.68(1H,m), 6.42 (1H,d,J=3.2 Hz), 7.13(1H,dd,J=8.4,1.2 Hz), 7.13–7.21(2H,m), 7.32–7.37(2H,m), 7.40(1H,d,J=3.2 Hz), 7.50(1H,d,J=8.4 Hz), 7.63(2H,br-s).
FAB-Mass; 381(MH+).

Example 121: Synthesis of 1-[1-(4-fluorophenethyl)piperdin-4-yl]-6-(3-hydydroxypropyl)indoline A solution of 1-[1-(4-fluorophenethyl)piperidin-4-yl]-6-formylindole (0.20 g) obtained in Example 130 in tetrahydrofuran (2 ml) was added dropwise at room temperature into a solution prepared by adding triethyl phosphonoacetate (0.14 g) to a suspension of sodium hydride (0.03 g) in tetrahydrofuran (5 ml). After 1 hr, a saturated aqueous solution (10 ml) of ammonium chloride was added thereto and the mixture was extracted with ethyl acetate. The extract was washed successively with water and brine, dried over magnesium sulfate, filtered and concentrated under reduced pressure. The residue was dissolved in ethanol (10 ml) and then hydrogenated in the presence of 10% palladium carbon (0.05 g) at ordinary temperature under atmospheric pressure. After 2 hr, the reaction mixturew were filtered and the filtrate was concentrated. The residue was dissolved in tetrahydrofuran (3 ml) and the resulting solution was added dropwise into a suspension of lithium aluminum hydride (0.03 g) in tetrahydrofuran (5 ml). After stirring the reaction mixtures at room temperature for 1 hr, water (0.03 ml), 5 N sodium hydroxide (0.09 ml) and further water (0.03 ml) were added thereto in this order. The resulting precipitate was filtered off. After washing with ethyl acetate, the filtrate was concentrated. The residue was purified by silica gel column chromatography (dichloromethane/methanol system) to give the title compound (0.05 g) as a pale yellow powder (yield: 23%)
m.p.: 131–133° C.
$^1$H-NMR(400 MHz,DMSO-$d_6$); δ(ppm) 1.90–2.05(4H,m), 2.20–2.29(2H,m), 2.55–2.62(2H,m), 2.74–2.81(2H,m), 2.81 (3H,s), 3.06–3.13(2H,m), 4.25(2H,d,J=6.4 Hz), 4.26–4.38 (1H,m), 6.42(1H,d,J=3.2 Hz), 7.02(1H,dd, J=8.0,1.2 Hz), 7.08–7.14(2H,m), 7.27–7.33(2H,m), 7.47–7.53(3H,m).
ESI-Mass; 381(MH+).

Example 322: Synthesis of 1-[1-(4-fluorophenethyl) piperidin-4-yl]-6-methanesulfonamidomethylindole 322-1) 1-[1-(4-Fluorophenethyl)piperidin-4-yl]-6-formylindole A suspension of 1-[1-(4-fluorophenethyl)piperidin-4-yl]-6-formylindoline (3.60 g) obtained in Example 130 and activated manganese dioxide (15.0 g) in chloroform (100 ml) was heated under reflux for 6 hr under vigorous stirring. Then the reaction mixtures were filtered through celite and the residue was washed with chloroform. After concentrating the filtrate under reduced pressure, the residue was recrystallized from ethyl acetate/hexane to give the title compound (2.45 g) as a yellow powder (yield: 68.4%).
$^1$H-NMR(400 MHz,CDCl$_3$); δ(ppm) 2.09–2.42(6H,m), 2.67–2.75(2H,m), 2.83–2.91(2H,m), 3.19–3.28(2H,br-d), 4.35–4.45(1H,m), 6.61(1H,d,J=3.2 Hz), 6.95–7.05(2H,m), 7.16–7.23(2H,m), 7.48(1H,d,J=3.2 Hz), 7.62(1H,dd,J=8.0, 1.2 Hz), 7.72(1H,d,J=8.0 Hz), 7.98(1H,s), 10.07(1H,s).

322-2) 1-[1-(4-Fluorophenethyl)piperidin-4-yl]-6-hydroxyiminomethylindole

1-[1-(4-Fluorophenethyl)piperidin-4-yl]-6-formylindole (3.78 g), hydroxylamine hydrochloride(0.90 g) and anhydrous sodium acetate (1.06 g) were stirred in ethanol (60 ml) at room temperature for 2 hr. Then the liquid reaction mixture was concentrated and the residue was partitioned between ethyl acetate (150 ml) and a 1 N aqueous solution (30 ml) of sodium hydroxide. The ethyl acetate layer was washed successively with water and brine, dried over magnesium sulfate and concentrated under reduced pressure. The residue was crystallized from ether/hexane and the crystals were collected by filtration, washed with hexane and dried to give the title compound (3.60 g) as a pale yellow powder (yield: 91.3%).
$^1$H-NMR(400 MHz,CDCl$_3$); δ(ppm) 2.03–37(6H,m), 2.61–2.74(2H,m), 2.81–2.91(2H,m), 3.15–3.27(2H,m), 4.20–4.32(1H,m), 6.51(0.5H,d,J=3.2 Hz), 6.68(0.5H,d,J=3.2 Hz), 6.95–7.02(2H,m), 7.14–7.22(2H,m), 7.31(0.5H,d,J=3.2 Hz), 7.32(0.5H,dd,J=8.0,1.2 Hz), 7.38(0.5H,dd,J=8.0,1.2 Hz), 7.45(0.5H,d,J=3.2 Hz), 7.58–7.63(1H,m), 7.66(0.5H,d, J=8.0 Hz), 7.74(0.5H,br-s), 8.32(0.5H,s).

322-3) 1-[1-(4-Fluorophenethyl)piperidin-4-yl]-6-aminomethylindole

Into a suspension of aluminum lithium hydride (1.0 g) in tetrahydrofuran (100 ml) was added dropwise at room temperature a solution of 1-[1-(4-fluorophenethyl)piperidin-4-yl]-6-hydroxyiminomethylindole (3.60 g) in tetrahydrofuran (50 ml) under ice cooling and stirring, and the resultant mixture was heated under reflux for 3 hr. Under cooling with ice water, water (1 ml), a 5 N aqueous solution (3 ml) of sodium hydroxide and further water (1 ml) were carefully added dropwise into the reaction mixtures in this order followed by vigorous stirring. The resulting precipitate was filtered off and the filtrate was concentrated under reduced pressure. Then the residue was purified by NH silica gel column chromatography (ethyl acetate) to give the title compound (2.56 g) as a pale yellow powder (yield: 73.9%).
$^1$H-NMR(400 MHz,CDCl$_3$); δ(ppm) 1.86–2.18(4H,m), 2.22–2.32(2H,m), 2.61–2.70(2H,m), 2.78–2.87(2H,m), 3.10–3.18(2H,m), 4.05(2H,d,J=4.2 Hz), 4.20–4.28(1H,m), 6.46(1H,d,J=3.2 Hz), 6.95–7.03(2H,m), 7.05(1H,dd,J=8.4, 1.6 Hz), 7.14–7.19(2H,m), 7.21(1H,d,J=3.2 Hz), 7.50–7.53 (1H,m), 7.53(1H,d,J=8.4 Hz).

322-4) 1-[1-(4-Fluorophenethyl)piperidin-4-yl]-6-methanesulfonamidomethylindole

Into a solution of 1-[1-(4-fluorophenethyl)piperidin-4-yl]-6-aminomethylindoline (0.12 g) obtained in the above Example and triethylamine (0.5 g) in ethyl acetate (15 ml) was added dropwise under ice cooling methanesulfonyl chloride (0.08 ml) and the resultant mixture was stirred at room temperature for 1 hr. After adding a 1 N aqueous solution (2 ml) of sodium hydroxide and water (15 ml), the reaction mixtures were extracted with ethyl acetate. The ethyl acetate layer was washed successively with water and brine, dried over magnesium sulfate and concentrated under reduced pressure. The residue was crystallized from ether/hexane and the crystals were collected by filtration, washed with hexane and dried to give the title compound (0.11 g) as a white powder (yield: 75%).
m.p.: 121–122° C.
$^1$H-NMR(400 MHz,DMSO-$d_6$); δ(ppm) 1.90–2.05(4H,m), 2.20–2.29(2H,m), 2.55–2.62(2H,m), 2.74–2.81(2H,m), 2.81 (3H,s), 3.06–3.13(2H,m), 4.25(2H,d,J=6.4 Hz), 4.26–4.38 (1H,m), 6.42(1H,d,J=3.2 Hz), 7.02(1H,dd,J=8.0,1.2 Hz), 7.08–7.14(2H,m), 7.27–7.33(2H,m), 7.47–7.53(3H,m).
ESI-Mass; 430(MH+).

Example 323: Synthesis of 1-[1-(4-fluorophenethyl) piperidin-4-yl]-6-isopropylsulfonamidomethylindole 1-[1-(4-Fluorophenethyl)piperidin-4-yl]-6-aminomethylindoline (0.20 g), triethylamine (0.3 ml) and isopropylsulfonyl chloride (0.1 ml) were treated as in Example 322-4) to give the title compound (0.06 g) as a white powder (yield: 23%).
m.p.: 90–92° C.
$^1$H-NMR(400 MHz,CDCl$_3$); δ(ppm) 1.38(6H,d,J=7.2 Hz), 2.05–2.18(4H,m), 2.22–2.36(2H,m), 2.60–2.75(2H,m), 2.79–2.90(2H,m), 3.05–3.25(3H,m), 4.20–4.35(1H,m), 4.35–4.50(3H,m), 6.52(1H,d,J=3.2 Hz), 6.99(2H,t,J=8.8 Hz), 7.05(1H,d,J=8.0 Hz), 7.19(2H,dd,J=5.4,8.8 Hz), 7.27 (1H,d,J=3.2 Hz), 7.38(1H,s), 7.60(1H,d,J=8.0 Hz).
MS m/e; 458(MH+).

Example 324: Synthesis of 1-[1-(4-fluorophenethyl) piperidin-4-yl]-6-n-propylsulfonamidomethylindole 1-[1-(4-Fluorophenethyl)piperidin-4-yl]-6-aminomethylindoline (0.25 g), triethylamine (0.4 ml) and n-propylsulfonyl chloride (0.3 ml) were treated as in Example 322-4) to give the title compound (0.17 g) as a beige powder (yield: 53%).
m.p.: 80–81° C.
$^1$H-NMR(400 MHz,CDCl$_3$); δ(ppm) 0.99(3H,t,J=7.4 Hz), 1.76–1.88(2H,m), 2.02–2.20(4H,m), 2.34–2.37(2H,m), 2.60–2.74(2H,m), 2.76–3.00(4H,m), 3.12–3.28(2H,m), 4.20–4.34(1H,m), 4.43(2H,d,J=5.6 Hz), 4.48(1H,br-s), 6.52 (1H,d,J=3.2 Hz), 6.99(2H,t,J=8.4 Hz), 7.05(1H,d,J=8.0 Hz), 7.19(2H,dd,J=5.8,8.4 Hz), 7.28(1H,d,J=3.2 Hz), 7.38(1H,s), 7.61(1H,d,J=8.0 Hz).

MS m/e; 458(MH+).

Example 325: Synthesis of 1-[1-(4-fluorophenethyl)piperidin-4-yl]-6-(3-chloropropyl)sulfonamidomethylindole 1-[1-(4-Fluorophenethyl)piperidin-4-yl]-6-aminomethylindoline (0.25 g), triethylamine (0.4 ml) and 3-chloropropylsulfonyl chloride (0.1 ml) were treated as in Example 322-4) to give the title compound (0.25 g) as a white powder (yield: 71%).
m.p.: 143–145° C.
$^1$H-NMR(400 MHz,CDCl$_6$); δ(ppm) 2.06–2.16(4H,m), 2.19–2.36(4H,m), 2.63–2.72(2H,m), 2.79–2.88(2H,m), 3.09 (2H,t,J=7.4 Hz), 3.15–3.24(2H,m), 3.59(2H,t,J=6.4 Hz), 4.20–4.34(1H,m), 4.44(2H,d,J=5.6 Hz), 4.56(1H,br-s), 6.52 (1H,d,J=3.2 Hz), 6.99(2H,t,J=8.4 Hz), 7.05(1H,d,J=8.4 Hz), 7.19(2H,dd,J=5.6,8.4 Hz), 7.28(1H,d,J=3.2 Hz), 7.38(1H,s), 7.62(1H,d,J=8.4 Hz).
MS m/e; 492, 494(MH+).

Example 326: Synthesis of 1-[1-( 4-fluorophenethyl)piperidin-4-yl]-6-(1,3-propanesultam-2-yl)methylindole 1-[1-(4-Fluorophenethyl)piperidin-4-yl]-6-(3-chloropropyl)sulfonamidomethylindole (144 mg) obtained in the above Example325 wasdissolved inN,N-dimethylformamide (4 ml). Then sodium hydride (40 mg, 60–70% oily) was added thereto at room temperature and the resultant mixture was stirred for 20 min. After adding water, the mixture was extracted with ethyl acetate and dried over magnesium sulfate. After evaporating the solvent, the residue was purified by silica gel column chromatography (ethyl acetate) to give the title compound (110 mg) as a colorless amorphous substance (yield: 83%).

This amorphous substance was dissolved in ethanol (5 ml) and oxalic acid (20 mg) dissolved in ethanol (1 ml) was added thereto. The resulting salt was powdered by adding ethyl acetate and collected by filtration to give an oxalate (82 mg) of the title compound as a white powder.
Oxalate:
m.p.: 171–172° C.
Free compound:
$^1$H-NMR(400 MHz,CDCl$_3$); δ(ppm) 2.10–2.38(4H,m), 2.22–2.36(4H,m), 2.62–2.72(2H,m), 2.78–2.88(2H,m), 3.06–3.28(6H,m), 4.20–4.38(1H,m), 4.30(2H,s), 6.52(1H,d, J=3.2 Hz), 6.99(2H,t,J=8.4 Hz), 7.07(1H,d,J=8.0 Hz), 7.19 (2H,dd,J=5.6 and 8.4 Hz), 7.27(1H,d,J=3.2 Hz), 7.37(1H,s), 7.59(1H,d,J=8.0 Hz).
MS m/e; 456(MH+).

Example 327: Synthesis of 1-[1-(4-fluorophenethyl)piperidin-4-yl]-6-propionylaminomethylindole 1-[1-(4-Fluorophenethyl)piperidin-4-yl]-6-propionylaminomethylindoline (0.16 g) obtained in Example 156 and activated manganese dioxide (0.8 g) were treated as in Example 288 to give the title compound (0.12 g) as a white powder
(yield: 75.3 ).
m.p.: 141–142° C.
$^1$H-NMR(400 MHz,CDCl$_3$); δ(ppm) 1.18(3H,t,J=7.2 Hz), 2.06–2.15(2H,m), 2.51(2H,q,J=7.2 Hz), 2.28–2.50(2H,m), 2.64–2.98(4H,m), 3.16–3.35(2H,m), 4.22–4.34(1H,m), 4.56 (2H,d,J=6 Hz), 6.51(1H,d,J=3.2 Hz), 6.96–7.05(2H,m), 7.16–7.23(2H,m), 7.24(1H,d,J=3.2 Hz), 7.36(1H,br-s), 7.58 (1H,d,J=8.0 Hz).
ESI-Mass; 408(MH+).

Example 328: Synthesis of 3-chloro-1-[1-(4-fluorophenethyl)piperidin-4-yl]-6-acetamidomethylindole 1-[1-(4-Fluorophenethyl)piperidin-4-yl]-6-acetamidomethylindole (0.1 g) obtained in Example was reacted with 1-chlorosuccinimide (0.04 g) in benzene (10 ml) at 80° C. for 1 hr. Then the liquid reaction mixture was diluted with ethyl acetate (20 ml), washed successively with water and brine, dried over magnesium sulfate and concentrated under reduced pressure. The residue was crystallized from ether/hexane and the crystals were collected by filtration, washed with hexane and dried to give the title compound (0.04 g) as a white powder (yield: 36.8%).
m.p.: 101–102° C.
$^1$H-NMR(400 MHz,CDCl$_3$); δ(ppm) 1.95–2.15(4H,m), 2.03 (3H,s), 2.20–2.50(2H,m), 2.72–3.00(4H,m), 3.28–3.40(2H, m), 4.20–4.30(1H,m), 4.54(2H,d,J=6.4 Hz), 6.95–7.04(2H, m), 7.10(1H,d,J=8.0 Hz), 7.17–7.24(3H,m), 7.35(1H,s), 7.55(1H,d,J=8.0 Hz).
ESI-Mass; 428(MH+).

Example 329: Synthesis of 1-[1-(4-fluorophenethyl)piperidin-4-yl]-6-(4-hydroxybutyroylamidomethyl)indole oxalate 4-Acetoxybutyric acid (0.07 g) synthesized in accordance with the method described in Tetrahedron., 45(24), 7783–7794, 1989. was reacted with 1,1'-carbonyldiimidazole (0.08 g) in chloroform (5 ml). Next, 1-[1-(4-fluorophenethyl)piperidin-4-yl]-6-aminomethylindole (0.13 g) obtained in Example 322-3) was added thereto and the resultant mixture was stirred at room temperature for 3 hr. After concentrating the reaction mixtures, a 5 N aqueous solution of sodium hydroxide (2 ml) and methanol (10 ml) were added to the residue. After reacting at 50° C. for 1 hr, the solvent was concentrated under reduced pressure and the residue was purified by silica gel column chromatography (dichloromethane/methanol system). The resulting pale yellow oil was converted into an oxalate in a conventional manner to give the oxalate (0.04 g) of the title compound as a pale brown amorphous substance (yield: 20.5%).
Oxalate:
$^1$H-NMR(400 MHz,DMSO-d$_6$); δ(ppm) 1.68(2H,m), 2.08–2.34(4H,m), 2.18(2H,t,J=7.6 Hz), 2.96–3.29(6H,m), 3.39(2H,t,J=6.8 Hz), 3.56–3.66(2H,m), 4.36(2H,d,J=5.2 Hz), 4.58–4.70(1H,m), 6.46(1H,d,J=3.6 Hz), 6.96(1H,d,J= 8.0 Hz), 7.15–7.23(2H,m), 7.32–7.46(3H,m), 7.50(1H,d,J= 8.0 Hz), 8.26–8.33(1H,m).
ESI-Mass; 438(MH+).

Example 330: Synthesis of 1-[1-(4-fluorophenethyl)piperidin-4-yl]-6-hydroxyethoxyindole 1-[1-(4-Fluorophenethyl)piperidin-4-yl]-6-hydroxyethoxyindoline (25.2 mg) obtained in Example 121 was dissolved in chloroform (5 ml). To the resultant solution was added activated manganese dioxide (138 mg). The resulting suspension was stirred at room temperature for 22 hr, then filtered through celite and washed with chloroform. The filtrate was concentrated under reduced pressure and crystallized from ethyl acetate/hexane to give the title compound (12.0 mg) as a white solid (yield: 48%).
$^1$H-NMR(400 MHZ,CDCl$_3$); δ(ppm) 2.05–2.13(4H,m), 2.22–2.30(2H,m), 2.64(2H,t,J=7.5 Hz), 2.83(2H,t,J=7.5 Hz), 3.18(2H,br-d,J=12.1 Hz), 4.00(2H,t,J=4.6 Hz), 4.09–4.17(1H,m), 4.17(2H,t,J=4.6 Hz), 6.46(1H,d,J=3.3 Hz), 6.80(1H,dd,J=8.6,2.2 Hz), 6.88(1H,d,J=2.2 Hz), 6.99 (2H,t,J=8.4 Hz), 7.15(1H,d,J=3.3 Hz), 7.18(2H,dd,J=8.4,5.5 Hz), 7.51(1H,d,J=8.6 Hz).
m.p.: 118–119° C.
Mass: FAB+383(M+H)+.

Example 331: Synthesis of 1-[1-(4-fluorophenethyl)piperidin-4-yl]-6-methanesulfonylindole 1-[1-(4-Fluorophenethyl)piperidin-4-yl]-6-methanesulfonylindoline (19.2 mg) obtained in Example 128 was dissolved in chloroform (5 ml). To the resultant solution was added activated manganese dioxide (100 mg).

The resulting suspension was stirred at room temperature for 22 hr and then at 60° C. for additional 22 hr. After the completion of the reaction, the reaction mixtures were filtered through celite and washed with chloroform. The filtrate was concentrated under reduced pressure and crystallized from ethyl acetate/hexane to give the title compound (5.0 mg) as a white solid (yield: 26%).

$^1$H-NMR(400 MHz,CDCl$_3$); δ(ppm) 2.06–2.24(4H,m), 2.32 (2H,td,J=11.6,2.0 Hz), 2.66(2H,t,J=7.2 Hz), 2.83(2H,t,J=7.2 Hz), 3.19(2H,br-d,J=9.9 Hz), 4.33–4.42(1H,m), 6.64(1H,d, J=3.3 Hz), 6.99(2H,t,J=8.8 Hz), 7.19(2H,dd,J=8.8,5.5 Hz), 7.49(1H,d,J=3.3 Hz), 7.61(1H,dd,J=7.3,1.1 Hz), 7.77(1H,d, J=7.3 Hz), 8.04(1H,br-s).

m.p.: 133–135° C.

Mass: FAB+401(M+H)+.

Example 332: Synthesis of 1-[1-(2,6-difluoro-3-pyridylethyl)piperidin-4-yl]indole 1-[1-(2,6-Difluoro-3-pyridylethyl)piperidin-4-yl]indoline (30.5 mg) obtained in Example 57 was dissolved in chloroform (5 ml). To the resultant solution was added activated manganese dioxide (185 mg). The resulting suspension was stirred at room temperature for 22 hr, filtered through celite and washed with chloroform. The filtrate was concentrated under reduced pressure to give the title compound (27.4 mg) as an oil (yield: 90%).

$^1$H-NMR(400 MHz,CDCl$_3$); δ(ppm) 2.00–2.15(4H,m), 2.28 (2H,td,J=11.7,3.1 Hz), 2.66(2H,t,J=8.1 Hz), 2.85(2H,t,J=8.1 Hz), 3.14(2H,br-d,J=11.7 Hz), 4.24–4.30(1H,m), 6.52(1H, d,J=3.1 Hz), 6.79(1H,dd,J=8.1,2.7 Hz), 7.10(1H,t,J=7.9 Hz), 7.21(1H,t,J=7.9 Hz), 7.23(1H,d,J=3.1 Hz), 7.37(1H,d,J=7.9 Hz), 7.63(1H,d,J=7.9,5.3 Hz), 7.76(1H,dd,J=17.2,8.1 Hz).

Mass; FAB+341(M+H).

Example 333: Synthesis of 1-[1-(4-fluorophenethyl)piperidin-4-yl]-6-fluoroindole 1-[1-(4-Fluorophenethyl)piperidin-4-yl]-6-fluoroindoline (28.8 mg) obtained in Example 103 was dissolved in chloroform (5 ml). To the resultant solution was added activated manganese dioxide (160 mg). The resulting suspension was stirred at room temperature for 22 hr, filtered through celite and washed with chloroform. The filtrate was concentrated under reduced pressure to give the title compound (20.1 mg) as an oil (yield: 70%).

$^1$H-NMR(400 MHz,CDCl$_3$); δ(ppm) 2.04–2.15(4H,m), 2.26 (2H,td,J=11.4,3.3 Hz), 2.65(2H,t,J=8.8 Hz), 2.82(2H,t,J=8.8 Hz), 3.18(2H,br-d,J=11.4 Hz), 4.08–4.17(1H,m), 6.50(1H, d,J=3.3 Hz), 6.87(1H,td,J=8.8,1.6 Hz), 6.99(2H,t,J=8.6 Hz), 7.03(2H,dd,J=10.4,1.6 Hz), 7.18(2H,dd,J=8.6,5.5 Hz), 7.22 (1H,d,J=3.3 Hz), 7.52(1H,dd,J=8.8,5.3 Hz).

Mass; FAB: 340(M+H)+.

Example 334: Synthesis of 1-[1-(4-fluorophenethyl)piperidin-4-yl]thiazolo[5,4-f]indole 1-[1-(4-Fluorophenethyl)piperidin-4-yl]thiazolo[5,4-f]indoline (23.7 mg) obtained in Example 234 was dissolved in chloroform (5 ml). To the resultant solution was added activated manganese dioxide (130 mg). The resulting suspension was stirred at room temperature for 22 hr. Then the reaction mixtures were filtered through celite and washed with chloroform. The filtrate was concentrated under reduced pressure and crystallized from ethyl acetate/hexane to give the title compound (12.6 mg) as a pale yellow solid (yield: 53%).

$^1$H-NMR(400 MHz,CDCl$_3$); δ(ppm) 2.07–2.18(4H,m), 2.24–2.35(2H,m), 2.66(2H,t,J=7.0 Hz), 2.83(2H,t,J=7.0 Hz), 3.21(2H,br-d,J=12.1 Hz), 4.36(1H,tt,J=11.7,4.4 Hz), 6.60(1H,d,J=3.5 Hz), 7.00(2H,t,J=8.6 Hz), 7.19(2H,dd,J= 8.6,5.5 Hz), 7.49(1H,d,J=3.5 Hz), 8.13(2H,s), 8.92(1H,s).

m.p.: 152–154° C.

Mass: FAB+380(M+H)+.

Example 335: Synthesis of 1-[1-(4-fluorophenethyl)piperidin-4-yl]-6-(N-methylmethanesulfonylamino)indole 1-[1-(4-Fluorophenethyl)piperidin-4-yl]-6-(N-methylmethanesulfonylamino)indoline (34.6 mg) obtained in Example 120 was dissolved in chloroform (5 ml). To the resultant solution was added activated manganese dioxide (190 mg). The resulting suspension was stirred at room temperature for 22 hr, then filtered through celite and washed with chloroform. The filtrate was concentrated under reduced pressure and crystallized from ethyl acetate/hexane to give the title compound (24.7 mg) as a white solid (yield: 72%).

$^1$H-NMR(400 MHz,CDCl$_3$); δ(ppm) 2.01–2.17(4H,m), 2.28 (2H,td,J=11.7,3.3 Hz), 2.65(2H,t,J=8.2 Hz), 2.83(2H,t,J=8.2 Hz), 2.88(3H,s), 3.17(2H,br-d,J=12.1 Hz), 3.39(3H,s), 4.25 (1H,tt,J=11.2,5.2 Hz), 6.52(1H,d,J=3.3 Hz), 6.99(2H,t,J=8.6 Hz), 7.04(1H,dd,J=8.4,1.8 Hz), 7.19(2H,dd,J=8.6,5.5 Hz), 7.30(1H,d,J=3.3 Hz), 7.47(1H,d,J=1.8 Hz), 7.61(1H,d,J=8.4 Hz).

m.p. 192–194° C.

Mass: FAB+430(M+H)+.

Example 336: Synthesis of 1-[1-(4-fluorophenethyl)piperidin-4-yl]-6-methanesulfonyloxyindole 1-[1-(4-Fluorophenethyl)piperidin-4-yl]-6-methanesulfonyloxyindoline (53.4 mg) obtained in Example 122 was dissolved in chloroform (5 ml). To the resultant solution was added activated manganese dioxide (300 mg). The resulting suspension was stirred at room temperature for 22 hr. Then the reaction mixtures were filtered through celite and washed with chloroform. The filtrate was concentrated under reduced pressure and crystallized from ethyl acetate/hexane to give the title compound (40.0 mg) as a white solid (yield: 75%).

$^1$H-NMR(400 MHz,DMSO-d$_6$); δ(ppm) 1.87–2.01(4H,m), 2.22(2H,br-t,J=10.6 Hz), 2.55(2H,t,J=7.9 Hz), 2.75(2H,t,J= 7.9 Hz), 3.06(2H,br-d,J=11.2 Hz), 3.34(3H,s), 4.32–4.41 (1H,m), 6.50(1H,d,J=2.6 Hz), 6.98(1H,dd,J=8.4,1.5 Hz), 7.09(2H,t,J=9.0 Hz), 7.27(2H,dd,J=9.0,5.7 Hz), 7.57(1H,d, J=1.5 Hz), 7.56(1H,d,J=8.4 Hz), 7.60(1H,d,J=2.6 Hz).

m.p.: 213–215° C.

Mass: FAB+417(M+H)+.

Example 337: Synthesis of 1-[1-(4-fluorophenethyl)piperidin-4-yl]-6-carbamoylindole 1-[1-(4-Fluorophenethyl)piperidin-4-yl]-6-carbamoylindoline (14.1 mg) obtained in Example 125 was dissolved in chloroform (5 ml). To the resultant solution was added activated manganese dioxide (80 mg). The resulting suspension was stirred at room temperature for 22 hr, then filtered through celite and washed with chloroform. The filtrate was concentrated under reduced pressure and crystallized from ethyl acetate/hexane to give the title compound (5.0 mg) as a white solid (yield: 36%).

$^1$H-NMR(400 MHz,CDCl$_3$); δ(ppm) 2.05–2.14(4H,m), 2.22–2.31(2H,m), 2.62–2.67(2H,m), 2.78–2.84(2H,m), 3.18 (2H,br-d, J=10.3 Hz), 4.35–4.44(1H,m), 6.57(1H,d,J=3.3 Hz), 6.99(2H,t,J=8.2 Hz), 7.18(2H,dd,J=8.2,5.3 Hz), 7.39 (1H,d,J=3.3 Hz), 7.40(1H,d,J=8.1 Hz), 7.64(1H,d,J=8.1 Hz), 8.10(1H,br-s).

m.p.: 238–240° C.

Mass: FAB+366(M+H)+.

Example 338: Synthesis of 1-[1-(4-fluorophenethyl)piperidin-4-yl]-6-(N-methylsulfamoylmethyl)indole 1-[1-(4-Fluorophenethyl)piperidin-4-yl]-6-(N-methylsulfamoylmethyl)indoline (30.4 mg) obtained in Example 164 was dissolved in chloroform (5 ml). To the resultant solution was added activated manganese dioxide (165 mg). The resulting suspension was stirred at room temperature for 22 hr. Then the reaction mixtures were filtered through celite and washed with chloroform. The filtrate was concentrated under reduced pressure and crystallized from ethyl acetate/hexane to give the title compound (24 mg) as a white solid (yield: 79%).

$^1$H-NMR(400 MHz,DMSO-d$_6$); δ(ppm) 1.99–2.04(4H,m), 2.17–2.25(2H,m), 2.54(2H,d,J=4.8), 2.55(2H,t,J=8.4 Hz), 2.76(2H,t,J=8.4 Hz), 3.08(2H,br-d,J=11.7 Hz), 4.25–4.35 (1H,m), 4.37(2H,s), 6.43(1H,d,J=3.1 Hz), 6.83(1H,q,J=4.8 Hz), 7.01(1H,d,J=8.4 Hz), 7.09(2H,t,J=8.8 Hz), 7.27(2H,dd, J=8.8,5.7 Hz), 7.50(1H,d,J=8.4 Hz), 7.51(1H,s), 7.52(1H,d, J-3.1 Hz).

m.p.: 172–175° C.

Mass: FAB+430(M+H)+.

Example 339: Synthesis of 1-[1-(4-fluorophenethyl) piperidin-4-yl]-6-acetamidoindole 1-[1-(4-Fluorophenethyl)piperidin-4-yl]-6-acetamidoindoline (32 mg) obtained in Example 115 was dissolved in chloroform (5 ml). To the resultant solution was added activated manganese dioxide (160 mg). The resulting suspension was stirred at room temperature for 22 hr, then filtered through celite and washed with chloroform. The filtrate was concentrated under reduced pressure and crystallized from ethyl acetate/hexane to give the title compound (23 mg) as a pale red solid (yield: 72%).

$^1$H-NMR(400 MHz,DMSO-d$_6$); δ(ppm) 1.85–2.00(4H,m), 2.02(3H,s), 2.13–2.23(2H,m), 2.55(2H,t,J=7.7 Hz), 2.75 (2H,t,J=7.7 Hz), 3.08(2H,br-d,J=11.7 Hz), 4.07–4.18(1H, m), 6.35(1H,d,J=2.2 Hz), 7.05(1H,d,J=8.6 Hz), 7.09(2H,t, J=9.0 Hz), 7.27(2H,dd,J=9.0,6.0 Hz), 7.39(1H,d,J=2.2 Hz), 7.40(1H,d,J=8.6 Hz), 7.92(1H,s), 9.85(1H,br-s).

m.p.: 195–196° C.

Mass: FAB+380(M+H)+.

Example 340: Synthesis of 1-[1-(4-fluorophenethyl) piperidin-4-yl]-6-(1,2-dihydroxypropan-3-yl) carbamoylmethylindole oxalate 1-[1-(4-Fluorophenethyl)piperidin-4-yl]-6-carboxymethylindoline (0.17 g) obtained in Example 146 was dissolved in N,N-dimethylformamide (5 ml). To the resultant solution was added 1,1-carbonyldiimidazole (0.09 g) and the resultant mixture was stirred under nitrogen atmosphere at room temperature for 15 min. Next, 1-amino-2,3-propanediol (0.40 g) dissolved in N,N-dimethylformamide (1 ml) was added thereto and the mixture was stirred for additional 7.5 hr. After evaporating the solvent under reduced pressure, water and ethyl acetate were added to the residue. The organic layer was separated, washed successively with water and brine and dried over magnesium sulfate. Then the solvent was evaporated under reduced pressure to give a pale brown viscous oil (0.14 g).

The resulting residue was dissolved in chloroform (30 ml) and manganese dioxide (0.27 g) was added thereto. After stirring the resultant mixture at 50° C. overnight, additional manganese dioxide (0.13 g) was added thereto followed by stirring for 3 hr. Next, the manganese dioxide was filtered off and the solvent was evaporated under reduced pressure. The residue was purified by silica gel column chromatography (chloroform/methanol system) to give a free title compound (0.07 g) as a pale brown amorphous substance, which was then converted into an oxalate in a conventional manner.

$^1$H-NMR(400 MHz,DMSO-d$_6$); δ(ppm) 2.07(2H,br-d), 2.18–2.27(2H,m), 2.84–3.06(7H,m), 3.17–3.28(3H,m), 3.45–3.53(3H,m), 3.53(2H,s), 4.50–4.58(1H,m), 6.43(1H,d, J=3.2 Hz), 6.95(1H,d,J=8.8 Hz), 7.16(2H,br-t), 7.32–7.36 (2H,m), 7.41–7.46(3H,m), 7.99(1H,t,J=5.4 Hz).

ESI-Mass; 454(MH+).

Example 341: Synthesis of 1-[1-(4-fluorophenethyl) piperidin-4-yl]-6-(pyridin-2-yl) methylcarbamoylmethylindole oxalate 1-[1-(4-Fluorophenethyl)piperidin-4-yl]-6-carboxymethyl-indoline (0.21 g) obtained in Example 146 was dissolved in N,N-dimethylformamide (5 ml). To the resultant solution was added 1,1-carbonyldiimidazole (0.11 g) and the resultant mixture was stirred under nitrogen atmosphere at room temperature for 15 min. Next, 2-aminomethylpyridine (287 ml) was added thereto and the mixture was stirred for additional 4 hr. After evaporating the solvent under reduced pressure, water and ethyl acetate were added to the residue. The organic layer was separated, washed successively with water and brine and dried over magnesium sulfate. Then the solvent was evaporated under reduced pressure to give a pale brown viscous oil (0.20 g).

The resulting residue was dissolved in chloroform (30 ml) and manganese dioxide (0.36 g) was added thereto. After stirring the resultant mixture at 50° C. overnight, additional manganese dioxide (0.18 g) was added thereto followed by stirring for 6 hr. Next, the manganese dioxide was filtered off and the solvent was evaporated under reduced pressure to give a free title compound (0.18 g) as a pale brown viscous oil, which was then converted into an oxalate in a conventional manner.

$^1$H-NMR(400 MHz,DMSO-d$_6$); δ(ppm) 2.09(2H,br-d), 2.25–2.34(2H,m), 2.92–3.00(4H,m), 3.09–3.17(2H,m), 3.52 (2H,br-d), 3.62(2H,s), 4.37(2H,d,J=5.8 Hz), 4.54–4.64(1H, m), 6.45(1H,d,J=3.4 Hz), 7.01(1H,d,J=8.0 Hz), 7.17(2H,br-t), 7.22–7.25(2H,m), 7.33–7.36(2H,m), 7.42(1H,d,J=1.6 Hz), 7.48(1H,d,J=8.0 Hz), 7.50(1H,s), 7.68–7.72(1H,m), 7.48(1H,d,J=3.4 Hz), 8.63(1H,t,J=5.8 Hz).

ESI-Mass; 471(MH+).

Example 342: Synthesis of 1-[1-(2-fluorophenethyl) piperidin-4-yl]-6-methylcarbamoylmethylindole 342-1) 1-[1-(2-Fluorophenethyl)piperidin-4-yl]-6-hydroxymethylindoline 1-[1-(2-Fluorophenethyl)piperidin-4-yl]-6-formylindoline (6.85 g) obtained in Example 348-3) was dissolved in methanol (50 ml) and tetrahydrofuran (25 ml), and the resultant solution was stirred under ice cooling. Then sodium borohydride was added thereto in portions. After confirming the disappearance of the starting material by thin layer chromatography, the solvent was evaporated under reduced pressure and ethyl acetate and an 8N aqueous solution of sodium hydroxide were added to the residue. The organic layer was separated, washed successively with water and brine and dried over magnesium sulfate. Then the solvent was evaporated under reduced pressure to give the title compound (8.10 g) as colorless crystals.

$^1$H-NMR(400 MHz,CDCl$_3$); δ(ppm) 1.72–1.84(4H,m), 2.13–2.19(2H,m), 2.60–2.64(2H,m), 2.84–2.88(2H,m), 2.93 (2H,t,J=8.4 Hz), 3.13(2H,br-d), 3.42(2H,t,J=8.4 Hz), 3.38–3.46(1H,m), 4.59(2H,s), 6.44(1H,s), 6.57(1H,d,J=7.2 Hz), 6.99–7.04(2H,m), 7.04–7.08(1H,m), 7.16–7.23(2H,m).

342-2) 1-[1-(2-Fluorophenethyl)piperidin-4-yl]-6-chloromethylindoline

Conc. hydrochloric acid (30 ml) was added to the 1-[1-(2-fluorophenethyl)piperidin-4-yl]-6-hydroxymethylindoline (7.49 g) obtained above and the resultant mixture was stirred at 80° C. overnight. Next, it was neutralized with a 5 N aqueous solution of sodium hydroxide under ice cooling and then the pH value thereof was adjusted to about pH 10 with a 10% aqueous solution of sodium carbonate followed by extraction with ethyl acetate. Then it was washed with brine and dried over magnesium sulfate. After evaporating the solvent under reduced pressure, the title compound (8.10 g) was obtained as pale brown crystals.
$^1$H-NMR(400 MHz,CDCl$_3$); δ(ppm) 1.72–1.85(4H,m), 2.14–2.21(2H,m), 2.60–2.65(2H,m), 2.84–2.89(2H,m), 2.93 (2H,t,J=8.4 Hz), 3.14(2H,br-d), 3.37–3.44(1H,m), 3.43(2H, t,J=8.4 Hz), 4.52(2H,s), 6.40(1H,d,J=1.2 Hz), 6.59(1H,dd, J=1.2,7.4 Hz), 6.99–7.04(2H,m), 7.05–7.09(1H,m), 7.16–7.24(2H,m).

342-3) 1-[1-(2-Fluorophenethyl)piperidin-4-yl]-6-cyanomethylindoline

Dimethyl sulfoxide (50 ml) was added to the 1-[1-(2-fluorophenethyl)piperidin-4-yl]-6-chloromethylindoline (6.51 g) obtained above. After dissolving, sodium cyanide (0.94 g) was added thereto and the resultant mixture was stirred at 50° C. for 2 hr. Then ice water was added thereto followed by extraction with ethyl acetate. Next, it was washed successively with a dilute aqueous solution of sodium chloride and a saturated aqueous solution of sodium chloride and dried over magnesium sulfate. After evaporating the solvent under reduced pressure, the residue was purified by NH-silica gel column chromatography (ethyl acetate/n-hexane system) to give the title compound (4.95 g) as a pale yellow viscous oil.
$^1$H-NMR(400 MHz,CDCl$_3$); δ(ppm) 1.72–1.83(4H,m), 2.14–2.21(2H,m), 2.61(2H,m), 2.84–2.88(2H,m), 2.94(2H, t,J=8.4 Hz), 3.13(2H,br-d), 3.35–3.44(1H,m), 3.44(2H,t,J= 8.4 Hz), 3.65(2H,s), 6.30(1H,s), 6.50(1H,d,J=7.2 Hz), 6.99–7.04(2H,m), 7.05–7.09(2H,m), 7.16–7.24(2H,m).

342-4) 1-[1-(2-Fluorophenethyl)piperidin-4-yl]-6-carboxymethylindoline

Water (10 ml) andconc. sulfuric acid (10 ml) were added to the 1-[1-(2-fluorophenethyl)piperidin-4-yl]-6-cyanomethylindoline (6.51 g) obtained above. After dissolution, the resultant mixture was heated under reflux. Then the reaction solution was ice-cooled and neutralized with an 8 N aqueous solution of sodium hydroxide and the pH value of the mixture was adjusted to pH 6 with 1 N hydrochloric acid. After extracting with chloroform, it was washed with brine and dried over magnesium sulfate. After evaporated the solvent under reduced pressure, the title compound (0.93 g) was obtained as a pale green powder.
$^1$H-NMR(400 MHz,CDCl$_3$); δ(ppm) 1.91–1.95(2H,m), 2.52 (2H,br-s), 2.80(2H,br-s), 2.90(2H,t,J=8.4 Hz), 3.13–3.17 (2H,m), 3.27–3.31(2H,m), 3.40(2H,t,J=8.4 Hz), 3.54–3.73 (3H,m), 3.55(2H,s), 6.39(1H,s), 6.55(1H,d,J=7.6 Hz), 6.97–7.13(3H,m), 7.25–7.35(2H,m).
ESI-Mass; 383(MH+).

342-5) 1-[1-(2-Fluorophenethyl)piperidin-4-yl]-6-methylcarbamoylmethylindole

1-[1-(2-Fluorophenethyl)piperidin-4-yl]-6-carboxymethyl-indoline (0.16 g) obtained in Example 146 was dissolved in N,N-dimethylformamide (5 ml). To the resultant solution was added 1,1-carbonyldiimidazole (0.08 g) and the resultant mixture was stirred under nitrogen atmosphere at room temperature for 15 min. Next, a 2 N solution (1.02 ml) of methylamine in tetrahydrofuran was added thereto and the resultant mixture was stirred for 2 hr. After evaporating the solvent under reduced pressure, water and ethyl acetate were added to the residue. The organic layer was separated, washed successively with water and brine and dried over magnesium sulfate. Then the solvent was evaporated under reduced pressure to give pale brown crystals (0.09 g).

The obtained crystals were dissolved in chloroform (20 ml) and manganese dioxide (0.20 g) was added thereto. After stirring the resultant mixture at 50° C. overnight, additional manganese dioxide (0.20 g) was added thereto followed by stirring for 7 hr. Next, the manganese dioxide was filtered off and the solvent was evaporated under reduced pressure. The residue was recrystallized from chloroform/n-hexane to give the title compound (0.06 g) as a pale brown powder.
m.p.: 136.5–137.4° C.
$^1$H-NMR(400 MHz,CDCl$_3$); δ(ppm) 2.08–2.13(4H,m), 2.28–2.35(2H,m), 2.67–2.71(2H,m), 2.73(3H,d,J=4.8 Hz), 2.88–2.92(2H,m), 3.20(2H,br-d), 3.72(2H,s), 4.21–4.28(1H, m), 5.40(1H,br-s), 6.53(1H,d,J=3.2 Hz), 6.96(1H,dd,J=1.2, 8.0 Hz), 7.01–7.06(1H,m), 7.06–7.10(1H,m), 7.18–7.24(4H, m), 7.61(1H,d,J=8.0 Hz).
ESI-Mass; 394(MH+).

Example 343: Synthesis of 1-[1-(2-fluorophenethyl) piperidin-4-yl]-6-(1-acetylpiperidin-4-yl) methylcarbamoylmethylindole oxalate 1-[1-(4-Fluorophenethyl)piperidin-4-yl]-6-carboxymethylindoline (0.20 g) obtained in Example 146 was dissolved in N,N-dimethylformamide (5 ml). To the resultant solution was added 1,1-carbonyldiimidazole (0.10 g) and the resultant mixture was stirred under nitrogen atmosphere at room temperature for 15 min. Next, 1-acetyl-4-aminomethyl-piperidine (0.25 g) dissolved in N,N-dimethylformamide (1 ml) was added thereto and the mixture was further stirred overnight. After evaporating the solvent under reduced pressure, water and ethyl acetate were added to the residue. The organic layer was separated, washed successively with water and brine and dried over magnesium sulfate. Then the solvent was evaporated under reduced pressure to give a pale brown viscous oil (0.20 g).

The resulting residue was dissolved in chloroform (30 ml) and manganese dioxide (0.33 g) was added thereto. After stirring the resultant mixture at 50° C. overnight, additional manganese dioxide (0.17 g) was added thereto followed by stirring for 6 hr. Next, the manganese dioxide was filtered off and the solvent was evaporated under reduced pressure to give the title compound (0.26 g) as a pale yellow amorphous substance.
$^1$H-NMR(400 MHz,CDCl$_3$); δ(ppm) 0.94–1.09(2H,m), 1.55–1.83(3H,m), 2.04(3H,s), 2.08–2.13(4H,m), 2.25–2.31 (2H,m), 2.46(1H,dt,J=2.4,12.8 Hz), 2.64–2.68(2H,m), 2.81–2.85(2H,m), 2.92–3.03(2H, m), 3.11–3.20(3H,m), 3.72(2H,s), 3.75(1H,br-d), 4.20–4.28(1H,m), 4.55(1H,br-d), 5.55(1H,t,J=6.0 Hz), 6.53(1H,d,J=2.8 Hz), 6.95–7.01(3H, m), 7.17–7.20(2H,m), 7.26–7.27(2H,m), 7.62(1H,d,J=8.0 Hz).
ESI-Mass; 519(MH+).

Example 344: Synthesis of 1-[1-(2-fluorophenethyl) piperidin-4-yl]-6-ethylcarbamoylmethylindole 1-[1-(2-Fluorophenethyl)piperidin-4-yl]-6-carboxymethylindoline (0.16 g) obtained in Example 342-4) was dissolved in N,N-dimethylformamide (5 ml). To the resultant solution was added 1,1-carbonyldiimidazole (0.08 g) and the resultant mixture was stirred under nitrogen atmosphere at room temperature for 15 min. Next, a 2 N solution (1.06 ml) of ethylamine in tetrahydrofuran was added thereto and the mixture was further stirred for 2 hr. After evaporating the solvent under reduced pressure, water and ethyl acetate were added to the residue. The organic layer was separated, washed successively with water and brine and dried over magnesium sulfate. Then the solvent was evaporated under reduced pressure to give pale brown crystals (0.11 g).

These crystals were dissolved in chloroform (20 ml) and manganese dioxide (0.23 g) was added thereto. After stirring the resultant mixture at 50° C. overnight, additional manganese dioxide (0.23 g) was added thereto followed by stirring for 7 hr. Next, the manganese dioxide was filtered off and the solvent was evaporated under reduced pressure. The residue was recrystallized from chloroform/n-hexane to give the title compound (0.07 g) as a pale brown powder.
m.p.: 147.0–148.6° C.
$^1$H-NMR(400 MHz,CDCl$_3$); δ(ppm) 1.02(3H,t,J=7.4 Hz), 2.08–2.13(4H,m), 2.28–2.35(2H,m), 2.67–2.71(2H,m), 2.88–2.92(2H,m), 3.19–3.26(4H,m), 3.70(2H,s), 4.21–4.29 (1H,m), 5.40(1H,br-t), 6.53(1H,d,J=3.2 Hz), 6.97(1H,dd,J= 1.6,8.0 Hz), 7.01–7.06(1H,m), 7.06–7.10(1H,m), 7.18–7.27 (4H,m), 7.61(1H,d,J=8.0 Hz).
ESI-Mass; 408(MH+).
Example 345: Synthesis of 1-[1-(2-fluorophenethyl) piperidin-4-yl]-6-(1-ethylpiperidin-4-yl) methylcarbamoylmethylindole oxalate 345-1) 1-Acetyl-4-aminomethylpiperidine Benzene (70 ml) was added to 4-aminomethylpiperidine (10.00 g) followed by dissolution. Next, benzaldehyde (9.30 g) was added thereto and the resultant mixture was heated under reflux for 3 hr with the use of a Dean-Stark reflux condenser. After evaporating the solvent under reduced pressure, benzene (70 ml) was added to the residue followed by dissolution. Next, triethylamine (67 ml) and acetic anhydride (9.1 ml) were added thereto and the resultant mixture was stirred under nitrogen atmosphere at room temperature for 3 days. The solvent was evaporated under reduced pressure.

Sodium hydrogensulfate monohydrate (13.3 g) was dissolved in water (80 ml) and the resulting residue was added thereto. The resultant mixture was stirred at room temperature for 2.5 hr. Then the reaction solution was washed with ether. The aqueous layer was ice-cooled and the pH value thereof was adjusted to pH 11 with a 5 N aqueous solution of sodium hydroxide followed by extraction with chloroform under salting out. Then the extract was dried over magnesium sulfate and the solvent was evaporated under reduced pressure to give the title compound (12.81 g) as a brown oil.
$^1$H-NMR(400 MHz,CDCl$_3$); δ(ppm) 1.04–1.19(2H,m), 1.50–1.57(1H,m), 1.74–1.84(2H,m), 2.09(3H,s), 2.54(1H, dt,J=2.8,12.8 Hz), 2.62(2H,d,J=6.8 Hz), 3.04(1H,dt,J=2.8, 12.8 Hz), 3.80–3.86(1H,m), 4.61–4.67(1H,m).

345-2) 1-Ethyl -4-aminomethylpiperdine

Lithium aluminum hydride (1.06 g) was suspended in tetrahydrofuran (70 ml) and the resultant suspension was stirred under nitrogen atmosphere under ice cooling. Next, 1-acetyl-4-aminomethylpiperidine (4.14 g). dissolved in tetrahydrofuran (30 ml) was added thereto and the resultant mixture was stirred at room temperature for 10 min and heated under reflux overnight. Then the reaction mixtures were ice-cooled and water (1.06 ml), a 5 N aqueous solution of sodium hydroxide (1.06 ml) and further water (3.18 ml) were successively added thereto. After stirring, the mixture was diluted with ethyl acetate and the insolubles were filtered off. The residue was purified by NH-silica gel column chromatography (chloroform/methanol system) to give the title compound (3.15 g) as a pale brown oil.

345-3) 1-[1-(4-Fluorophenethyl)piperidin-4-yl]-6-(1-ethylpiperidin-4-yl)methylcarbamoylmethylindole oxalate 1-[1-(4-Fluorophenethyl)piperidin-4-yl]-6-carboxymethylindoline (0.29 g) obtained in Example 146 was dissolved in N,N-dimethylformamide (5 ml). To the resultant solution was added 1,1-carbonyldiimidazole (0.15 g) and the resultant mixture was stirred under nitrogen atmosphere at room temperature for 15 min. Next, 1-ethyl-4-aminomethylpiperidine (0.32 g) dissolved in N,N-dimethylformamide (1 ml) was added thereto and the mixture was stirred for additional 3 hr. After evaporating the solvent under reduced pressure, water and ethyl acetate were added to the residue. The organic layer was separated, washed successively with water and brine and dried over magnesium sulfate. Then the solvent was evaporated under reduced pressure to give a pale brown viscous oil (0.30 g).

The obtained residue was dissolved in chloroform (30 ml) and manganese dioxide (0.51 g) was added thereto. After stirring the resultant mixture at 50° C. overnight, additional manganese dioxide (0.51 g) was added thereto followed by stirring for 13.5 hr. After further adding manganese dioxide (0.51 g), the resultant mixture was stirred overnight. Next, the manganese dioxide was filtered off and the solvent was evaporated under reduced pressure. The residue was purified by silica gel column chromatography (chloroform/methanol system) to give a free title compound (0.26 g) as a brown viscous oil, which was then converted into an oxalate in a conventional manner.
$^1$H-NMR(400 MHz,DMSO-d$_6$); δ(ppm) 1.12(3H,t,J=6.6 Hz), 1.27–1.35(2H,m), 1.54–1.64(1H,m), 1.73(2H,br-d), 1.92–2.08(4H,m), 2.30(2H,br-t), 2.55(2H,br-t), 2.62–2.66 (2H,m), 2.78–2.86(4H,m), 2.97(2H,br-t), 3.14(2H,br-d), 3.23(2H,br-d), 3.50(2H,s), 4.26–4.34(1H,m), 6.40(1H,d,J= 3.2 Hz), 6.93(1H,d,J=8.0 Hz), 7.12(2H,br-t), 7.28–7.32(2H, m), 7.41–7.45(2H,m), 8.09(1H,t,J=5.8 Hz).
ESI-Mass; 505(MH+).
Example 346: Synthesis of 1-[1-(2-fluorophenethyl) piperidin-4-yl]-6-(2-hydroxyethyl)carbamoylmethylindole 1-[1-(2-Fluorophenethyl)piperidin-4-yl]-6-carboxymethylindoline (0.20 g) obtained in Example 342-4) was dissolved in N,N-dimethylformamide (5 ml). To the resultant solution was added 1,1-carbonyldiimidazole (0.10 g) and the resultant mixture was stirred under nitrogen atmosphere at room temperature for 15 min. Next, ethanolamine (161 ml) was added thereto and the mixture was stirred overnight. After evaporating the solvent under reduced pressure, water and ethyl acetate were added to the residue. The organic layer was separated, washed successively with water and brine and dried over magnesium sulfate. Then the solvent was evaporated under reduced pressure to give pale brown crystals (0.14 g).

These crystals were dissolved in chloroform (30 ml) and manganese dioxide (0.28 g) was added thereto. After stirring the resultant mixture at 50° C. overnight, the manganese dioxide was filtered off and the solvent was evaporated under reduced pressure. The residue was recrystallized from ethyl acetate/n-hexane to give the title compound (0.07 g) as a pale gray powder.
m.p.: 127.7–128.6° C.
$^1$H-NMR(400 MHz,CDCl$_3$); δ(ppm) 2.08–2.21(4H,m), 2.31 (2H,br-t), 2.68–2.71(2H,m), 2.88–2.92(2H,m), 3.21(2H,br-d), 3.37(2H,dt,J=4.8,4.8 Hz), 3.67(2H,t,J=4.8 Hz), 3.74(2H, s), 4.20–4.27(1H,m), 5.90(1H,br-s), 6.51(1H,d,J=3.2 Hz), 6.96–7.10(3H,m), 7.18–7.26(3H,m), 7.32(1H,s), 7.61(1H,d, J=8.0 Hz).
ESI-Mass; 424(MH+).
Example 347: Synthesis of 1-[1-(4-fluorophenethyl) piperidin-4-yl]-6-(1,3-dioxolan-2-yl) methylcarbamoylmethylindole 1-[1-(4-Fluorophenethyl)piperidin-4-yl]-6-carboxymethylindoline (0.22 g) obtained in Example 342-4) was dissolved in N,N-dimethylformamide (5 ml). To the resultant solution was added 1,1-carbonyldiimidazole (0.11 g) and the resultant mixture was stirred under nitrogen atmosphere at room temperature for 15 min. Next, 2-aminomethyl-1,3-dioxolane (0.12 g) dissolved in N,N- dimethylformamide (1 ml) was added thereto and the mixture was stirred overnight. After evaporating the solvent under reduced pressure, water and ethyl acetate were added to the residue. The organic layer was separated, washed successively with water and brine and dried over magnesium sulfate. Then the solvent was evaporated under reduced pressure to give pale brown crystals (0.20 g).

These crystals were dissolved in chloroform (20 ml) and manganese dioxide (0.38 g) was added thereto. After stirring the resultant mixture at 50° C. overnight, additional manganese dioxide (0.38 g) was added thereto and the mixture was stirred for 10.5 hr. Next, the manganese dioxide was filtered off and the solvent was evaporated under reduced pressure. The residue was recrystallized from chloroform/n-hexane to give the title compound (0.15 g) as colorless needles.

m.p.: 173.8–174.6° C.

$^1$H-NMR(400 MHz,CDCl$_3$); δ(ppm) 2.05–2.12(4H,m), 2.25–2.31(2H,m), 2.64–2.68(2H,m), 2.81–2.85(2H,m), 3.18 (2H,br-d), 3.43(2H,dd,J=3.6,6.0 Hz), 3.73(2H,s), 3.75–3.79 (4H,m), 4.21–4.29(1H,m), 4.90(1H,t,J=3.6 Hz), 5.67(1H,t, J=6.0 Hz), 6.51(1H,d,J=3.2 Hz), 6.96–7.01(3H,m), 7.17–7.20(2H,m), 7.25–7.28(2H,m), 7.60(1H,d,J=8.0 Hz).

ESI-Mass; 466(MH+).

Example 348: Synthesis of 1-1-(2-fluorophenethyl) piperidin-4-yl]-6-aminomethylindole 348-1) 1-(2-Fluorophenethyl)piperidin-4-one An aqueous solution (400 ml) of N,N-dimethyl-4-oxopiperidinium iodide (49.6 g) was added dropwise under reflux into a solution of 2-fluorophenethylamine (25 g) and potassium carbonate (56.6 g) in water (400 ml) and ethanol (800 ml). After the completion of the addition, the reaction solution was further heated under reflux for 45 min. Then ethanol was evaporated under reduced pressure and the residue was extracted with chloroform. The chloroform layer was washed with brine and dried over magnesium sulfate. After evaporating the solvent under reduced pressure, the residue was dissolved in a mixture of ethyl acetate with chloroform (1:1) and filtered through silica gel. The filtrate was concentrated under reduced pressure to give the title compound (31.2 g) as a yellow oil (yield: 80.2%).

$^1$H-NMR(400 MHz,CDCl$_3$); δ(ppm) 2.46–2.55(4H,m), 2.71–2.80(2H,m), 2.80–2.93(6H,m), 6.98–7.10(2H,m), 7.16–7.25(2H,m).

348-2) 1-[1-(2-Fluorophenethyl)piperidin-4-yl]-6-bromoindoline

Triacetoxylated sodium borohydride (15.0 g) was added under ice cooling to a liquid mixture of 6-bromoindoline (9.0 g), 1-(2-fluorophenethyl)piperidin-4-one (11.0 g) and acetic acid (12.5 ml) in 1,2-dichloroethane (140 ml). Then the reaction mixtures were stirred at room temperature overnight. The reaction mixtures were diluted with ethyl acetate (400 ml) and then an 8 N aqueous solution (70 ml) of sodium hydroxide was added thereto. The organic layer was separated, extracted with 5 N hydrochloric acid (100 ml) and then basified with an 8 N aqueous solution of sodium hydroxide. Then it was extracted with ethyl acetate and washed successively with water and brine. The ethyl acetate layer was dried over magnesium sulfate and the solvent was evaporated distilled off under reduced pressure to give the title compound (12.2 g) as a pale yellow solid (yield: 66.6%). 2.10(2H,dt,J=7.6,2.8 Hz), 2.48–2.53(2H,m), 2.77(2H,t, J=8.4 Hz), 2.83(2H,t,J=8.4 Hz), 2.96–3.03(2H, br-d), 3.37(2H,t,J=8.4 Hz), 3.34–3.43(1H,m), 6.57(1H,d,J= 1.2 Hz), 6.61(1H,dd,J=7.6,1.2 Hz), 6.90(1H,d,J=7.6 Hz), 7.10–7.16(2H,m), 7.21–7.28(1H,m), 7.33(1H,dt,J=7.6,1.2 Hz).

ESI-Mass; 404(MH+).

348-3) 1-[1-(2-Fluorophenethyl)piperidin-4-yl]-6-formylindoline

A 1.6 M solution (24 ml) of n-(butyllithium) in hexane was added dropwise at −78° C. over 10 min into a solution of 1-[1-(2-fluorophenethyl)piperidin-4-yl]-6-bromoindoline (12 g) obtained in Example 348-2) in tetrahydrofuran (200 ml). After 10 min, dimethylformamide (3.5 ml) was added thereto and the resultant mixture was allowed to warm to room temperature. Then a saturated aqueous solution (100 ml) of ammonium chloride and ethyl acetate (200 ml) were added thereto and the layers were separated. The organic layer was washed with brine, dried over anhydrous magnesium sulfate and concentrated under reduced pressure. The resulting obtained was purified by silica gel column chromatography (ethyl acetate/ethanol system) to give the title compound (9.6 g) as a yellow powder (yield: 91.5%).

m.p.: 86–87° C.

$^1$H-NMR(400 MHz,DMSO-d$_6$); δ(ppm) 1.56–1.71(4H,m), 2.07–2.16(2H,m), 2.48–2.56(2H,m), 2.77(2H,t,J=8.0 Hz), 2.94–3.06(4H,m), 3.39–3.50(3H,m), 6.82(1H,s), 7.10–7.17 (3H,m), 7.20–7.29(2H,m), 7.31–7.37(1H,m), 9.83(1H,s).

ESI-Mass; 353(MH+).

348-4) 1-[1-(2-Fluorophenethyl)piperidin-4-yl]-6-formylindole

A suspension of 1-[1-(2-fluorophenethyl)piperidin-4-yl]-6-formylindoline (2.50 g) obtained in Example 348-3) and activated manganese dioxide (5.0 g) in chloroform (100 ml) was heated under reflux for 4 hr under vigorous stirring. Further, activated manganese dioxide (5.0 g×1, 2.5 g×2) was added to the reaction mixture at 1 hr intervals and the resultant mixture was reacted for additional 2 hr. The reaction solution was filtered through celite and the residue was washed with chloroform. The filtrate was concentrated under reduced pressure to give the title compound (1.94 g) as a yellow powder (yield: 78.0%).

m.p.: 128–1291° C.

$^1$H-NMR(400 MHz,DMSO-d$_6$); δ(ppm) 2.09–2.42(6H,m), 2.67–2.75(2H,m), 2.83–2.91(2H,m), 3.19–3.28(2H,br-d), 4.35–4.45(1H,m), 6.61(1H,d,J=3.2 Hz), 6.95–7.05(2H,m), 7.16–7.23(2H,m), 7.48(1H,d,J=3.2 Hz), 7.62(1H,dd,J=8.0, 1.2 Hz), 7.72(1H,d,J=8.0 Hz), 7.98(1H,s), 10.07(1H,s).

Mass; 351(MH+).

348-5) 1-[1-(2-Fluorophenethyl)piperidin-4-yl]-6-aminomethylindole

A mixture of 1-[1-(2-fluorophenethyl)piperidin-4-yl]-6-formylindole (1.94 g) obtained in Example 348-4), hydroxylamine hydrochloride (0.5 g) and anhydrous sodium acetate (0.55 g) in methanol (60 ml) was stirred at room temperature for 1 hr. Then the reaction mixtures were concentrated and the residue was partitioned between ethyl acetate (150 ml) and a 1 N aqueous solution (30 ml) of sodium hydroxide. The ethyl acetate layer was washed successively with water and brine, dried over magnesium sulfate and concentrated under reduced pressure to give 1-[1-(2-fluorophenethyl) piperidin-4-yl]-6-hydroxyiminomethylindole (1.96 g) as an ivory powder (yield: 96.8%).

A solution of 1-[1-(2-fluorophenethyl)piperidin-4-yl]-6-hydroxyiminomethylindole (1.95 g) in tetrahydrofuran (50 ml) was added dropwise at room temperature under ice cooling and stirring into a suspension of lithium aluminum hydride (0.4 g) in tetrahydrofuran (100 ml). Then the resultant mixture was heated under reflux for 3 hr. Under ice watar cooling, water (1 ml), a 5 N aqueous solution of sodium hydroxide (3 ml) and further water (1 ml) were carefully added dropwise into the reaction mixtures and the mixture was further vigorously stirred. The resulting precipitate was collected by filtration and washed with tetrahydrofuran. The filtrate was concentrated under reduced pressure. The residue was purified by NH-silica gel column chromatography (ethyl acetate) to give the title compound (0.92 g) as a brown wax (yield: 49.1%).

¹H-NMR(400 MHz,DMSO-d₆); δ(ppm) 1.80–2.04(4H,m), 2.22–2.30(2H,m), 2.56–2.62(2H,m), 2.79–2.85(2H,m), 3.06–3.13(2H,m), 3.80(2H,s), 4.27–4.38(1H,m), 6.38(1H,d, J=2.8 Hz), 6.97(1H,br-d), 7.12–7.18(2H,m), 7.23–7.29(1H, m), 7.34–7.39(1H,m), 7.41–7.45(2H,m), 7.47(1H,br-s).

Example 349: Synthesis of 1-[1-(4-chlorophenethyl) piperidin-4-yl]-6-acetamidomethylindole 1-[1-(4-Chlorophenethyl)piperidin-4-yl]-6-acetamidomethylindoline (120 mg) obtained in Example 98, activated manganese dioxide (480 mg) and chloroform (10 ml) were treated as in Example 285 to give the title compound (95 mg) as a white powder (yield: 80 ).

¹H-NMR(400 MHz,CDCl₃); δ(ppm) 2.03(3H,s), 2.04–2.16 (4H,m), 2.24–2.40(2H,m), 2.64–2.76(2H,m), 2.81–2.95(2H, m), 3.12–3.29(2H,m), 4.23–4.33(1H,m), 4.55(2H,d,J=5.6 Hz), 5.79(1H,br-s), 6.51(1H,d,J=3.6 Hz), 7.03(1H,d,J=8.0 Hz), 7.17(2H,d,J=8.4 Hz), 7.25(1H,d,J=3.6 Hz), 7.28(2H,d, J=8.4 Hz), 7.36(1H,s), 7.59(1H,d,J=8.0 Hz).

m.p.: 148–149° C.
Mass: FAB+410(M+H).

Example 350: Synthesis of 1-[1-(3-fluorophenethyl) piperidin-4-yl]-6-acetamidomethylindole 1-[1-(3-Fluorophenethyl)piperidin-4-yl]-6-acetamidomethylindoline (130 mg) obtained in Example 135, activated manganese dioxide (520 mg) and chloroform (10 ml) were treated as in Example 285 to give the title compound (110 mg) as a white powder (yield: 85%).

¹H-NMR(400 MHz,CDCl₃); δ(ppm) 2.03(3H,s), 2.04–2.16 (4H,m), 2.24–2.40(2H,m), 2.60–2.78(2H,m), 2.80–2.99(2H, m), 3.11–3.33(2H,m), 4.22–4.33(1H,m), 4.55(2H,d,J=5.2 Hz), 5.78(1H,br-s), 6.51(1H,d,J=3.2 Hz), 6.89–6.98(2H,m), 7.00–7.11(2H,m), 7.24–7.30(2H,m), 7.36(1H,s), 7.59(1H,d, J=8.0 Hz).

m.p.: 134–135° C.
Mass: FAB+394(M+H).

Example 351: Synthesis of 1-[1-(4-methoxyphenethyl)-piperidin-4-yl]-6-acetamidomethylindole 1-[1-(4-Methoxyphenethyl)piperidin-4-yl]-6-acetamidomethylindoline (110 mg) obtained in Example 97, activated manganese dioxide (440 mg) and chloroform (10 ml) were treated as in Example 285 to give the title compound (90 mg) as pale yellow prisms (yield: 82%).

¹H-NMR(400 MHz,CDCl₃); δ(ppm) 2.03(3H,s), 2.05–2.15 (4H,m), 2.25–2.35(2H,m), 2.63–2.76(2H,m), 2.79–2.90(2H, m), 3.17–3.30(2H,m), 3.80(3H,s), 4.22–4.31(1H,m), 4.52 (2H,d,J=5.2 Hz), 5.73(1H,br-s), 6.51(1H,d,J=3.6 Hz), 6.86 (2H,d,J=8.4 Hz), 7.03(1H,d,J=8.0 Hz), 7.16(2H,d,J=8.4 Hz), 7.25(1H,d,J=3.6 Hz), 7.36(1H,s), 7.59(1H,d,J=8.0 Hz).

m.p.: 101–102° C.
Mass: FAB+406(M+H).

Example 352: Synthesis of 1-[F1-(2-fluorophenethyl) piperidin-4-yl]-6-acetamidomethylindole 1-[1-(2-Fluorophenethyl)piperidin-4-yl]-6-acetamidomethylindoline (110 mg) obtained in Example 134, activated manganese dioxide (440 mg) and chloroform (10 ml) were treated as in Example 285 to give the title compound (90 mg) as pale yellow needles (yield: 82%).

¹H-NMR(400 MHz,CDCl₃); δ(ppm) 2.03(3H,s), 2.05–2.16 (4H,m), 2.31–2.43(2H,m), 2.69–2.82(2H,m), 2.86–2.99(2H, m), 3.17–3.31(2H,m), 4.23–4.35(1H,m), 4.55(2H,d,J=5.6 Hz), 5.75(1H,br-s), 6.51(1H,d,J=3.6 Hz), 6.99–7.13(3H,m), 7.15–7.27(3H,m), 7.37(1H,s), 7.59(1H,d,J=8.0 Hz).

m.p.: 101–102° C.
Mass: FAB+394(M+H).

Example 353: Synthesis of 1-[1-(4-fluorophenethyl) piperidin-4-yl]-6-(2,4-imidazolidinedion-3-yl)methylindole 1-[1-(4-Fluorophenethyl)piperidin-4-yl]-6-(2,4-imidazolidinedion-3-yl)methylindoline (110 mg) obtained in Example 207, activated manganese dioxide (550 mg) and chloroform (10 ml) were treated as in Example 285 to give the title compound (80 mg) as a pale yellow powder (yield: 74%).

¹H-NMR(400 MHz,CDCl₃); δ(ppm) 2.05–2.13(4H,m), 2.26–2.36(2H,m), 2.63–2.70(2H,m), 2.80–2.87(2H,m), 3.14–3.20(2H,m), 3.93(2H,s), 4.21–4.33(1H,m), 4.79(2H,s), 5.83(1H,br-s), 6.49(1H,d,J=3.2 Hz), 6.96–7.03(2H,m), 7.15–7.22(3H,m), 7.25(1H,d,J=3.2 Hz), 7.48(1H,s), 7.56 (1H,d,J=8.0 Hz).

m.p.: 156–157° C.
Mass: FAB+435(M+H).

Example 354: Synthesis of 1-[1-(4-fluorophenethyl) piperidin-4-yl]-6-isobutyrylaminomethylindole 1-[1-(4-Fluorophenethyl)piperidin-4-yl]-6-isobutyrylaminomethylindoline (110 mg) obtained in Example 158, activated manganese dioxide (550 mg) and chlorof orm (10 ml) were treated as in Example 285 to give the title compound (95 mg) as white needles (yield: 87%).

¹H-NMR(400 MHz,CDCl₃); δ(ppm) 1.19(6H,d,J=7.6 Hz), 2.06–2.15(4H,m), 2.26–2.43(2H,m), 2.38(1H,septet,J=7.6 Hz), 2.65–2.75(2H,m), 2.81–2.91(2H,m), 3.18–3.27(2H,m), 4.22–4.31(1H,m), 4.56(2H,d,J=5.6 Hz), 5.75(1H,br-s), 6.51 (1H,d,J=3.2 Hz), 6.96–7.05(3H,m), 7.16–7.22(2H,m), 7.25 (1H,d,J=3.2 Hz), 7.33(1H,s), 7.59(1H,d,J=8.0 Hz).

m.p.: 97–98° C.
Mass: FAB+422(M+H).

Example 355: Synthesis of 1-[1-(4-fluorophenethyl) piperidin-4-yl]-6-(2-imidazolidonyl)methylindole 1-[1-(4-Fluorophenethyl)piperidin-4-yl]-6-(2-imidazolidonyl)methylindoline (80 mg) obtained in Example 206, activated manganese dioxide (400 mg) and chloroform (10 ml) were treated as in Example 285 to give the title compound (32 mg) as a pale yellow powder (yield: 48%).

¹H-NMR(400 MHz,CDCl₃); δ(ppm) 2.04–2.18(4H,m), 2.28–2.42(2H,m), 2.65–2.78(2H,m), 2.81–2.96(2H,m), 3.12–3.41(6H,m), 4.25–4.36(2H,m), 4.49(2H,s), 6.52(1H,d, J=3.2 Hz), 6.99(1H,d,J=8.0 Hz), 7.00–7.09(2H,m), 7.17–7.23(2H,m), 7.26(1H,d,J=3.2 Hz), 7.33(1H,s), 7.58 (1H,d,J=8.0 Hz).

m.p.: 130–131° C.
Mass: FAB+421(M+H).

Example 356: Synthesis of 1-{1-[4-(4-fluorophenyl)butyl]-piperidin-4-yl}-6-acetamidomethylindole 1-{1-[4-(4-Fluorophenyl)butyl]piperidin-4-yl}-6-acetamidomethylindoline (110 mg) obtained in Example 227, activated manganese dioxide (550 mg) and chloroform (10 ml) were treated as in Example 285 to give the title compound (56 mg) as a white powder (yield: 51%).

¹H-NMR(400 MHz,CDCl₃); δ(ppm) 1.62–1.72(4H,m), 2.04 (3H,s), 2.05–2.17(4H,m), 2.24–2.39(2H,m), 2.60–2.79(2H, m), 2.81–2.92(2H,m), 3.10–3.22(2H,m), 4.23–4.35(1H,m), 4.55(2H,d,J=5.6 Hz), 5.83(1H,br-s), 6.50(1H,d,J=3.2 Hz), 6.95–7.01(2H,m), 7.03(1H,d,J=8.0 Hz), 7.12–7.17(2H,m), 7.23(1H,d,J=3.2 Hz), 7.26(1H,s), 7.58(1H,d,J=8.0 HZ).

m.p.: 59–60° C.
Mass: FAB+422(M+H).

Example 357: Synthesis of 1-[1-(2,4-difluorophenethyl)-piperidin-4-yl]-6-acetamidomethylindole 1-[1-(2,4-Difluorophenethyl)piperidin-4-yl]-6-acetamidomethylindoline (100 mg) obtained in Example 224, activated manganese dioxide (500 mg) and chloroform (10 ml) were treated as in Example 285 to give the title compound (83 mg) as an oil. This oil was then crystallized from ethyl acetate by using oxalic acid (15 mg) to give the oxalate (46 mg) of the title compound as pale yellow prisms (yield: 42%).
$^1$H-NMR(400 MHz,DMSO-d$_6$); δ(ppm) 2.00–2.28(4H,m), 2.05(3H,s), 2.81–3.16(6H,m), 3.44–3.54(2H,m), 4.28(2H,d, J=5.2 Hz), 4.52–4.63(1H,m), 6.47(1H,d,J=3.6 Hz), 6.99–7.16(3H,m), 7.32–7.40(1H,m), 7.44(1H,d,J=3.6 Hz), 7.51–7.58(2H,m), 8.23(1H,t,J=5.2 Hz).
m.p.: 103–106° C.
Mass: FAB+412(M+H).

Example 358: Synthesis of 1-[1-(4-fluorophenethyl) piperidin-4-yl]-6-(2-pyrrolidon-1-yl)methylindole 1-[1-(4-Fluorophenethyl)piperidin-4-yl]-6-(2-pyrrolidon-1-yl) methylindoline (80 mg) obtained in Example 202, activated manganese dioxide (400 mg) and chloroform (10 ml) were treated as in Example 285 to give the title compound (69 mg) as an oil. This oil was then crystallized from ethyl acetate by using oxalic acid (13 mg) to give the oxalate (54 mg) of the title compound as a white powder (yield: 61%).
$^1$H-NMR(400 MHz,DMSO-d$_6$); δ(ppm) 1.83–1.92(2H,m), 2.05–2.25(4H,m), 2.27(2H,t,J=8.0 Hz), 2.89–3.24(6H,m), 3.20(2H,t,J=8.0 Hz), 3.46–3.56(2H,m), 4.44(2H,s), 4.54–4.66(1H,m), 6.45(1H,d,J=2.8 Hz), 6.89(1H,d,J=8.0 Hz), 7.13–7.19(2H,m), 7.30–7.36(2H,m), 7.40–7.46(2H,m), 7.50(1H,d,J=8.0 Hz).
m.p.: 179–180° C.
Mass: FAB+420(M+H).

Example 359: Synthesis of 1-[1-(4-fluorophenethyl) piperidin-4-yl]-6-N-methylacetamidomethylindole 1-[1-(4-Fluorophenethyl)piperidin-4-yl]-6-N-methylacetamidomethylindoline (140 mg) obtained in Example 163, activated manganese dioxide (700 mg) and chloroform (10 ml) were treated as in Example 285 to give the title compound (120 mg) as an oil. This oil was then crystallized from ethyl acetate by using oxalic acid (24 mg) to give the oxalate (90 mg) of the title compound as a pale red powder (yield: 58%).
$^1$H-NMR(400 MHz,DMSO-d$_6$); δ(ppm) 2.05(1.5H,s), 2.10 (1.5H,s), 2.05–2.26(4H,m), 2.78(1.5H,s), 2.87(1.5H,s), 2.90–3.04(4H,m), 3.09–3.18(2H,m), 3.46–3.56(2H,m), 4.52–4.66(3H,m), 6.44(0.5H,d,J=2.8 Hz), 6.47(0.5H,d,J=2.8 Hz), 6.86–6.92(1H,m), 7.13–7.20(2H,m), 7.30–7.46(4H,m), 7.48(0.5H,d,J=8.0 Hz), 7.53(0.5H,d,J=8.0 Hz).
m.p.: 148–149° C.
Mass: FAB+408(M+H).

Example 360: Synthesis of 1-{1-[3-(4-fluorophenyl) propyl]-piperidin-4-yl}-6-acetamidomethylindole 1-{1-[3-(4-Fluorophenyl)propyl]piperidin-4-yl}-6-acetamidomethylindoline (110 mg) obtained in Example 226, activatedmanganese dioxide (550 mg) andchloroform (10 ml) were treated as in Example 285 to give the title compound (113 mg) as an oil. This oil was crystallized from diethyl ether with the use of oxalic acid (25 mg) to give the oxalate (90 mg) of the title compound as a pale red amorphous substance (yield: 67%).
$^1$H-NMR(400 MHz,DMSO-d$_6$); δ(ppm) 1.84(3H,s), 1.87–1.97(2H,m), 2.01–2.09(2H,m), 2.14–2.26(2H,m), 2.60–2.67(2H,m), 2.86–2.99(4H,m), 3.41–3.50(2H,m), 4.32 (2H,d,J=5.6 Hz), 4.53–4.61(1H,m), 6.43(1H,d,J=3.2 Hz), 6.94(1H,d,J=8.0 Hz), 7.08–7.15(2H,m), 7.24–7.30(2H,m), 7.39(1H,d,J=3.2 Hz), 7.40(1H,s), 7.47(1H,d,J=8.0 Hz), 8.30 (1H,t,J=5.6 Hz).
Mass; FAB+408(M+H).

Example 361: Synthesis of 1-[1-(4-fluorophenethyl) piperidin-4-yl]-6-N-methylaminomethylindole A mixture of 1-[1-(4-fluorophenethyl)piperidin-4-yl]-6-formylindole (400 mg) obtained in Example 130, methylamine hydrochloride (150 mg), sodium triacetoxyborohydride (480 mg), acetic acid (300 mg) and dichioroethane (10 ml) was stirred at room temperature for 2 days. Then a saturated aqueous solution of sodium bicarbonate and ethyl acetate were added to the reaction mixtures. The organic layer was separated, washed with brine, dried over anhydrous magnesium sulfate and concentrated under reduced pressure. The resulting residue was purified by Chromatorex NH-silica gel column chromatography (hexane/ethyl acetate system) to give the title compound (140 mg) as an oil. This oil was crystallized from ethyl acetate by using oxalic acid (34 mg) to give the oxalate (140 mg) of the title compound as a white powder (yield: 27%).
$^1$H-NMR(400 MHz,DMSO-d$_6$); δ(ppm) 1.88–2.05(4H,m), 2.16–2.25(2H,m), 2.41(3H,s), 2.53–2.60(2H,m), 2.73–2.78 (2H,m), 3.04–3.12(2H,m), 3.96(2H,s), 4.20(1H,br-s), 4.24–4.34(1H,m), 6.42(1H,d,J=3.2 Hz), 7.02(1H,d,J=8.0 Hz), 7.06–7.13(2H,m), 7.25–7.30(2H,m), 7.49(1H,d,J=3.2 Hz), 7.50(1H,d,J=8.0 Hz), 7.55(1H,s).
m.p.: 195–196° C.
Mass: FAB+366(M+H).

Example 362: Synthesis of 1-[1-(4-fluorophenethyl) piperidin-4-yl]-6-(n-butyryl)aminomethylindole A mixture of 1-[1-(4-fluorophenethyl)piperidin-4-yl]-6-aminomethylindole (200 mg) obtained in Example 322-3), n-butyric anhydride (158 mg) and pyridine (3 ml) was stirred at room temperature for 2 days. Then a saturated aqueous solution of sodium bicarbonate and ethyl acetate were added to the liquid reaction mixture. The organic layer was separated, washed with brine, dried over anhydrous magnesium sulfate and concentrated under reduced pressure. The resulting residue was purified by silica gel column chromatography (hexane/ethyl acetate system) to give the title compound (170 mg) as an oil. This oil was crystallized from ethyl acetate by using oxalic acid (36 mg) to give the oxalate (170 mg) of the title compound as a white amorphous substance (yield: 58%).
$^1$H-NMR(400 MHz,DMSO-d$_6$); δ(ppm) 0.85(3H,t,J=7.2 Hz), 1.53(2H,q,J=7.2 Hz), 1.98–2.18(6H,m), 2.69–3.02(6H, m), 3.35–3.44(2H,m), 4.34(2H,d,J=6.0 Hz), 4.41–4.53(1H, m), 6.42(1H,d,J=3.2 Hz), 6.93(1H,d,J=8.4 Hz), 7.10–7.18 (2H,m), 7.27–7.35(2H,m), 7.39(1H,s), 7.42(1H,d,J=3.2 Hz), 7.47(1H,d,J=8.4 Hz), 8.26(1H,t,J=6.0 Hz).
Mass: FAB+422(M+H).

Example 363: Synthesis of 1-[1-(4-fluorophenethyl) piperidin-4-yl]-6-cyclopropanecarboxamidomethylindole 1-[1-(4-Fluorophenethyl)piperidin-4-yl]-6-cyclopropanecarboxamidomethylindoline (90 mg) obtained in Example 159, activated manganese dioxide (450 mg) and chloroform (10 ml) were treated as in Example 285 to give the title compound (60 mg) as a white powder (yield: 73%).
$^1$H-NMR(400 MHz,CDCl$_3$); δ(ppm) 0.72–0.79(2H,m), 0.99–1.04(2H,m), 1.31–1.42(1H,m), 2.05–2.17(4H,m), 2.22–2.35(2H,m), 2.63–2.75(2H,m), 2.82–2.93(2H,m), 3.12–3.25(2H,m), 4.23–4.34(1H,m), 4.58(2H,d,J=5.6 Hz), 5.89(1H,br-s), 6.51(1H,d,J=3.2 Hz), 6.97–7.03(2H,m), 7.06 (1H,d,J=8.0 Hz), 7.17–7.23(2H,m), 7.25(1H,d,J=3.2 Hz), 7.36(1H,s), 7.60(1H,d,J=8.0 Hz).
m.p.: 116–117° C.
Mass: FAB+420(M+H).

Example 364: Synthesis of 1-[1-(4-fluorophenethyl) piperidin-4-yl]-6-hydroxyacetamidomethylindole A mixture of 1-[1-(4-fluorophenethyl)piperidin-4-yl]-6-aminomethylindole (150 mg) obtained in Example 322-3), acetoxyacetyl chloride (64 mg), pyridine (3 ml) and tetrahydrofuran (5 ml) was stirred under ice cooling for 30 min. Then ice water and ethyl acetate were added to the reaction mixtures. The organic layer was separated, washed with brine, dried over anhydrous magnesium sulfate and concentrated under reduced pressure. To the resulting residue were added methanol (10 ml) and potassium carbonate (100 mg) followed by stirring for 30 min. Then ice water and ethyl acetate were added to the reaction mixtures. The organic layer was separated, washed with brine, dried over anhydrous magnesium sulfate and concentrated under reduced pressure. The obtained residue was purified by silica gel column chromatography (ethyl acetate/ethanol system) to give the title compound (140 mg) as white scales (yield: 80%).
$^1$H-NMR(400 MHz,DMSO-d6); δ(ppm) 1.87–1.99(4H,m), 2.19–2.25(2H,m), 2.52–2.59(2H,m), 2.72–2.78(2H,m), 3.03–3.11(2H,m), 3.82(2H,d,J=6.0 Hz), 4.23–4.33(1H,m), 4.37(2H,d,J=6.0 Hz), 5.48(1H,t,J=6.0 Hz), 6.38(1H,d,J=3.2 Hz), 6.95(1H,d,J=8.0 Hz), 7.06–7.13(2H,m), 7.24–7.30(2H,m), 7.42(1H,d,J=8.0 Hz), 7.45(1H,d,J=3.2 Hz), 7.46(1H,s), 8.14(1H,t,J=6.0 Hz).
m.p.: 76–78° C.
Mass: FAB+410(M+H).

Example 365: Synthesis of 1-[1-(4-fluorophenethyl)piperidin-4-yl]-6-difluoroacetamidomethylindole Under ice cooling, N,N'-carbonyldiimidazole (160 mg) was added to a solution of difluoroacetic acid (96 mg) in dimethylformamide (5 ml) and the resultant mixture was stirred for 30 min. Next, a solution of 1-[1-(4-fluorophenethyl)piperidin-4-yl]-6-aminomethylindole (150 mg) obtained in Example 322-3) in dimethylformamide (5 ml) was added thereto and the resultant mixture was stirred at room temperature for 2 hr. Then a saturated aqueous solution of sodium bicarbonate and ethyl acetate were added to the reaction mixtures. The organic layer was separated, washed with brine, dried over anhydrous magnesium sulfate and concentrated under reduced pressure. The resulting residue was purified by silica gel column chromatography (hexane/ethyl acetate system) to give the title compound (120 mg) as a white powder (yield: 65%).
$^1$H-NMR(400 MHz,CDCl$_3$); δ(ppm) 2.05–2.15(4H,m), 2.24–2.35(2H,m), 2.63–2.70(2H,m), 2.79–2.86(2H,m), 3.14–3.22(2H,m), 4.20–4.30(1H,m), 4.62(2H,d,J=5.6 Hz), 5.95(1H,t,J=54.2 Hz), 6.52(1H,d,J=3.6 Hz), 6.61(1H,br-s), 6.96–7.02(2H,m), 7.03(1H,d,J=8.0 Hz), 7.15–7.21(2H,m), 7.27(1H,d,J=3.6 Hz), 7.33(1H,s), 7.61(1H,d,J=8.0 Hz).
m.p.: 79–80° C.
Mass: FAB+430(M+H).

Example 366: Synthesis of 1-[1-(4-fluorophenethyl)piperidin-4-yl]-6-fluoroacetamidomethylindole Under ice cooling, ethyl chlorocarbonate (96 μl) was added to a suspension of sodium fluoroacetate (100 mg) in dimethylformamide (5 ml) and the resultant mixture was stirred for 20 min. Next, a solution of 1-[1-(4-fluorophenethyl)piperidin-4-yl]-6-aminomethylindole (150 mg) obtainedinExample 322-3) indimethylformamide (5 ml) was added thereto and the resultant mixture was stirred at room temperature for 2 hr. Then a saturated aqueous solution of sodium bicarbonate and ethyl acetate were added to the reaction mixtures. The organic layer was separated, washed with brine, dried over anhydrous magnesium sulfate and concentrated under reduced pressure. The resulting residue was purified by silica gel column chromatography (hexane/ethyl acetate system) to give the title compound (100 mg) as a white powder (yield: 57%).
$^1$H-NMR(400 MHz,CDCl$_3$); δ(ppm) 2.08–2.16(4H,m), 2.26–2.35(2H,m), 2.64–2.71(2H,m), 2.81–2.88(2H,m), 3.16–3.24(2H,m), 4.21–4.31(1H,m), 4.63(2H,d,J=5.6 Hz), 4.85(2H,d,J=47.6 Hz), 6.52(1H,d,J=3.2 Hz), 6.60(1H,br-s), 6.96–7.02(2H,m), 7.04(1H,d,J=8.0 Hz), 7.16–7.21(2H,m), 7.27(1H,d,J=3.2 Hz), 7.34(1H,s), 7.61(1H,d,J=8.0 Hz).
m.p.: 106–108° C.
Mass: FAB+412(M+H).

Example 367: Synthesis of 1-[1-(4-fluorophenethyl)piperidin-4-yl]-6-(3-chloropropionylamino)methylindole Under ice cooling, a mixture of 1-[1-(4-fluorophenethyl)piperidin-4-yl]-6-aminomethylindole (150 mg) obtained in Example 322-3), 3-chloropropionyl chloride (70 mg) and pyridine (5 ml) was stirred for 2 hr. Then a saturated aqueous solution of sodium bicarbonate and ethyl acetate were added to the reaction mixtures. The organic layer was separated, washed with brine, dried over anhydrous magnesium sulfate and concentrated under reduced pressure. The resulting residue was purified by silica gel column chromatography (ethyl acetate/methanol system) to give the title compound (30 mg) as a white powder (yield: 16%).
$^1$H-NMR(400 MHz,CDCl$_3$); δ(ppm) 2.04–2.15(4H,m), 2.22–2.32(2H,m), 2.62–2.69(2H,m), 2.65(2H,t,J=6.4 Hz), 2.80–2.87(2H,m), 3.13–3.22(2H,m), 3.86(2H,t,J=6.4 Hz), 4.20–4.30(1H,m), 4.59(2H,d,J=5.6 Hz), 5.99(1H,br-s), 6.51(1H,d,J=3.2 Hz), 6.97(1H,d,J=8.0 Hz), 6.98–7.04(2H,m), 7.16–7.21(2H,m), 7.24(1H,d,J=3.2 Hz), 7.35(1H,s), 7.58(1H,d,J=8.0 Hz).
m.p.: 121–122° C.
Mass: FAB+442(M+H).

Example 368: Synthesis of 1-[1--(4-fluorophenethyl)piperidin-4-yl]-6-imidazocarbonylaminomethylindole Under ice cooling, N,N'-carbonyldiimidazole (160 mg) was added to a solution of 1-[1-(4-fluorophenethyl)piperidin-4-yl]-6-aminomethylindole (150 mg) obtained in Example 322-3) in dimethylformamide (5 ml) and the resultant mixture was stirred for 30 min. Then ice water and ethyl acetate were added to the reaction mixtures. The organic layer was separated, washed with brine, dried over anhydrous magnesium sulfate and concentrated under reduced pressure. The resulting residue was purified by silica gel column chromatography (ethyl acetate/ethanol system) to give the title compound (140 mg) as an oil. This oil was then crystallized from ethyl acetate by using oxalic acid (28 mg) to give the oxalate (150 mg) of the title compound as a white powder (yield: 65%).
$^1$H-NMR(400 MHz,DMSO-d$_6$); δ(ppm) 1.99–2.23(4H,m), 2.69–2.81(2H,m), 2.84–3.02(4H,m), 3.33–3.43(2H,m), 4.47–4.57(1H,m), 4.54(2H,d,J=5.6 Hz), 6.44(1H,d,J=2.8 Hz), 7.01(1H,s), 7.03(1H,d,J=8.0 Hz), 7.10–7.18(2H,m), 7.27–7.35(2H,m), 7.45(1H,d,J=2.8 Hz), 7.51(1H,d,J=8.0 Hz), 7.53(1H,s), 7.71(1H,s), 8.27(1H,s), 9.08(1H,t,J=5.6 Hz).
m.p.: 156–157° C.
Mass: FAB+446(M+H).

Example 369: Synthesis of 1-[1-(4-fluorophenethyl)piperidin-4-yl]-6-(3-hydroxypropionylamino)methylindole A mixture of 1-[1-(4-fluorophenethyl)piperidin-4-yl]-6-aminomethylindole (150 mg) obtained in Example 322-3), propiolactone (30 mg) and toluene (10 ml) was heated under reflux for 2 hr. Then the reaction solution was concentrated under reduced pressure and the residue was purified by silica gel column chromatography (ethyl acetate/ethanol system) to give the title compound (150 mg) as an oil. This oil was then crystallized from ethyl acetate by using oxalic acid (32 mg) to give the oxalate (100 mg) of the title compound as a pale yellow amorphous substance (yield: 45%).
$^1$H-NMR(400 MHz,DMSO-d$_6$); δ(ppm) 2.03–2.25(4H,m), 2.29(2H,t,J=6.8 Hz), 2.91–2.98(4H,m), 3.05–3.16(2H,m), 3.44–3.54(2H,m), 3.64(2H,t,J=6.8 Hz), 4.35(2H,d,J=6.0 Hz), 4.50–4.60(1H,m), 6.43(1H,d,J=3.2 Hz), 6.94(1H,d,J=8.4 Hz), 7.12–7.20(2H,m), 7.29–7.36(2H,m), 7.41(1H,d,J=3.2 Hz), 7.43(1H,s), 7.46(1H,d,J=8.4 Hz), 8.28(1H,t,J=6.0 Hz).
Mass; FAB+424(M+H).

Example 370: Synthesis of 1-[1-(4-fluorophenethyl)piperidin-4-yl]-3-formyl-6-acetamidomethylindole Phosphorus oxychloride (0.1 g) was added at 0° C. to a solution of 1-[1-(4-fluorophenethyl)piperidin-4-yl]-6-acetamidomethylindole (0.22 g) obtained in Example 285 in N,N-dimethylformamide (5 ml). The resultant mixture was stirred for 10 min and then reacted at 70° C. for 2 hr. After adding a 2 N aqueous solution of sodium hydroxide (20 ml), the reaction solution was extracted with ethyl acetate. The extract was washed successively with water and brine, dried over magnesium sulfate and concentrated under reduced pressure. The resulting residue was filtered through silica gel (15 g) and washed with ethyl acetate/methanol. The filtrate was concentrated to give the title compound (0.16 g) as a pale yellow amorphous substance (yield: 67.9%).
$^1$H-NMR(400 MHz,DMSO-d$_6$); δ(ppm) 2.04(3H,s), 2.14–2.37(4H,m), 2.37–2.49(2H,m), 2.73–2.82(2H,m), 2.87–2.95(2H,m), 3.25–3.35(2H,m), 4.28–4.38(1H,m), 4.55 (2H,d,J=5.6 Hz), 6.00–2.29(2H,t,J=6.8 Hz), 2.91–2.98(4H, m), 3.05–3.16(2H,m), 3.44–3.54(2H,m), 3.64(2H,t,J=6.8 Hz), 4.35(2H,d,J=6.0 Hz), 4.50–4.60(1H,m), 6.43(1H,d,J=3.2 Hz), 6.94(1H,d,J=8.4 Hz), 7.12–7.20(2H,m), 7.29–7.36(2H,m), 7.41(1H,d,J=3.2 Hz), 7.43(1H,s), 7.46(1H,d,J=8.4 Hz), 8.28(1H,t,J=6.0 Hz).
Mass; FAB+424(M+H).

Example 370: Synthesis of 1-[1-(4-fluorophenethyl)piperidin-4-yl]-3-formyl-6-acetamidomethylindole Phosphorus oxychloride (0.1 g) was added at 0° C. to a solution of 1-[1-(4-fluorophenethyl)piperidin-4-yl]-6-acetamidomethylindole (0.22 g) obtained in Example 285 in N,N-dimethylformamide (5 ml). The resultant mixture was stirred for 10 min and then reacted at 70° C. for 2 hr. After adding a 2 N aqueous solution of sodium hydroxide (20 ml), the reaction solution was extracted with ethyl acetate. The extract was washed successively with water and brine, dried over magnesium sulfate and concentrated under reduced pressure. The resulting residue was filtered through silica gel (15 g) and washed with ethyl acetate/methanol. The filtrate was concentrated to give the title compound (0.16 g) as a pale yellow amorphous substance (yield: 67.9%).
$^1$H-NMR(400 MHz,DMSO-d$_6$); δ(ppm) 2.04(3H,s), 2.14–2.37(4H,m), 2.37–2.49(2H,m), 2.73–2.82(2H,m), 2.87–2.95(2H,m), 3.25–3.35(2H,m), 4.28–4.38(1H,m), 4.55 (2H,d,J=5.6 Hz), 6.00–6.12(1H,m), 6.97–7.04(2H,m), 7.17–7.24(3H,m), 7.44(1H,br-s), 7.84(1H,s), 8.25(1H,d,J=8.0 Hz), 9.97(1H,s).
ESI-Mass; 422(MH+).

Example 371: Synthesis of 1-[1-(4-fluorophenethyl)piperidin-4-yl]-3-hydroxyimino-6-acetamidomethylindole A liquid mixture of 1-[1-(4-fluorophenethyl)piperidin-4-yl]-3-formyl-6-acetamidomethylindole (0.09 g) obtained in Example 370, hydroxylamine hydrochloride (0.02 g) and anhydrous sodium acetate (0.03 g) in methanol (10 ml) was stirred at room temperature for 1 hr. Then the reaction mixtures were concentrated and the residue was partitioned between ethyl acetate (20 ml) and a 1 N aqueous solution (10 ml) of sodium hydroxide. The ethyl acetate layer was washed successively with water and brine, dried over magnesium sulfate and concentrated under reduced pressure. Then the residue was crystallized from ether/hexane, collected by filtration, washed with hexane and dried to give the title compound (0.08 g) as a pale yellow powder (yield: 88.5%).
$^1$H-NMR(400 MHz,DMSO-d$_6$); δ(ppm) 1.87(3H,s), 1.91–2.03(4H,m), 2.20–2.30(2H,m), 2.56–2.62(2H,m), 2.74–2.80(2H,m), 3.06–3.3(2H,m), 4.33–4.38(1H,m), 7.03–7.15(3H,m), 7.27–7.33(2H,m), 7.45–7.50(1H,m), 7.77 (1H,d,J=8.0 Hz), 7.83(0.5H,d,J=8.0 Hz), 7.91(0.5H,d,J=8.0 Hz), 8.20(0.5H,s), 8.26(0.5H,s), 8.30–8.35(1H,m), 10.54 (0.5H,s), 11.27(0.5H,s).

Example 372: Synthesis of 1-[1-(4-fluorophenethyl)piperidin-4-yl]-3-hydroxymethyl-6-acetamidomethylindole Sodium borohydride (0.01 g) was added to a solution of 1-[1-(4-fluorophenethyl)piperidin-4-yl]-3-formyl-6-acetamidomethylindole (0.04 g) obtained in Example 370 in methanol (10 ml) and the resultant mixture was stirred at room temperature for 0.5 hr. Then the reaction solution was concentrated and the residue was partitioned between ethyl acetate (40 ml) and water (10 ml). The ethyl acetate layer was washed successively with water and brine, dried over magnesium sulfate and concentrated under reduced pressure. Then the residue was treated with ether/hexane to give the title compound (0.03 g) as a pale yellow amorphous substance (yield: 74.6%).
$^1$H-NMR(400 MHz,DMSO-d$_6$); δ(ppm) 1.86(3H,s), 1.87–2.00(4H,m), 2.18–2.27(2H,m), 2.54–2.61(2H,m), 3.05–3.12(2H,m), 4.22–4.32(1H,m), 4.33(2H,d,J=5.6 Hz), 4.60(2H,d,J=5.6 Hz), 4.76(1H,t,J=5.6 Hz), 6.94(1H,dd,J=8.0,1.2 Hz), 7.08–7.15(2H,m), 7.25–7.33(2H,m), 7.36(1H, br-d), 8.26–8.32(1H,m).

Example 373: Synthesis of 1-[1-(4-fluorophenethyl)piperidin-4-yl]-6-chloroacetamidomethylindole A mixture of 1-[1-(4-fluorophenethyl)piperidin-4-yl]-6-aminomethylindole (150 mg) obtained in Example 322-3), chloroacetyl chloride (60 mg), triethylamine (50 mg) and acetonitrile (5 ml) was stirred under ice cooling for 2 hr. Then a saturated aqueous solution of sodium bicarbonate and ethyl acetate were added to the reaction solution. The organic layer was separated, washed with brine, dried over anhydrous magnesium sulfate and concentrated under reduced pressure. The resulting residue was purified by silica gel column chromatography (hexane/ethyl acetate system) to give the title compound (90 mg) as white needles (yield: 49%).
$^1$H-NMR(400 MHz,CDCl$_3$); δ(ppm) 2.06–2.13(4H,m), 2.24–2.33(2H,m), 2.63–2.69(2H,m), 2.80–2.86(2H,m), 3.14–3.22(2H,m), 4.09(2H,s), 4.20–4.30(1H,m), 4.59(2H,d, J=5.6 Hz), 6.52(1H,d,J=3.2 Hz), 6.89(1H,br-s), 6.90–7.02 (2H,m), 7.04(1H,d,J=8.0 Hz), 7.16–7.21(2H,m), 7.26(1H,d, J=3.2 Hz), 7.33(1H,s), 7.61(1H,d,J=8.0 Hz).
m.p.: 143–144° C.
Mass: FAB+428(M+H).

Example 374: Synthesis of 1-[1-(4-fluorophenethyl)piperidin-4-yl]-6-bromoacetamidomethylindole 1-[1-(4-Fluorophenethyl)piperidin-4-yl]-6-aminomethylindole (370 mg) obtained in Example 322-3), bromoacetyl chloride (220 mg), triethylamine (140 mg) and acetonitrile (10 ml) were treated as in Example 373 to give the title compound (320 mg) as an oil (yield: 65%).
$^1$H-NMR(400 MHz,CDCl$_3$); δ(ppm) 2.05–2.13(4H,m), 2.25–2.33(2H,m), 2.62–2.70(2H,m), 2.79–2.85(2H,m), 3.15–3.24(2H,m), 3.92(2H,s), 4.19–4.29(1H,m), 4.58(2H,d, J=5.6 Hz), 6.53(1H,d,J=3.2 Hz), 6.90(1H,br-s), 6.92–7.04 (3H,m), 7.15–7.21(2H,m), 7.25(1H,d,J=3.2 Hz), 7.34(1H,s), 7.60(1H,d,J=8.0 Hz).

Example 375: Synthesis of 1-[1-(4-fluorophenethyl)piperidin-4-yl]-6-(N,N-dimethylaminoacetamido)methylindole A mixture of 1-[1-(4-fluorophenethyl)piperidin-4-yl]-6-bromoacetamidomethylindole (170 mg) obtained in Example 374, a 2 M solution (2.2 ml) of dimethylamine in tetrahydrofuran and dimethylformamide (5 ml) was stirred at room temperature for 2 hr. Then water and ethyl acetate were added to the reaction solution. The organic layer was separated, washed with brine, dried over anhydrous magnesium sulfate and concentrated under reduced pressure. The resulting residue was purified by Chromatorex NH silica gel column chromatography (hexane/ethyl acetate system) to give the title compound (35 mg) as an oil.

This oil was crystallized from ethyl acetate by using oxalic acid (7 mg) to give the oxalate (18 mg) of the title compound as a white powder (yield: 9.4%).
$^1$H-NMR(400 MHz,DMSO-$d_6$); δ(ppm) 1.96–2.16(4H,m), 2.39–2.44(2H,m), 2.60(6H,s), 2.82–2.94(4H,m), 3.30–3.71 (4H,m), 4.41(2H,d,J=5.6 Hz), 4.42–4.52(1H,m), 6.43(1H,d, J=2.8 Hz), 6.96(1H,d,J=8.0 Hz), 7.10–7.19(2H,m), 7.27–7.34(2H,m), 7.45(1H,s), 7.46(1H,d,J=2.8 Hz), 7.49 (1H,d,J=8.0 Hz), 8.53(1H,t,J=5.6 Hz).
m.p.: 112–113° C.
Mass: FAB+437(M+H).

Example 376: Synthesis of 1-[1-(4-fluorophenethyl) piperidin-4-yl]-6-[(piperidin-1-yl)acetamido]methylindole 1-[1-(4-Fluorophenethyl)piperidin-4-yl]-6-bromoacetamidomethylindole (150 mg) obtained in Example 374, piperidine (187 mg) and dimethylformamide (5 ml) were treated as in Example 375 to give the oxalate (20 mg) of the title compound as a white powder (yield: 11 ).
$^1$H-NMR(400 MHz,DMSO-$d_6$); δ(ppm) 1.40–1.50(2H,m), 1.60–1.71(4H,m), 2.00–2.08(2H,m), 2.12–2.26(2H,m), 2.37–2.52(2H,m), 2.70–3.10(8H,m), 3.39–3.49(2H,m), 3.52–3.63(2H,m), 4.42(2H,d,J=6.0 Hz), 4.45–4.58(1H,m), 6.43(1H,d,J=3.2 Hz), 6.96(1H,d,J=8.0 Hz), 7.10–7.19(2H, m), 7.26–7.34(2H,m), 7.44(1H,d,J=3.2 Hz), 7.47(1H,s), 7.49(1H,d,J=8.0 Hz), 8.76(1H,t,J=6.0 Hz).
m.p.: 113–114° C.
Mass: FAB+477(M+H).

Example 377: Synthesis of 1-[1-(4-fluorophenethyl) piperidin-4-yl]-6-(3-bromopropionylamino)methylindole 1-[1-(4-Fluorophenethyl)piperidin-4-yl]-6-aminomethylindole (370 mg) obtained in Example 322-3), 3-bromopropionyl chloride (240 mg), triethylamine (140 mg) and acetonitrile (10 ml) were treated as in Example 373 to give the title compound (290 mg) as an oil (yield: 57%).
$^1$H-NMR(400 MHz,CDCl$_3$); δ(ppm) 2.02–2.10(2H,m), 2.14–2.26(2H,m), 2.29–2.40(2H,m), 2.68–2.76(2H,m), 2.80 (2H,t,J=6.4 Hz), 2.85–2.92(2H,m), 3.18–3.26(2H,m), 3.70 (2H,t,J=6.4 Hz), 4.20–4.30(1H,m), 4.62(2H,d,J=6.0 Hz), 6.15(1H,br-s), 6.50(1H,d,J=3.2 Hz), 6.96–7.04(3H,m), 7.16–7.24(2H,m), 7.25(1H,d,J=3.2 Hz), 7.37(1H,s), 7.58 (1H,d,J=8.0 Hz).

Example 378: Synthesis of 1-[1-(4-fluorophenethyl) piperidin-4-yl]-6-(3-N,N-dimethylaminopropionyl) aminomethylindole A mixture of 1-[1-(4-fluorophenethyl)piperidin-4-yl]-6-(3-bromopropionylamino)methylindole (150 mg) obtained in Example 377, a 2 M solution (5.0 ml) of dimethylamine in tetrahydrofuran and toluene (5 ml) was heated at 80 to 90° C. for 1.5 days. Then water and ethyl acetate were added to the reaction mixtures. The organic layer was separated, washed with brine, dried over anhydrous magnesium sulfate and concentrated under reduced pressure. The resulting residue was purified by Chromatorex NH-silica gel column chromatography (hexane/ethyl acetate system) to give the title compound (140 mg) as an oil. This oil was crystallized from ethyl acetate by using oxalic acid (28 mg) to give the oxalate (110 mg) of the title compound as a white powder (yield: 66%).
$^1$H-NMR(400 MHz,DMSO-$d_6$); δ(ppm) 1.90–1.99(2H,m), 2.00–2.12(2H,m), 2.38–2.45(2H,m), 2.55(2H,t,J=7.2 Hz), 2.61(6H,s), 2.70–2.76(2H,m), 2.78–2.85(2H,m), 3.11(2H,t, J=7.2 Hz), 3.16–3.24(2H,m), 4.37(2H,d,J=5.6 Hz), 4.38–4.42(1H,m), 6.40(1H,d,J=2.8 Hz), 6.94(1H,d,J=8.0 Hz), 7.08–7.14(2H,m), 7.25–7.32(2H,m), 7.42(1H,s), 7.45 (1H,d,J=2.8 Hz), 7.47(1H,d,J=8.0 Hz), 8.58(1H,t,J=5.6 Hz).
m.p.: 104–105° C.
Mass: FAB+451(M+H).

Example 379: Synthesis of 1-[1-(4-fluorophenethyl) piperidin-4-yl]-6-[3-(piperidin-1-yl)propionylamino] methylindole 1-[1-(4-Fluorophenethyl)piperidin-4-yl]-6-(3-bromopropionylamino)methylindole (140 mg) obtained in Example 377, piperidine (85 mg) and toluene (5 ml) were treated as in Example 378 to give the oxalate (80 mg) of the title compound as a white powder (yield: 44%).
$^1$H-NMR(400 MHz,DMSO-$d_6$); δ(ppm) 1.39–1.49(2H,m), 1.57–1.66(4H,m), 1.90–2.11(4H,m), 2.35–2.60(4H,m), 2.71–3.01(8H,m), 3.06–3.14(2H,m), 3.18–3.25(2H,m), 4.36 (2H,d,J=4.8 Hz), 4.37–4.45(1H,m), 6.41(1H,d,J=3.2 Hz), 6.94(1H,d,J=8.0 Hz), 7.06–7.14(2H,m), 7.23–7.31(2H,m), 7.42(1H,s), 7.45(1H,d,J=3.2 Hz), 7.47(1H,d,J=8.0 Hz), 8.56 (1H,t,J=4.8 Hz).
m.p.: 108–109° C.
Mass: FAB+491(M+H).

Example 380: Synthesis of 1-[1-(2-fluorophenethyl) piperidin-4-yl]-6-propionylaminomethylindole 1-[1-(2-Fluorophenethyl)piperidin-4-yl]-6-aminomethylindole (150 mg) obtained in Example 348, propionyl chloride (43 mg), triethylamine (47 mg) and acetonitrile (5 ml) were treated as in Example 373 to give the title compound (105 mg) as a white powder (yield: 60%).
$^1$H-NMR(400 MHz,CDCl$_3$); δ(ppm) 1.19(3H,t,J=7.6 Hz), 2.00–2.16(4H,m), 2.25(2H,q,J=7.6 Hz), 2.26–2.50(2H,m), 2.61–2.82(2H,m), 2.85–3.05(2H,m), 3.20–3.34(2H,m), 4.19–4.33(1H,m), 4.56(2H,d,J=5.6 Hz), 5.75(1H,br-s), 6.51 (1H,d,J=3.2 Hz), 7.06–7.13(3H,m), 7.15–7.29(3H,m), 7.36 (1H,s), 7.59(1H,d,J=8.4 Hz).
m.p.: 118–119° C.
Mass: FAB+408(M+H).

Example 381: Synthesis of 1-[1-(2-fluorophenethyl) piperidin-4-yl]-6-fluoroacetamidomethylindole 1-[1-(2-Fluorophenethyl)piperidin-4-yl]-6-aminomethylindole (150 mg) obtained in Example 348, sodium fluoroacetate (100 mg), ethyl chlorocarbonate (96 μl) and dimethylformamide (10 ml) were treated as in Example 373 to give the oxalate (100 mg) of the title compound as a white powder (yield: 46%).
$^1$H-NMR(400 MHz,DMSO-$d_6$); δ(ppm) 2.05–2.12(2H,m), 2.15–2.28(2H,m), 2.93–3.05(4H,m), 3.09–3.17(2H,m), 3.49–3.58(2H,m), 4.41(2H,d,J=6.0 Hz), 4.52–4.63(1H,m), 4.83(2H,d,J=47.2 Hz), 6.44(1H,d,J=3.2 Hz), 6.98(1H,d,J= 8.4 Hz), 7.15–7.22(2H,m), 7.27–7.35(1H,m), 7.36–7.46(3H, m), 7.48(1H,d,J=8.4 Hz), 8.68(1H,t,J=6.0 Hz).
m.p.: 168–169° C.
Mass: FAB+412(M+H).

Example 382: Synthesis of 1-[1-(2-fluorophenethyl) piperidin-4-yl]-6-(3-hydroxypropionylamino)methylindole 1-[1-(2-Fluorophenethyl)piperidin-4-yl]-6-aminomethylindole (110 mg) obtained in Example 348, β-propiolactone (23 mg) and toluene (10 ml) were treated as in Example 373 to give the title compound (90 mg) as a white powder (yield: 69%).
$^1$H-NMR(400 MHz,CDCl$_3$); δ(ppm) 1.99–2.06(4H,m), 2.28–2.39(2H,m), 2.51(2H,t,J=5.2 Hz), 2.69–2.78(2H,m), 2.91–2.99(2H,m), 3.23–3.30(2H,m), 3.95(2H,t,J=5.2 Hz), 4.14–4.24(1H,m), 4.63(2H,d,J=6.0 Hz), 6.28(1H,br-s), 6.45 (1H,d,J=3.2 Hz), 6.98(1H,d,J=8.8 Hz), 7.02–7.12(2H,m), 7.14(1H,d,J=3.2 Hz), 7.19–7.27(2H,m), 7.57(1H,d,J=8.8 Hz), 7.58(1H,s).
m.p.: 58–59° C.
Mass: FAB+424(M+H).
Example 383: Synthesis of 1-[1-(2-fluorophenethyl) piperidin-4-yl]-6-hydroxyacetamidomethylindole 1-[1-(2-Fluorophenethyl)piperidin-4-yl]-6-aminomethylindole (150 mg) obtained in Example 348 and acetoxyacetyl chloride (64 mg) were treated as in Example 373 to give the title compound (110 mg) as a white powder (yield: 62%).
$^1$H-NMR(400 MHz,DMSO-$d_6$); δ(ppm) 1.87–2.03(4H,m), 2.19–2.26(2H,m), 2.54–2.60(2H,m), 2.76–2.83(2H,m), 3.04–3.11(2H,m), 3.82(2H,d,J=6.0 Hz), 4.23–4.33(1H,m), 4.37(2H,d,J=6.0 Hz), 5.47(1H,t,J=6.0 Hz), 6.38(1H,d,J=3.2 Hz), 6.95(1H,d,J=8.0 Hz), 7.10–7.17(2H,m), 7.21–7.28(1H, m), 7.32–7.38(1H,m), 7.42(1H,d,J=8.0 Hz), 7.44(1H,d,J= 3.2 Hz), 7.45(1H,s), 8.14(1H,t,J=6.0 Hz).
m.p.: 151–152° C.
Mass: FAB+410(M+H).
Example 384: Synthesis of 1-[1-(4-fluorophenethyl) piperidin-4-yl]-6-methoxycarbonylaminomethylindole 1-[1-(4-Fluorophenethyl)piperidin-4-yl]-6-aminomethylindole (150 mg) obtained in Example 322-3), methyl chlorocarbonate (47 mg), triethylamine (50 mg) andacetonitrile (5 ml) were treated as in Example 373 to give the title compound (120 mg) as white needles (yield: 68%).
$^1$H-NMR(400 MHz,CDCl$_3$); δ(ppm) 2.02–2.12(4H,m), 2.20–2.31(2H,m), 2.60–2.68(2H,m), 2.78–2.85(2H,m), 3.12–3.20(2H,m), 3.70(3H,s), 4.19–4.29(1H,m), 4.48(2H,d, J=6.0 Hz), 5.13(1H,br-s), 6.49(1H,d,J=3.2 Hz), 6.95–7.01 (2H,m), 7.03(1H,d,J=8.0 Hz), 7.15–7.20(2H,m), 7.22(1H, J=3.2 Hz), 7.31(1H,s), 7.58(1H,d,J=8.0 Hz).
m.p.: 117–118° C.
Mass: FAB+410(M+H).
Example 385: Synthesis of 1-[1-(4-fluorophenethyl) piperidin-4-yl]-6-N,N-dimethylaminocarbonylaminomethylindole 1-[1-(4-Fluorophenethyl)piperidin-4-yl]-6-aminomethylindole (150 mg) obtained in Example 322-3), dimethylcarbamyl chloride (54 mg), triethylamine (50 mg) and acetonitrile (5 ml) were treated as in Example 373 to give the title compound (130 mg) as a white powder (yield: 72%).
$^1$H-NMR(400 MHz,CDCl$_3$); δ(ppm) 2.04–2.11(4H,m), 2.23–2.30(2H,m), 2.62–2.68(2H,m), 2.79–2.85(2H,m), 2.90 (6H,s), 3.13–3.20(2H,m), 4.20–4.30(1H,m), 4.53(2H,d,J= 5.2 Hz), 4.70(1H,br-s), 6.49(1H,d,J=3.2 Hz), 6.95–7.02(2H, m), 7.07(1H,d,J=8.0 Hz), 7.16–7.21(2H,m), 7.23(1H,d,J= 3.2 Hz), 7.35(1H,s), 7.58(1H,d,J=8.0 Hz).
m.p.: 115–116° C.
Mass: FAB+423(M+H).
Example 386: Synthesis of 1-{1-[2-(3-pyridyl)ethyl]-piperidin-4-yl}-6-acetamidomethylindole
386-1) Synthesis of 1-(piperidin-4-yl)-6-acetamidomethyl-indole 1-(Piperidin-4-yl)-6-acetamidomethylindoline (0.6 g) obtained in Production Example 52 and activated manganese dioxide (3.0 g) were heated under reflux in chloroform (30 ml) for 8 hr. Then the reaction mixtures were filtered through celite. The residue was washed with chloroform and the filtrate was concentrated under reduced pressure. The resulting residue was purified by NH-silica gel column chromatography (ethyl acetate/methanol system) to give the title compound (0.45 g) as a brown amorphous substance (yield: 75.5%).
$^1$H-NMR(400 MHz,DMSO-$d_6$); δ(ppm) 1.75–1.90(4H,m), 1.86(3H,s), 2.64–2.74(2H,m), 3.04–3.10(2H,m), 4.30–4.39 (1H,m), 4.33(2H,d,J=6.0 Hz), 6.41(1H,d,J=3.0 Hz), 6.93 (1H,dd,J=8.0,1.2 Hz), 7.41(1H,br-s), 7.42(1H,d,J=3.0 Hz), 7.47(1H,d,J=8.0 Hz), 8.24–8.31(1H,m).
386-2) 1-{1-[2-(3-Pyridyl)ethyl]piperidin-4-yl}-6-acetamidomethylindole Potassium carbonate (0.5 g) was added to a solution of 1-(piperidin-4-yl)-6-acetamidomethylindole (0.10 g) obtained in Example 386-1) and 3-(2-bromoethyl)pyridine (0.07 g) obtained in Production Example 26-2 in N,N-dimethylformamide (5 ml) and the resultant mixture was stirred at 70° C. for 6 hr. Then the reaction mixtures were concentrated under reduced pressure and the residue was partitioned between ethyl acetate (40 ml) and water (15 ml) followed by extraction with ethyl acetate. The ethyl acetate layer was washed with brine, dried over magnesium sulfate and concentrated under reduced pressure. The residue was purified by silica gel column chromatography (chloroform/methanol system) to give the title compound (0.06 g) as a pale yellow wax (yield: 75.5%).

Then the obtained product was converted into an oxalate in a conventional manner to give the oxalate (0.06 g) of the title compound as a pale yellow amorphous substance.
Oxalate:
$^1$H-NMR(400 MHz,DMSO-$d_6$); δ(ppm) 1.87(3H,s), 2.00–2.09(2H,m), 2.14–2.27(2H,m), 2.75–2.86(2H,m), 2.93–3.09(4H,m), 3.38–3.46(2H,m), 4.35(2H,d,J=6.0 Hz), 4.47–4.60(1H,m), 6.44(1H,d,J=3.2 Hz), 6.96(1H,d,J=8.0 Hz), 7.36(1H,dd,J=8.0,4.4 Hz), 7.43–7.47(2H,m), 7.49(1H, d,J=8.0 Hz), 7.71–7.76(1H,m), 8.30–8.37(1H,m), 8.46(1H, dd,J=8.0,1.6 Hz), 8.53(1H,d,J=1.6 Hz).
ESI-Mass; 377(MH+).
Example 387: Synthesis of 3-cyano-1-[1-(4-fluorophenethyl)-piperidin-4 -yl]-6-acetamidomethylindole 1,1'-Carbonyldiimidazole (0.04 g) was added to a solution of 1-[1-(4-fluorophenethyl)piperidin-4-yl]-3-hydroxyimino-6-acetamidomethylindole (0.07 g) obtained in Example 371 in chloroform (10 ml) and the resultant mixture was stirred at room temperature for 0.5 hr. Then the reaction mixtures were concentrated and the residue was partitioned between ethyl acetate (40 ml) and water (10 ml). The ethyl acetate layer was washed successively with water and brine, dried over magnesium sulfate and concentrated under reduced pressure. The residue was purified by NH-silica gel column chromatography (ethyl acetate) to give the title compound (0.04 g) as a white powder (yield: 57.6%).
m.p.: 130–131° C.
$^1$H-NMR(400 MHz,DMSO-$d_6$); δ(ppm) 1.88(3H,s), 2.09–2.29(4H,m), 2.82–3.14(6H,m), 3.42–3.52(2H,m), 4.39 (2H,d,J=5.2 Hz), 4.64–4.74(1H,m), 7.14–7.24(3H,m), 7.32–7.38(2H,m), 7.62(1H,d,J=8.4 Hz), 7.68(1H,s), 8.43 (1H,s).
Example 388: Synthesis of 1-{4-[(1-hydroxyethyl) phenethyl]-piperidin-4-yl}-6-acetamidomethylindole Potassium carbonate (0.5 g) was added to a solution of 1-(piperidin-4-yl)-6-acetamidomethylindole (0.10 g) obtained in Example 386-1) and 4-(1-hydroxyethyl) phenethyl bromide (0.07 g) obtained in Production Example 19 in N,N-dimethylformamide (5 ml) and the resultant mixture was stirred at 70° C. for 6 hr. Then the reaction mixtures were concentrated under reduced pressure and the residue was partitioned between chloroform (40 ml) and water (15 ml). The chloroform layer was washed with brine, dried over magnesium sulfate and concentrated under reduced pressure. The residue was purified by silica gel column chromatography (chloroform/methanol system) to give the title compound (0.07 g) as a pale yellow wax (yield: 45.3%).

Then the resulting product was converted into an oxalate in a conventional manner to give the oxalate (0.06 g) of the title compound as a pale yellow powder.
Oxalate:
m.p.: 105–107° C.
$^1$H-NMR(400 MHz,DMSO-$d_6$); δ(ppm) 1.31(2H,d,J=6.4 Hz), 1.87(3H,s), 2.09–2.17(2H,m), 2.30–2.43(2H,m), 2.99–3.05(2H,m), 3.16–3.33(4H,m), 3.62–3.70(2H,m), 4.35 (2H,d,J=6.0 Hz), 4.64–4.74(2H,m), 6.47(1H,d,J=3.2 Hz), 6.97(1H,d,J=8.0 Hz), 7.25(2H,d,J=8.0 Hz), 7.32(2H,d,J=8.0 Hz), 7.43(1H,d,J=3.2 Hz), 7.48(1H,br-s), 7.50(1H,d,J=8.0 Hz), 8.33–8.38(1H,m).
ESI-Mass; 420(MH+).

Example 389: Synthesis of 1-[1-( 4-bromophenethyl) piperidin-4-yl]-6-acetamidomethylindole Potassium carbonate (1.0 g) was added to a solution of 1-(piperidin-4-yl)-6-acetamidomethylindole (0.20 g) obtained in Example 386-1) and 4-bromophenethyl bromide (0.16 g) obtained in Production Example 4 in N,N-dimethylformamide (15 ml) and the resultant mixture was stirred at 70° C. for 6 hr. Then the reaction mixtured were concentrated under reduced pressure and the residue was partitioned between chloroform (40 ml) and water (15 ml). The chloroform layer was washed with brine, dried over magnesium sulfate and concentrated under reduced pressure. The residue was purified by silica gel column chromatography (chloroform/methanol system) and then crystallized from ethyl acetate/hexane to give the title compound (0.25 g) as a pale yellow powder (yield: 74.6%).
m.p.: 140–141° C.
$^1$H-NMR(400 MHz,DMSO-$d_6$); δ(ppm) 1.86(3H,s), 1.88–2.03(4H,m), 2.19–2.28(2H,m), 2.56–2.62(2H,m), 2.73–2.79(2H,m), 3.05–3.12(2H,m), 4.26–4.35(1H,m), 4.34 (2H,d,J=6.0 Hz), 6.41(1H,d,J=3.2 Hz), 6.97(1H,d,J=8.0 Hz), 7.25(2H,d,J=8.0 Hz), 7.32(2H,d,J=8.0 Hz), 4.64–6.93(1H, dd,J=8.0,1.2 Hz), 7.23(2H,d,J=8.0 Hz), 7.40(1H,br-s), 7.45–7.50(4H,m), 8.25–8.31(1H,m).
ESI-Mass; 455 (MH+).

Example 390: Synthesis of 1-[1-(2-fluorophenethyl) piperidin-4-yl]-6-formylindole 1-[1-(2-Fluorophenethyl)piperidin-4-yl]-6-hydroxymethylindoine (0.49 g) obtained in Example 342-1) was dissolved in chloroform (40 ml). To the resultant solution was added manganese dioxide (1.20 g) and the resultant mixture was stirred at 50° C. overnight. After adding additional manganese dioxide (0.60 g), the mixture was further stirred for 7 hr. After further adding manganese dioxide (0.60 g), the mixture was stirred overnight. After furthermore adding manganese dioxide (0.60 g), the mixture was stirred for 10 hr. After furthermore adding manganese dioxide (0.60 g), the mixture was stirred overnight. Next, the manganese dioxide was filtered off and the solvent was evaporated under reduced pressure to give the title compound (0.40 g) as a pale yellow powder.
$^1$H-NMR(400 MHz,CDCl$_3$); δ(ppm) 2.07–2.13(4H,m), 2.27–2.34(2H,m), 2.67–2.71(2H,m), 2.87–2.91(2H,m), 3.19 (2H,br-d), 4.32–4.40(1H,m), 6.59(1H,d,J=3.2 Hz), 7.00–7.03(1H,m), 7.05–7.10(1H,m), 7.17–7.25(2H,m), 7.46 (1H,d,J=3.2 Hz), 7.61(1H,dd,J=0.8,8.0 Hz), 6.71(1H,d,J= 8.0 Hz), 7.97(1H,s), 10.06(1H,s).
ESI-Mass; 351(MH+).

Example 391: Synthesis of 1-[1-( 2-fluorophenethyl) piperidin-4-yl]-6-hydroxymethylindole 1-[1-(2-Fluorophenethyl)piperidin-4-yl]-6-formylindole (0.21 g) obtained in Example 348-4) was dissolved in methanol (10 ml) andtetrahydrofuran (5 ml) andthe resultant solution was stirred under ice cooling. Then sodium borohydride was added thereto in portions. After confirming the disappearance of the starting material by thin layer chromatography, the solvent was evaporated under reduced pressure. Then a 2 N aqueous solution of sodium hydroxide was added to the residue followed by extraction with ethyl acetate. The extract was washed successively with water and brine and dried over magnesium sulfate. After evaporating the solvent under reduced pressure, the residue was recrystallized from chloroform/n-hexane to give the title compound (0.17 g) as a colorless powder.
m.p.: 116.8–117.5° C.
$^1$H-NMR(400 MHz,CDCl$_3$); δ(ppm) 2.07–2.16(4H,m), 2.26–2.33(2H,m), 2.66–2.70(2H,m), 2.87–2.91(2H,m), 3.19 (2H,br-d), 4.23–4.31(1H,m), 4.82(2H,s), 6.51(1H,d,J=3.6 Hz), 7.01–7.11(3H,m), 7.17–7.26(3H,m), 7.43(1H,s), 7.61 (1H,d,J=8.0 Hz).
ESI-Mass; 353(MH+).

Example 392: Synthesis of 1-[1-(4-fluorophenethyl) piperidin-4-yl]-6-(1-hydroxyethyl)indole oxalate 1-[1-(4-Fluorophenethyl)piperidin-4-yl]-6-formylindoline (0.15 g) obtained in Example 130 was dissolved in tetrahydrofuran (5 ml) and stirred under ice cooling. To the resultant solution was added a 1.0 M solution (0.5 ml) of methylmagnesium bromide in ether and the mixture was stirred for 30 min. Then a saturated aqueous solution of ammonium chloride, water and ethyl acetate were added to the reaction solution. The organic layer was separated, washed successively with water and brine and dried over magnesium sulfate. After evaporating the solvent under reduced pressure, a free title compound (0.13 g) was obtained as a pale brown viscous oil, which was then converted into an oxalate in a conventional manner.
$^1$H-NMR(400 MHz,DMSO-$d_6$); δ(ppm) 1.38(3H,d,J=6.4 Hz), 2.10(2H,br-d), 2.24–2.33(2H,m), 2.98–3.02(2H,m), 3.06(2H,br-t), 3.16–3.20(2H,m), 3.56(2H,br-d), 4.63–4.70 (1H,m), 6.44(1H,d,J=3.2 Hz), 7.03(1H,d,J=8.4 Hz), 7.18 (2H,br-t), 7.34–7.37(2H,m), 7.41(1H,d,J=3.2 Hz), 7.47(1H, d,J=8.4 Hz), 7.53(1H,s).
ESI-Mass; 367(MH+).

Example 393: Synthesis of 1-[1-(4-fluorophenethyl) piperidin-4-yl]-6-ureidomethylindole 1,1-Carbonyldiimidazole (0.16 g) and imidazole (0.13 g) were added to tetrahydrofuran (5 ml) and the resultant mixture was stirred under nitrogen atmosphere under ice cooling. Next, 1-[1-(4-fluorophenethyl)piperidin-4-yl]-6-aminomethylindoline (0.33 g) obtained in Example 132 dissolved in tetrahydrofuran (3 ml) was added dropwise thereinto. After stirring for 15 min, a saturated solution (2 ml) of ammonia in ethanol was further added thereto and the resultant mixture was stirred under ice cooling for 10 min and then at room temperature overnight. Next, water and ethyl acetate were added to the reaction solution. The organic layer was separated, washed with brine and dried over magnesium sulfate. After evaporating the solvent under reduced pressure, the residue was purified by silica gel column chromatography (chloroform/methanol system) to give the title compound as colorless crystals. Then these crystals were recrystallized from chloroform/ethyl acetate/ n-hexane to give the title compound (0.07 g) as colorless needles.
m.p. 171.9–172.8° C.
$^1$H-NMR(400 MHz,CDCl$_3$); δ(ppm) 2.02–2.10(4H,m), 2.20–2.26(2H,m), 2.60–2.64(2H,m), 2.78–2.82(2H,m), 3.12 (2H,br-d), 4.16–4.24(1H,m), 4.37(2H,d,J-5.4 Hz), 4.58(2H, s), 5.34(1H,t,J=5.4 Hz), 6.47(1H,d,J=3.2 Hz), 6.96–7.00 (3H,m), 7.15–7.18(2H,m), 7.21(1H,d,J=3.2 Hz), 7.29(1H,s), 7.54(1H,d,J=8.0 Hz).

ESI-Mass; 395(MH+).

Example 394: Synthesis of 1-[1-(4-fluorophenethyl)piperidin-4-yl]-6-(3-methylureido)methylindole 1-[1-(4-Fluorophenethyl)piperidin-4-yl]-6-aminomethylindoline (0.17 g) obtained in Example 132 was dissolved in tetrahydrofuran (5 ml) and the resultant solution was stirred under nitrogen atmosphere. After adding methyl isothiocyanate (40.4 ml), the mixture was stirred for additional 50 min. Then additional methyl isothiocyanate (40.4 ml) was added thereto and the mixture was further stirred for 30 min. After evaporating the solvent under reduced pressure, the residue was purified by NH-silica gel column chromatography (ethyl acetate/n-hexane system) to give the title compound (0.14 g) as a pink amorphous substance.
$^1$H-NMR(400 MHz,CDCl$_3$); δ(ppm) 2.07–2.12(4H,m), 2.26–2.33(2H,m), 2.64–2.68(2H,m), 2.81–2.85(2H,m), 2.96(3H,br-d), 3.17(2H,br-d), 4.22–4.30(1H,m), 4.71(2H,br-s), 5.87(1H,br-s), 6.09(1H,br-s), 6.52(1H,d,J=3.2 Hz), 6.99(2H,br-t), 7.05(1H,d,J=8.0 Hz), 7.17–7.20(2H,m), 7.27(1H,d,J=3.2 Hz), 7.37(1H,s), 7.61(1H,d,J=8.0 Hz).
ESI-Mass; 425(MH+).

Example 395: Synthesis of 3,3-dimethyl-1-[1-(4-fluorophenethyl)piperidin-4-yl]-6-acetamidoindoline 395-1) 3,3-Dimethyl-1-[1-(4-fluorophenethyl)piperidin-4-yl]-6-aminomethylindoline Into a solution of 3,3-dimethyl-1-[1-(4-fluoro-phenethyl)piperidin-4-yl]-6-bromoindoline (1.50 g) obtained in Example 293 in tetrahydrofuran (50 ml) was added dropwise at −78° C. a 1.6 M solution (3 ml) of n-butyllithium in hexane. After 10 min, dimethylformamide (0.3 ml) was added thereto and the resultant mixture was warmed to room temperature. Then a saturated aqueous solution of ammonium chloride (20 ml) and ethyl acetate (100 ml) were added thereto and the layers were separated. The organic layer was washed with brine, dried over anhydrous magnesium sulfate and concentrated under reduced pressure. From the resulting residue, 3,3-dimethyl-1-[1-(4-fluorophenethyl)piperidin-4-yl]-6-formylindoline (0.68 g) was separated by silica gel column chromatography (ethyl acetate). Then it was suspended in a solution of hydroxylammonium chloride (0.15 g) and anhydrous sodium acetate (0.18 g) in ethanol (20 ml) and stirred at room temperature for 2 hr. The reaction mixtures were concentrated under reduced pressure and diluted with ethyl acetate (50 ml), a 2 N aqueous solution of sodium hydroxide (10 ml) and water (10 ml). The organic layer was separated, washed with brine and dried over magnesium sulfate. After evaporating the solvent, the obtained 3,3-dimethyl-1-[1-(4-fluorophenethyl)piperidin-4-yl]-6-hydroxyiminomethylindoline (0.55 g) was dissolved in tetrahydrofuran (5 ml). The resultant solution was added dropwise under ice cooling and stirring into a suspension of lithium aluminum hydride (0.07 g) in tetrahydrofuran (50 ml) and then heated under reflux for 3 hr. Under ice water cooling, water (0.07 ml), a 5 N aqueous solution (0.21 ml) of sodium hydroxide and further water (0.07 ml) were carefully added dropwise into the reaction mixtures in this order followed by vigorous stirring. The resulting precipitate was filtered off and the filtrate was concentrated under reduced pressure. The residue was purified by NH-silica gel column chromatography (ethyl acetate/methanol system) to give the title compound (0.23 g) as a brown amorphous substance (total yield: 17.4%)
$^1$H-NMR(400 MHz,CDCl$_3$); δ(ppm) 1.24(6H,s), 1.78–2.10(4H,m), 2.38–2.51(2H,m), 2.72–2.83(2H,m), 2.89–2.98(2H,m), 3.17(2H,s), 3.20–3.35(2H,m), 3.42–3.55(1H,m), 6.61(1H,s), 6.88(1H,d,J=8.0 Hz), 6.94–7.01(3H,m), 7.14–7.20(2H,m).

395)-2 3,3-Dimethyl-1-[1-(4-fluorophenethyl)piperidin-4-yl]-6-acetamidomethylindoline Under ice cooling, acetyl chloride (0.05 ml) was added dropwise into a solution of 3,3-dimethyl-1-[1-(4-fluorophenethyl)piperidin-4-yl]-6-aminomethylindoline (0.22 g) obtained above and triethylamine (0.5 ml) in tetrahydrofuran (10 ml) and the resultant mixture was stirred at room temperature for 1 hr. Then a 1 N aqueous solution (5 ml) of sodium hydroxide and water (10 ml) were added to the reaction mixture, which was extracted with ethyl acetate, washed with brine and dried over magnesium sulfate. After evaporating the solvent, the residue was purified by silica gel column chromatography (chloroform/methanol system) and crystallized from ethyl acetate/hexane to give the title compound (0.18 g) as a yellowish white powder (yield: 73.7%).
m.p.: 131–133° C.
$^1$H-NMR(400 MHz,DMSO-d$_6$); δ(ppm) 1.21(6H,s), 1.83(3H,s), 1.80–2.06(4H,m), 2.98–3.20(4H,m), 3.07(2H,s), 3.21–3.42(2H,m), 3.58–3.68(1H,m), 4.14(2H,d,J=6 Hz), 6.41(1H,s), 6.50(1H,br-d), 6.94(1H,br-d), 7.14–7.22(2H,m), 7.28–7.38(2H,m), 8.17–8.21(1H,m).
ESI-Mass; 428(MH+).

Example 396: Synthesis of 2,2-dimethyl-1-[1-(4-fluorophenethyl)piperidin-4-yl]-6-methoxyindoline 396-1N-(1-Acetylpiperidin-4-yl)-3-methoxyaniline Under ice cooling, sodium triacetoxyborohydride (12.0 g) was added to a liquid mixture of m-anisidine (4.40 g), 1-acetylpiperidin-4-one (5.0 g) and acetic acid (8 ml) in dichloroethane (80 ml). Then the reaction mixtures were stirred at room temperature overnight. The reaction mixtures were diluted with ethyl acetate (200 ml) and a 5 N aqueous solution (35 ml) of sodium hydroxide was added thereto. The organic layer was separated, washed successively with water and brine and dried over magnesium sulfate. After evaporating the solvent under reduced pressure, the residue was purified by silica gel column chromatography (ethyl acetate/hexane system) to give the title compound (7.80 g) as a brown oil (yield: 87.9%).
$^1$H-NMR(400 MHz,CDCl$_3$); δ(ppm) 1.30–1.45(2H,m), 2.06–2.18(2H,m), 2.11(3H,s), 2.76–2.85(1H,m), 3.13–3.22(1H,m), 3.43–3.51(1H,m), 3.78(3H,s), 3.76–3.93(1H,m), 4.46–4.53(1H,m), 6.24(1H,br-s), 6.28–6.36(2H,m), 7.11(1H,t,J=8.0 Hz).

396-2) N-(1-Acetylpiperidin-4-yl)-N-(2-methyl-2-propen-1-yl)-3-methoxyaniline

A mixture of N-(l-acetylpiperidin-4-yl)-3-methoxyaniline (2.0 g), 3-chloro-2-methylpropene (10 ml) and potassium carbonate (5.0 g) in dimethylformamide (50 ml) was reacted at 80° C. for 6 hr. Then the reaction mixtures were concentrated under reduced pressure and partitioned between ethyl acetate and water. The ethyl acetate layer was washed successively with water and brine and dried over magnesium sulfate. After evaporating the solvent under reduced pressure, the residue was purified by silica gel column chromatography (ethyl acetate/hexane system) to give the title compound (1.55 g) as a yellow oil (yield: 63.6%).
$^1$H-NMR(400 MHz,CDCl$_3$); δ(ppm) 1.46–1.60(2H,m), 1.73(3H,s), 1.86–1.98(2H,m), 2.11(3H,s), 2.58(1H,dt,J=8.8,2.4 Hz), 3.14(1H,dt,J=8.8,2.4 Hz), 3.59(2H,s), 3.77(3H,s), 3.80–3.94(2H,m), 4.73–4.81(1H,s), 4.87(2H,d,J=9.2 Hz), 6.22–6.37(3H,m), 7.12(1H,t,J=8.0 Hz).

396-3) 2,2-Dimethyl-1-[1-(4-fluorophenethyl)piperidin-4-yl]-6-methoxyindoline

Under nitrogen atmosphere, N-(1-acetylpiperidin-4-yl)-N-(2-methyl-2-propen-1-yl)-3-methoxyaniline (1.50 g) was heated under reflux in the presence of zinc chloride (2.0 g)

in xylene (30 ml) for 4 hr. After cooling the reaction mixtures, a 5 N aqueous solution (20 ml) of sodium hydroxide and ethyl acetate (100 ml) were added thereto and the resultant mixture was stirred for 30 min. The ethyl acetate layer was separated, washed successively with water and brine and dried over magnesium sulfate. After evaporating the solvent, the residue was dissolved in ethanol (30 ml). Then a 5 N aqueous solution (10 ml) of sodium hydroxide was added thereto and the mixture was heated under reflux for 2.5 hr. After concentrating the mixture, the residue was partitioned between ethyl acetate and water followed by extraction with ethyl acetate. The ethyl acetate layer was washed with brine, dried over magnesium sulfate and concentrated under reduced pressure. The resulting residue was purified by silica gel column chromatography (ethyl acetate/hexane system) to give a yellow oily mixture (0.91 g) containing 2,2-dimethyl-1-(piperidin-4-yl)-6-methoxyindoline.

This mixture was reacted with 4-fluorophenethyl bromide (0.8 g) in N,N-dimethylformamide (20 ml) in the presence of potassium carbonate (1.5 g) at 70° C. for 6 hr. Then the reaction mixtures were concentrated under reduced pressure and the residue was partitioned between water and ethyl acetate followed by extraction with ethyl acetate. The ethyl acetate layer was washed with brine, dried over magnesium sulfate and concentrated under reduced pressure. The resulting residue was purified by high performance liquid chromatography (ODS column, acetonitrile/water/70% perchloric acid system). After concentrating the solvent, the residue was basified, extracted with ethyl acetate, washed with water, dried and concentrated to give the title compound (0.31 g) as a pale yellow oil.

Next, this product was converted into an oxalate in a conventional manner to give a pale greenish blue powder.
Oxalate:
m.p.: 228° C. (decomp.).
$^1$H-NMR(400 MHz,DMSO-$d_6$); δ(ppm) 1.22(6H,s), 1.58–1.69(2H,m), 2.50–2.75(4H,m), 2.94–3.11(4H,m), 3.15–3.25(2H,m), 3.36–3.61(3H,m), 3.66(3H,s), 6.01(1H,d, J=8 Hz), 6.22(1H,s), 6.82(1H,d,J=8 Hz), 7.14–7.24(2H,m), 7.30–7.38(2H,m).
ESI-Mass; 383(MH+).

Example 397: Synthesis of 1-[1-(4-fluorophenethyl)piperidin-4-yl]-6-(3-methylureido)methylindole Under ice cooling, methyl isocyanate (0.02 g) was added dropwise into a solution of 1-[1-(4-fluorophenethyl)piperidin-4-yl]-6-aminomethylindoline (0.09 g) obtained in Example 132 in ethyl acetate (10 ml) and the resultant mixture was stirred at room temperature for 1 hr. The resulting precipitate was collected by filtration, washed with ether/hexane and dried to give the title compound (0.07 g) as a white powder (yield: 67%).
m.p.: 192° C. (decomp.).
$^1$H-NMR(400 MHz,DMSO-$d_6$); δ(ppm) 1.88–2.04(4H,m), 2.19–2.27(2H,m), 2.54–2.61(2H,m), 2.57(3H,d,J=4.4 Hz), 2.74–2.80(2H,m), 3.09(2H,br-d), 4.25–4.34(1H,m), 4.28 (2H,d,J=6.0 Hz), 5.73–5.78(1H,m), 6.26–6.32(1H,m), 6.40 (1H,d,J=3.2 Hz), 6.94(1H,d,J=8.0 Hz), 7.08–7.14(2H,m), 7.27–7.32(2H,m), 7.39(1H,s), 7.44–7.48(2H,m).
ESI-Mass; 409(MH+).

The Chemical formula of the compounds of Ex. 294 to 397 are cited below.
Referential Example 1: Synthesis of 1-{1-[2-(5-oxo-7-methyl-5H-pyrimidinor[2,1][1,3]thiazol-6-yl)ethyl]piperidin-4-yl}indoline

[Co. No. 5 disclosed in WO96/23784]

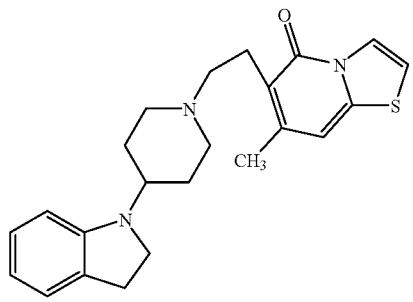

1-[1-(2-Aminoethyl)piperazin-4-yl]indoline (192 mg) was dissolved in DMF (5 ml) and then 7-methyl-6-(2-chloroethyl)-5H-pyrimidino[2,1-b][1,3]thiazol-5-one (239 mg) and triethylamine (0.159 ml) were added thereto. Next, the resultant mixture was stirred at 80° C. for 11 hr and then at 100° C for 8 hr. After adding water, the reaction solution was extracted with ethyl acetate. The organic layer was washed with brine and dried over magnesium sulfate. After evaporating the solvent, the resulting residue was purified by silica gel column chromatography (methanol/methylene chloride system) to give the title compound (46 mg) as an oil.

$^1$H-NMR (400 MHz, CDCl$_3$):

δ(ppm) 1.60–1.89(6H, m), 2.15–2.24(2H, m), 2.45(3H, s), 2.51–2.58(2H, m), 2.82–2.88(2H, m), 2.94(2H, t, J=8.2 Hz), 3.14–3.22(2H, m), 3.39(2H, t, J=8.2 Hz), 3.36–3.44(1H, m), 6.41(1H, d, J=7.6 Hz), 6.60(1H, t, J=7.6 Hz), 6.92(1H, d, J=4.8 Hz), 7.01–7.07(2H, m), 7.91(1H, d, J=4.8 Hz).

FAB-Mass: 395(MH+).

Ex. 294

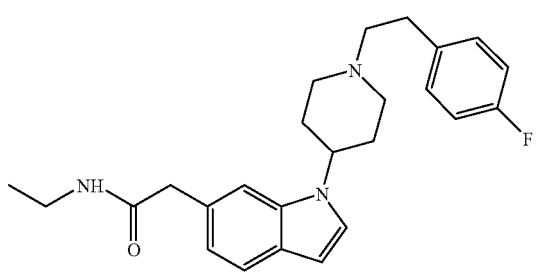

Ex. 295

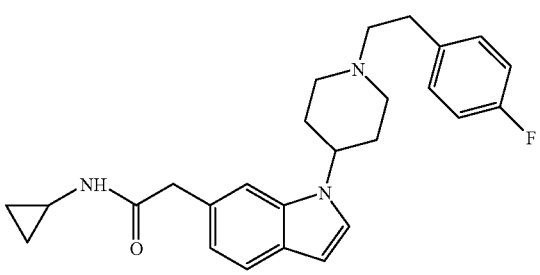

Ex. 296
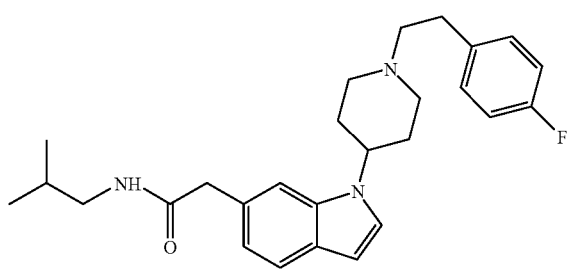
Ex. 297
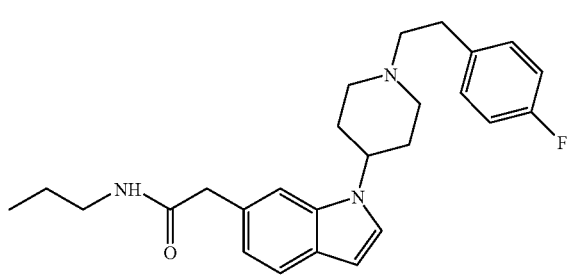
Ex. 298
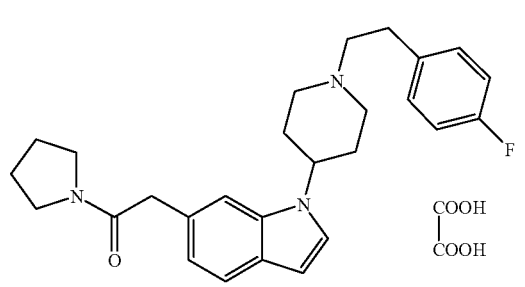
Ex. 299
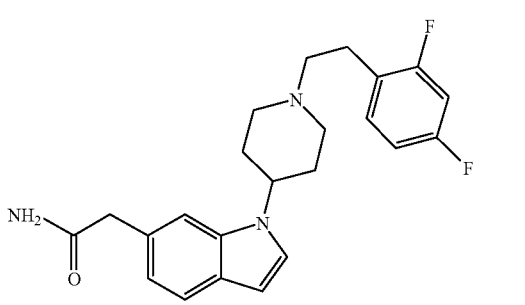
Ex. 300
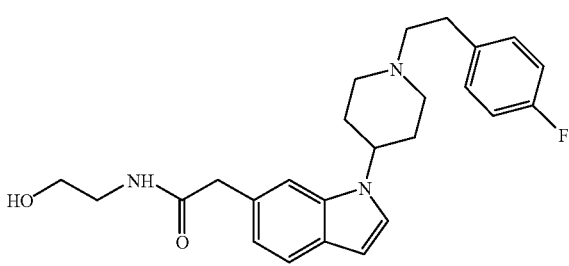
Ex. 301
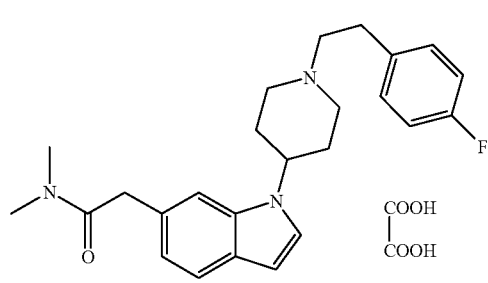
Ex. 302
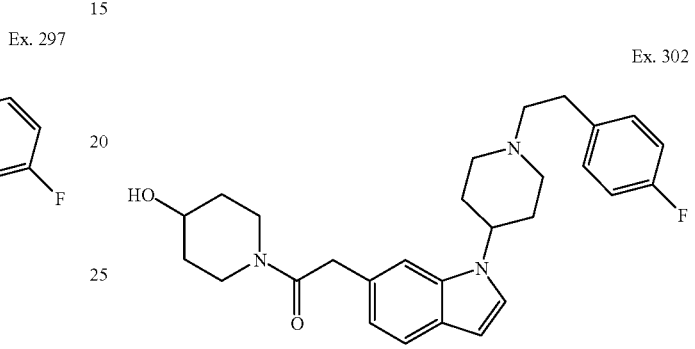
Ex. 303
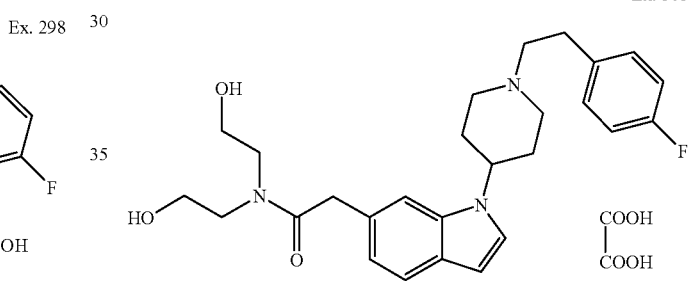
Ex. 304
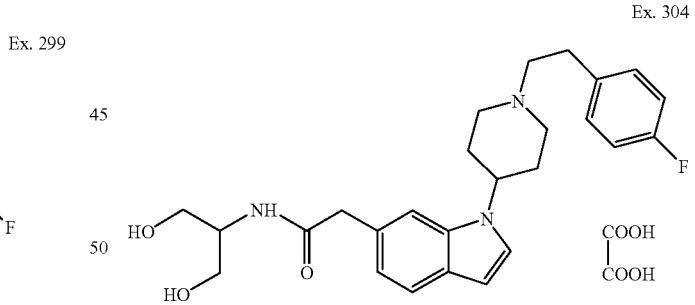
Ex. 305
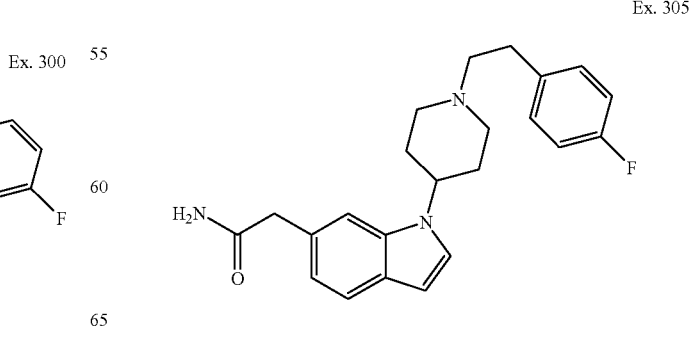

Ex. 306
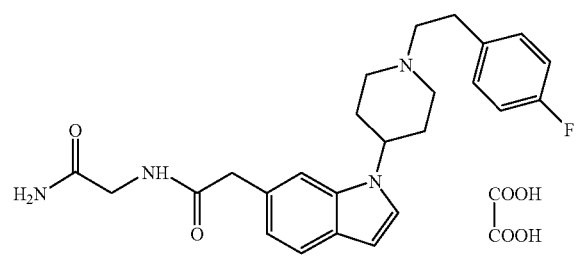
Ex. 311-1
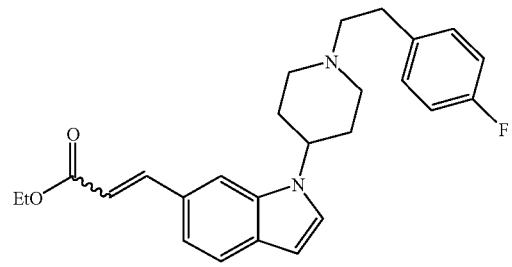
Ex. 307
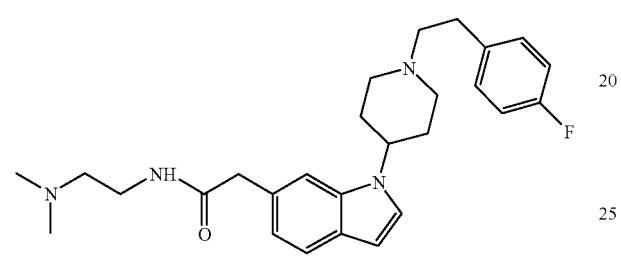
Ex. 311-2
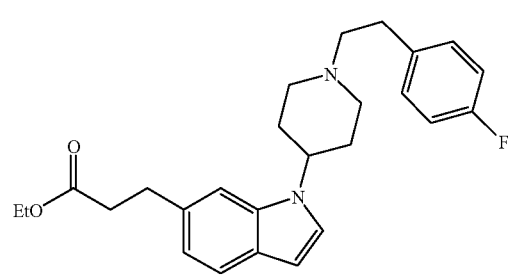
Ex. 308
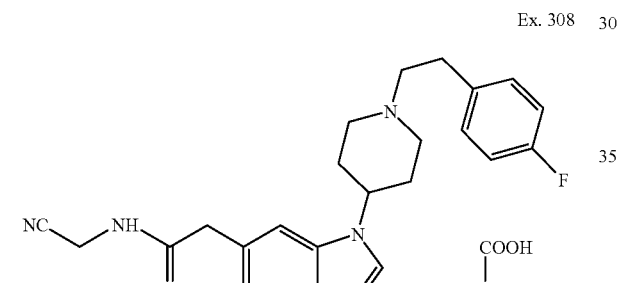
Ex. 311-3
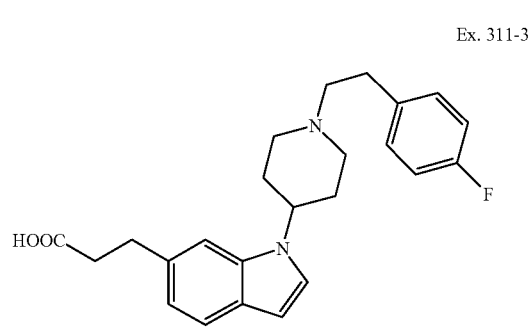
Ex. 309
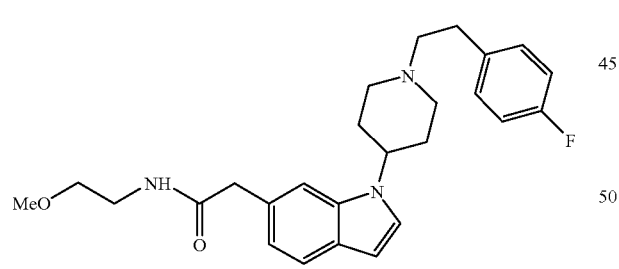
Ex. 311-4
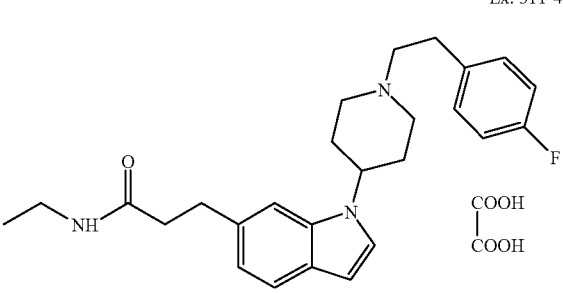
Ex. 310
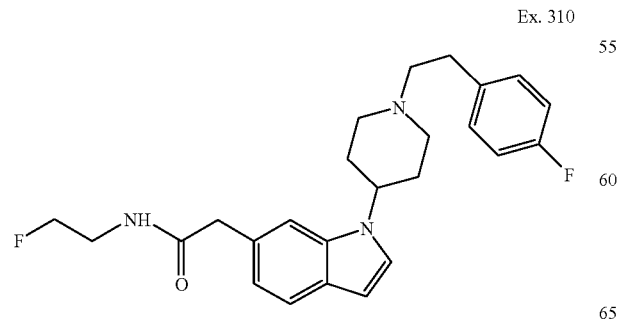
Ex. 312
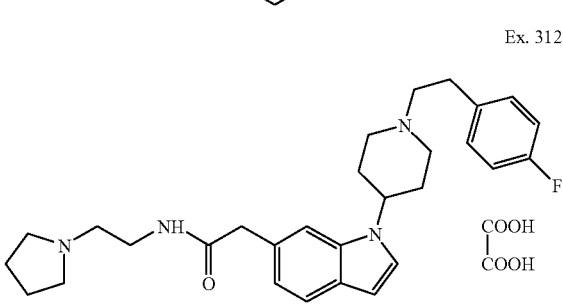

-continued
Ex. 313
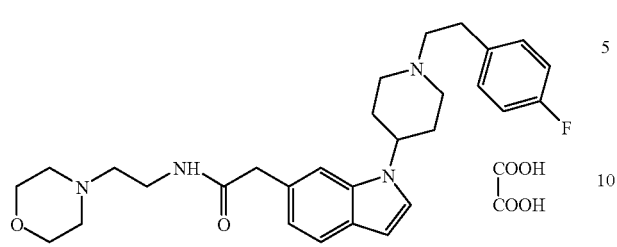
Ex. 314
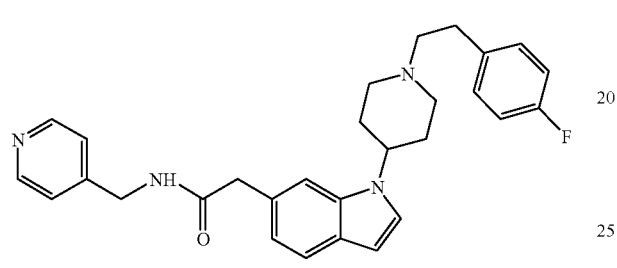
Ex. 315
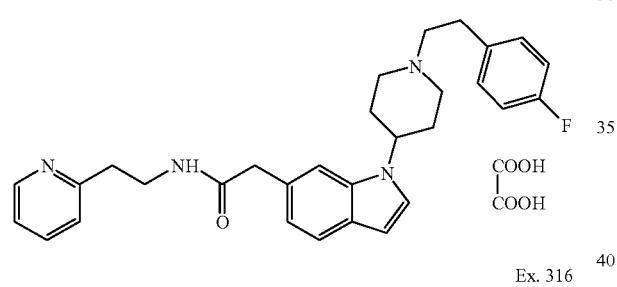
Ex. 316
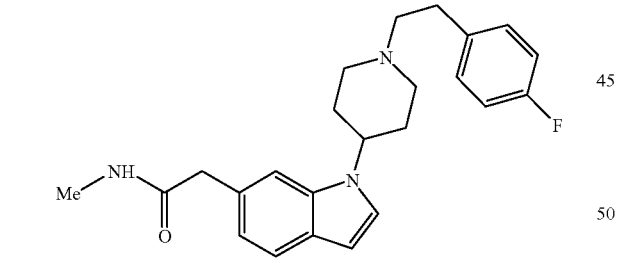
Ex. 317
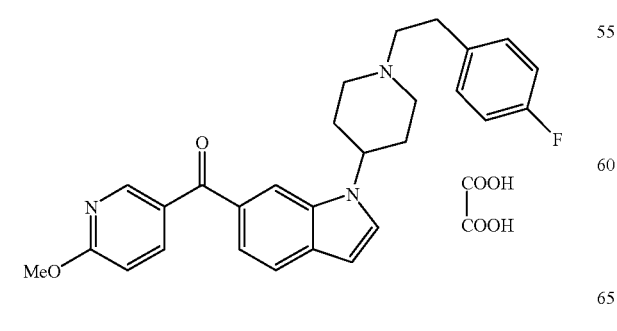
-continued
Ex. 318
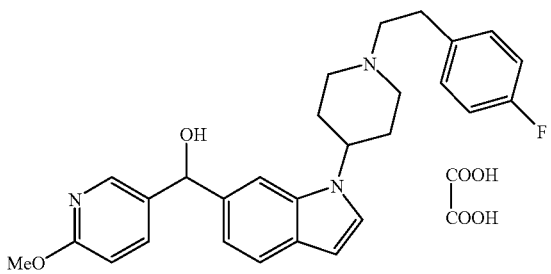
Ex. 319
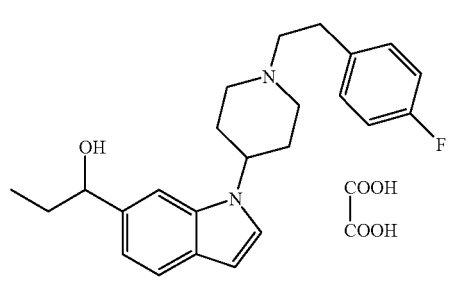
Ex. 320
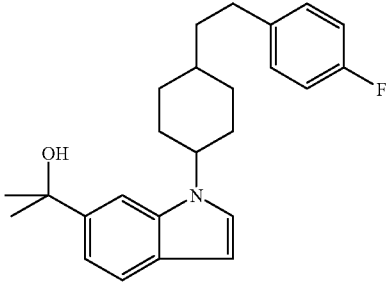
Ex. 321
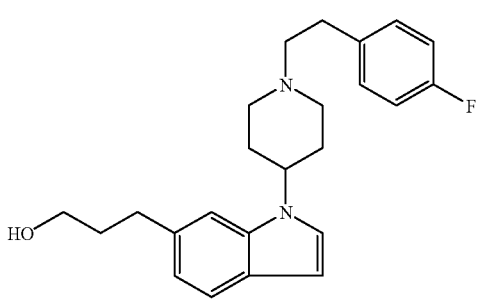
Ex. 322-1
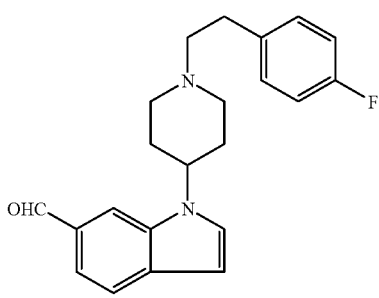

Ex. 322-2
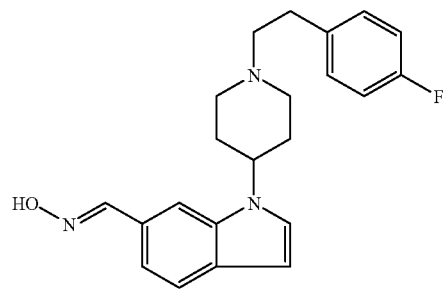
Ex. 325
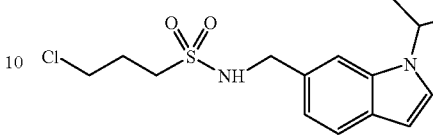
Ex. 322-3
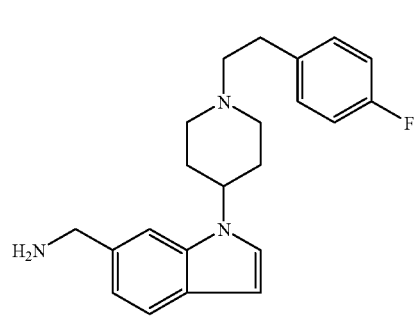
Ex. 326
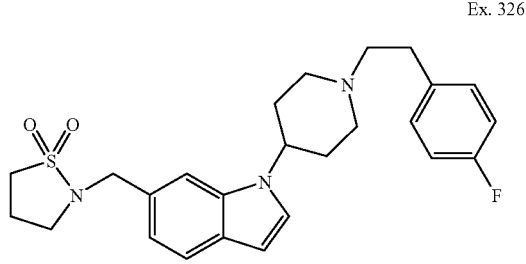
Ex. 322-4
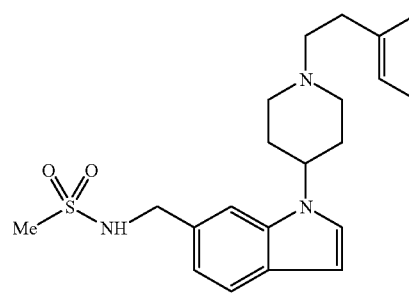
Ex. 327
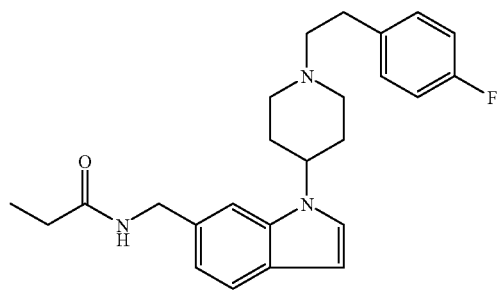
Ex. 323
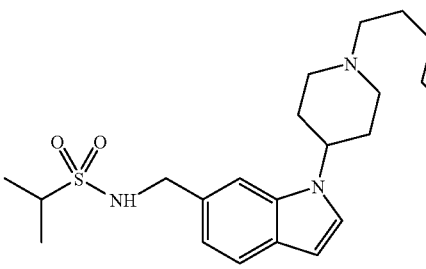
Ex. 328
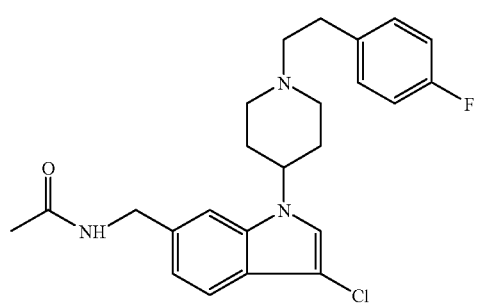
Ex. 324
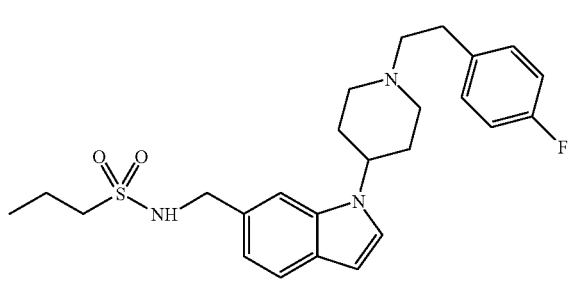
Ex. 329
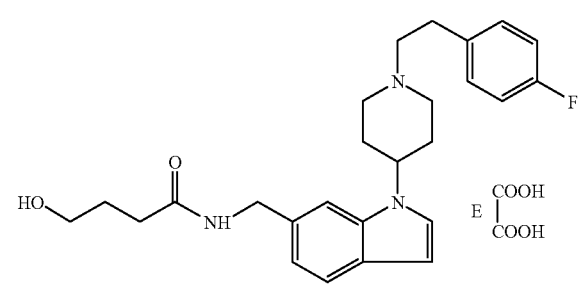

-continued

Ex. 330 — 1-[1-(4-fluorophenethyl)piperidin-4-yl]-6-(2-hydroxyethoxy)-1H-indole

Ex. 331 — 1-[1-(4-fluorophenethyl)piperidin-4-yl]-6-(methylsulfonyl)-1H-indole

Ex. 332 — 2,6-difluoro-3-{2-[4-(1H-indol-1-yl)piperidin-1-yl]ethyl}pyridine

Ex. 333 — 6-fluoro-1-[1-(4-fluorophenethyl)piperidin-4-yl]-1H-indole

Ex. 334 — 5-[1-(4-fluorophenethyl)piperidin-4-yl]-5H-[1,3]thiazolo[4',5':4,5]benzo[1,2-b]pyrrole Ex. 335 — N-{1-[1-(4-fluorophenethyl)piperidin-4-yl]-1H-indol-6-yl}-N-methylmethanesulfonamide Ex. 336 — 1-[1-(4-fluorophenethyl)piperidin-4-yl]-1H-indol-6-yl methanesulfonate Ex. 337 — 1-[1-(4-fluorophenethyl)piperidin-4-yl]-1H-indole-6-carboxamide Ex. 338 — ({1-[1-(4-fluorophenethyl)piperidin-4-yl]-1H-indol-6-yl}methanesulfonyl)-N-methylamine Ex. 339 — N-{1-[1-(4-fluorophenethyl)piperidin-4-yl]-1H-indol-6-yl}acetamide Ex. 340
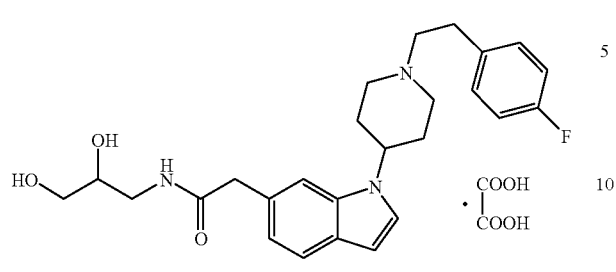
Ex. 341
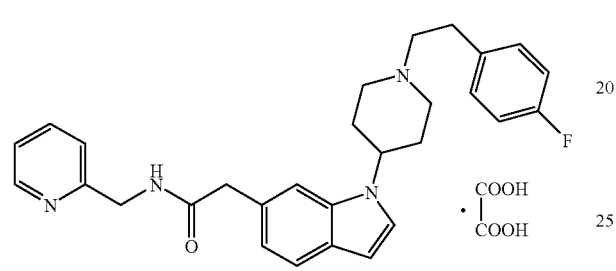
Ex. 342-1
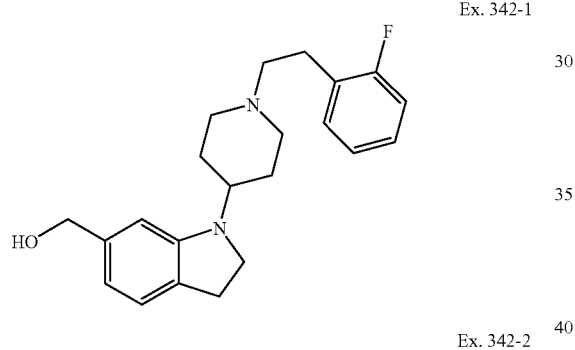
Ex. 342-2
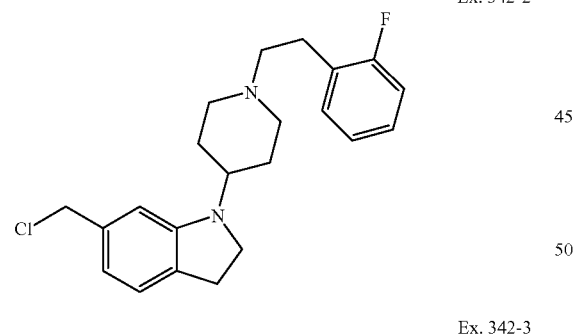
Ex. 342-3
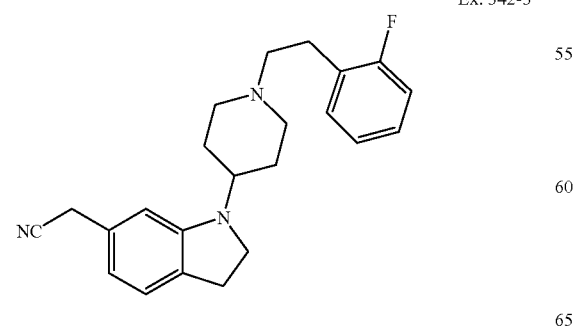
Ex. 342-4
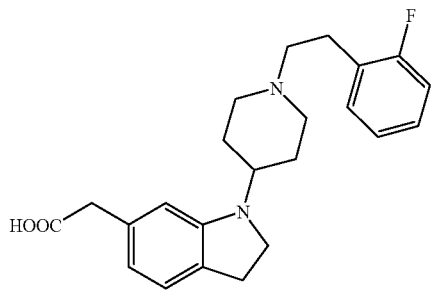
Ex. 342-5
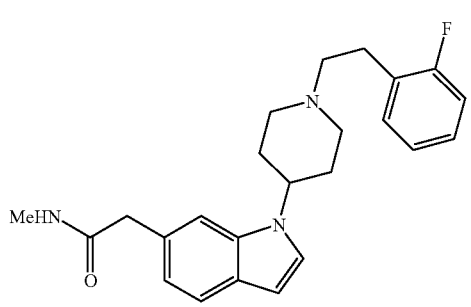
Ex. 343
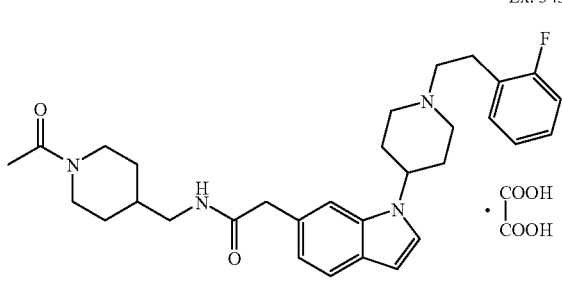
Ex. 344
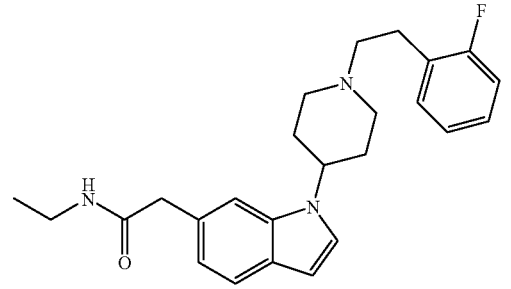
Ex. 345-1
Ex. 345-2
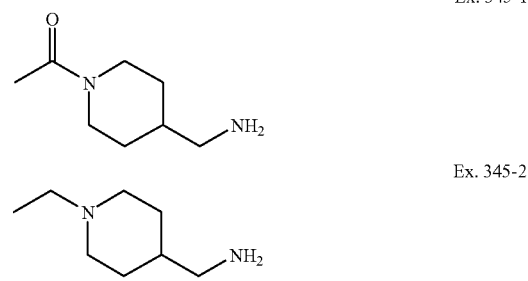

Ex. 345-3
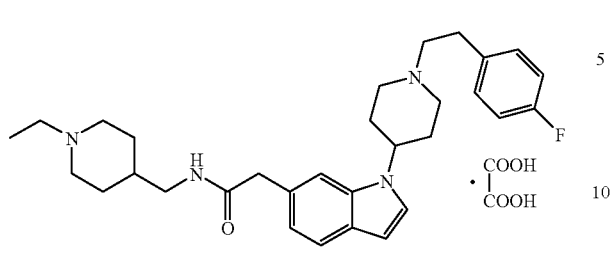
Ex. 346
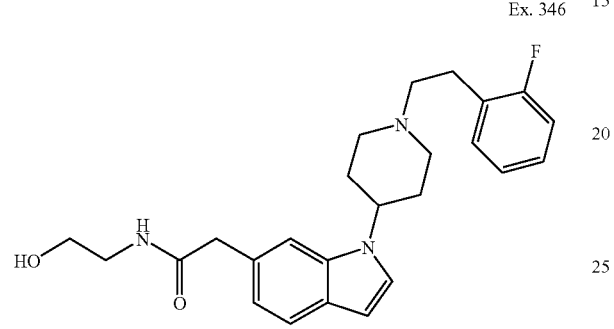
Ex. 347
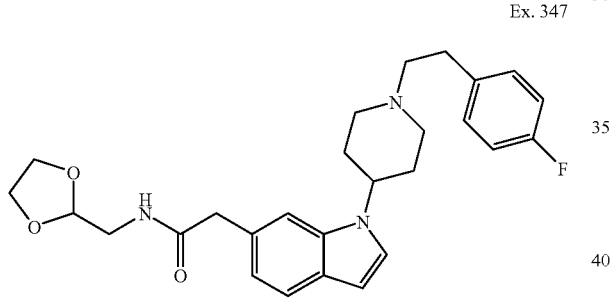
Ex. 348-1
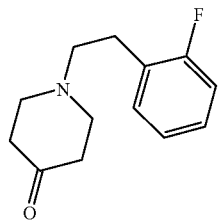
Ex. 348-2
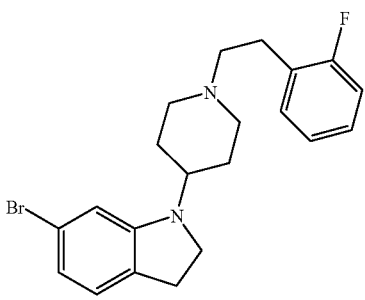
Ex. 348-3
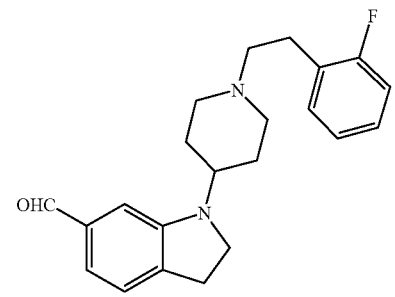
Ex. 348-4
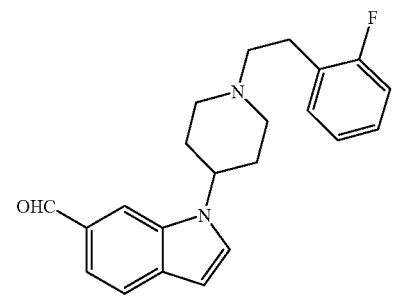
Ex. 348-5
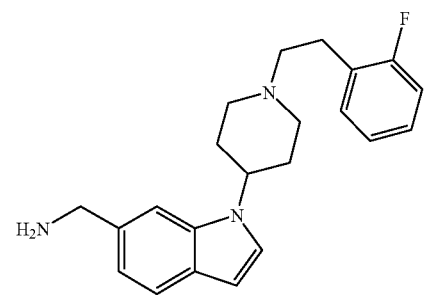
Ex. 349
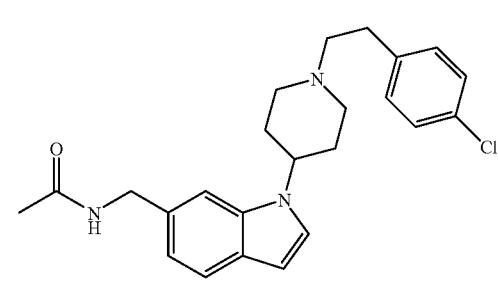
Ex. 350
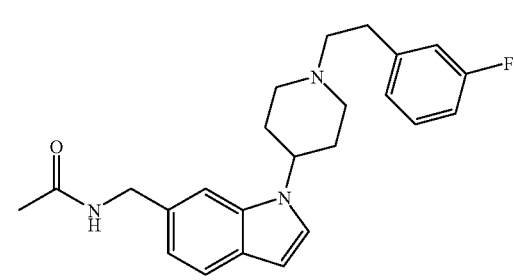

Ex. 351
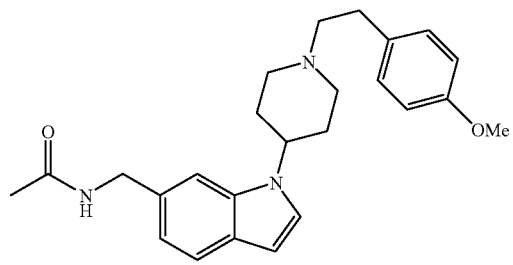
Ex. 352
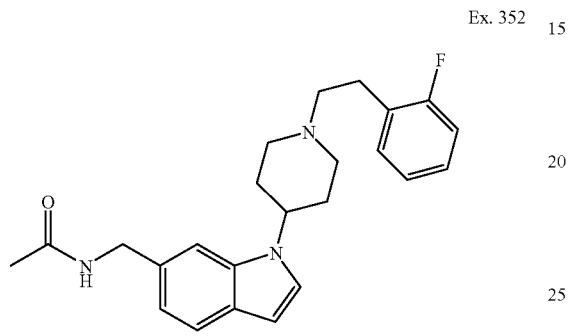
Ex. 353
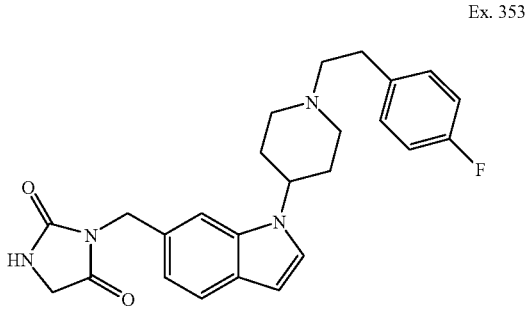
Ex. 354
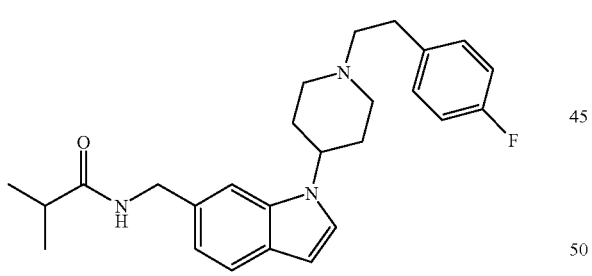
Ex. 355
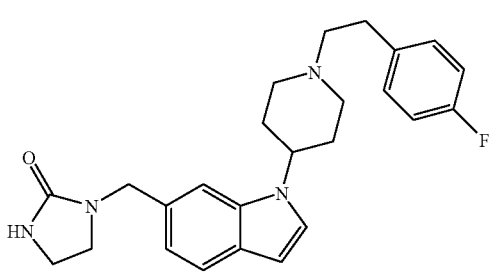
Ex. 356
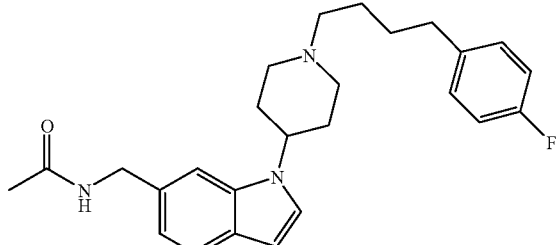
Ex. 357
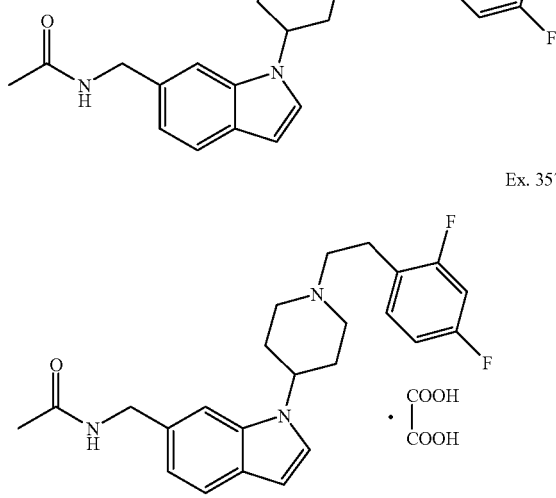
Ex. 358
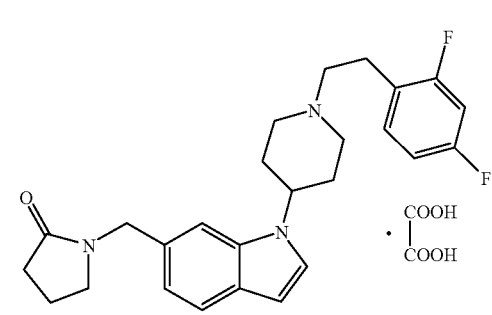
Ex. 359
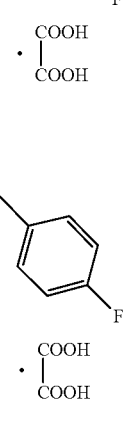
Ex. 360
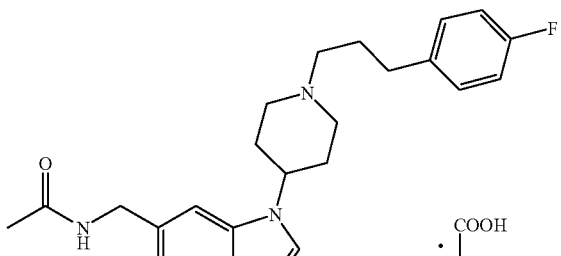

Ex. 361
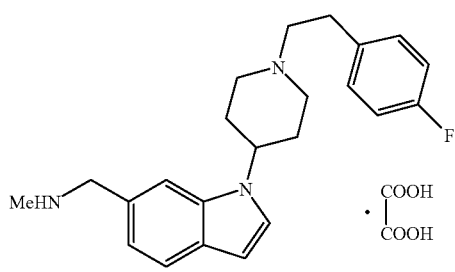
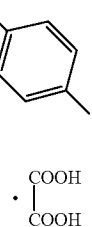
Ex. 362
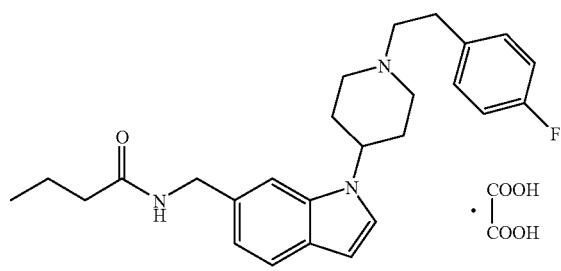
Ex. 363
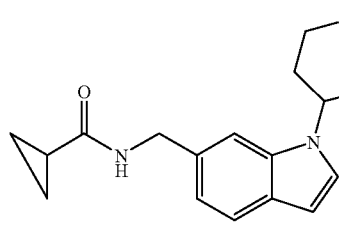
Ex. 364
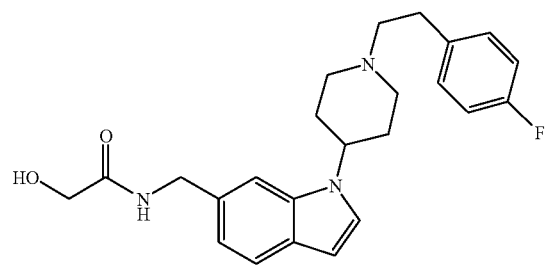
Ex. 365
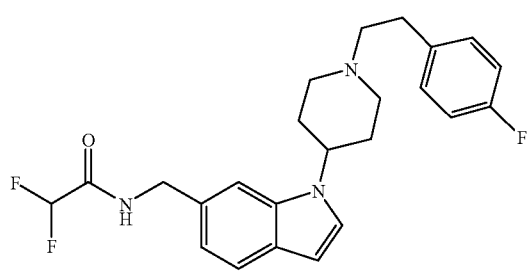
Ex. 366
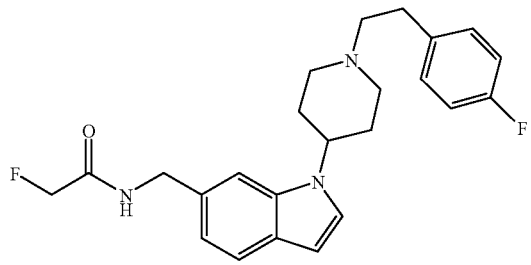
Ex. 367
Ex. 368
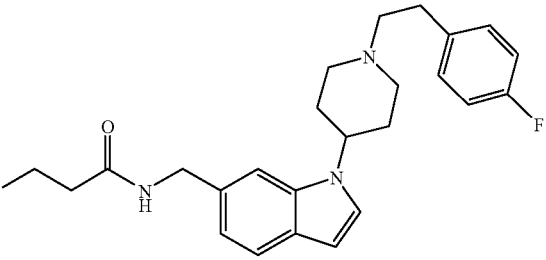
Ex. 369
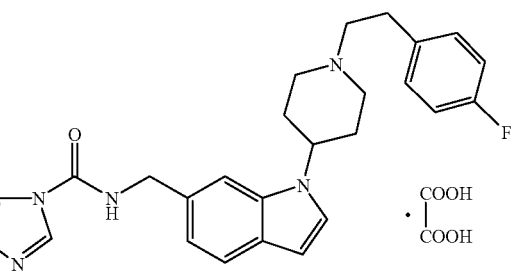
Ex. 370
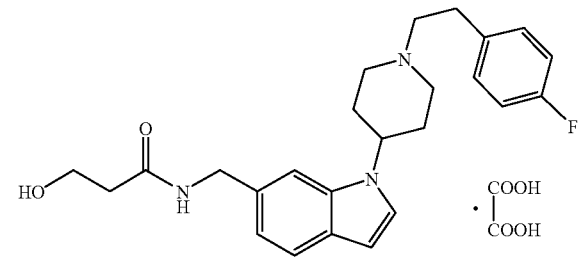
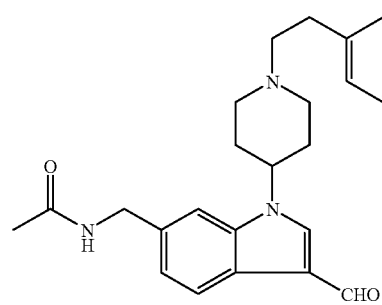

Ex. 371

Ex. 372

Ex. 373

Ex. 374

Ex. 375

Ex. 376

Ex. 377

Ex. 378

Ex. 379

Ex. 380

Ex. 381
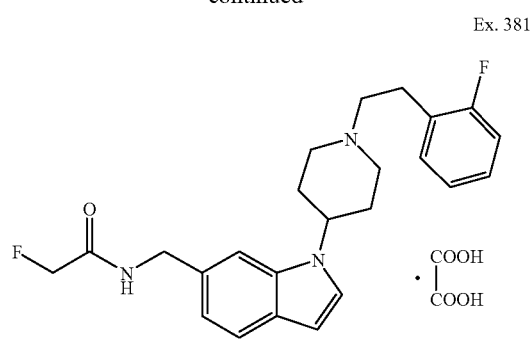 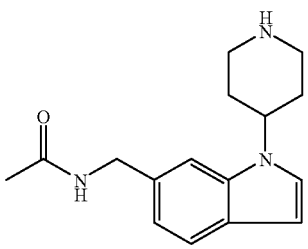
Ex. 386-1
Ex. 382
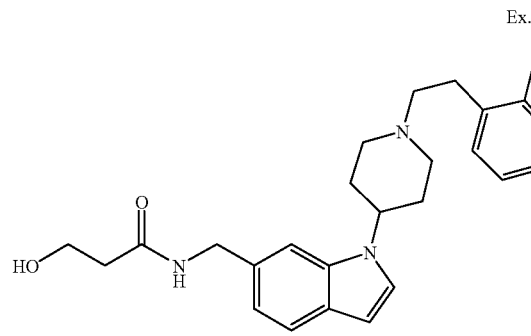
Ex. 386-2
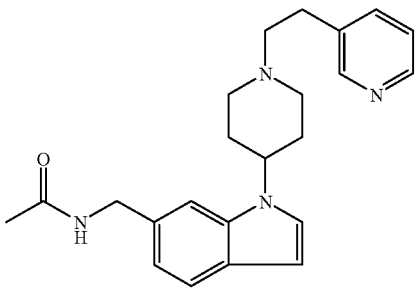
Ex. 383
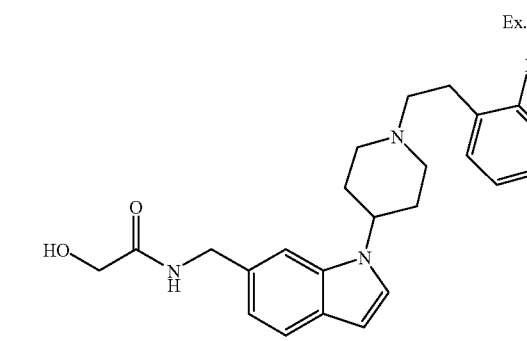
Ex. 387
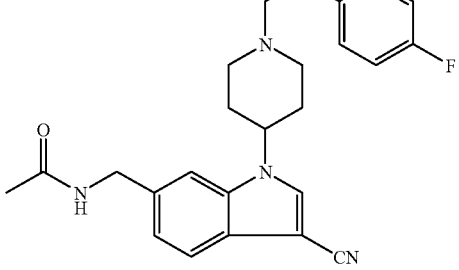
Ex. 384
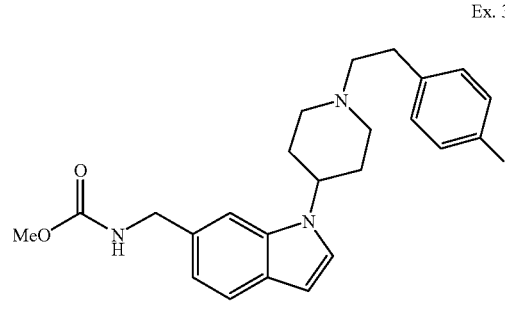
Ex. 388
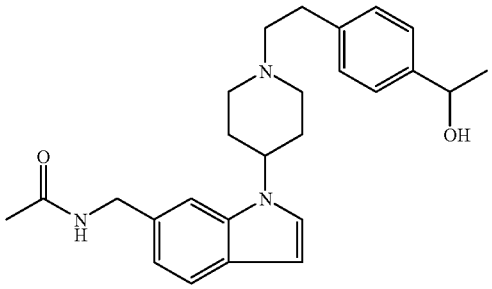
Ex. 385
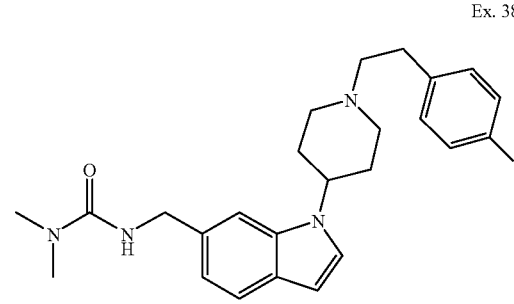
Ex. 389
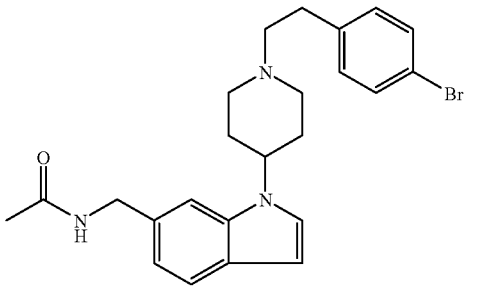

Ex. 390
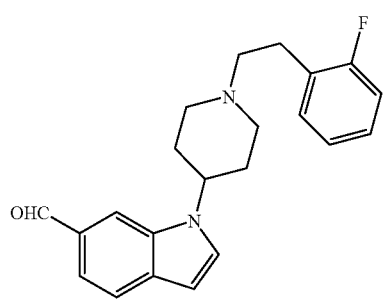
Ex. 391
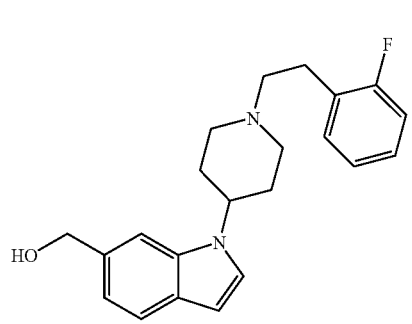
Ex. 392
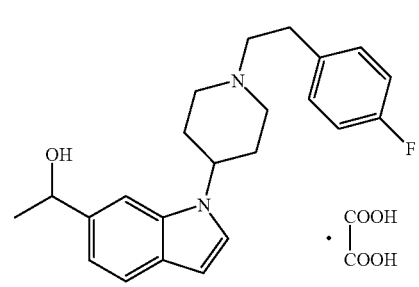
Ex. 393
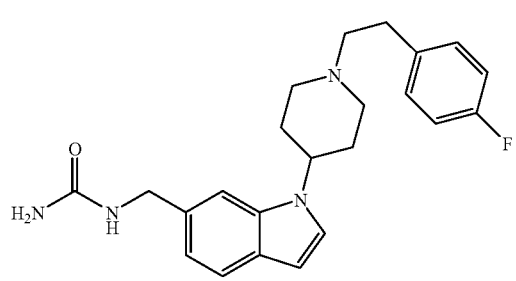
Ex. 394
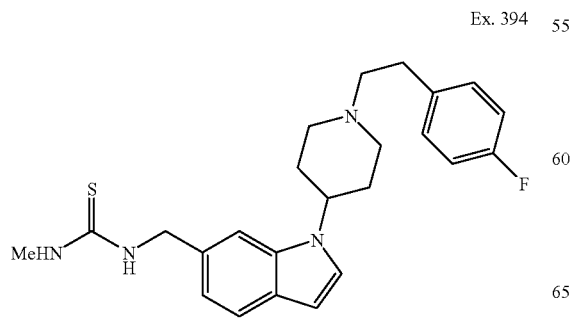
Ex. 395-1
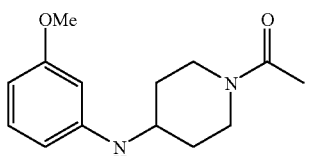
Ex. 395-2
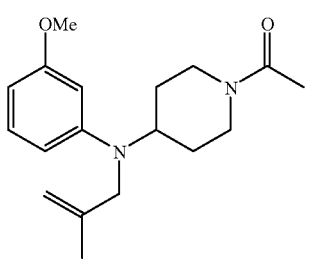
Ex. 396-1
Ex. 396-2
Ex. 396-3
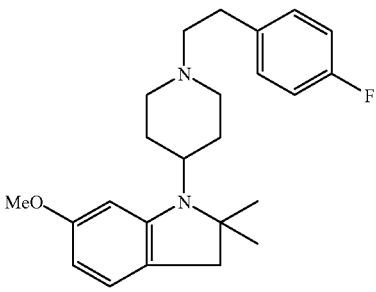

-continued

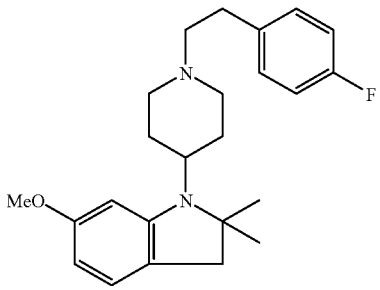
Ex. 396-3

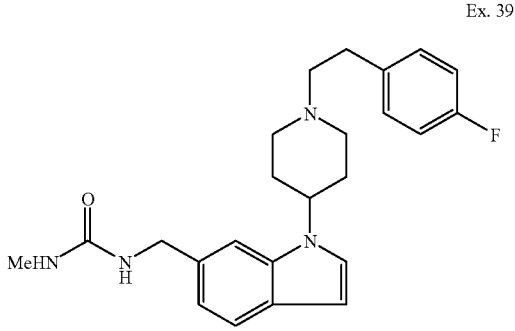
Ex. 397

What is claimed is:
1. A compound of formula (I):

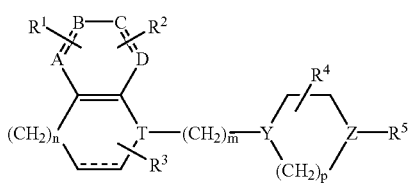

wherein A, B, C, D, and T are the same or different from one another and each represents methine or nitrogen, provided that one and only one of them represents nitrogen;
the bond represented by the following formula:

represents a single or double bond;
Y and Z are the same or different from each other and each represents methine, nitrogen, a group represented by the following formula:

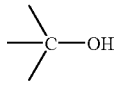

or a group represented by the following formula:

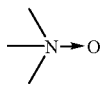

provided at least one of them represents nitrogen;
$R^1$ and $R^2$ are the same or different from each other and each represents hydrogen, halogeno, hydroxy, lower alkylsulfonylaminoalkyl, lower halogenated-alkylsulfonylaminoalkyl, 2-pyrrolidinon-1-yl, 1-hydroxy-1- (methoxypyridyl)methyl, methoxypyridylcarbonyl, 1,3-propanesultum-2-yl, lower hydroxypiperidyl -carbonylalkyl, lower hydroxyalkylamidoalkyl, lower halogenated-alkylamidoalkyl, lower dihalogenatedalkylamidoalkyl, lower hydroxyalkylamidoalkyl, optionally substituted amino, nitro, lower alkyl, lower alkoxy, lower acyl, lower alkoxyalkoxy, cyano, lower alkylsulfonyl, sulfonylamido, hydroxy-lower alkyl, hydroxy-lower alkoxy, lower alkoxycarbonylamino, lower alkylsulfonylamino, N-lower alkylalkylsulfonylamino, lower acylamino, optionally substituted aminoalkyl, optionally N-substituted lower acylaminoalkyl, optionally substituted aryl, optionally substituted arylsulfonylamino, lower alkylsulfonyloxy, hydroxyiminomethyl, (2-pyrrolidonl-yl) methyl, (2-piperidon-1-yl) methyl, optionally substituted heteroaryl, optionally substituted aralkyl, optionally substituted heteroarylalkyl, cycloalkylcarbonylaminoalkyl, optionally substituted ureido, optionally substituted ureido-lower alkyl, succinimido, (succinimido-1-yl)-lower alkyl, amido, optionally substituted carbamoyl, optionally substituted carbamoyl-lower alkyl, optionally substituted thiocarbamoyllower alkyl, formyl, aromatic acyl, heteroarylcarbonyl, halogenated lower alkyl, (2-imidazolidinon -1-yl)methyl, (2,4-imidazolidinedion-3-yl)methyl, (2-oxazolidon3-yl) methyl, (glutarimido-1-yl)methyl, optionally substituted heteroarylhydroxyalkyl, cyano-lower alkyl, 1-hydroxy lower cycloalkyl, (2,4-thiazolidinedion-3-yl)methyl, optionally substituted 4-piperidylmethyl, heteroarylacyl, pyrrolidinylcarbonyl-lower alkyl, optionally substituted aminosulfonylalkyl, carboxy-lower alkyl, or lower alkylamidoalkyl; or alternatively optionally substituted heterocycle or alkylenedioxy, provided these rings may be substituted;

$R^3$ represents hydrogen, halogeno, lower alkyl, hydroxy, hydroxy-lower alkyl, lower alkoxy, formyl, optionally substituted aralkyloxy, hydroxy-lower alkoxy, optionally substituted sulfamoyl, or optionally N-substituted sulfamoyl-lower alkyl;

$R^4$ represents hydrogen, lower alkyl, hydroxy-lower alkyl, lower alkoxyalkyl, optionally aryl-substituted aryloxyalkyl, or optionally aryl-substituted aralkyloxyalkyl;

$R^5$ represents lower alkyl, lower acyl, lower alkoxycarbonyl, aromatic acyl, or a group represented by the following formula:

$-Q^1-(CH_2)_s-Q^2-R^6$ wherein $Q^1$ and $Q^2$ are both single bonds, or one of them is a single bond while the other represents oxygen, carbonyl, a group represented by —NHCO—, a group represented by —NHSO$_2$—, or a group represented by >CH—$R^7$, wherein $R^7$ represents hydroxy, lower alkyl or halogeno:

s represents 0 or an integer of 1 to 6; and $R^6$ represents optionally substituted aryl, optionally substituted benzoheteroaryl, 1,4-benzodioxanyl, 1,3-benzodioxolyl, benzothiazolyl, or cyano;

n represents 1;

m represents 0 or an integer of 1 to 6; and p represents an integer of 1 to 3, or a pharmacologically acceptable salt thereof.

2. A compound of formula:

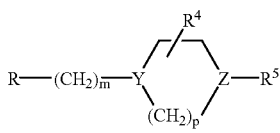

wherein R represents a substituent of the formula:

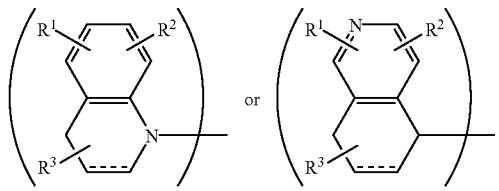

wherein the bond represented by the following formula:

and $R^1$, $R^2$, $R^3$, $R^4$, $R^5$, Y, Z, m, and p are each as defined in claim 1, and pharmacologically acceptable salts thereof.

3. The compound of claim 1 or a pharmacologically acceptable salt thereof, wherein m is 0 and p is 2.

4. The compound of claim 1 or a pharmacologically acceptable salt thereof, wherein Y is methine and Z is nitrogen.

5. The compound of claim 1 or a pharmacologically acceptable salt thereof, which is a compound selected from among the following ones:
- (267) 1-{1-[2-(4-methoxyphenyl)ethyl]piperidin-4-yl}-7-methoxy-1,2,3,4-tetrahydroquinoline,
- (268) 1-{1-[2-(4-fluorophenyl)ethyl]piperidin-4-yl}-7-methoxy-1,2,3,4-tetrahydro-quinoline,
- (269) 1-[1-(4-cyanopropyl)piperidin-4-yl]-7-methoxy-1,2,3,4-tetrahydroquinoline,
- (270) 1-{1-[2-(2-thienyl)ethyl]piperidin-4-yl}-1-7-methoxy-1,2,3,4-tetrahydroquinoline,
- (271) 1-{1-[2-(4-fluorophenyl)ethyl]piperidin-4-yl}-7,8-dimethoxy- 1,2,3,4-tetrahydroquinoline,
- (272) 1-{1-[2-(4-fluorophenyl)ethyl]piperidin-4-yl}-7,8-methylenedioxy-1,2,3,4-tetrahydroquinoline,
- (273) 1-{1-[2-(4-fluorophenyl)ethyl]piperidin-4-yl}-7-methoxy-8-methyl-1,2,3,4-tetrahydroquinoline,
- (274) 1-{1-[2-(4-fluorophenyl)-2-oxoethyl]piperidin-4-yl}-7-methoxy-1,2,3,4-tetrahydroquinoline,
- (275) 1-{1-[2-(4-fluorophenyl)-2-hydroxyethyl]piperidin-4-yl}-7-methoxy-1,2,3,4-tetrahydroquinoline,
- (276) 1-{1-[2-(4-fluorophenyl)-2-fluoroethyl]piperidin-4-yl}-7-methoxy-1,2,3,4-tetrahydroquinoline, and
- (283) 5-{4-[2-(4-fluorophenyl)ethyl]piperazin-1-yl}-5,6,7,8-tetrahydroisoquiline.

6. A pharmaceutical composition comprising a therapeutically effective amount of the compound of claim 1 or its salt in combination with a pharmaceutically acceptable carrier.

7. An agent for treating and ameliorating diseases against which serotonin antagonism is efficacious, which contains as the active ingredient the compound of claim 1 or a pharmacologically acceptable salt thereof.

8. A compound for treating and ameliorating spastic paralysis, which comprises as the active ingredient an effective amount of the compound of claim 1 or a pharmacologically acceptable salt thereof.

9. A muscle relaxant composition which contains as the active ingredient an effective amount of the compound of claim 1 or a pharmacologically acceptable salt thereof.

10. A process for producing a compound of the formula:

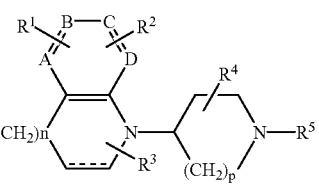

wherein the bond represented by the following formula:

and A, B, C, D, $R^1$, $R^2$, $R^3$, $R^4$, $R^5$, n, and p are each as defined in claim 1, which comprises removing, if necessary, the protecting group from a 1,4-substituted cyclic amine derivative (IX) represented by the following formula:

(IX)

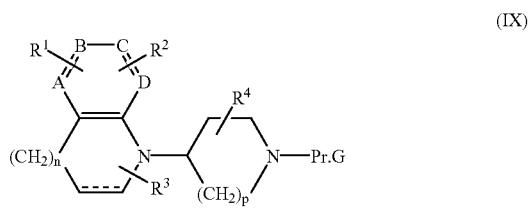

wherein the bond represented by the following formula:

and A, B, C, D, $R^1$, $R^2$, $R^3$, $R^4$, n, and p are each as defined in claim 1; and Pr.G represents hydrogen or a protecting group, and then reacting the same with L-$R^5$ wherein $R^5$ is as defined in claim 1; and L represents a leaving group.

11. A process for producing a compound of claim 1, which comprises reacting a fused cyclic amine represented by the following formula:

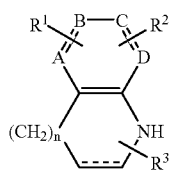

wherein the bond represented by the following formula:

and A, B, C, D, $R^1$, $R^2$, $R^3$ and n are each as defined in claim 1 with a cyclic ketone (VIII) represented by the following formula:

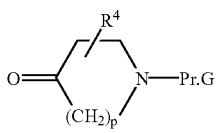
(VIII)

wherein $R^4$, p, and Pr.G are each as defined in claim 1 in the presence of a reducing agent to thereby give a 1,4-substituted cyclic amine derivative (IX), removing, if necessary, the protecting group therefrom and further reacting the same with L-$R^5$.

12. A compound of the formula:

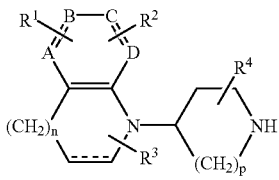

wherein the bond represented by the following formula:

----- and A, B, C, D, $R^1$, $R^2$, $R^3$, $R^4$, n, and p are each as defined in claim 1, provided that the case where $R^1$, $R^2$, $R^3$ and $R^4$ are all hydrogen atoms is excluded.

13. A method for antagonizing serotonin, which comprises administering an effective dose of the compound of claim 1, or a pharmacologically acceptable salt thereof, to a person in need of such treatment.

14. The compound of claim 1, in which the bond represented by the following formula in the formula (I):

----- is a single bond, represented by the formula (XXI)

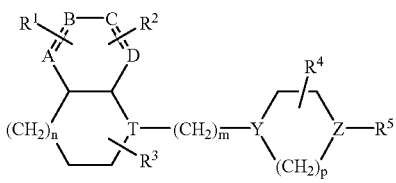
(XXI)

or a pharmacologically acceptable salt thereof.

15. The compound of claim 1, which m is 0 in the formula (I), represented by the formula (XXII)

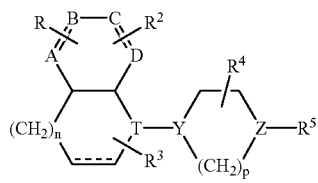
(XXII)

or a pharmacologically acceptable salt thereof.

16. The compound of claim 1, in which m is 1 to 6 in the formula (I) or a pharmacologically acceptable salt thereof.

17. A compound of the formula (XXIII)

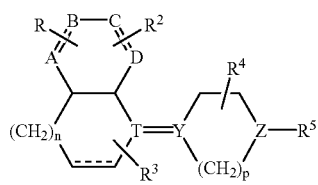
(XXIII)

or a pharmacologically acceptable salt thereof.

18. The compound of claim 1, in which the bond represented by the following formula in the formula (I):

----- is a double bond, represented by the formula (XXIV):

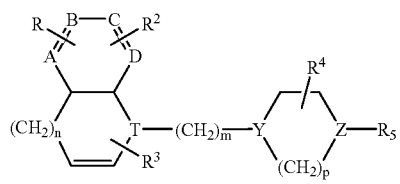
(XXIV)

or a pharmacologically acceptable salt thereof.

19. The compound of claim 1, in which the T is nitrogen.

* * * * *